US011342511B2

United States Patent
Baba et al.

(10) Patent No.: US 11,342,511 B2
(45) Date of Patent: May 24, 2022

(54) AZOLINE RING-CONTAINING COMPOUND, ELECTRON TRANSPORT/INJECTION LAYER MATERIAL CONTAINING THE SAME, AND ORGANIC ELECTROLUMINESCENT ELEMENT USING THE SAME

(71) Applicant: JNC CORPORATION, Tokyo (JP)

(72) Inventors: Daisuke Baba, Chiba (JP); Yohei Ono, Chiba (JP); Katsuya Masuda, Chiba (JP)

(73) Assignee: SK MATERIALS JNC CO., LTD., Gyeonggi-Do (KR)

(*) Notice: Subject to any disclaimer, the term of this patent is extended or adjusted under 35 U.S.C. 154(b) by 1017 days.

(21) Appl. No.: 15/745,900

(22) PCT Filed: Jul. 20, 2016

(86) PCT No.: PCT/JP2016/071228
§ 371 (c)(1),
(2) Date: Jan. 18, 2018

(87) PCT Pub. No.: WO2017/014226
PCT Pub. Date: Jan. 26, 2017

(65) Prior Publication Data
US 2018/0212156 A1 Jul. 26, 2018

(30) Foreign Application Priority Data
Jul. 21, 2015 (JP) .............................. JP2015-143862

(51) Int. Cl.
| H01L 51/54 | (2006.01) |
| H01L 51/00 | (2006.01) |
| C07D 233/06 | (2006.01) |
| C07D 263/12 | (2006.01) |
| C07D 471/04 | (2006.01) |
| C07D 207/20 | (2006.01) |
| C07D 401/14 | (2006.01) |
| C07D 413/14 | (2006.01) |
| H01L 51/50 | (2006.01) |

(52) U.S. Cl.
CPC ........ H01L 51/0069 (2013.01); C07D 207/20 (2013.01); C07D 233/06 (2013.01); C07D 263/12 (2013.01); C07D 401/14 (2013.01); C07D 413/14 (2013.01); C07D 471/04 (2013.01); H01L 51/0052 (2013.01); H01L 51/0054 (2013.01); H01L 51/0056 (2013.01); H01L 51/0058 (2013.01); H01L 51/0067 (2013.01); H01L 51/0072 (2013.01); H01L 51/5072 (2013.01); H01L 51/5076 (2013.01); H01L 51/5092 (2013.01)

(58) Field of Classification Search
None
See application file for complete search history.

(56) References Cited

U.S. PATENT DOCUMENTS

| 2003/0215667 A1 | 11/2003 | Xie | |
| 2006/0172147 A1 | 8/2006 | Matsuura et al. | |
| 2010/0190994 A1* | 7/2010 | Lee | C09K 11/06 548/110 |
| 2010/0193773 A1 | 8/2010 | Yamamoto et al. | |
| 2010/0249349 A1* | 9/2010 | Chebotareva | C08G 61/10 526/259 |
| 2011/0166143 A1 | 7/2011 | Bretschneider et al. | |

(Continued)

FOREIGN PATENT DOCUMENTS

| CN | 1820550 | 8/2006 |
| CN | 101503393 | 8/2009 |
| CN | 102127073 A * | 7/2011 |

(Continued)

OTHER PUBLICATIONS

Machine translation of CN-102127073. (Year: 2011).*
J. Am. Chem. Soc. 2006, 128, 13038-13039. (Year: 2006).*
J. Am. Chem. Soc. 2009, 131, 4592-4593. (Year: 2009).*
Office Action dated Mar. 31, 2020 in corresponding Japanese Patent Application No. 2017-529904 with English language translation.
Beinhoff et al., "Synthesis and Spectroscopic Properties of Arene-Substituted Pyrene Derivatives as Model Compounds for Fluorescent Polarity Probes," European Journal of Organic Chemistry, 2001, vol. 20, pp. 3819-3829.

(Continued)

*Primary Examiner* — Andrew K Bohaty
(74) *Attorney, Agent, or Firm* — Wenderoth, Lind & Ponack, L.L.P.

(57) ABSTRACT

An object is to provide an azoline ring-containing compound which achieves characteristics required for an organic EL element, such as a driving voltage, a quantum efficiency, and element lifetime in a well-balanced manner, and particularly can obtain a high quantum efficiency, for example, in a case where the azoline ring-containing compound is used for the organic EL element. The above object is achieved by an azoline ring-containing compound represented by the following general formula (1).

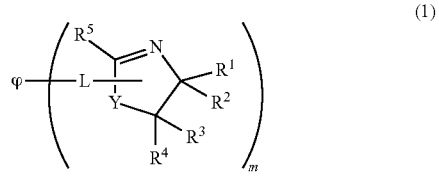

(1)

In formula (1), φ represents an m-valent group derived from an aromatic hydrocarbon having 6 to 40 carbon atoms or the like, Y represents —O—, —S—, or >N—Ar, $R^1$ to $R^5$ each represent a hydrogen atom or an alkyl having 1 to 4 carbon atoms, and L represents a phenylene group or the like.

24 Claims, 1 Drawing Sheet

(56) References Cited

U.S. PATENT DOCUMENTS

2014/0221362 A1 8/2014 Bretschneider et al.
2016/0118598 A1 4/2016 Baba et al.

FOREIGN PATENT DOCUMENTS

| CN | 103313712 | 9/2013 |
|---|---|---|
| CN | 103329619 | 9/2013 |
| JP | 2003-123983 | 4/2003 |
| JP | 2013-184909 | 9/2013 |
| WO | 2003/060956 | 7/2003 |
| WO | 2008/085655 | 7/2008 |
| WO | 2008/117976 | 10/2008 |
| WO | 2010/150988 | 12/2010 |
| WO | 2011/045224 | 4/2011 |
| WO | 2012/068161 | 5/2012 |
| WO | 2014/163173 | 10/2014 |

OTHER PUBLICATIONS

Vingiello et al., "3- and 4-(7-Benz[a]Anthracenyl)Phenyl-2-Oxazolines and 3- And 4-(9-Anthracenyl)Phenyl-2-Oxazolines and Their Hydrochloride Salts," Organic Preparations and Procedures International, 1971, vol. 3, No. 2, pp. 103-107.

Vingiello et al., "3- and 4- (Benz[a]Anthracenyl)Phenyl-2-Thiazolines and 3- and 4-(9-Anthracenyl)Phenyl-2-Thiazolines. A New Method of Preparation of Thiazolines", Organic Preparations and Procedures International: The New Journal for Organic Synthesis, 1971, vol. 3, No. 5, pp. 235-238.

Astley et al., "Uncatalysed coupling of an activated aryl chloride with aryllithium and aryl Grignard reagents", Tetrahedron Letters, 2004, vol. 45, pp. 7315-7317.

Kandasamy et al., "Mercury chalcogenolates of a ligand having both sterically more bulkier and intramolecularly coordinating features: first isolation of a novel air stable mercury tellurolate", 2005, vol. 358, pp. 207-212.

Office Action dated Sep. 11, 2020 in corresponding Chinese Patent Application No. 201680024128.9, with Machine translation.

Decision to Grant a Patent dated Jul. 14, 2020 in corresponding Japanese Patent Application 2017-529904, with Machine translation.

International Search Report dated Oct. 18, 2016 in International Application No. PCT/JP2016/071228.

Krasavin, M., "Novel diversely substituted 1-heteroaryl-2-imidazolines for fragment-based drug discovery", Tetrahedron Letters, 2012, 53 23), pp. 2876-2880, ISSN: 0040-4039.

Sasada, T. et al., "An Unprecedented Approach to 4,5-Disubstituted Pyrimidine Derivatives by a $ZnCl_2$-Catalyzed Three-Component Coupling Reaction", Organic Letters, 2009,11(10), pp. 2161-2164, ISSN:1523-7060.

Ghosh, S. et al., "Synthesis of 4-oxazolinephenylboronic acid and heterobiaryl oxazolines via a Suzuki reaction", Journal of Chemical Research, 2009, (4), pp. 205-207, ISSN: 1745-5198.

Ackermann, L. et al., "Well-Defined Ruthenium(II) Carboxylate as Catalyst for Direct C-H/C-0 Bond Arylations with Phenols in Water", Organic Letters, 2012,14(8), pp. 2146-2149, ISSN: 1523-7052.

Tobisu, M. et al., "Nickel-Catalyzed Suzuki—Miyaura Reaction of Aryl Fluorides", Journal of the American Chemical Society, 2011, 133(48), p. 19505-19511, ISSN:0002-7863.

Jain, P. et al., "Nicotinic Acid Adenine Dinucleotide Phosphate Analogues Containing Substituted Nicotinic Acid: Effect of Modification of $Ca^{2+}$ Release$^+$", Journal of Medicinal Chemistry, 2010, 53(21), pp. 7599-7612, ISSN: 0022-2623.

Ye, W. et al., "Highly Active Ruthenium (II) Complex Catalysts Bearing an Unsymmetrical NNN Ligand in the (Asymmetric) Transfer Hydrogenation of Ketones", Chemistry—A European Journal, 2011,17(17), pp. 4737-4741, ISSN:0947-6539.

Ye, W. et al., "Ruthenium(II) Pyrazolyl-Pyridyl-Oxazolinyl Complex Catalysts for the Asymmetric Transfer Hydrogenation of Ketones", Chemistry—A European Journal, 2012,18(35), pp. 10843-10846, ISSN:0947-6539.

Oi, S. et al., "Nitrogen-directed *ortho*-arylation and -heteroarylation of aromatic rings catalyzed by ruthenium complexes", Tetrahedron, 2008, 64(26), pp. 6051-6059, ISSN: 0040-4020.

Li, P. et al., "NCN palladium pincer via transmercuration. Synthesis of [2-(2-oxazoliny)-6-(2-pyridyl)] phenylpalladium(II) chloride and its catalytic activity in Suzuki coupling", Inorganic Chemistry Communications,2013, 32, pp. 78-81.

Bellamy, E. et al., "*Ortho*-directed functionalization of arenes using magnesate bases+", Chemical Communications, 2010, 46(37), pp. 7043-7045, ISSN: 1359-7345.

M. Uchida et al., "Relationships between the Structures of Pyridylsilole Derivatives and the Performance for Organic Electroluminescent Device", Proceedings of the 10th International Workshop on Inorganic and Organic Electroluminescence (2000).

Office Action dated Apr. 2, 2021 in corresponding Chinese Patent Application No. 201680024128.9, with English translation.

\* cited by examiner

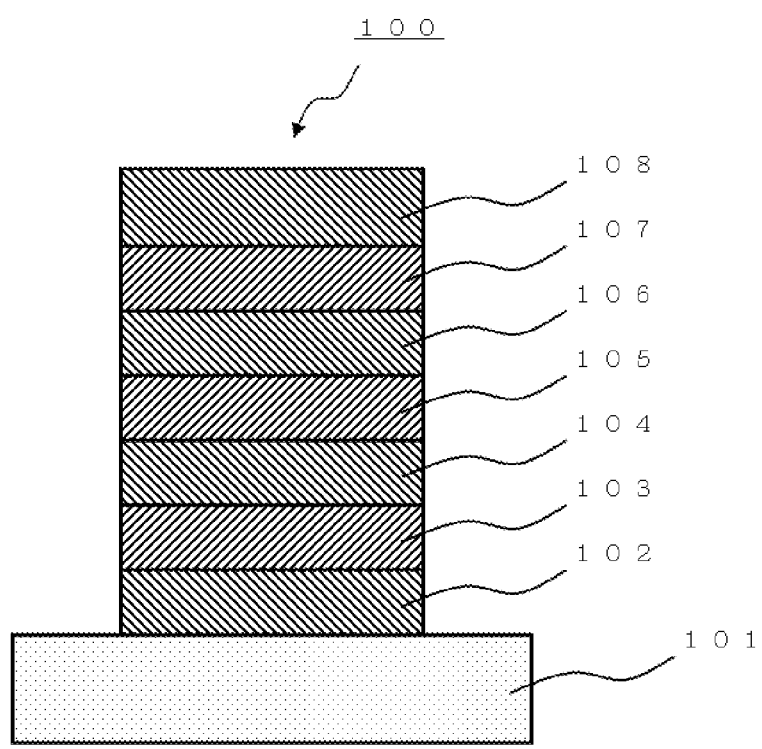

AZOLINE RING-CONTAINING COMPOUND, ELECTRON TRANSPORT/INJECTION LAYER MATERIAL CONTAINING THE SAME, AND ORGANIC ELECTROLUMINESCENT ELEMENT USING THE SAME

TECHNICAL FIELD

The present invention relates to a novel compound containing an azoline ring (oxazoline ring, thiazoline ring, or imidazoline ring), an electron transport/injection layer material containing the compound, an organic electroluminescent element (hereinafter, referred to as an organic EL element or simply abbreviated as an "element") using the material, and the like.

BACKGROUND ART

In recent years, an organic EL element has attracted attention as a next-generation full color flat panel display, and active studies have been conducted. In order to promote practical application of the organic EL element, it is indispensable to reduce power consumption of the element (reduction in voltage and increase in external quantum yield) and to prolong lifetime of the element. In order to achieve these, a new electron transport/injection layer material has been developed.

Particularly, an object is to reduce power consumption of a blue electroluminescent element and to prolong lifetime thereof, and various electron transport/injection layer materials have been studied. For example, as described in Patent Literature 1 and Non Patent Literature 1, it is known that an organic EL element can be driven at a low voltage by using a pyridine derivative or a bipyridine derivative as an electron transport/injection layer material. Some of the organic EL elements have been put into practical use. However, characteristics thereof are insufficient for the organic EL elements to be adopted in more displays.

In addition, studies using benzimidazole or a benzothiazole derivative as an electron transport/injection layer material for an organic EL element have also been made (see Patent Literatures 2 to 4). Like the organic EL element using a pyridine derivative and a bipyridine derivative, some of the organic EL elements using benzimidazole and a benzothiazole derivative have been put into practical use. However, characteristics thereof are insufficient and further improvement is required.

CITATION LIST

Patent Literature

Patent Literature 1: JP 2003-123983 A
Patent Literature 2: US 2003/215667 A
Patent Literature 3: WO 2003/060956 A
Patent Literature 4: WO 2008/117976 A

Non Patent Literature

Non Patent Literature 1: Proceedings of the 10$^{th}$ International Workshop on Inorganic and Organic Electroluminescence (2000)

SUMMARY OF INVENTION

Technical Problem

As described above, generally, a compound used for the electron transport/injection layer material is a nitrogen-containing aromatic ring-based compound such as a pyridine-based compound, a benzimidazole-based compound, or a benzothiazole-based compound, and an aliphatic ring-based compound has not been studied. The present invention has been achieved in view of such related art and problems of the related art. One object of the present invention is to provide an electron transport/injection layer material which achieves characteristics required for an organic EL element, such as a driving voltage, a quantum efficiency, and element lifetime in a well-balanced manner, and can obtain a high quantum efficiency particularly. Another object of the present invention is to provide an organic EL element using the material.

Solution to Problem

As a result of intensive studies, the present inventors have succeeded in synthesizing a novel compound containing an azoline ring (oxazoline ring, thiazoline ring, or imidazoline ring), have found that characteristics such as a driving voltage, a quantum efficiency, and element lifetime are improved, particularly the quantum efficiency is improved by using this compound for an electron transport/injection layer of an organic EL element, and have completed the present invention based on this finding.

The above object is achieved by the following items.

[1] An azoline ring-containing compound represented by the following general formula (1).

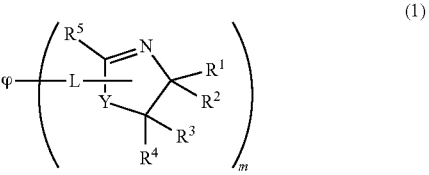

(1)

In formula (1), φ represents an m-valent group derived from an aromatic hydrocarbon having 6 to 40 carbon atoms or an m-valent group derived from an aromatic heterocyclic ring having 2 to 40 carbon atoms, and at least one hydrogen atom of φ may be substituted by an alkyl having 1 to 6 carbon atoms, an aryl having 6 to 18 carbon atoms, or a heteroaryl having 2 to 18 carbon atoms, Y's each independently represent —O—, —S—, or >N—Ar, Ar represents an aryl having 6 to 12 carbon atoms or a heteroaryl having 2 to 12 carbon atoms, at least one hydrogen atom of Ar may be substituted by an alkyl having 1 to 4 carbon atoms, an aryl having 6 to 12 carbon atoms, or a heteroaryl having 2 to 12 carbon atoms, and $R^1$ to $R^5$ each independently represent a hydrogen atom or an alkyl having 1 to 4 carbon atoms, with the proviso that at least one of Ar in the >N—Ar and the $R^1$ to $R^5$ is a moiety bonded to L, L's are each independently selected from the group consisting of a divalent group represented by the following formula (L-1) and a divalent group represented by the following formula (L-2),

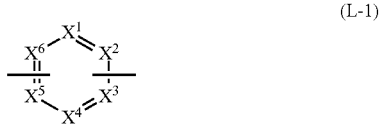

(L-1)

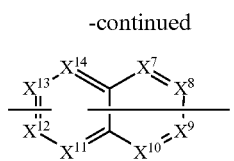
(L-2)

in formula (L-1), $X^1$ to $X^6$ each independently represent =$CR^6$— or =N—, at least two of $X^1$ to $X^6$ each represent =$CR^6$—, $R^6$'s in two =$CR^6$'s in $X^1$ to $X^6$ are each a moiety bonded to φ or an azoline ring, and $R^6$'s in the other =$CR^6$'s- each represent a hydrogen atom, in formula (L-2), $X^7$ to $X^{14}$ each independently represent =$CR^6$— or =N—, at least two of $X^7$ to $X^{14}$ each represent =$CR^6$—, $R^6$'s in two =$CR^6$'s in $X^7$ to $X^{14}$ are each a moiety bonded to φ or an azoline ring, and $R^6$'s in the other =$CR^6$—'s each represent a hydrogen atom, at least one hydrogen atom of L may be substituted by an alkyl having 1 to 4 carbon atoms, an aryl having 6 to 10 carbon atoms, or a heteroaryl having 2 to 10 carbon atoms, m represents an integer of 1 to 4, and when m represents 2 to 4, groups formed by an azoline ring and L may be the same as or different from one another, and at least one hydrogen atom in a compound represented by formula (1) may be substituted by a deuterium atom.

[2] The azoline ring-containing compound according to [1], represented by the following general formula (2-1) or (2-2).

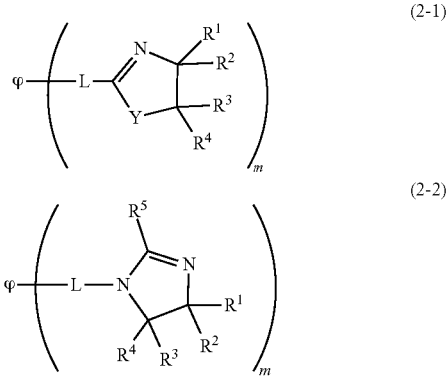

In formulas (2-1) and (2-2), φ represents an m-valent group derived from an aromatic hydrocarbon having 6 to 40 carbon atoms or an m-valent group derived from an aromatic heterocyclic ring having 2 to 40 carbon atoms, and at least one hydrogen atom of φ may be substituted by an alkyl having 1 to 6 carbon atoms, an aryl having 6 to 18 carbon atoms, or a heteroaryl having 2 to 18 carbon atoms, in formula (2-1), Y's each independently represent —O—, —S—, or >N—Ar, Ar represents an aryl having 6 to 12 carbon atoms or a heteroaryl having 2 to 12 carbon atoms, and at least one hydrogen atom of Ar may be substituted by an alkyl having 1 to 4 carbon atoms, an aryl having 6 to 12 carbon atoms, or a heteroaryl having 2 to 12 carbon atoms, in formula (2-1), $R^1$ to $R^4$ each independently represent a hydrogen atom or an alkyl having 1 to 4 carbon atoms, with the proviso that $R^1$ and $R^2$ are the same as each other and $R^3$ and $R^4$ are the same as each other, in formula (2-2), $R^4$ to $R^5$ each independently represent a hydrogen atom or an alkyl having 1 to 4 carbon atoms, with the proviso that $R^1$ and $R^2$ are the same as each other and $R^3$ and $R^4$ are the same as each other, in formulas (2-1) and (2-2), L's are each independently selected from the group consisting of a divalent group represented by the following formula (L-1) and a divalent group represented by the following formula (L-2),

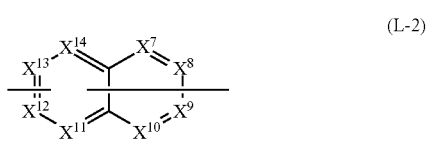

in formula (L-1), $X^1$ to $X^6$ each independently represent =$CR^6$— or =N—, at least two of $X^1$ to $X^6$ each represent =$CR^6$—, $R^6$'s in two =$CR^6$'s in $X^1$ to $X^6$ are each a moiety bonded to φ or an azoline ring, and $R^6$'s in the other =$CR^6$—'s each represent a hydrogen atom, in formula (L-2), $X^7$ to $X^{14}$ each independently represent =$CR^6$— or =N—, at least two of $X^7$ to $X^{14}$ each represent =$CR^6$—, $R^6$'s in two =$CR^6$'s in $X^7$ to $X^{14}$ are each a moiety bonded to φ or an azoline ring, and $R^6$'s in the other =$CR^6$—'s each represent a hydrogen atom, at least one hydrogen atom of L may be substituted by an alkyl having 1 to 4 carbon atoms, an aryl having 6 to 10 carbon atoms, or a heteroaryl having 2 to 10 carbon atoms, m represents an integer of 1 to 4, and when m represents 2 to 4, groups formed by an azoline ring and L may be the same as or different from one another, and at least one hydrogen atom in a compound represented by formula (2-1) or (2-2) may be substituted by a deuterium atom.

[3] The azoline ring-containing compound according to [1] or [2], in which φ is selected from the group consisting of monovalent groups represented by the following formulas (φ1-1) to (φ1-18), divalent groups represented by the following formulas (φ2-1) to (φ2-34), trivalent groups represented by the following formulas (φ3-1) to (φ3-3), and tetravalent groups represented by the following formulas (φ4-1) and (φ4-2), and at least one hydrogen atom of φ may be substituted by an alkyl having 1 to 6 carbon atoms, an aryl having 6 to 18 carbon atoms, or a heteroaryl having 2 to 18 carbon atoms.

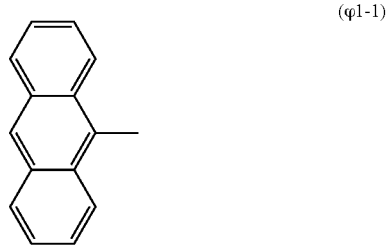

-continued
(φ1-2)
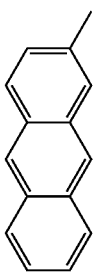
(φ1-3)
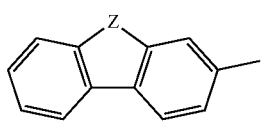
(φ1-4)
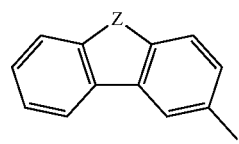
(φ1-5)
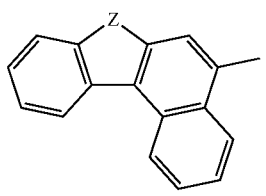
(φ1-6)
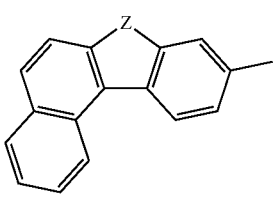
(φ1-7)
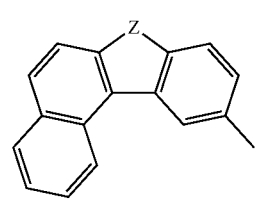
(φ1-8)
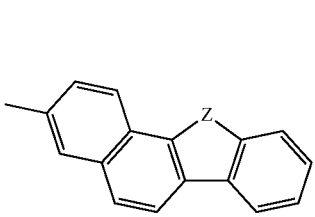
(φ1-9)
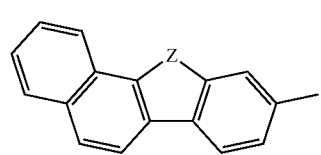
-continued
(φ1-10)
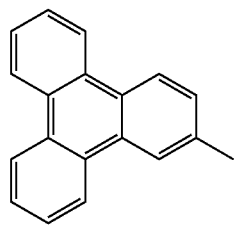
(φ1-11)
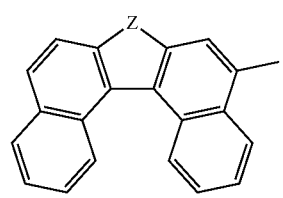
(φ1-12)
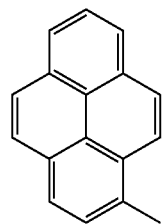
(φ1-13)
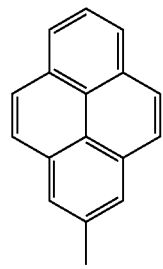
(φ1-14)
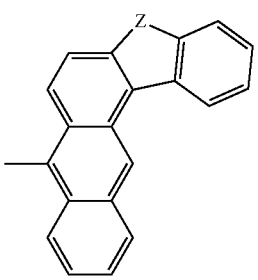
(φ1-15)
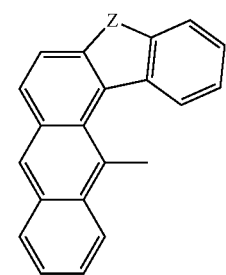

-continued
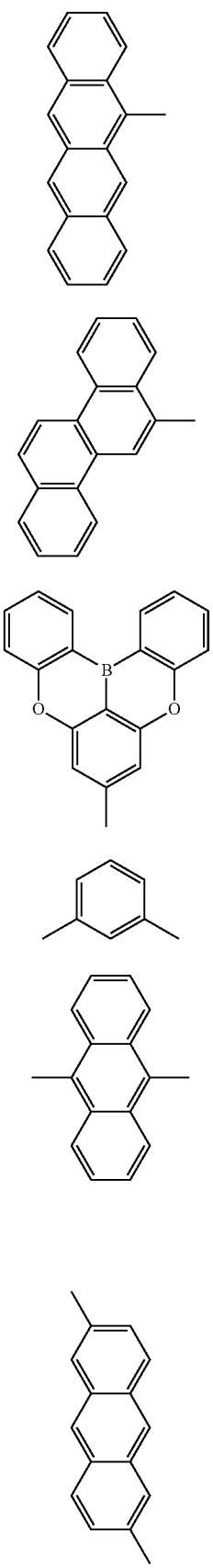
(φ1-16)
(φ1-17)
(φ1-18)
(φ2-1)
(φ2-2)
(φ2-3)
-continued
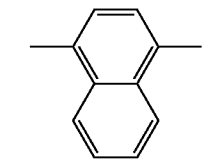
(φ2-4)
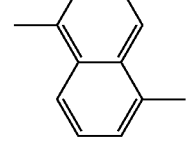
(φ2-5)
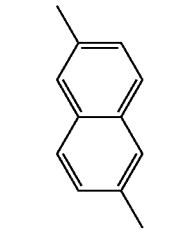
(φ2-6)
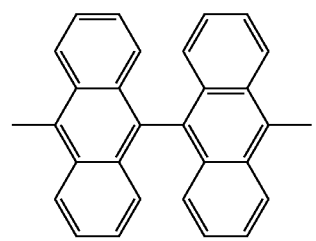
(φ2-7)
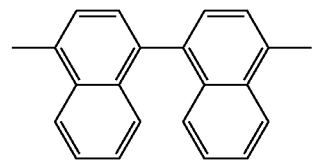
(φ2-8)
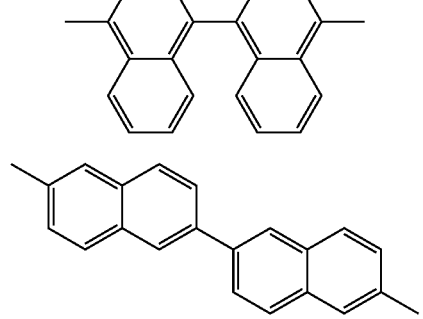
(φ2-9)
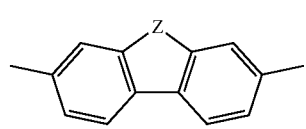
(φ2-10)
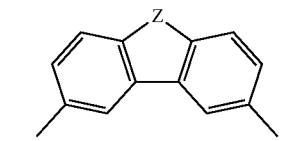
(φ2-11)
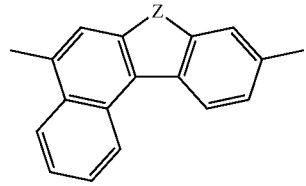
(φ2-12)

(φ2-13)
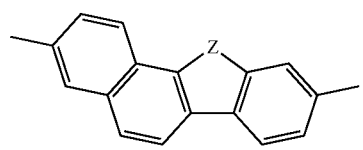
(φ2-14)
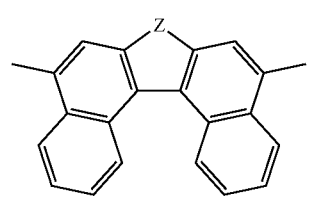
(φ2-15)
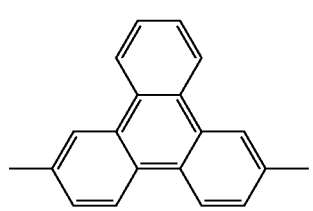
(φ2-16)
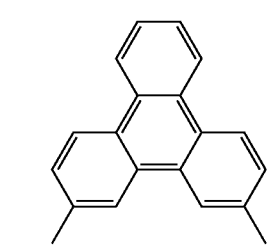
(φ2-17)
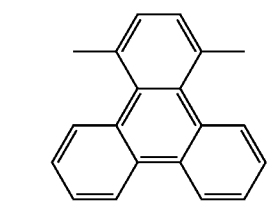
(φ2-18)
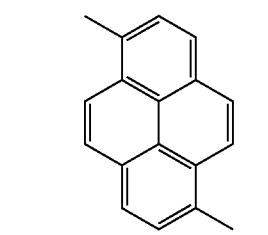
(φ2-19)
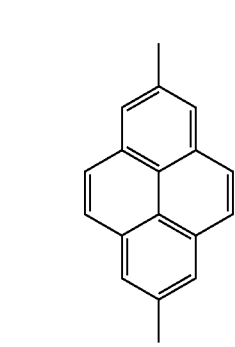
(φ2-20)
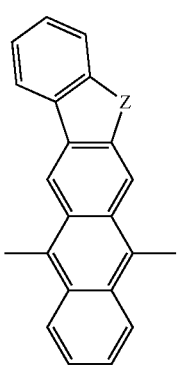
(φ2-21)
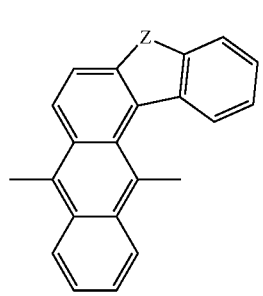
(φ2-22)
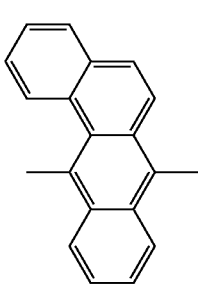
(φ2-23)
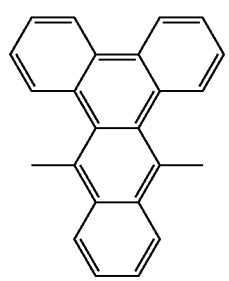
(φ2-24)
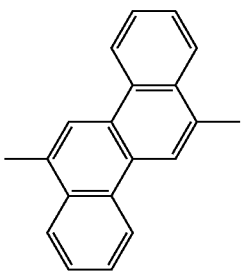

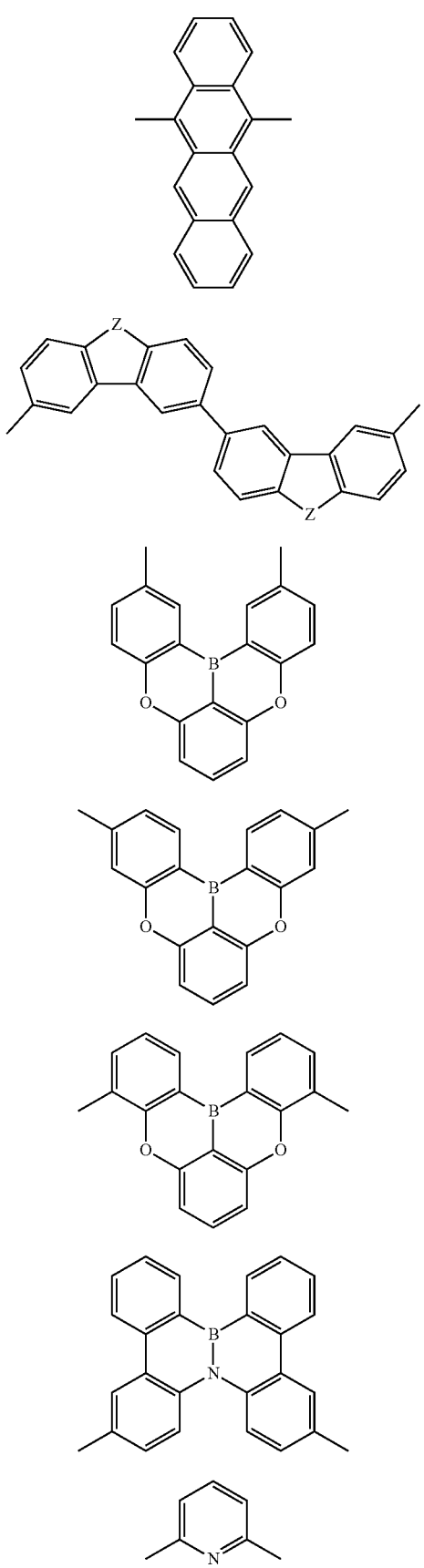

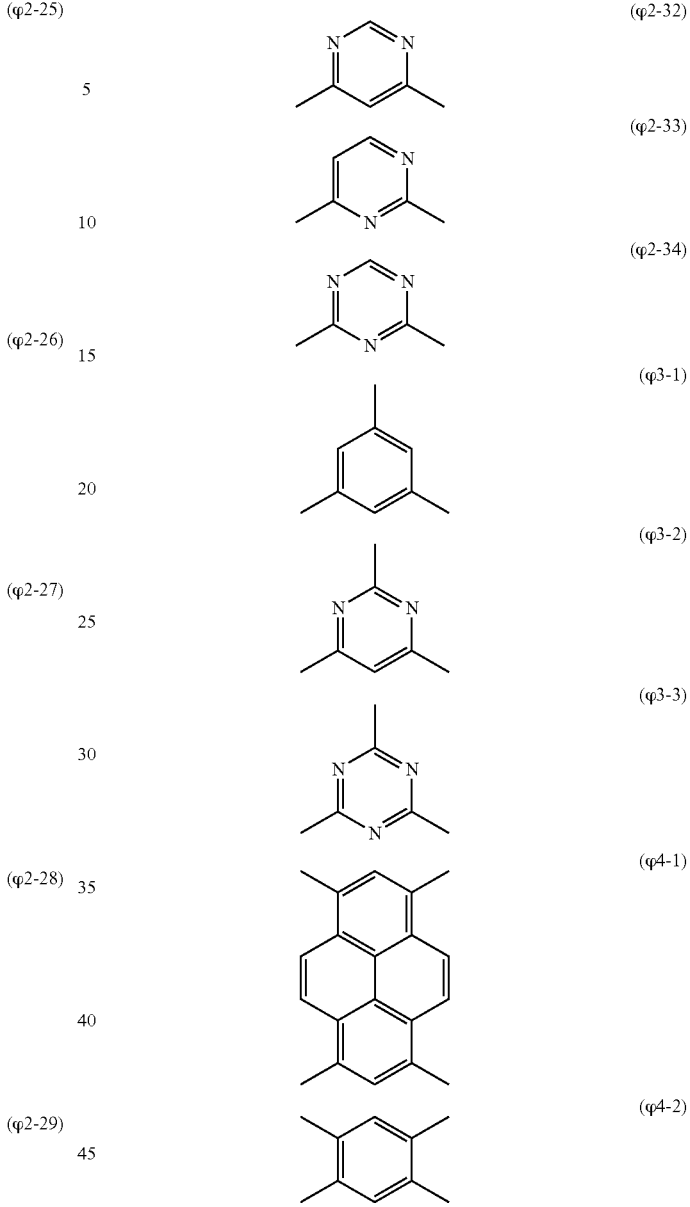

Z in the above formulas represents >CR$_2$, >N—Ar, >N-L, —O—, or —S—, R's in >CR$_2$ each independently represent an alkyl having 1 to 4 carbon atoms, an aryl having 6 to 12 carbon atoms, or a heteroaryl having 2 to 12 carbon atoms, R's may be bonded to each other to form a ring, Ar in >N—Ar represents an aryl having 6 to 12 carbon atoms or a heteroaryl having 2 to 12 carbon atoms, and L in >N-L represents L in the above general formula (1), (2-1), or (2-2).

[4] The azoline ring-containing compound according to any one of [1] to [3], in which L represents a divalent group of a ring selected from the group consisting of benzene, naphthalene, pyridine, pyrazine, pyrimidine, pyridazine, triazine, quinoline, isoquinoline, naphthyridine, phthalazine, quinoxaline, quinazoline, cinnoline, and pteridine, and at least one hydrogen atom of L may be substituted by an alkyl having 1 to 4 carbon atoms, an aryl having 6 to 10 carbon atoms, or a heteroaryl having 2 to 10 carbon atoms.

[5] The azoline ring-containing compound according to any one of [1] to [4], in which Ar in >N—Ar as Y or Z is selected from the group consisting of phenyl, naphthyl, pyridinyl, pyrazinyl, pyrimidinyl, pyridazinyl, triazinyl, quinolinyl, isoquinolinyl, naphthyridinyl, phthalazinyl, quinoxalinyl, quinazolinyl, cinnolinyl, and pteridinyl, and at least one hydrogen atom of Ar in >N—Ar as Y may be substituted by an alkyl having 1 to 4 carbon atoms or an aryl having 6 to 10 carbon atoms.

[6] The azoline ring-containing compound according to any one of [1] to [5], in which $R^1$ to $R^4$ each independently represent a hydrogen atom or an alkyl having 1 to 4 carbon atoms, with the proviso that $R^1$ and $R^2$ are the same as each other, $R^3$ and $R^4$ are the same as each other, and not all of $R^1$ to $R^4$ represent hydrogen atoms simultaneously, and m represents 1 or 2, and when m represents 2, groups formed by an azoline ring and L are the same as each other.

[7] The azoline ring-containing compound according to [1], represented by any one of the following formulas (1-1-108), (1-2-1), (1-2-2), (1-2-102), and (1-3-2).

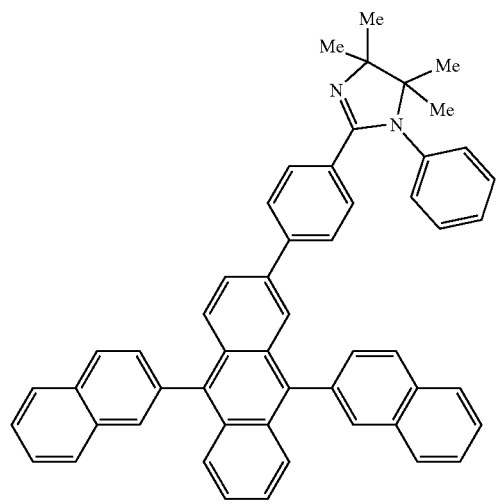

(1-1-108)

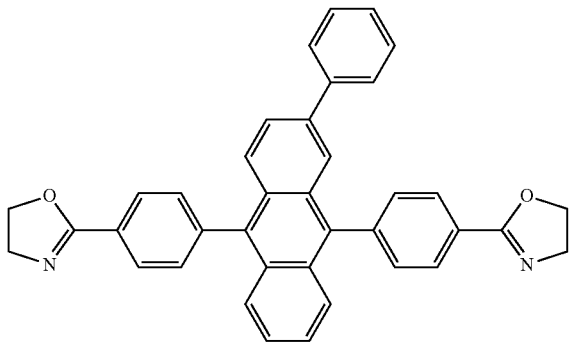

(1-2-1)

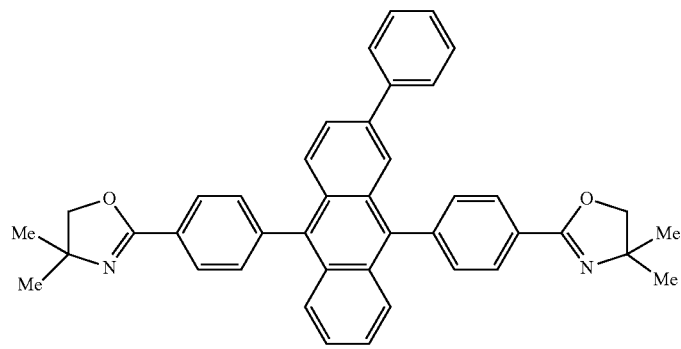

(1-2-2)

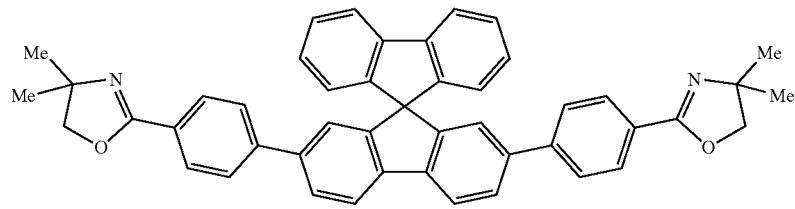

(1-2-102)

(1-3-2)
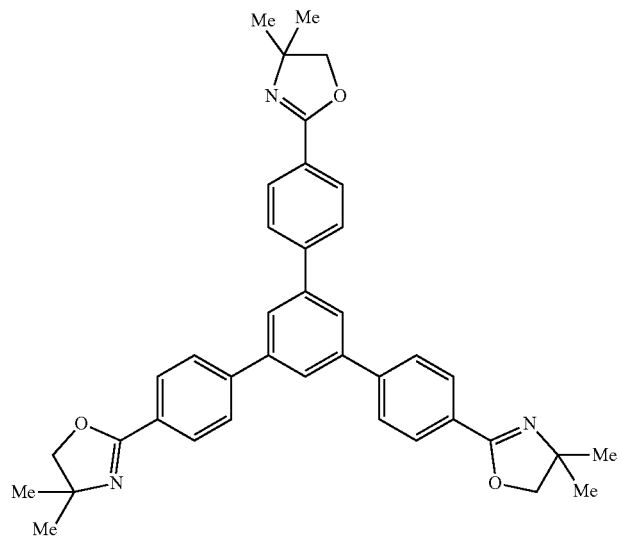
[8] The azoline ring-containing compound according to [1], represented by any one of the following formulas (1-2-22), (1-2-146), (1-2-402), (1-2-522), and (1-3-8).
(1-2-22)
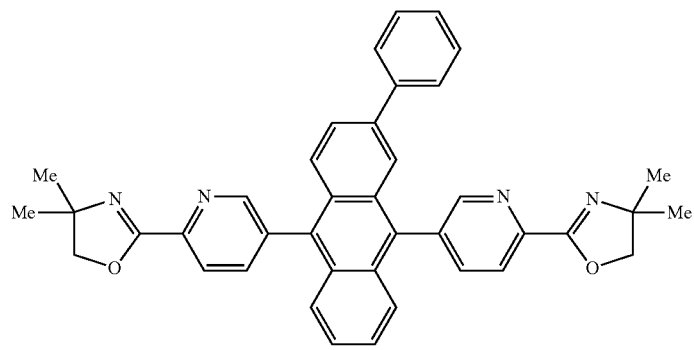
(1-2-146)
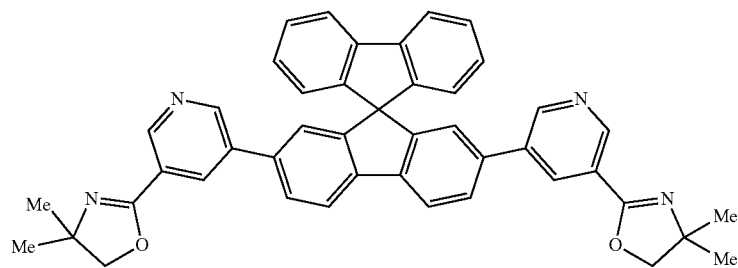
(1-2-402)
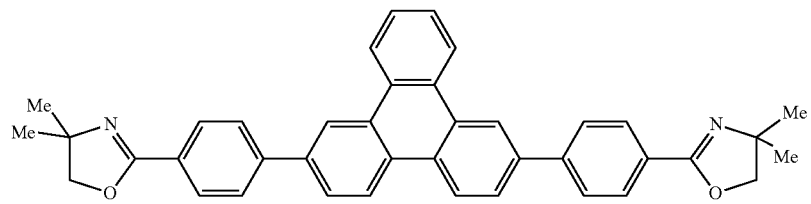

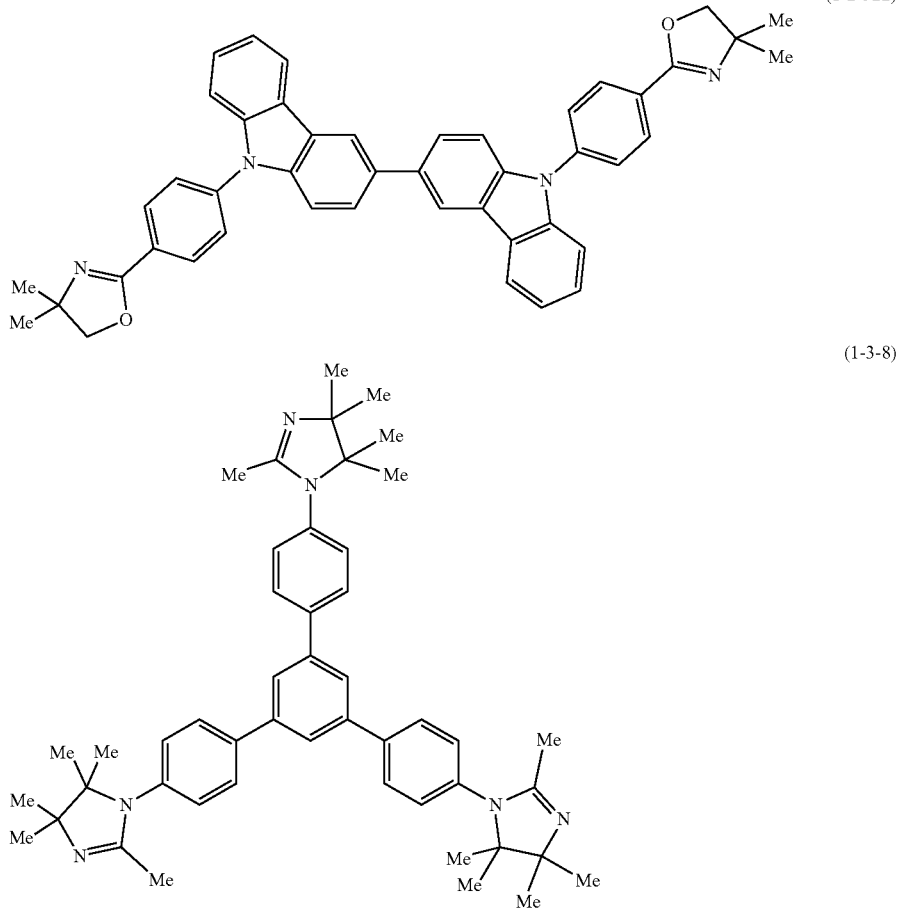

(1-2-522)

(1-3-8)

[9] The azoline ring-containing compound according to any one of [1] to [3], in which φ is selected from the group consisting of divalent groups represented by the following formulas (φ2-1), (φ2-31), (φ2-32), (φ2-33), and (φ2-34), and at least one hydrogen atom of φ may be substituted by an aryl having 6 to 18 carbon atoms,

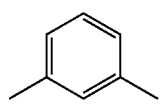
(φ2-1)

(φ2-31)

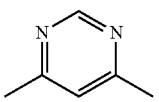
(φ2-32)

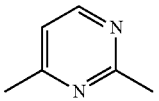
(φ2-33)

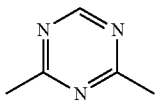
(φ2-34)

L represents a divalent group of a ring selected from the group consisting of benzene, pyridine, pyrazine, pyrimidine, pyridazine, and triazine, and at least one hydrogen atom of L may be substituted by an alkyl having 1 to 4 carbon atoms, an aryl having 6 to 10 carbon atoms, or a heteroaryl having 2 to 14 carbon atoms, Ar in >N—Ar as Y is selected from the group consisting of phenyl, pyridinyl, pyrazinyl, pyrimidinyl, pyridazinyl, and triazinyl, and at least one hydrogen atom of the Ar may be substituted by an alkyl having 1 to 4 carbon atoms or an aryl having 6 to 10 carbon atoms, $R^1$ to $R^4$ each independently represent a hydrogen atom or an alkyl having 1 to 4 carbon atoms, with the proviso that $R^1$ and $R^2$ are the same as each other, $R^3$ and $R^4$ are the same as each other, and not all of $R^1$ to $R^4$ represent hydrogen atoms simultaneously, and m represents 2, and groups formed by an azoline ring and L are the same as each other.

[10] The azoline ring-containing compound according to [1], represented by any one of the following formulas (1-2-1022), (1-2-1025), (1-2-1026), (1-2-1027), (1-2-1031), and (1-2-1035).

(1-2-1022)
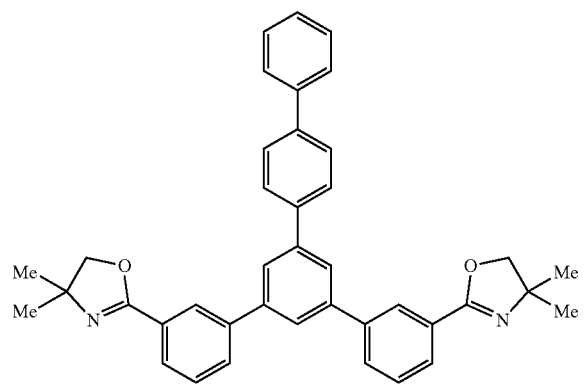
(1-2-1025)
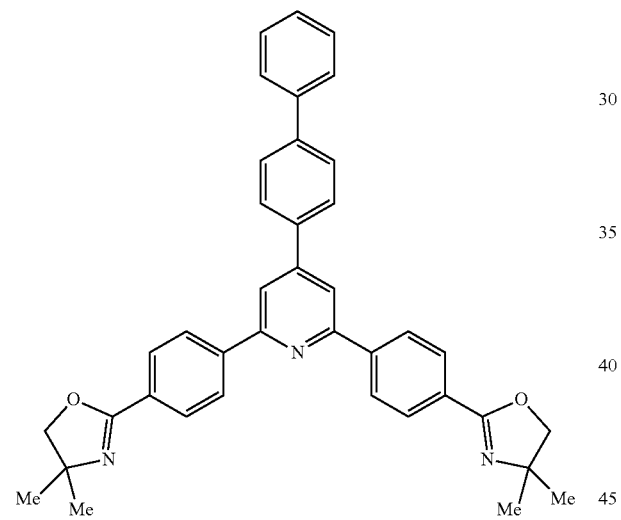
(1-2-1026)
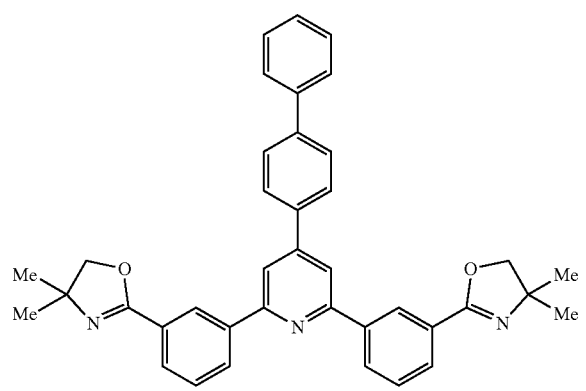
(1-2-1027)
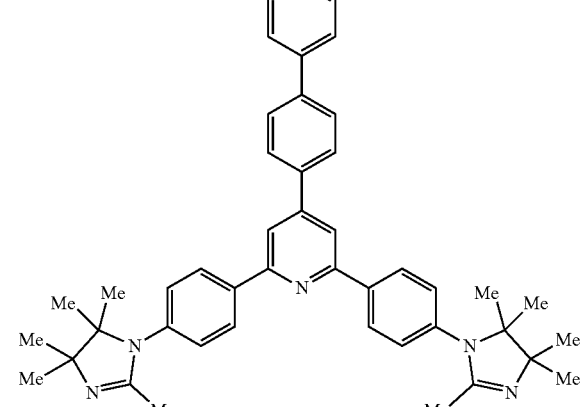
(1-2-1031)
(1-2-1035)
[11] An electron transport material or an electron injection layer material, containing the azoline ring-containing compound according to any one of [1] to [10].

[12] An organic electroluminescent element including: a pair of electrodes formed of an anode and a cathode; a light emitting layer disposed between the pair of electrodes; and an electron transport layer and/or an electron injection layer disposed between the cathode and the light emitting layer and containing the material according to [11].

[13] The organic electroluminescent element according to [12], in which at least one of the electron transport layer and the electron injection layer further contains at least one selected from the group consisting of a quinolinol-based metal complex, a bipyridine derivative, a phenanthroline derivative, and a borane derivative.

[14] The organic electroluminescent element according to [12] or [13], in which at least one of the electron transport layer and the electron injection layer further contains at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

[15] A display apparatus or a lighting apparatus including the organic electroluminescent element according to any one of [12] to [14].

ADVANTAGEOUS EFFECTS OF INVENTION

According to a particularly preferred embodiment of the present invention, the novel compound of the present invention is characterized by being stable even when a voltage is applied to the compound in a thin film state, and having high charge transport ability. The compound is suitable, for example, as a charge transport material in an organic EL element. Use of the compound for an electron transport/injection layer of the organic EL element makes it possible to improve characteristics such as a driving voltage, a quantum efficiency, and element lifetime in a well-balanced manner. Among these characteristics, the compound particularly contributes to improvement of the quantum efficiency. In addition, use of this organic EL element makes it possible to manufacture a high-performance display apparatus such as a full-color display.

BRIEF DESCRIPTION OF DRAWINGS

FIG. 1 is a schematic cross-sectional view illustrating an organic electroluminescent element according to the present embodiment.

DESCRIPTION OF EMBODIMENTS

<Description of Azoline Ring-Containing Compound>

An azoline ring-containing compound according to the present invention is a compound represented by the following general formula (1).

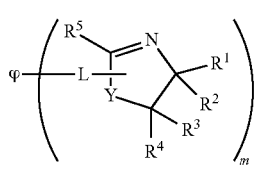

(1)

In formula (1), $\varphi$ is a core portion, a 5-membered ring formed by containing N and Y (—O—, —S—, or >N—Ar) is an azoline ring portion, and L is a linking portion for bonding the core portion $\varphi$ to the azoline ring portion. The azoline ring portion is a functional moiety most affecting characteristics of the azoline ring-containing compound. Basically, the core portion $\varphi$ and the linking portion L have a role of causing m (m=1 to 4) azoline ring portions to be present in the compound. However, particularly in order to use the compound as an electron transport/injection layer material of an organic EL element, the compound preferably adopts such a specific structure as described below. The compound includes m (m=1 to 4) conjugates formed of the linking portion L and the azoline ring. However, in a case where a plurality of the conjugates is present, the structures of these conjugates may be the same as or different from one another, and preferably are the same.

In formula (1), $\varphi$ represents an m-valent group derived from an aromatic hydrocarbon having 6 to 40 carbon atoms or an m-valent group derived from an aromatic heterocyclic ring having 2 to 40 carbon atoms, and at least one hydrogen atom of $\varphi$ may be substituted by an alkyl having 1 to 6 carbon atoms, an aryl having 6 to 18 carbon atoms, or a heteroaryl having 2 to 18 carbon atoms.

In formula (1), Y's each independently represent —O—, —S—, or >N—Ar, Ar represents an aryl having 6 to 12 carbon atoms or a heteroaryl having 2 to 12 carbon atoms, and at least one hydrogen atom of Ar may be substituted by an alkyl having 1 to 4 carbon atoms, an aryl having 6 to 12 carbon atoms, or a heteroaryl having 2 to 12 carbon atoms.

In formula (1), $R^1$ to $R^5$ each independently represent a hydrogen atom or an alkyl having 1 to 4 carbon atoms.

However, any one of Ar in >N—Ar as the Y and the $R^1$ to $R^5$ is a moiety bonded to L, and the azoline ring portion can have four bonding moieties. Among these four bonding forms, a form in which the moiety of $R^5$ of the azoline ring is bonded to the linking portion L, as represented by the following general formula (2-1), and a form in which the moiety of Ar in >N—Ar as Y of the azoline ring is bonded to the linking portion L, as represented by the following general formula (2-2) are preferable.

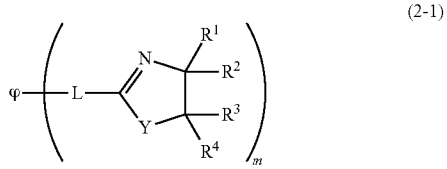

(2-1)

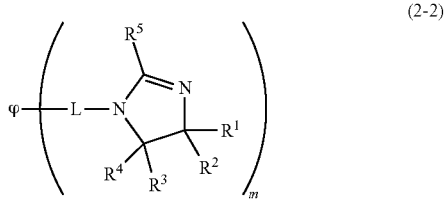

(2-2)

L's are each independently selected from the group consisting of a divalent group represented by the following formula (L-1) and a divalent group represented by the following formula (L-2).

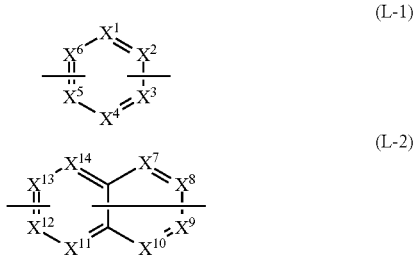

(L-1)

(L-2)

In formula (L-1), $X^1$ to $X^6$ each independently represent =$CR^6$— or =N—, at least two of $X^1$ to $X^6$ each represent =$CR^6$—, $R^6$'s in two =$CR^6$'s in $X^1$ to $X^6$ are each a moiety bonded to φ or an azoline ring, and $R^6$'s in the other =$CR^6$—'s each represent a hydrogen atom.

In formula (L-2), $X^7$ to $X^{14}$ each independently represent =$CR^6$— or =N—, at least two of $X^7$ to $X^{14}$ each represent =$CR^6$—, $R^6$'s in two =$CR^6$'s- in $X^7$ to $X^{14}$ are each a moiety bonded to φ or an azoline ring, and $R^6$'s in the other =$CR^6$—'s each represent a hydrogen atom.

At least one hydrogen atom of L may be substituted by an alkyl having 1 to 4 carbon atoms, an aryl having 6 to 10 carbon atoms, or a heteroaryl having 2 to 10 carbon atoms.

m represents an integer of 1 to 4, preferably an integer of 1 to 3, more preferably 1 or 2, and still more preferably 2.

At least one hydrogen atom in a compound represented by formula (1), a compound represented by formula (2-1), and a compound represented by formula (2-2) may be substituted by a deuterium atom.

<Core Portion φ>

The "aromatic hydrocarbon" and the "aromatic heterocyclic ring" in φ mean an "aryl" and a "heteroaryl", respectively in a case where φ is monovalent (m=1). Each of the "aromatic hydrocarbon" and the "aromatic heterocyclic ring" means a group having a corresponding valence with the structure of the aryl or the heteroaryl as it is in a case where φ is divalent to tetravalent (m=2 to 4). Hereinafter, φ will be described using the group name of an aryl or a heteroaryl, but the structure is the same also in a case where φ is divalent to tetravalent.

The "aromatic hydrocarbon" will be described as a monovalent aryl. The "aromatic hydrocarbon" is an aryl having 6 to 40 carbon atoms. A list of the aryl having 6 to 40 carbon atoms in ascending order of desirability includes an aryl having 6 to 30 carbon atoms, an aryl having 6 to 25 carbon atoms, an aryl having 6 to 20 carbon atoms, an aryl having 6 to 18 carbon atoms, an aryl having 6 to 16 carbon atoms, an aryl having 6 to 14 carbon atoms, an aryl having 6 to 12 carbon atoms, and an aryl having 6 to 10 carbon atoms. The aryl having 6 to 10 carbon atoms is the most preferable.

Specific examples of the "aryl" include: phenyl which is amonocyclic aryl; (2-, 3-, 4-) biphenylyl which is a bicyclic aryl; (1-, 2-) naphthyl which is a fused bicyclic aryl; acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; triphenylene-(1-, 2-)yl, pyrene-(1-, 2-, 4-)yl, and naphthacene-(1-, 2-, 5-)yl which are fused tetracyclic aryls; and perylene-(1-, 2-, 3-)yl and pentacene-(1-, 2-, 5-, 6-)yl which are fused pentacyclic aryls, although not being limited thereto.

The "aromatic heterocyclic ring" will be described as a monovalent heteroaryl. The "aromatic heterocyclic ring" is a heteroaryl having 2 to 40 carbon atoms. A list of the heteroaryl having 2 to 40 carbon atoms in ascending order of desirability includes a heteroaryl having 2 to 30 carbon atoms, a heteroaryl having 2 to 25 carbon atoms, a heteroaryl having 2 to 20 carbon atoms, a heteroaryl having 2 to 18 carbon atoms, a heteroaryl having 2 to 16 carbon atoms, a heteroaryl having 2 to 14 carbon atoms, a heteroaryl having 2 to 12 carbon atoms, and a heteroaryl having 2 to 10 carbon atoms. The heteroaryl having 2 to 10 carbon atoms is the most preferable. Examples of these "heteroaryls" include a heteroaryl containing 1 to 5 heteroatoms selected from an oxygen atom, a sulfur atom, and a nitrogen atom in addition to a carbon atom as a ring-constituting atom.

Specific examples of the "heteroaryl" include furyl, thienyl, pyrrolyl, oxazolyl, isoxazolyl, triazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl, benzofuranyl, isobenzofuranyl, benzo[b]thienyl, indolyl, isoindolyl, 1H-indazolyl, benzoimidazolyl, benzoxazolyl, benzothiazolyl, 1H-benzotriazolyl, quinolyl, isoquinolyl, cinnolyl, quinazolyl, quinoxalinyl, phthalazinyl, naphthyridinyl, purinyl, pteridinyl, carbazolyl, acridinyl, phenoxazinyl, phenothiazinyl, phenazinyl, phenoxathiinyl, thianthrenyl, and indolizinyl, although not being limited thereto.

Examples of φ include monovalent groups represented by the following formulas (φ1-1) to (φ1-18), divalent groups represented by the following formulas (φ2-1) to (φ2-34), trivalent groups represented by the following formulas (φ3-1) to (φ3-3), and tetravalent groups represented by the following formulas (φ4-1) and (φ4-2).

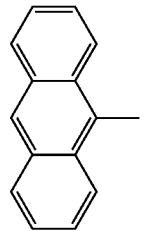

(φ1-1)

(φ1-2)

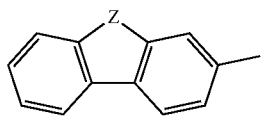

(φ1-3)

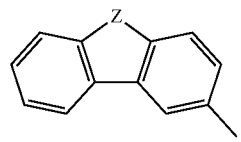

(φ1-4)

(φ1-5)
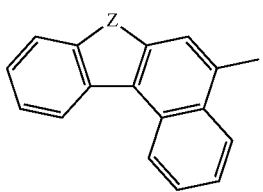
(φ1-6)
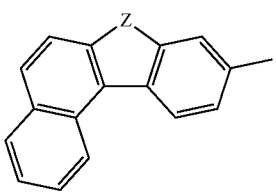
(φ1-7)
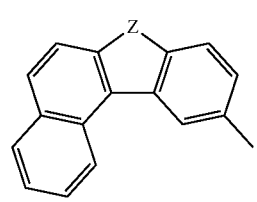
(φ1-8)
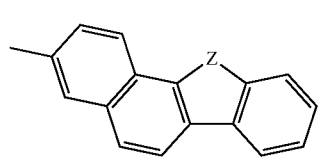
(φ1-9)
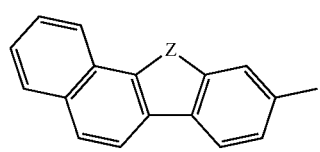
(φ1-10)
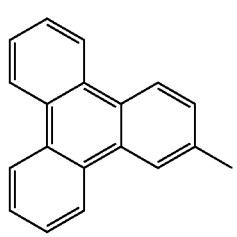
(φ1-11)
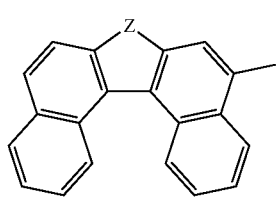
(φ1-12)
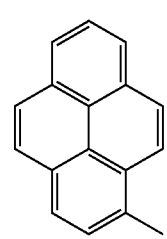
(φ1-13)
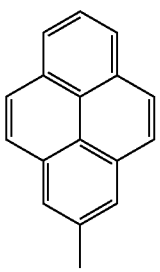
(φ1-14)
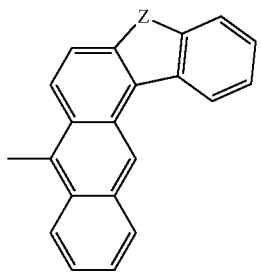
(φ1-15)
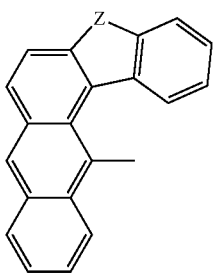
(φ1-16)
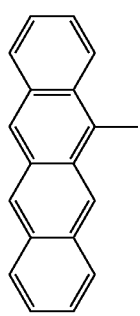
(φ1-17)
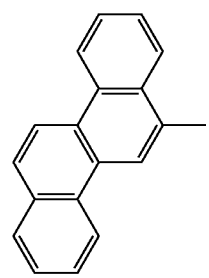

-continued
(φ1-18)
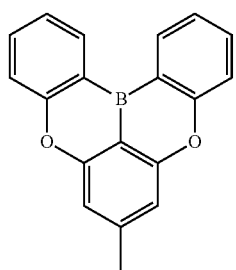
(φ2-1)
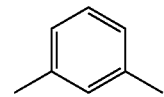
(φ2-2)
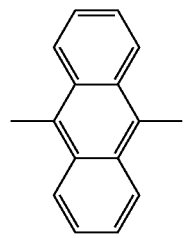
(φ2-3)
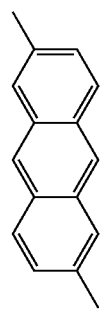
(φ2-4)
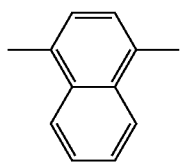
(φ2-5)
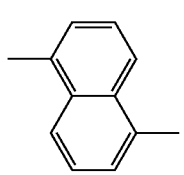
(φ2-6)
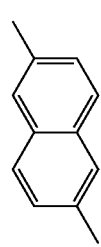
-continued
(φ2-7)
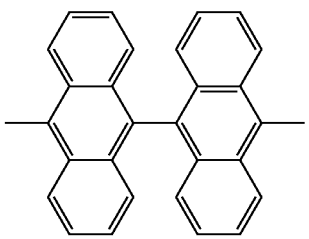
(φ2-8)
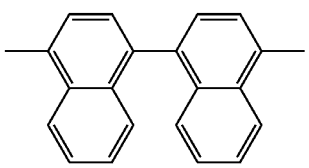
(φ2-9)
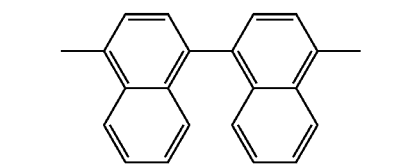
(φ2-10)
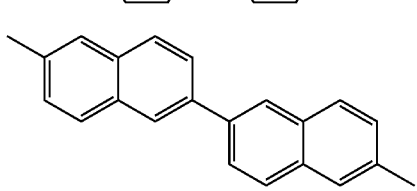
(φ2-11)
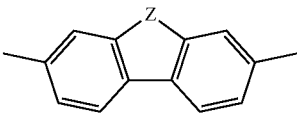
(φ2-12)
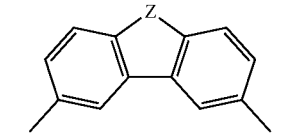
(φ2-13)
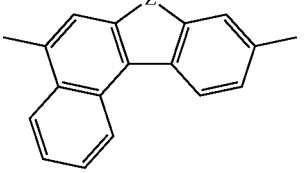
(φ2-14)
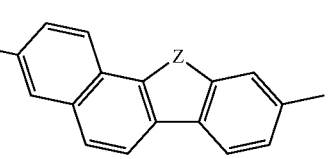
(φ2-15)
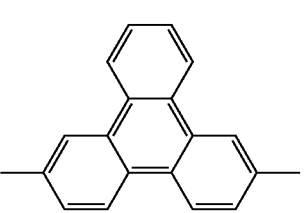

-continued
(φ2-16)
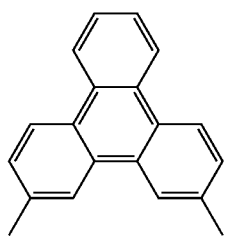
(φ2-17)
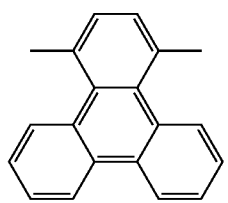
(φ2-18)
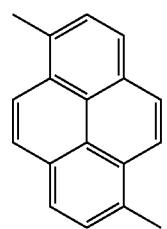
(φ2-19)
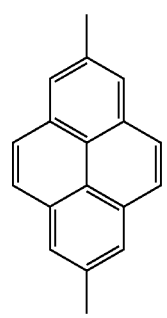
(φ2-20)
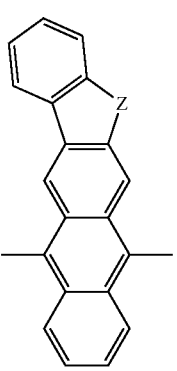
(φ2-21)
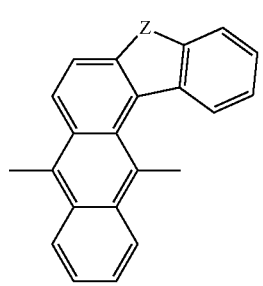
-continued
(φ2-22)
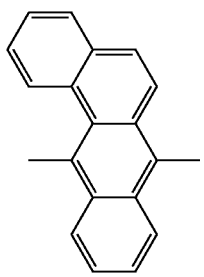
(φ2-23)
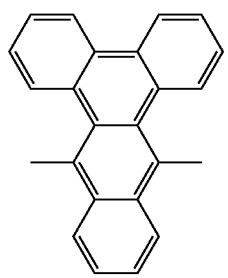
(φ2-24)
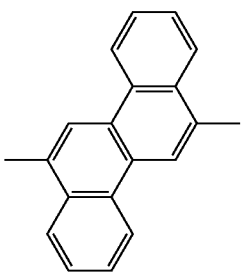
(φ2-25)
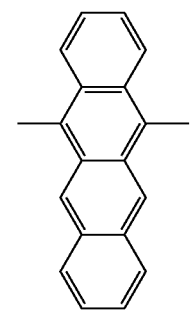
(φ2-26)
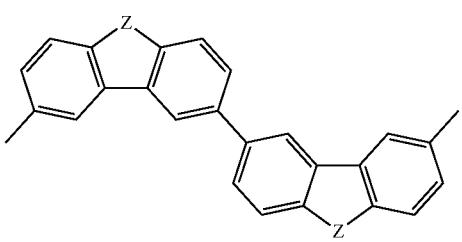

(φ2-27)
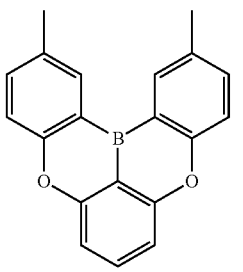

(φ2-28)
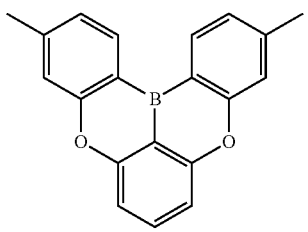

(φ2-29)
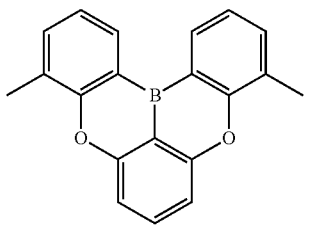

(φ2-30)
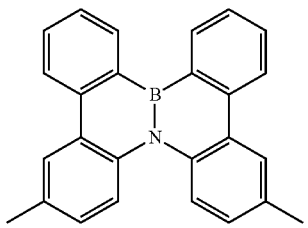

(φ2-31)
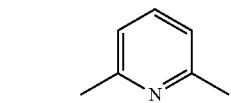

(φ2-32)
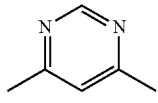

(φ2-33)
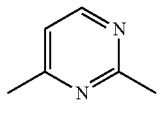

(φ2-34)
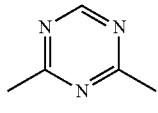

(φ3-1)
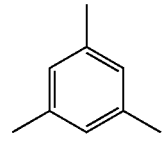

(φ3-2)
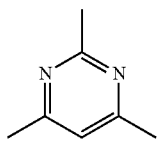

(φ3-3)
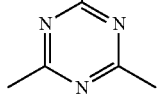

(φ4-1)
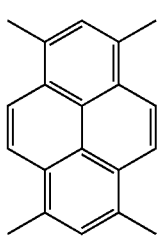

(φ4-2)
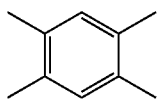

A straight line extending outward in the structural formula indicated by φ means a bond with the linking portion L. One bond is indicated in a monovalent group, two bonds are indicated in a divalent group, three bonds are indicated in a trivalent group, and four bonds are indicated in a tetravalent group.

Z in the above formulas of φ represents >CR$_2$, >N—Ar, >N-L, —O—, or —S—, R's in >CR$_2$ each independently represent an alkyl having 1 to 4 carbon atoms, an aryl having 6 to 12 carbon atoms, or a heteroaryl having 2 to 12 carbon atoms, R's may be bonded to each other to form a ring, Ar in >N—Ar represents an aryl having 6 to 12 carbon atoms or a heteroaryl having 2 to 12 carbon atoms, and L in >N-L represents the linking portion L. Incidentally, in a case where Z represents >N-L, it is assumed that there is no bond with the linking portion L already indicated by a straight line in the structural formula according to the number of >N-L. For example, in formula (φ2-26), in a case where two Z's each represent >N-L, the two bonds already indicated by straight lines are removed, and in a case where one of Z's represents >N-L, any one of the bonds already indicated by straight lines is removed. Examples of the case where R's are bonded to each other to form a ring include a case where two phenyls are bonded at ortho positions to each other with a single bond or two alkyls are bonded to each other to form a spiro ring.

Incidentally, as the alkyl in R, those exemplified in the following description can be cited specifically, and as the aryl and heteroaryl in R and Ar, those exemplified in the above description can be cited specifically.

φ is preferably selected from the group consisting of divalent groups represented by the above formulas (φ2-1), (φ2-4), (φ2-5), (φ2-6), (φ2-31), (φ2-32), (φ2-33), and (φ2-34), is more preferably selected from the group consisting of divalent groups represented by the above formulas (φ2-1), (φ2-31), and (φ2-32), (φ2-33), and (φ2-34).

At least one hydrogen atom of φ may be substituted by an alkyl having 1 to 6 carbon atoms, an aryl having 6 to 18 carbon atoms, or a heteroaryl having 2 to 18 carbon atoms. As this heteroaryl, those exemplified in the above description can be cited specifically. In a case where φ is a divalent group represented by the above formula (φ2-1), (φ2-31), (φ2-32), (φ2-33), or (φ2-34), at least one hydrogen atom of φ may be substituted by an aryl preferably having 6 to 18 carbon atoms (for example, (2-, 3-, 4-)biphenylyl group).

The "aryl having 6 to 18 carbon atoms" is preferably an aryl having 6 to 16 carbon atoms, more preferably an aryl having 6 to 14 carbon atoms, still more preferably an aryl having 6 to 12 carbon atoms, and most preferably an aryl having 6 to 10 carbon atoms.

Specific examples of the "aryl" include: phenyl which is amonocyclic aryl; (2-, 3-, 4-) biphenylyl which is a bicyclic aryl; (1-, 2-)naphthyl which is a fused bicyclic aryl; terphenylyl (m-terphenyl-2'-yl, m-terphenyl-4'-yl, m-terphenyl-5'-yl, o-terphenyl-3'-yl, o-terphenyl-4'-yl, p-terphenyl-2'-yl, m-terphenyl-2-yl, m-terphenyl-3-yl, m-terphenyl-4-yl, o-terphenyl-2-yl, o-terphenyl-3-yl, o-terphenyl-4-yl, p-terphenyl-2-yl, p-terphenyl-3-yl, or p-terphenyl-4-yl) which is a tricyclic aryl; acenaphthylene-(1-, 3-, 4-, 5-)yl, fluorene-(1-, 2-, 3-, 4-, 9-)yl, phenalene-(1-, 2-)yl, and (1-, 2-, 3-, 4-, 9-)phenanthryl which are fused tricyclic aryls; and triphenylene-(1-, 2-)yl, pyrene-(1-, 2-, 4-)yl, and naphthacene-(1-, 2-, 5-)yl which are fused tetracyclic aryls, although not being limited thereto.

The "alkyl having 1 to 6 carbon atoms" may be either a linear alkyl having 1 to 6 carbon atoms or a branched alkyl having 3 to 6 carbon atoms. The alkyl having 1 to 6 carbon atoms is preferably an alkyl having 1 to 4 carbon atoms (branched alkyl having 3 or 4 carbon atoms).

Specific examples of the alkyl include methyl (Me), ethyl (Et), n-propyl, isopropyl (i-Pr), n-butyl, isobutyl, s-butyl, t-butyl (t-Bu), n-pentyl, isopentyl, neopentyl, t-pentyl, n-hexyl, 1-methylpentyl, 4-methyl-2-pentyl, 3,3-dimethylbutyl, and 2-ethylbutyl.

A position on φ substituted by a substituent is not particularly limited. However, some φ's have a chemically highly reactive moiety. Therefore, by introducing a substituent into such a moiety, chemical stability of a material can be improved. For example, a 9-position and a 10-position of an anthracene ring are chemically active moieties, and hydrogen atoms at these positions tend to react chemically. Therefore, by introducing a substituent(s) into a 9-position and/or a 10-position of an anthracene ring in advance, chemical stability of a material can be improved. A substituent selected for this purpose is an alkyl having 1 to 6 carbon atoms, an aryl having 6 to 18 carbon atoms, or a heteroaryl having 2 to 18 carbon atoms, and particularly preferably an aryl having 6 to 18 carbon atoms or a heteroaryl having 2 to 18 carbon atoms. A similar effect is also obtained by substitution of a structure formed of the azoline ring portion and the linking portion L by an active moiety instead of the substituent. Incidentally, φ having an anthracene structure has been specifically described above, but this also applies to another ring structure exemplified as φ.

The core portion φ may be a multimer structure formed by bonding a plurality of aryls or heteroaryls having the same structure via a single bond. Specific examples thereof include a dimer structure such as a group represented by the above formula (φ2-7), (φ2-8), (φ2-9), or (φ2-26). However, the core portion φ may have a trimer or higher structure, and preferably has a dimer structure. However, the total number of carbon atoms of the formed multimer structure is required to be within a range of 6 to 40 when the multimer is classified into an aromatic hydrocarbon, and within a range of 2 to 40 when the multimer is classified into an aromatic heterocyclic ring. Other examples are illustrated below. Note that Z in each formula is as described above.

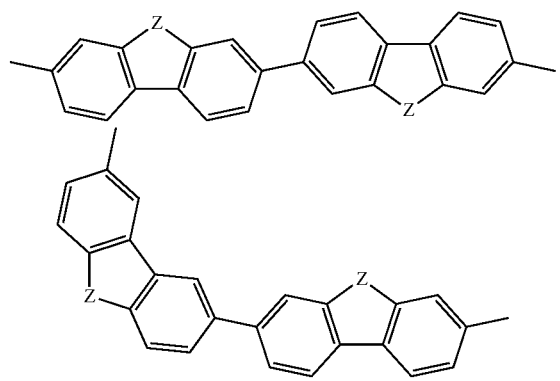

<Azoline Ring Portion>

Y's each independently represent —O—, —S—, or >N—Ar, Ar represents an aryl having 6 to 12 carbon atoms or a heteroaryl having 2 to 12 carbon atoms, and at least one hydrogen atom of Ar may be substituted by an alkyl having 1 to 4 carbon atoms, an aryl having 6 to 12 carbon atoms, or a heteroaryl having 2 to 12 carbon atoms. As the alkyl, aryl, or heteroaryl, those exemplified in the above description for the core portion φ can be cited specifically.

$R^2$ to $R^5$ each independently represent a hydrogen atom or an alkyl having 1 to 4 carbon atoms. As the alkyl, those exemplified in the above description for the core portion φ can be cited specifically. In $R^2$ to $R^4$, preferably, $R^2$ and $R^2$ are the same as each other, and $R^3$ and $R^4$ are the same as each other. In a more preferable form, not all of $R^2$ to $R^4$ represent hydrogen atoms simultaneously.

An example of the azoline ring portion is illustrated below.

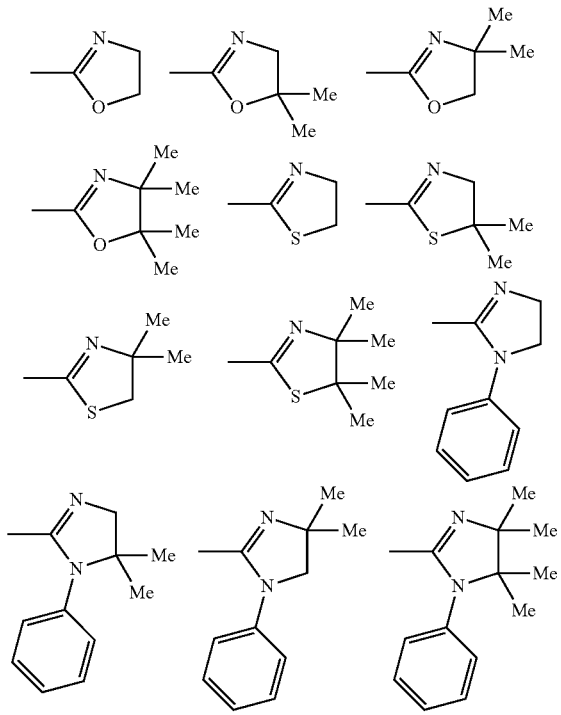

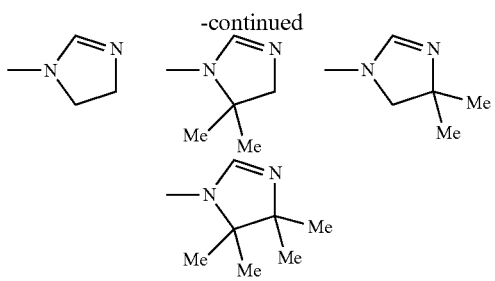

Preferable examples of the azoline ring include oxazolin-2-yl, 4,4-dimethyloxazolin-2-yl, 5,5-dimethyloxazolin-2-yl, 4,4,5,5-tetramethyloxazolin-2-yl, thiazolin-2-yl, 4,4-dimethylthiazolin-2-yl, 5,5-dimethylthiazolin-2-yl, 4,4,5,5-tetramethylthiazolin-2-yl, 1-phenylimidazolin-2-yl, 4,4-dimethyl-1-phenylimidazolin-2-yl, 5,5-dimethyl-1-phenylimidazolin-2-yl, 4,4,5,5-tetramethyl-1-phenylimidazolin-2-yl, imidazolin-1-yl, 4,4-dimethylimidazolin-1-yl, 5,5-dimethylimidazolin-1-yl, 4,4,5,5-tetramethylimidazolin-1-yl, 2,4,4-trimethylimidazolin-1-yl, 2,5,5-trimethylimidazolin-1-yl, and 2,4,4,5,5-pentamethylimidazolin-1-yl.

More preferable examples of the azoline ring include 4,4-dimethyloxazolin-2-yl, 5,5-dimethyloxazolin-2-yl, 4,4,5,5-tetramethyloxazolin-2-yl, 4,4-dimethylthiazolin-2-yl, 5,5-dimethylthiazolin-2-yl, 4,4,5,5-tetramethylthiazolin-2-yl, 4,4,5,5-tetramethyl-1-phenylimidazolin-2-yl, 4,4,5,5-tetramethylimidazolin-1-yl, and 2,4,4,5,5-pentamethylimidazolin-1-yl.

Particularly preferable examples of the azoline ring include 4,4,5,5-tetramethyloxazolin-2-yl, 4,4,5,5-tetramethyl-1-phenylimidazolin-2-yl, 4,4,5,5-tetramethylimidazolin-1-yl, and 2,4,4,5,5-pentamethylimidazolin-1-yl.

Other particularly preferable examples of the azoline ring include 4,4-dimethyloxazolin-2-yl, 5,5-dimethyloxazolin-2-yl, 4,4,5,5-tetramethyloxazolin-2-yl, 4,4,5,5-tetramethyl-1-phenylimidazolin-2-yl, 4,4,5,5-tetramethylimidazolin-1-yl, and 2,4,4,5,5-pentamethylimidazolin-1-yl.

<Linking portion L>

L's are each independently selected from a divalent group represented by formula (L-1) and a divalent group represented by formula (L-2). Examples of a group represented by formula (L-1) include a divalent group of a ring selected from the group consisting of benzene, pyridine, pyrazine, pyrimidine, pyridazine, and triazine. A divalent group of benzene or pyridine is preferable, and a divalent group (phenylene) of benzene is particularly preferable. Examples of a group represented by formula (L-2) include a divalent group of a ring selected from the group consisting of naphthalene, quinoline, isoquinoline, naphthyridine, phthalazine, quinoxaline, quinazoline, cinnoline, and pteridine. A divalent group of naphthalene is preferable.

At least one hydrogen atom of L may be substituted by an alkyl having 1 to 4 carbon atoms, an aryl having 6 to 10 carbon atoms, or a heteroaryl having 2 to 10 carbon atoms. As the alkyl, aryl, or heteroaryl, those exemplified in the above description for the core portion φ can be cited specifically.

<Molecular Weight of Azoline Ring-Containing Compound>

The compound according to the present invention has a molecular weight of 400 to 1,500, preferably 400 to 1,300, more preferably 400 to 1,200, still more preferably 400 to 1,000, particularly preferably 500 to 800. By setting the molecular weight within these ranges, in a case of forming an organic layer of an organic EL element, for example, by vapor-depositing the compound according to the present invention, vapor deposition can be performed more suitably, and a more heat-resistant thin film can be formed. In order to design a compound structure having an optimum molecular weight, it is only required to adjust the molecular weight of each of the core portion φ, the linking portion L, and the azoline ring portion. For example, in a case where the core portion φ is a monovalent group, one linking portion L and one azoline ring portion are present, and therefore the molecular weight tends to be small. Therefore, an increase in the molecular weight of a skeleton itself of each portion or substitution of each portion by a substituent can increase the molecular weight. This applies also to a case where the core portion is a divalent or higher group having a small molecular weight. The molecular weight can be increased by selecting a divalent group represented by formula (L-1) or (L-2) as the linking portion L. Meanwhile, in a case where the molecular weight of the skeleton itself of each portion is large and the entire molecular weight is too large, it is only required to adjust the molecular weight by reducing the valence of the core portion φ or eliminating a substituent.

<Specific Combination of Particularly Preferable Moieties>

The azoline ring-containing compound according to the present invention may be formed of any combination as long as being a compound constituted by the core portion φ, the azoline ring portion, and the linking portion L described above, but particularly preferably has the following structural characteristics.

First, among the azoline rings, particularly an imidazoline ring may be aromatized under a condition of sublimation purification or the like. Therefore, a tetra-substitute in which all of $R^1$ to $R^4$ are alkyls (particularly methyls) is preferable. In a case where an oxazoline ring substituted by an alkyl group is used for an EL element, element lifetime is often improved. Therefore, a case where at least one of "each of $R^4$ and $R^{2}$" and "each of $R^3$ and $R^{4}$" represents an alkyl (particularly a methyl) is preferable.

<Specific Example of Compound Represented by Formula (1)>

Specific examples of the compound of the present invention are represented by the formulas listed below, but the present invention is not limited by the disclosure of these specific structures. Compounds represented by the following formulas (1-1-1) to (1-1-318) are classified into a compound of m=1. Compounds represented by the following formulas (1-2-1) to (1-2-1018) and (1-2-1021) to (1-2-1168) are classified into a compound of m=2. Compounds represented by the following formulas (1-3-1) to (1-3-179) are classified into a compound of m=3. Compounds represented by the following formulas (1-4-1) to (1-4-18) are classified into a compound of m=4.

(1-1-1)

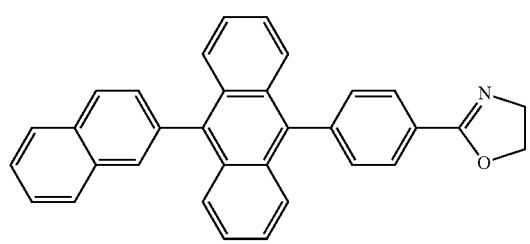

(1-1-2)
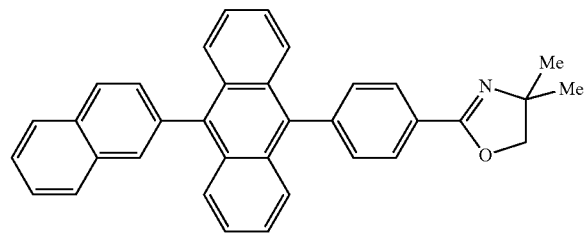
(1-1-3)
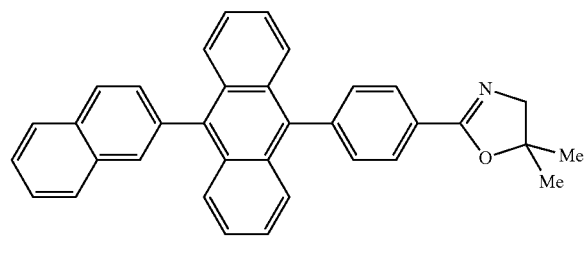
(1-1-4)
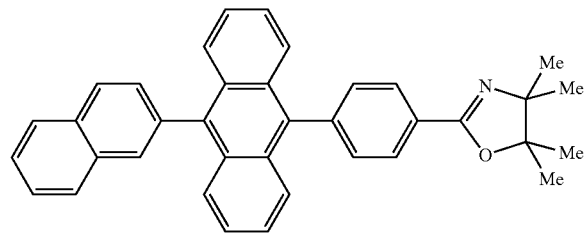
(1-1-5)
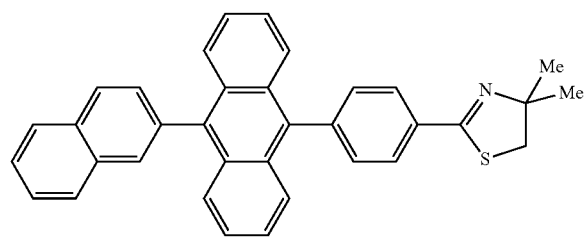
(1-1-6)
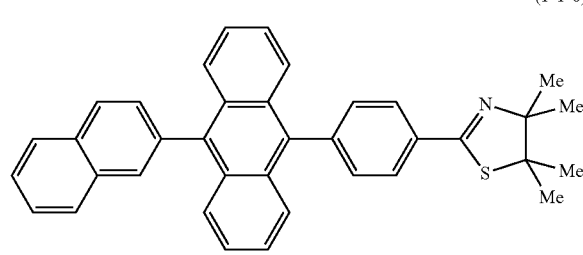
(1-1-7)
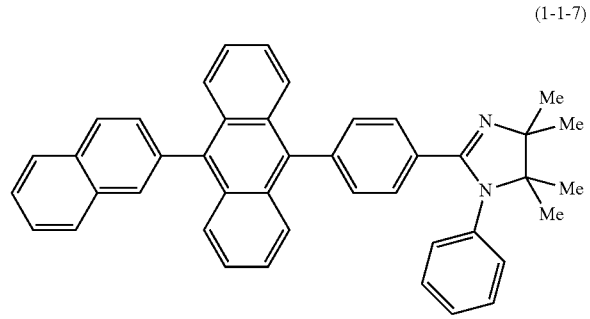
(1-1-8)
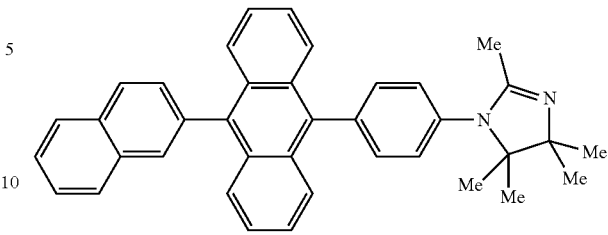
(1-1-9)
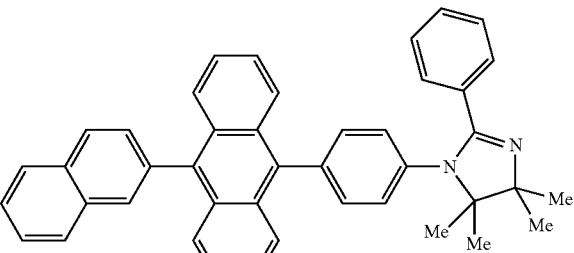
(1-1-11)
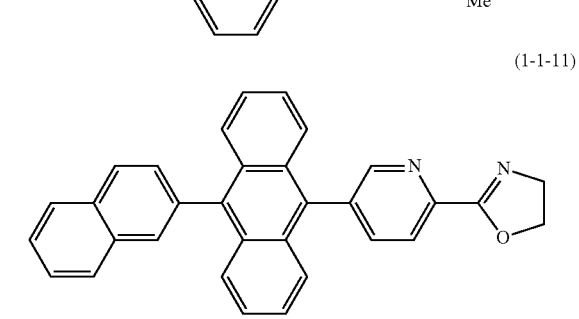
(1-1-12)
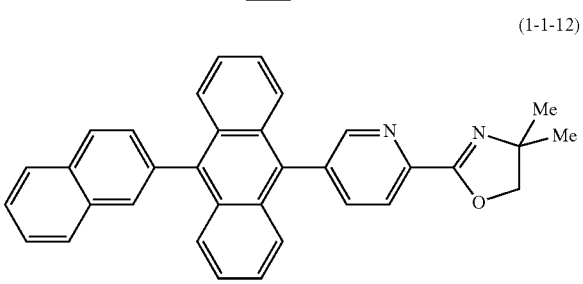
(1-1-13)
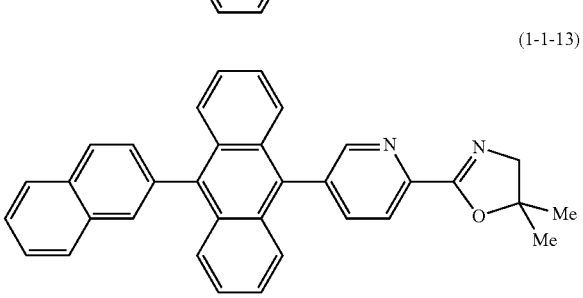
(1-1-14)
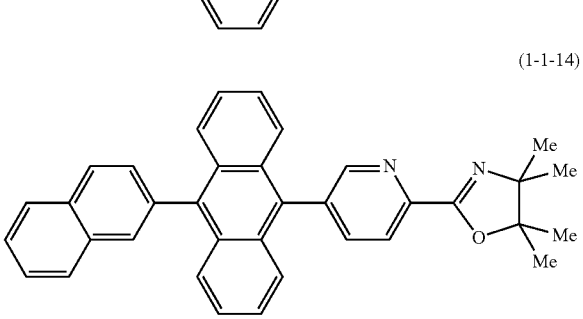

(1-1-15)
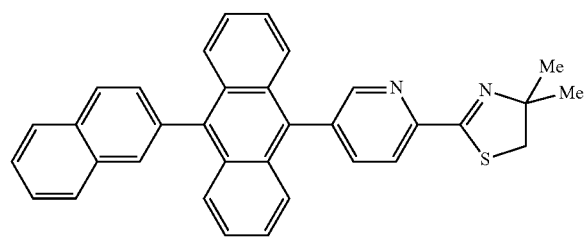
(1-1-16)
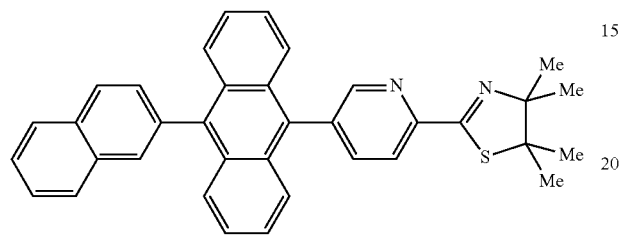
(1-1-17)
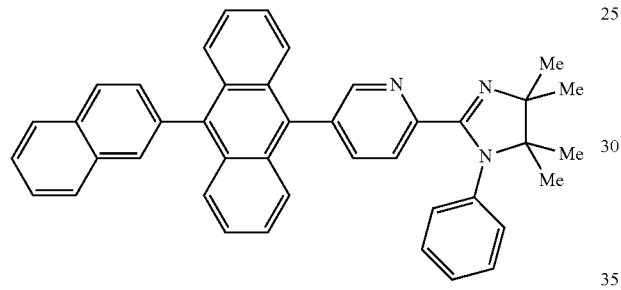
(1-1-18)
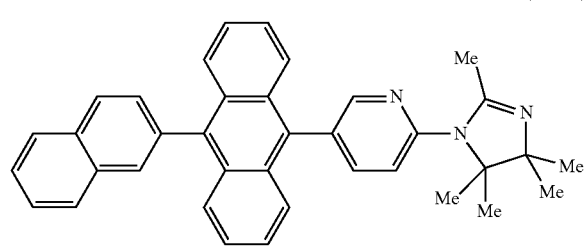
(1-1-19)
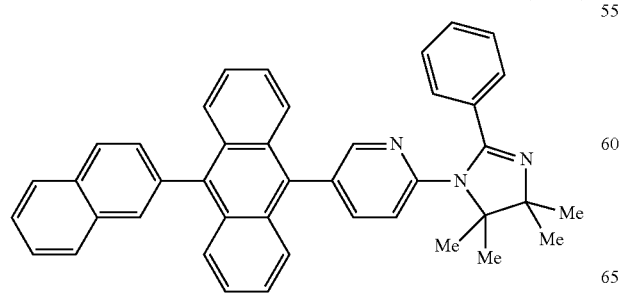
(1-1-21)
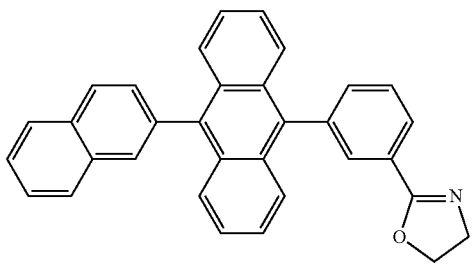
(1-1-22)
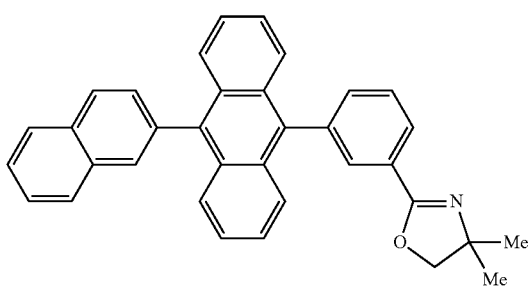
(1-1-23)
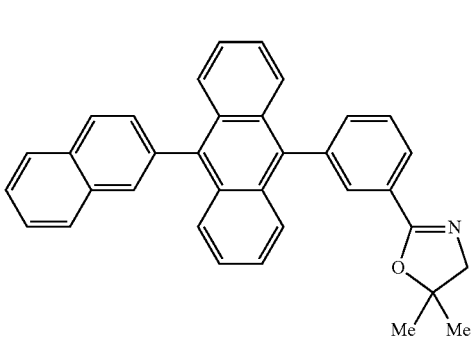
(1-1-24)
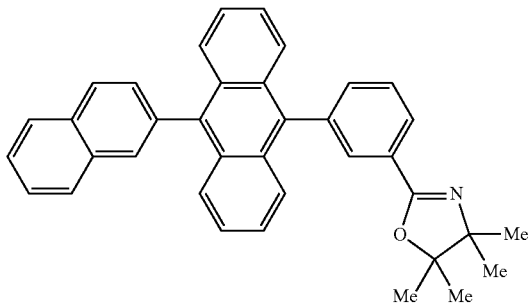
(1-1-25)
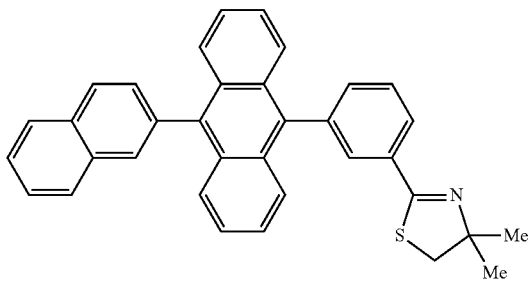

(1-1-26)
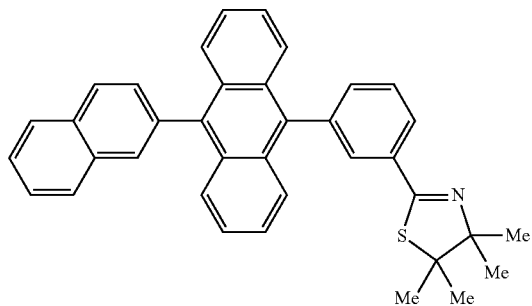
(1-1-27)
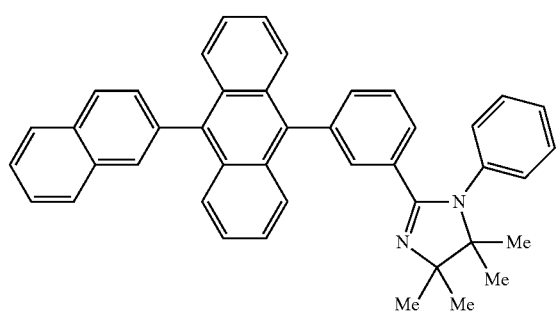
(1-1-28)
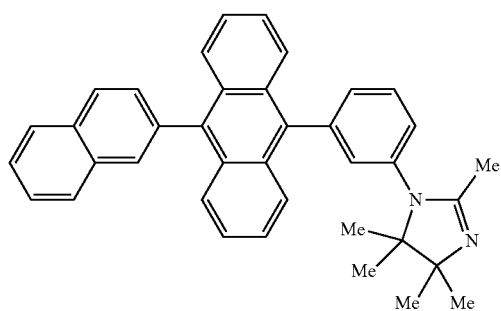
(1-1-29)
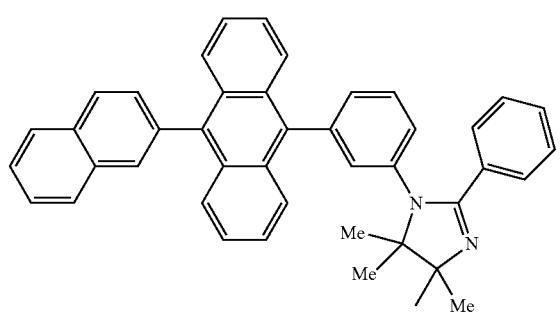
(1-1-31)
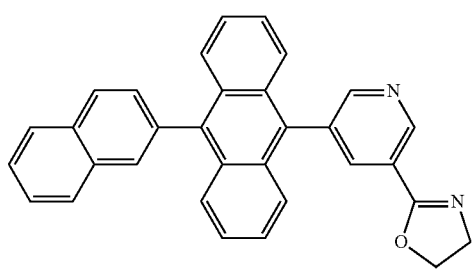
(1-1-32)
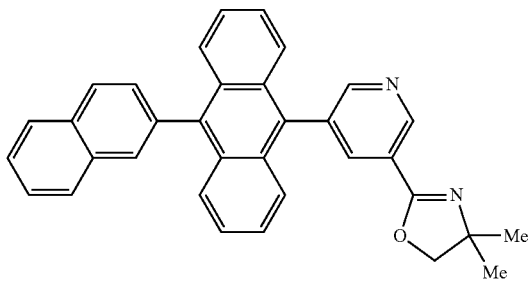
(1-1-33)
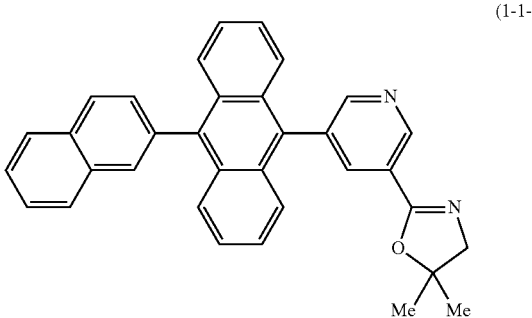
(1-1-34)
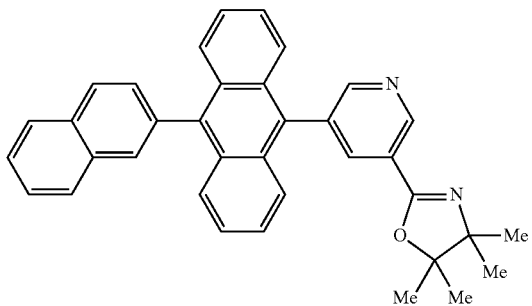
(1-1-35)
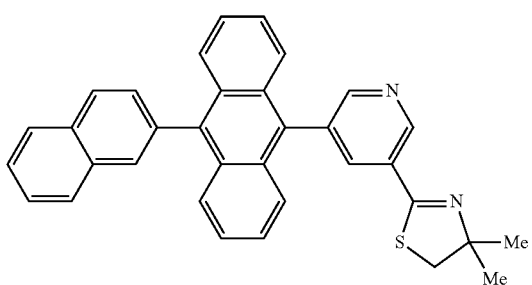
(1-1-36)
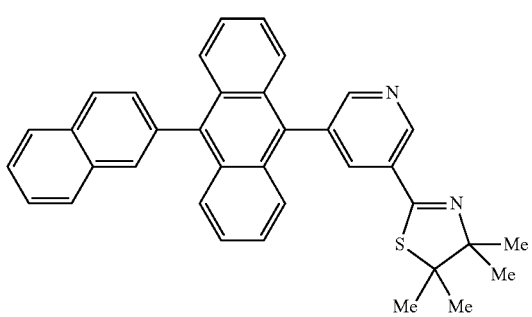

(1-1-37)
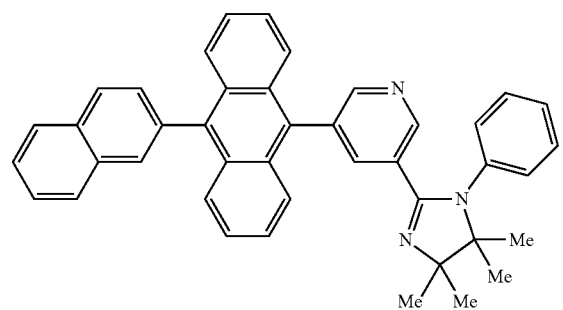
(1-1-38)
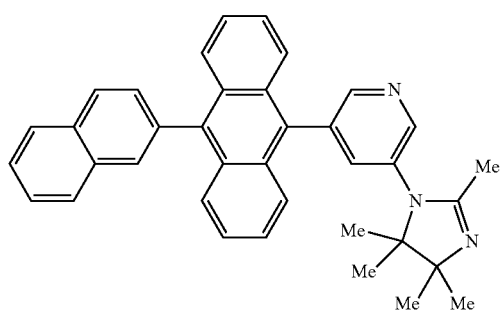
(1-1-39)
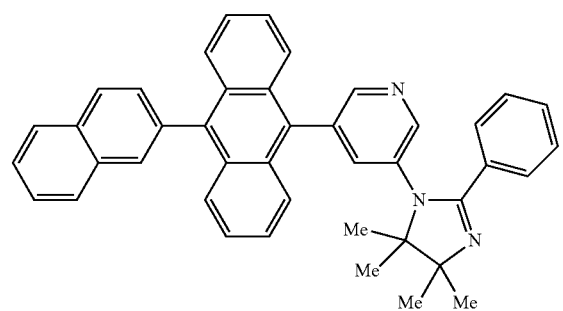
(1-1-41)
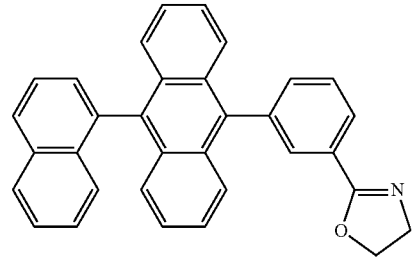
(1-1-42)
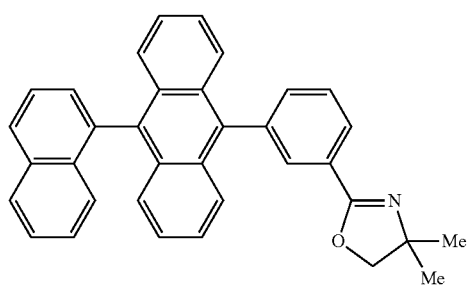
(1-1-43)
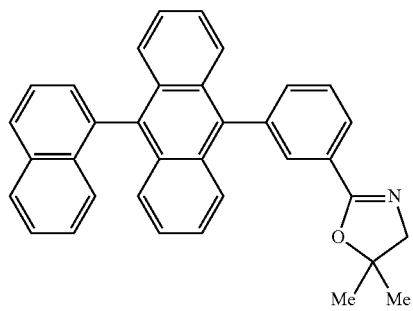
(1-1-44)
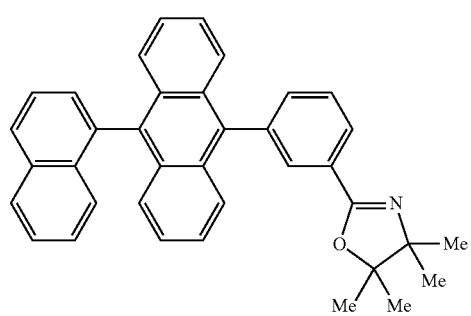
(1-1-45)
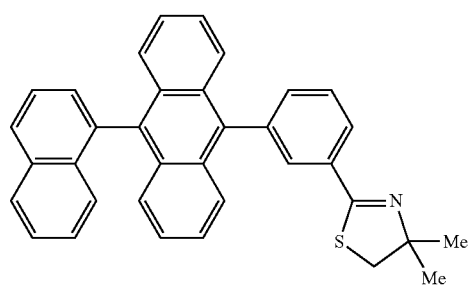
(1-1-46)
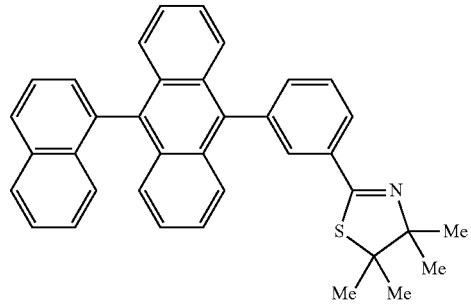
(1-1-47)
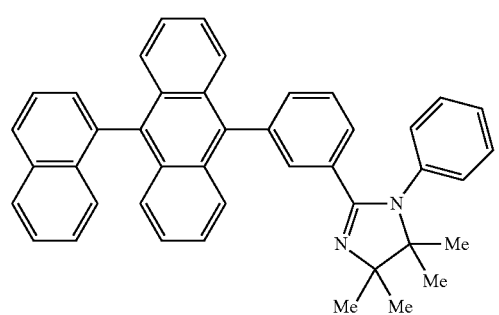

(1-1-48)
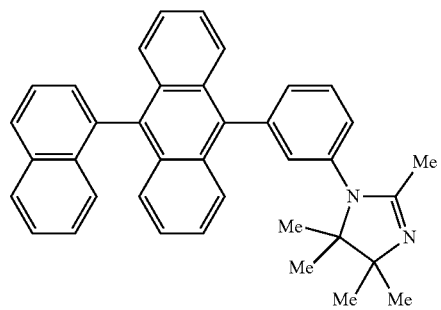
(1-1-49)
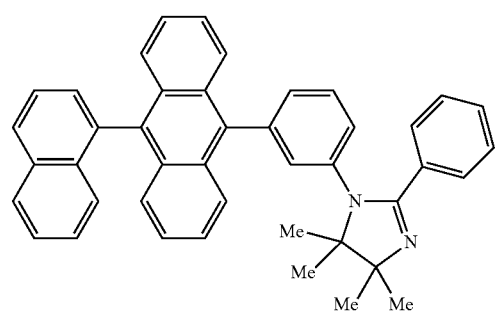
(1-1-51)
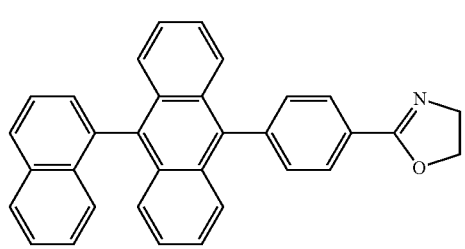
(1-1-52)
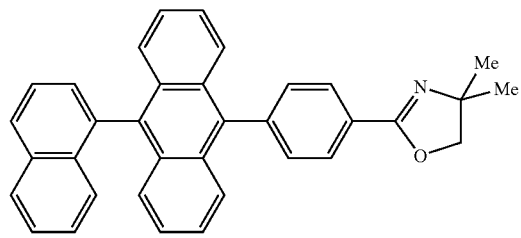
(1-1-53)
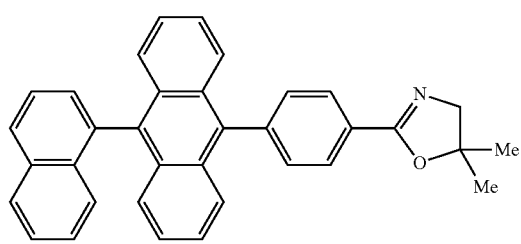
(1-1-54)
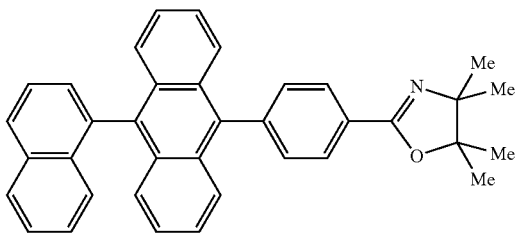
(1-1-55)
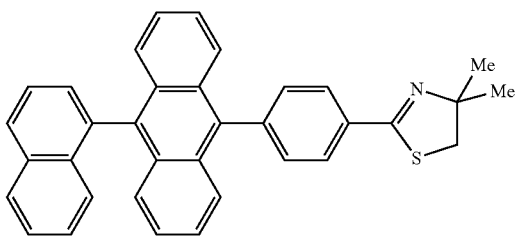
(1-1-56)
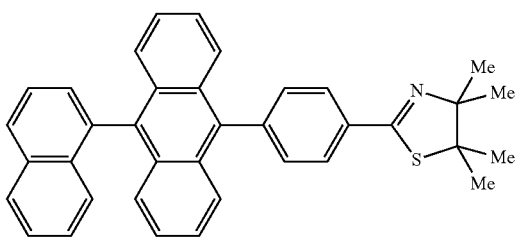
(1-1-57)
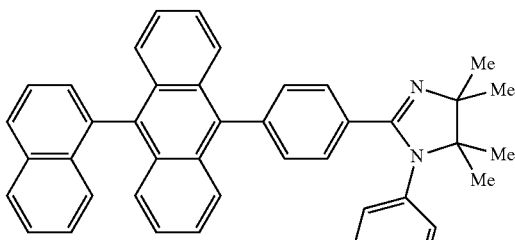
(1-1-58)
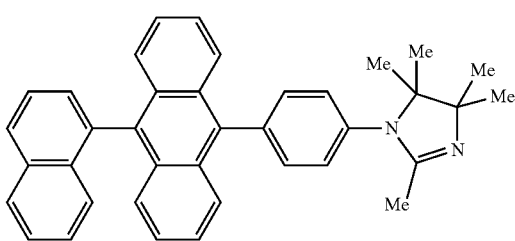
(1-1-59)

(1-1-61)
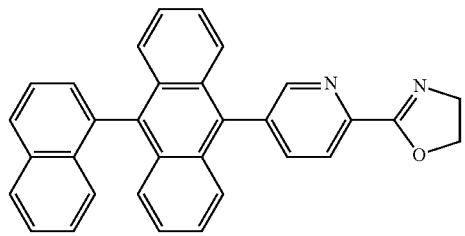
(1-1-62)
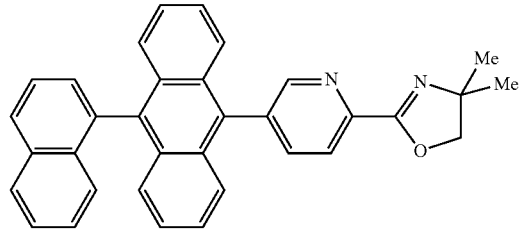
(1-1-63)
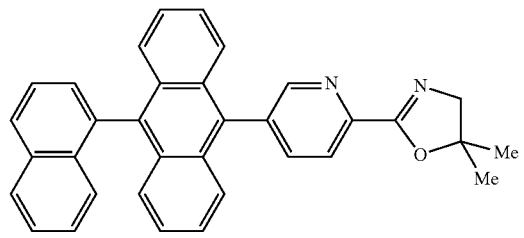
(1-1-64)
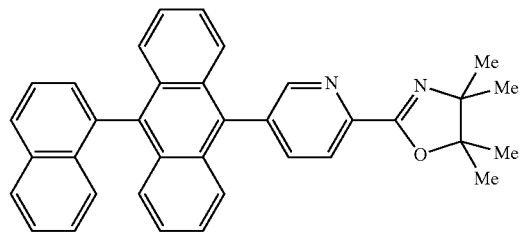
(1-1-65)
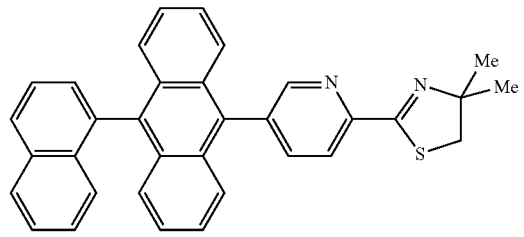
(1-1-66)
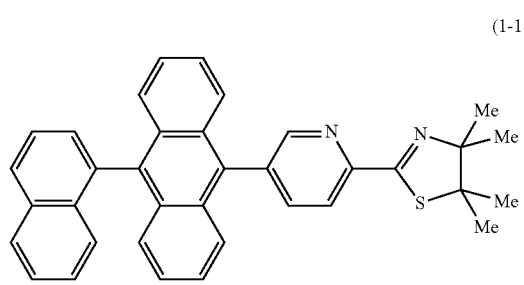
(1-1-67)
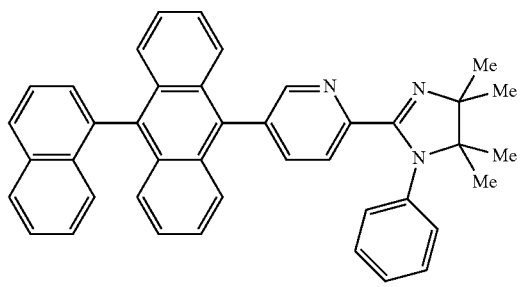
(1-1-68)
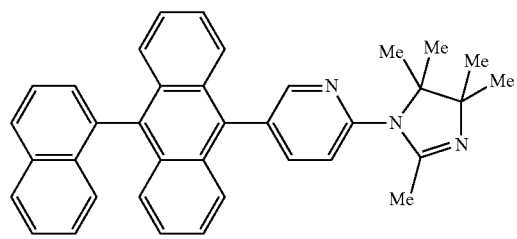
(1-1-69)
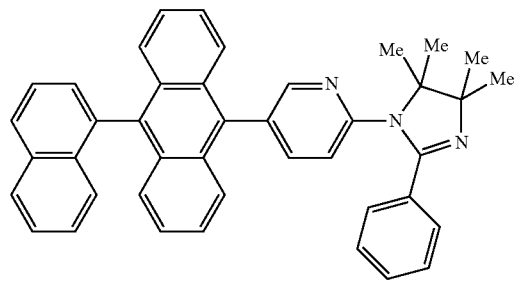
(1-1-71)
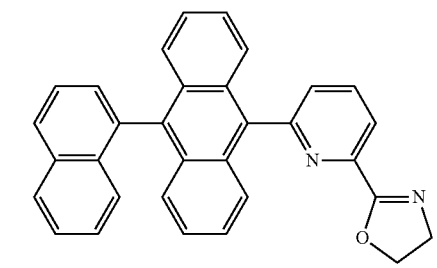
(1-1-72)
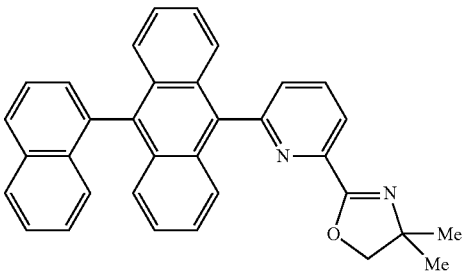

(1-1-73)
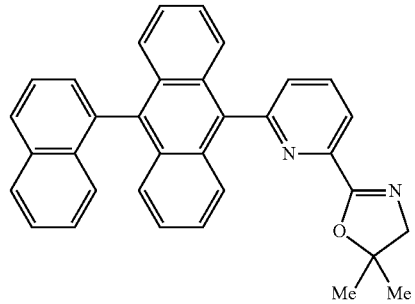
(1-1-74)
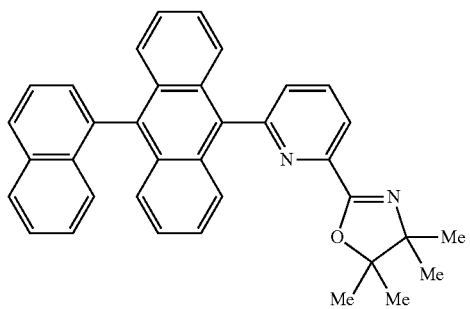
(1-1-75)
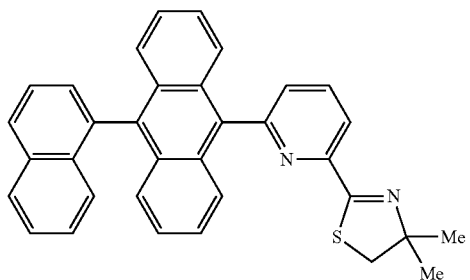
(1-1-76)
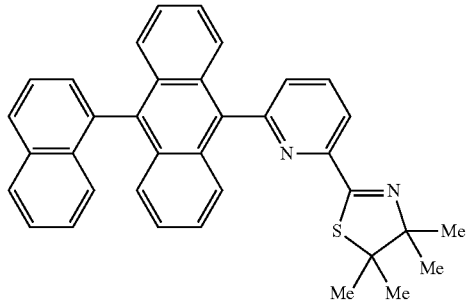
(1-1-77)
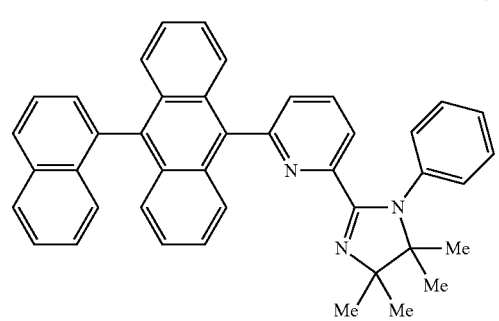
(1-1-78)
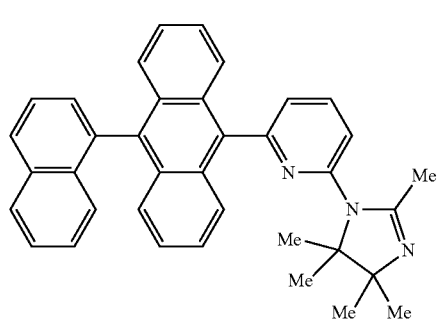
(1-1-79)
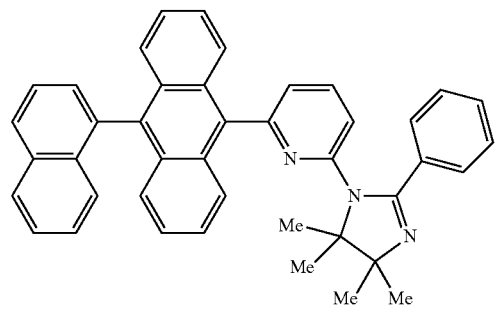
(1-1-81)
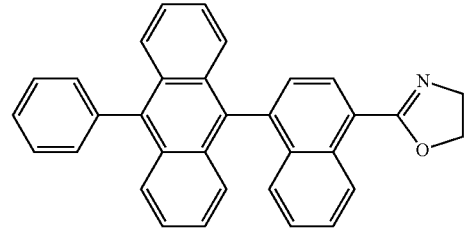
(1-1-82)
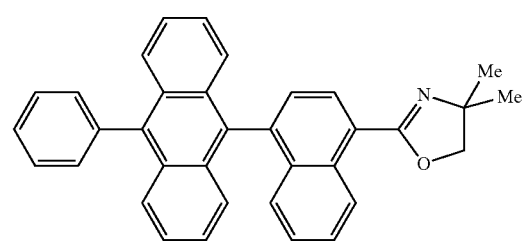
(1-1-83)
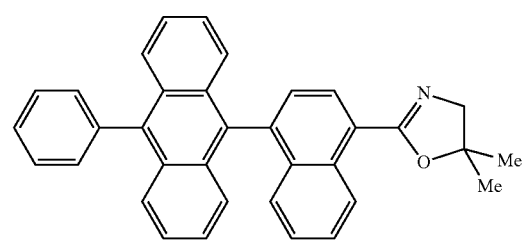

(1-1-84)
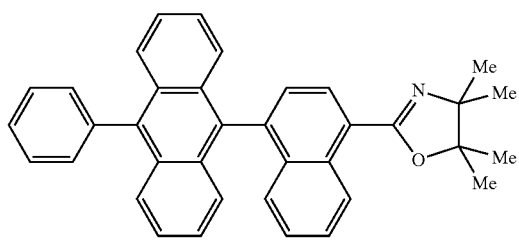
(1-1-85)
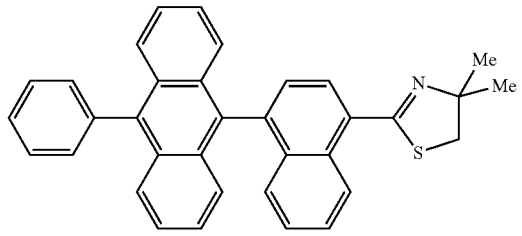
(1-1-86)
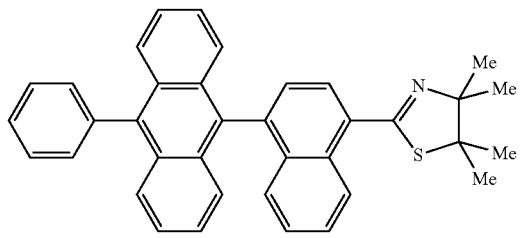
(1-1-87)
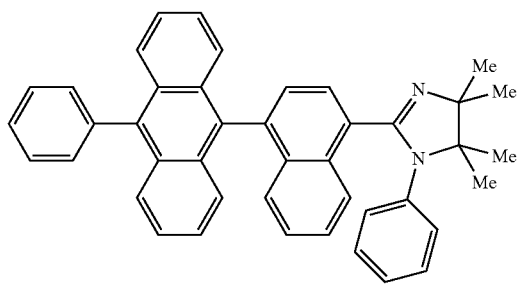
(1-1-88)
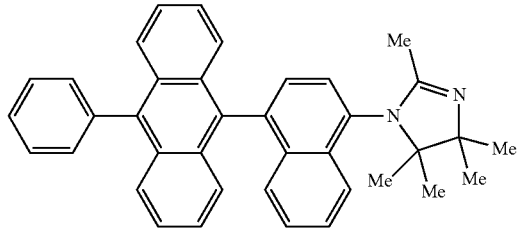
(1-1-89)
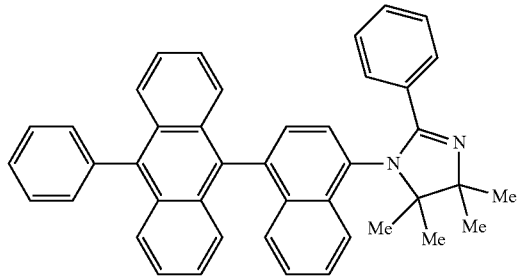
(1-1-91)
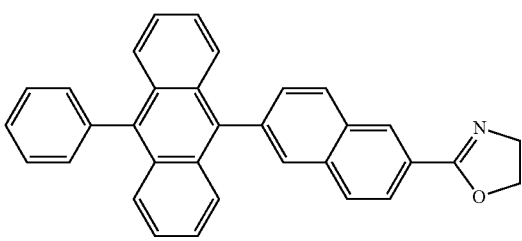
(1-1-92)
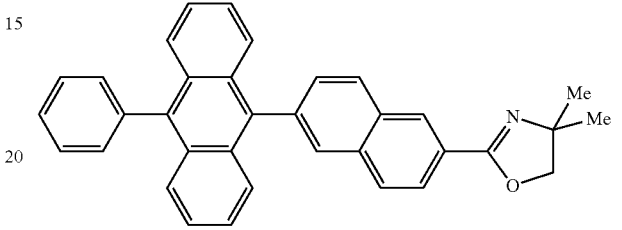
(1-1-93)
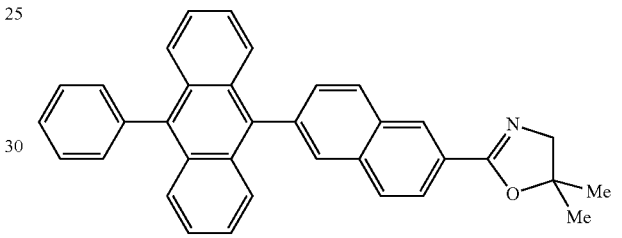
(1-1-94)
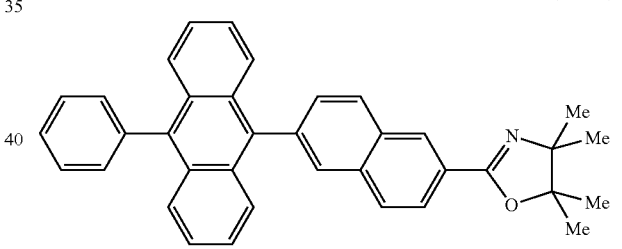
(1-1-95)
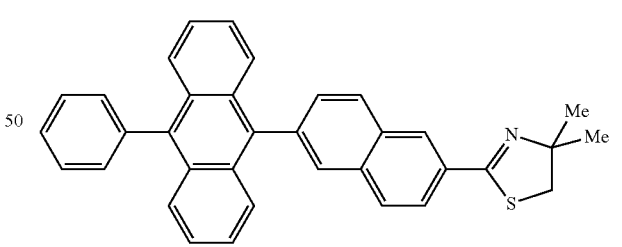
(1-1-96)
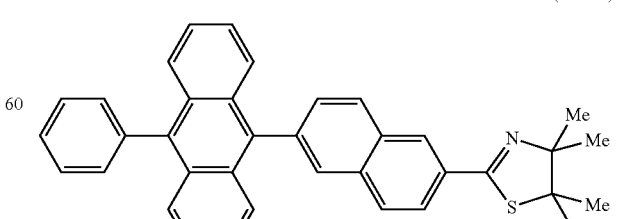

(1-1-97)
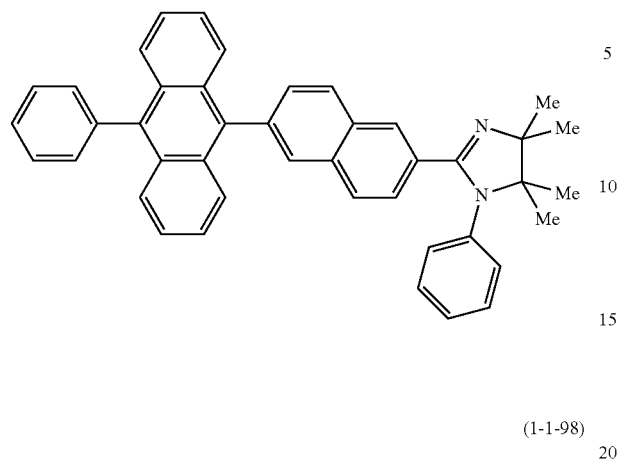
(1-1-98)
(1-1-99)
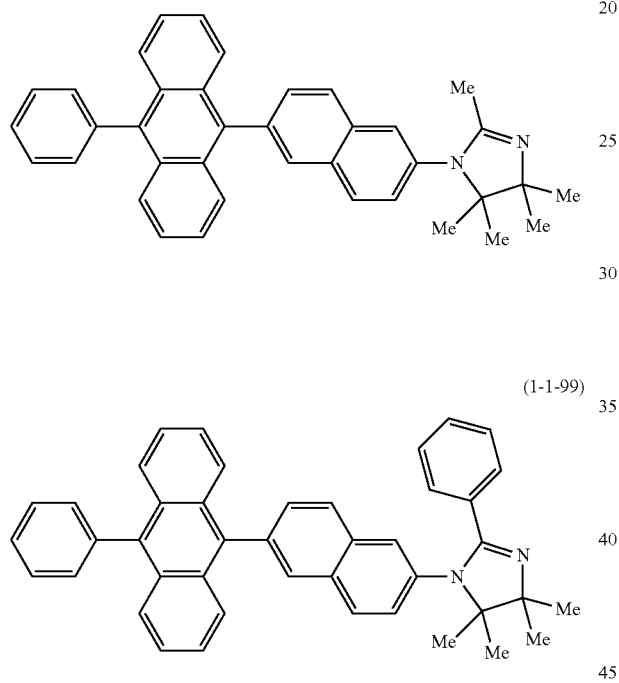
(1-1-101)
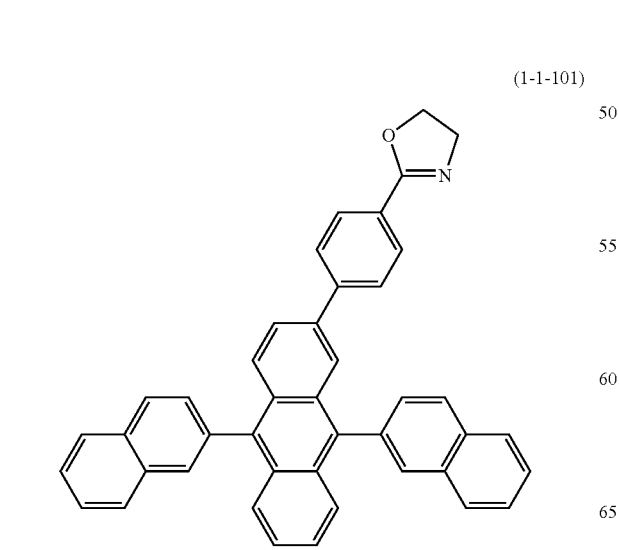
(1-1-102)
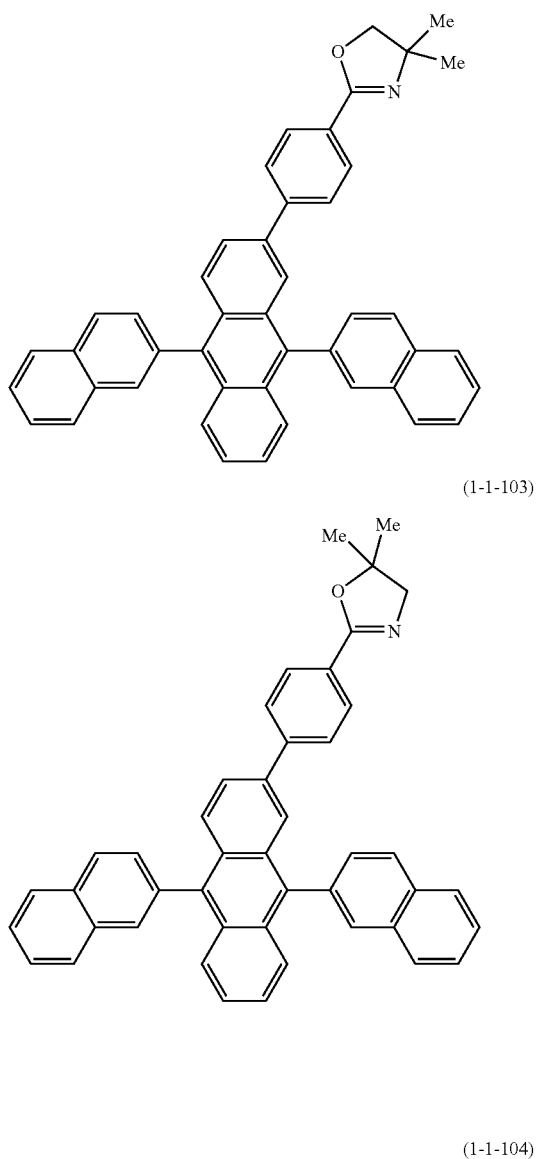
(1-1-103)
(1-1-104)

(1-1-105)
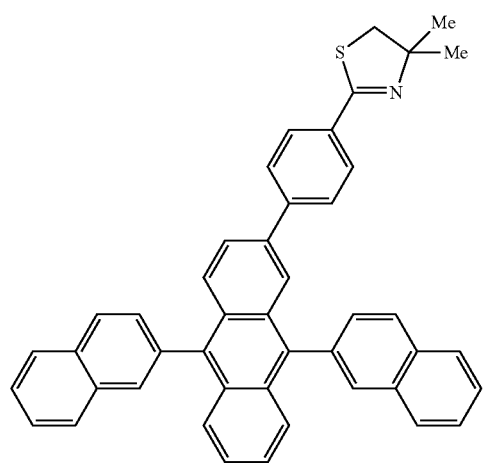
(1-1-106)
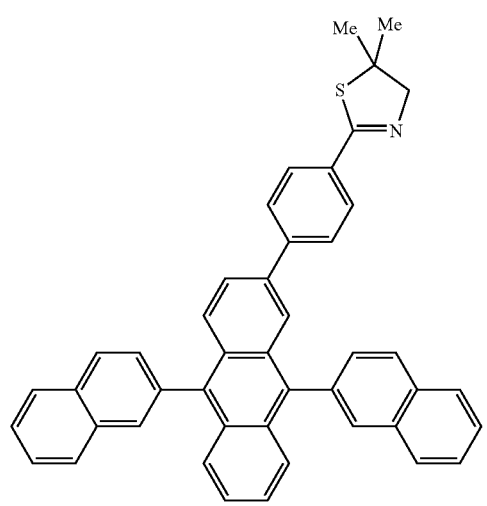
(1-1-108)
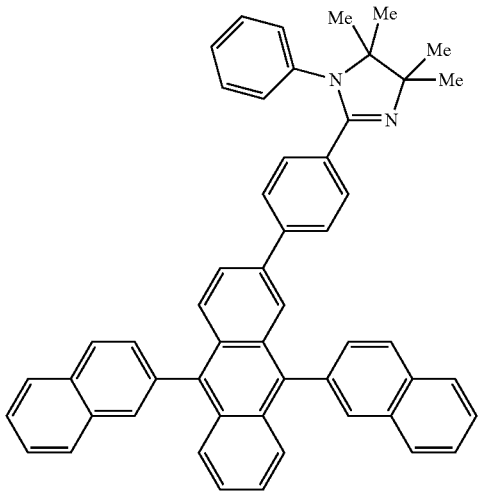
(1-1-109)
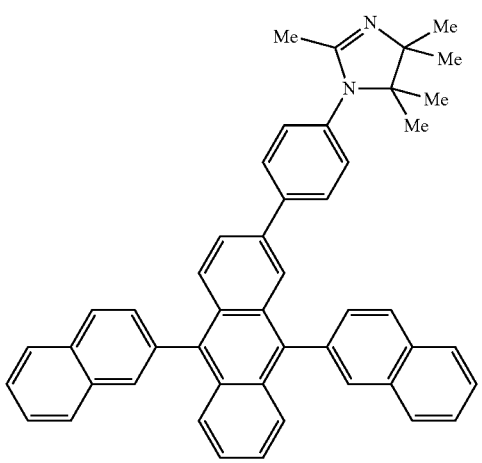

(1-1-111)
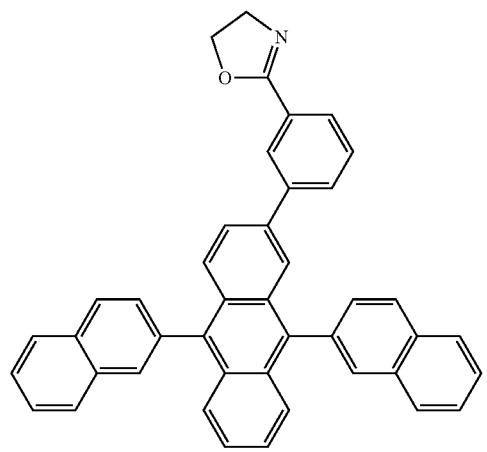
(1-1-112)
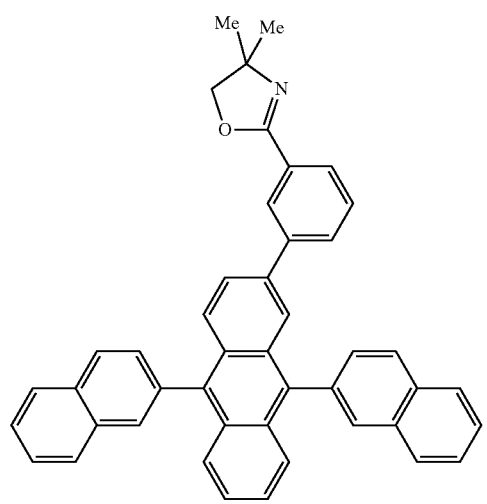
(1-1-113)
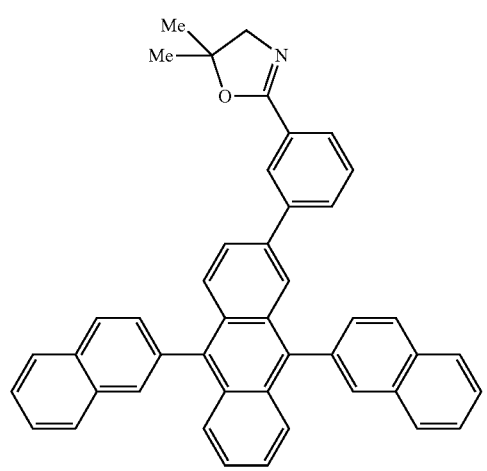
(1-1-114)
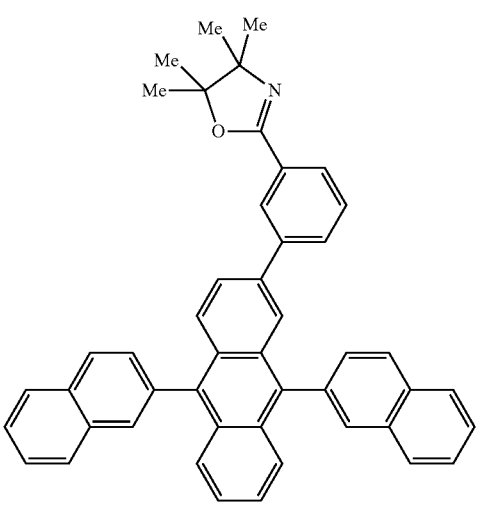
(1-1-115)
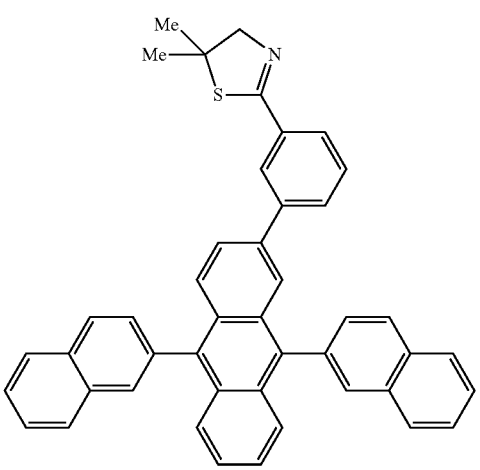
(1-1-116)
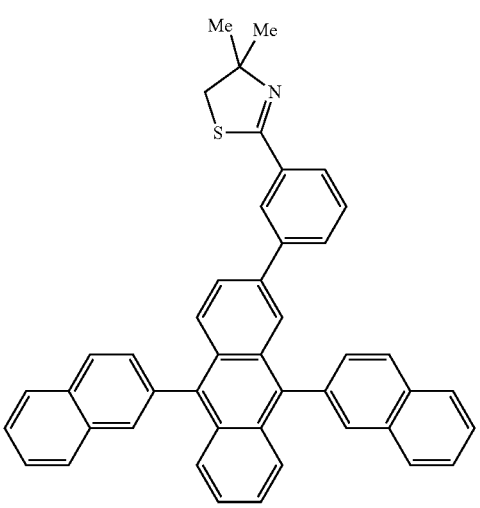

(1-1-117)
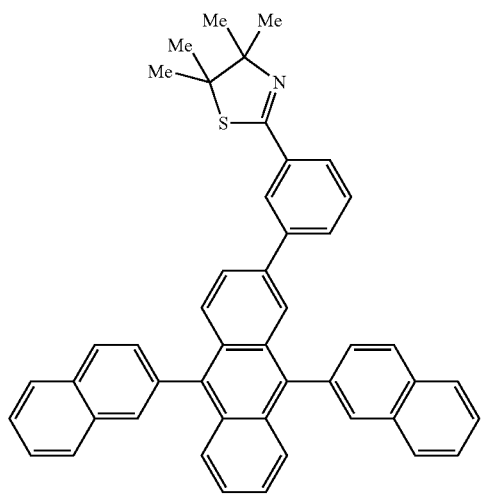
(1-1-118)
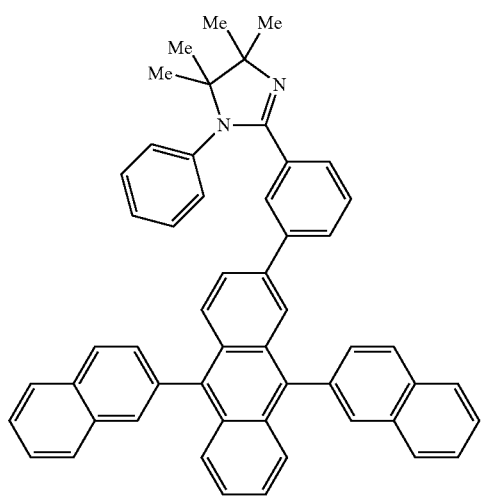
(1-1-119)
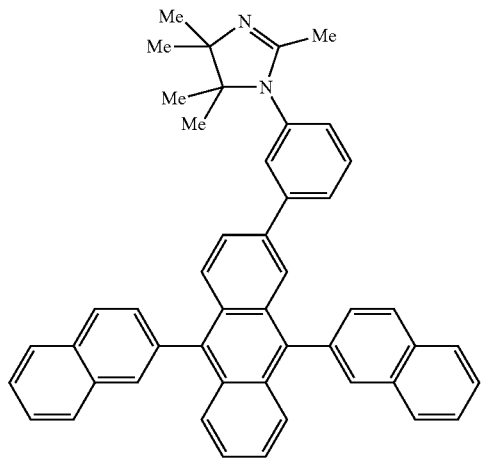
(1-1-120)
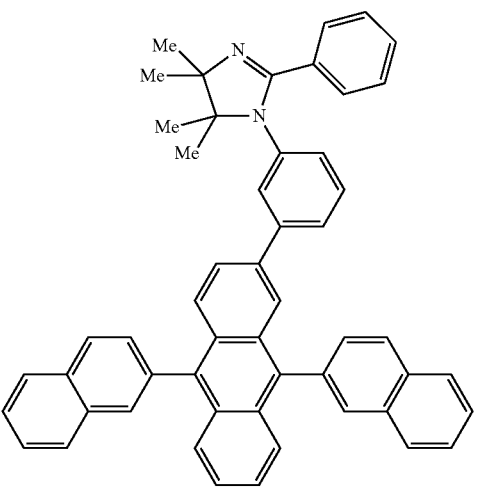
(1-1-121)
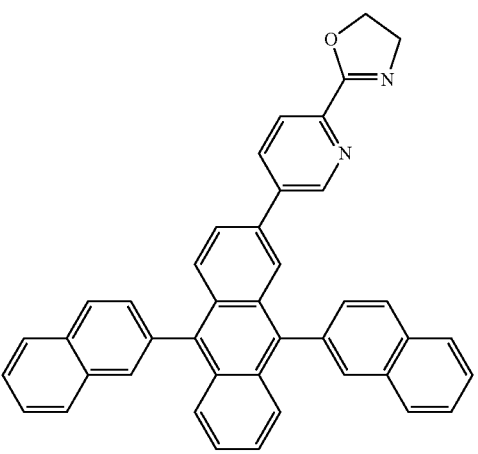
(1-1-122)
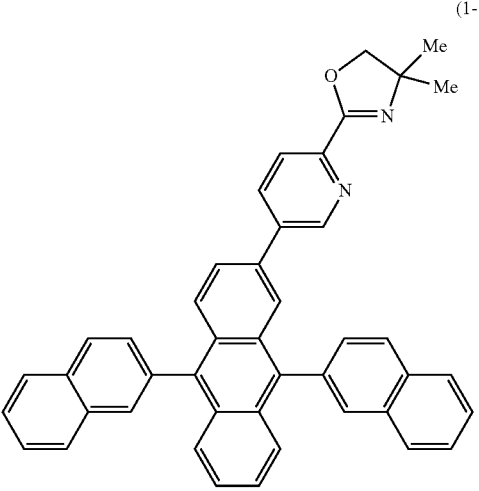

(1-1-123)
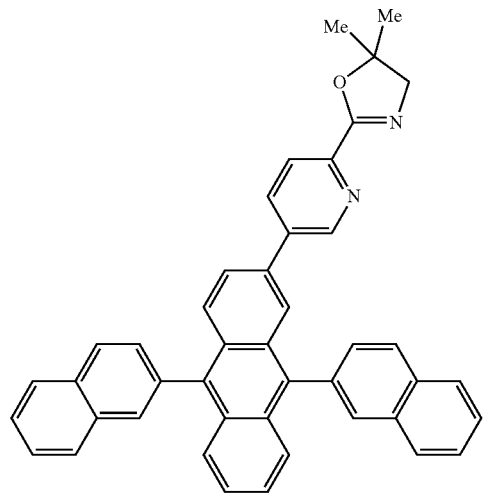
(1-1-124)
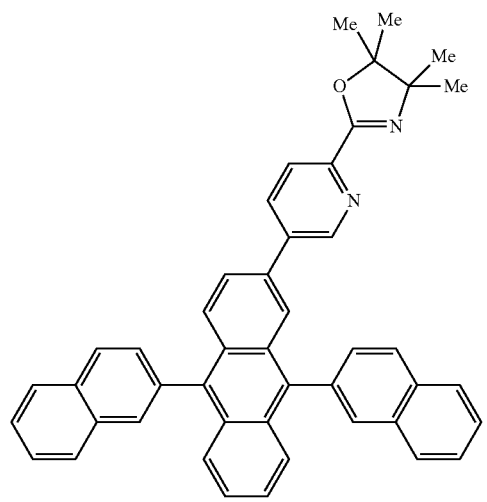
(1-1-125)
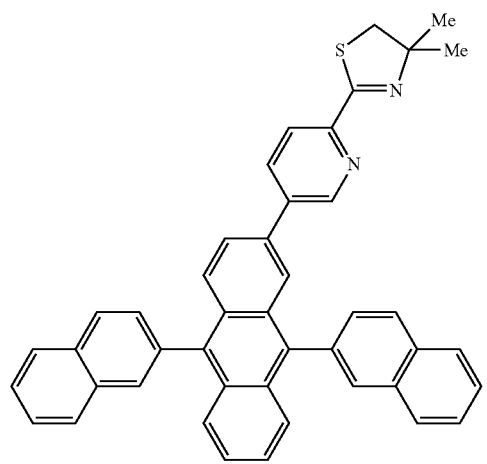
(1-1-126)
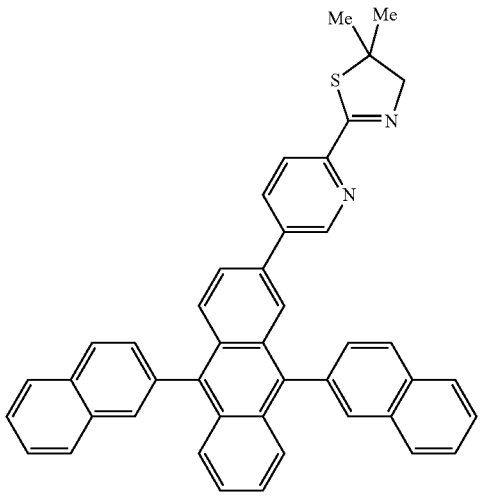
(1-1-127)
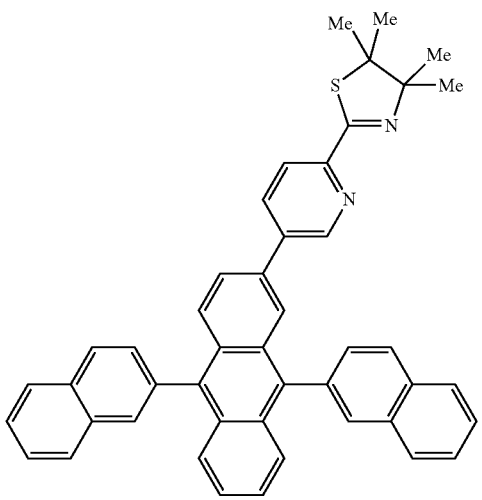
(1-1-128)
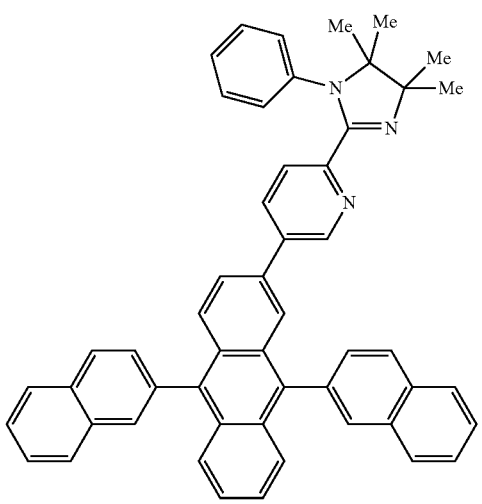

(1-1-129)
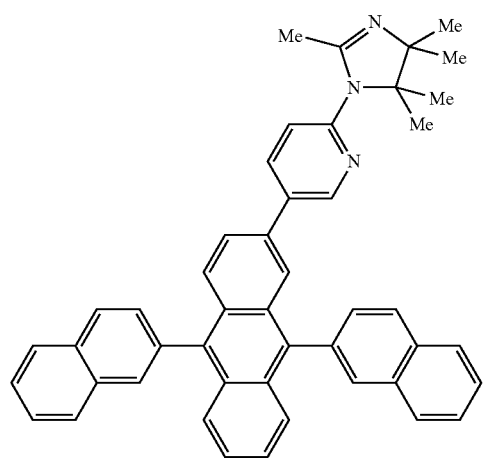
(1-1-130)
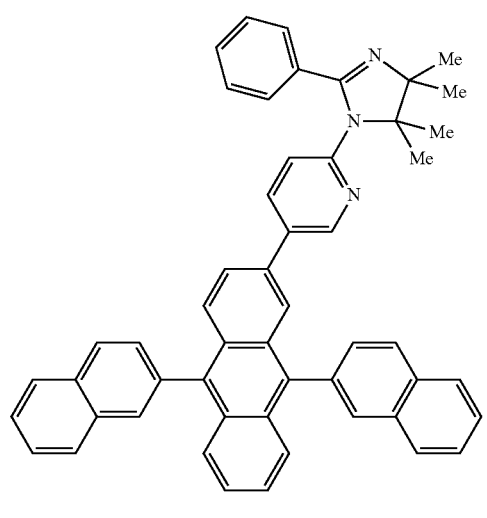
(1-1-131)
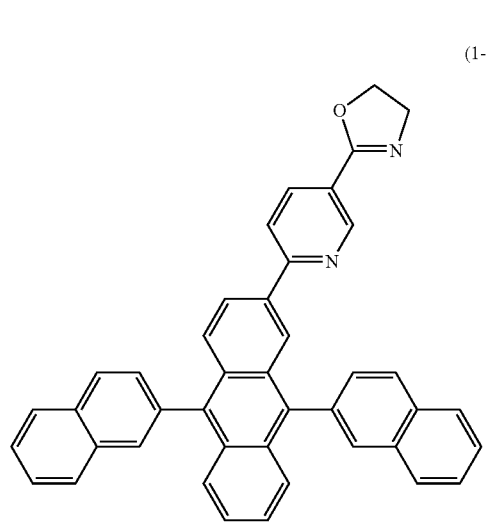
(1-1-132)
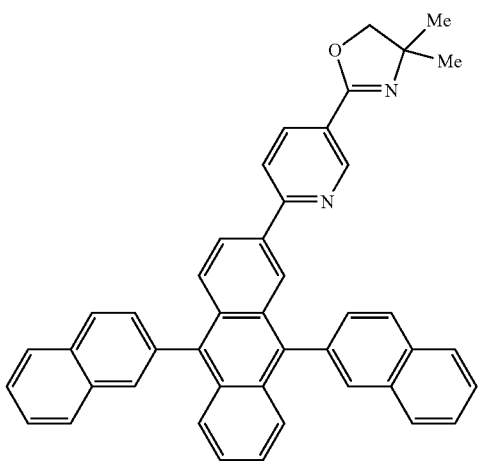
(1-1-133)
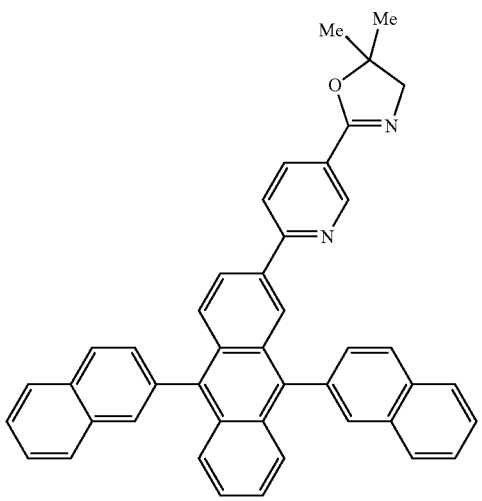
(1-1-134)
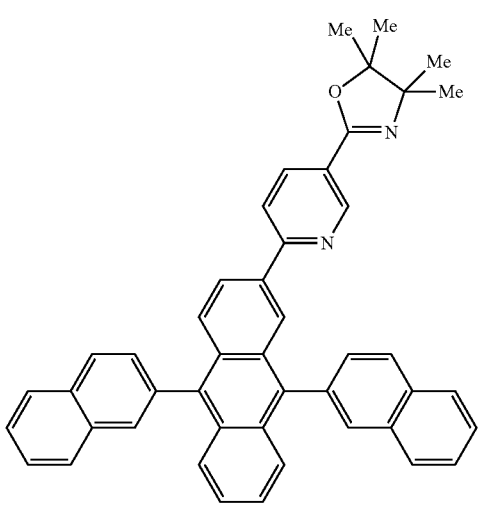

(1-1-135)
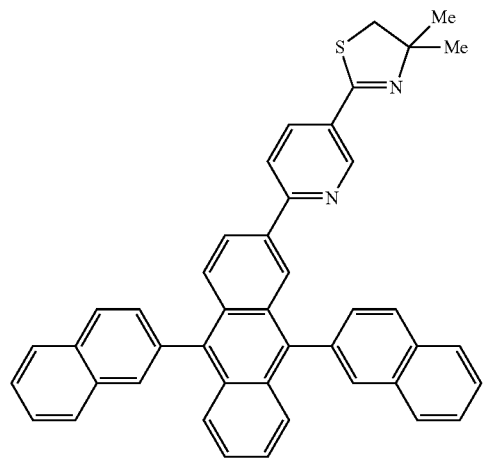
(1-1-136)
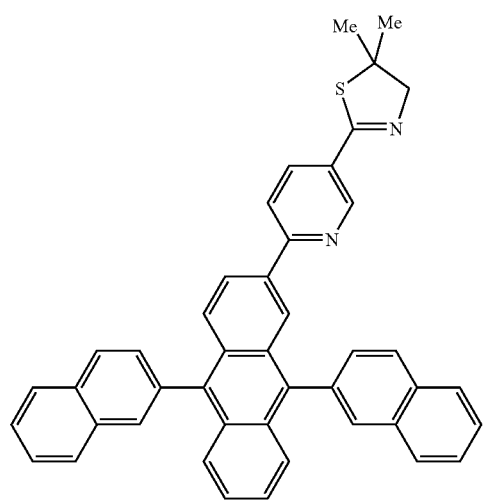
(1-1-137)
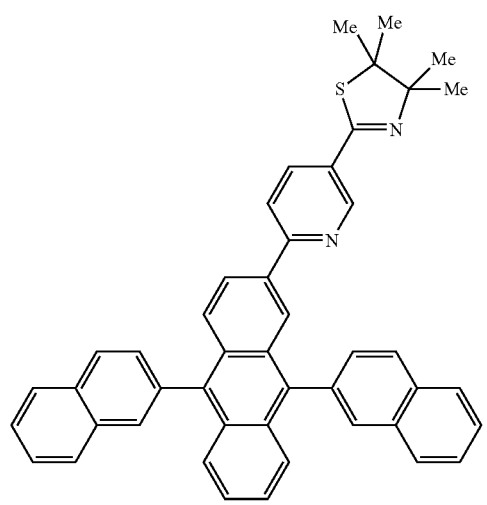
(1-1-138)
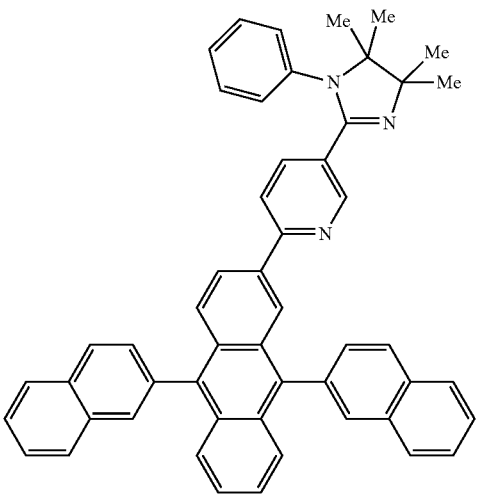
(1-1-139)
(1-1-140)
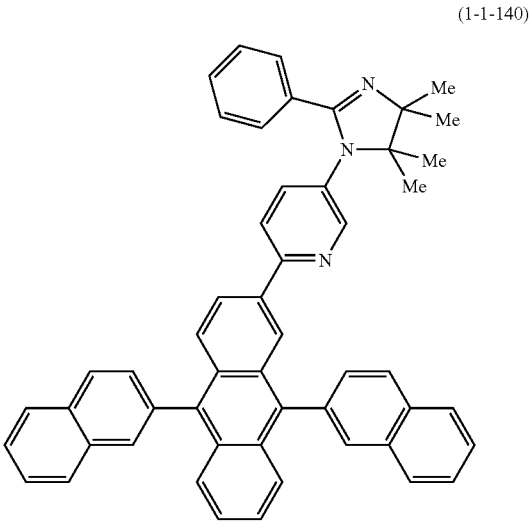

(1-1-141)
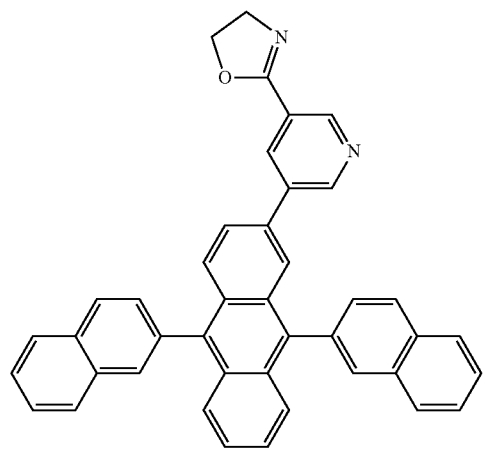
(1-1-142)
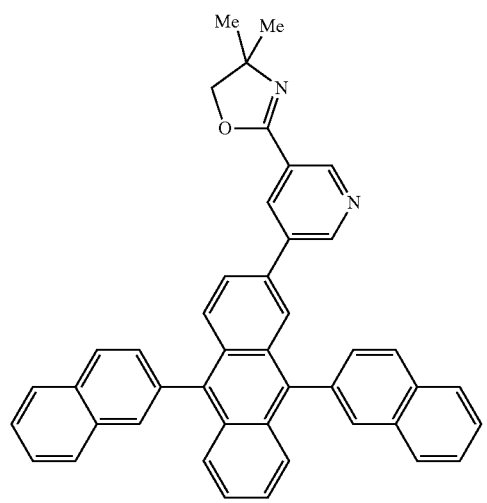
(1-1-143)
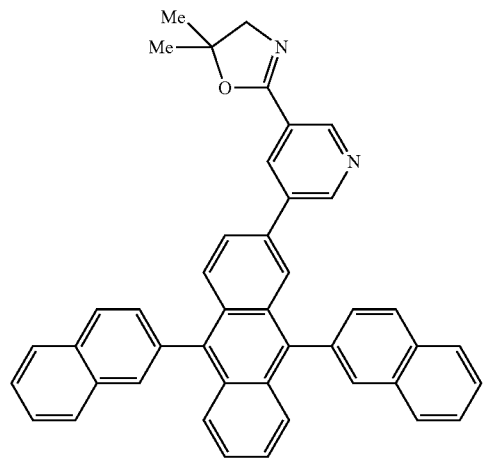
(1-1-144)
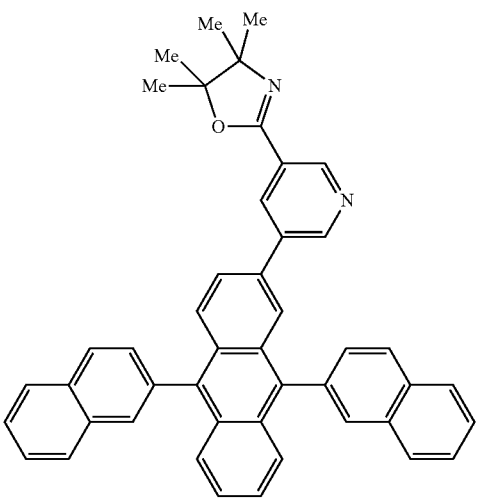
(1-1-145)
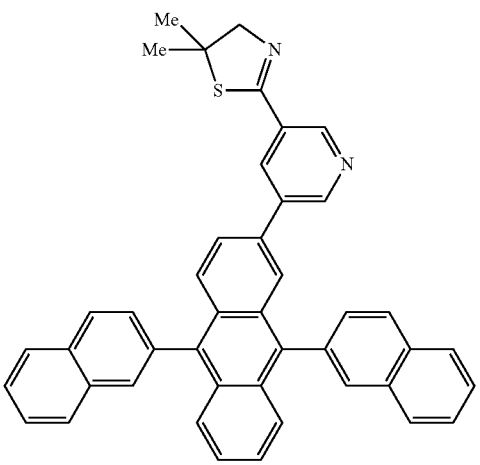
(1-1-146)
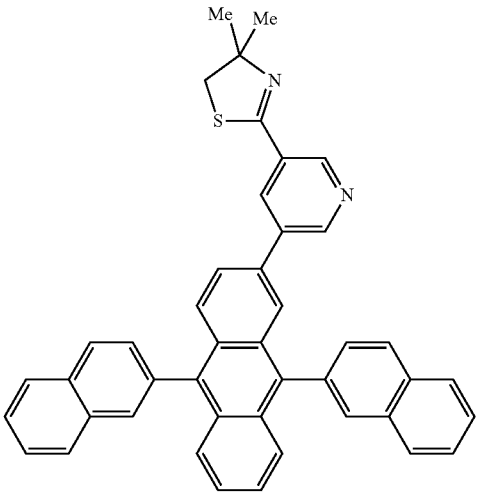

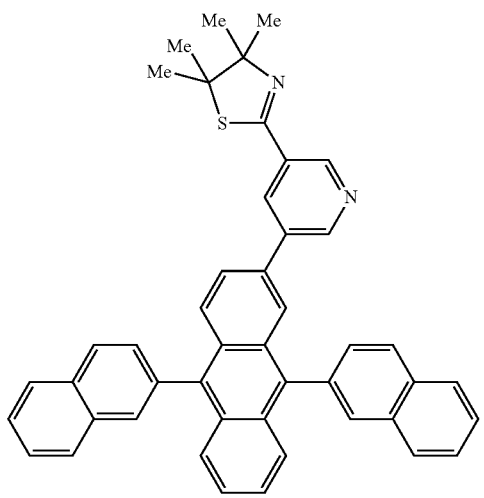
(1-1-147)
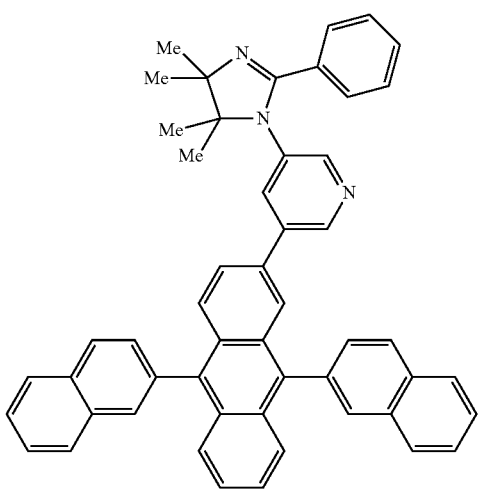
(1-1-150)
(1-1-148)
(1-1-151)
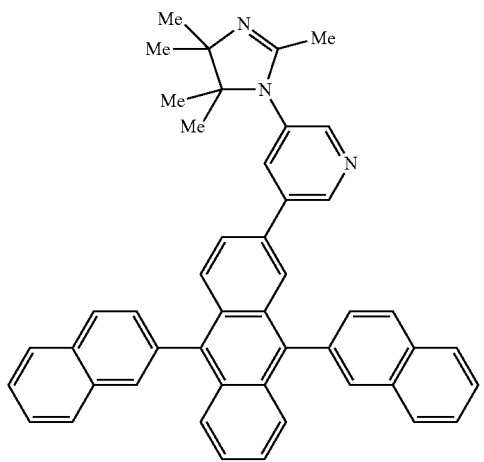
(1-1-149)
(1-1-152)

-continued
(1-1-153)
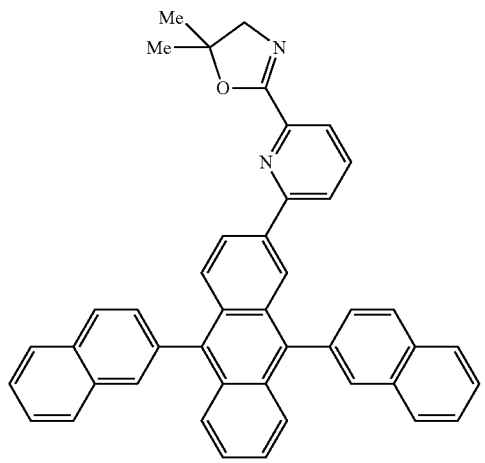
(1-1-154)
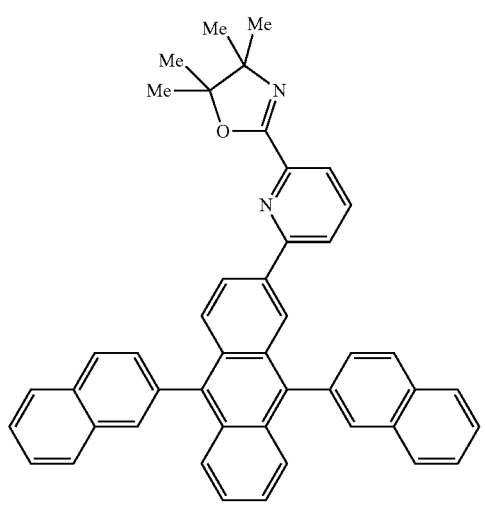
(1-1-155)
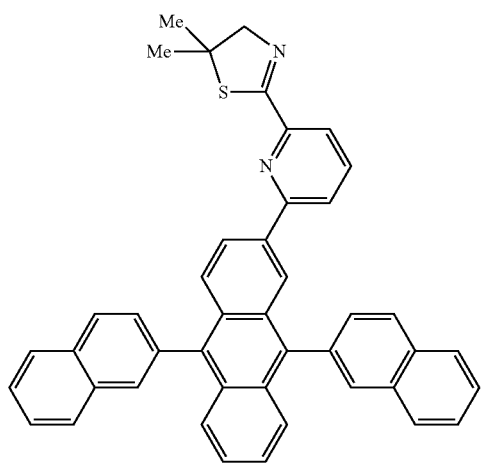
-continued
(1-1-156)
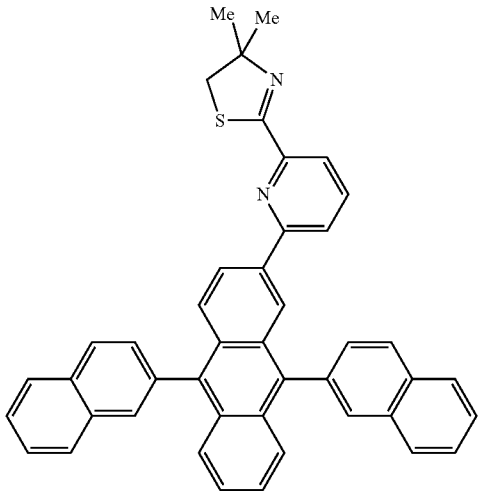
(1-1-157)
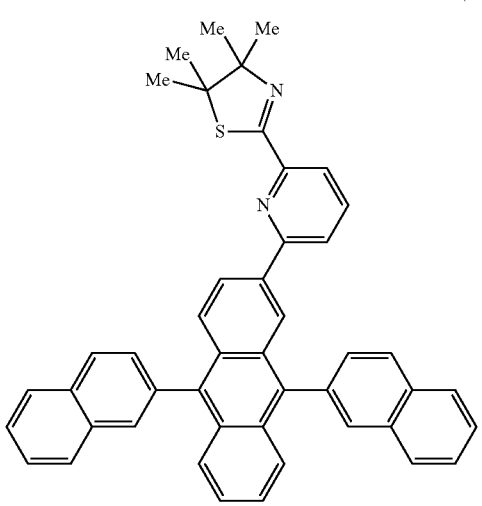
(1-1-158)
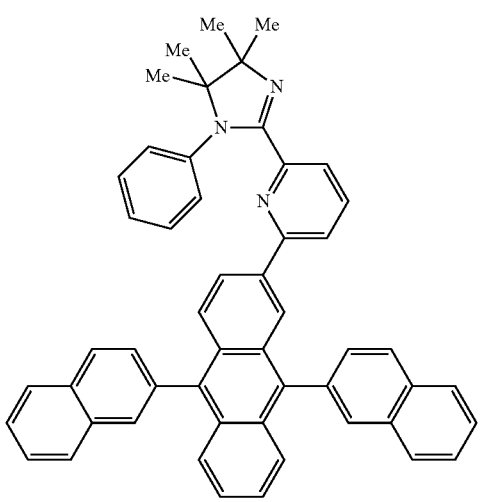

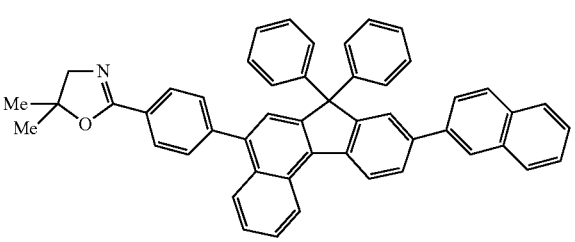
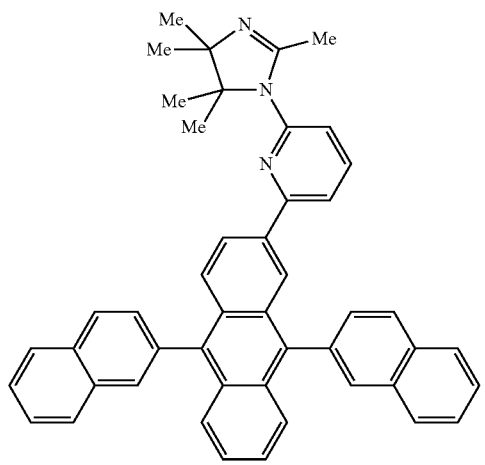

(1-1-168)
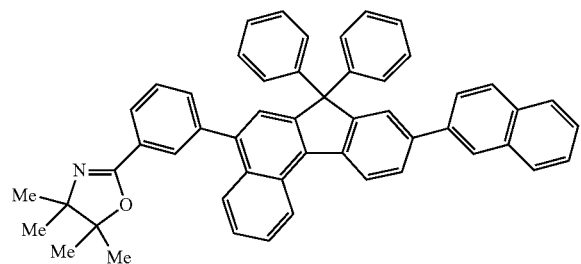
(1-1-171)
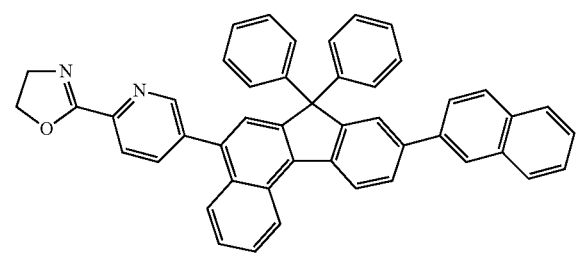
(1-1-172)
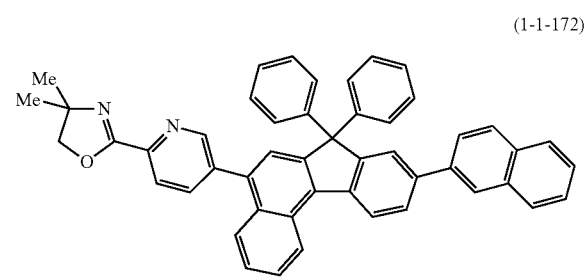
(1-1-173)
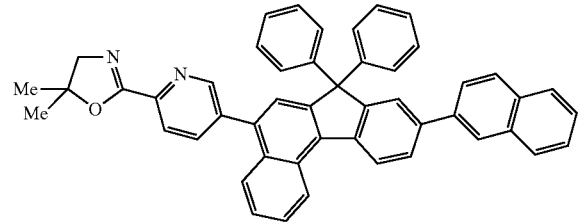
(1-1-174)
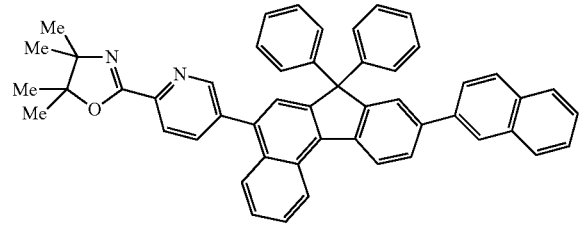
(1-1-175)
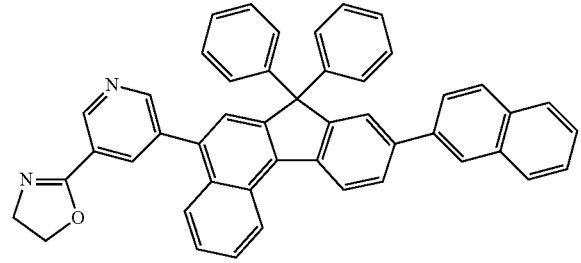
(1-1-176)
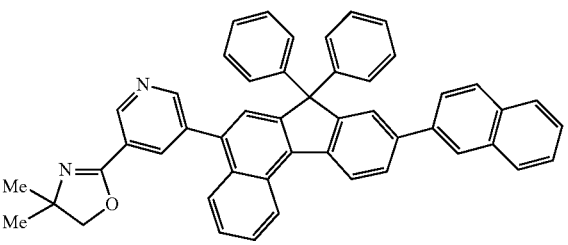
(1-1-177)
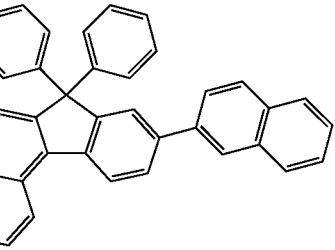
(1-1-178)
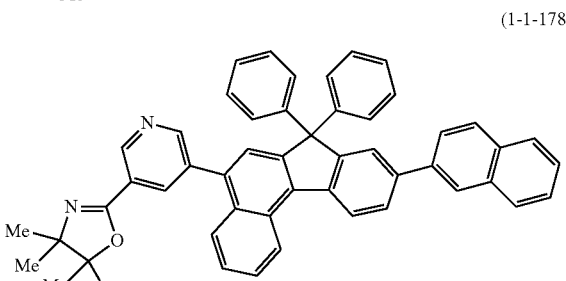
(1-1-181)
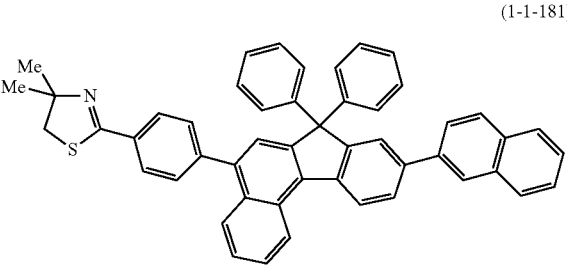
(1-1-182)
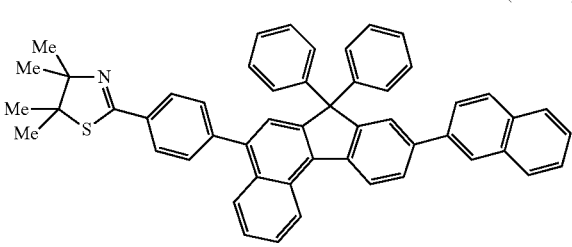
(1-1-183)
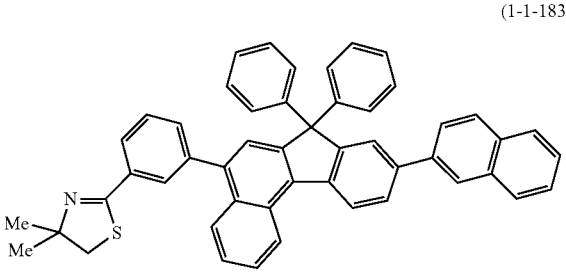

(1-1-184)
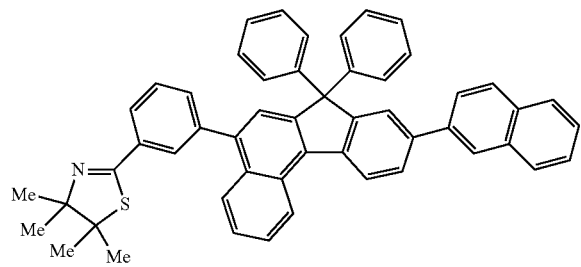
(1-1-185)
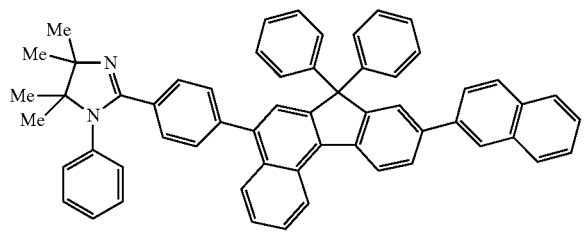
(1-1-186)
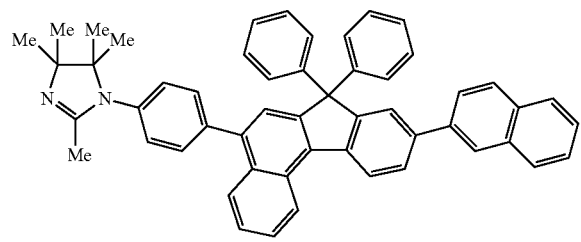
(1-1-187)
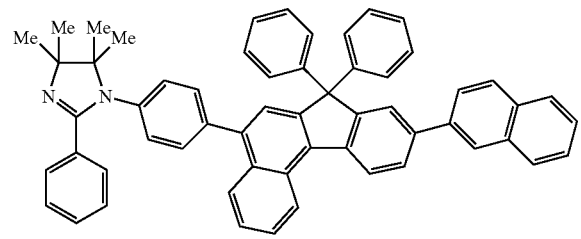
(1-1-188)
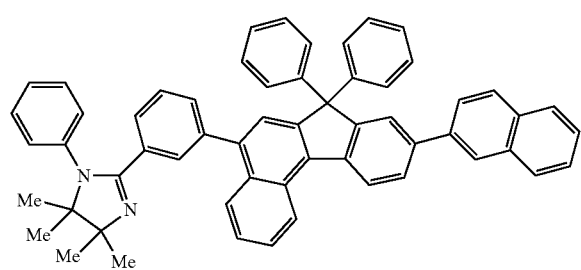
(1-1-189)
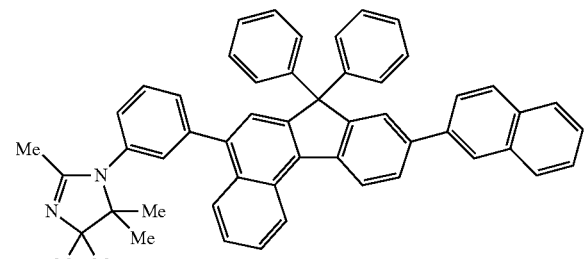
(1-1-191)
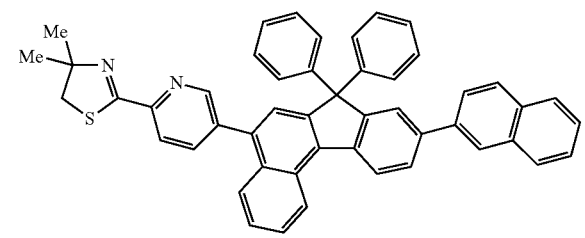
(1-1-192)
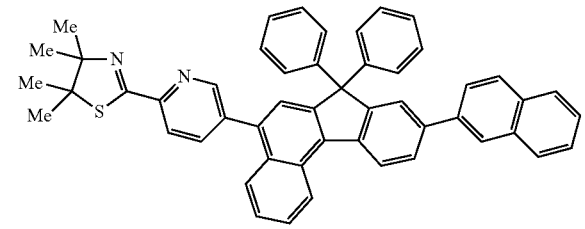
(1-1-193)
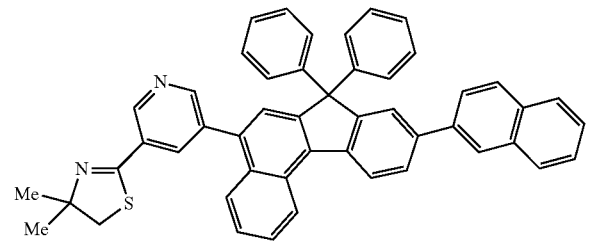
(1-1-194)
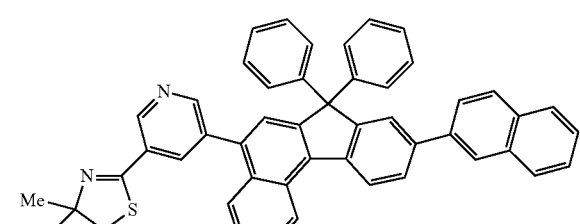
(1-1-195)
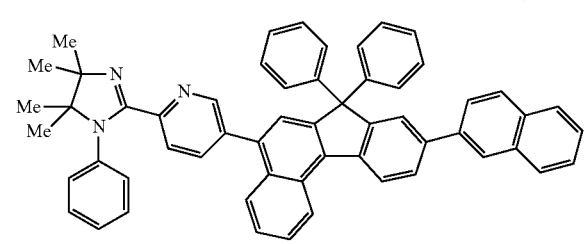

(1-1-196)
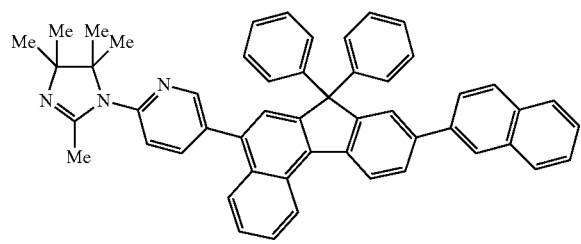
(1-1-202)
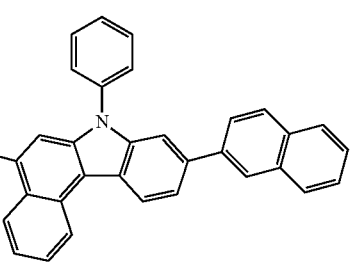
(1-1-197)
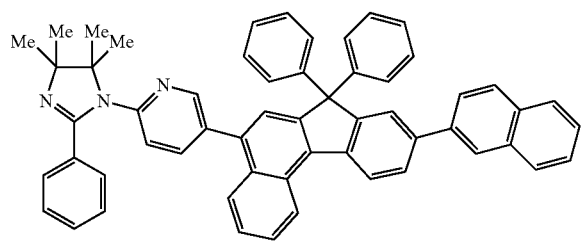
(1-1-203)
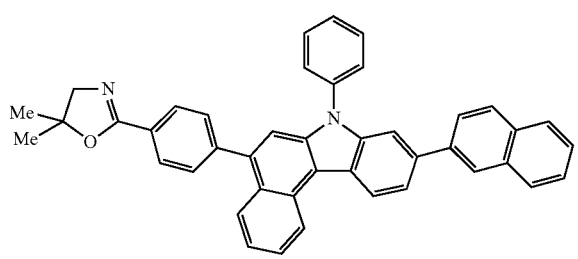
(1-1-198)
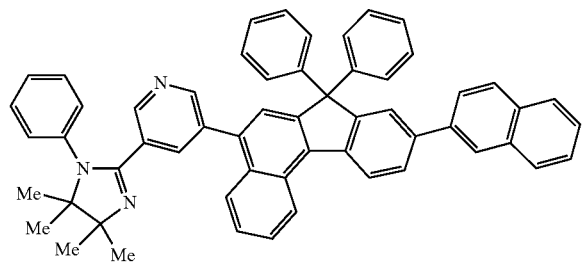
(1-1-204)
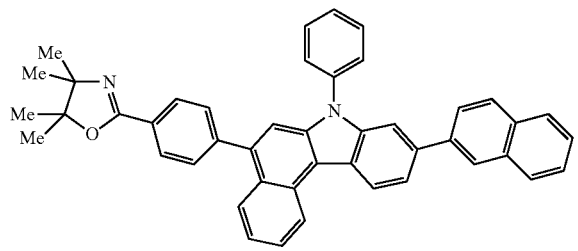
(1-1-199)
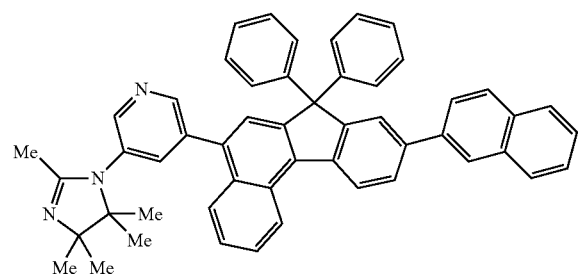
(1-1-205)
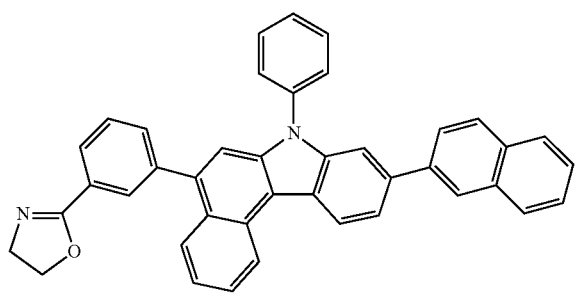
(1-1-201)
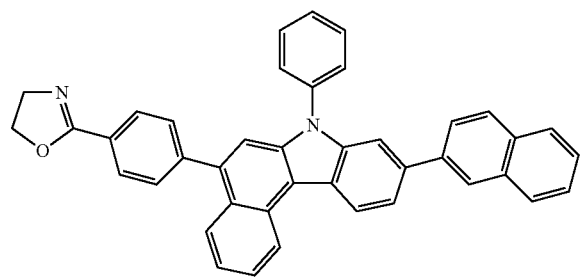
(1-1-206)
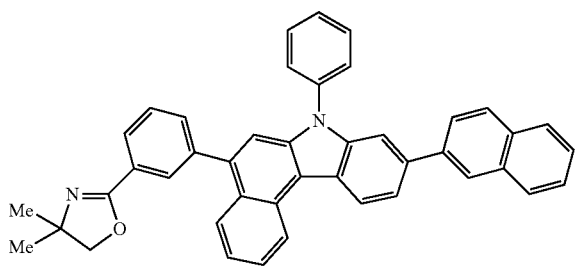

(1-1-207)
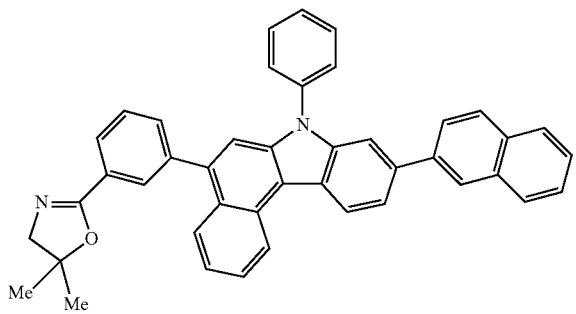
(1-1-214)
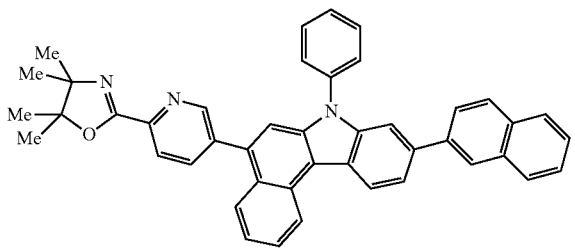
(1-1-208)
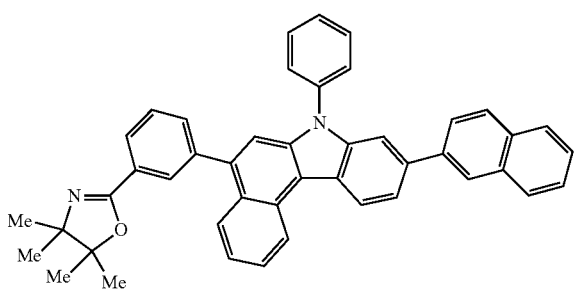
(1-1-215)
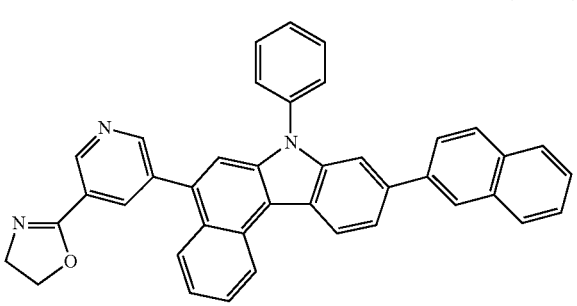
(1-1-211)
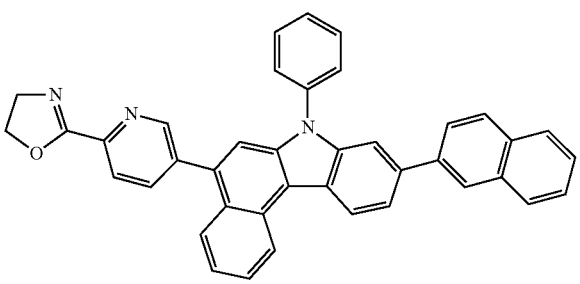
(1-1-216)
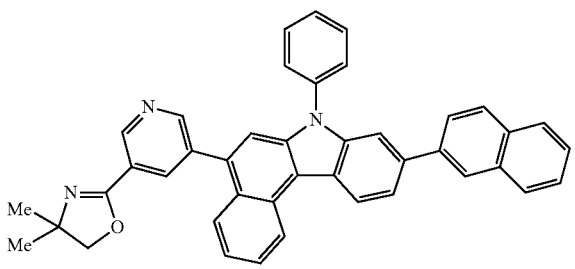
(1-1-212)
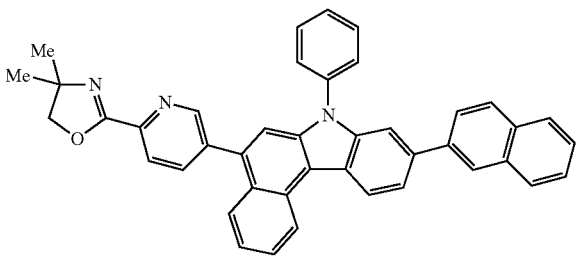
(1-1-217)
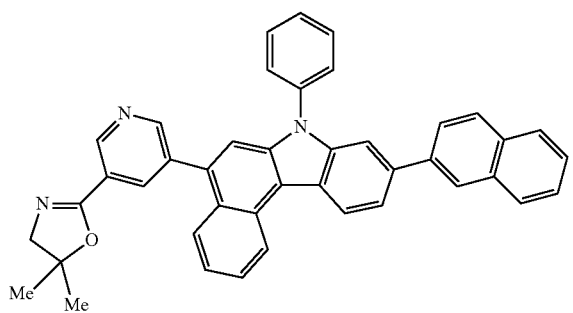
(1-1-213)
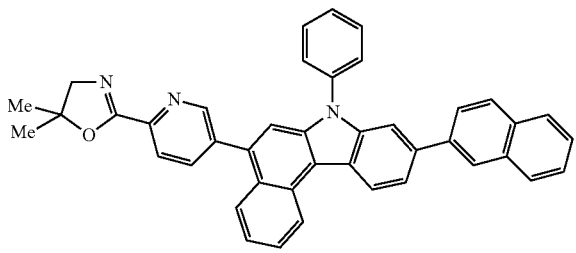
(1-1-218)
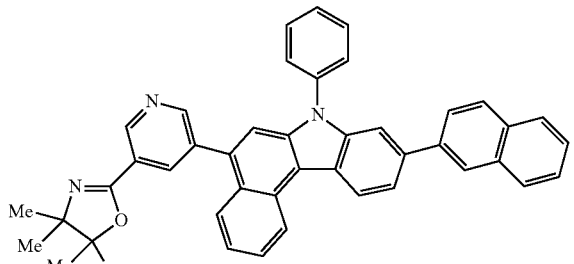

(1-1-221)
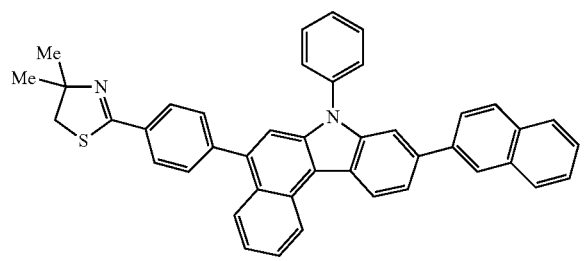
(1-1-222)
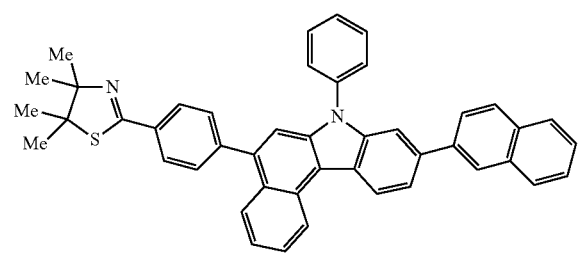
(1-1-223)
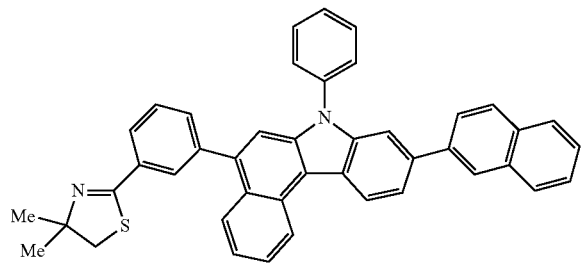
(1-1-224)
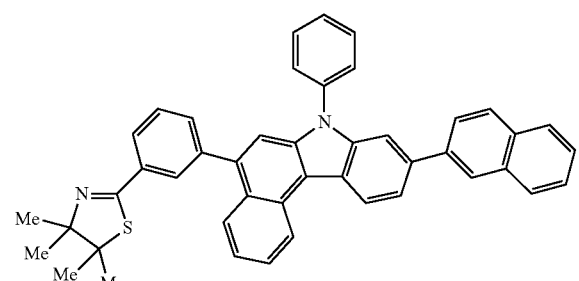
(1-1-225)
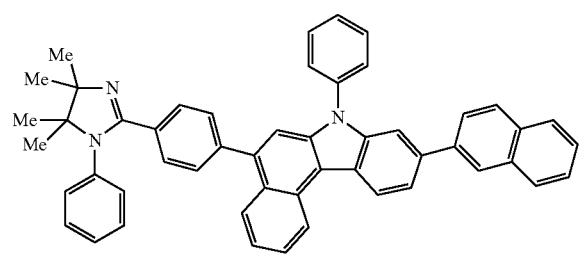
(1-1-226)
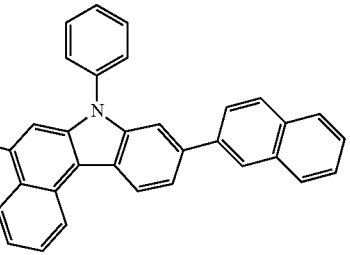
(1-1-227)
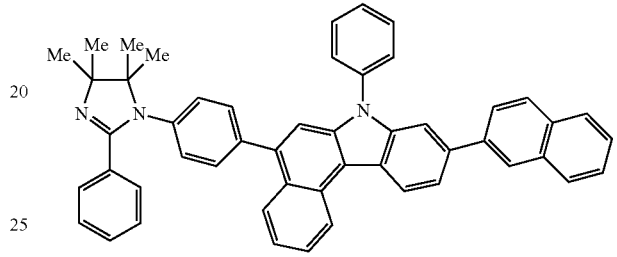
(1-1-228)
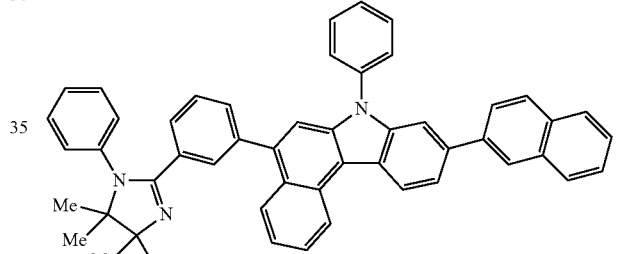
(1-1-229)
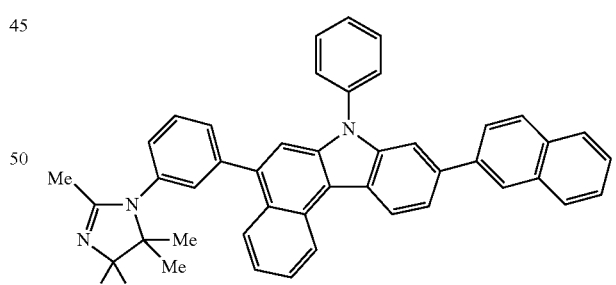
(1-1-231)
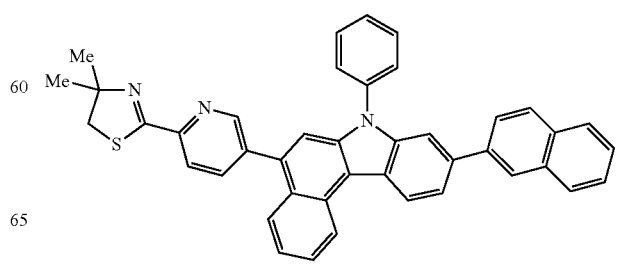

(1-1-232)
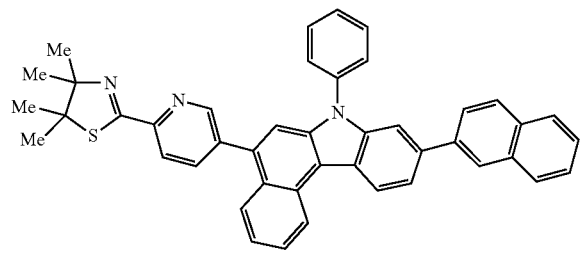
(1-1-233)
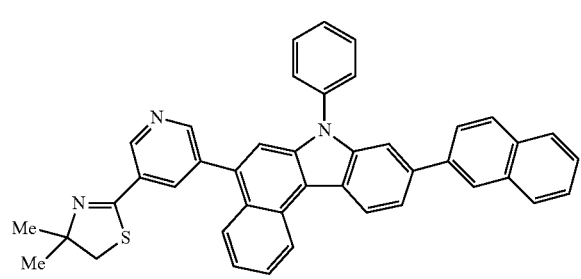
(1-1-234)
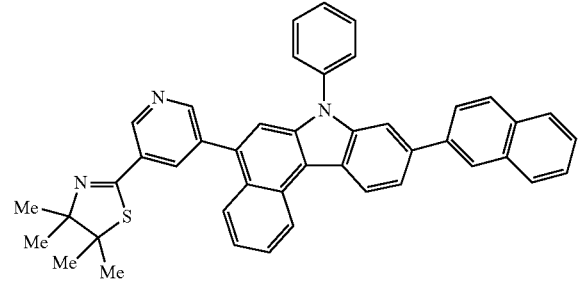
(1-1-235)
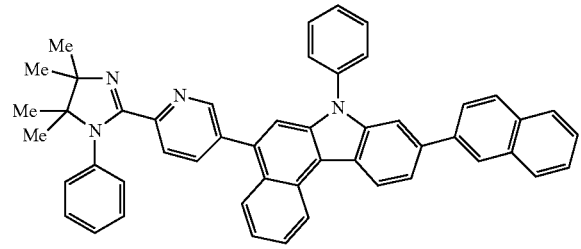
(1-1-236)
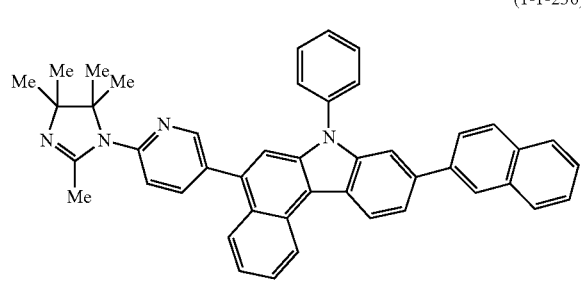
(1-1-237)
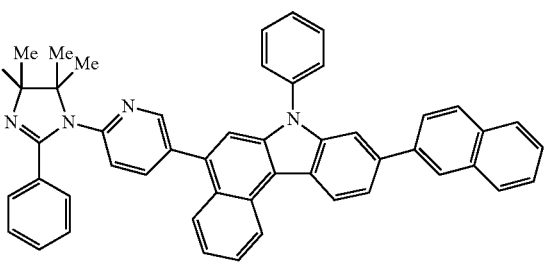
(1-1-238)
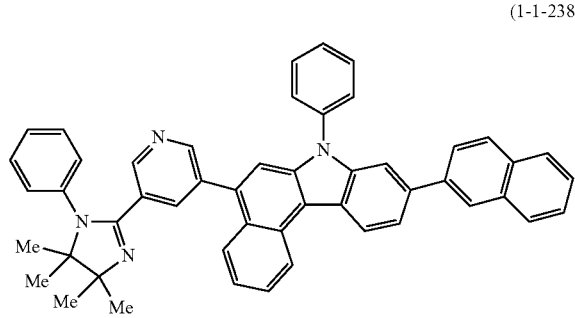
(1-1-239)
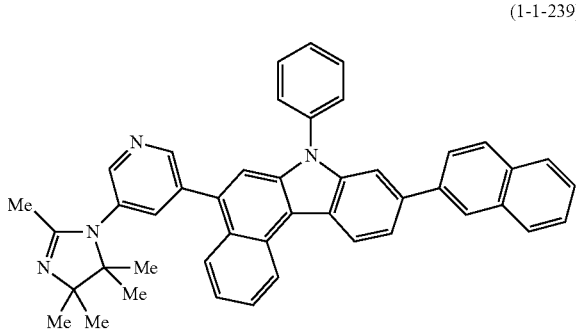
(1-1-261)
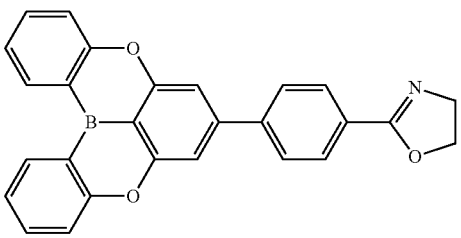
(1-1-262)
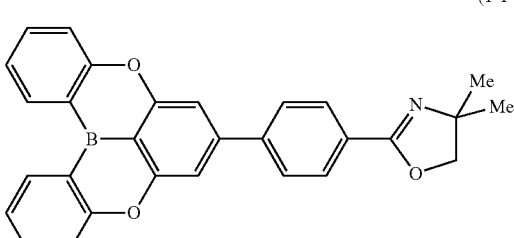

(1-1-263)
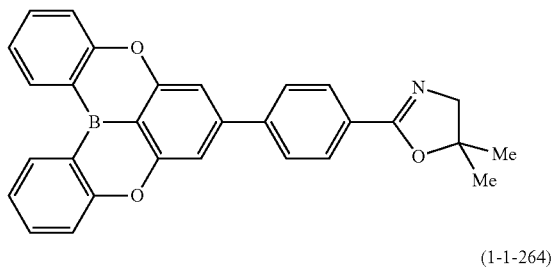
(1-1-264)
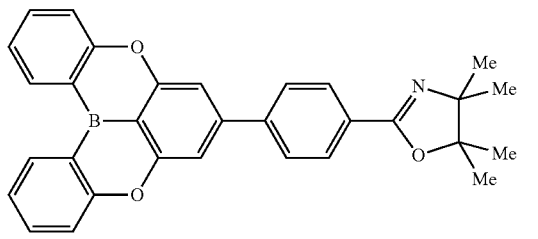
(1-1-265)
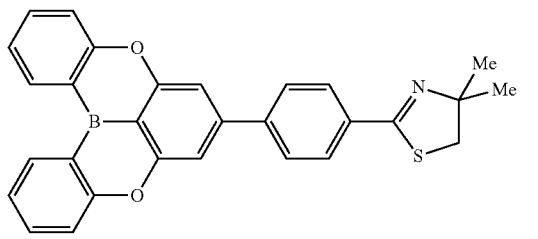
(1-1-266)
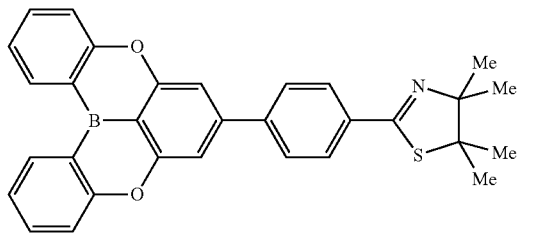
(1-1-267)
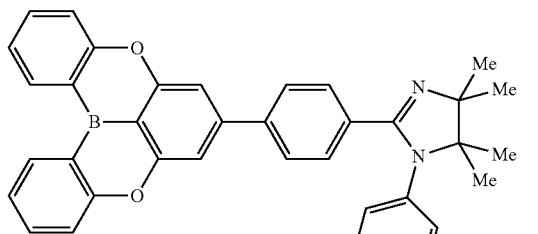
(1-1-268)
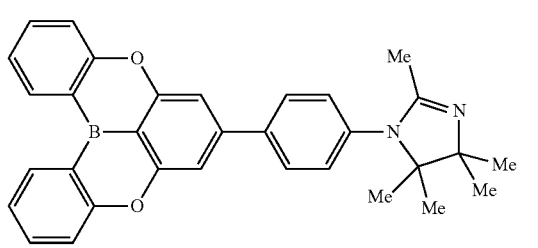
(1-1-269)
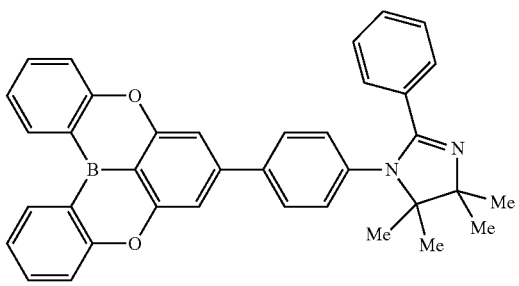
(1-1-270)
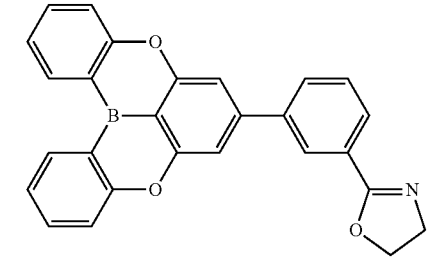
(1-1-271)
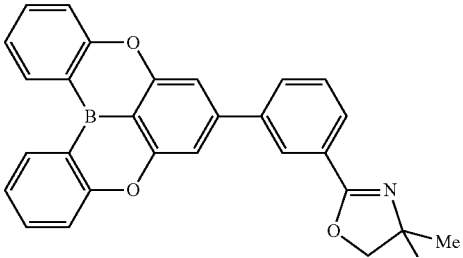
(1-1-272)
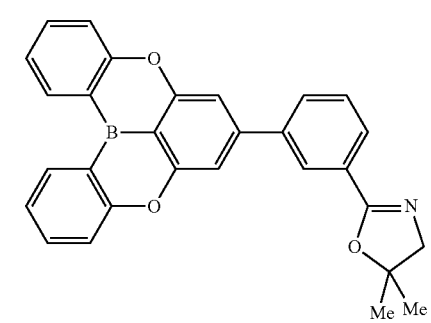
(1-1-273)
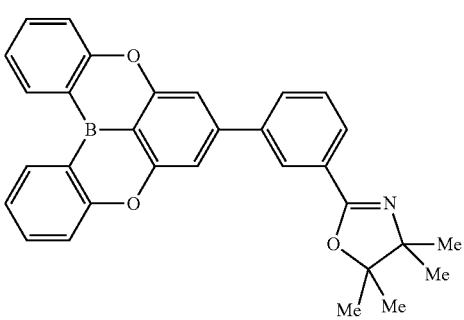

(1-1-274)
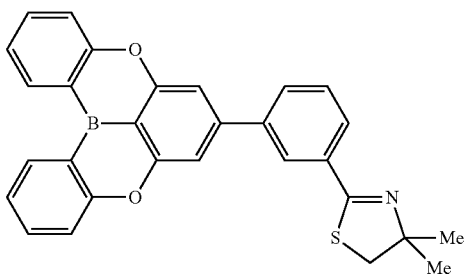
(1-1-275)
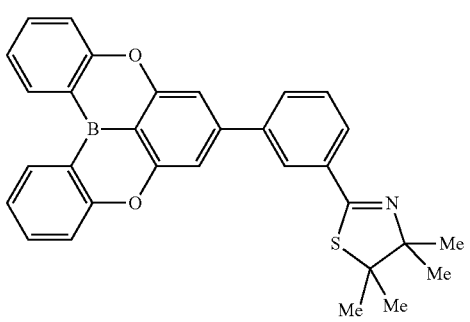
(1-1-276)
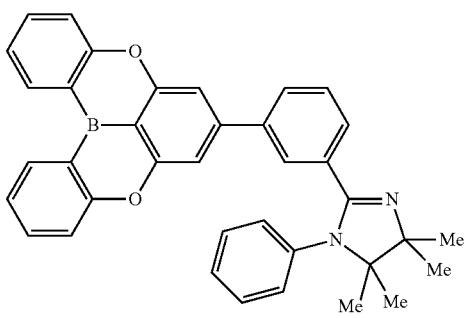
(1-1-277)
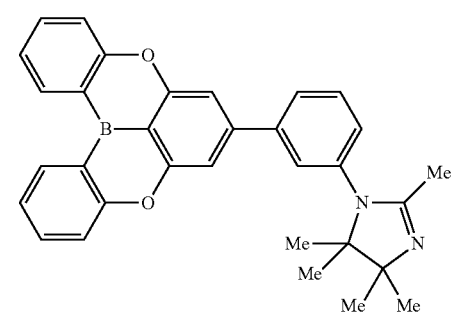
(1-1-278)
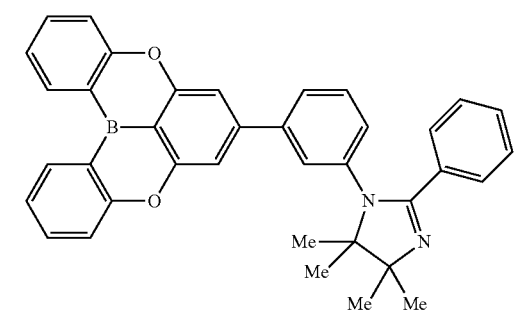
(1-1-281)
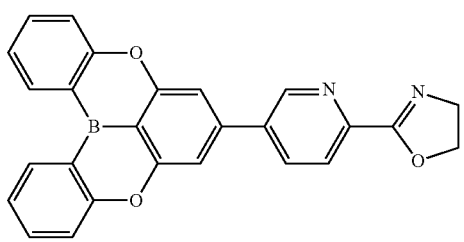
(1-1-282)
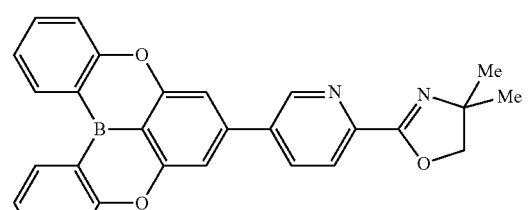
(1-1-283)
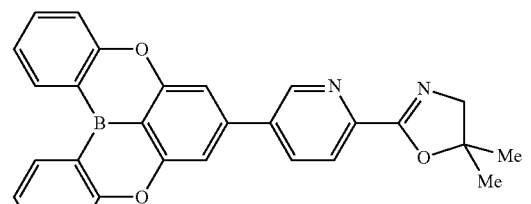
(1-1-284)
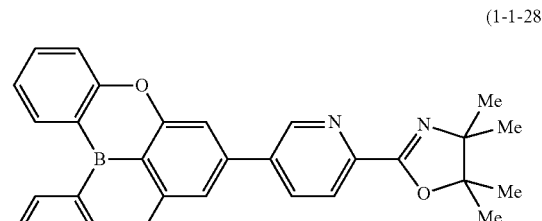
(1-1-285)
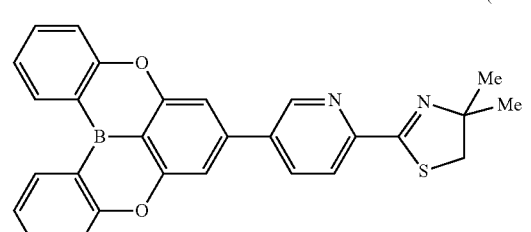
(1-1-286)
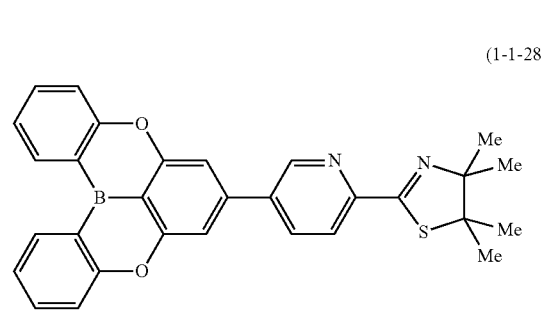

(1-1-287)
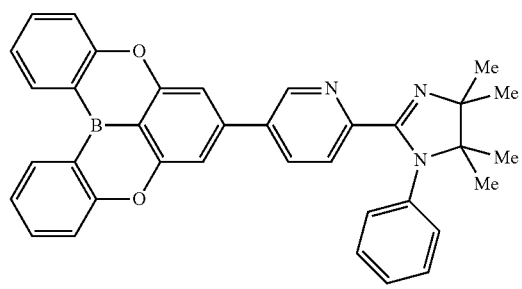
(1-1-288)
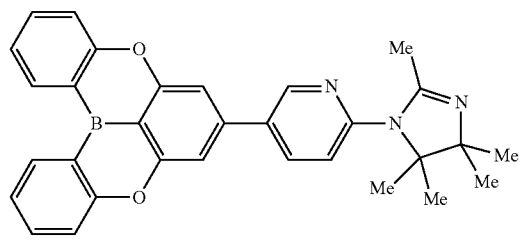
(1-1-289)
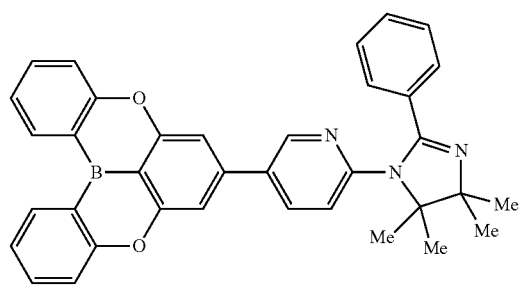
(1-1-290)
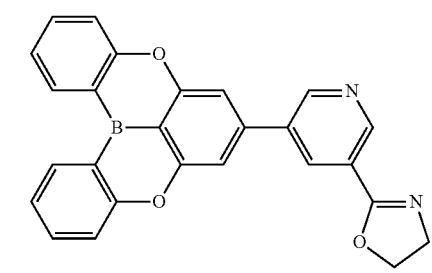
(1-1-291)
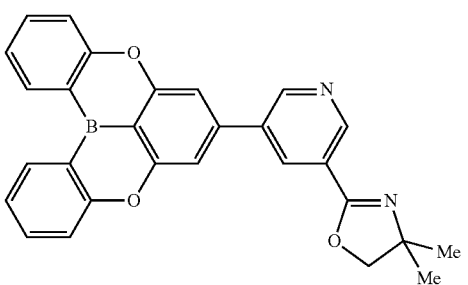
(1-1-292)
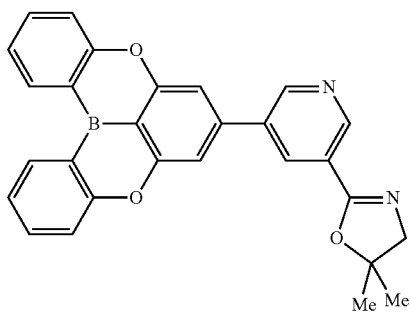
(1-1-293)
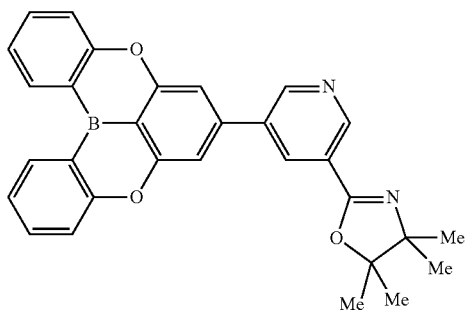
(1-1-294)
(1-1-295)
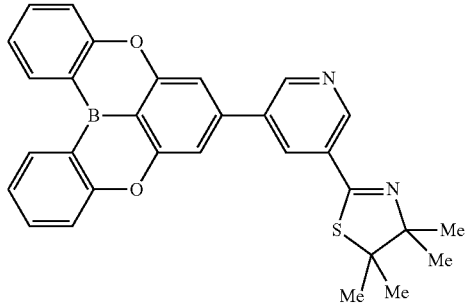
(1-1-296)
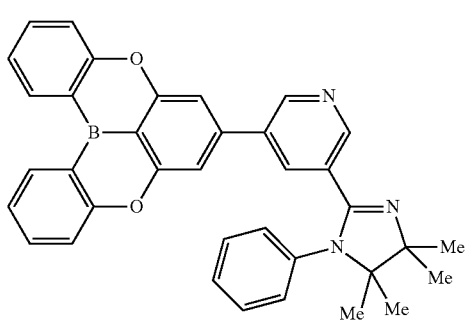

-continued
(1-1-297)
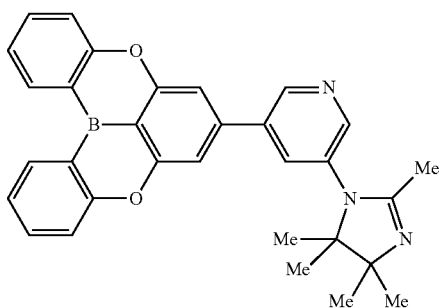
(1-1-298)
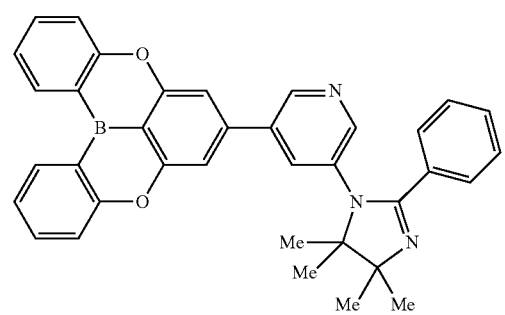
(1-1-301)
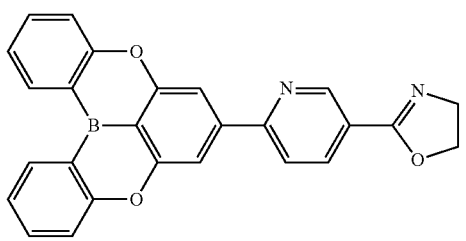
(1-1-302)
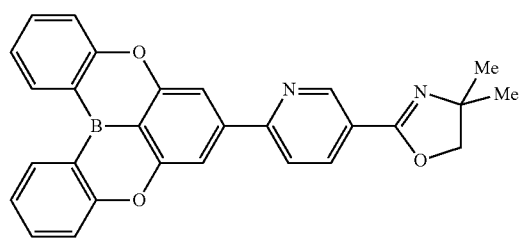
(1-1-303)
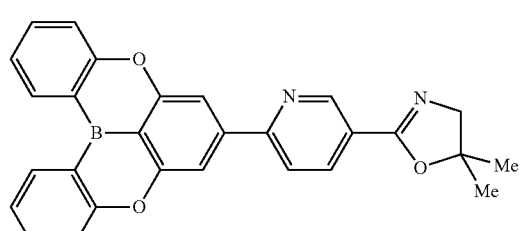
-continued
(1-1-304)
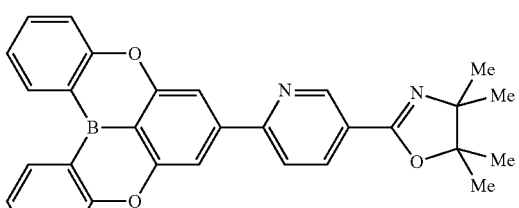
(1-1-305)
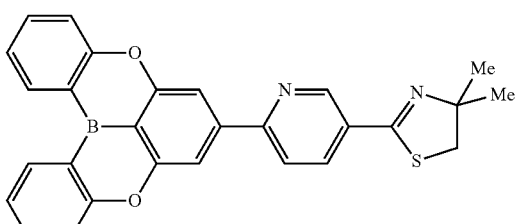
(1-1-306)
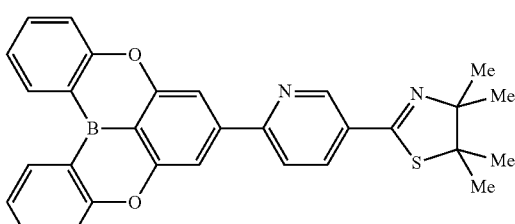
(1-1-307)
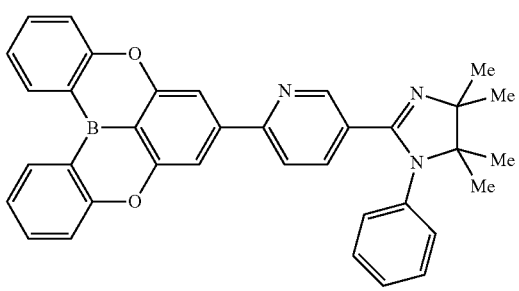
(1-1-308)
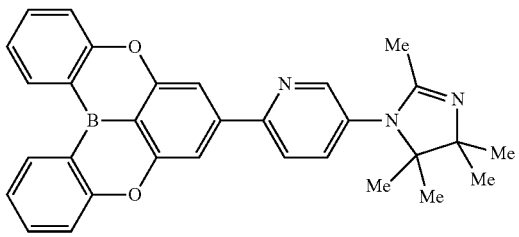
(1-1-309)
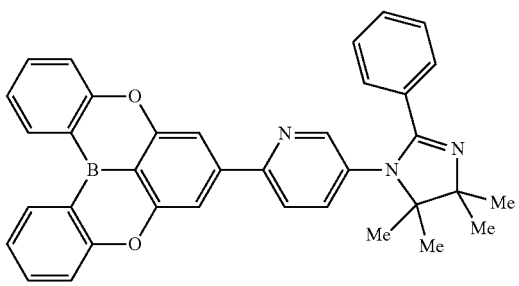

(1-1-310)
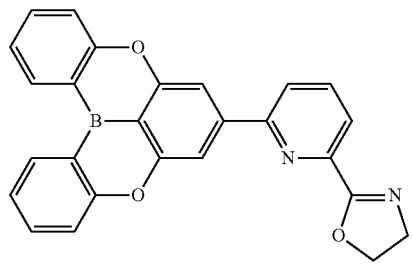
(1-1-311)
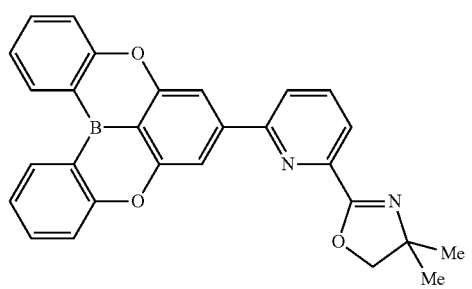
(1-1-312)
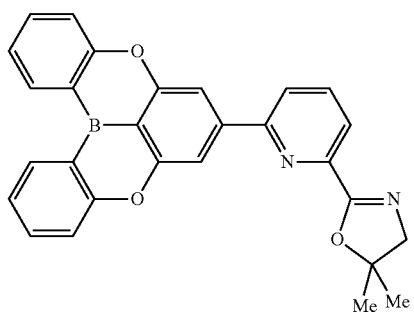
(1-1-313)
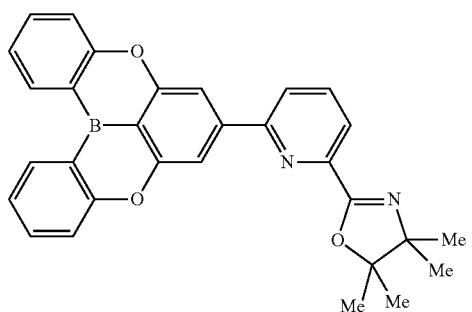
(1-1-314)
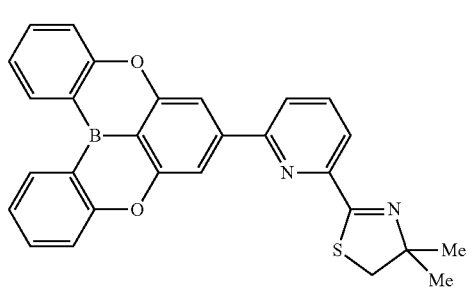
(1-1-315)
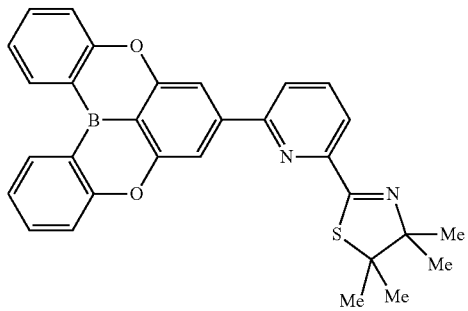
(1-1-316)
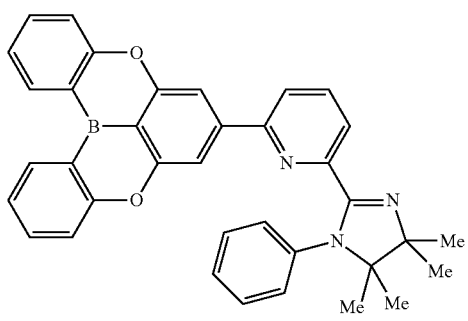
(1-1-317)
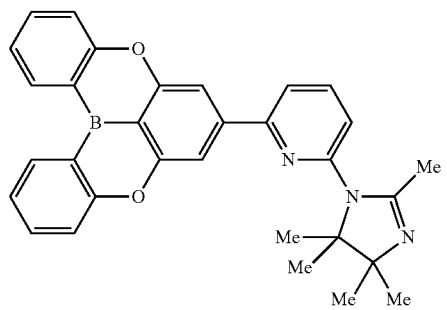
(1-1-318)
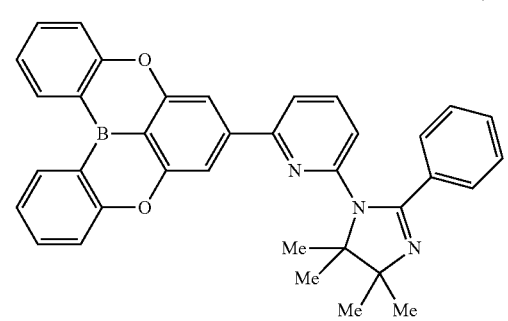

(1-2-1)
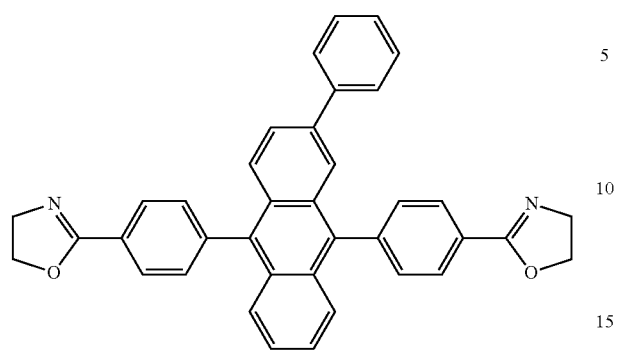
(1-2-2)
(1-2-3)
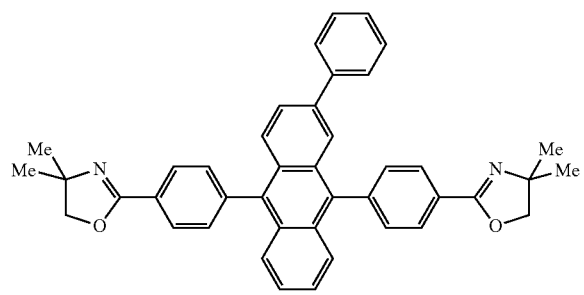
(1-2-4)
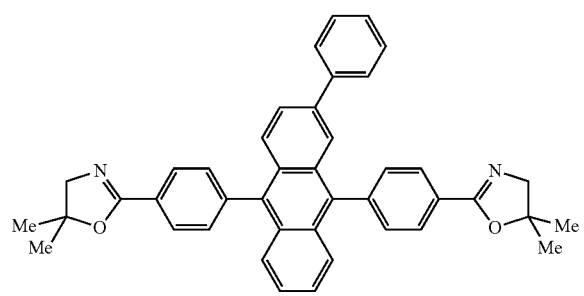
(1-2-5)
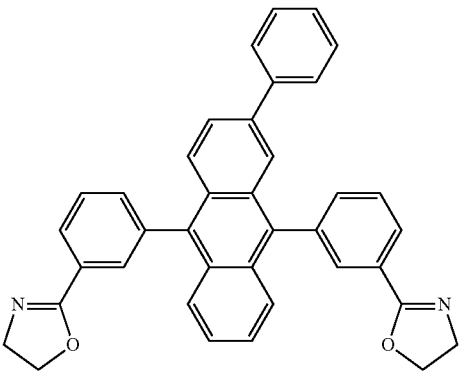
(1-2-6)
(1-2-7)
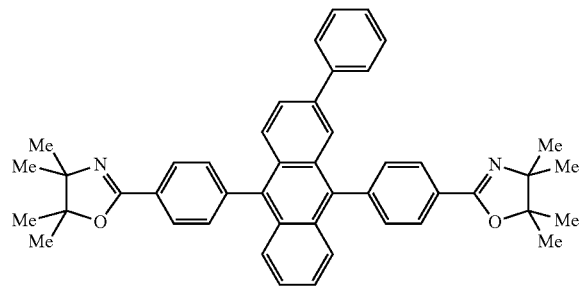
(1-2-8)

(1-2-11)
(1-2-12)
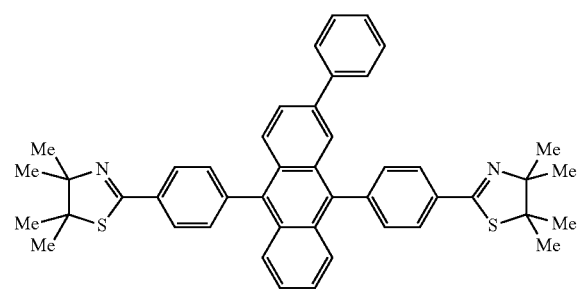
(1-2-13)
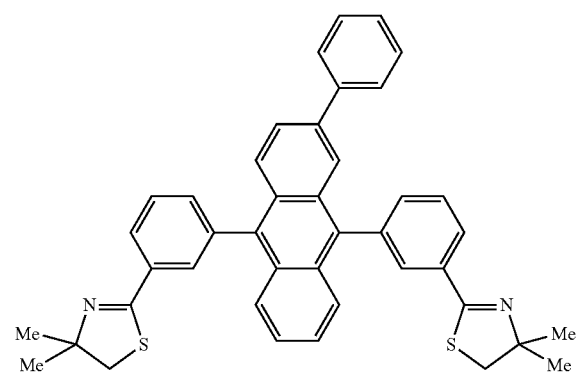
(1-2-14)
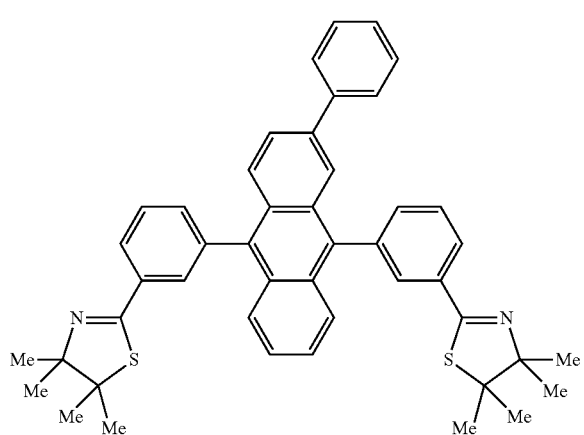
(1-2-15)
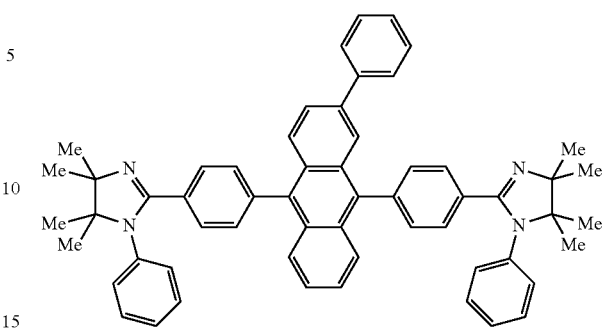
(1-2-16)
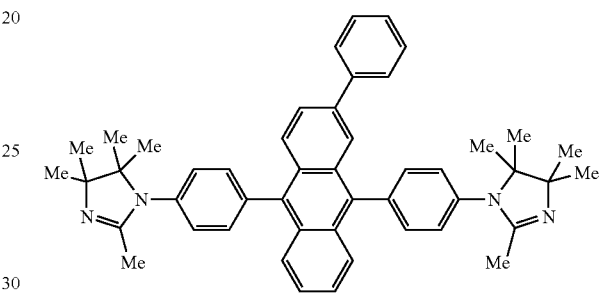
(1-2-17)
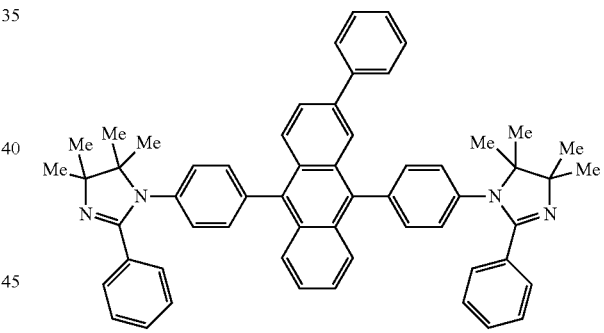
(1-2-18)

(1-2-19)
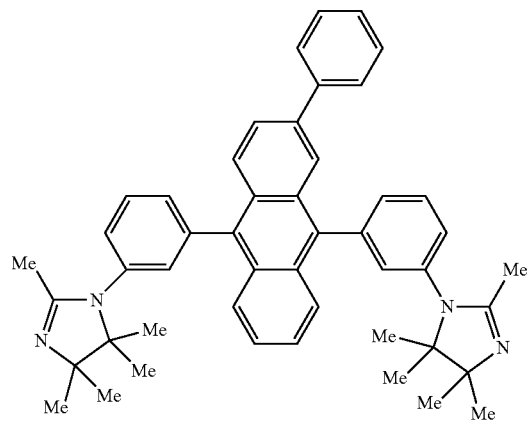
(1-2-20)
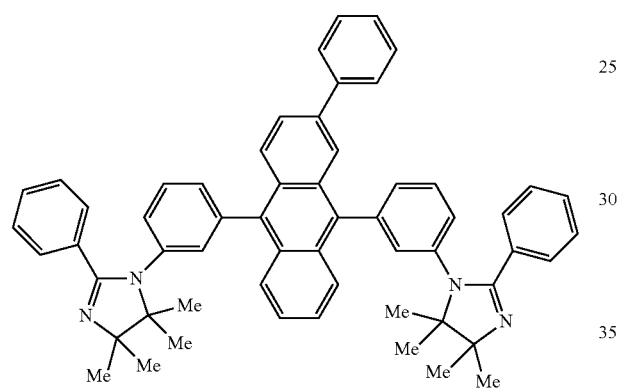
(1-2-21)
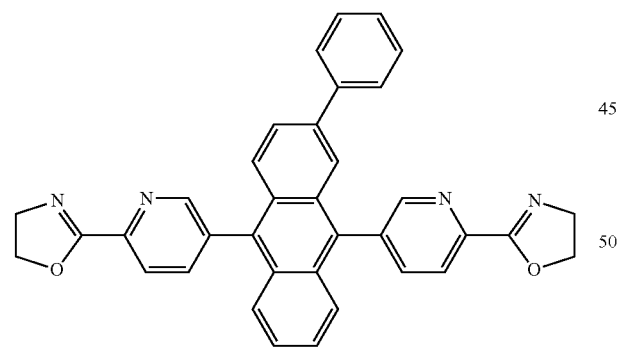
(1-2-22)
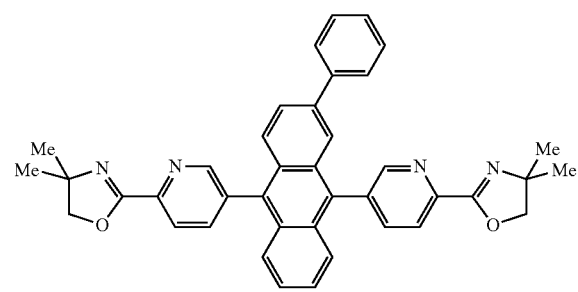
(1-2-23)
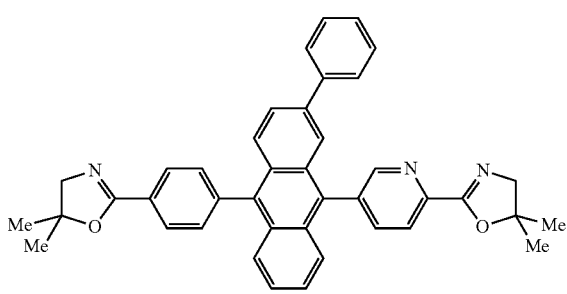
(1-2-24)
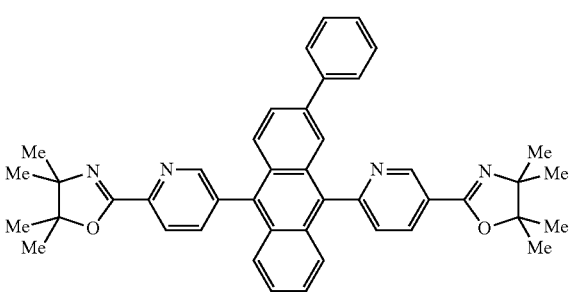
(1-2-25)
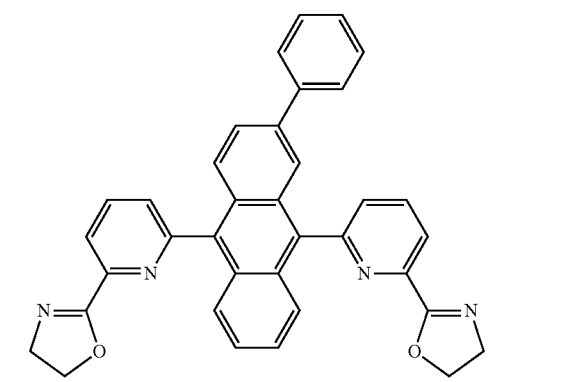
(1-2-26)
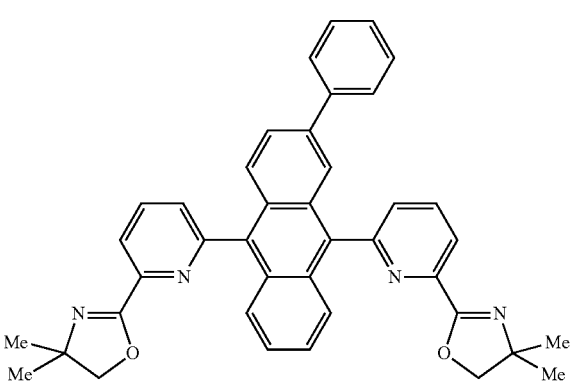

-continued
(1-2-27)
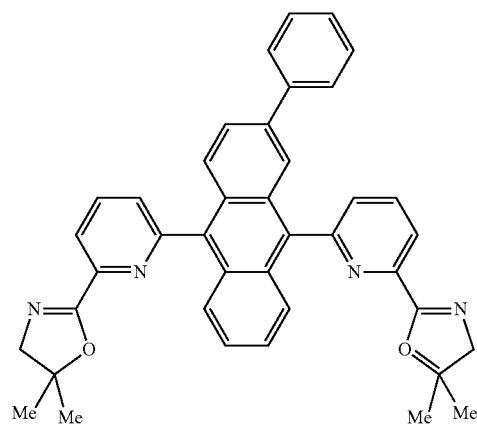
(1-2-28)
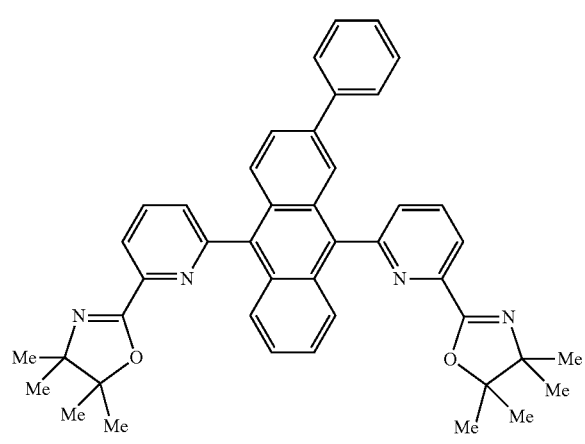
(1-2-31)
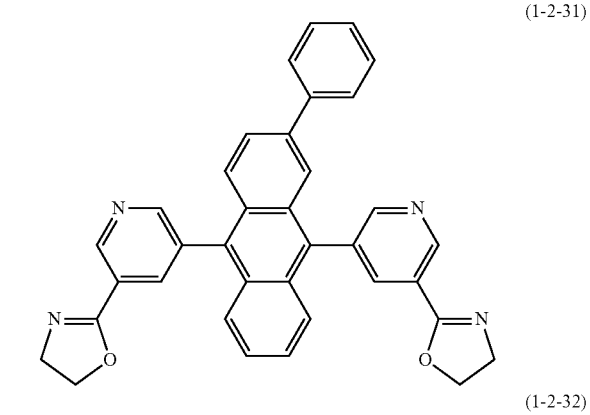
(1-2-32)
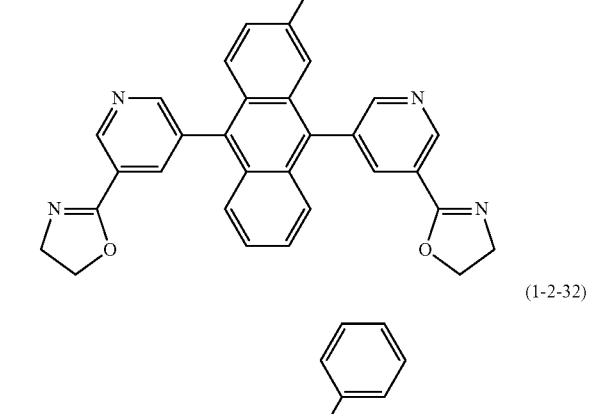
(1-2-33)
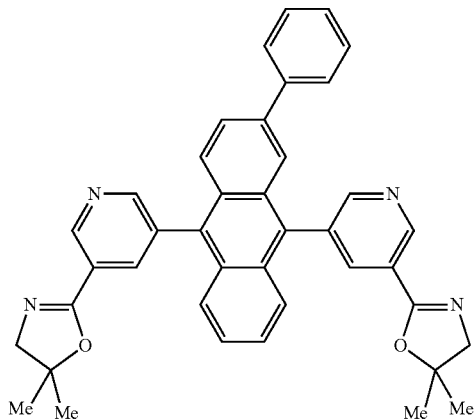
(1-2-34)
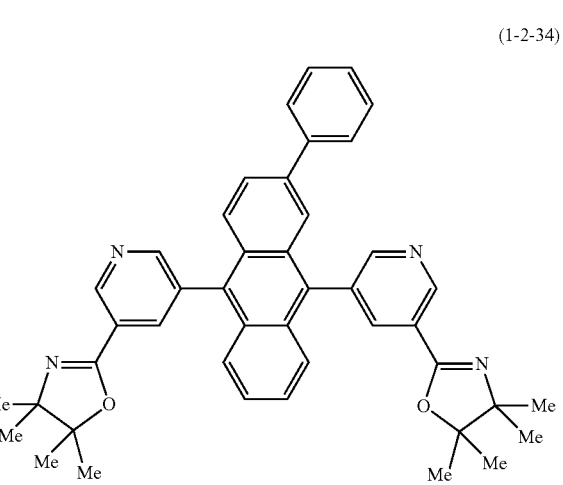
(1-2-35)
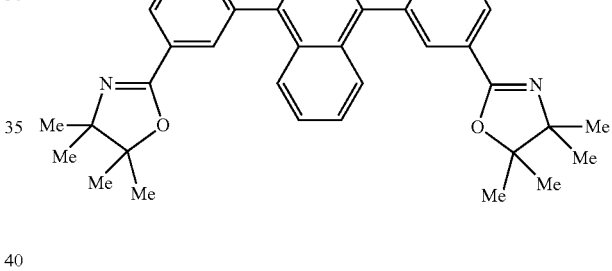
(1-2-36)
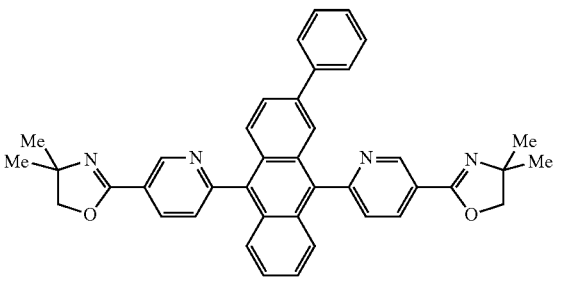

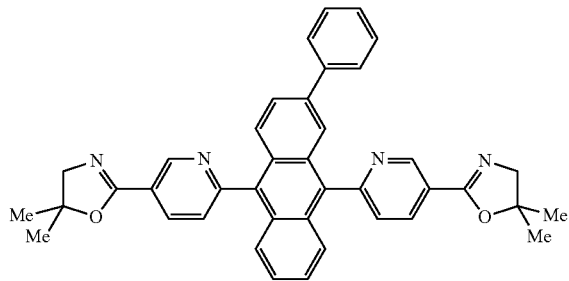
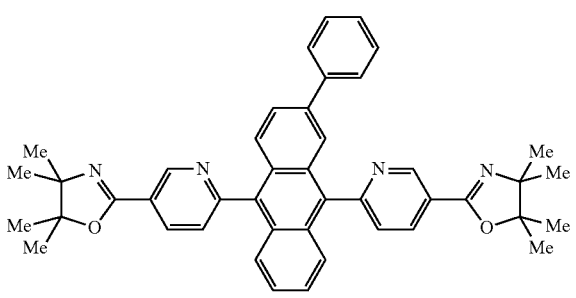
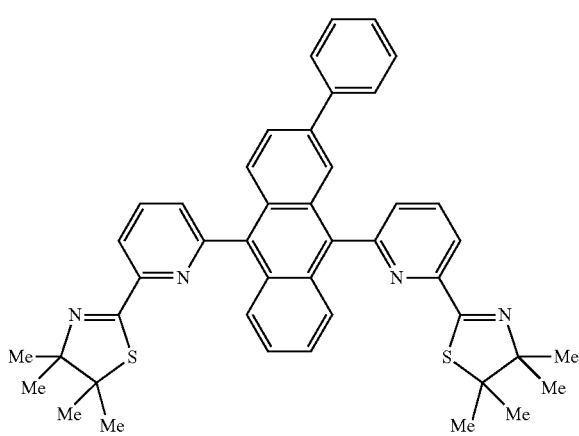

(1-2-48) 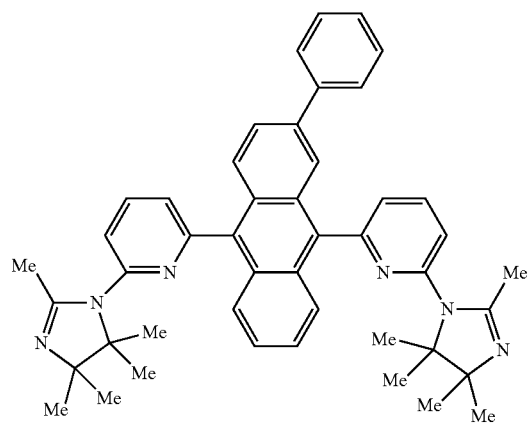
(1-2-49) 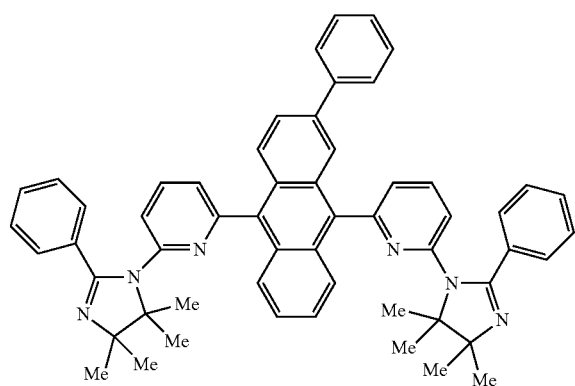
(1-2-51) 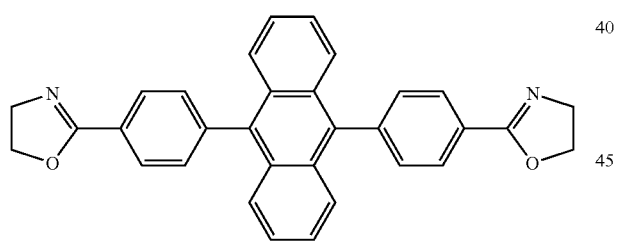
(1-2-52) 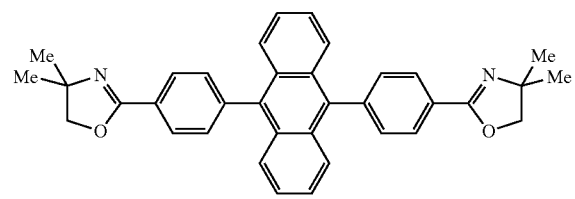
(1-2-53) 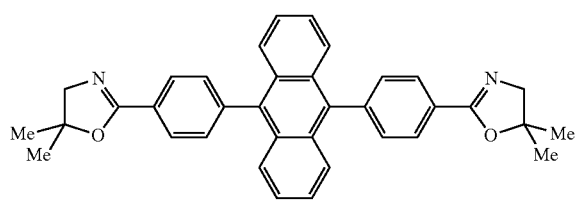
(1-2-54) 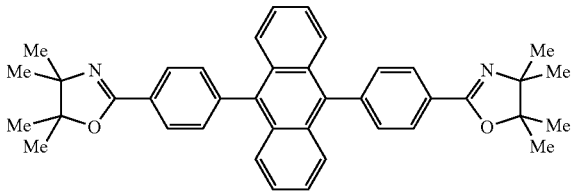
(1-2-55) 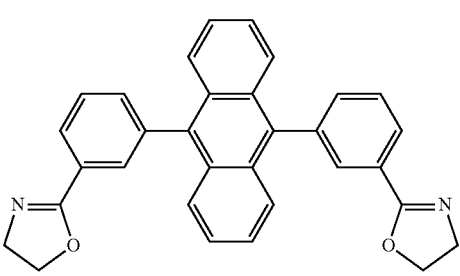
(1-2-56) 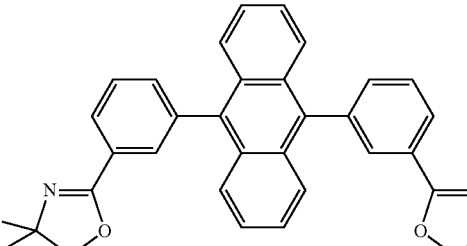
(1-2-57) 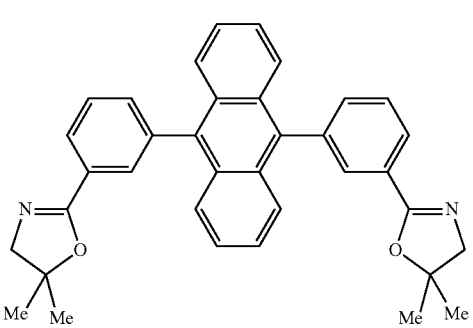
(1-2-58) 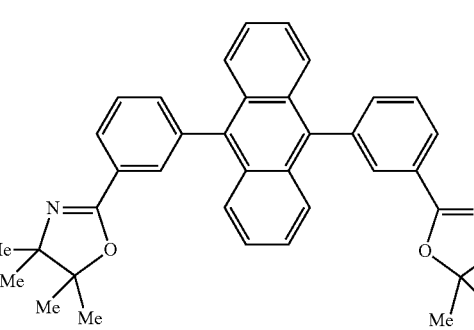

(1-2-61)
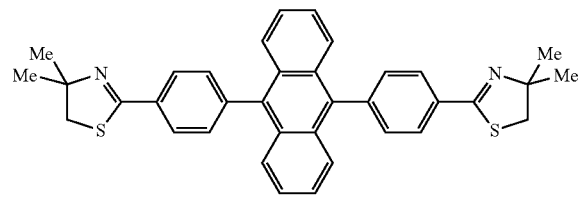
(1-2-67)
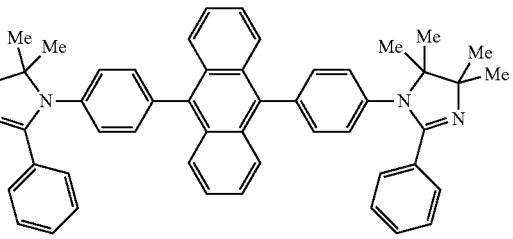
(1-2-62)
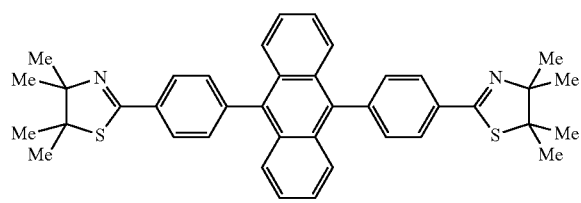
(1-2-63)
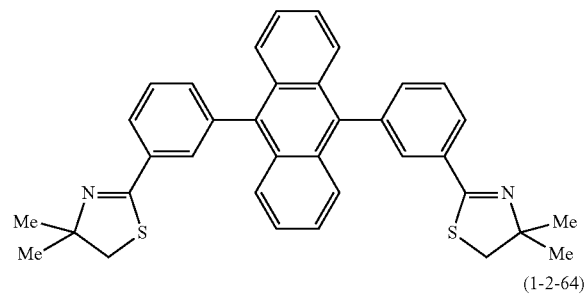
(1-2-68)
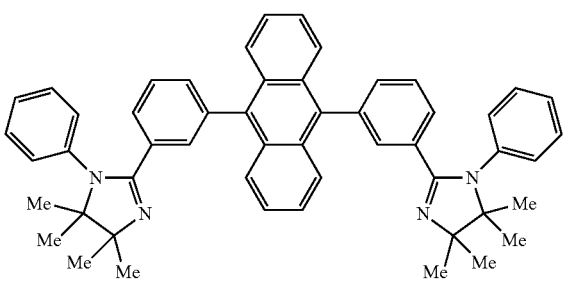
(1-2-64)
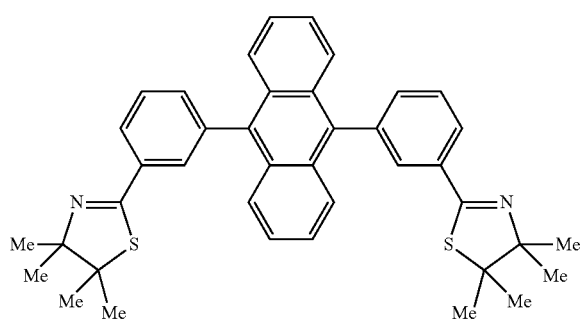
(1-2-69)
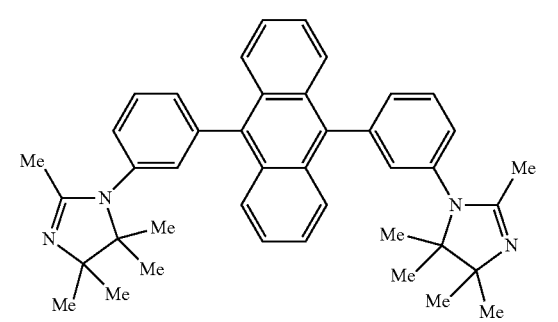
(1-2-65)
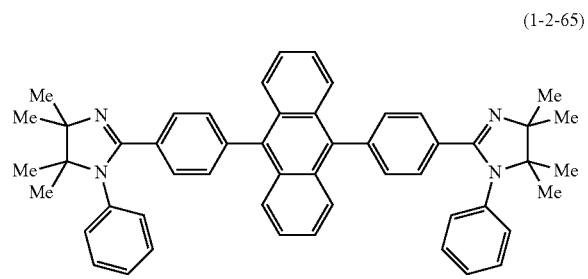
(1-2-70)
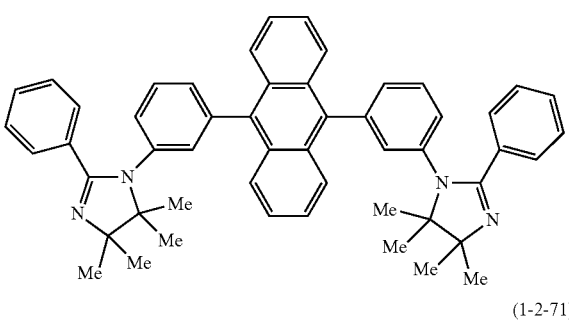
(1-2-66)
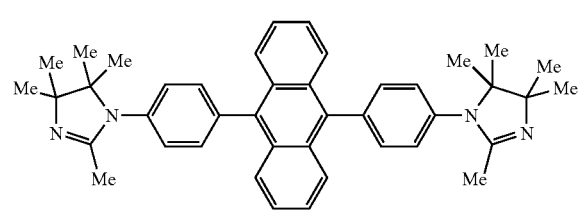
(1-2-71)
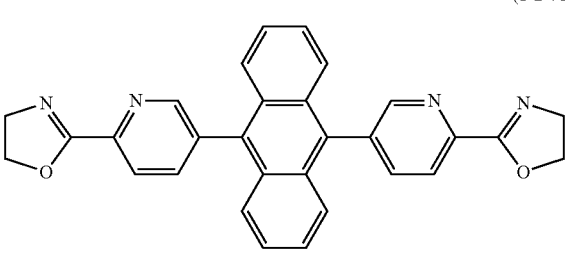

-continued
(1-2-72)
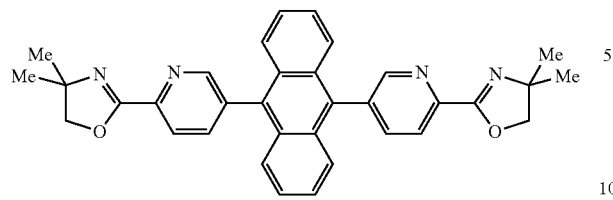
(1-2-73)
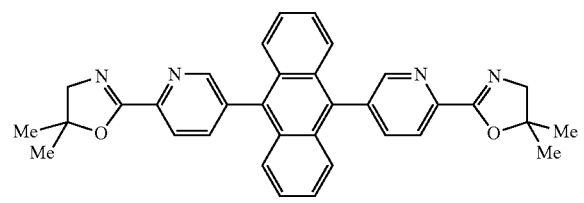
(1-2-74)
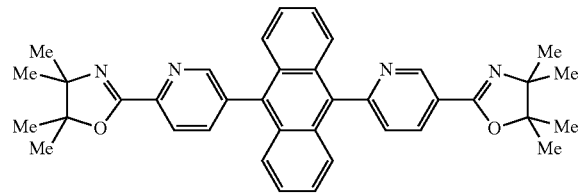
(1-2-75)

(1-2-76)
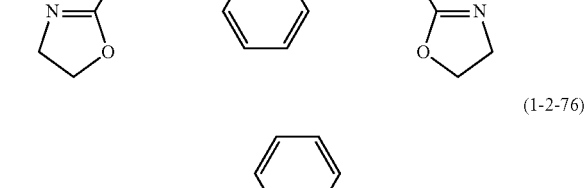
(1-2-77)
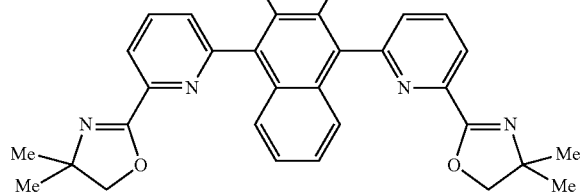
-continued
(1-2-78)
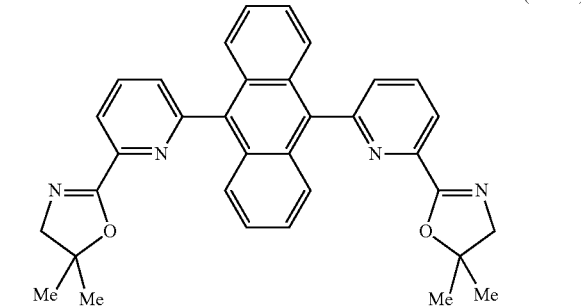
(1-2-81)
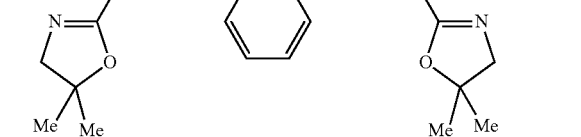
(1-2-82)
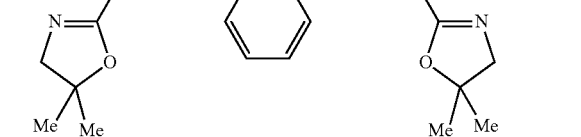
(1-2-83)
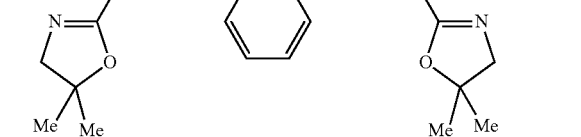
(1-2-84)
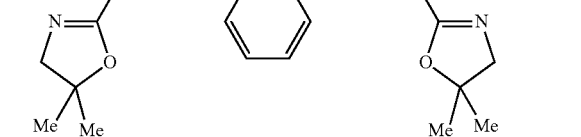

(1-2-85)
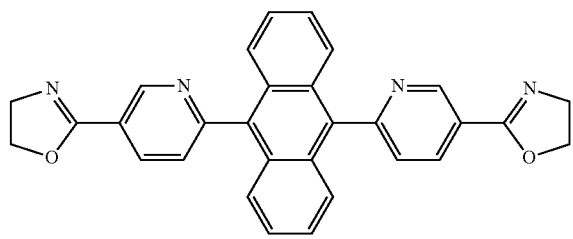
(1-2-86)
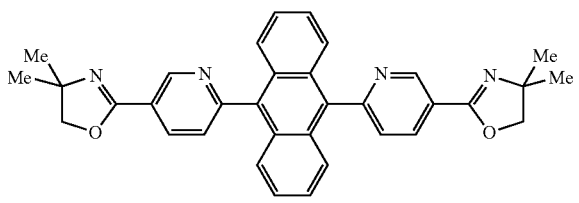
(1-2-87)
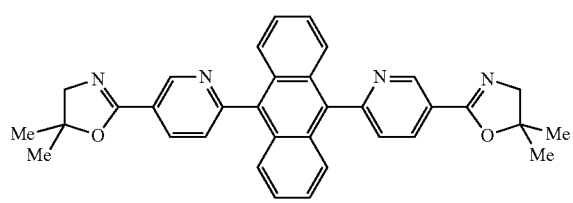
(1-2-88)
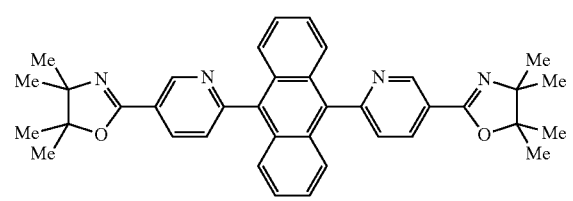
(1-2-91)
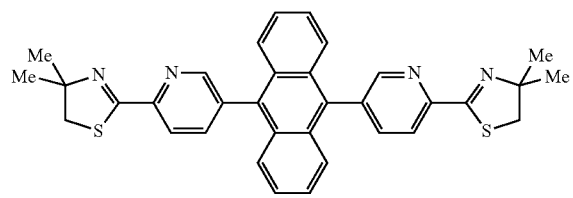
(1-2-92)
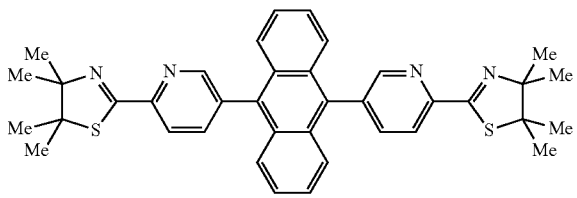
(1-2-93)
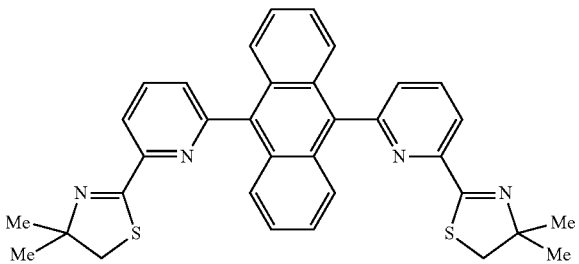
(1-2-94)
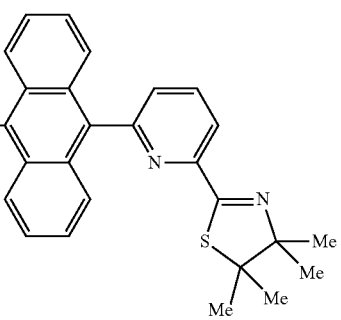
(1-2-95)
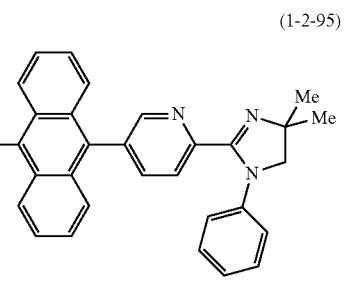
(1-2-96)
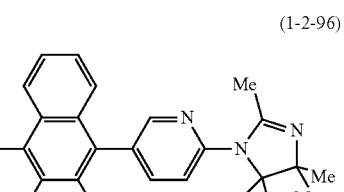
(1-2-97)
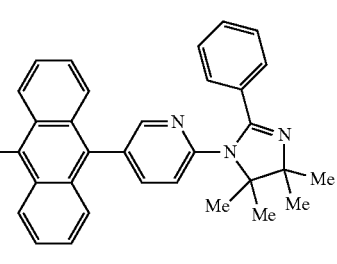

(1-2-98)
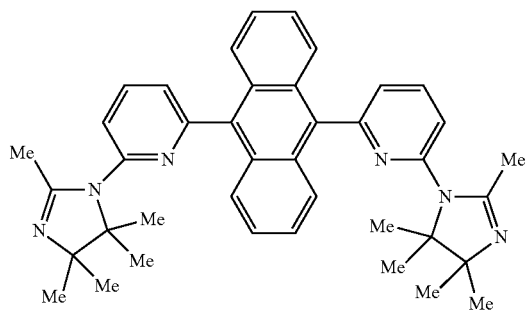
(1-2-99)
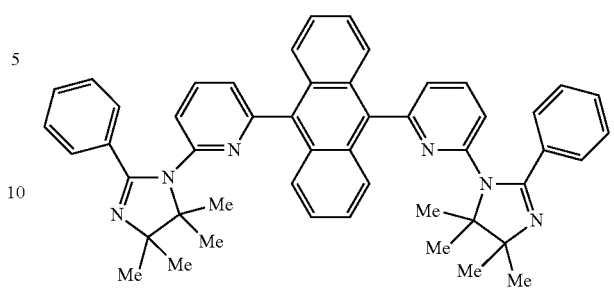
(1-2-101)
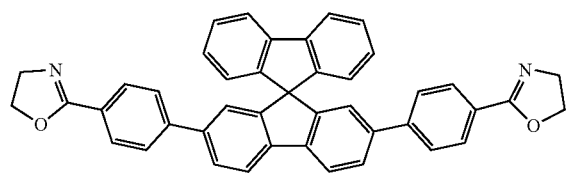
(1-2-102)
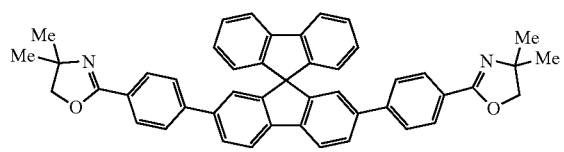
(1-2-103)
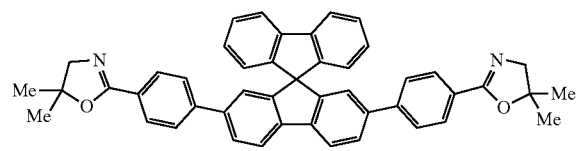
(1-2-104)
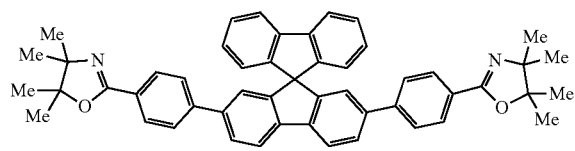
(1-2-105)
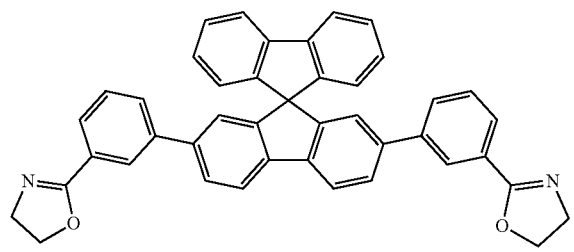
(1-2-106)
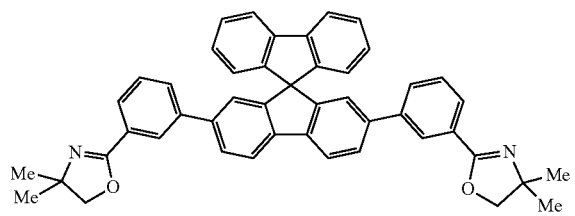
(1-2-107)
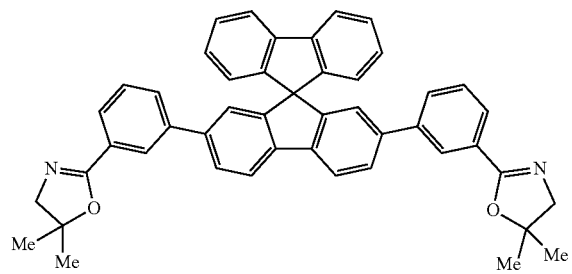
(1-2-108)
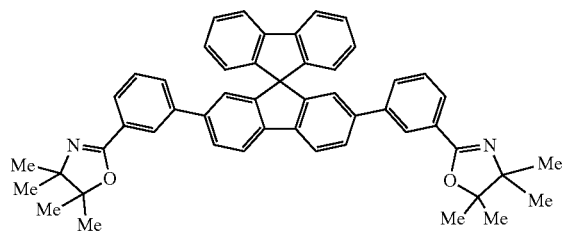
(1-2-111)
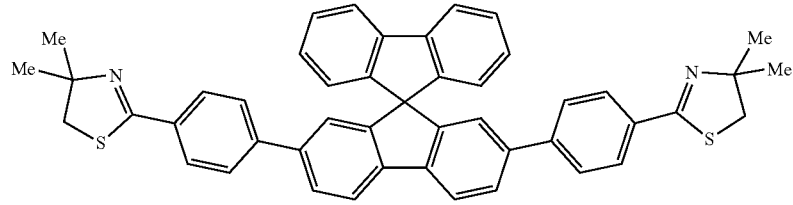

-continued
(1-2-112)
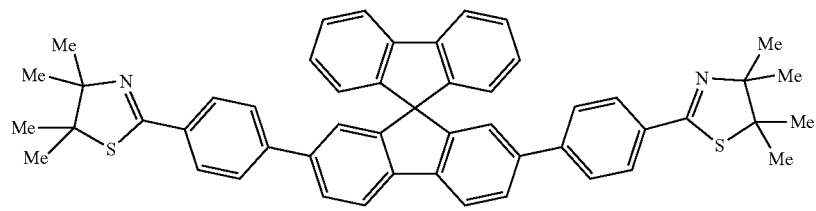
(1-2-113) (1-2-114)
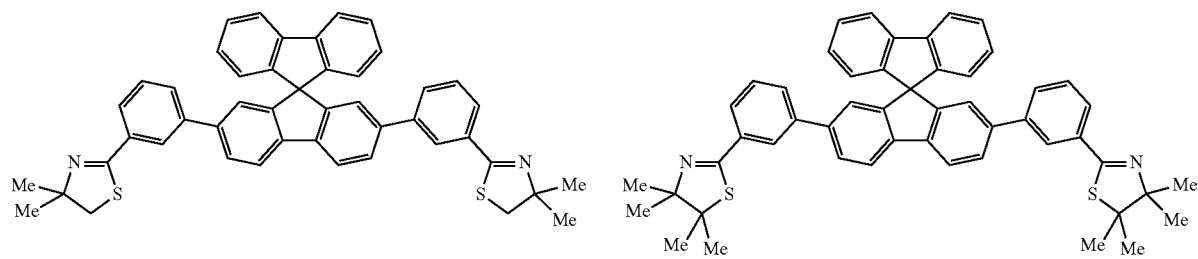
(1-2-115)
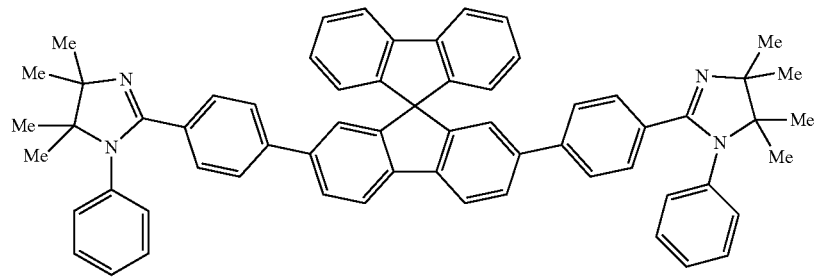
(1-2-116)
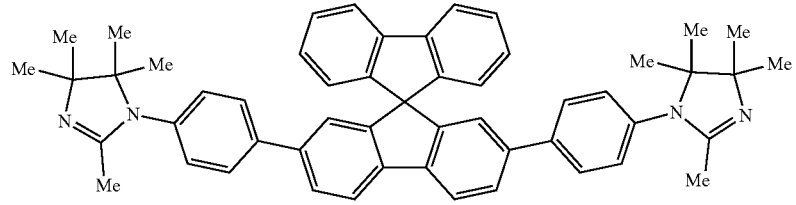
(1-2-117)
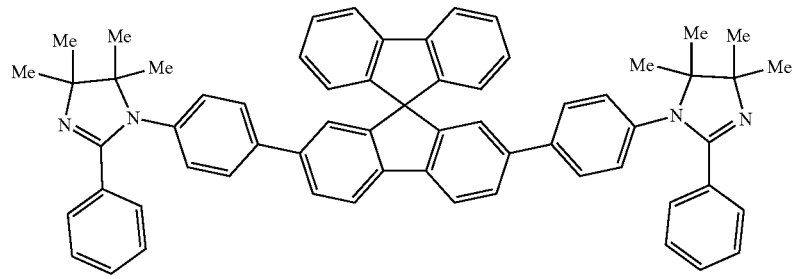
(1-2-118) (1-2-119)
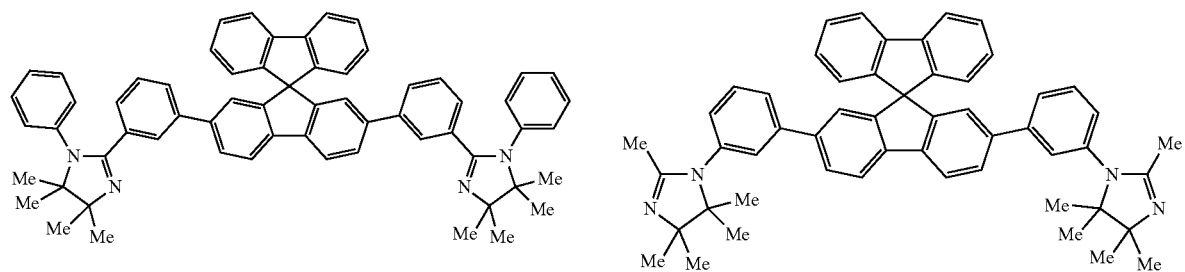

-continued
(1-2-120)
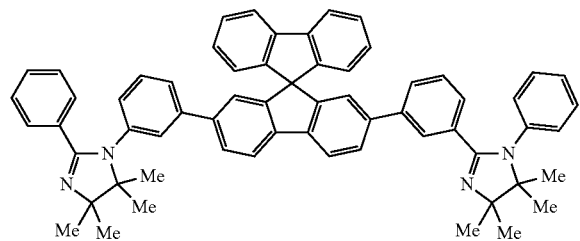
(1-2-121)
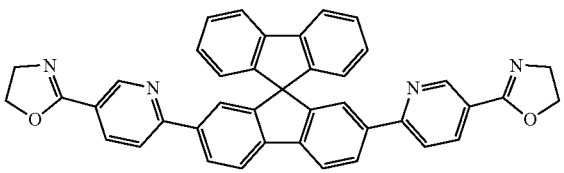
(1-2-122)
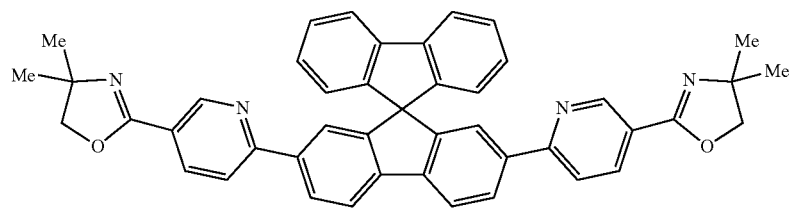
(1-2-123)
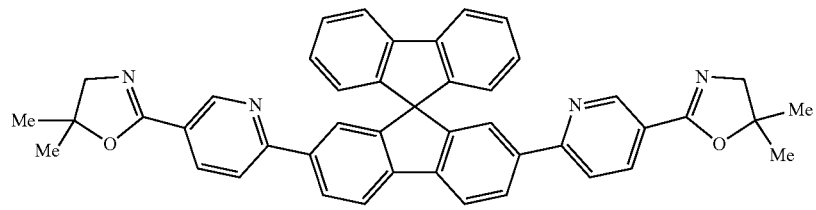
(1-2-124)
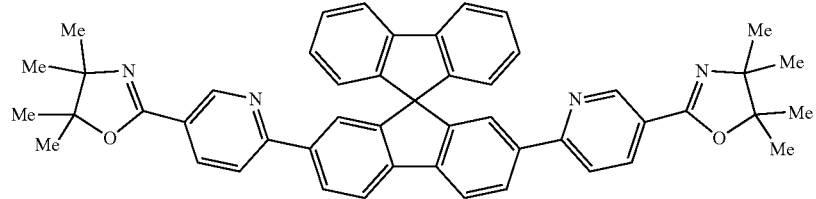
(1-2-125)
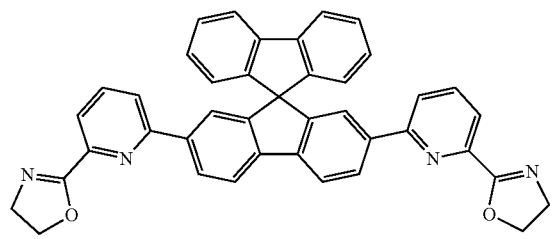
(1-2-126)
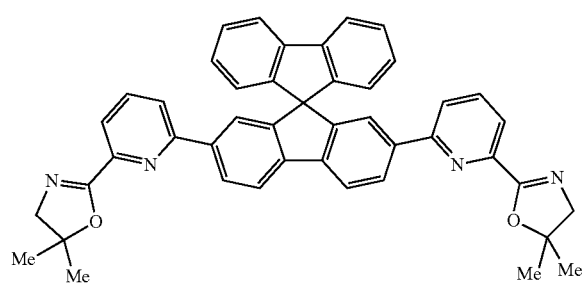
(1-2-127)
(1-2-128)
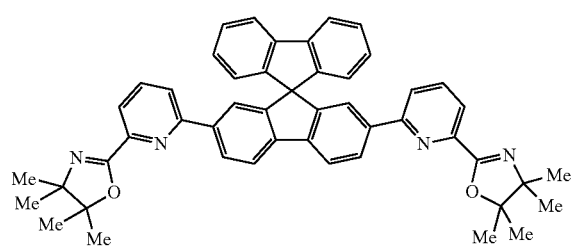

-continued
(1-2-131)
(1-2-132)
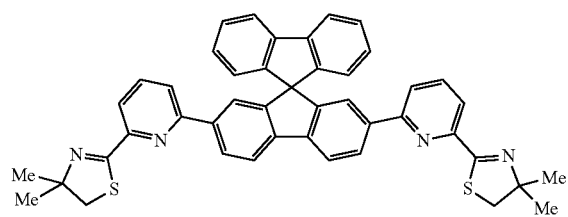
(1-2-133)
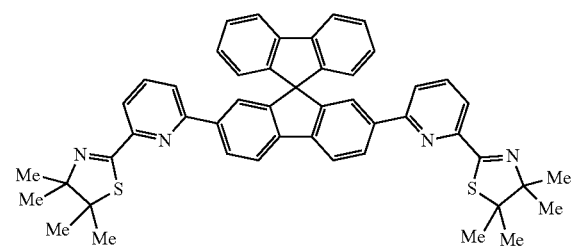
(1-2-134)
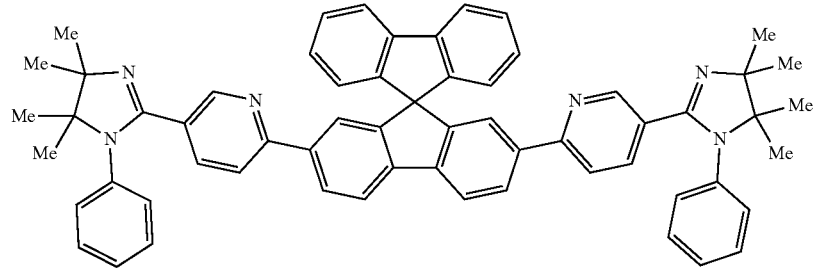
(1-2-135)
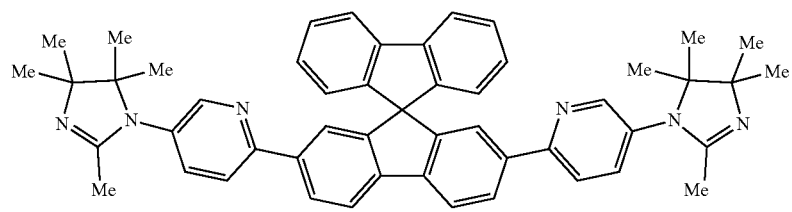
(1-2-136)
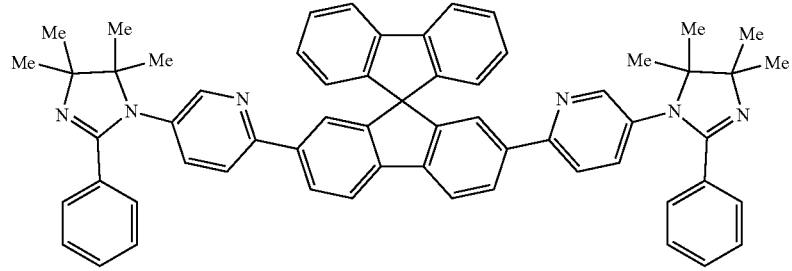
(1-2-137)

-continued
(1-2-138)
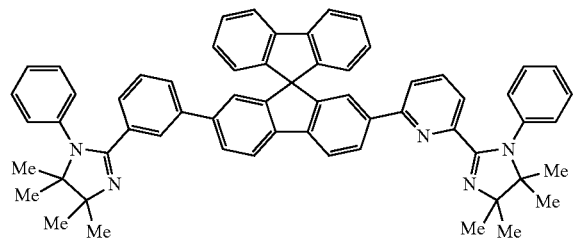
(1-2-139)
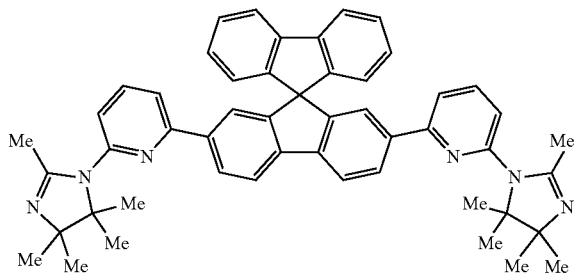
(1-2-140)
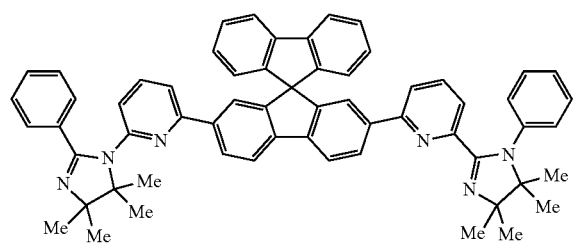
(1-2-141)
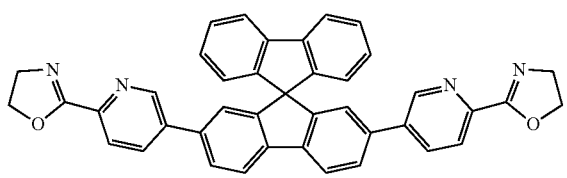
(1-2-142)
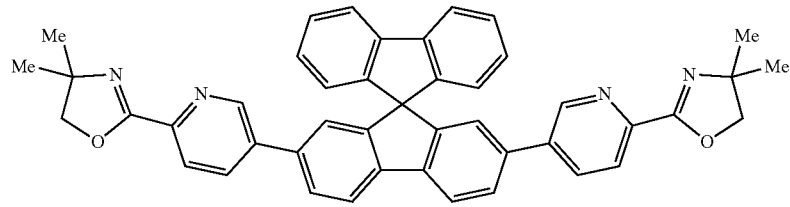
(1-2-143)
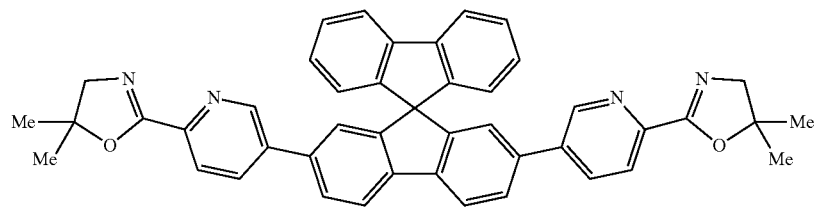
(1-2-144)
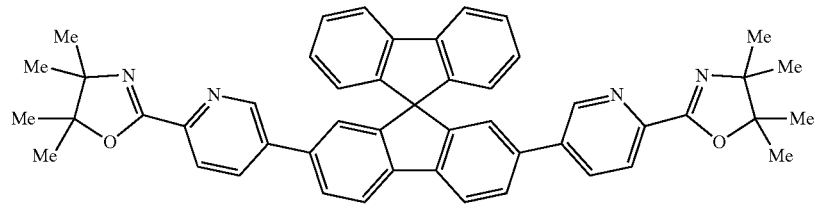
(1-2-145)
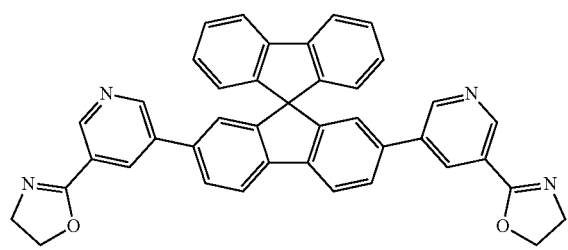
(1-2-146)
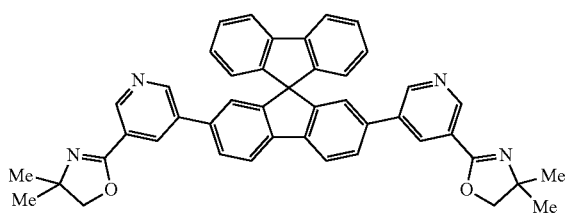

(1-2-147)
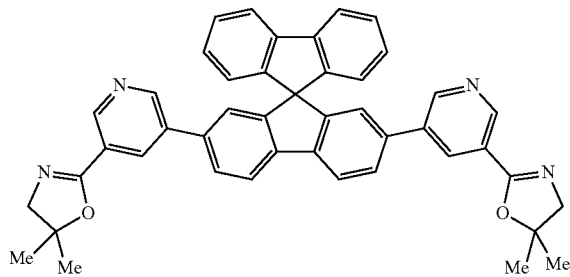
(1-2-148)
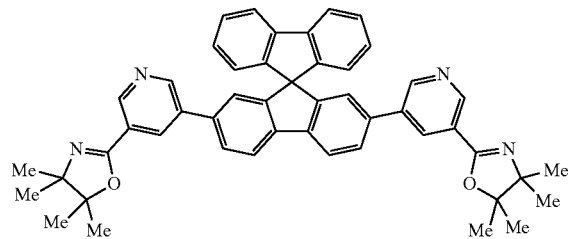
(1-2-151)
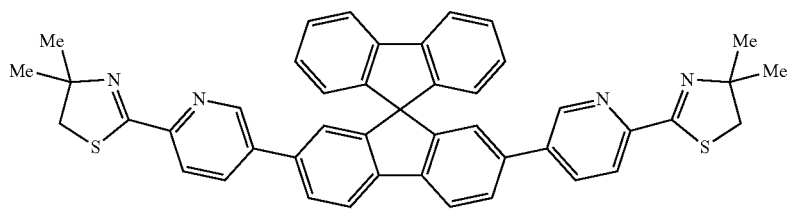
(1-2-152)
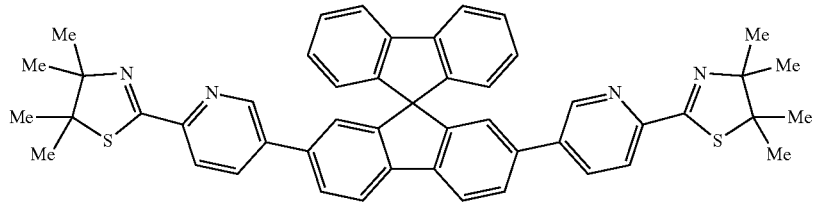
(1-2-153) (1-2-154)
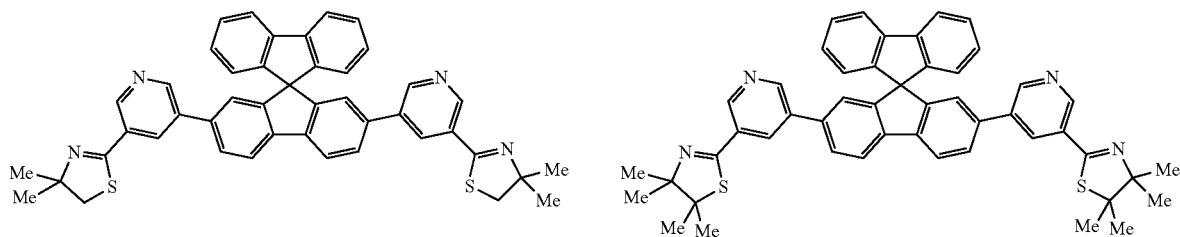
(1-2-155)
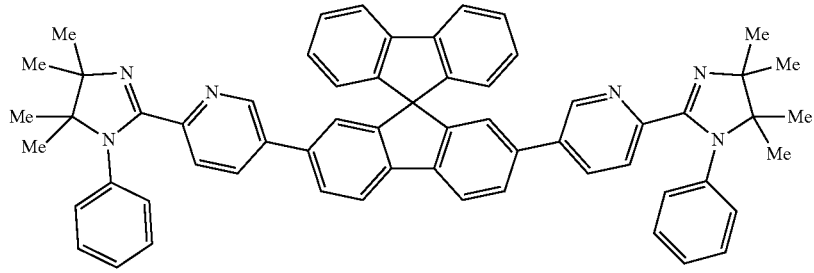
(1-2-156)
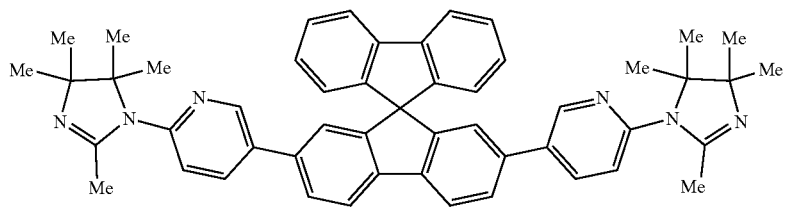

(1-2-157)
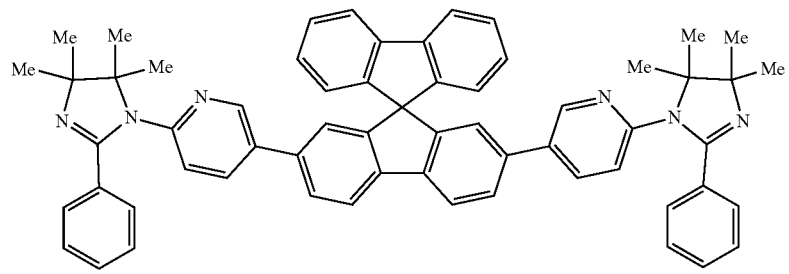
(1-2-158) (1-2-159)
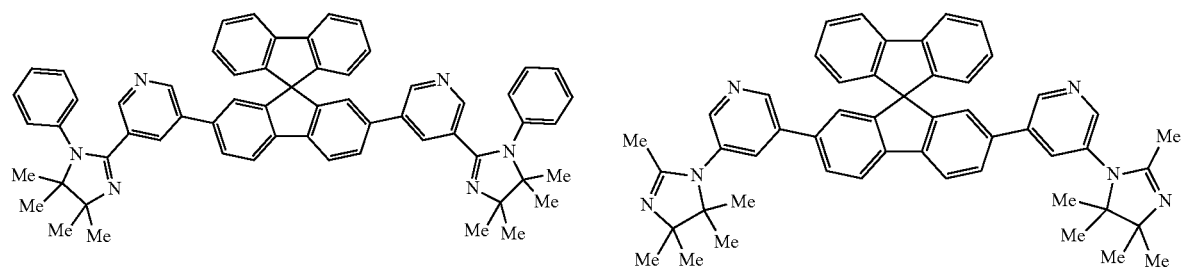
(1-2-160) (1-2-161)
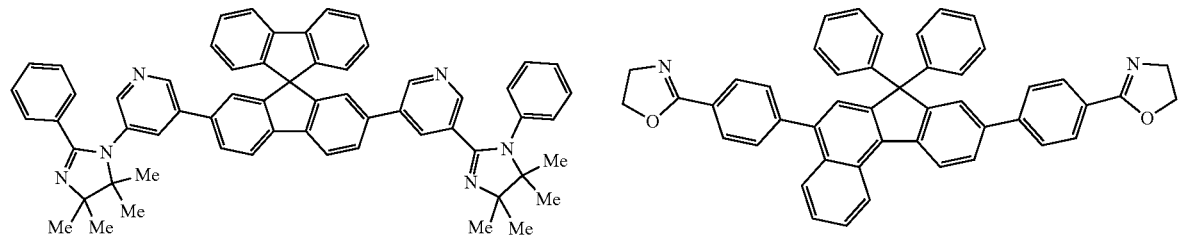
(1-2-162)
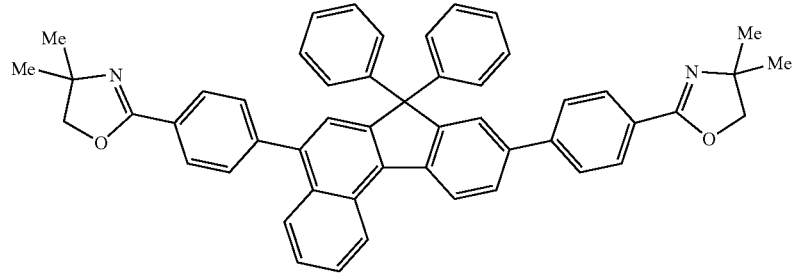
(1-2-163)
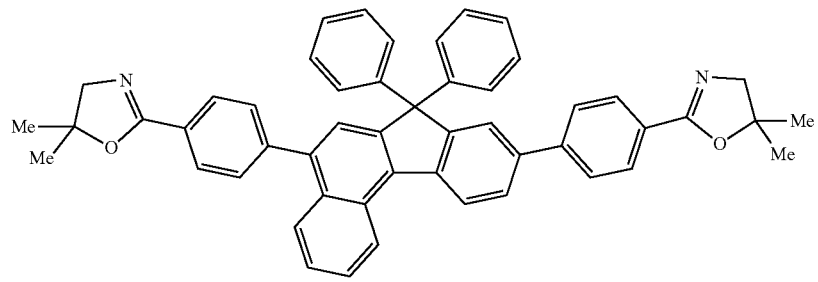

(1-2-164)
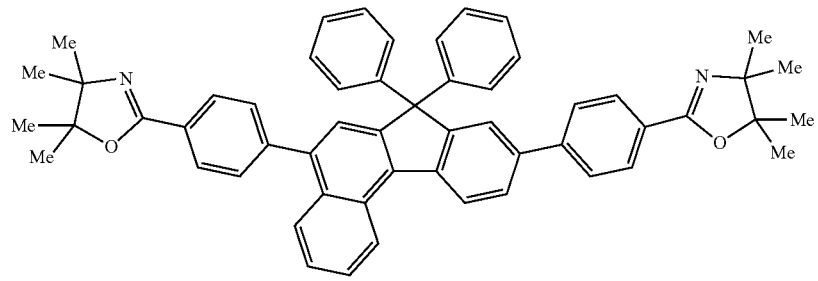
(1-2-165)
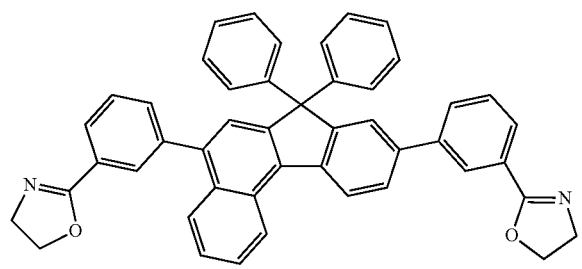
(1-2-166)
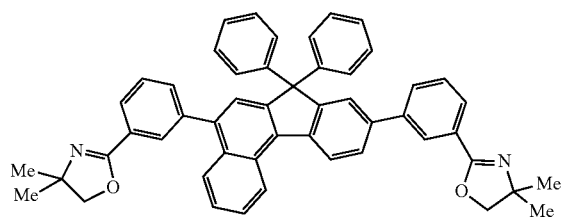
(1-2-167)
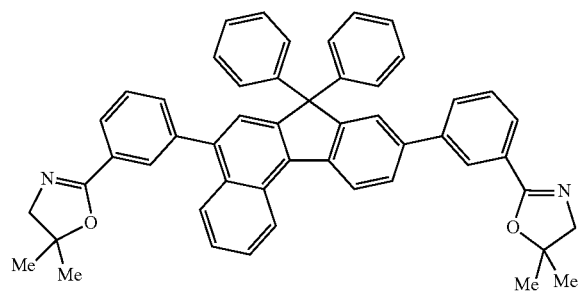
(1-2-168)
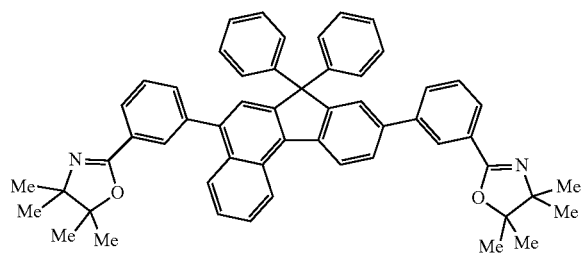
(1-2-171)
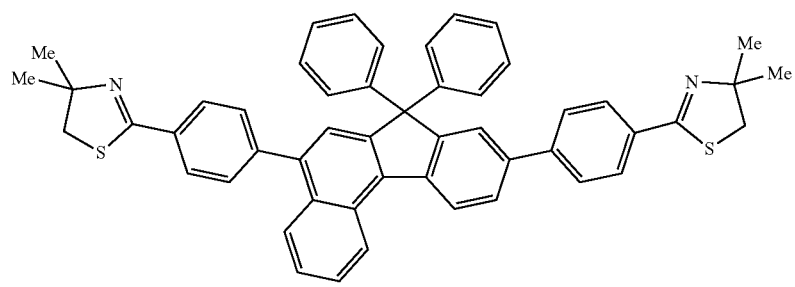
(1-2-172)
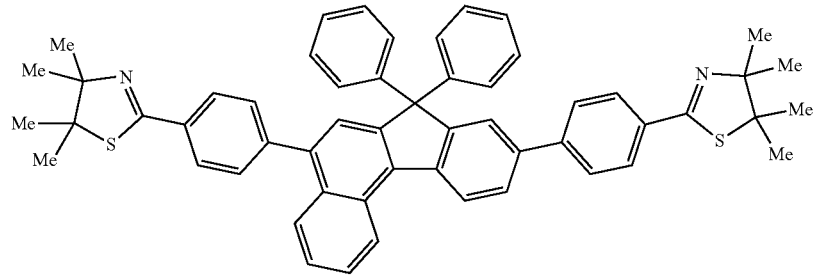

-continued
(1-2-173)
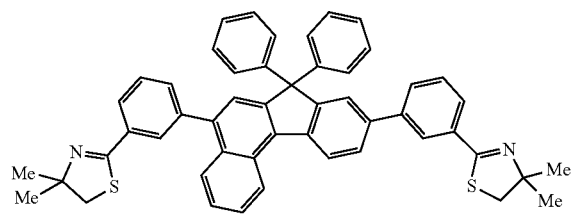
(1-2-174)
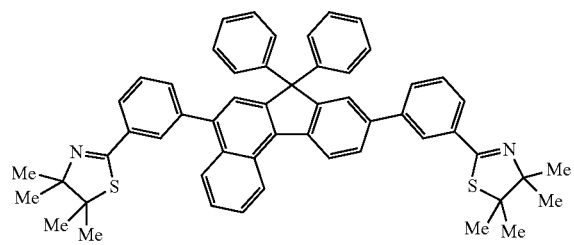
(1-2-175)
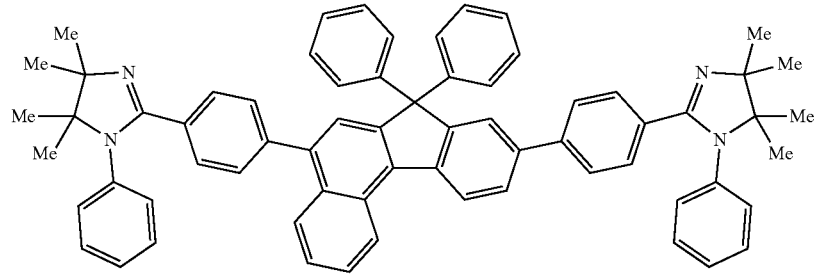
(1-2-176)
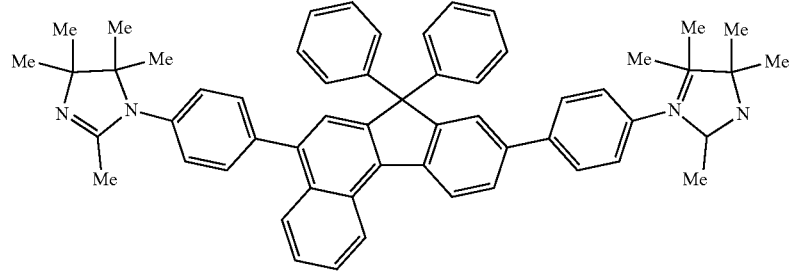
(1-2-177)
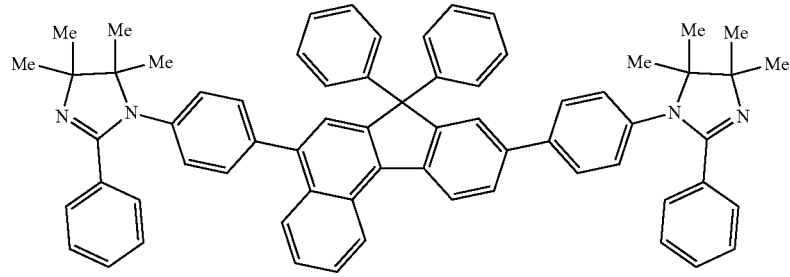
(1-2-178)
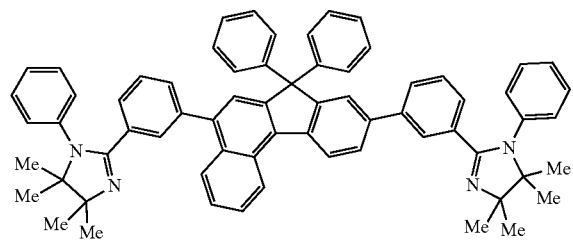
(1-2-179)
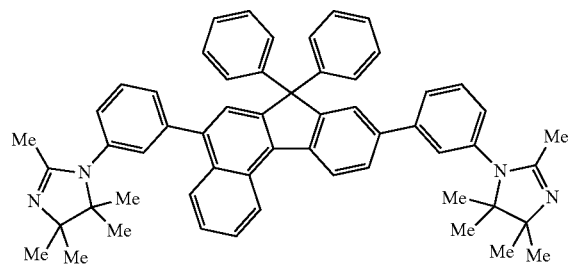

(1-2-180)
(1-2-181)
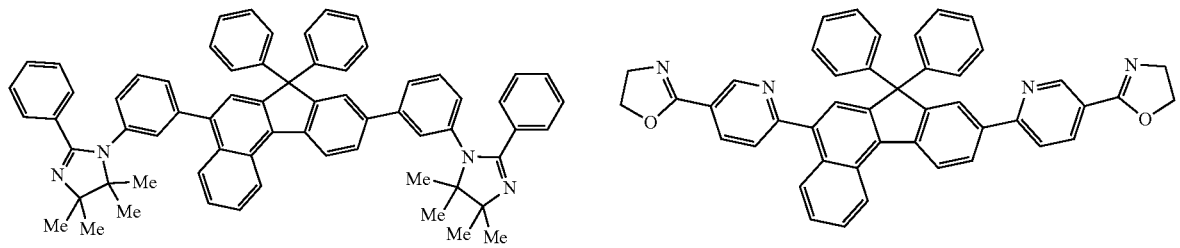
(1-2-182)
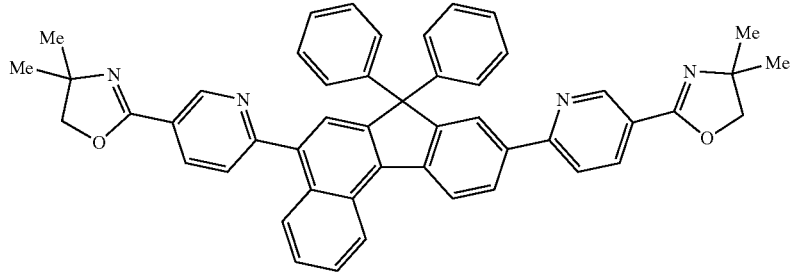
(1-2-183)
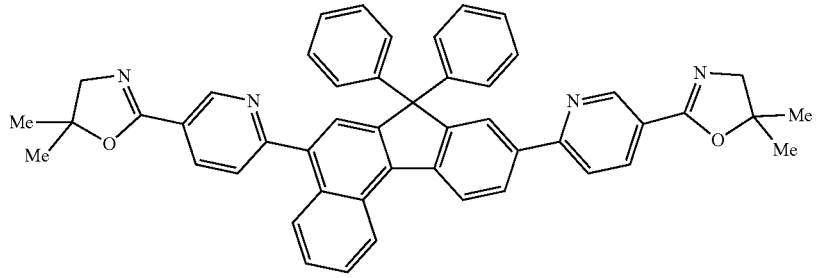
(1-2-184)
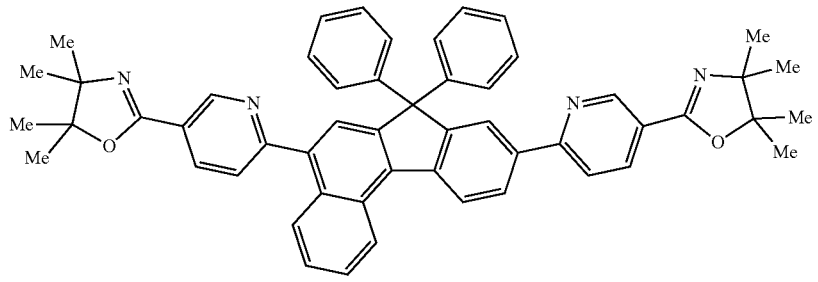
(1-2-185)
(1-2-186)
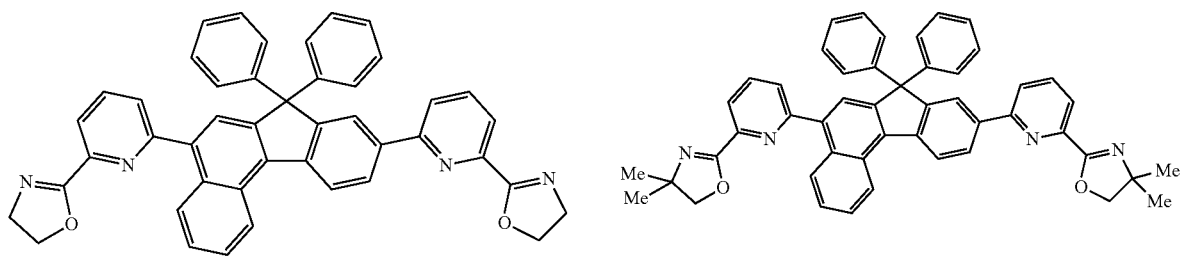

-continued
(1-2-187)
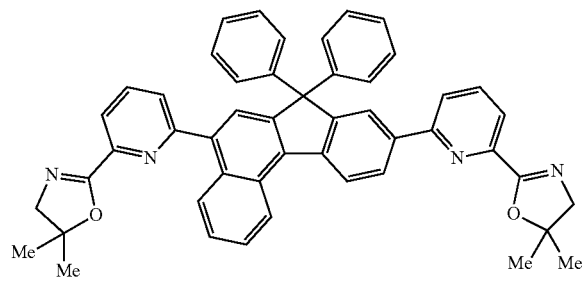
(1-2-188)
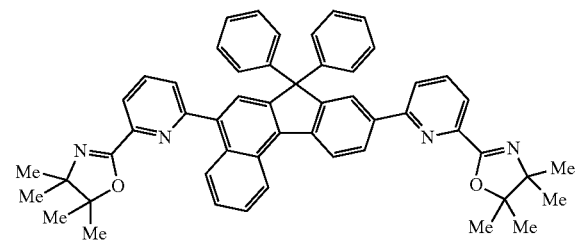
(1-2-191)
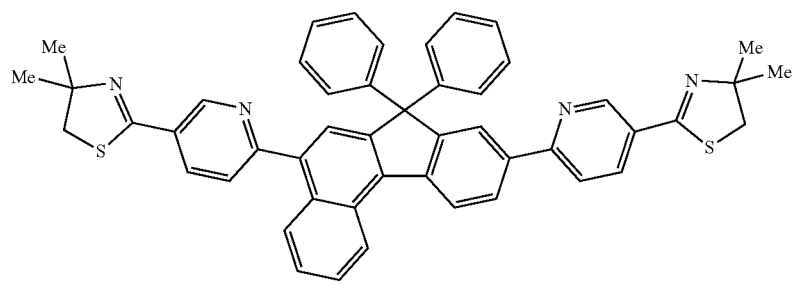
(1-2-192)
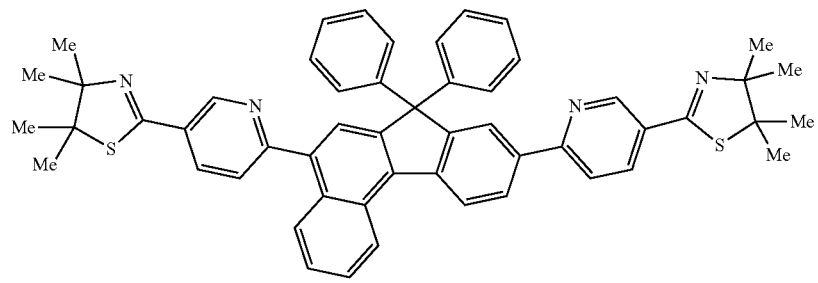
(1-2-193)
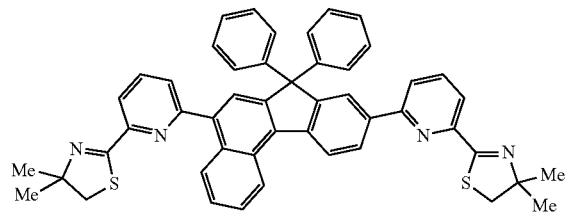
(1-2-194)
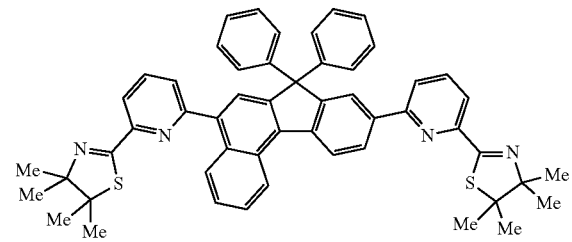
(1-2-195)
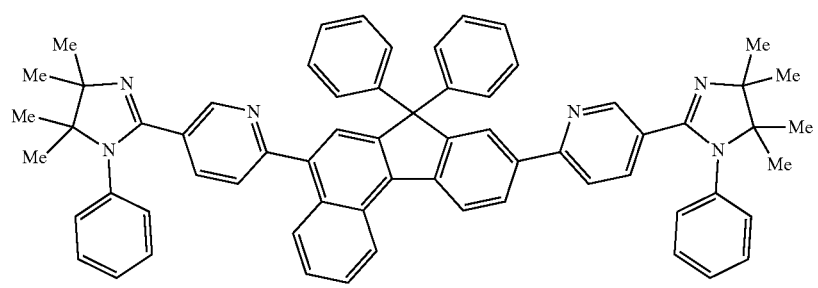

(1-2-196)
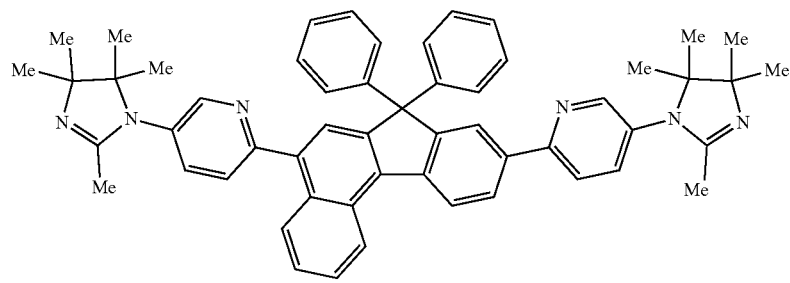
(1-2-197)
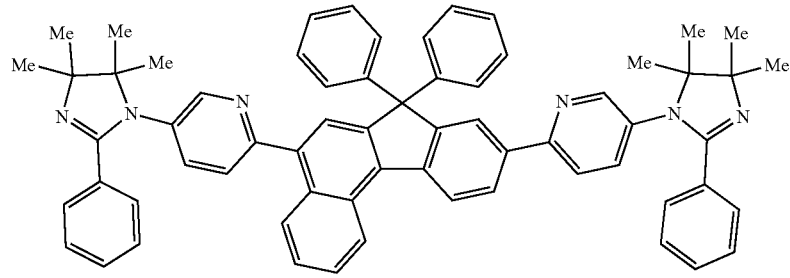
(1-2-198) (1-2-199)
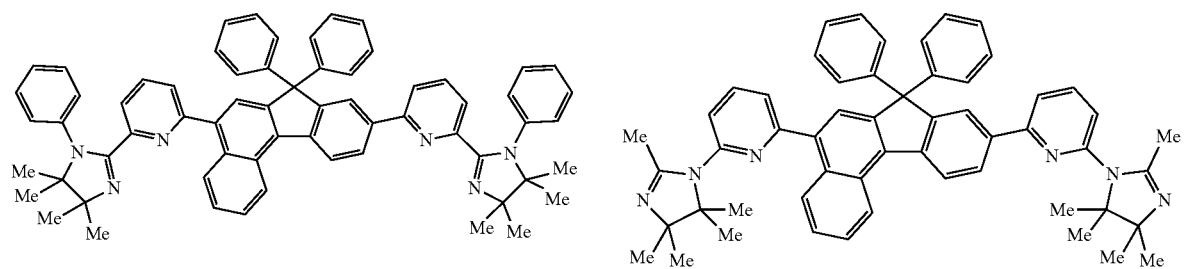
(1-2-200) (1-2-201)
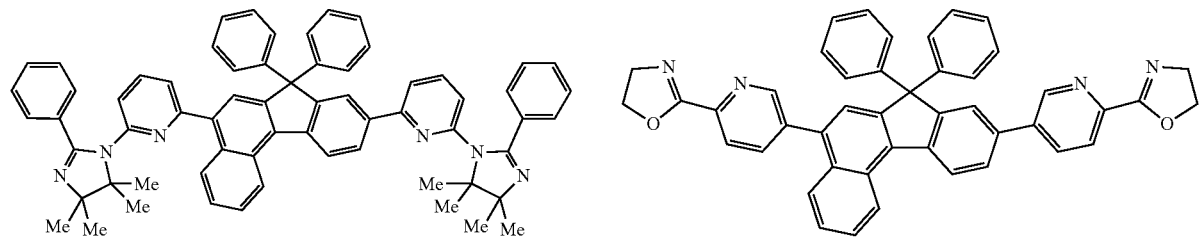
(1-2-202)
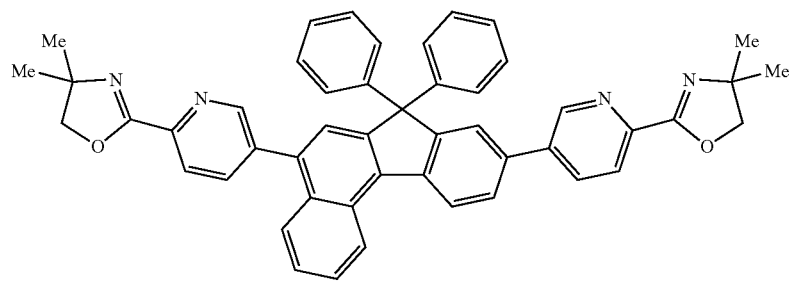

(1-2-203)
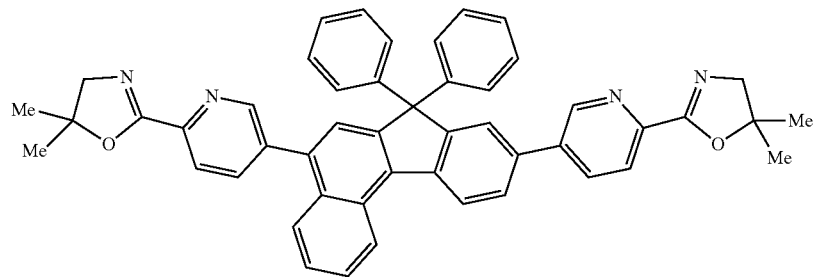
(1-2-204)
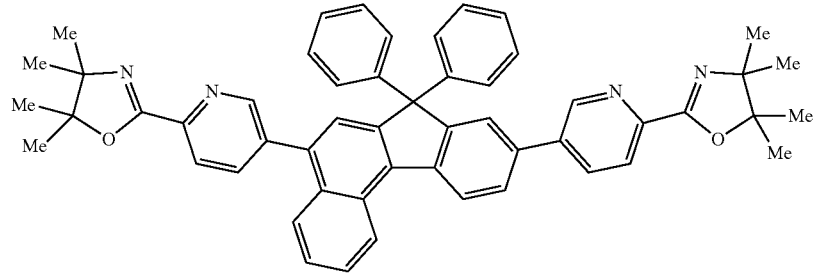
(1-2-205)
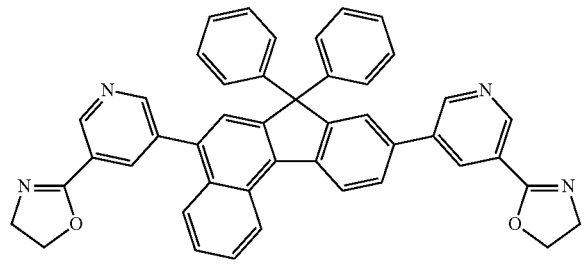
(1-2-206)
(1-2-207)
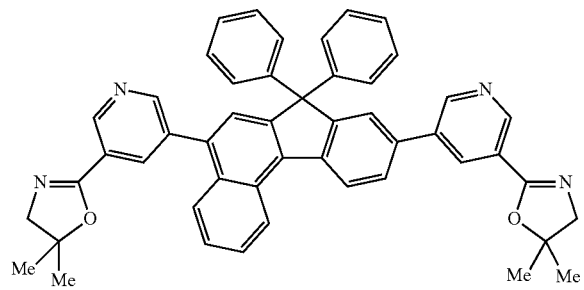
(1-2-208)
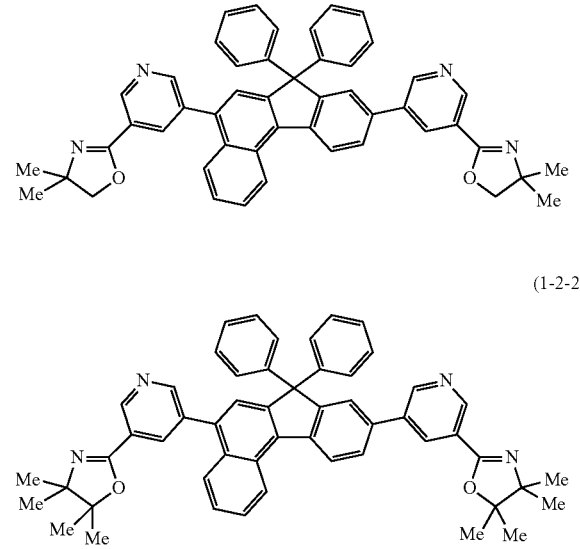
(1-2-211)
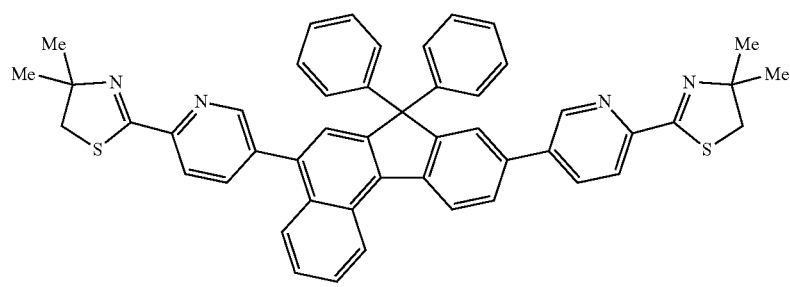

(1-2-212)
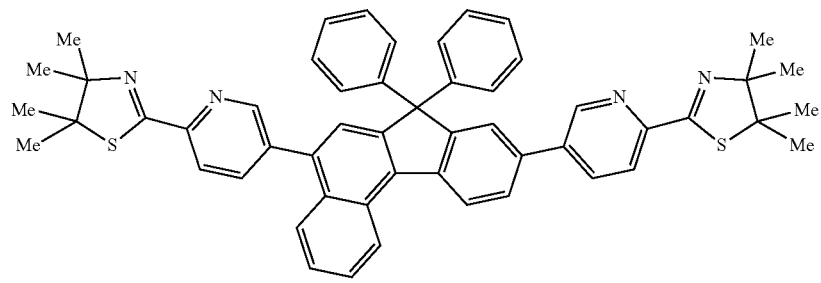
(1-2-213) (1-2-214)
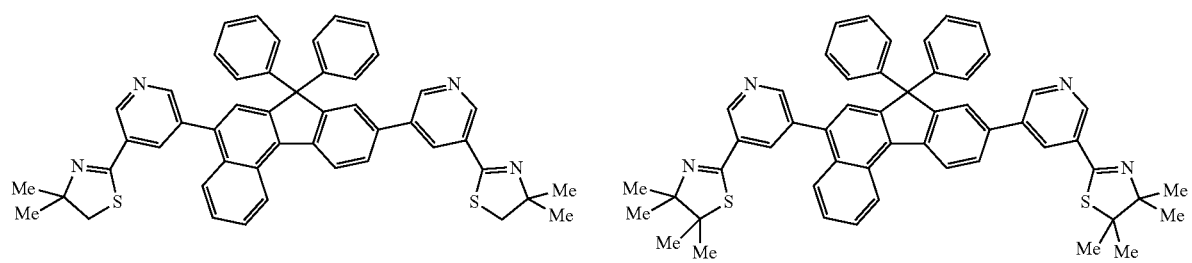
(1-2-215)
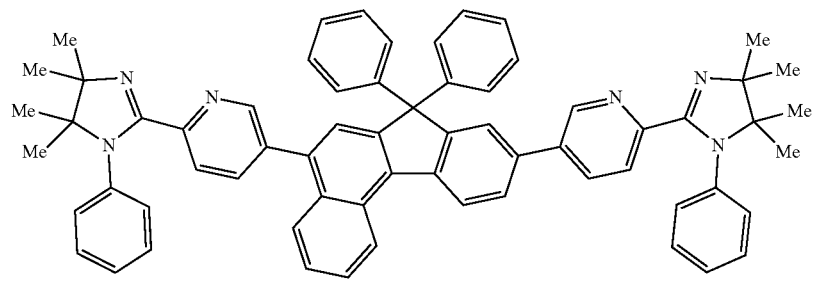
(1-2-216)
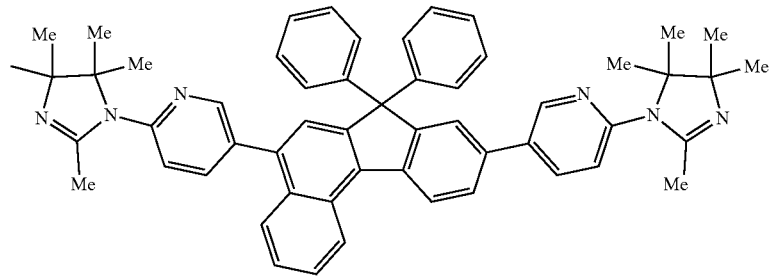
(1-2-217)
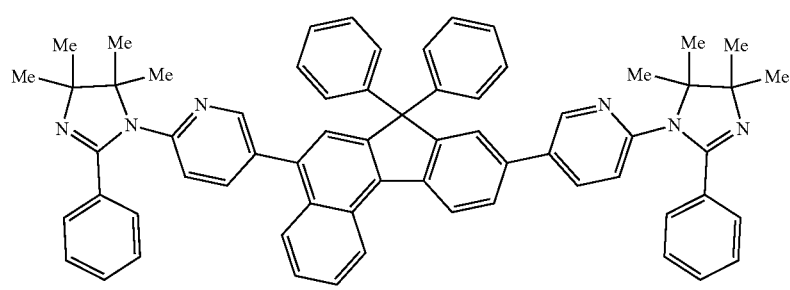

-continued
(1-2-218)
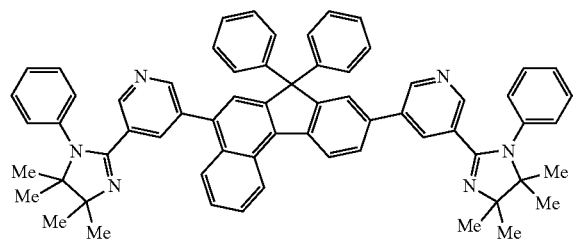
(1-2-219)
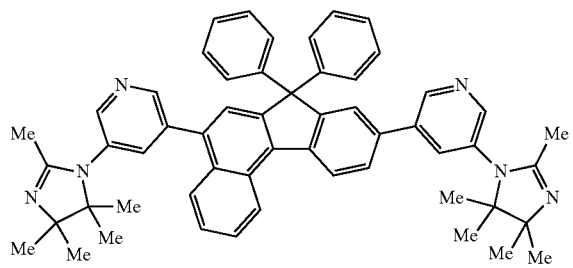
(1-2-220)
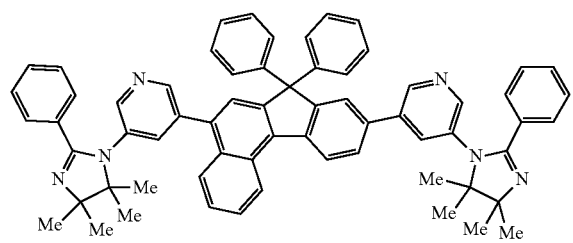
(1-2-221)
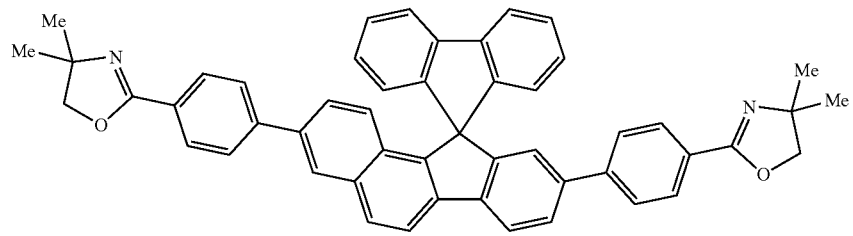
(1-2-222)
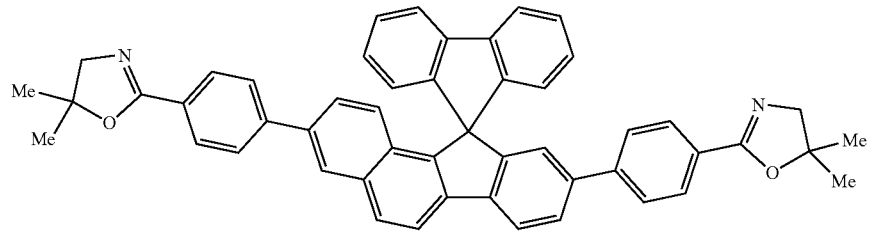
(1-2-223)
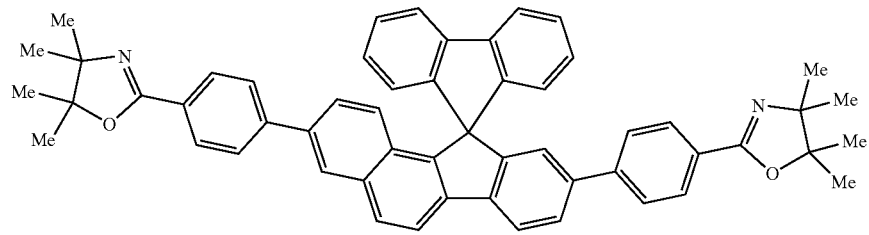
(1-2-224)
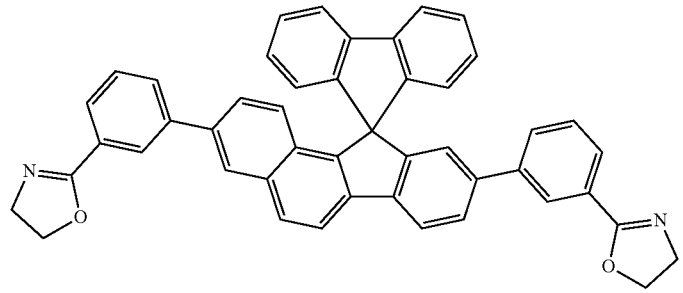
(1-2-225)

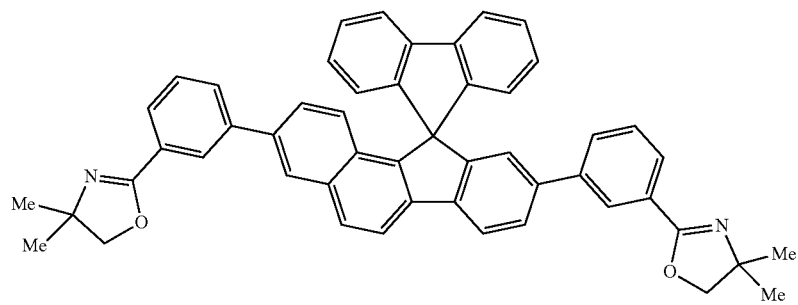
(1-2-226)
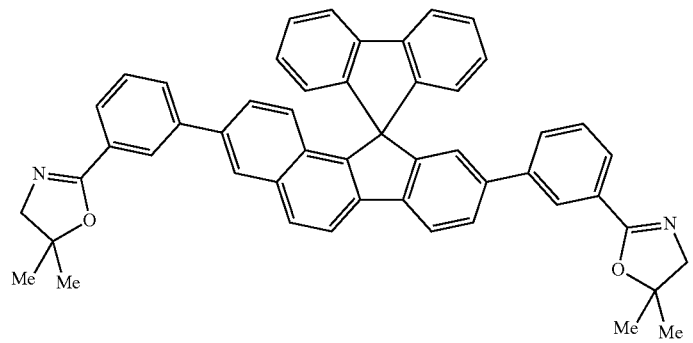
(1-2-227)
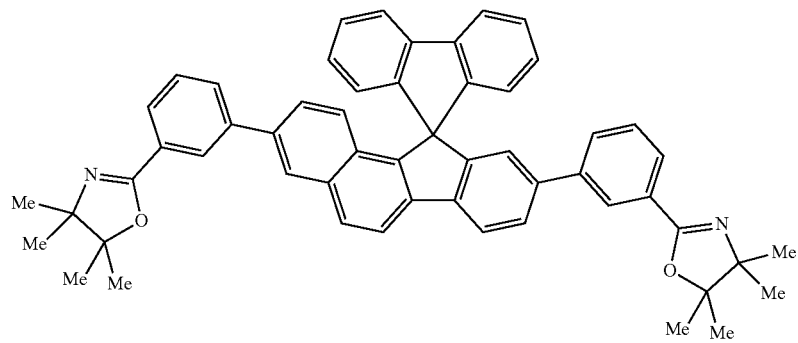
(1-2-228)
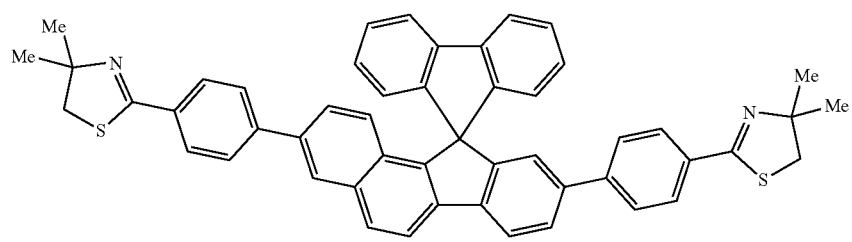
(1-2-231)
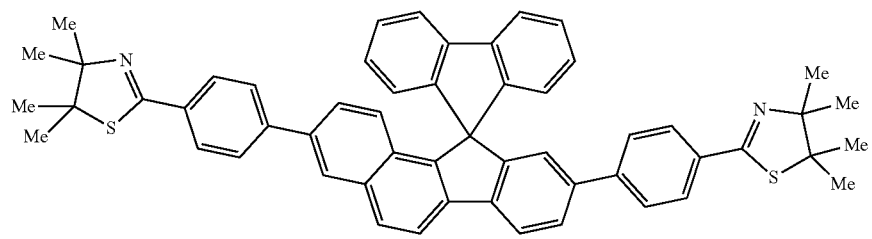
(1-2-232)

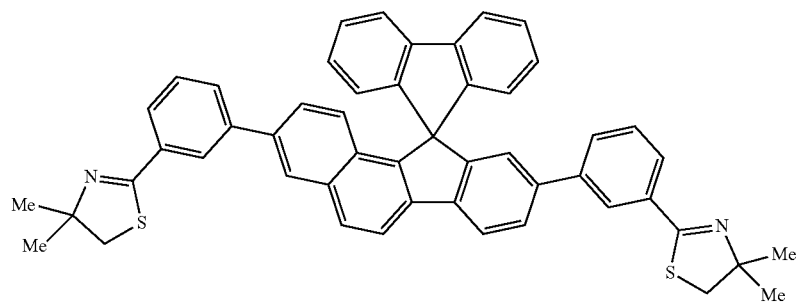
(1-2-233)
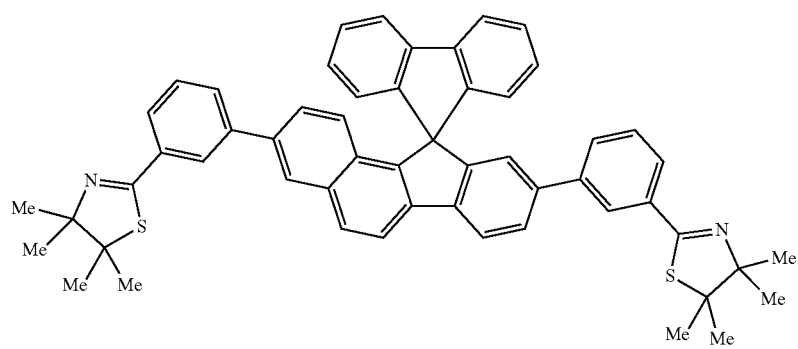
(1-2-234)
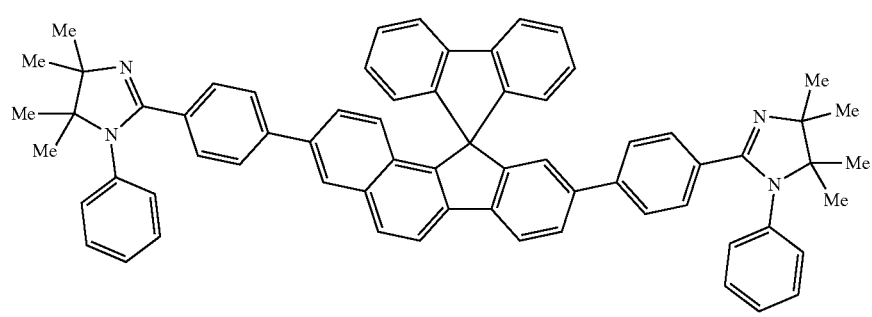
(1-2-235)
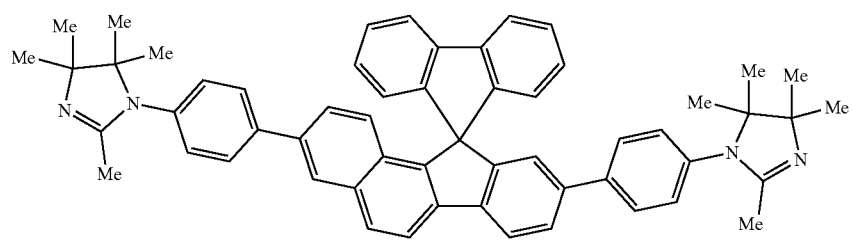
(1-2-236)
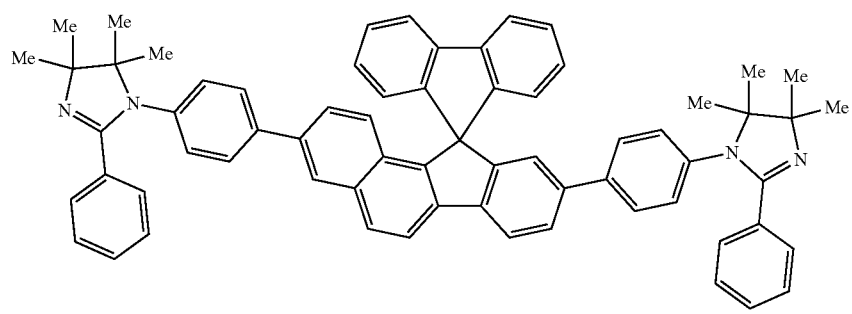
(1-2-237)

-continued
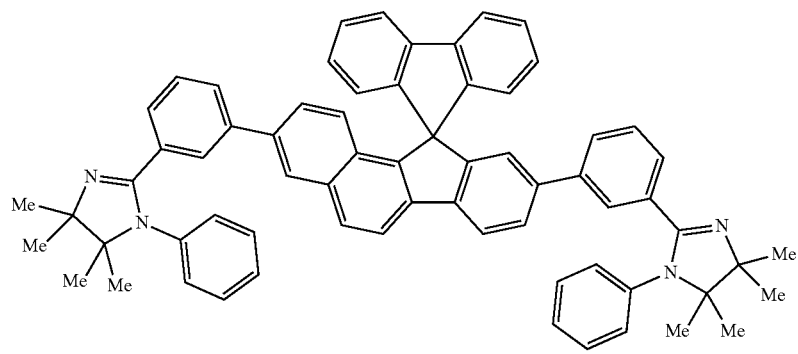
(1-2-238)
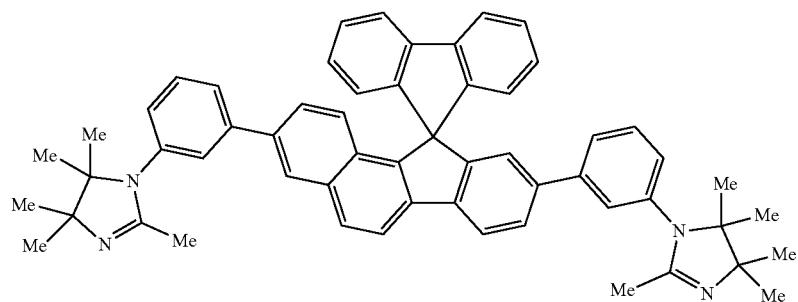
(1-2-239)
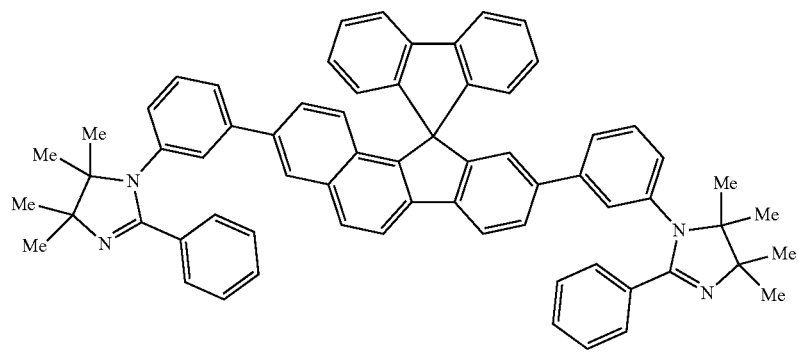
(1-2-240)
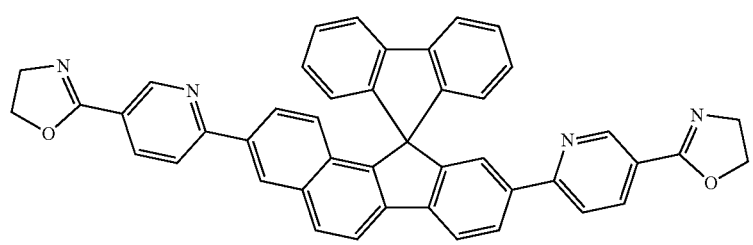
(1-2-241)
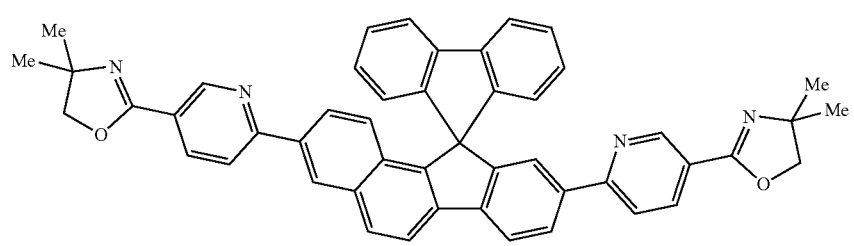
(1-2-242)

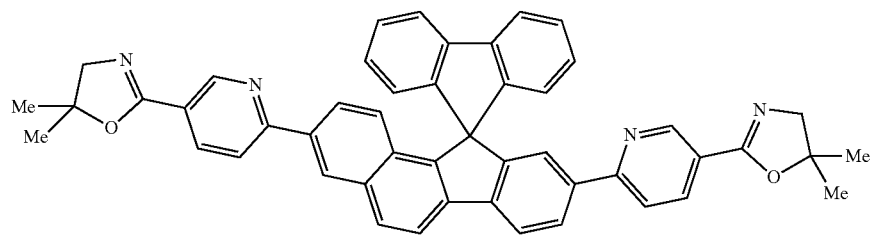
(1-2-243)
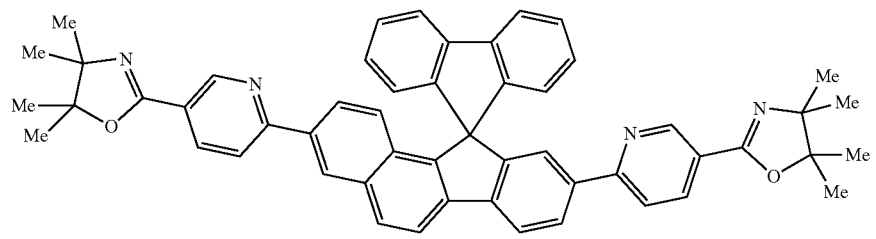
(1-2-244)
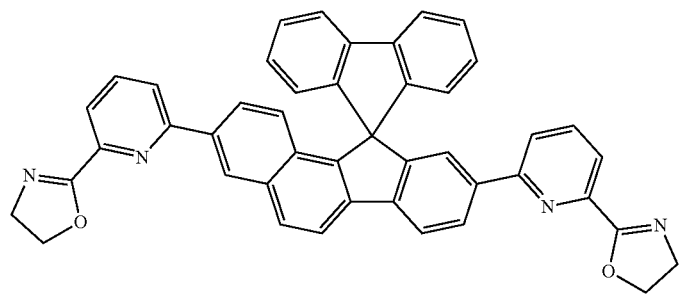
(1-2-245)
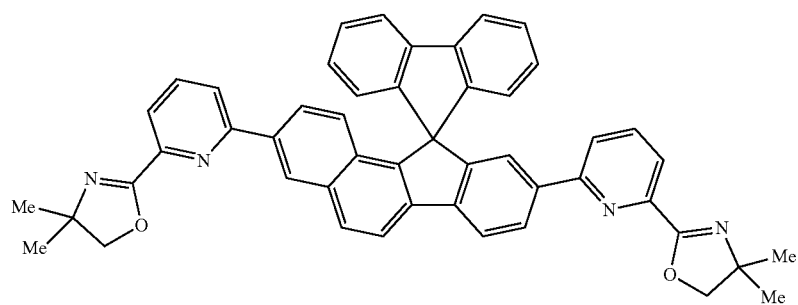
(1-2-246)
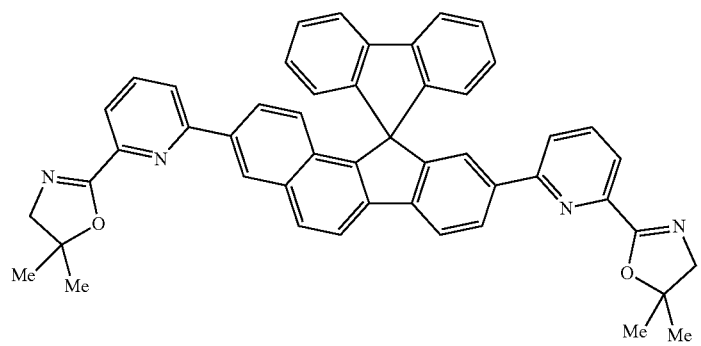
(1-2-247)

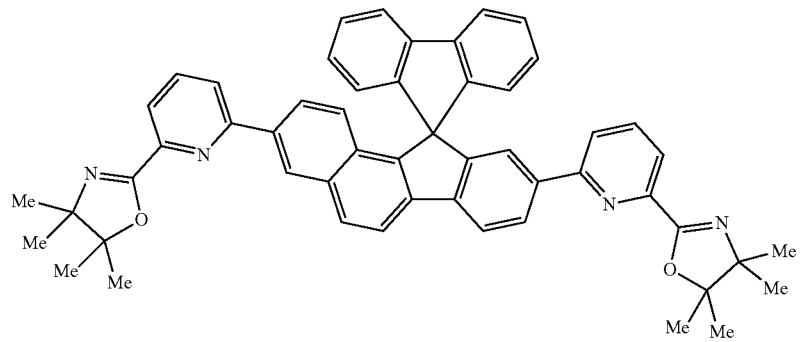
(1-2-248)
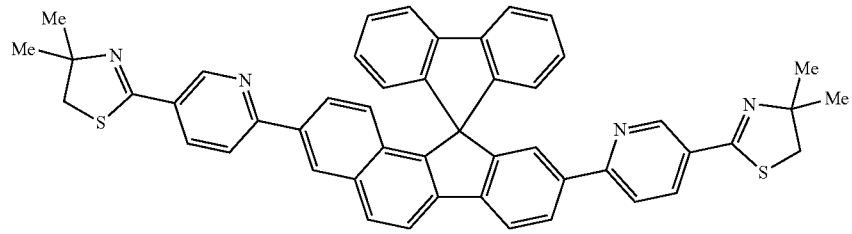
(1-2-251)
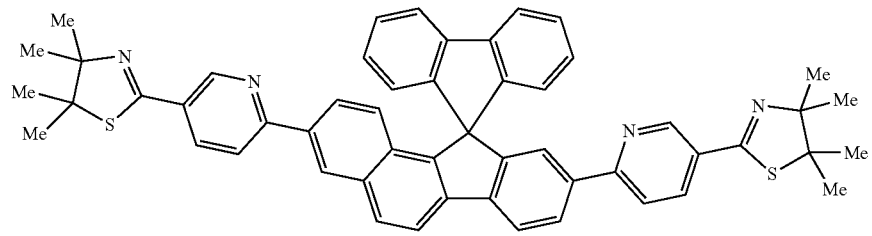
(1-2-252)
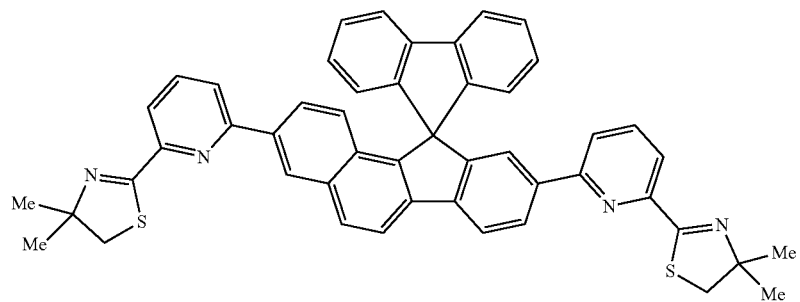
(1-2-253)
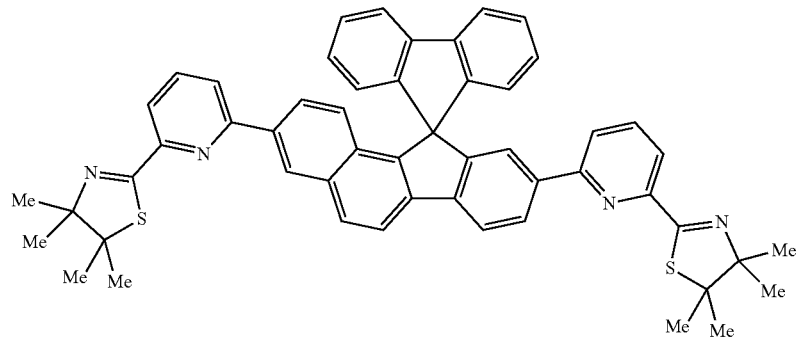
(1-2-254)

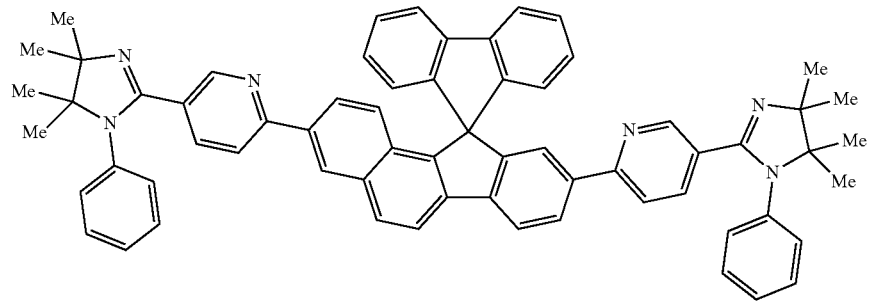
(1-2-255)
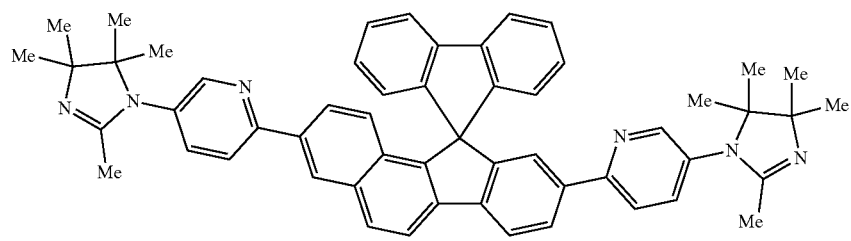
(1-2-256)
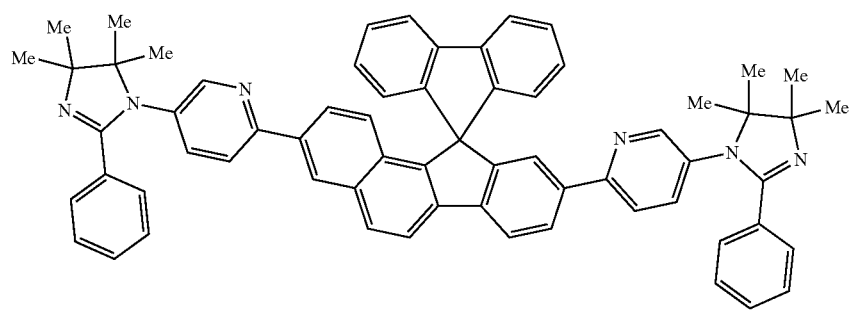
(1-2-257)
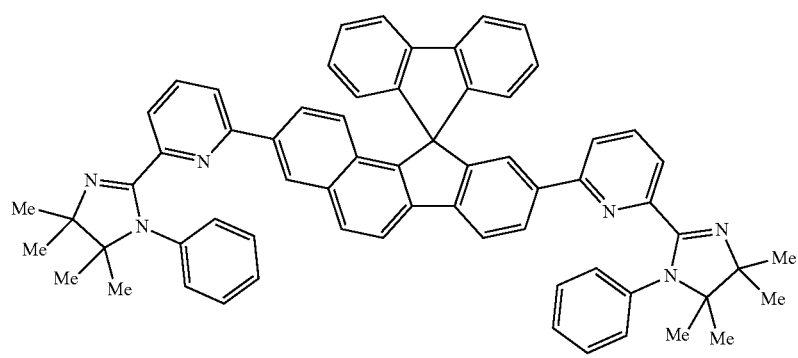
(1-2-258)
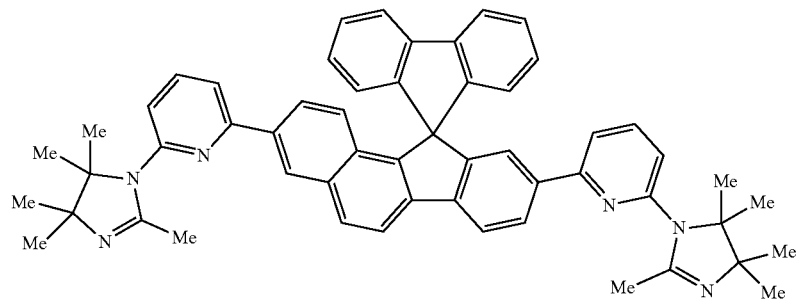
(1-2-259)

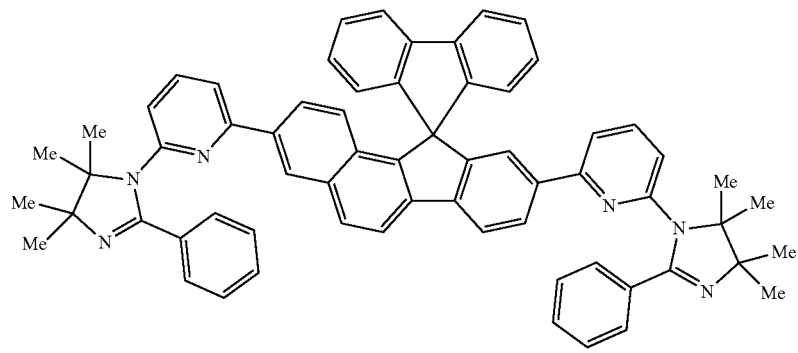
(1-2-260)
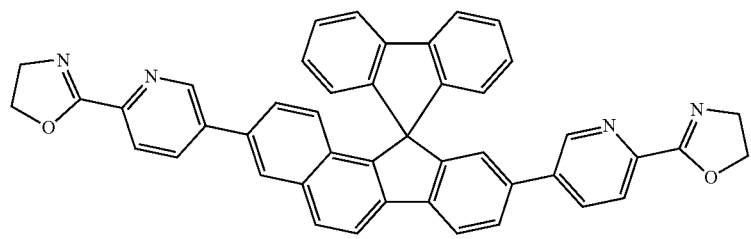
(1-2-261)
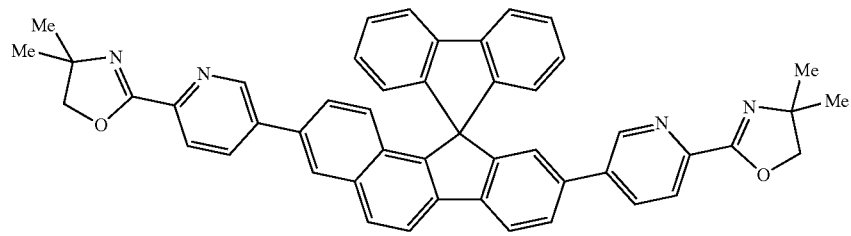
(1-2-262)
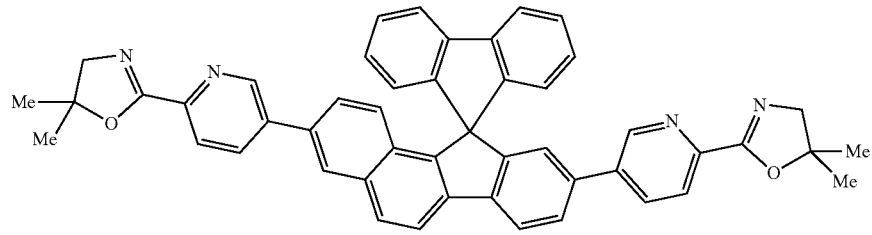
(1-2-263)
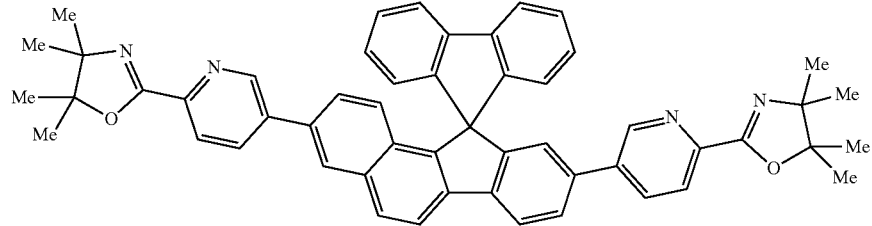
(1-2-264)
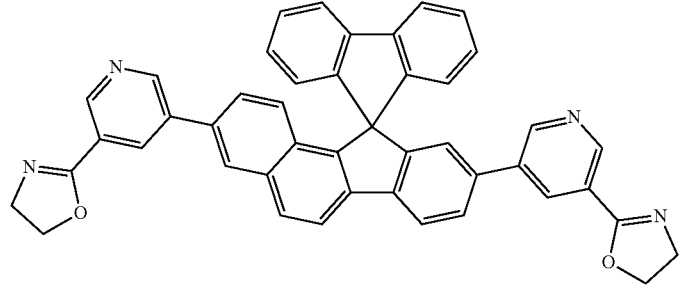
(1-2-265)

-continued
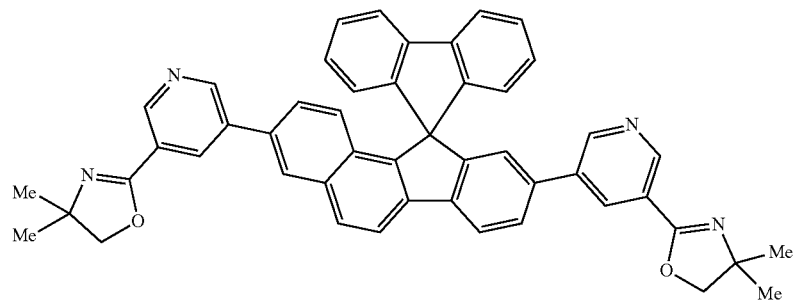
(1-2-266)
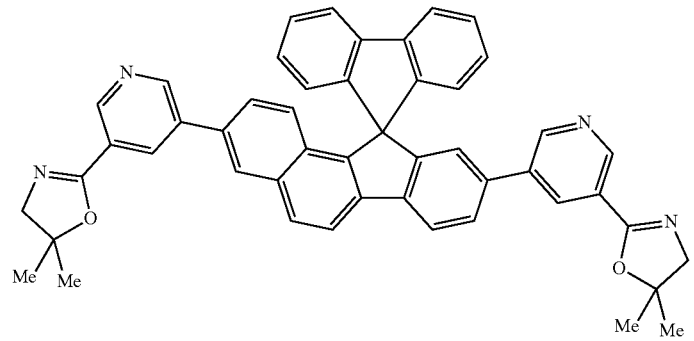
(1-2-267)
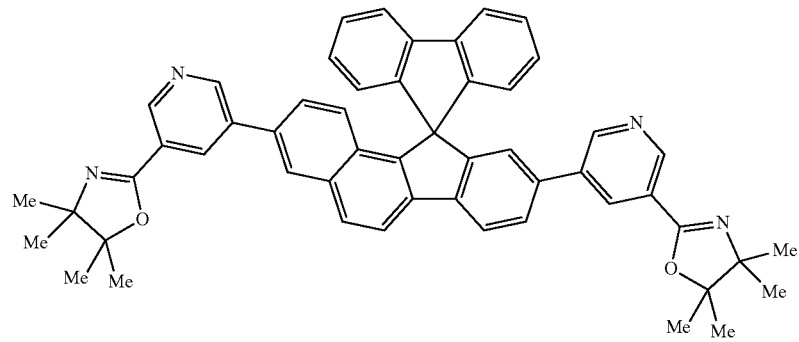
(1-2-268)
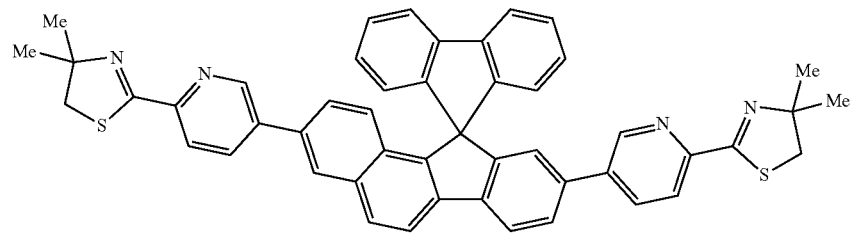
(1-2-271)
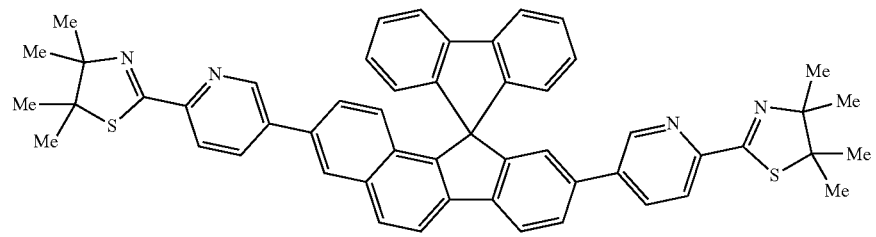
(1-2-172)

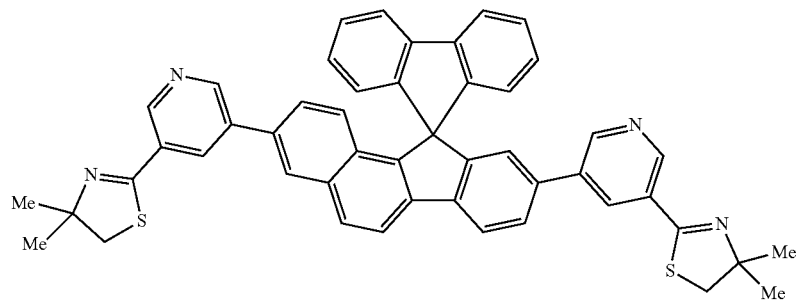
(1-2-273)
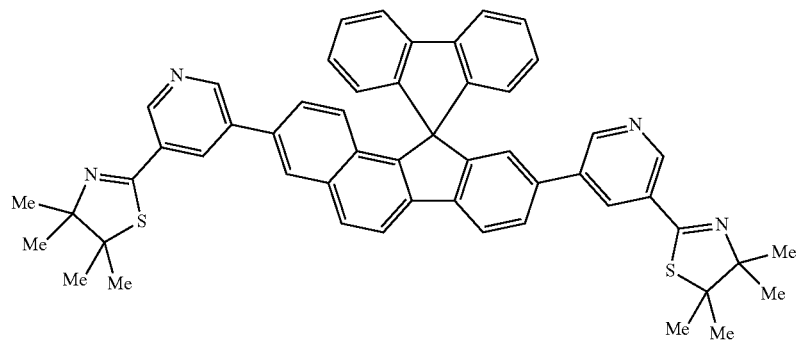
(1-2-274)
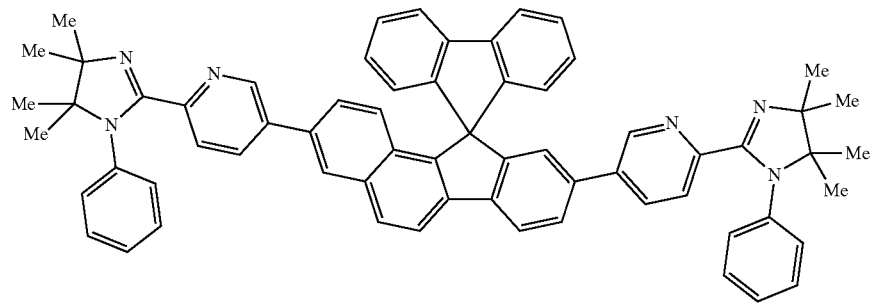
(1-2-275)
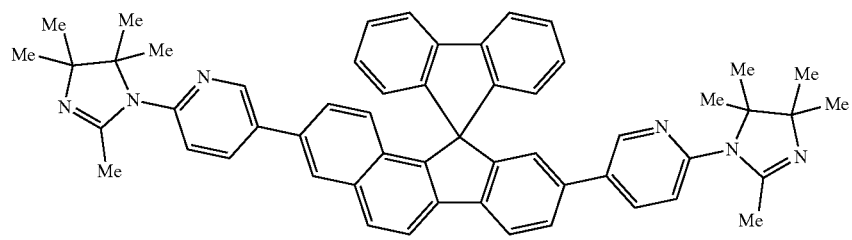
(1-2-276)
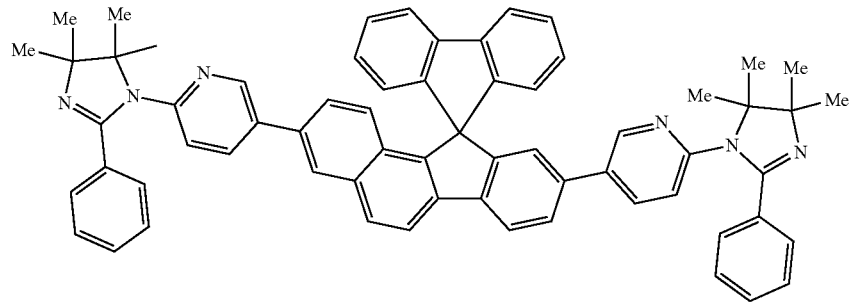
(1-2-277)

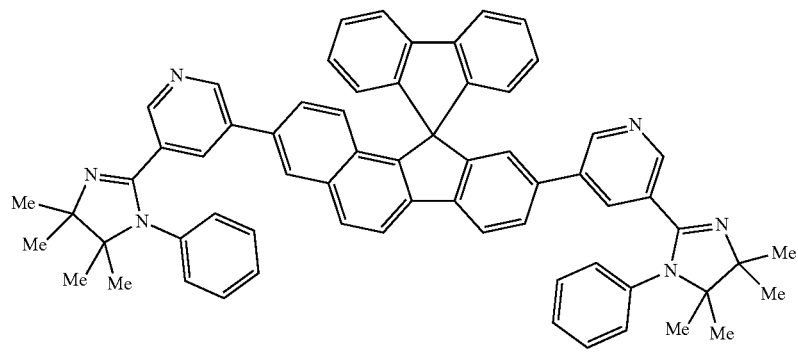
(1-2-278)
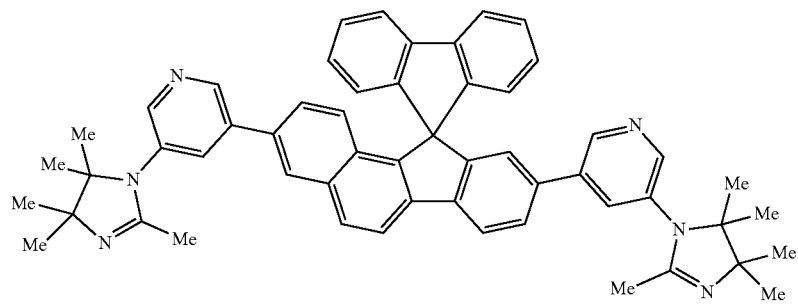
(1-2-279)
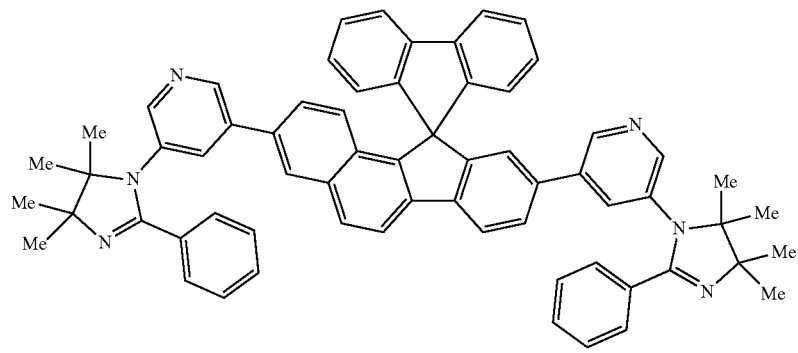
(1-2-280)
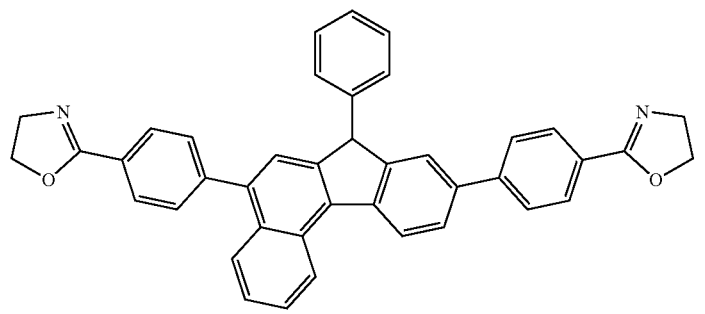
(1-2-281)
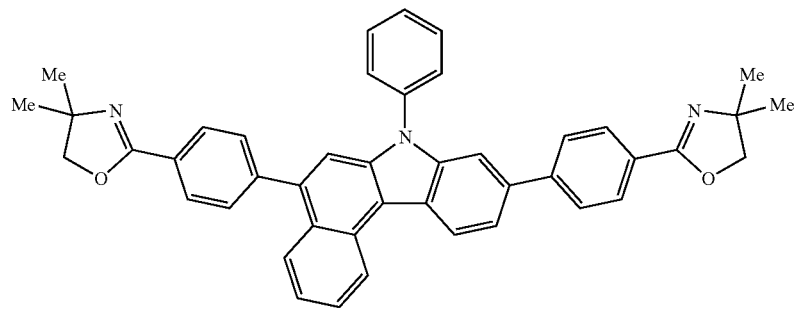
(1-2-282)

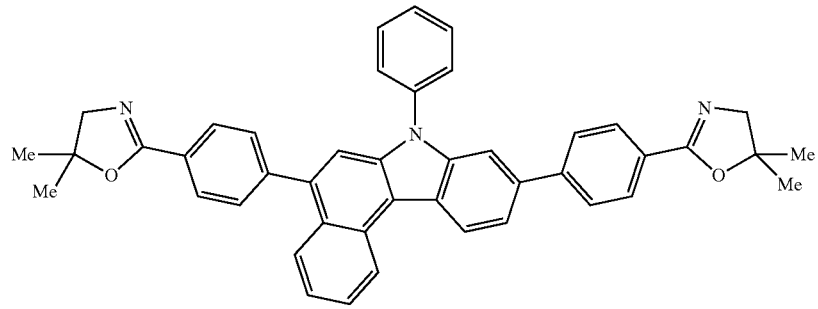
(1-2-283)
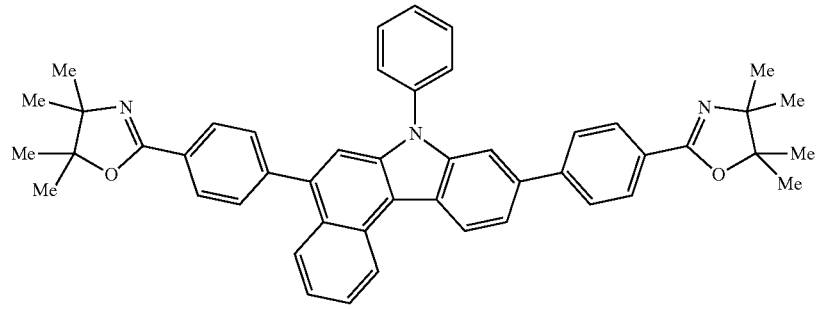
(1-2-284)
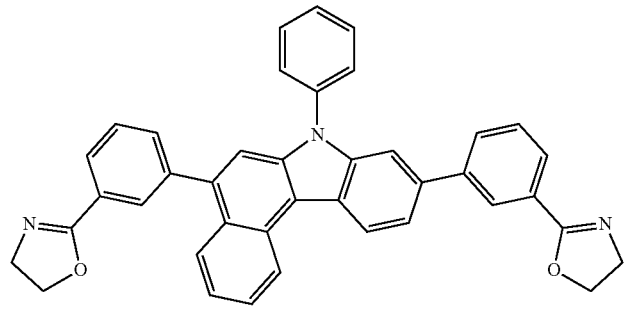
(1-2-285)
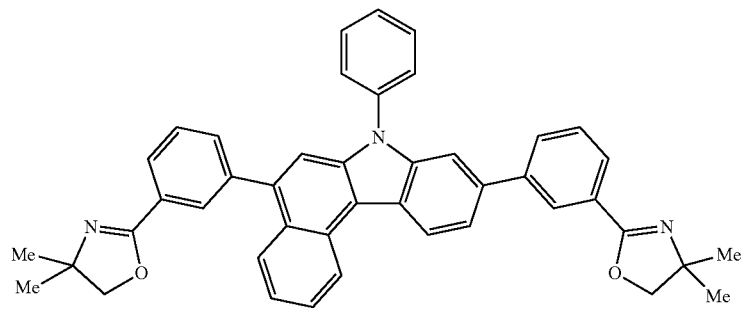
(1-2-286)
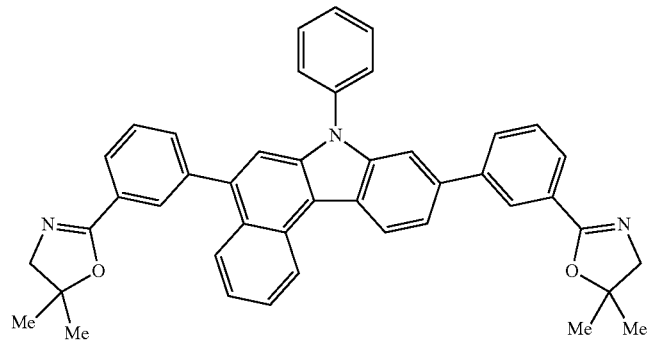
(1-2-287)

-continued
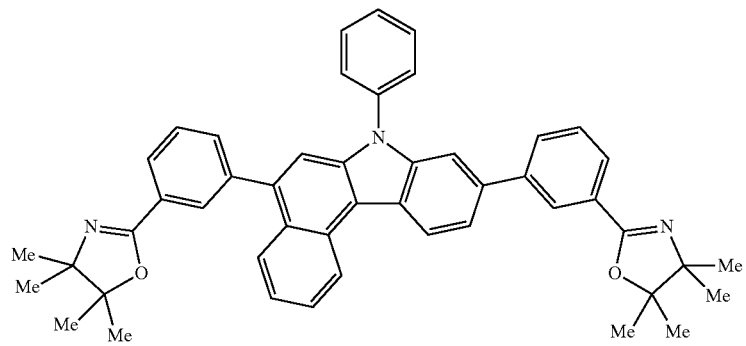
(1-2-288)
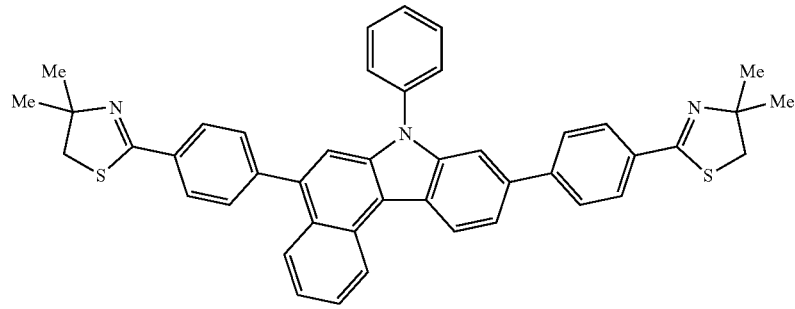
(1-2-291)
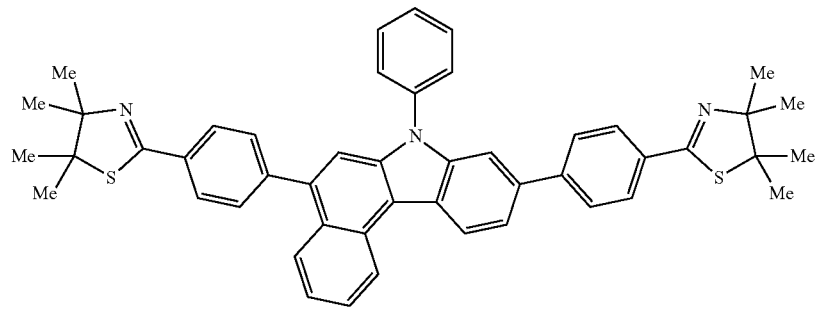
(1-2-292)
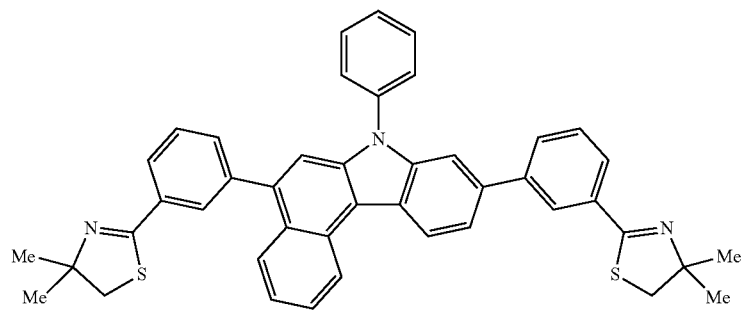
(1-2-293)
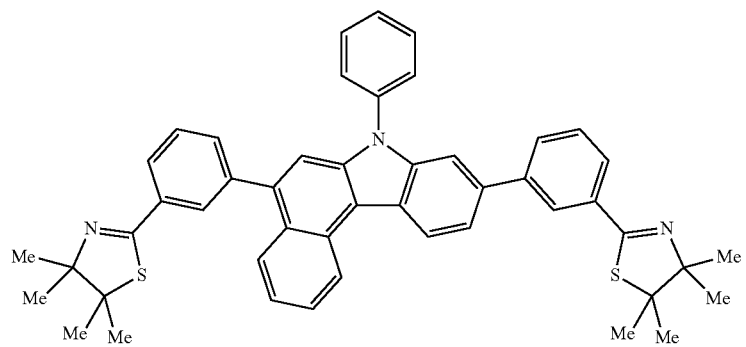
(1-2-294)

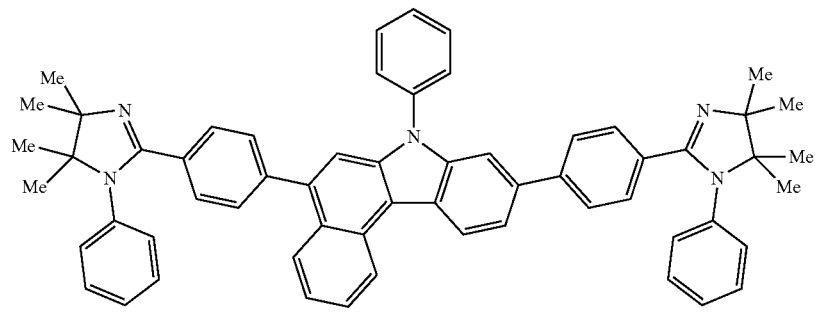
(1-2-295)
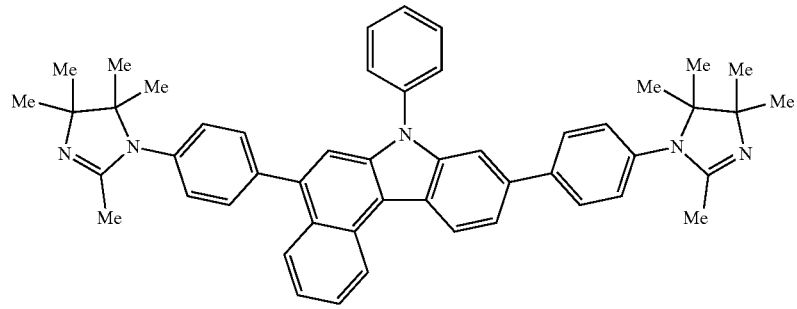
(1-2-296)
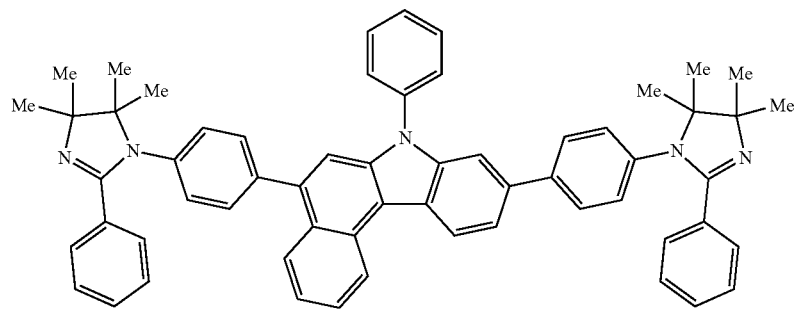
(1-2-297)
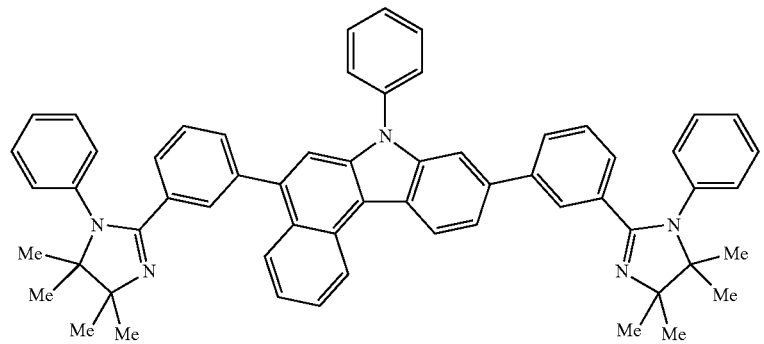
(1-2-298)
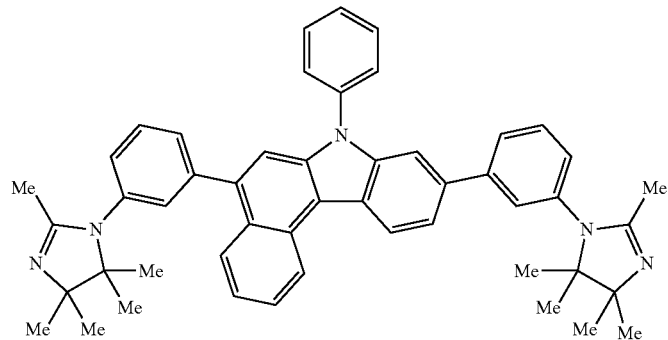
(1-2-299)

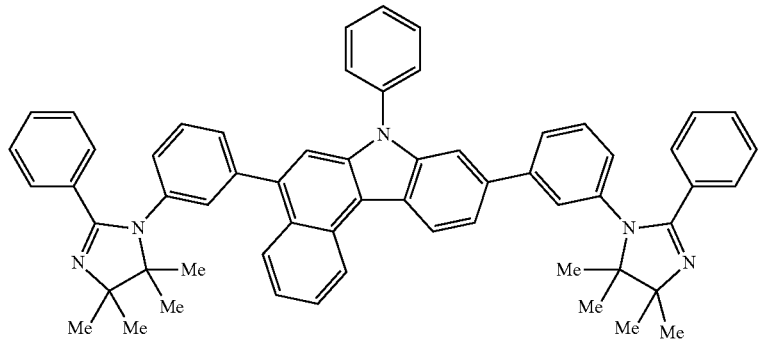
(1-2-300)
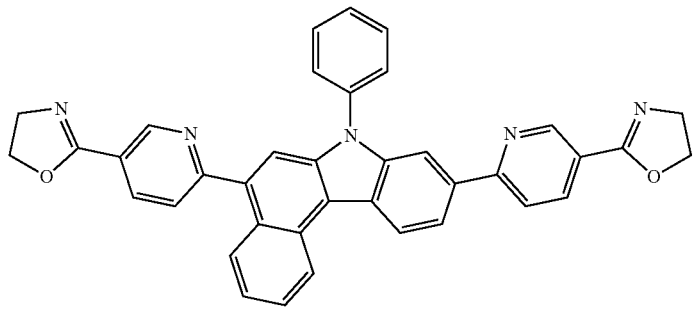
(1-2-301)
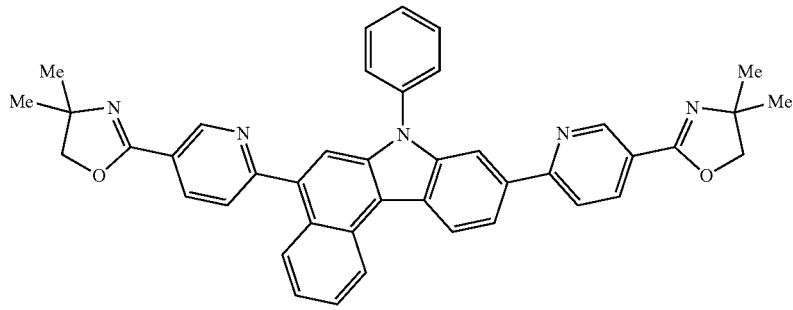
(1-2-302)
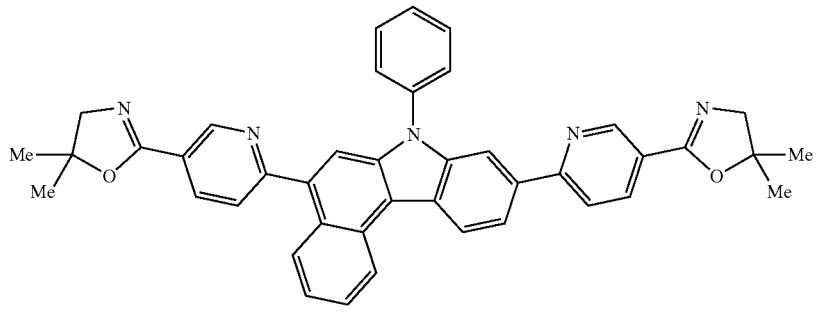
(1-2-303)
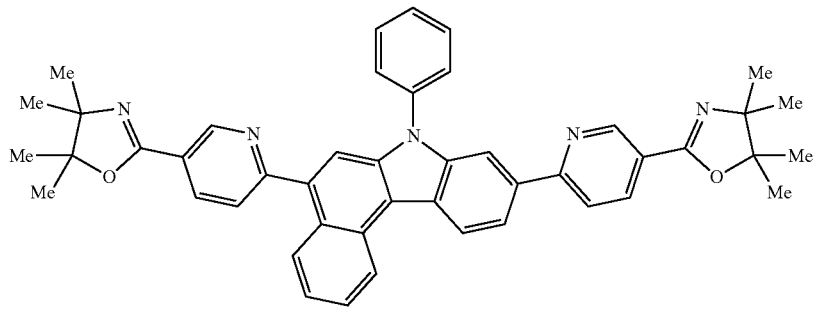
(1-2-304)

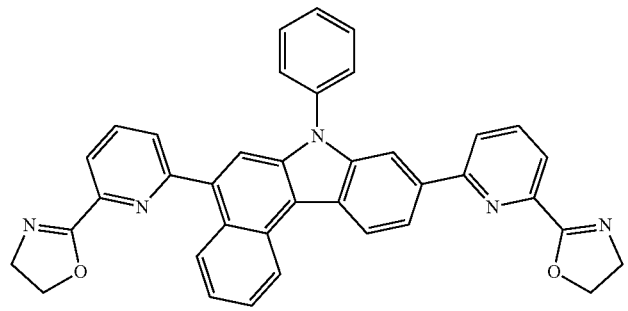
(1-2-305)
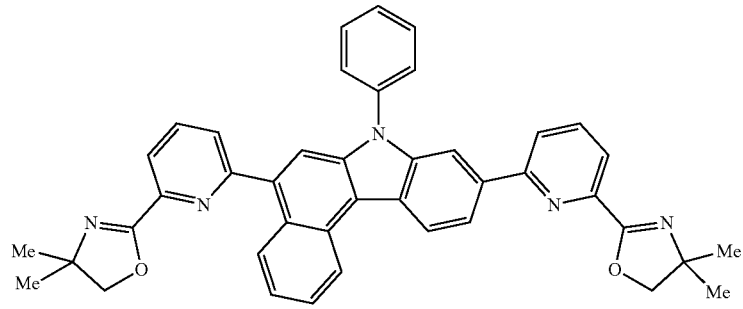
(1-2-306)
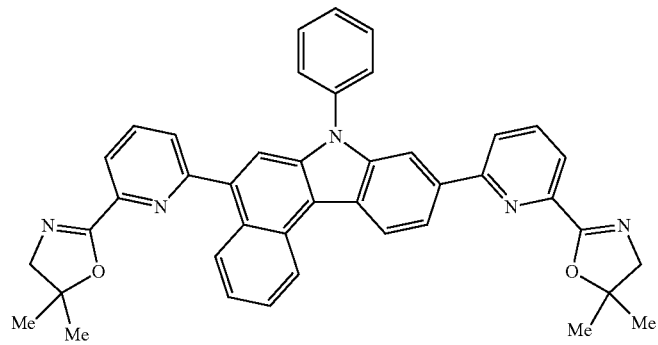
(1-2-307)
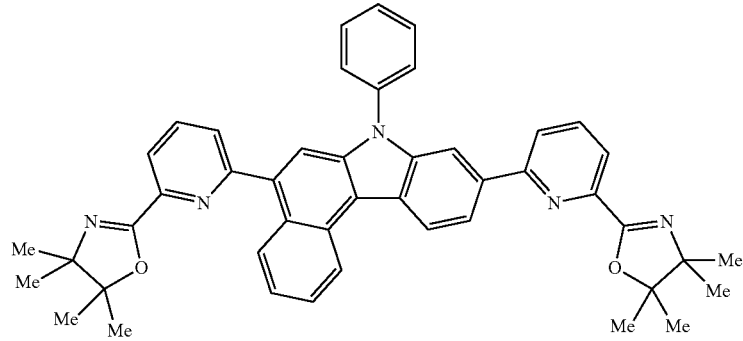
(1-2-308)
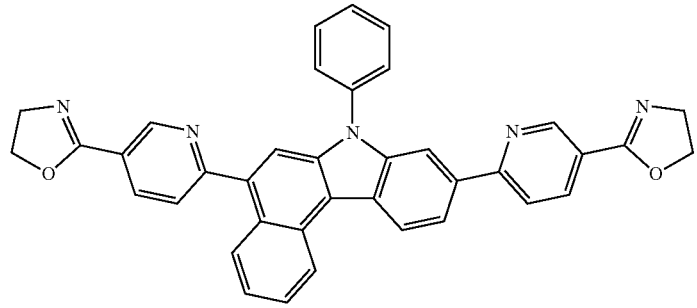
(1-2-311)

(1-2-312)
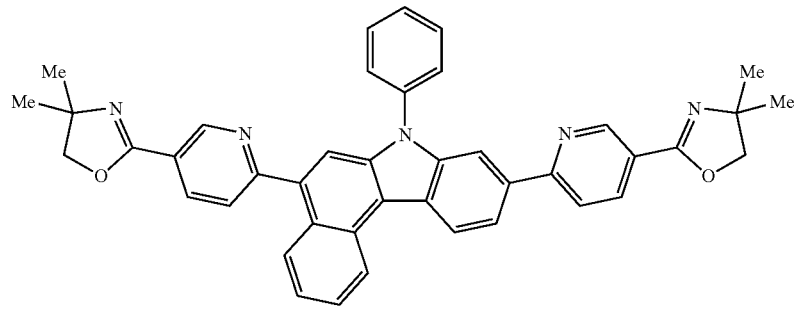
(1-2-313)
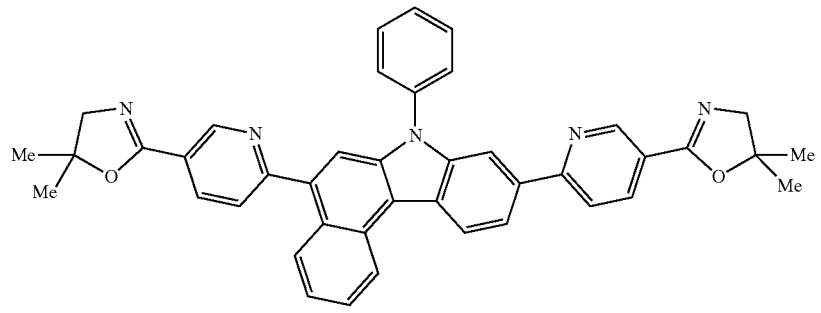
(1-2-314)
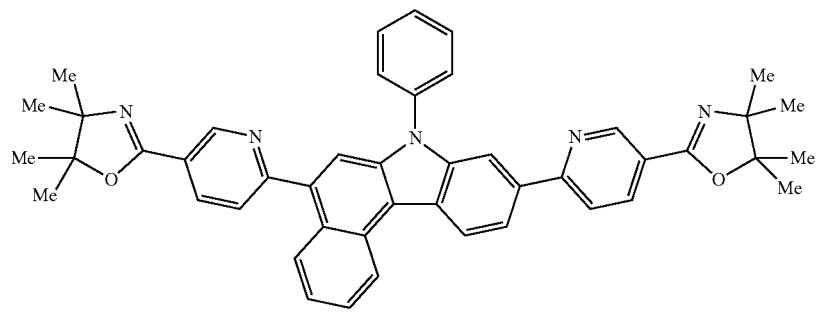
(1-2-315)
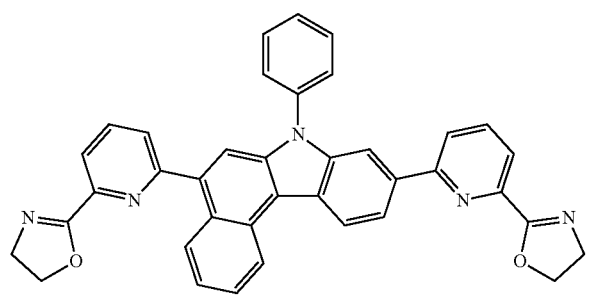
(1-2-316)
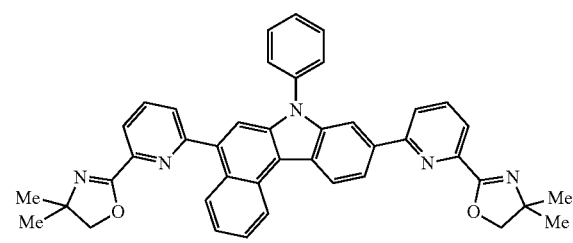
(1-2-317)
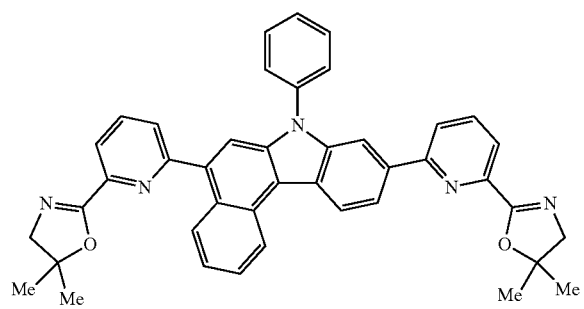
(1-2-318)
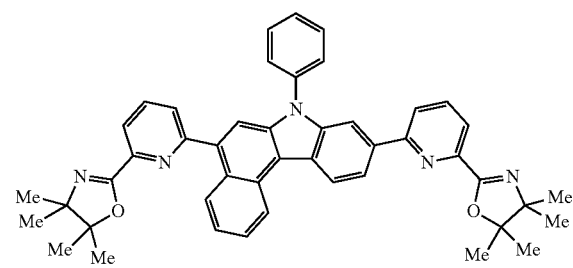

-continued
(1-2-321)
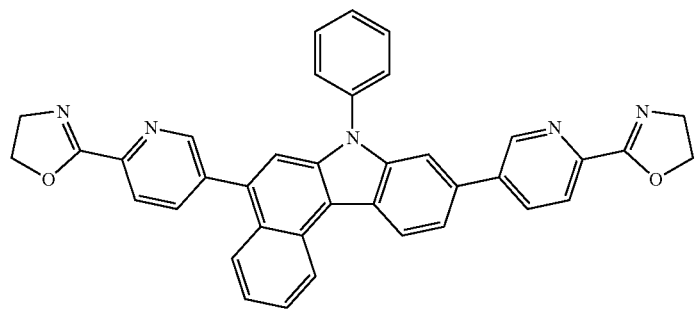
(1-2-322)
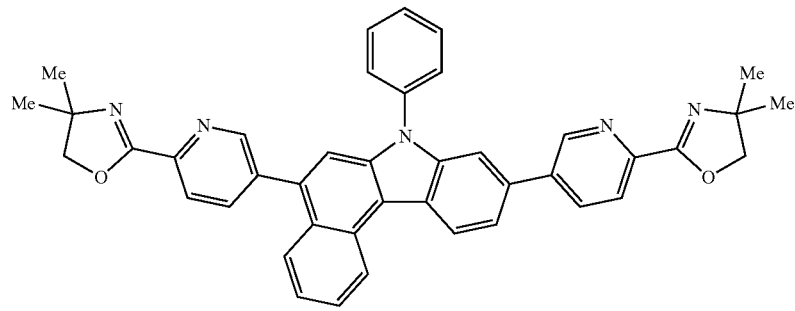
(1-2-323)
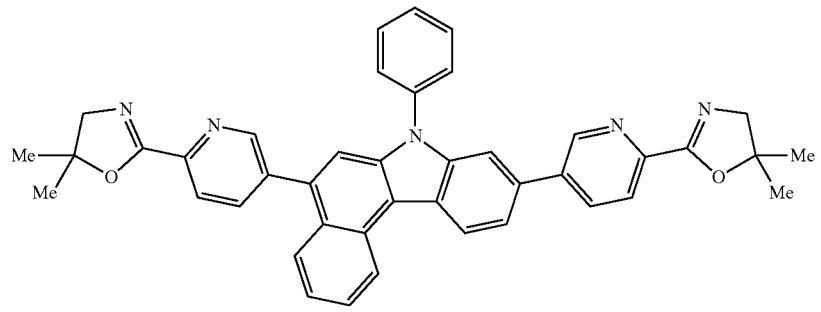
(1-2-324)
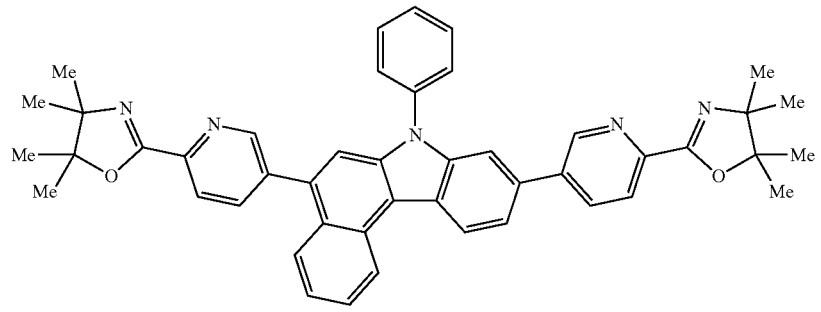
(1-2-325)
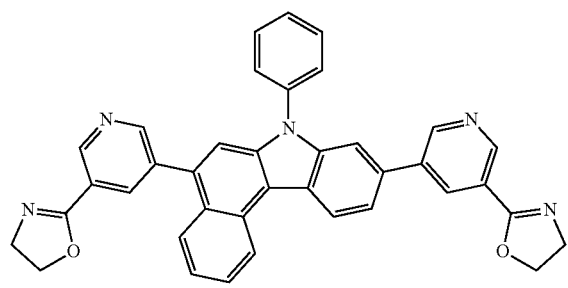
(1-2-326)
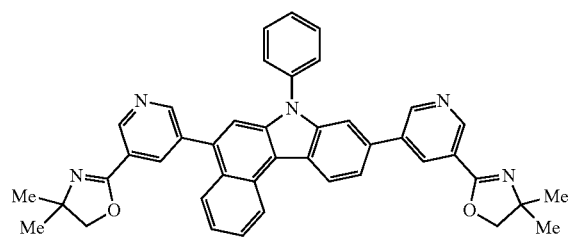

-continued
(1-2-327)
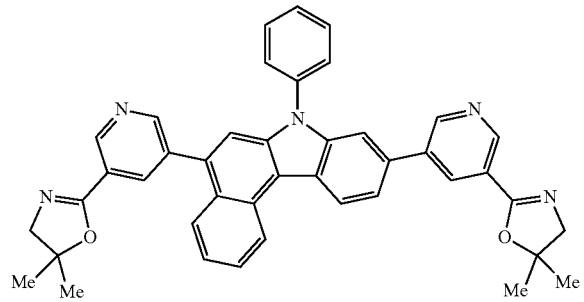
(1-2-328)
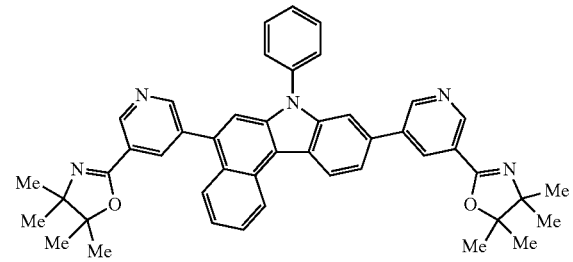
(1-2-331)
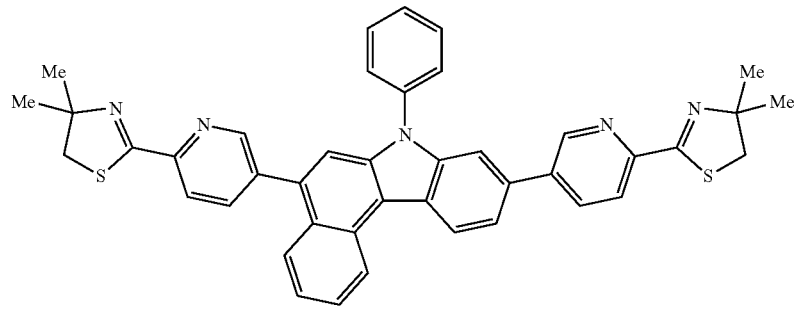
(1-2-332)
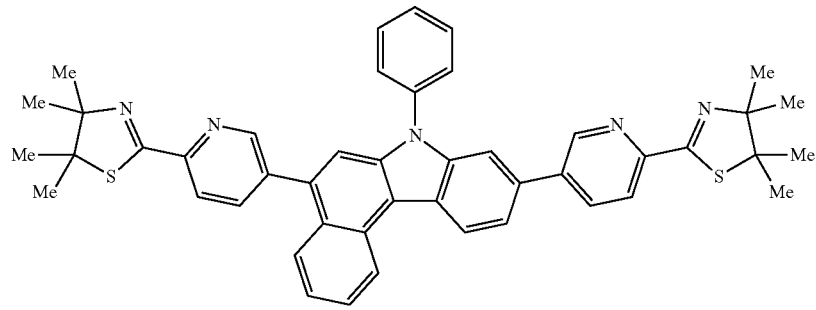
(1-2-333)
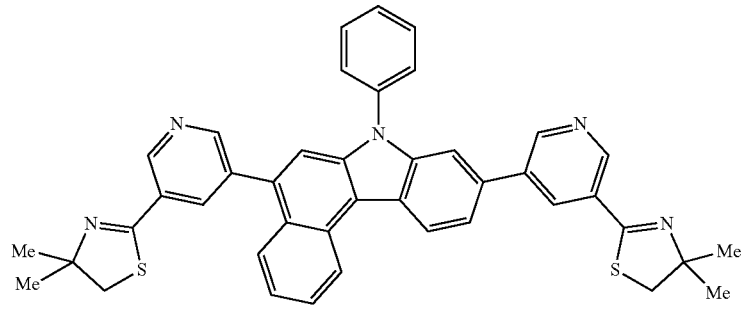
(1-2-334)
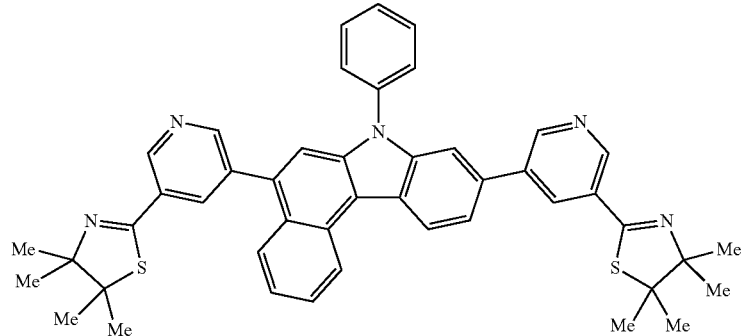

-continued
(1-2-335)
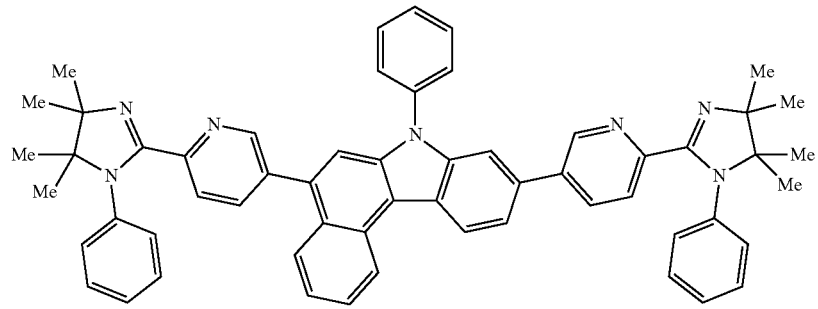
(1-2-336)
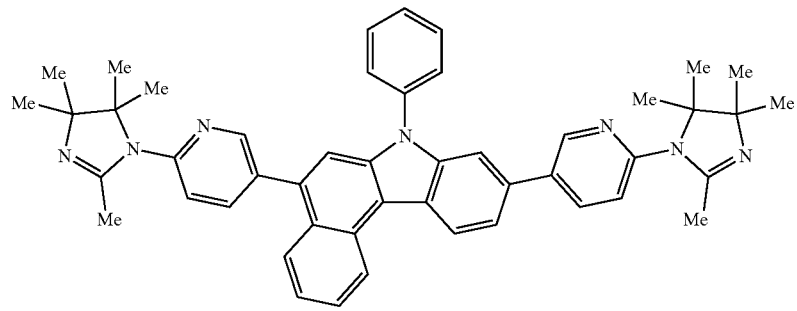
(1-2-337)
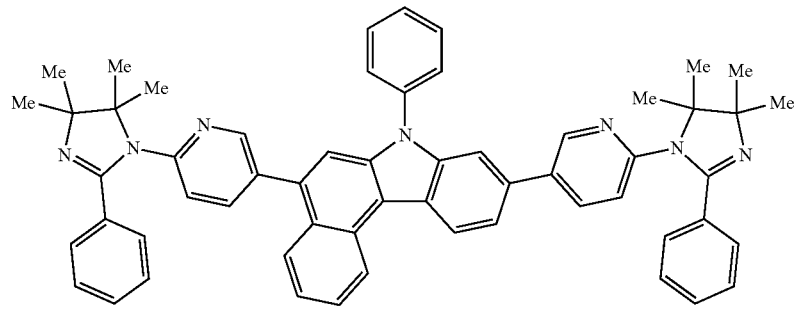
(1-2-338)
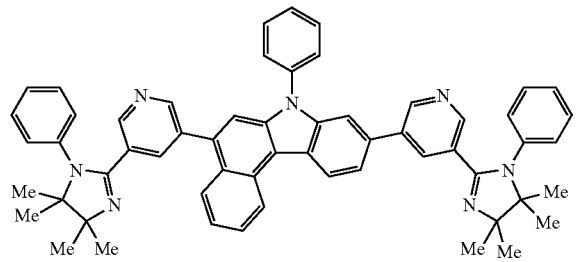
(1-2-339)
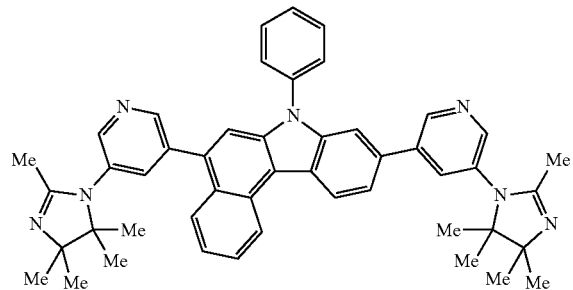
(1-2-340)
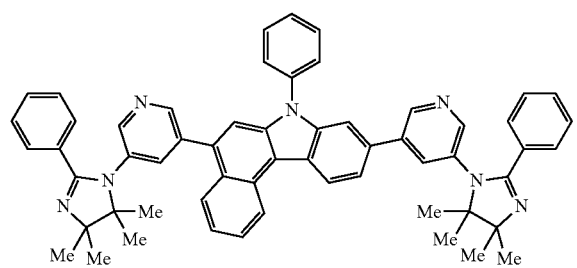
(1-2-341)
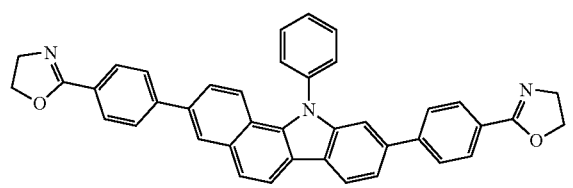

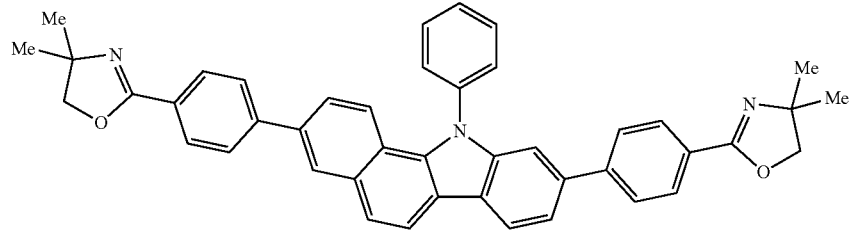
(1-2-342)
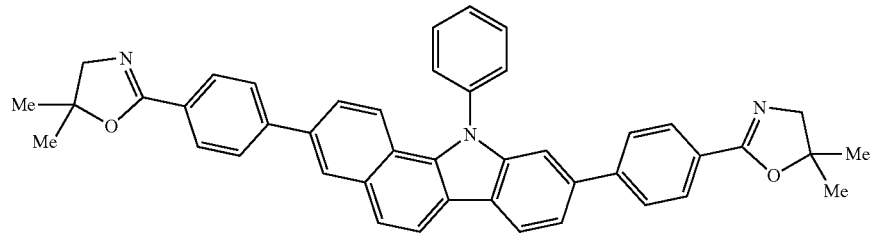
(1-2-343)
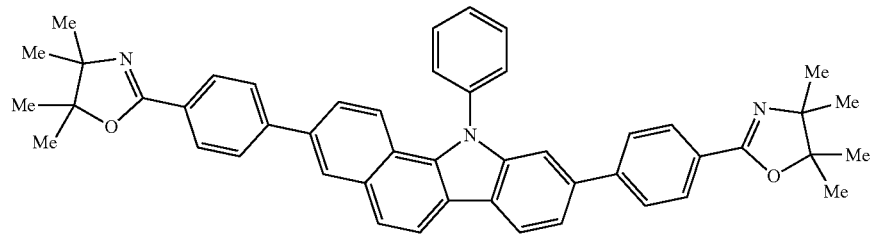
(1-2-344)
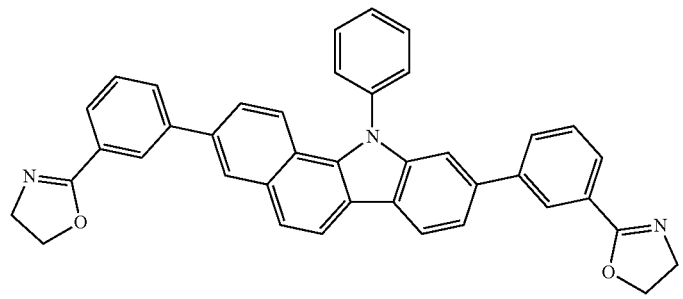
(1-2-345)
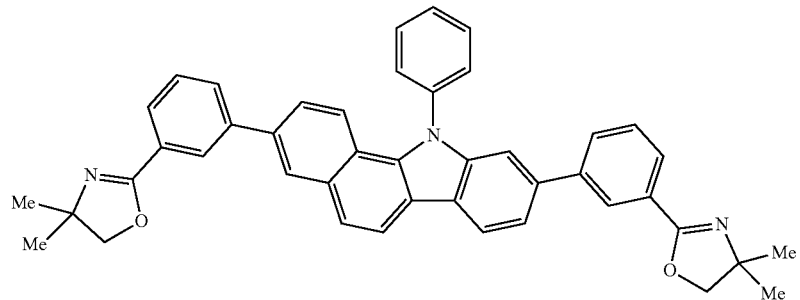
(1-2-346)

-continued
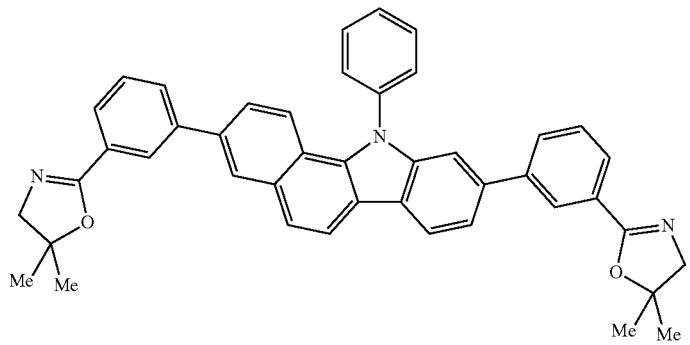
(1-2-347)
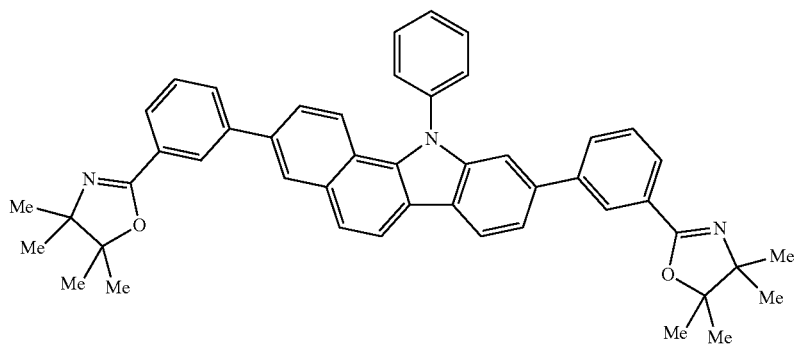
(1-2-348)
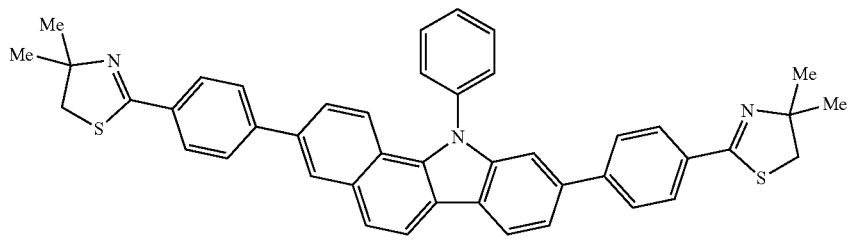
(1-2-351)
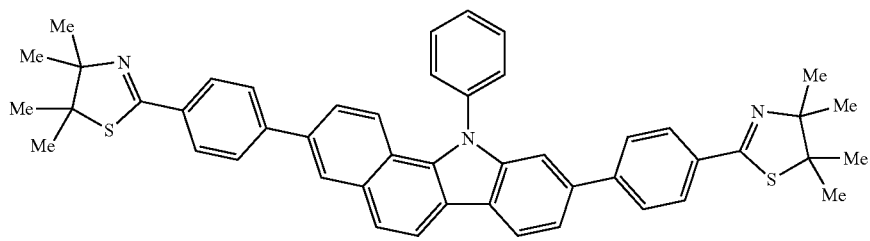
(1-2-352)
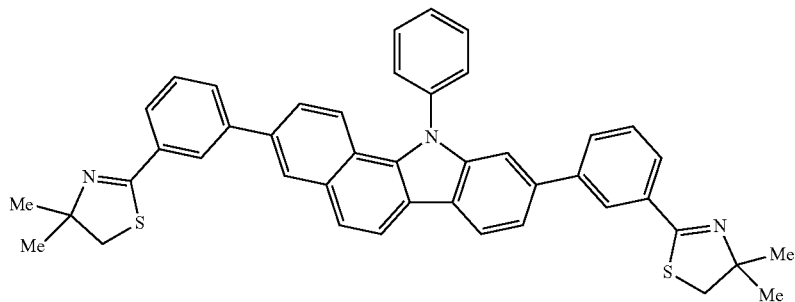
(1-2-353)

-continued
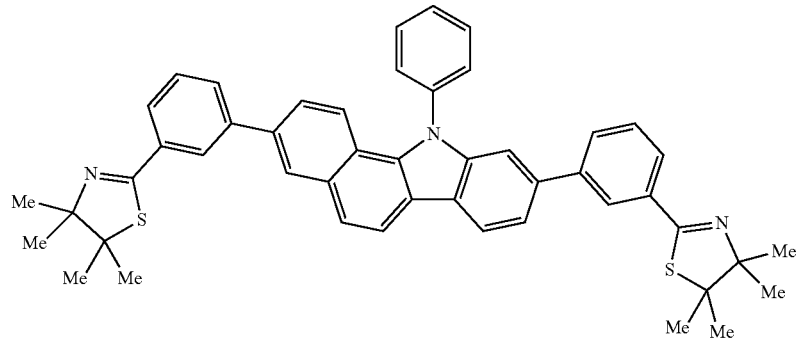
(1-2-354)
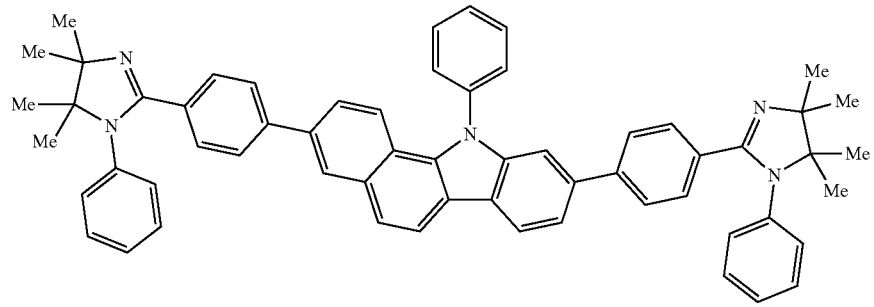
(1-2-355)
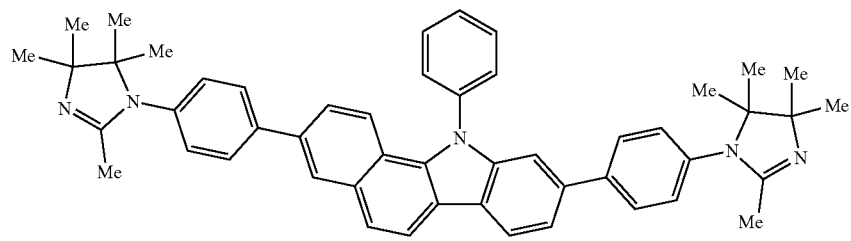
(1-2-356)
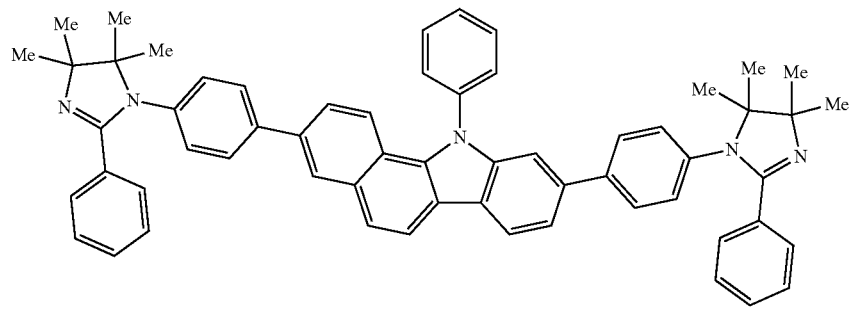
(1-2-357)
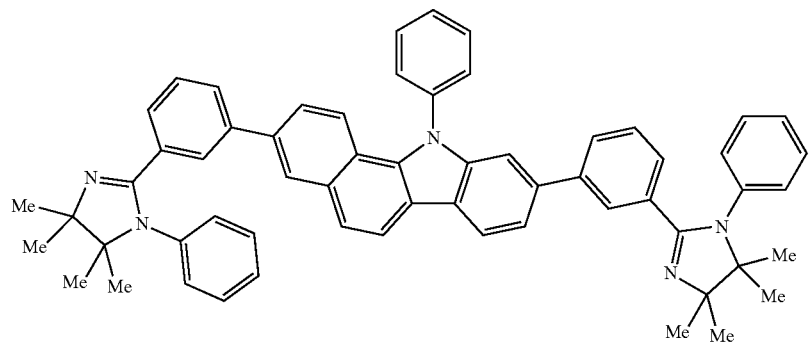
(1-2-358)

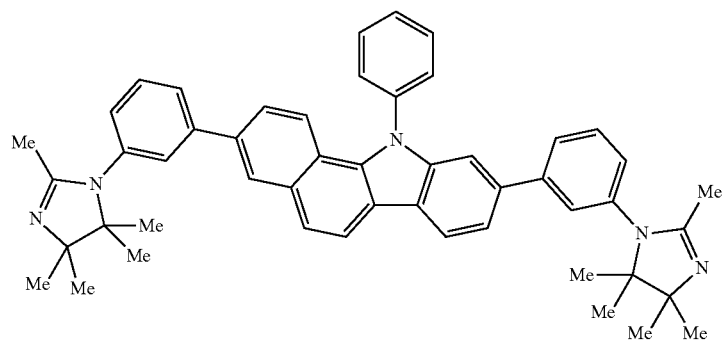
(1-2-359)
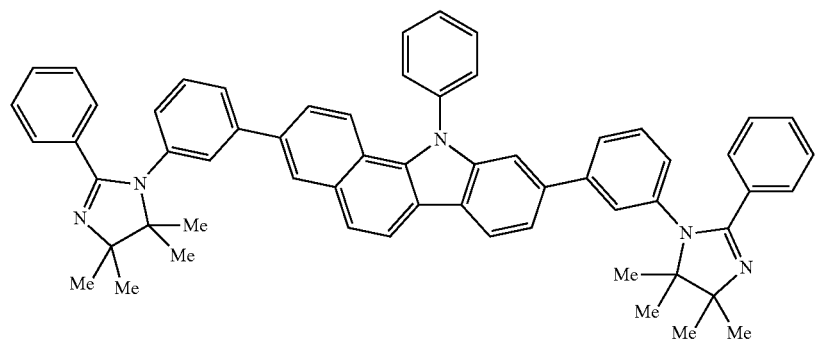
(1-2-360)
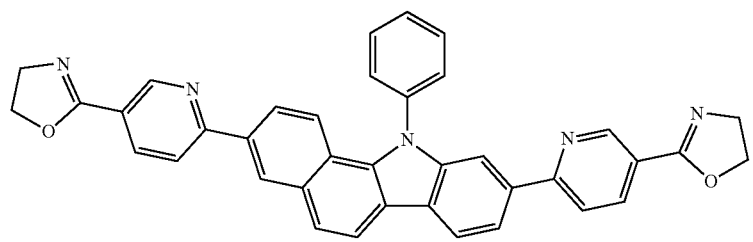
(1-2-361)
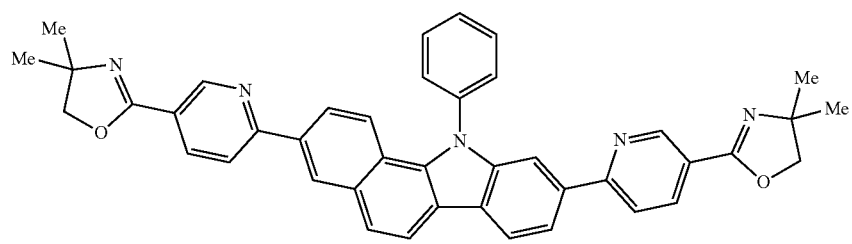
(1-2-362)
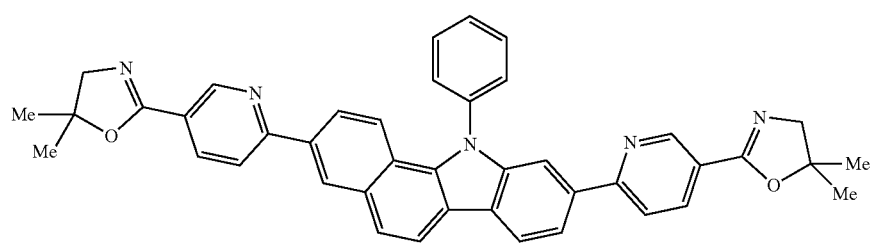
(1-2-363)

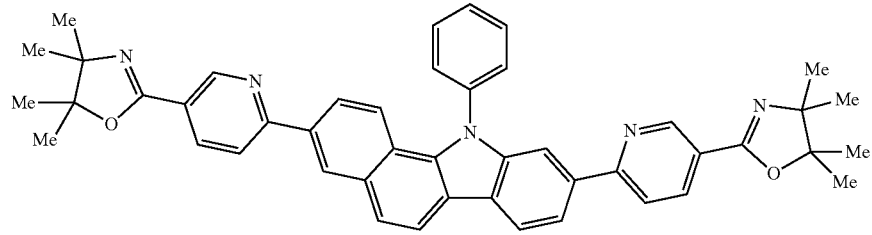
(1-2-364)
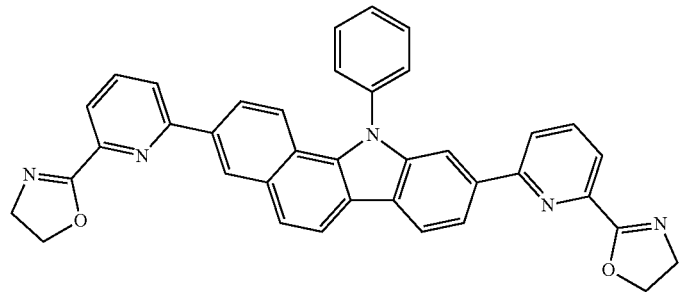
(1-2-365)
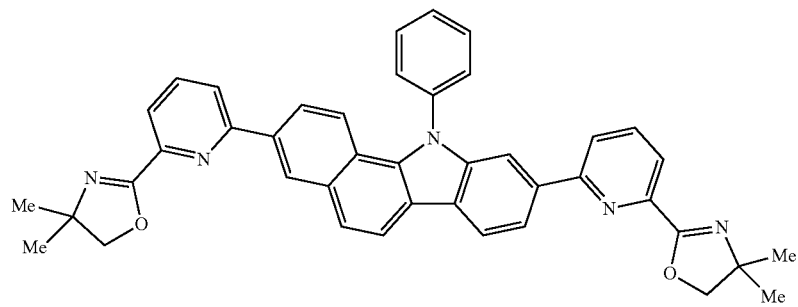
(1-2-366)
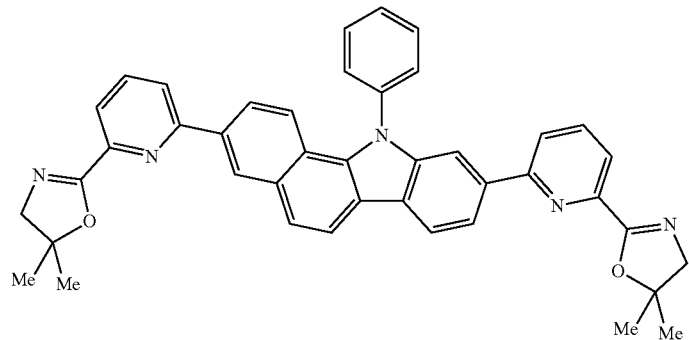
(1-2-367)
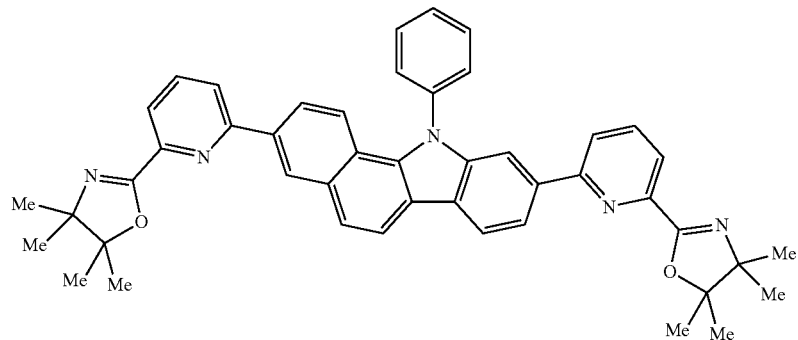
(1-2-368)

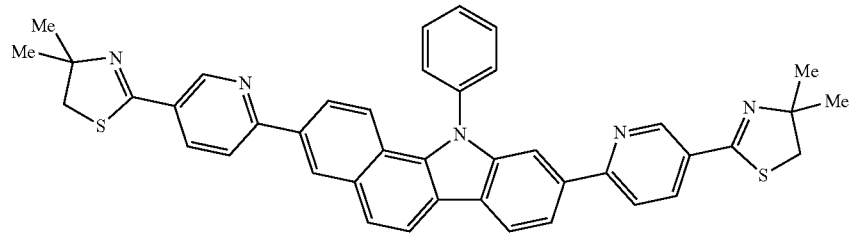
(1-2-371)
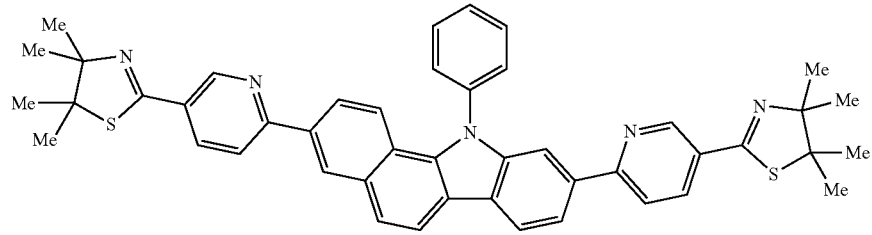
(1-2-372)
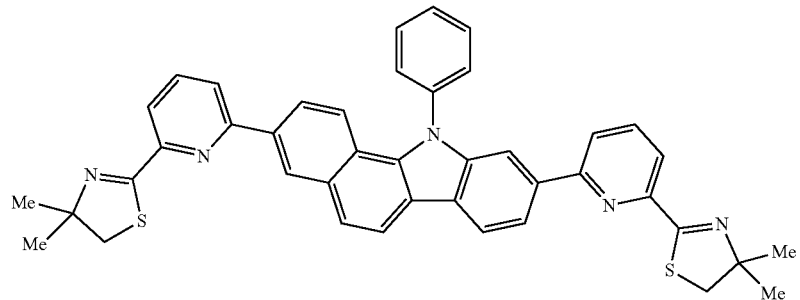
(1-2-373)
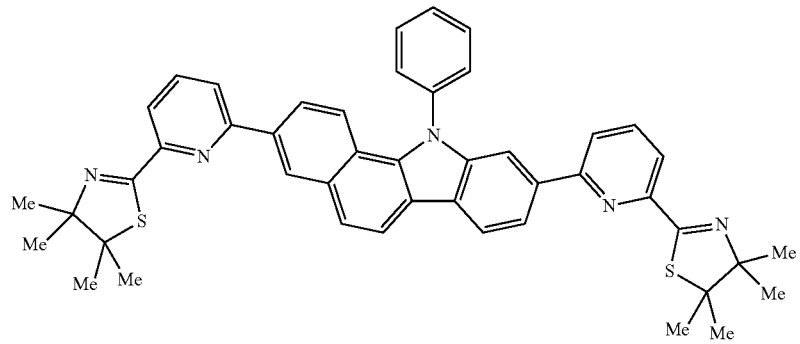
(1-2-374)
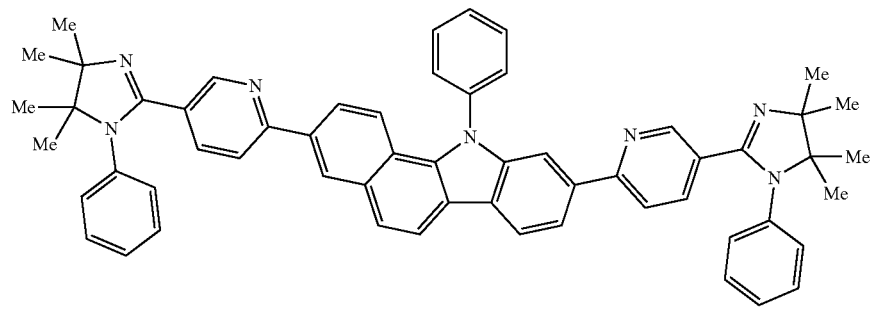
(1-2-375)

-continued
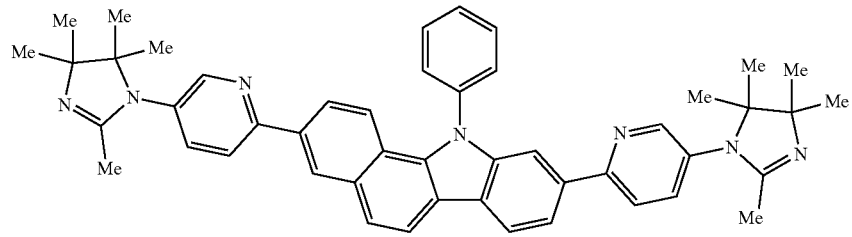
(1-2-376)
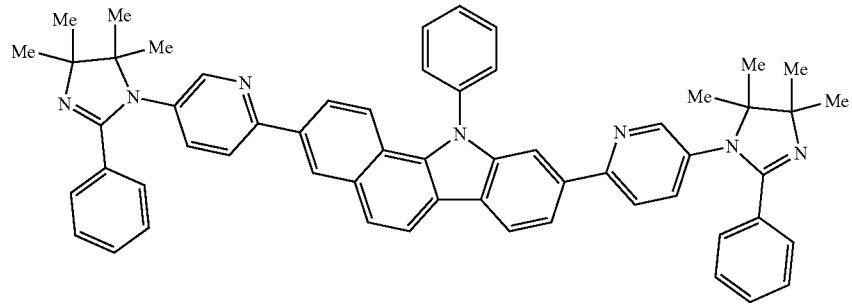
(1-2-377)
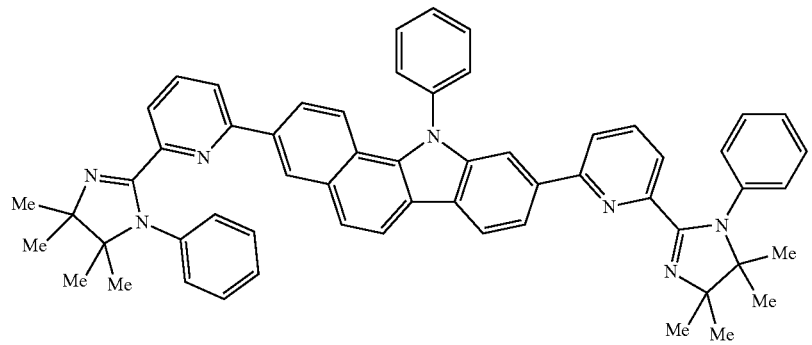
(1-2-378)
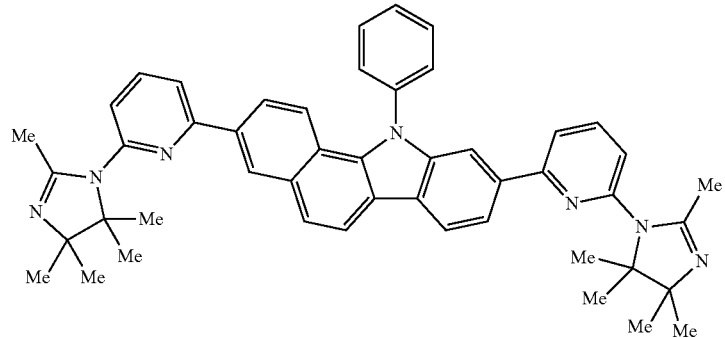
(1-2-379)
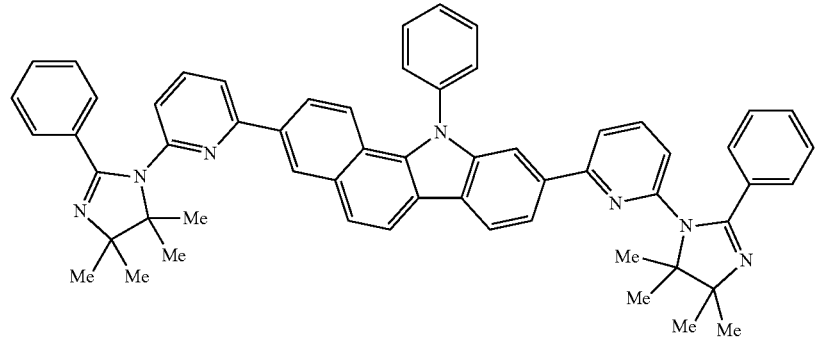
(1-2-380)

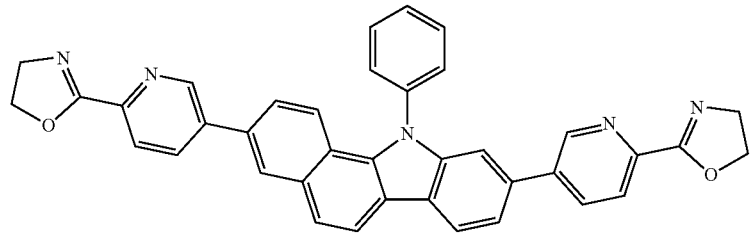
(1-2-381)
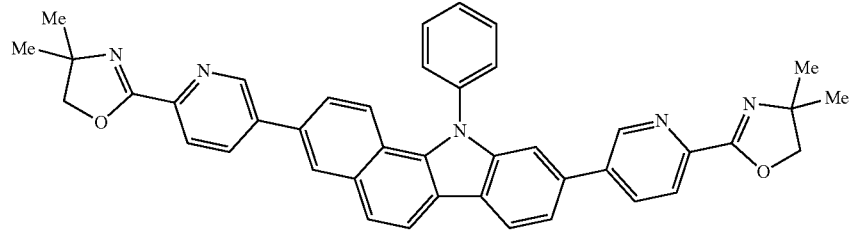
(1-2-382)
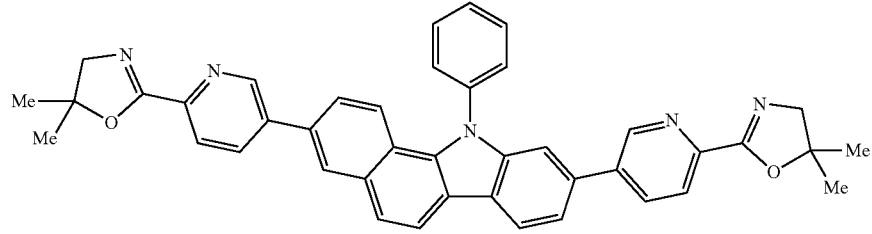
(1-2-383)
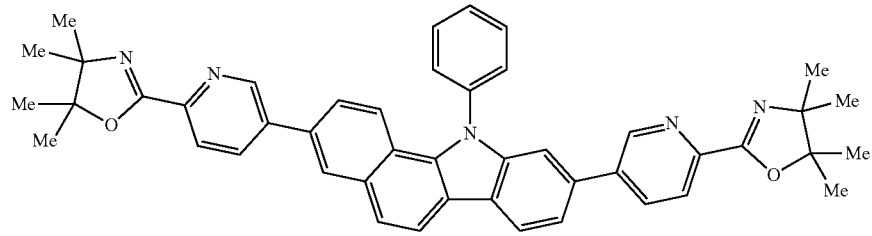
(1-2-384)
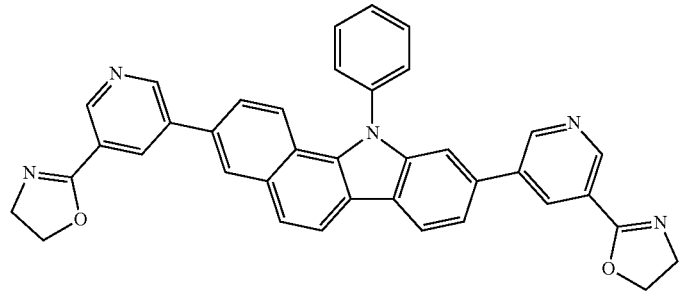
(1-2-385)
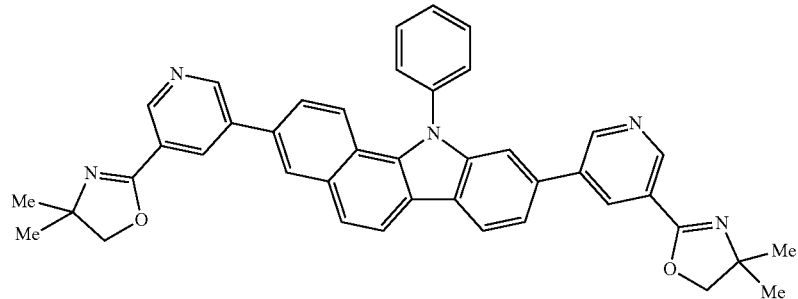
(1-2-386)

-continued
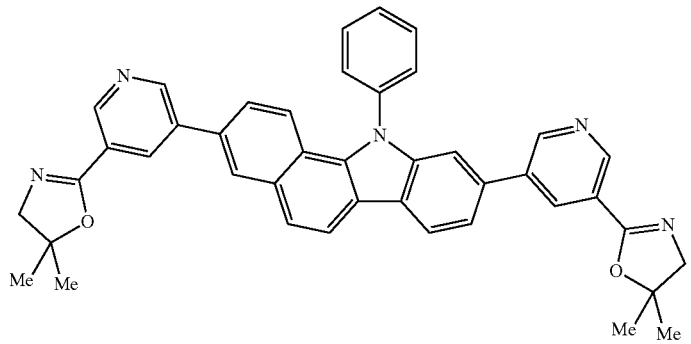
(1-2-387)
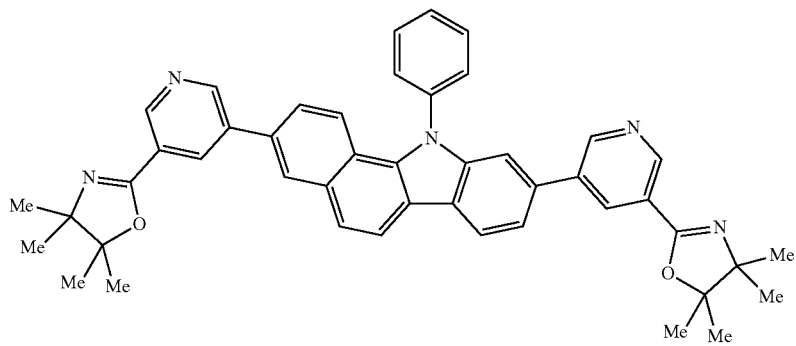
(1-2-388)
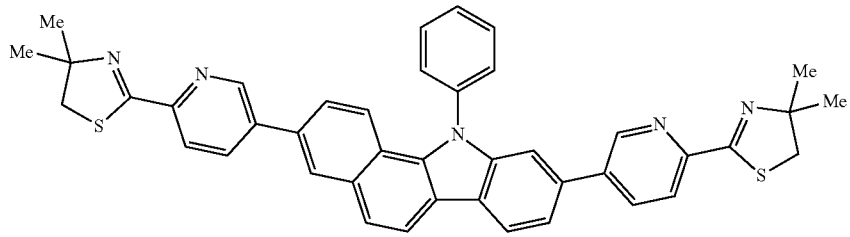
(1-2-391)
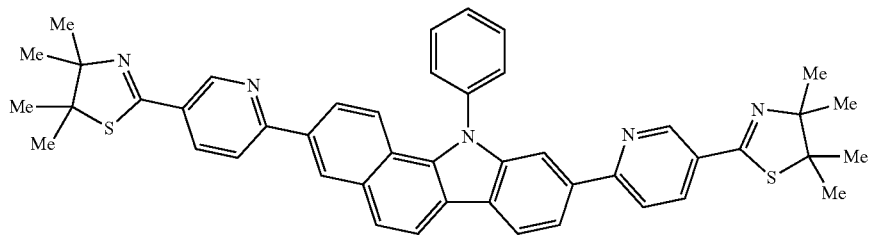
(1-2-392)
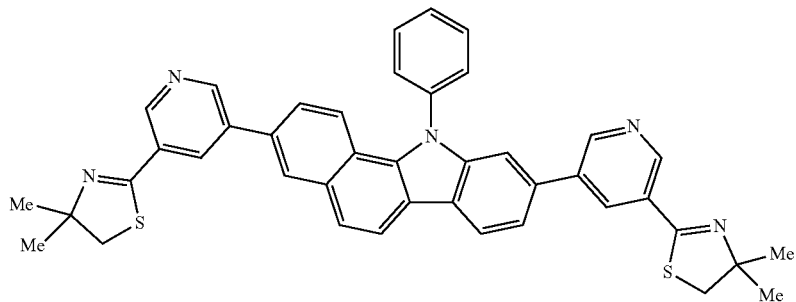
(1-2-393)

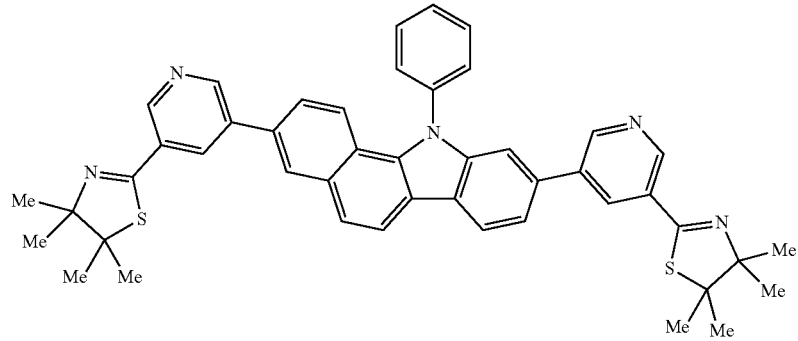
(1-2-394)
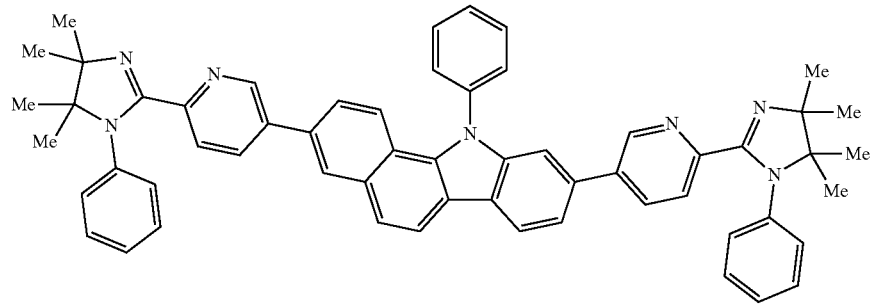
(1-2-395)
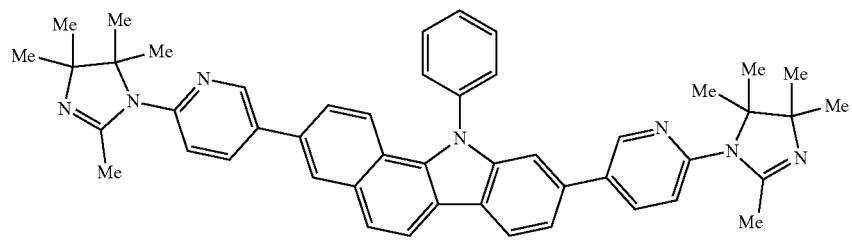
(1-2-396)
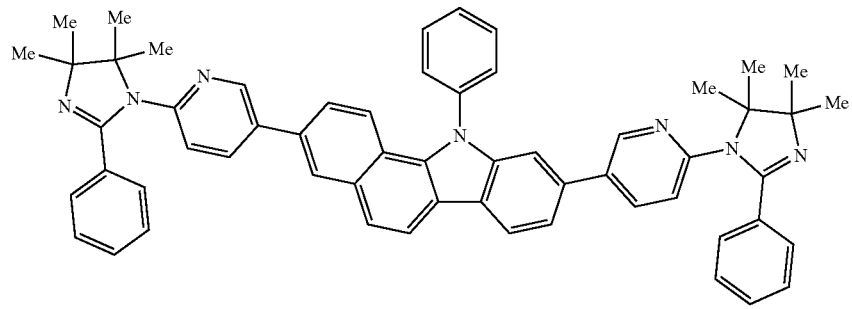
(1-2-397)
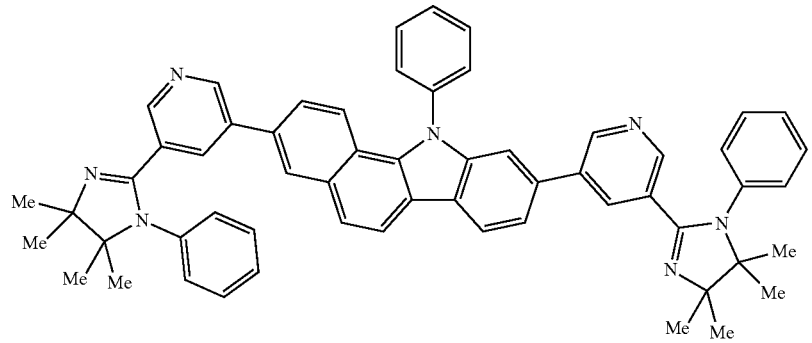
(1-2-398)

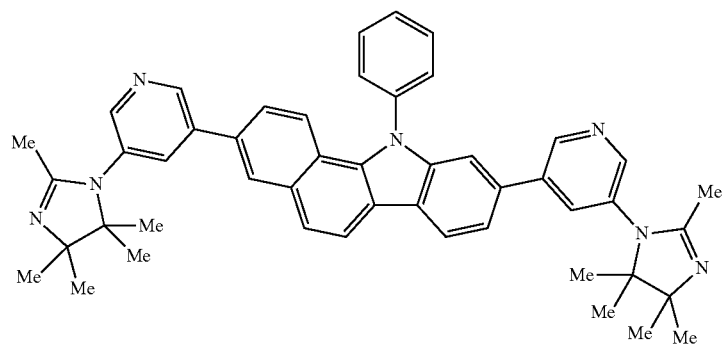
(1-2-399)
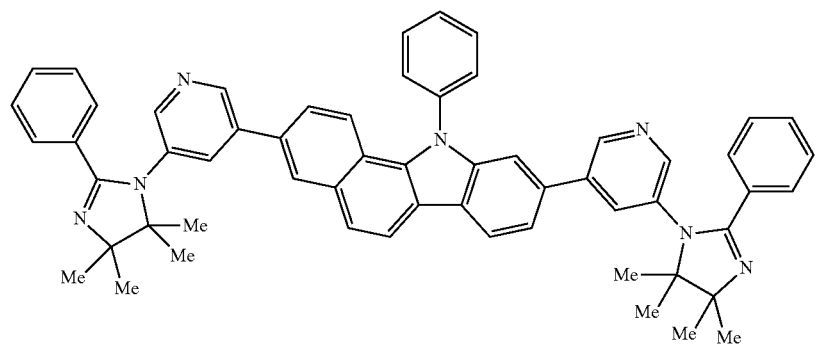
(1-2-400)
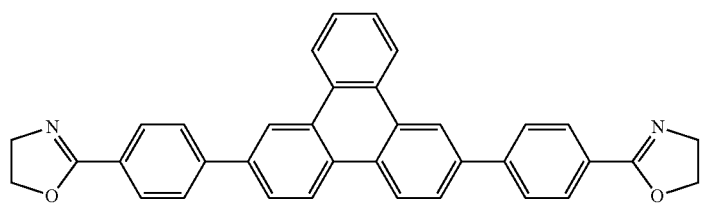
(1-2-401)
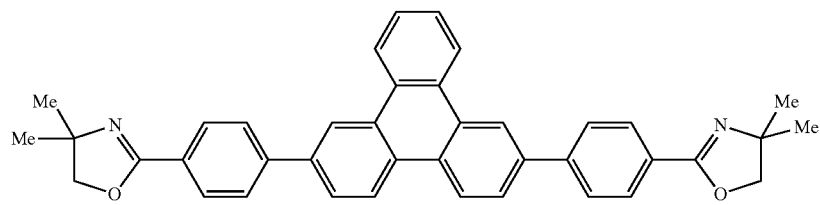
(1-2-402)
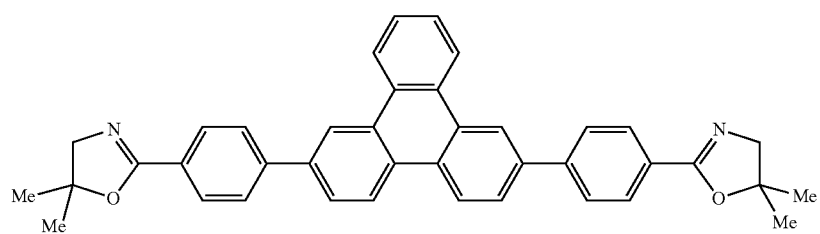
(1-2-403)
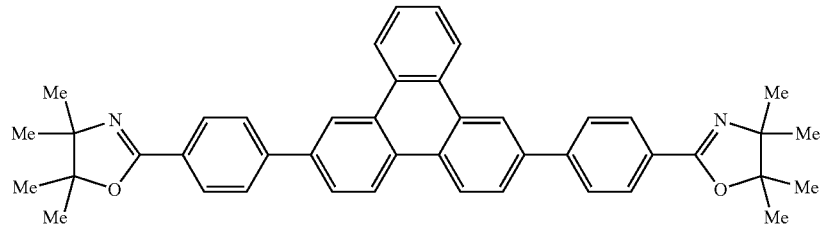
(1-2-404)

-continued
(1-2-405)
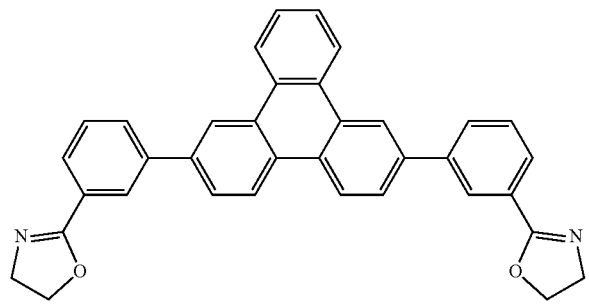
(1-2-406)
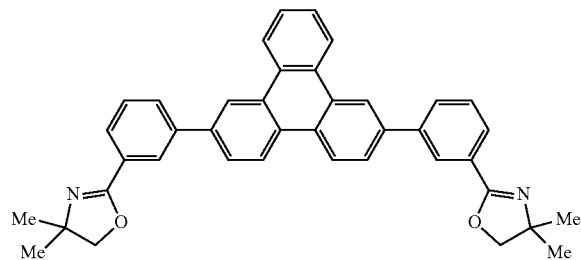
(1-2-407)
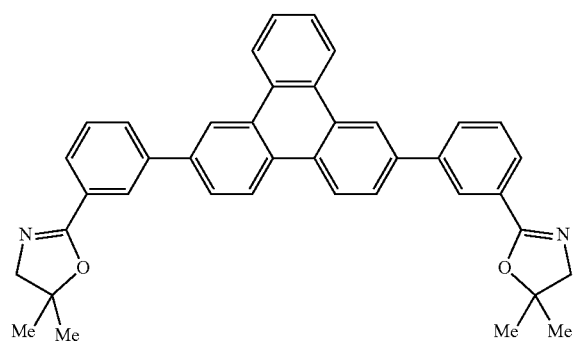
(1-2-408)
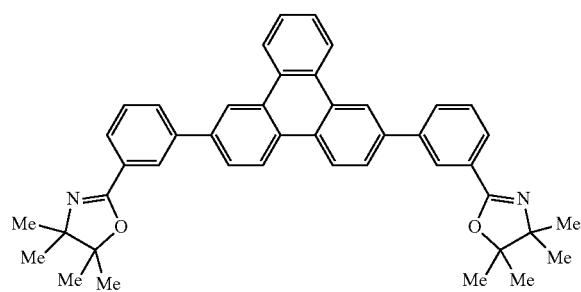
(1-2-411)
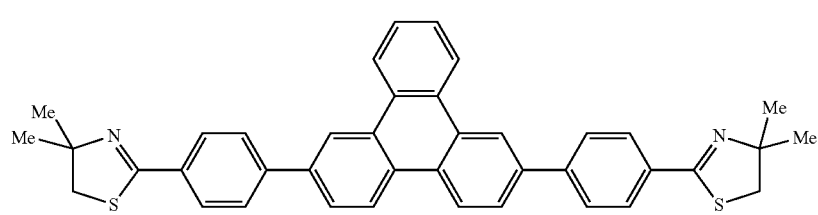
(1-2-412)
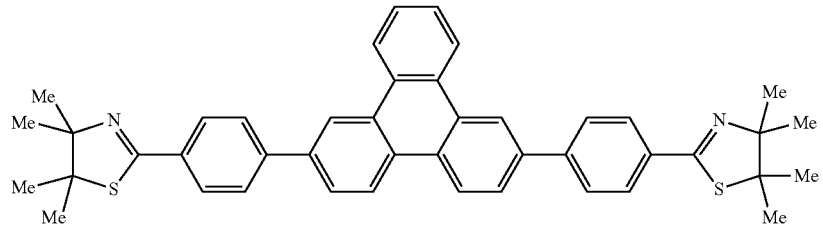
(1-2-413)
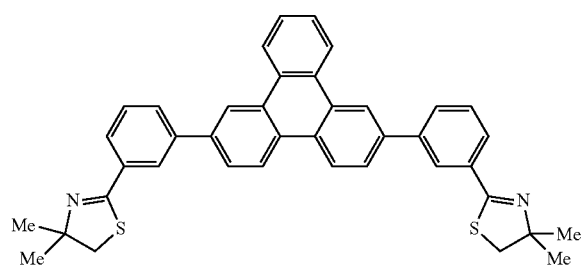
(1-2-414)
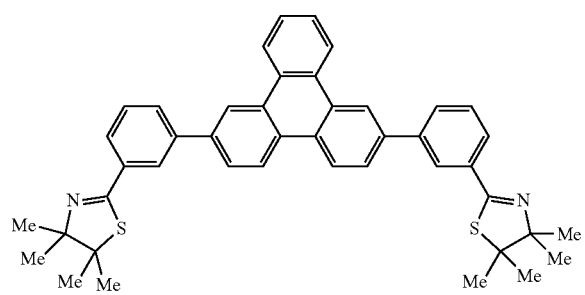

-continued
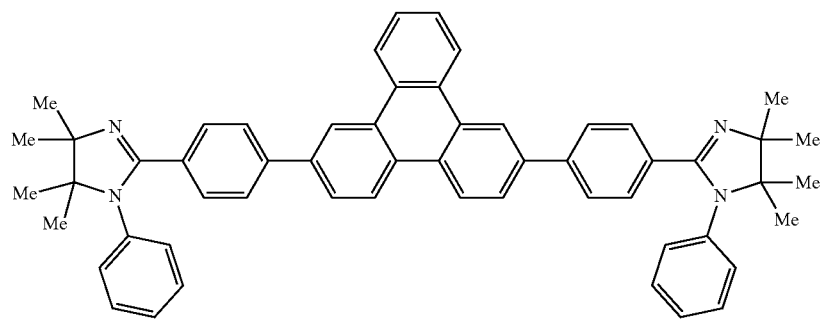
(1-2-415)
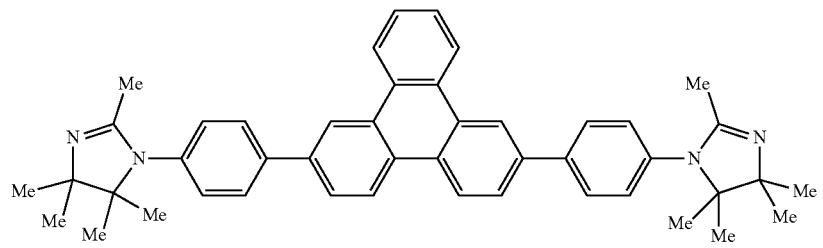
(1-2-416)
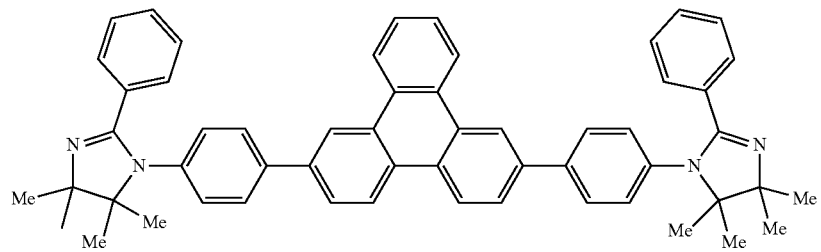
(1-2-417)
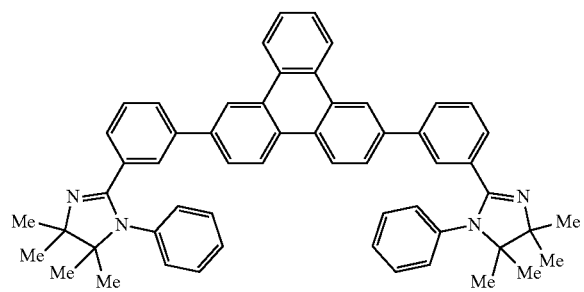
(1-2-418)
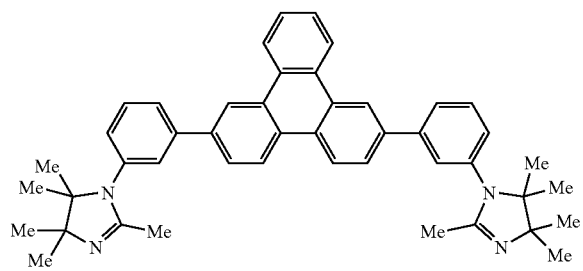
(1-2-419)
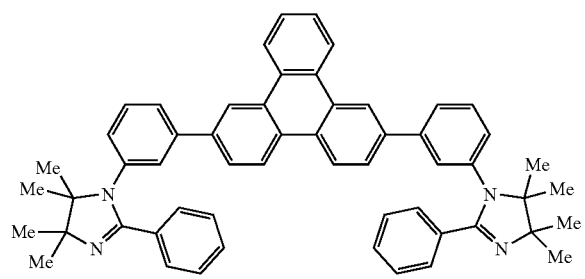
(1-2-420)
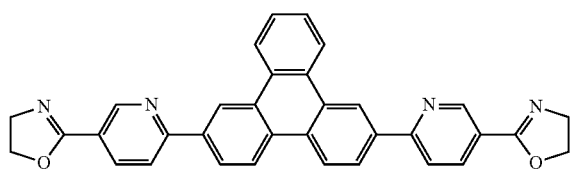
(1-2-421)
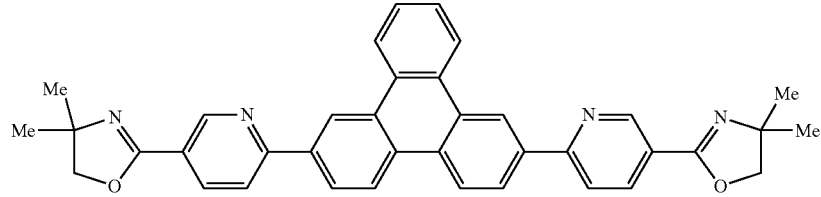
(1-2-422)

-continued
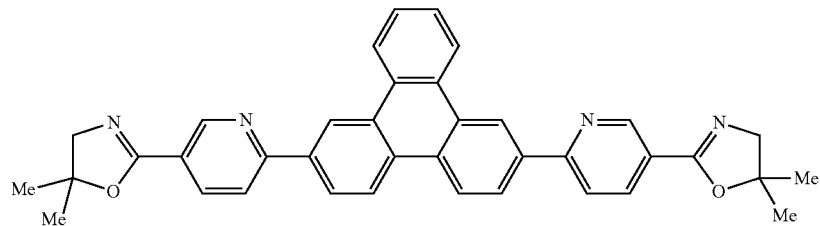
(1-2-423)
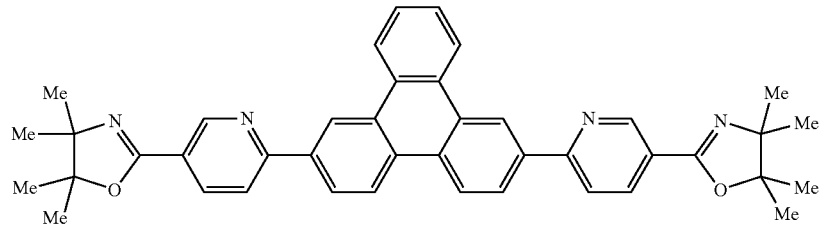
(1-2-424)
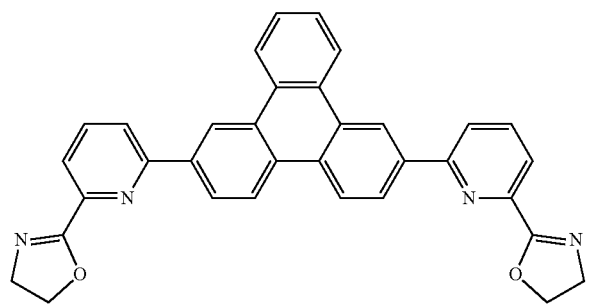
(1-2-425)
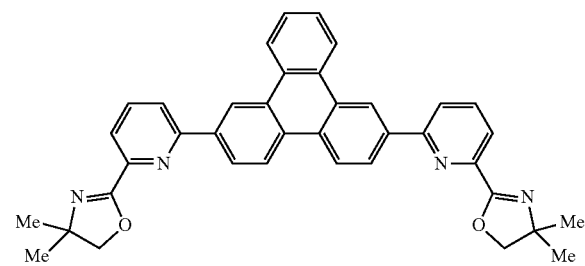
(1-2-426)
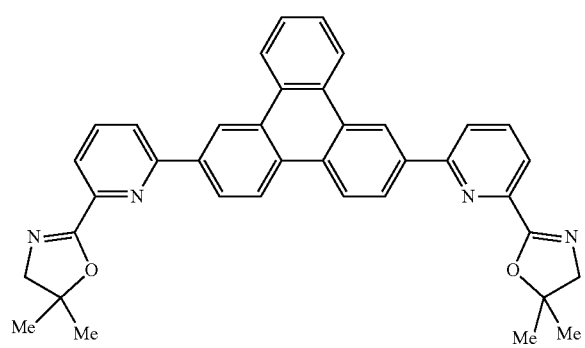
(1-2-427)
(1-2-428)
(1-2-431)
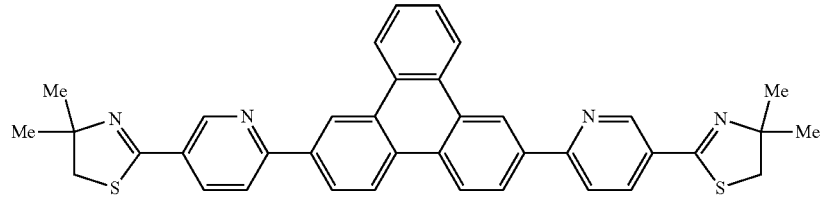
(1-2-432)
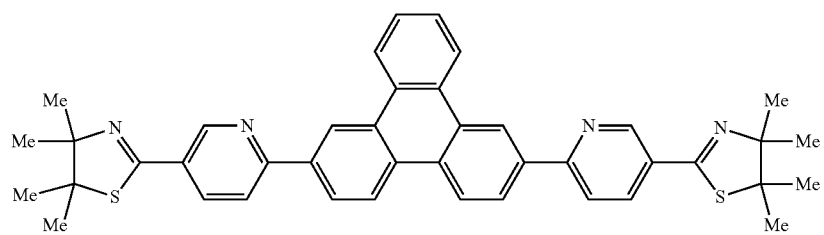

(1-2-433)
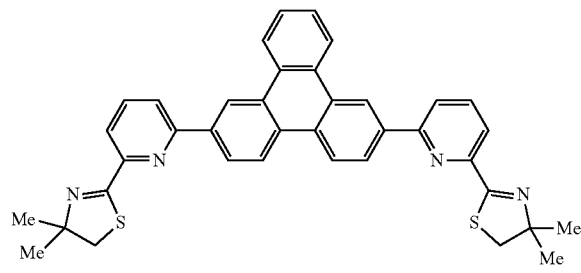
(1-2-434)
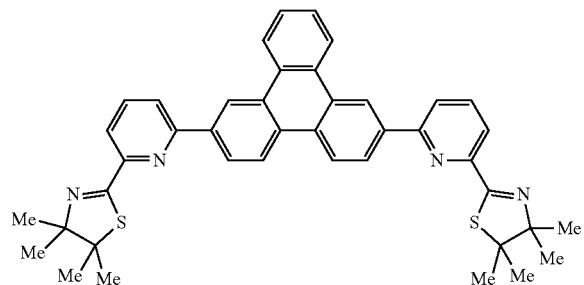
(1-2-435)
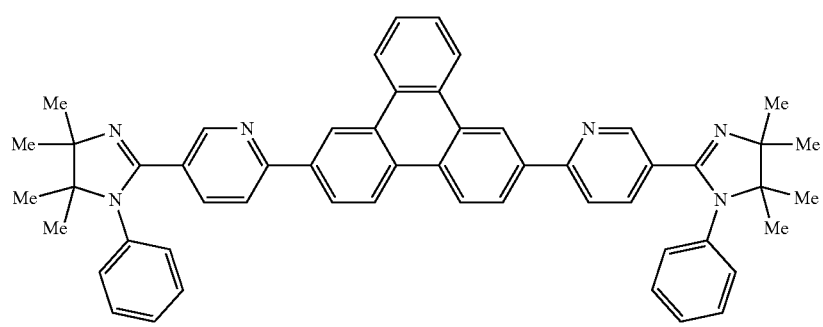
(1-2-436)
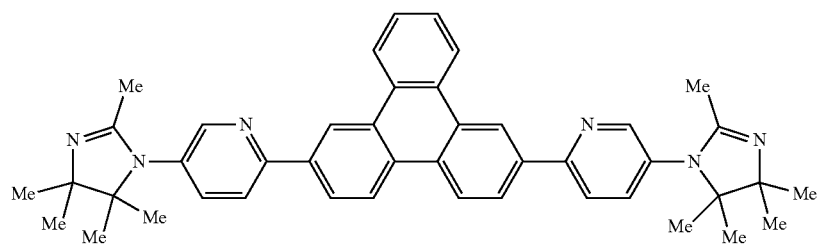
(1-2-437)
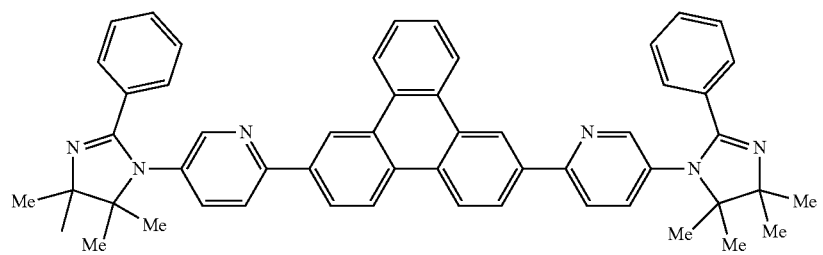
(1-2-438)
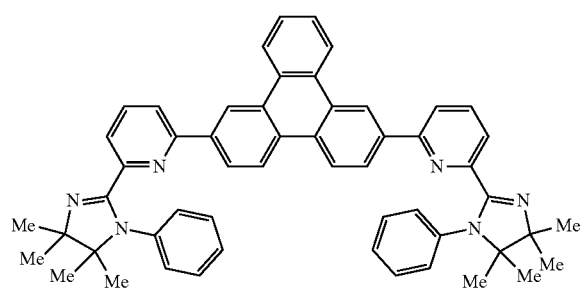
(1-2-439)
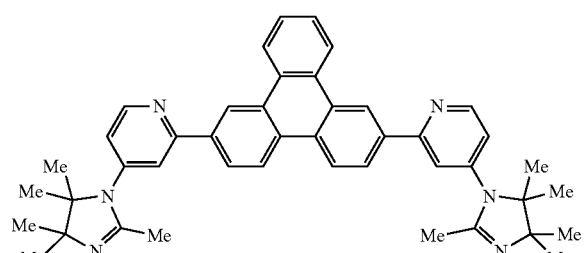

-continued
(1-2-441)
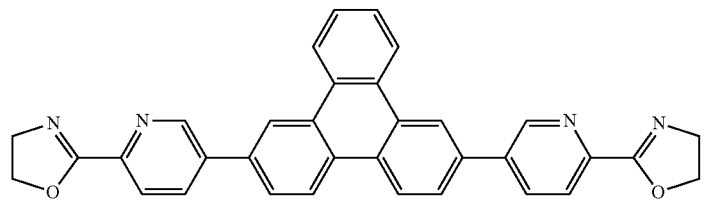
(1-2-442)
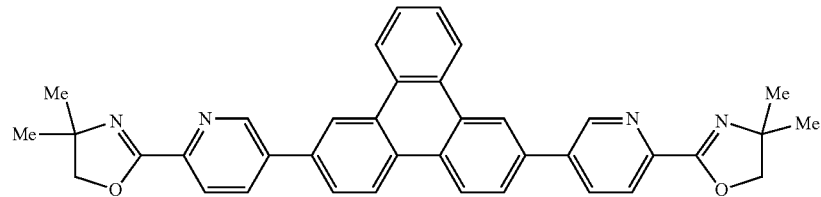
(1-2-443)
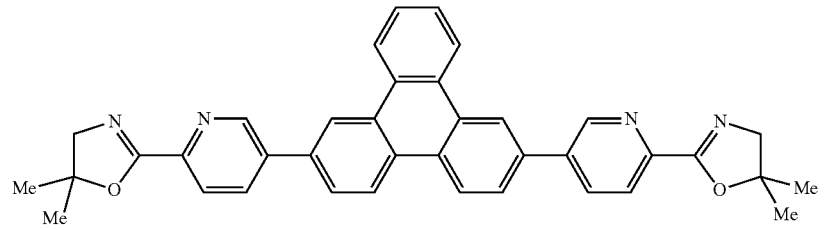
(1-2-444)
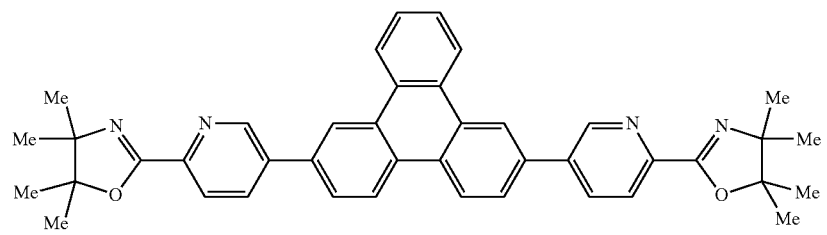
(1-2-445)
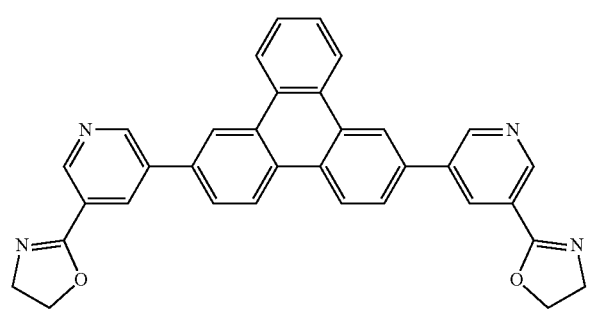
(1-2-446)
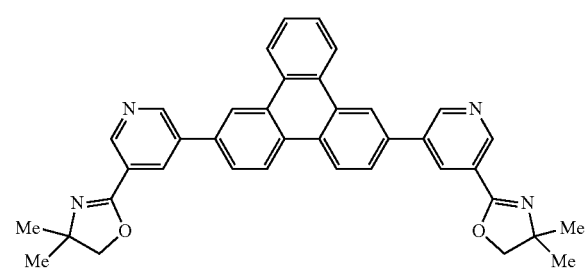
(1-2-447)
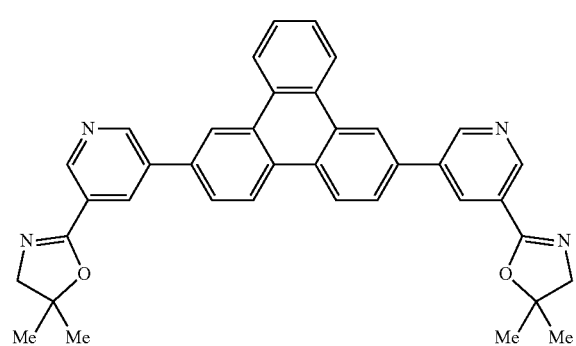
(1-2-448)
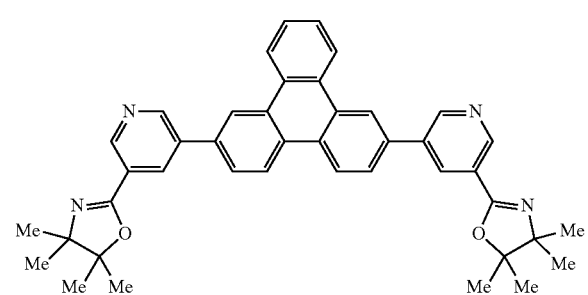

-continued
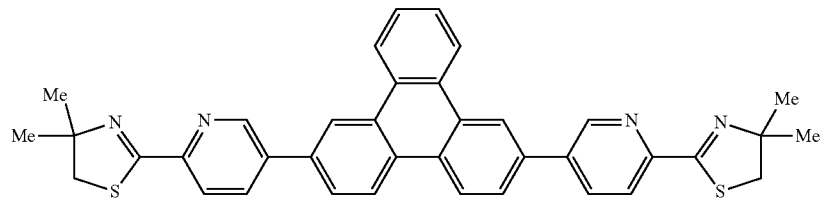
(1-2-451)
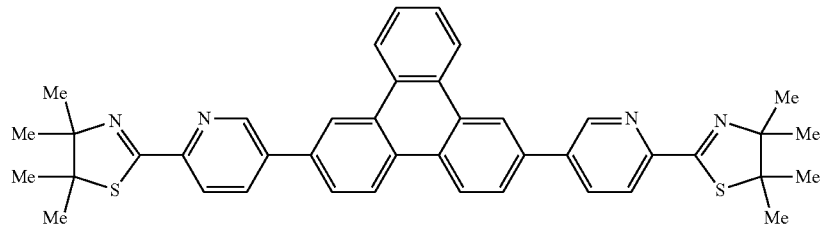
(1-2-452)
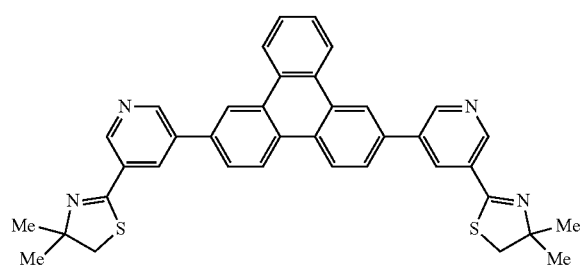
(1-2-453)
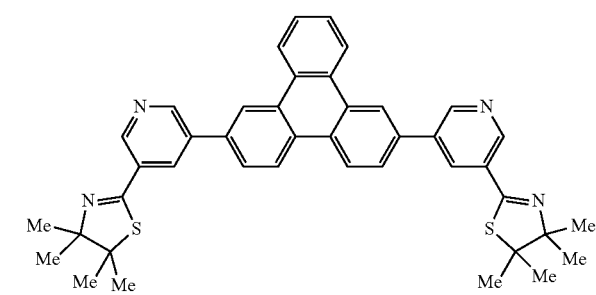
(1-2-454)
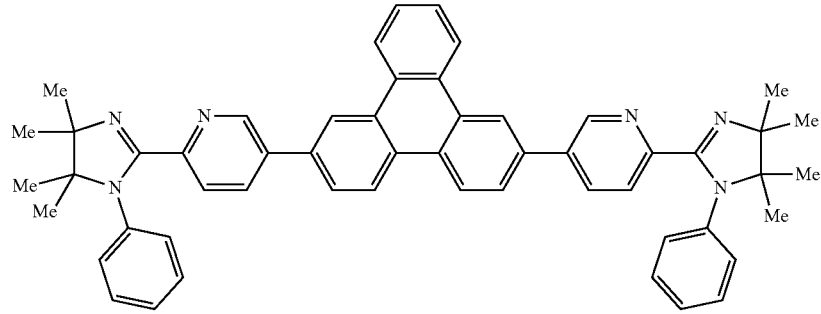
(1-2-455)
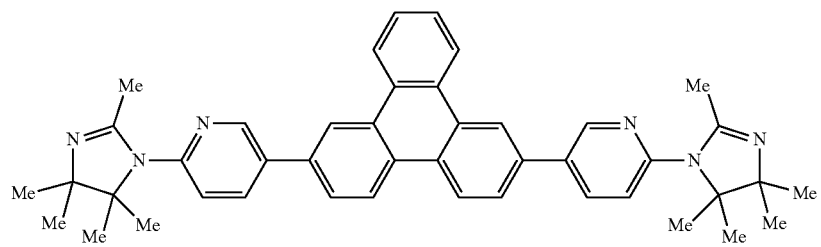
(1-2--456)
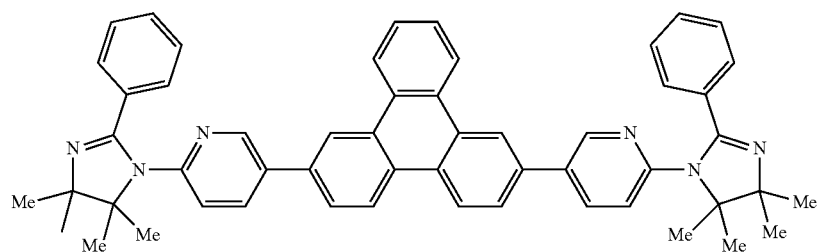
(1-2-457)

-continued
(1-2-458)
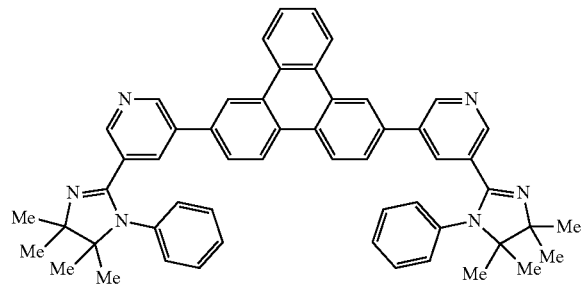
(1-2-459)
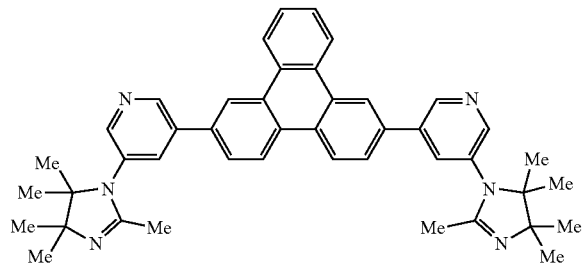
(1-2-461)
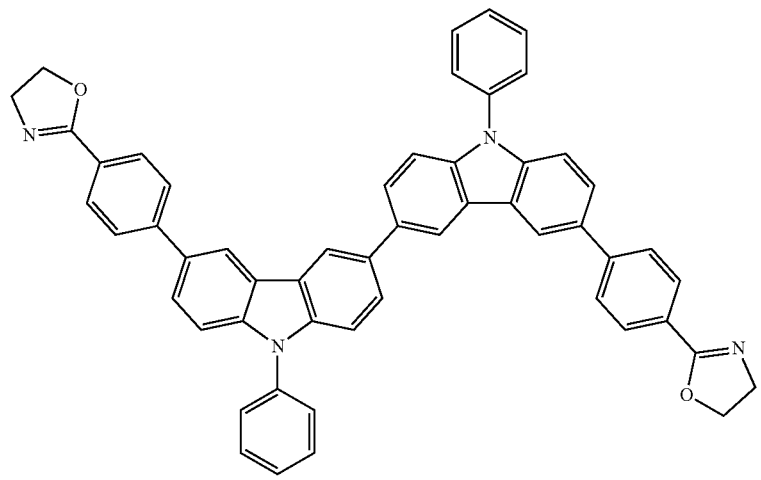
(1-2-462)
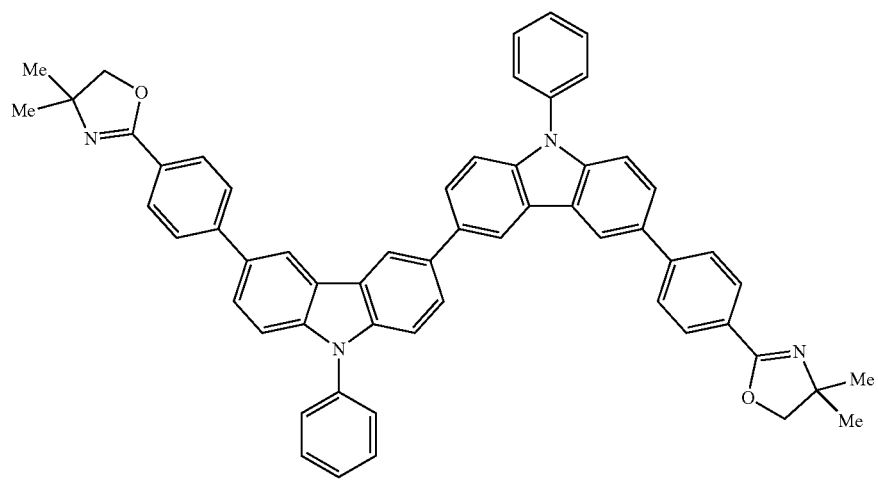

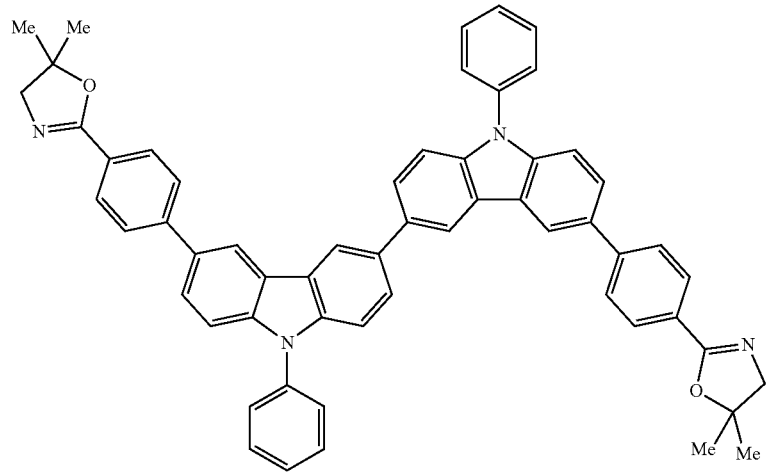
(1-2-463)
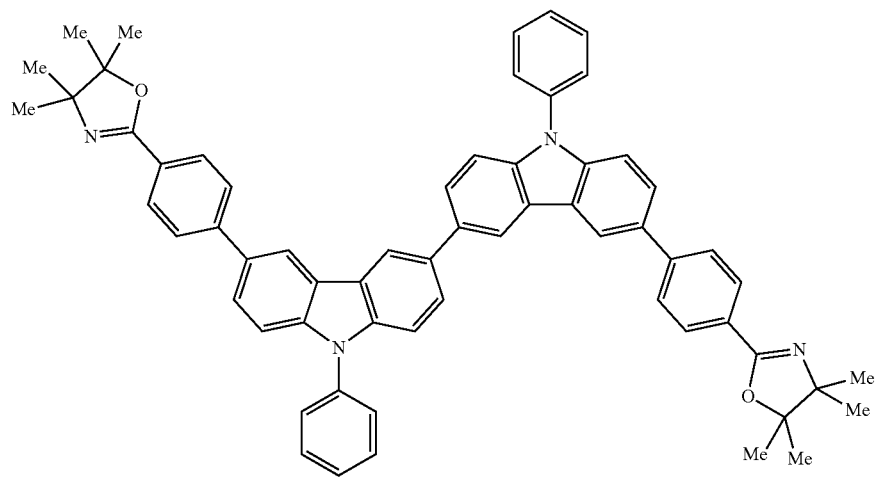
(1-2-464)
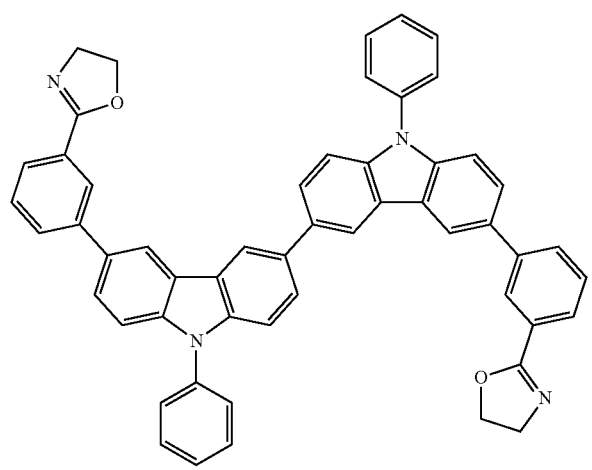
(1-2-465)
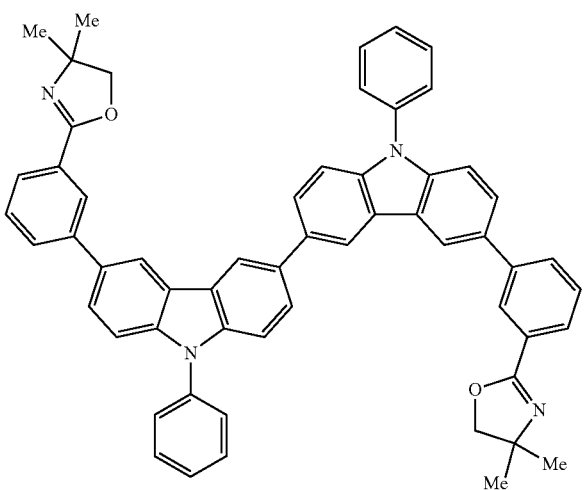
(1-2-466)

-continued
(1-2-467)
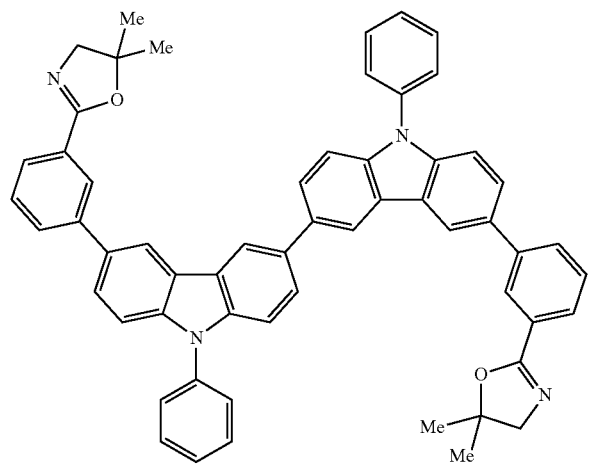
(1-2-468)
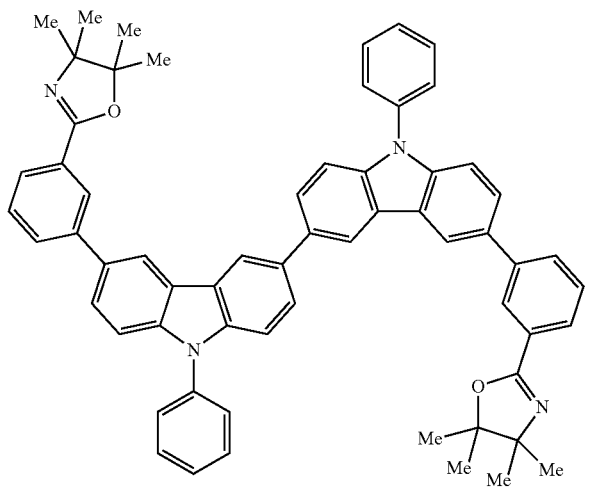
(1-2-471)
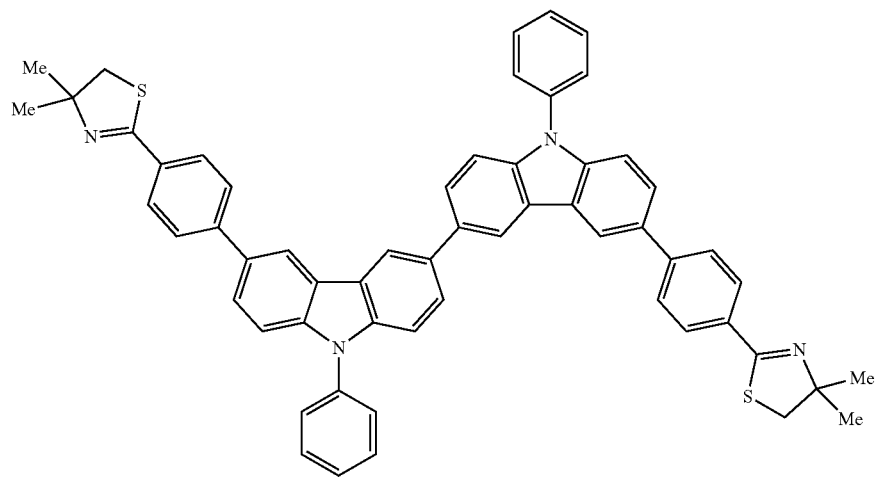
(1-2-472)
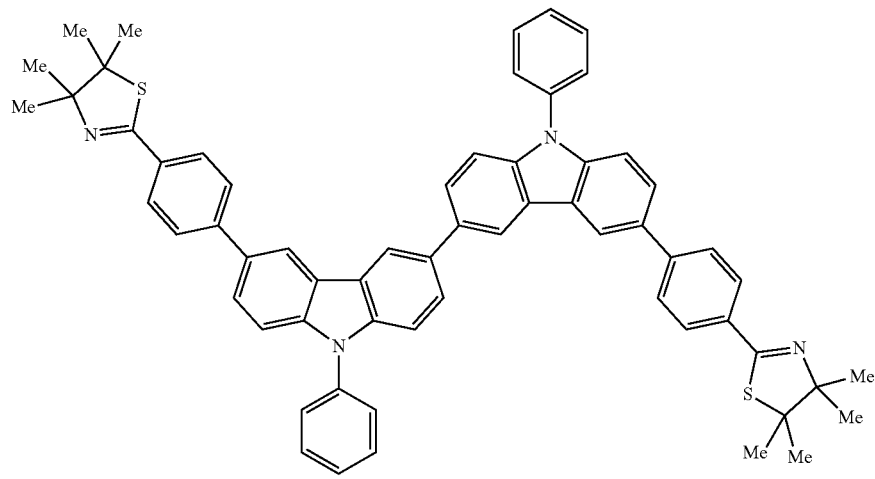

(1-2-473)
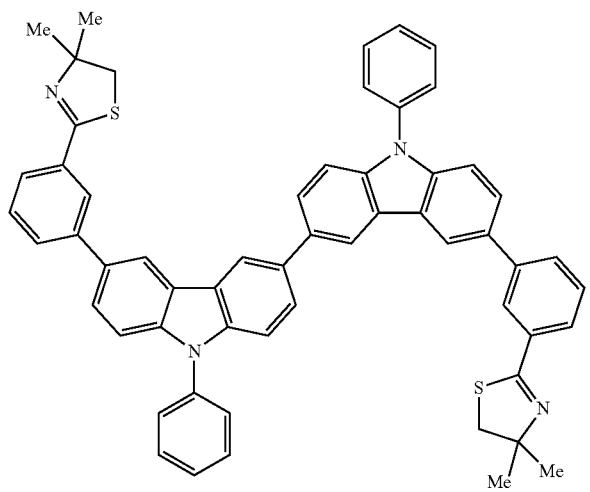
(1-2-474)
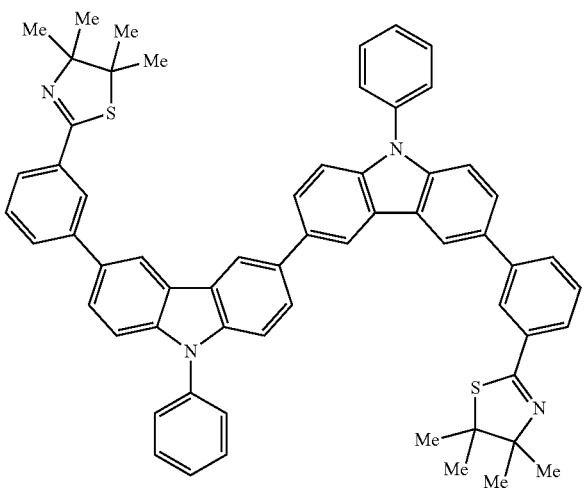
(1-2-475)
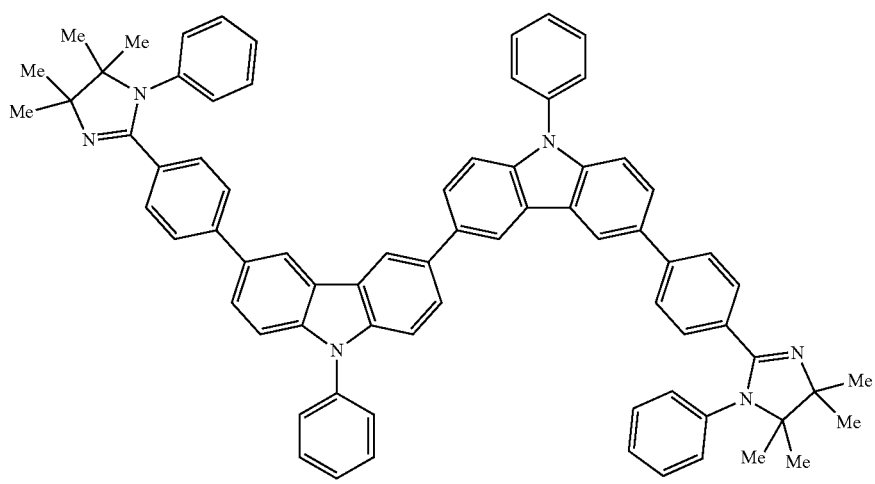
(1-2-476)
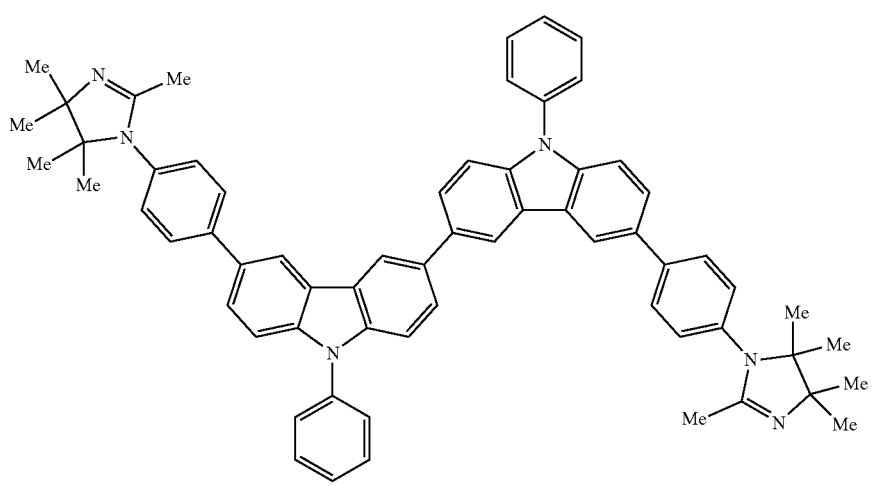

(1-2-477)
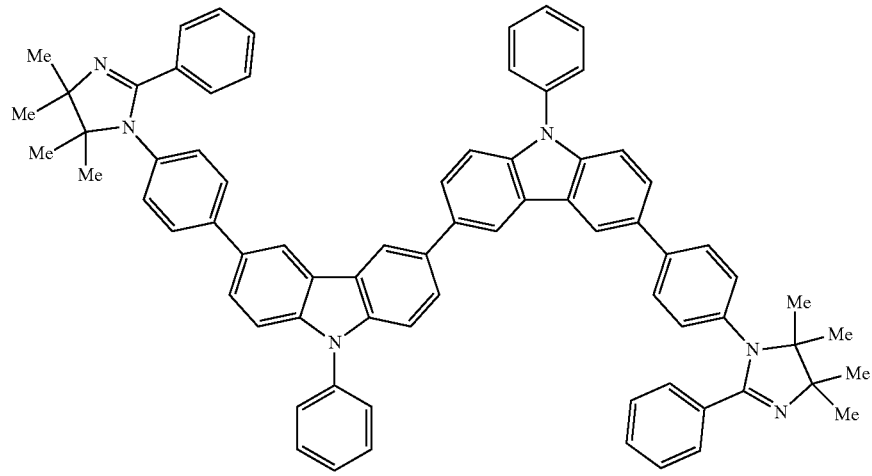
(1-2-478)
(1-2-479)
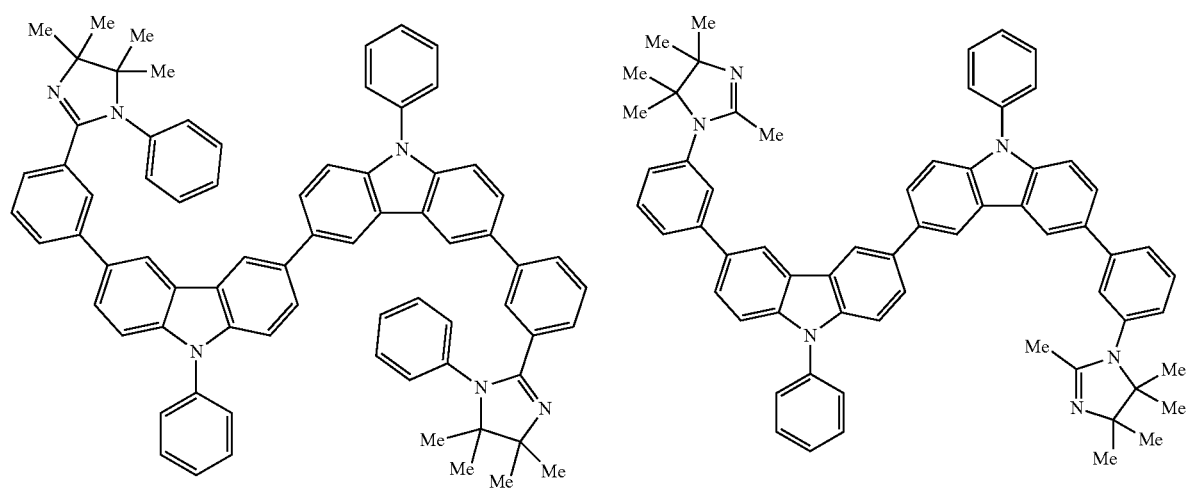
(1-2-480)
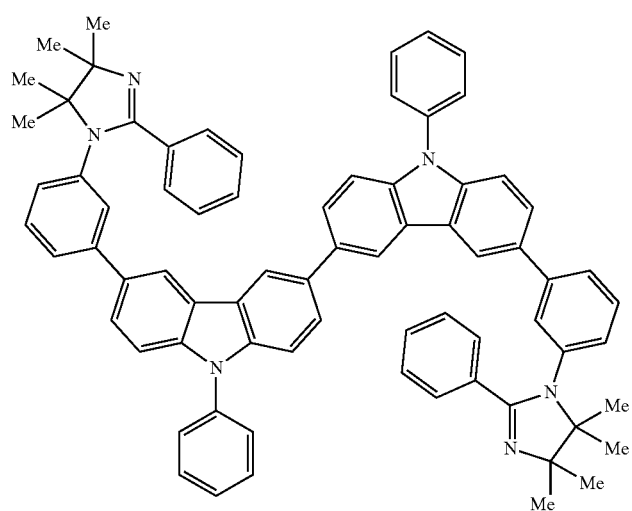

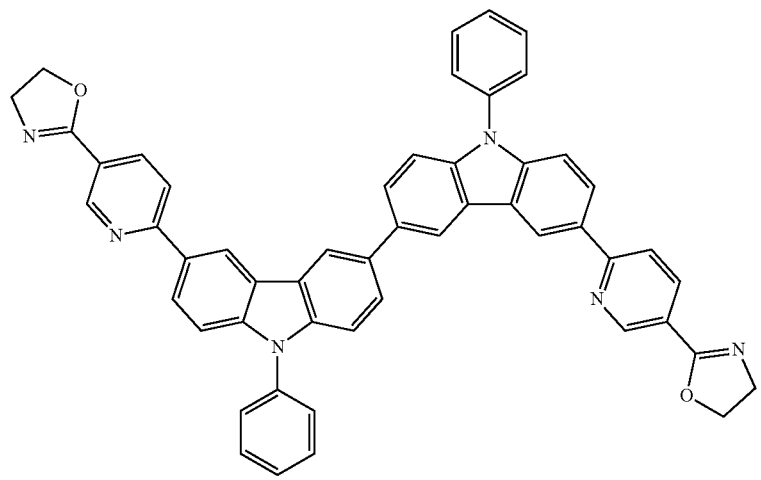
(1-2-481)
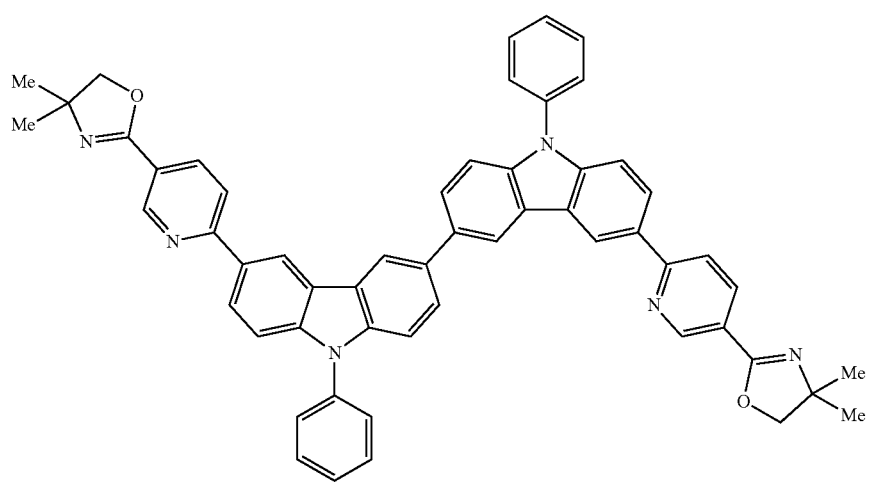
(1-2-482)
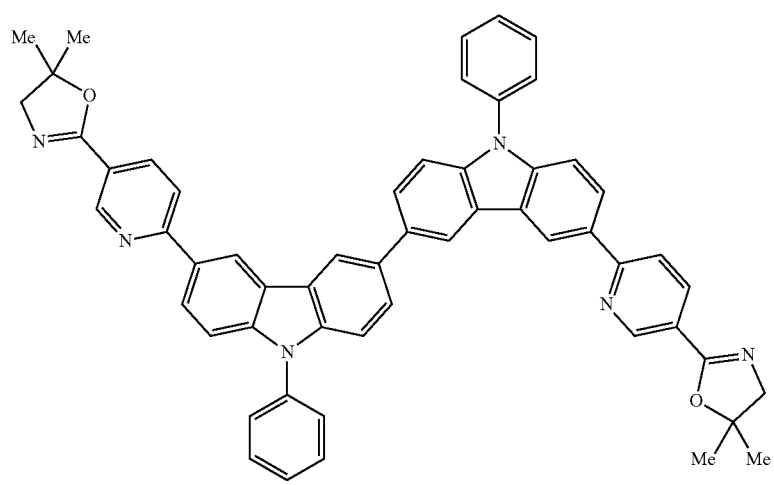
(1-2-483)

(1-2-484)
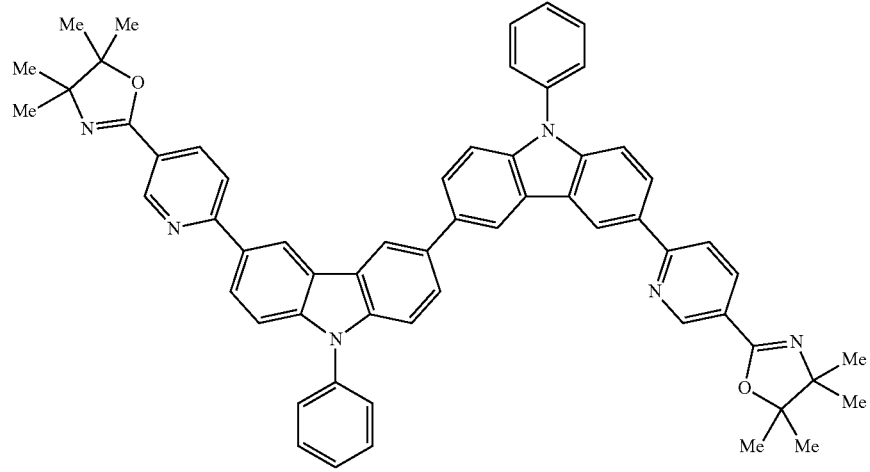
(1-2-485) (1-2-486)
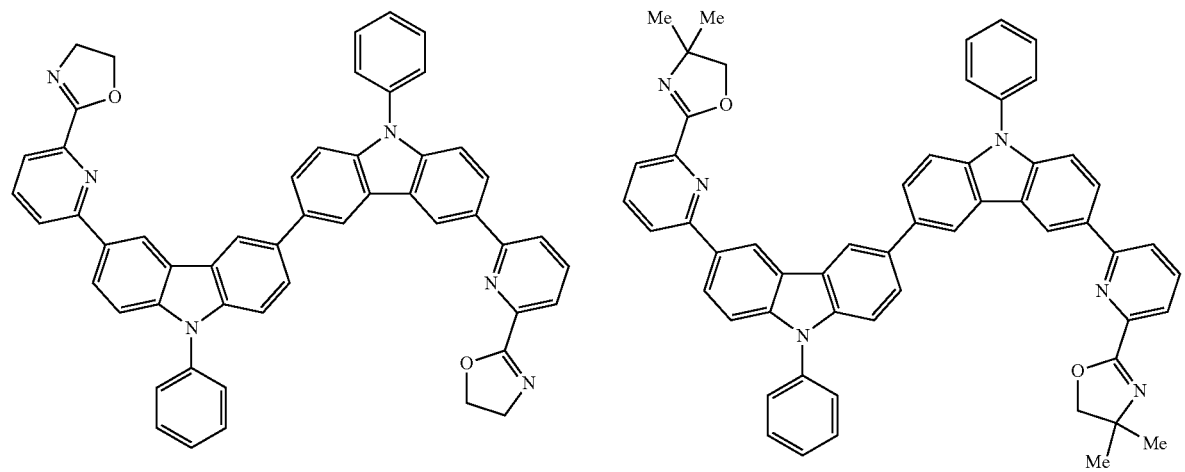
(1-2-487) (1-2-488)
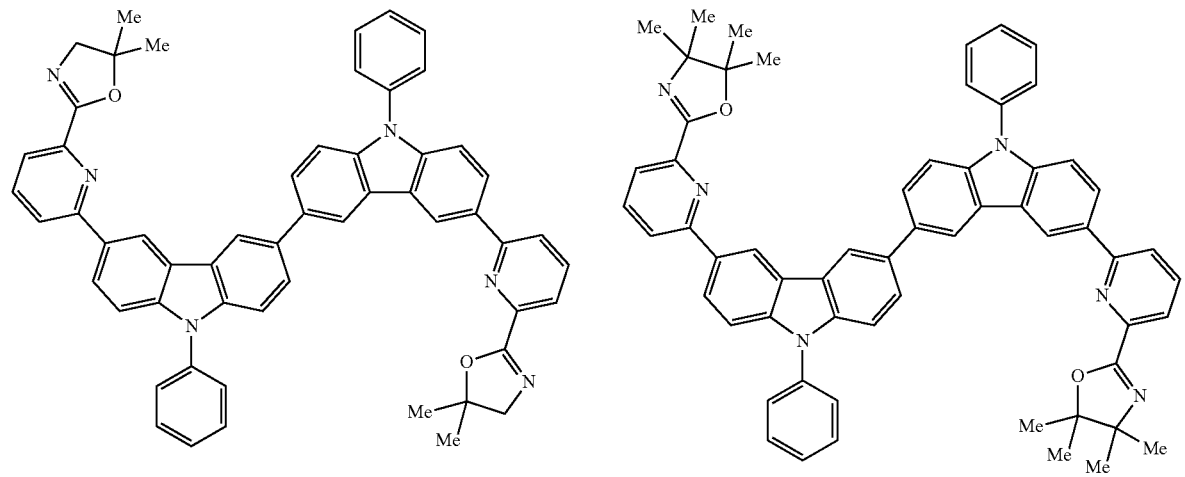

(1-2-491)
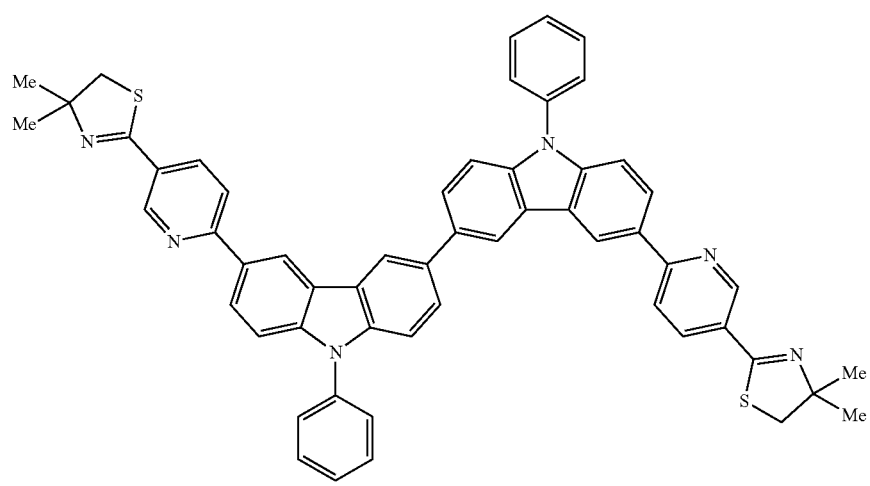
(1-2-492)
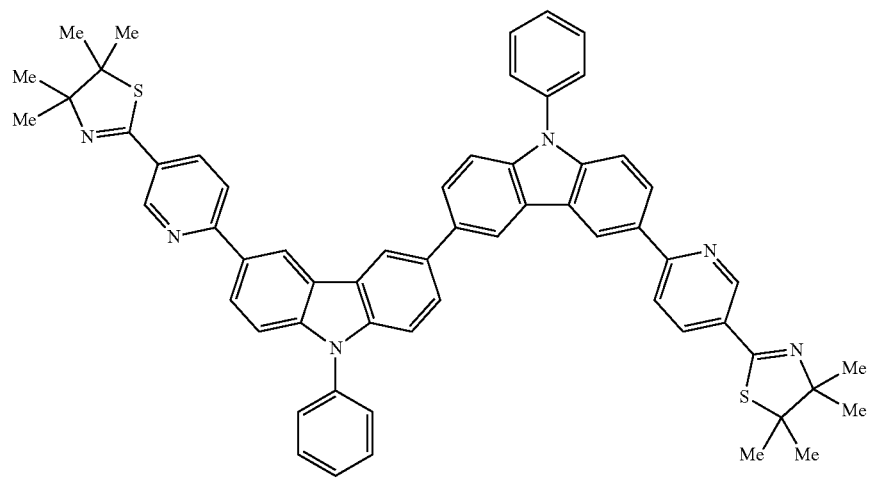
(1-2-493)
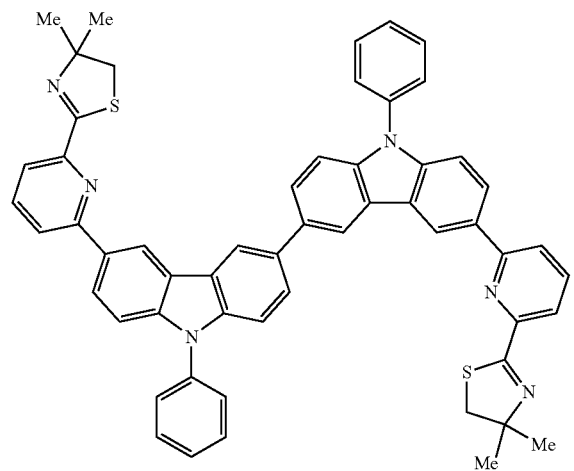
(1-2-494)
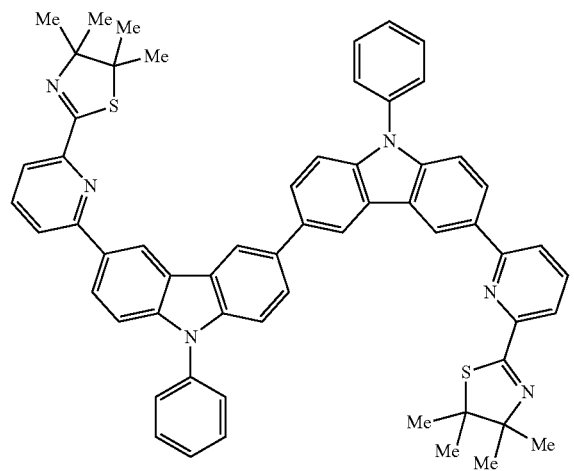

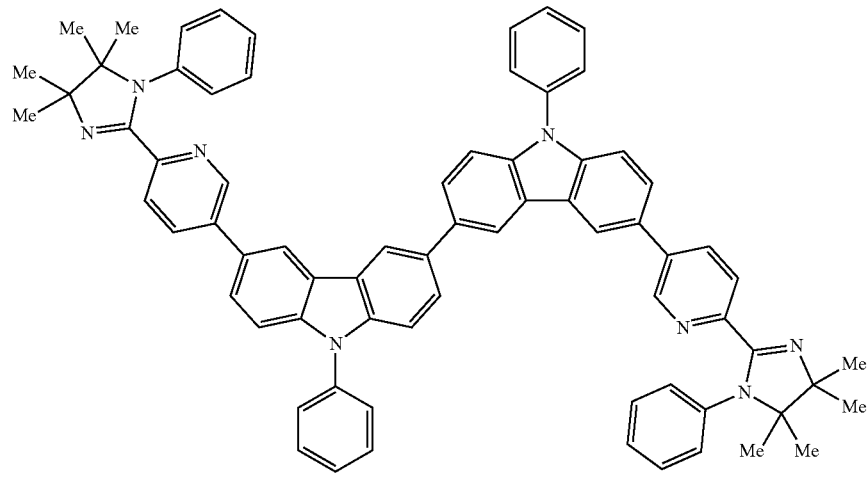
(1-2-495)
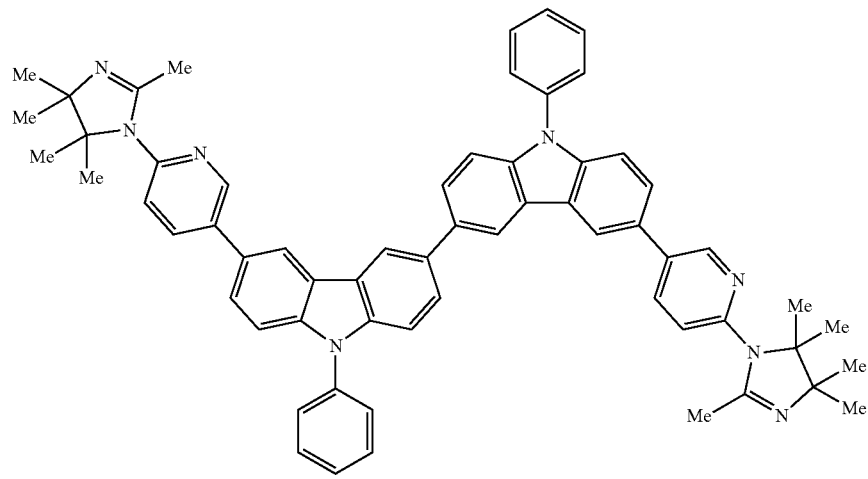
(1-2-496)
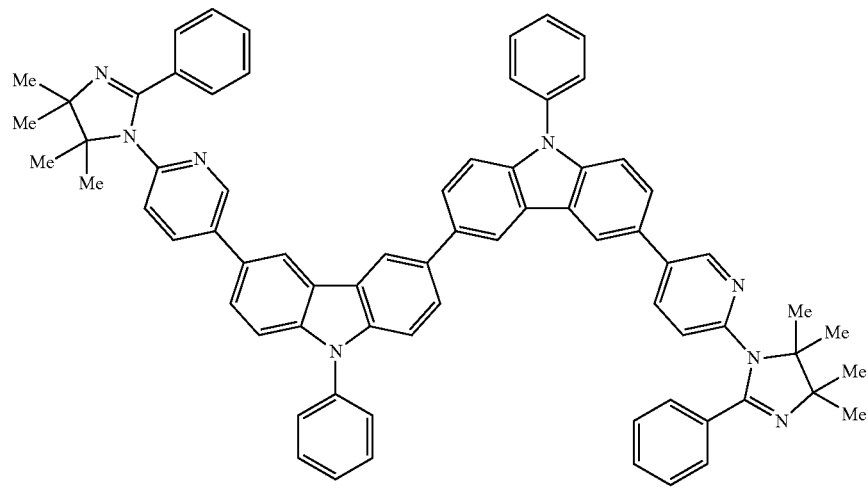
(1-2-497)

(1-2-498)
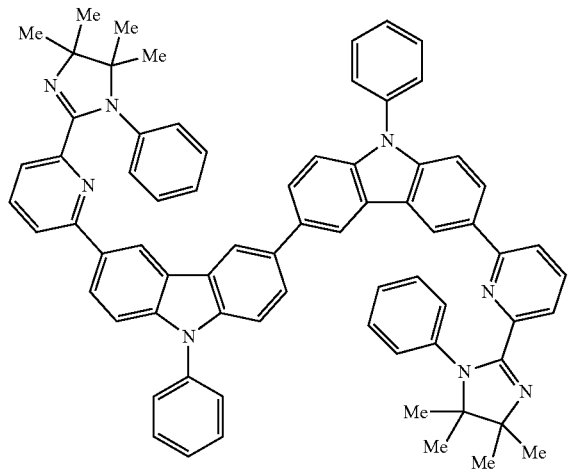
(1-2-499)
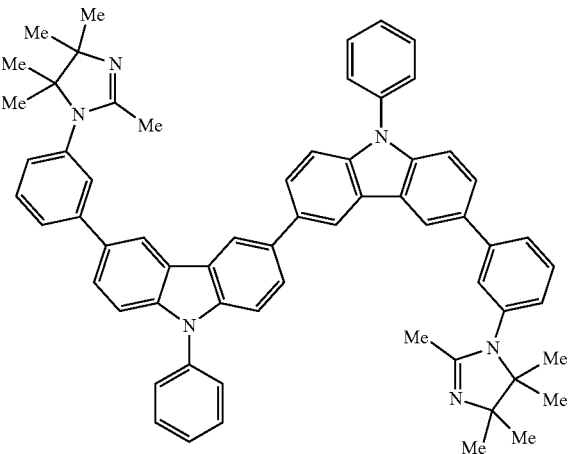
(1-2-500)
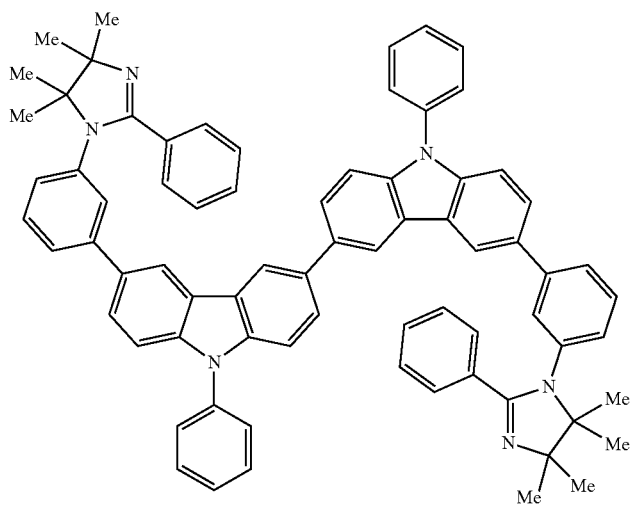
(1-2-501)
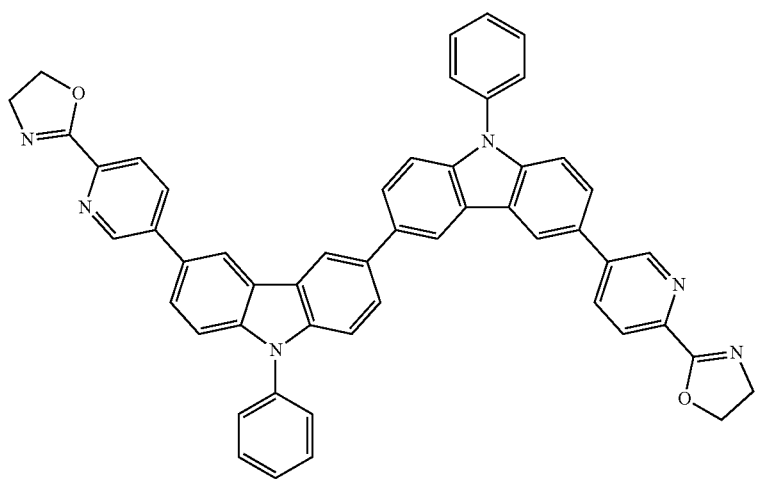

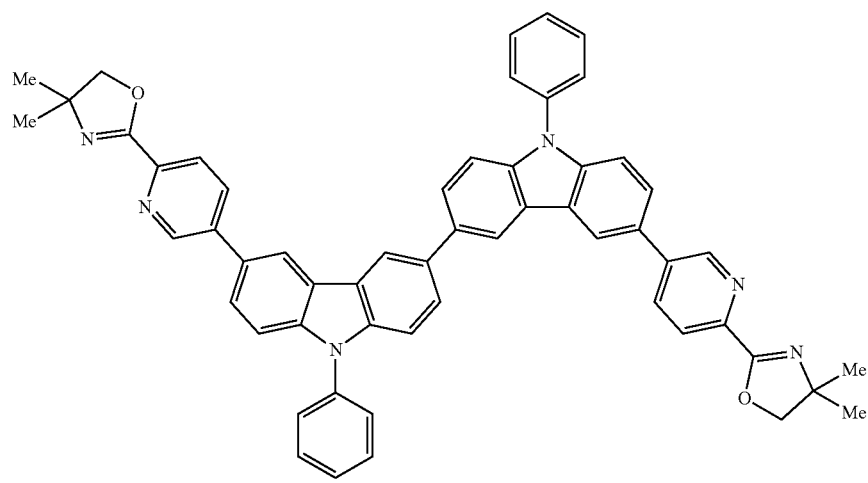
(1-2-502)
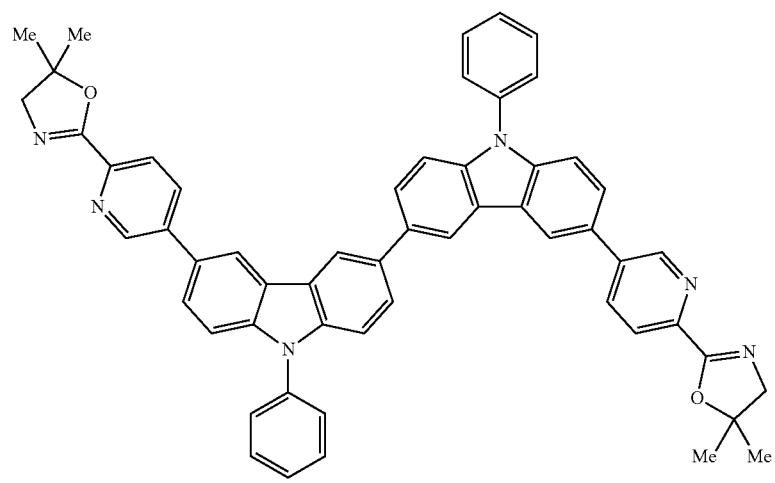
(1-2-503)
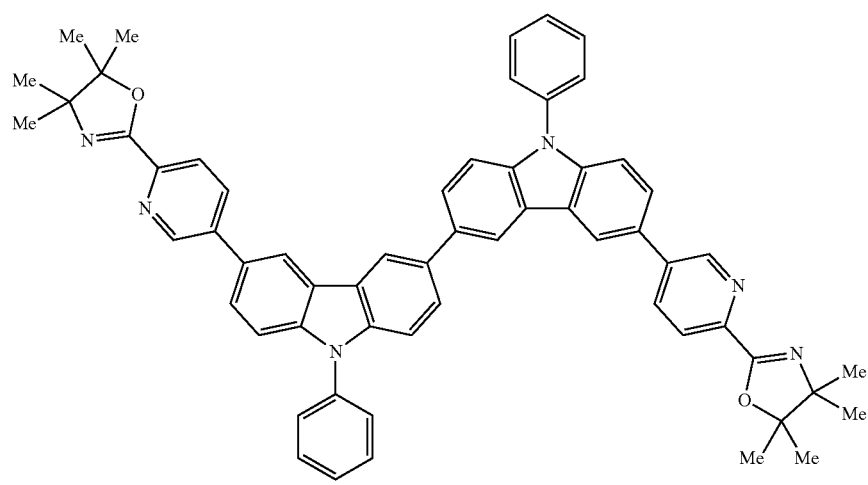
(1-2-504)

-continued
(1-2-505)
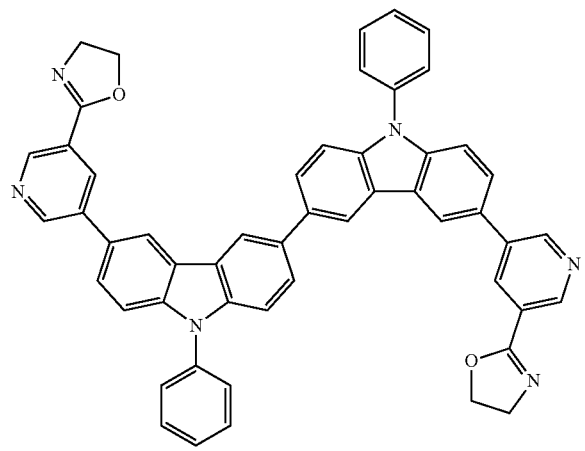
(1-2-506)
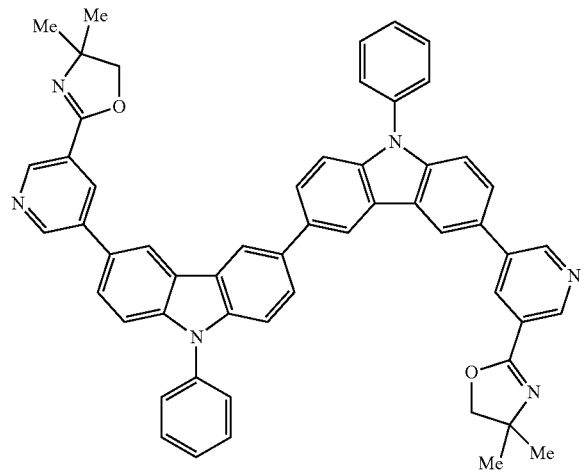
(1-2-507)
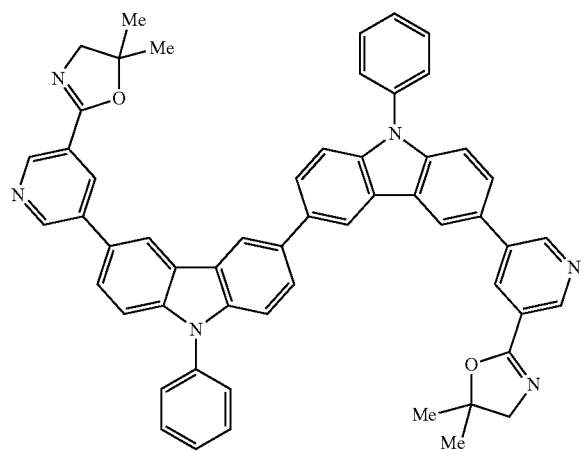
(1-2-508)
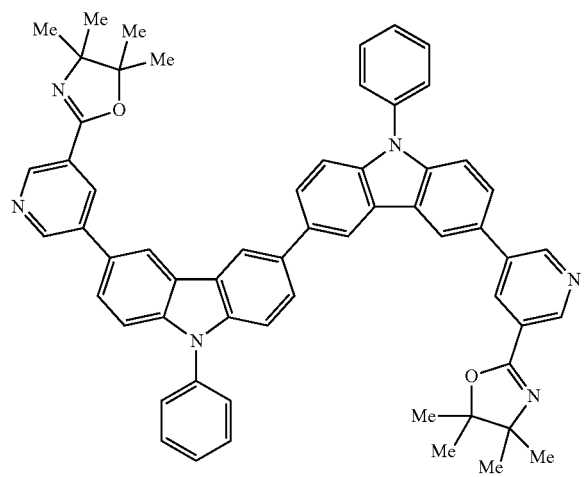
(1-2-511)
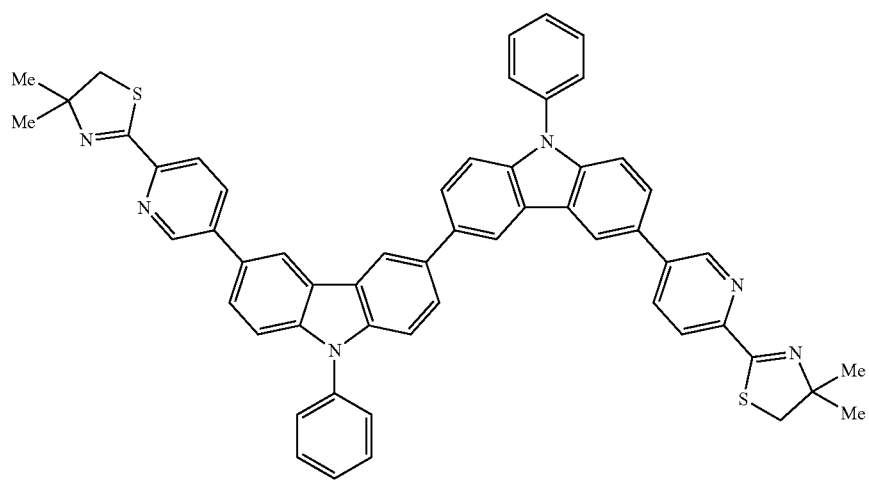

(1-2-512)
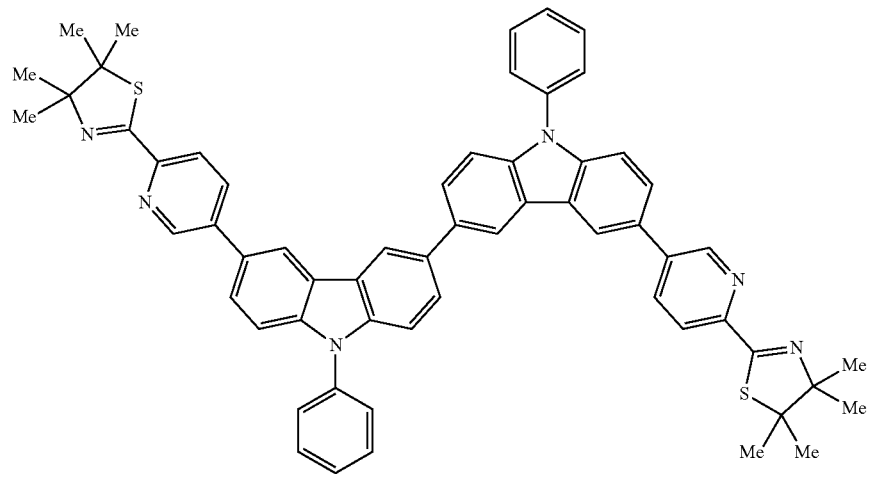
(1-2-513)
(1-2-514)
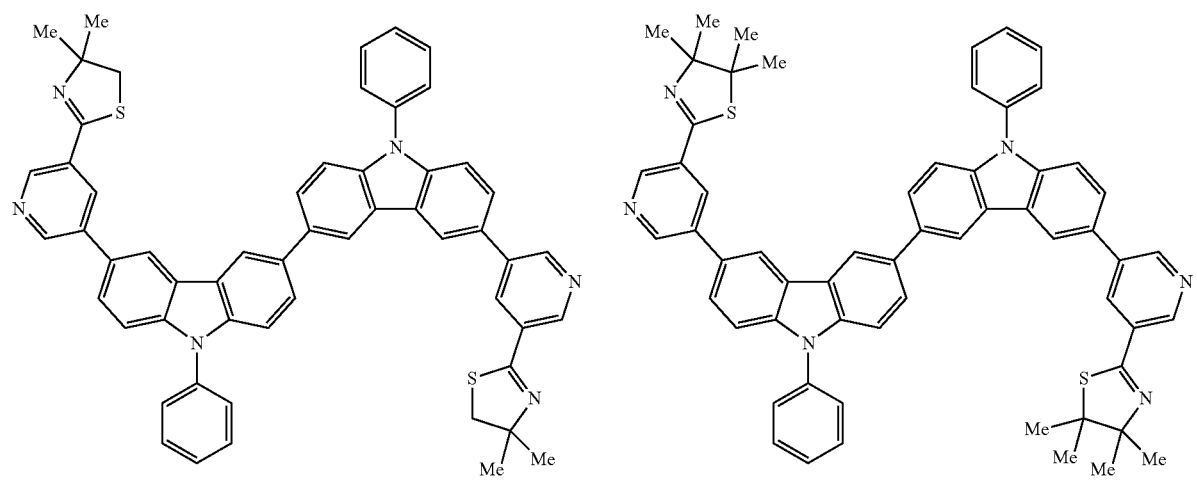
(1-2-515)
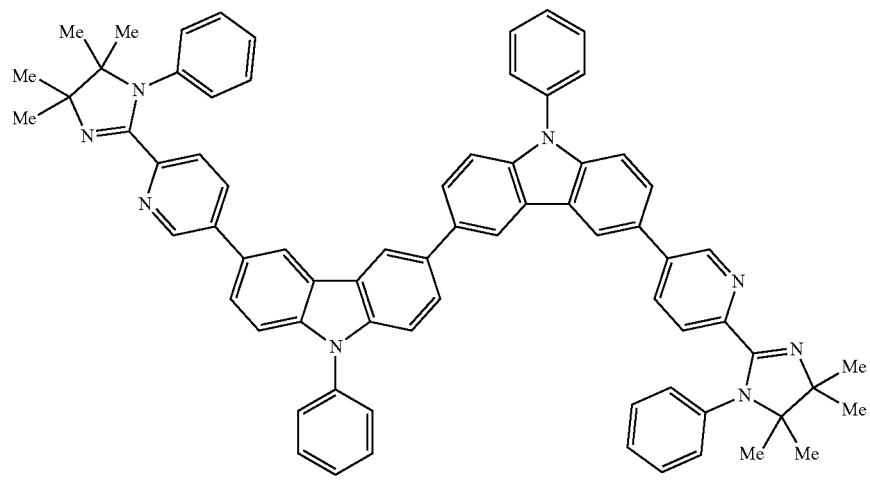

(1-2-516)
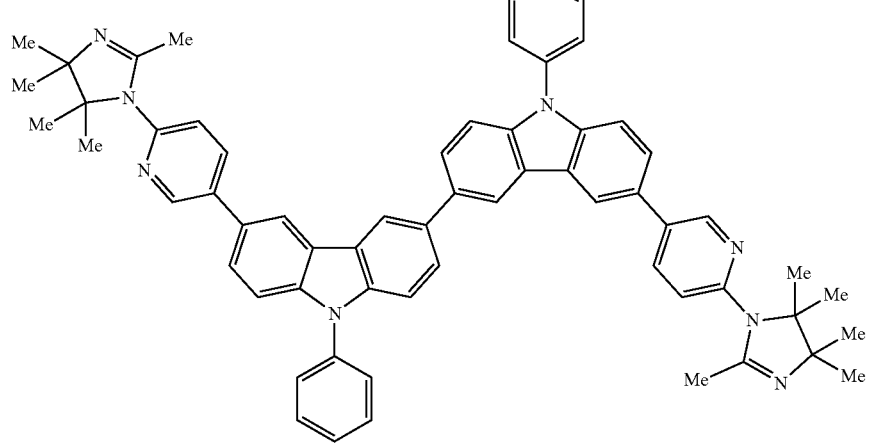
(1-2-517)
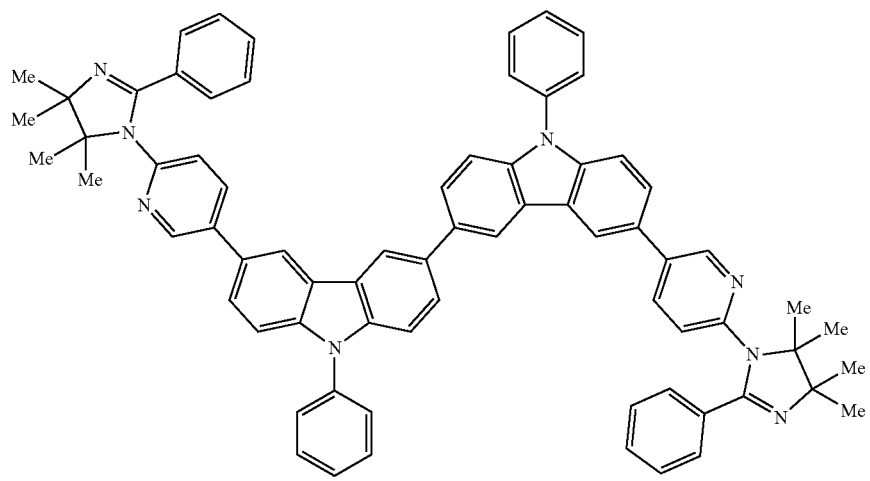
(1-2-518)
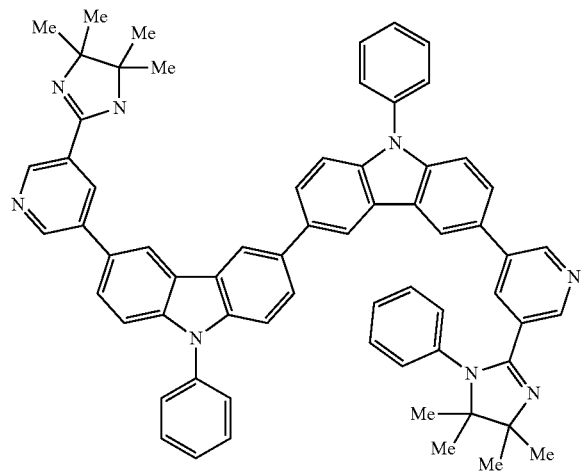
(1-2-519)
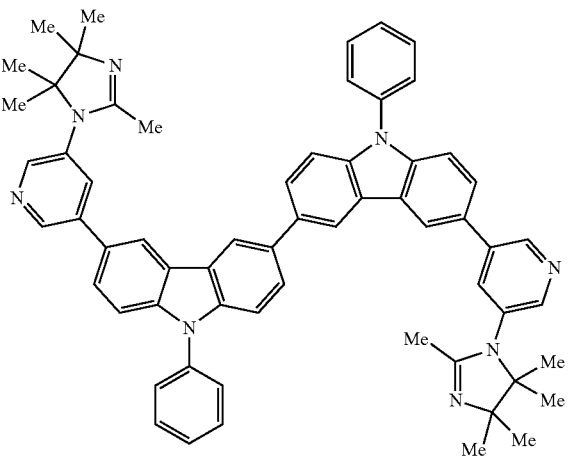

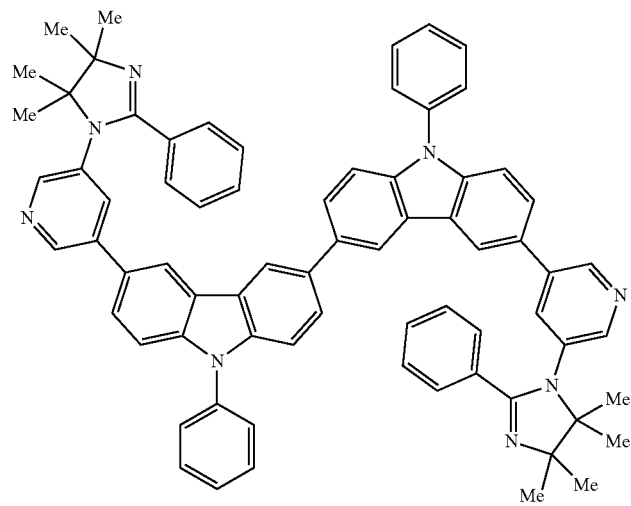
(1-2-520)
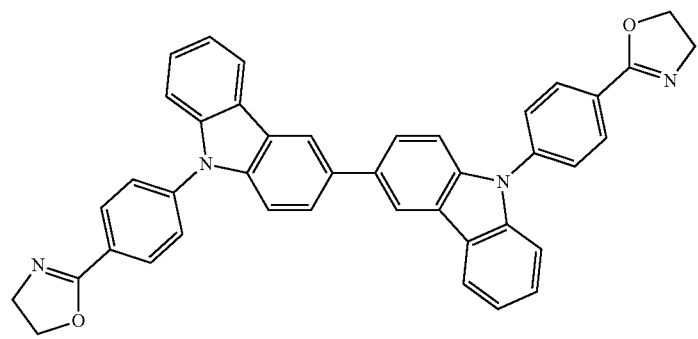
(1-2-521)
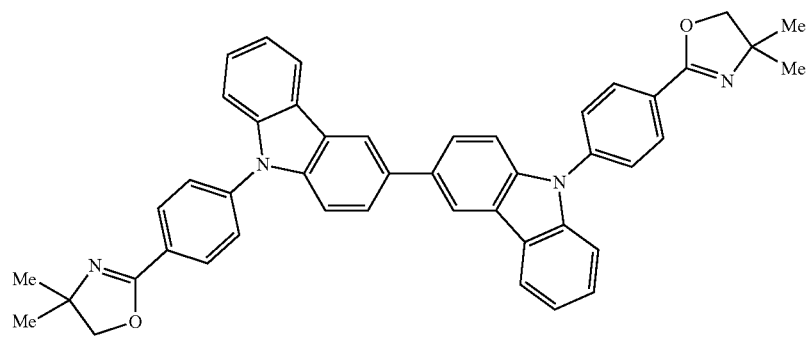
(1-2-522)
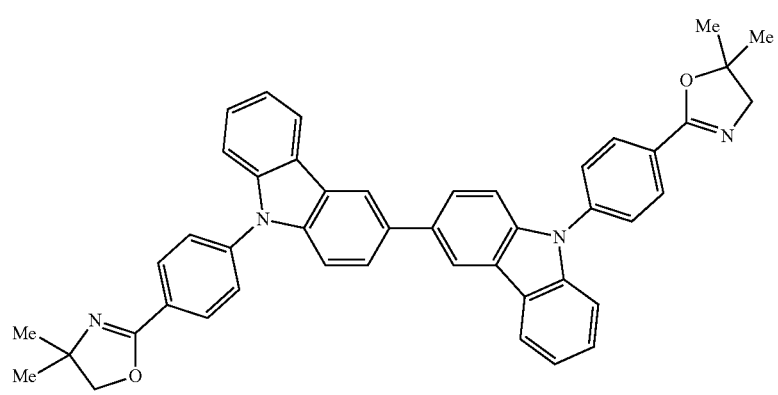
(1-2-523)

-continued
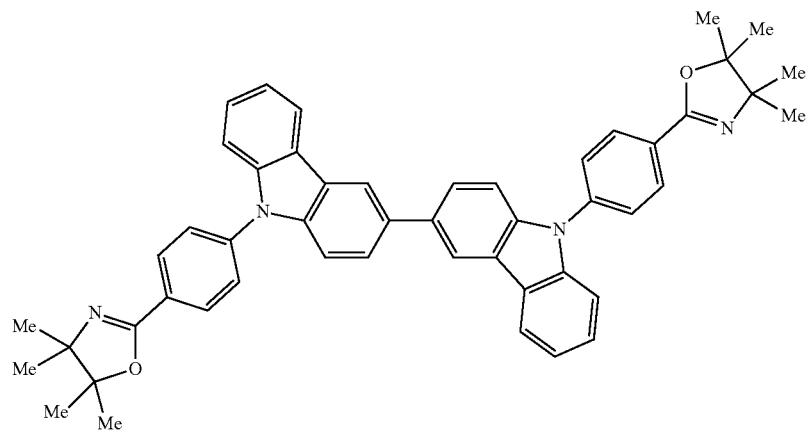
(1-2-524)
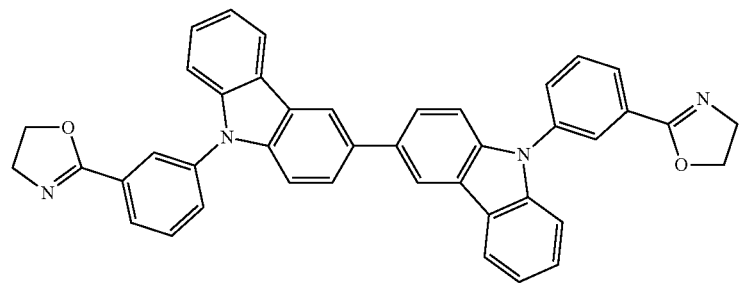
(1-2-525)
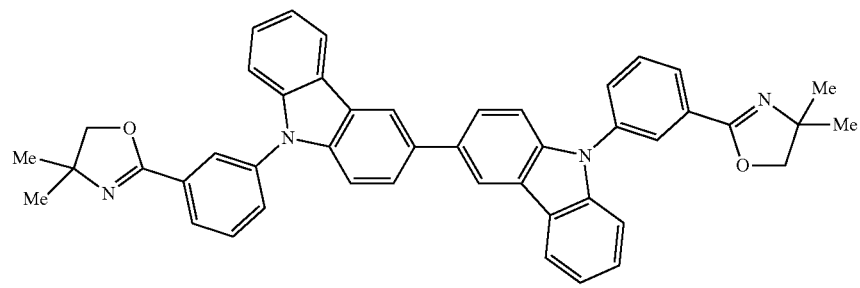
(1-2-526)
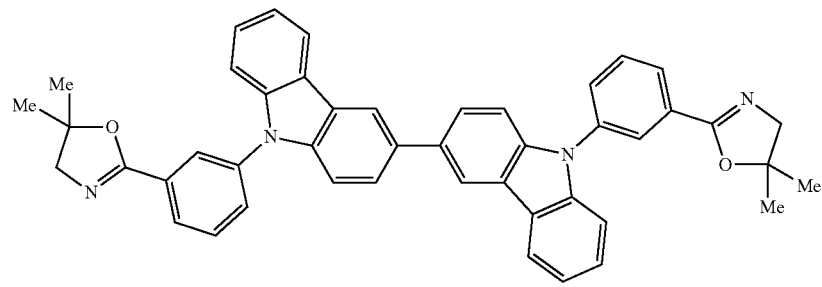
(1-2-527)
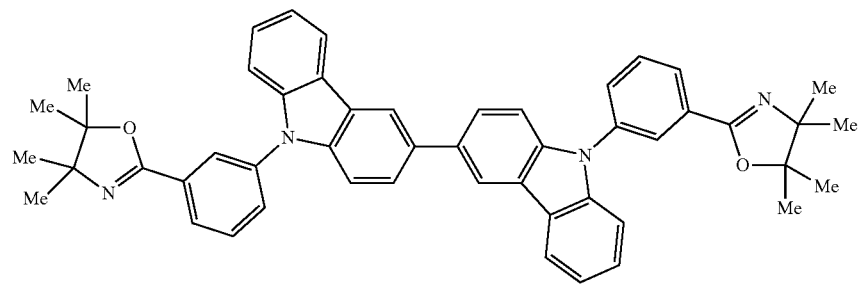
(1-2-528)

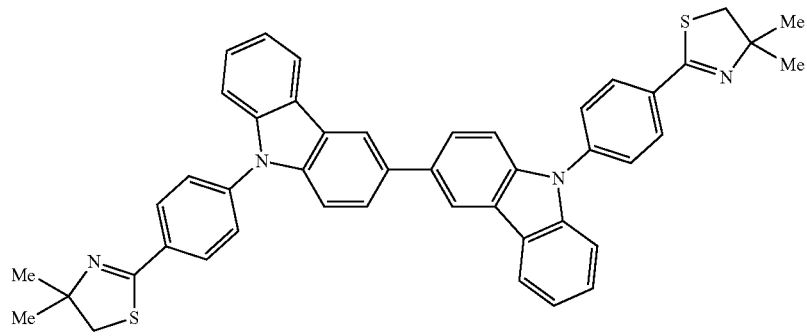
(1-2-531)
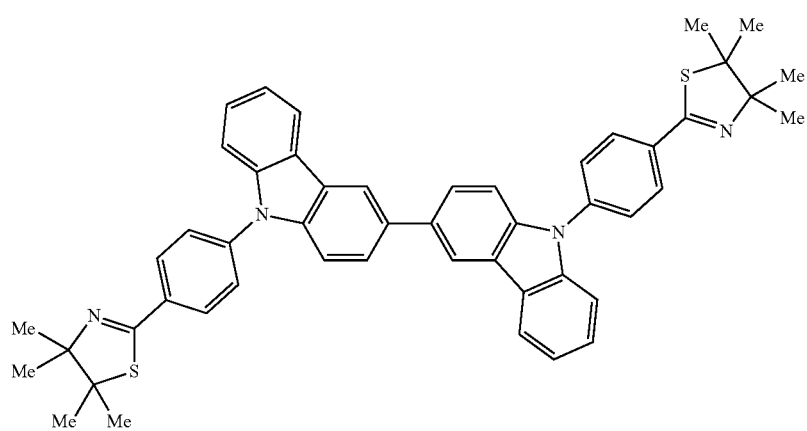
(1-2-532)
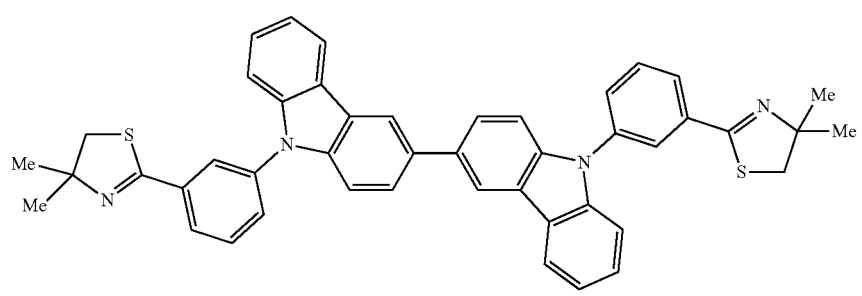
(1-2-533)
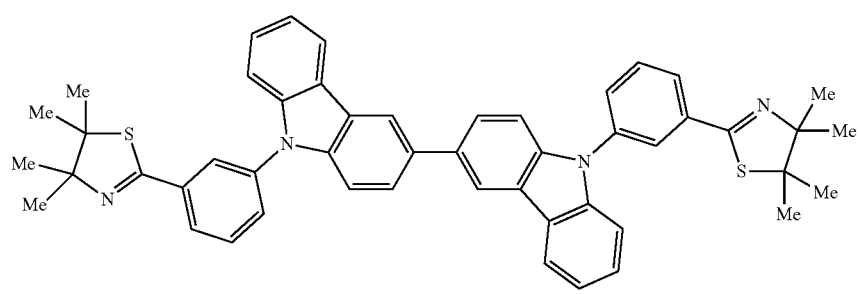
(1-2-534)

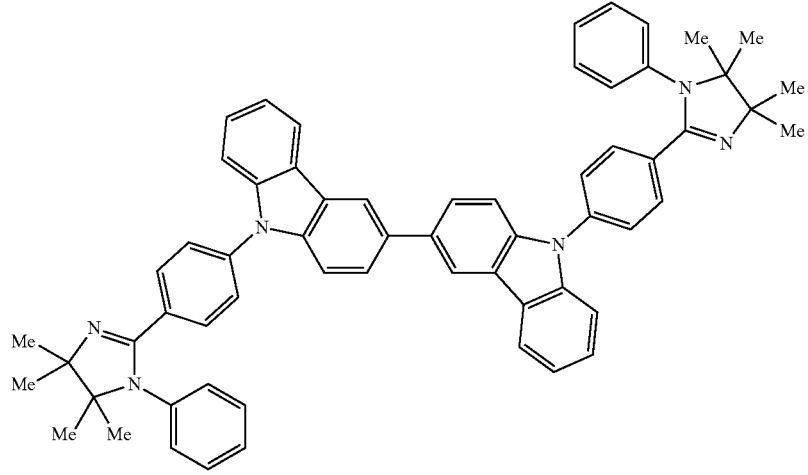 (1-2-535)
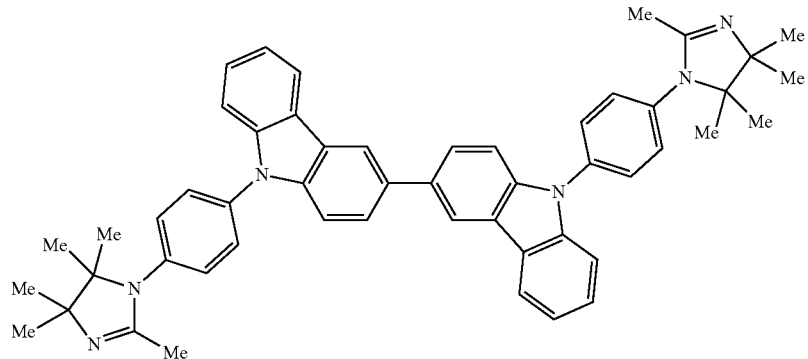 (1-2-536)
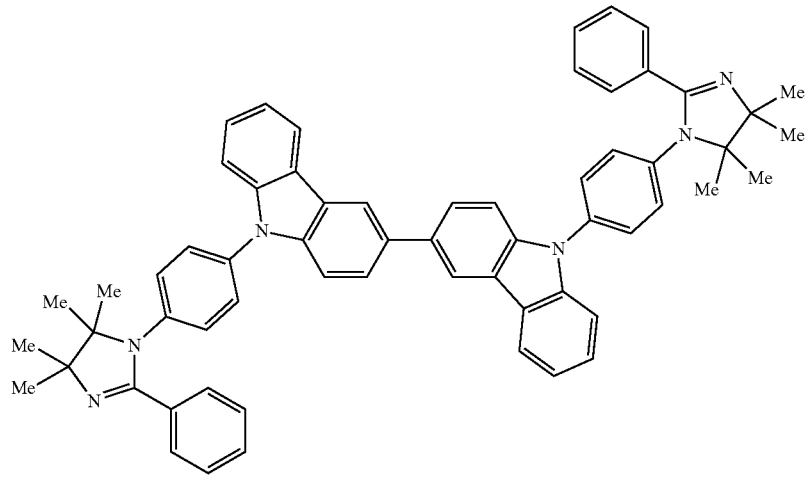 (1-2-537)
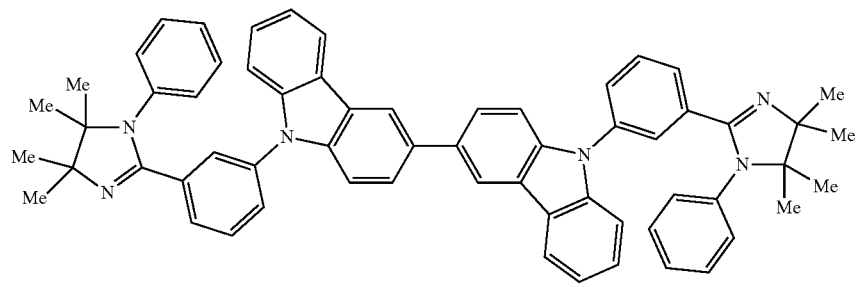 (1-2-538)

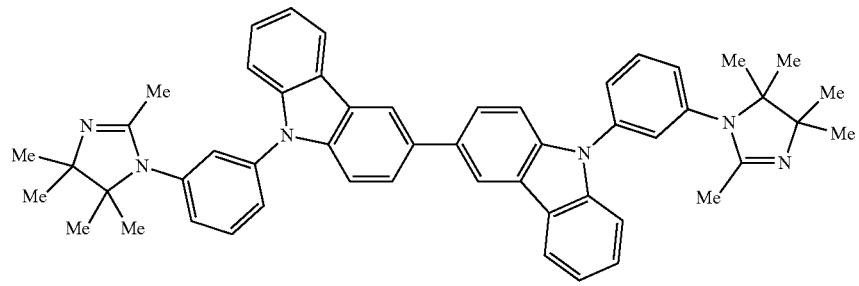
(1-2-539)
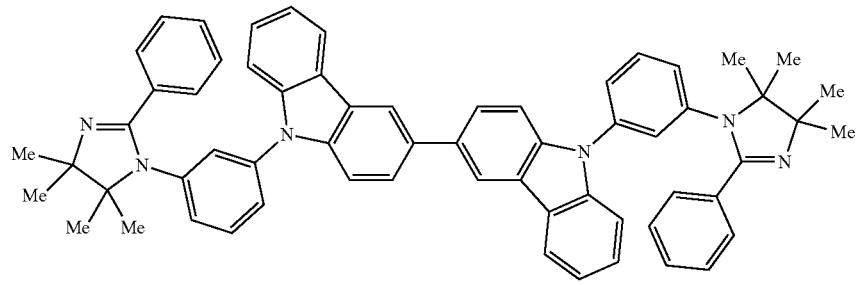
(1-2-540)
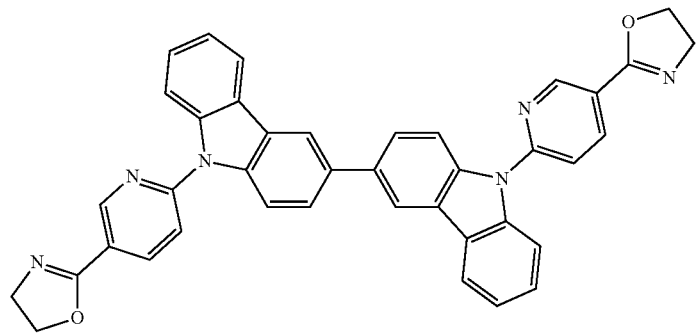
(1-2-541)
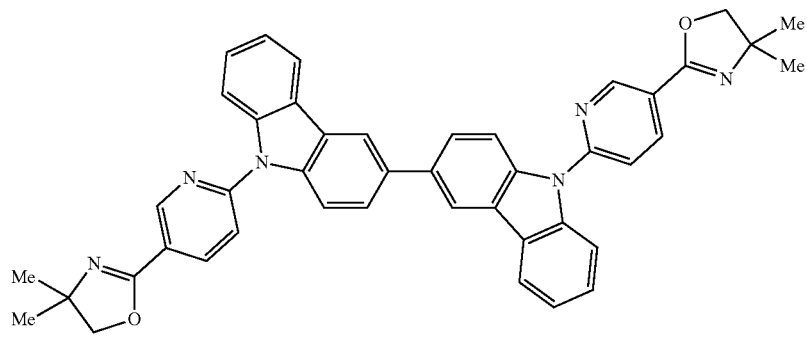
(1-2-542)
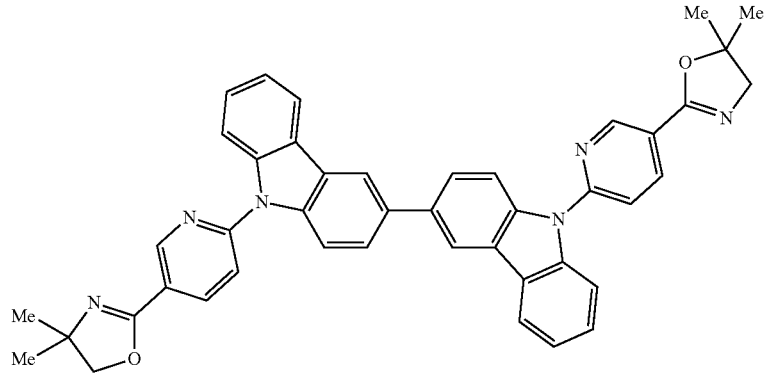
(1-2-543)

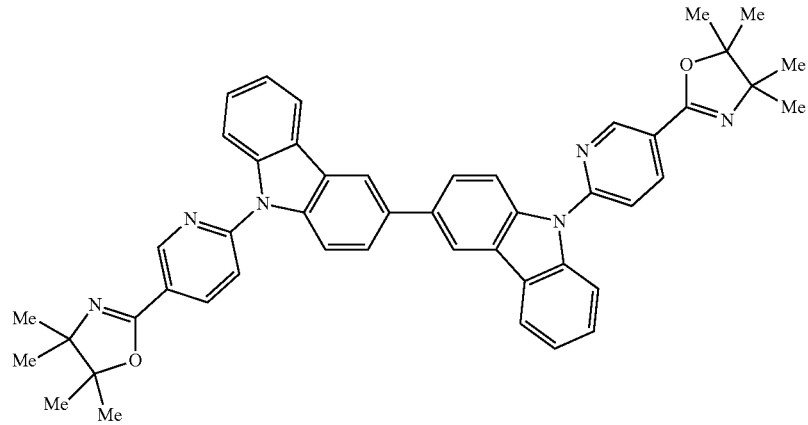
(1-2-544)
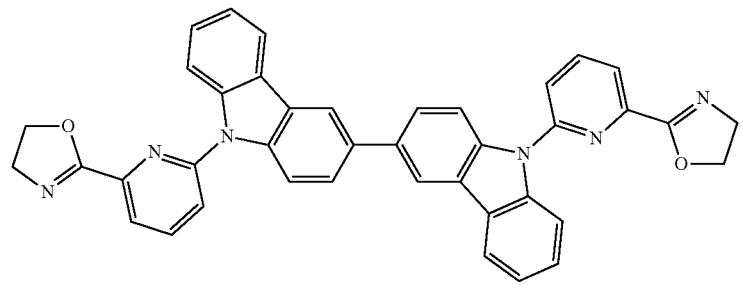
(1-2-545)
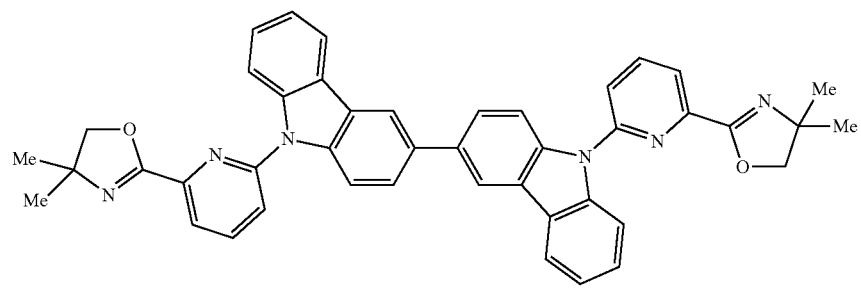
(1-2-546)
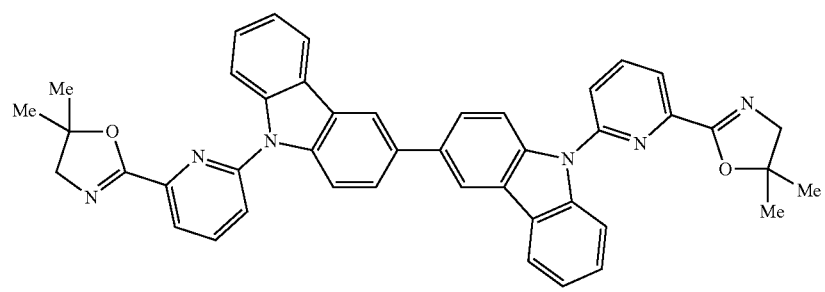
(1-2-547)
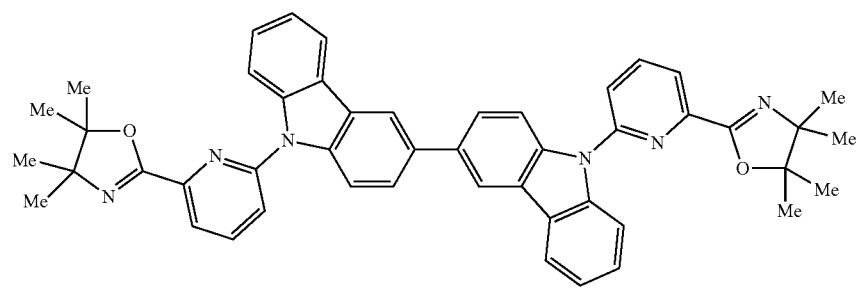
(1-2-548)

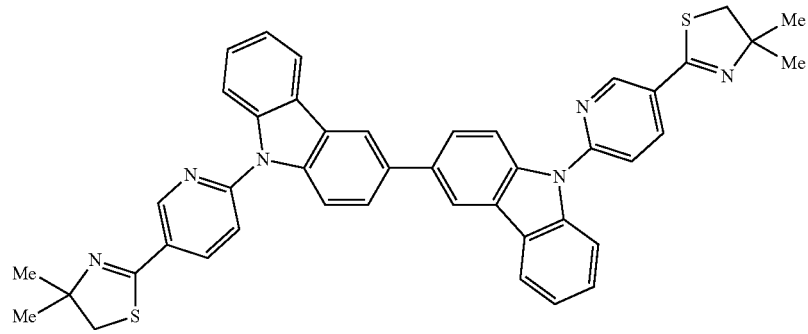
(1-2-551)
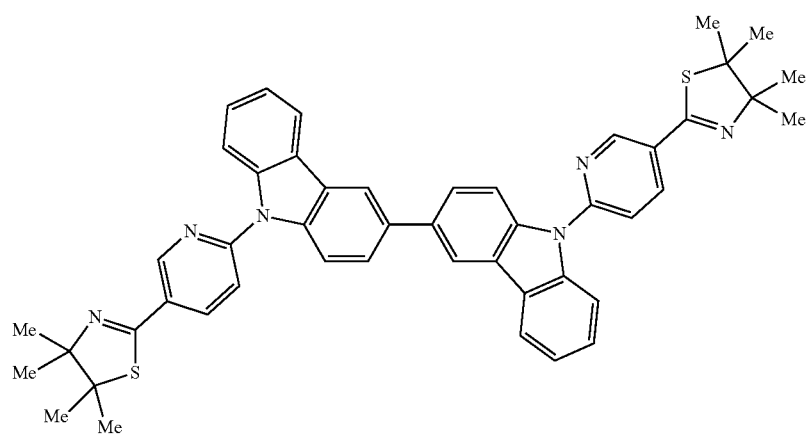
(1-2-552)
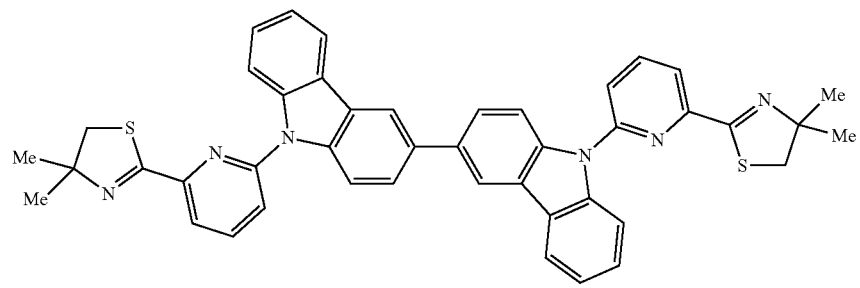
(1-2-553)
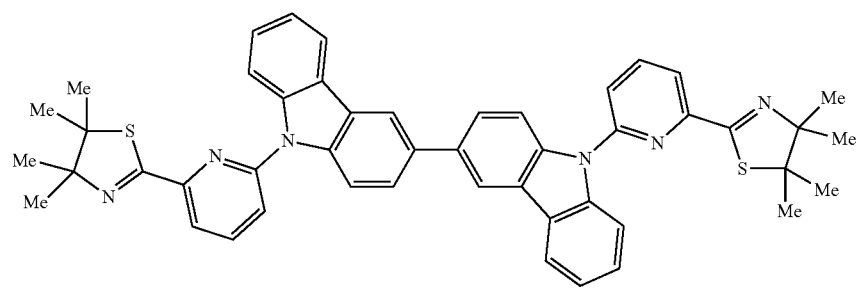
(1-2-554)

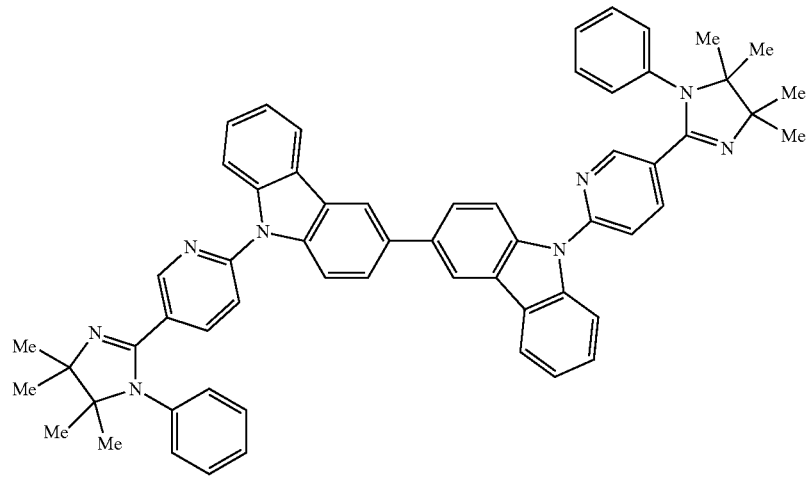
(1-2-555)
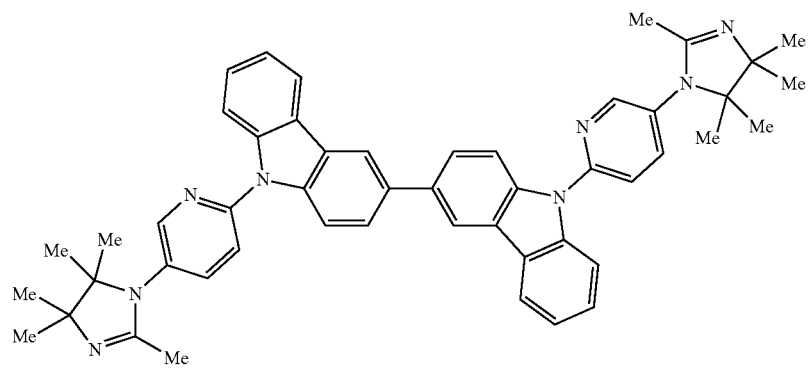
(1-2-556)
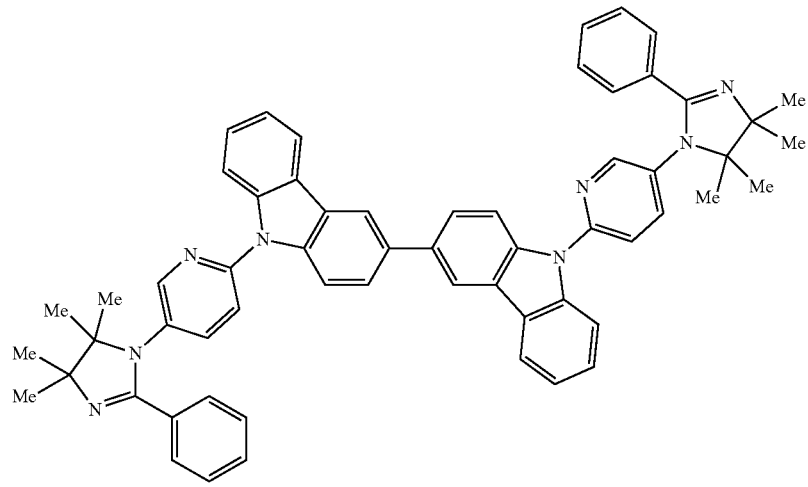
(1-2-557)
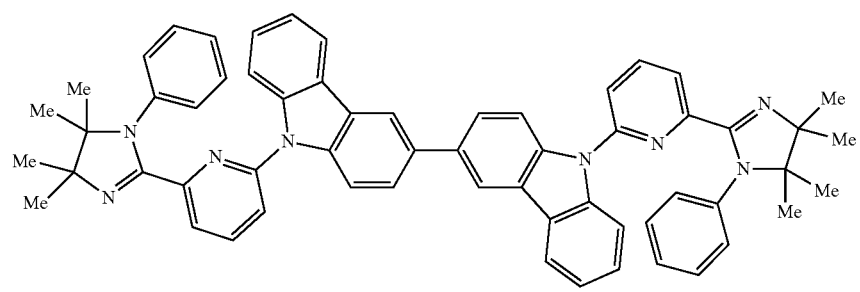
(1-2-558)

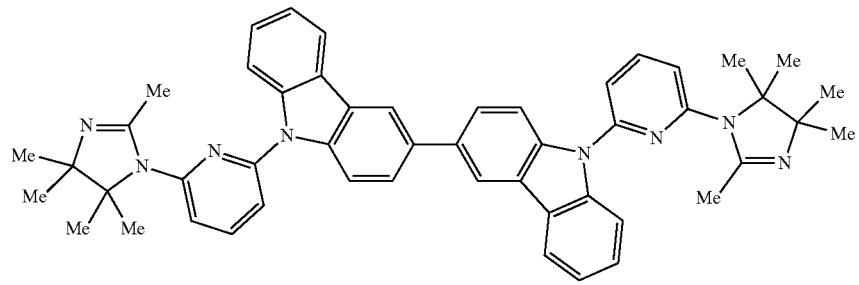
(1-2-559)
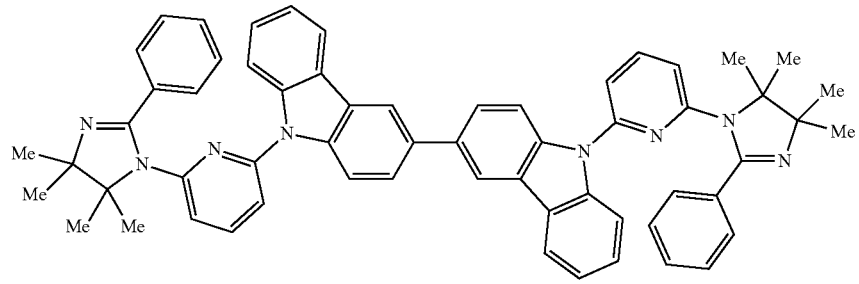
(1-2-560)
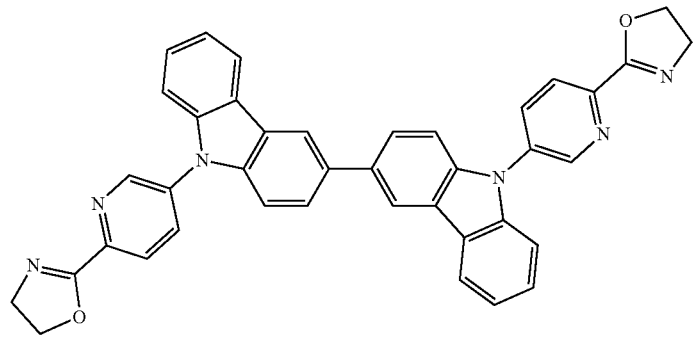
(1-2-561)
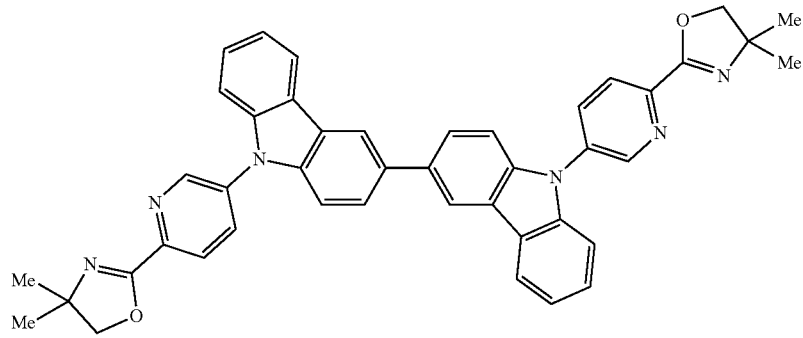
(1-2-562)
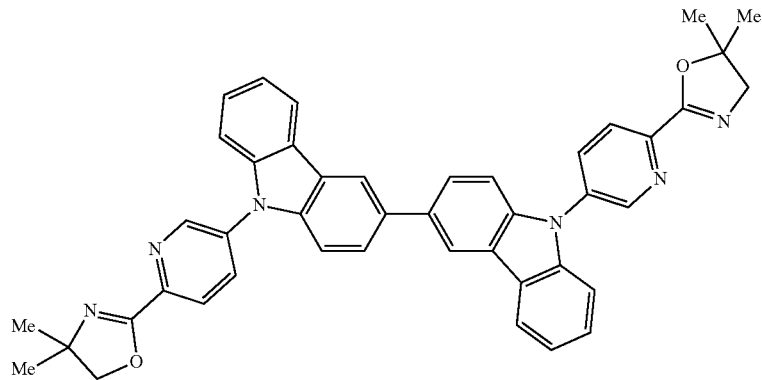
(1-2-563)

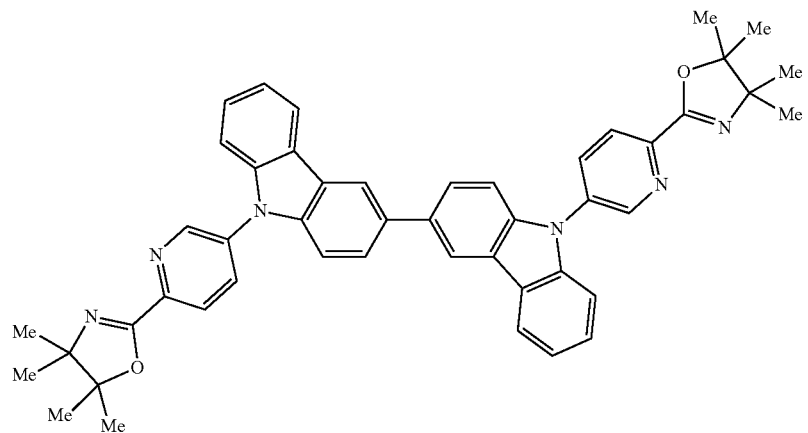
(1-2-564)
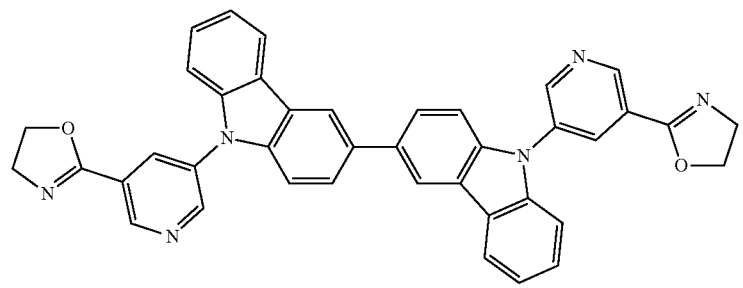
(1-2-565)
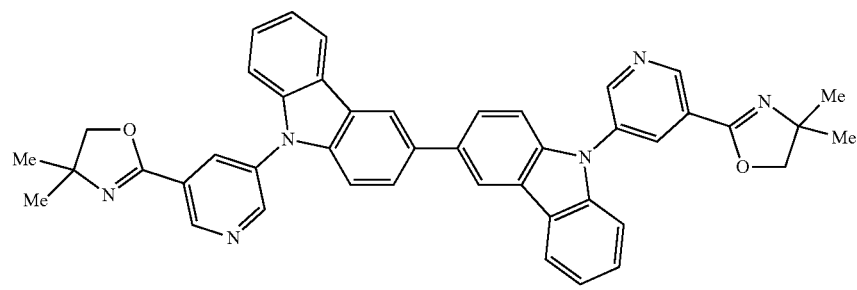
(1-2-566)
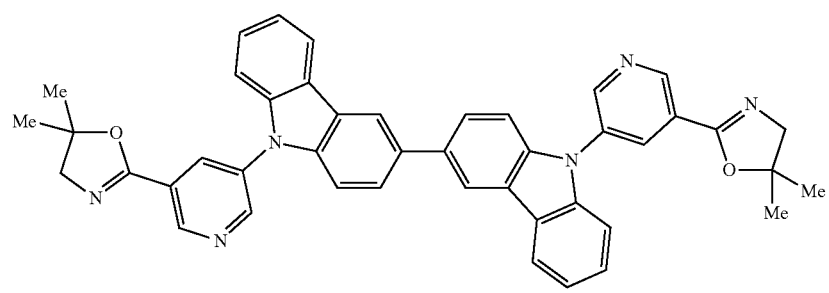
(1-2-567)
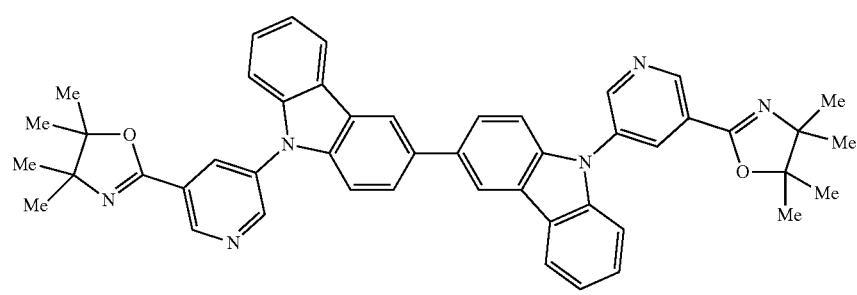
(1-2-568)

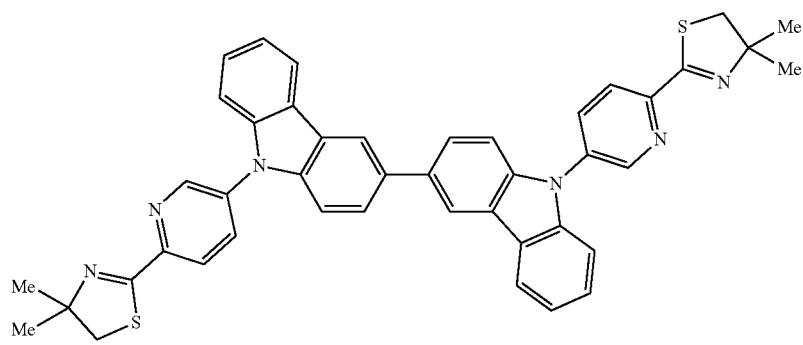
(1-2-571)
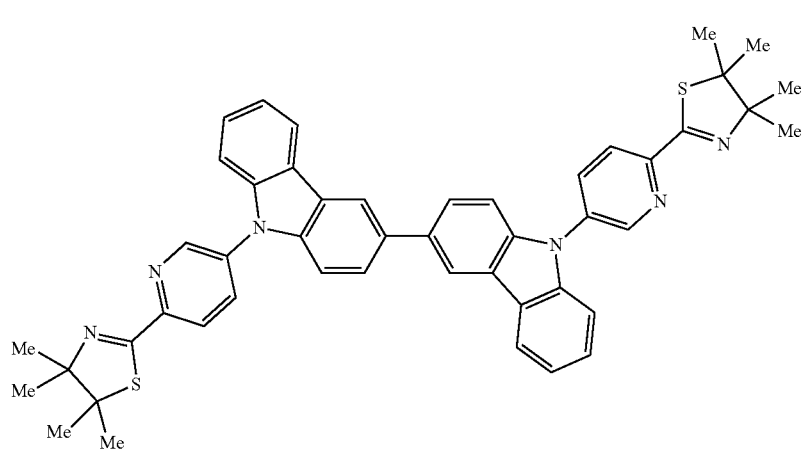
(1-2-572)
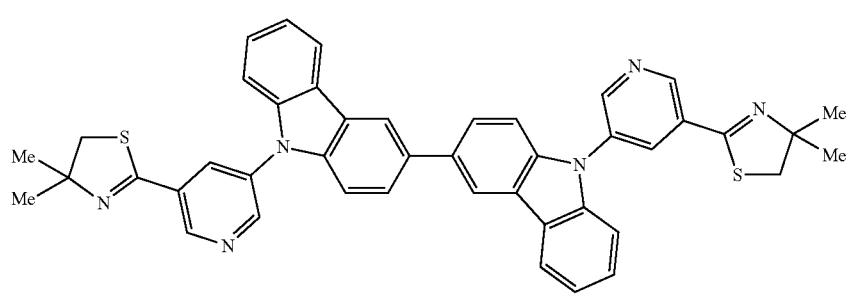
(1-2-573)
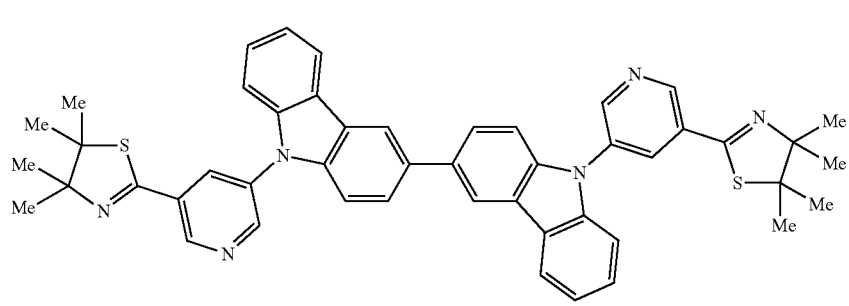
(1-2-574)

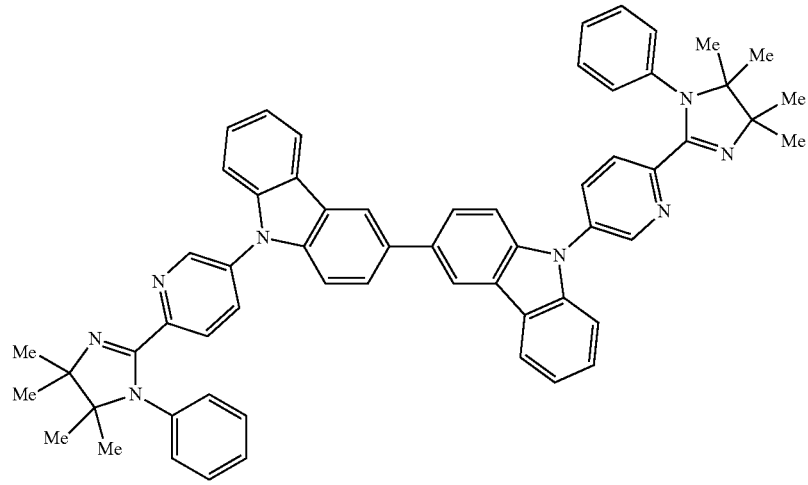
(1-2-575)
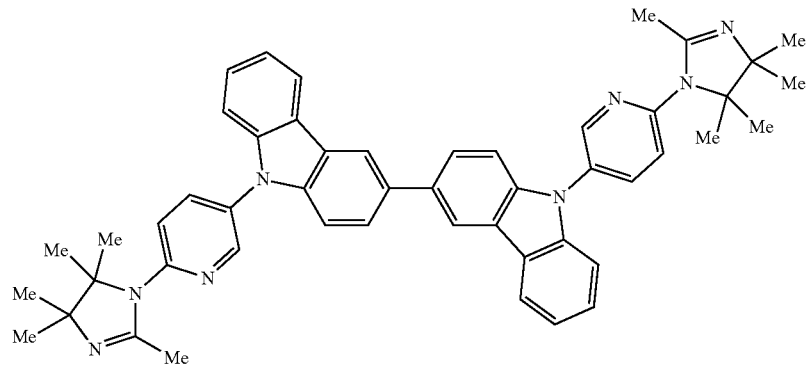
(1-2-576)
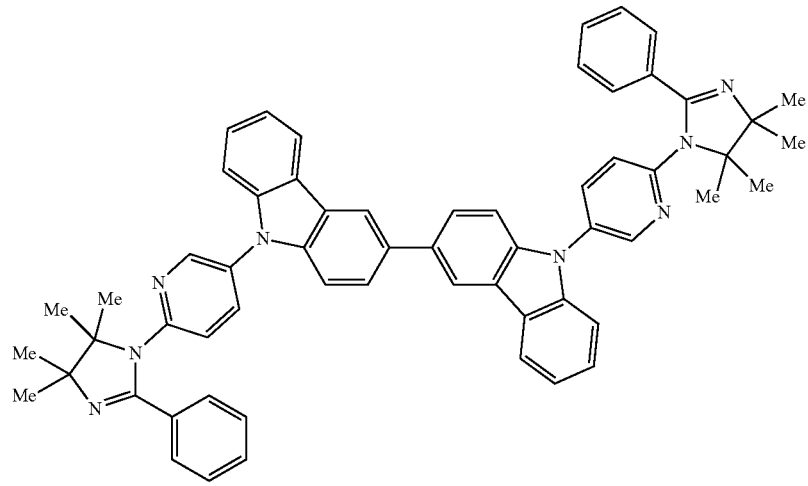
(1-2-577)
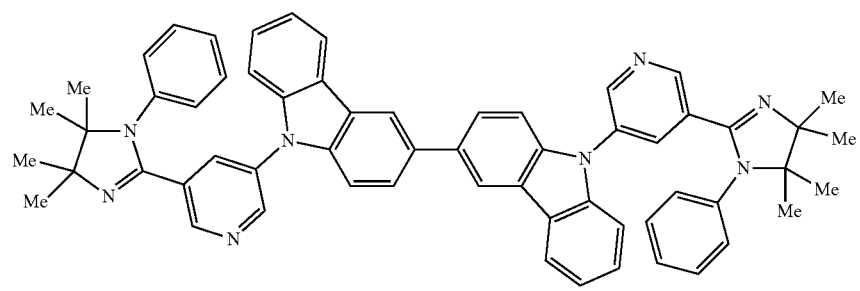
(1-2-578)

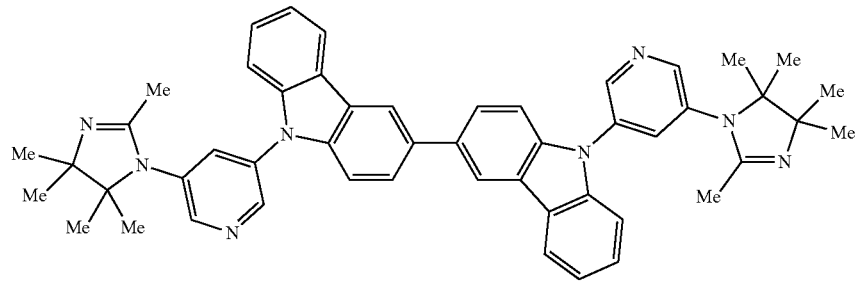
(1-2-579)
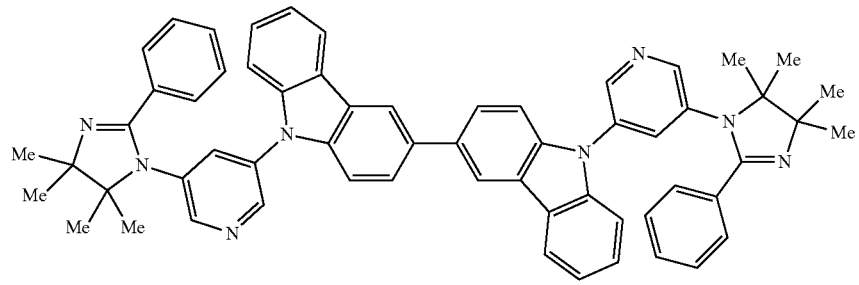
(1-2-580)
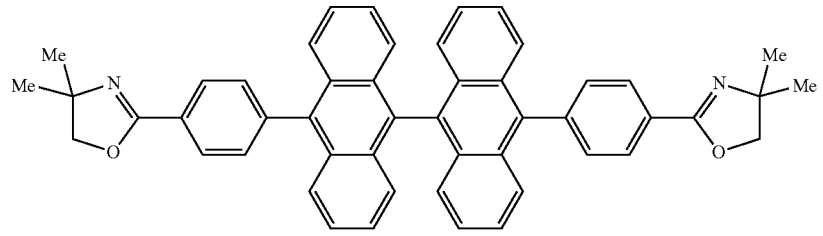
(1-2-581)
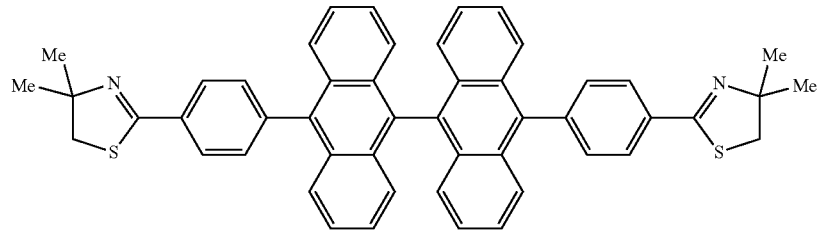
(1-2-582)
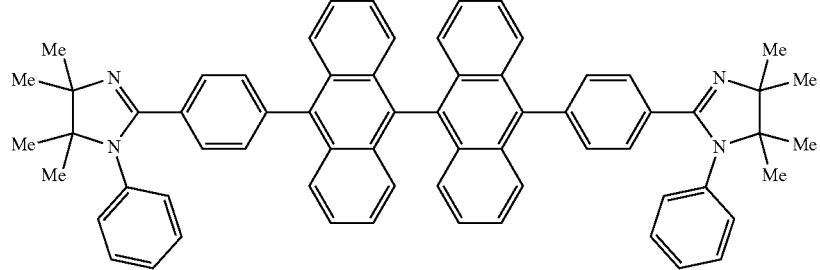
(1-2-583)
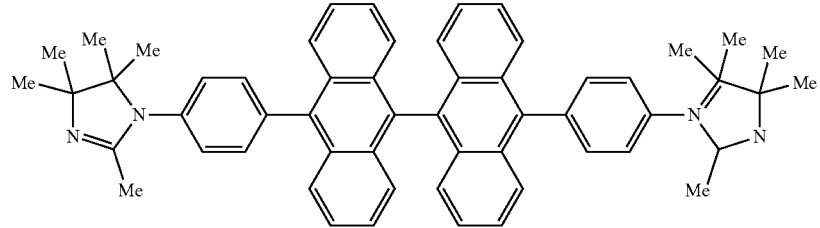
(1-2-584)

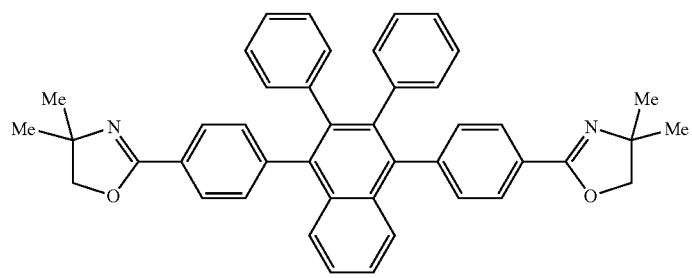
(1-2-585)
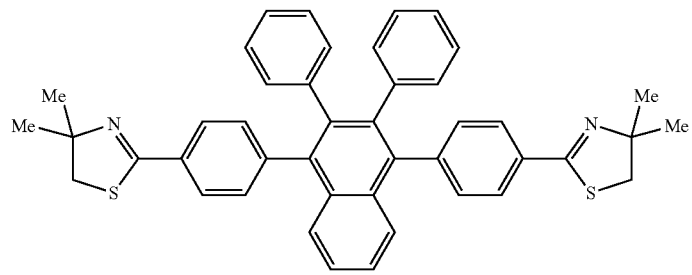
(1-2-586)
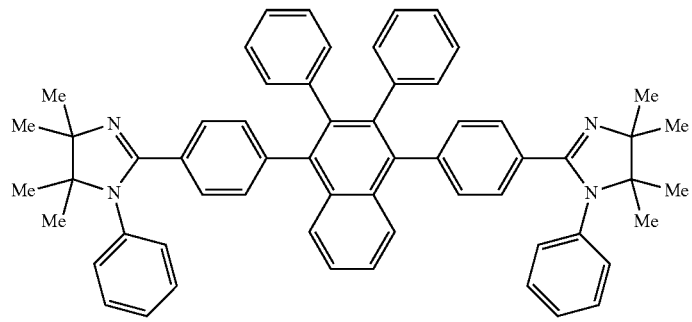
(1-2-587)
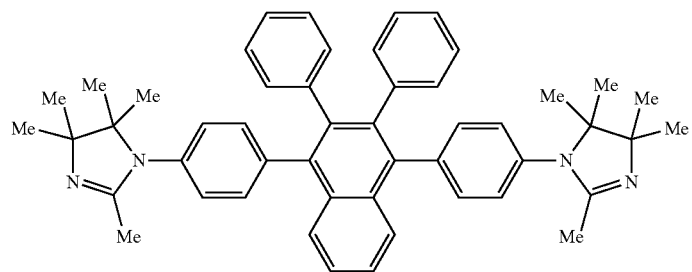
(1-2-588)
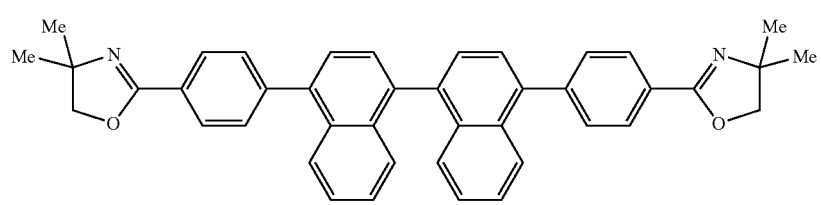
(1-2-589)
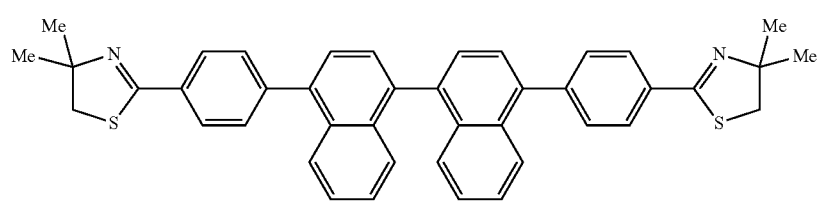
(1-2-590)

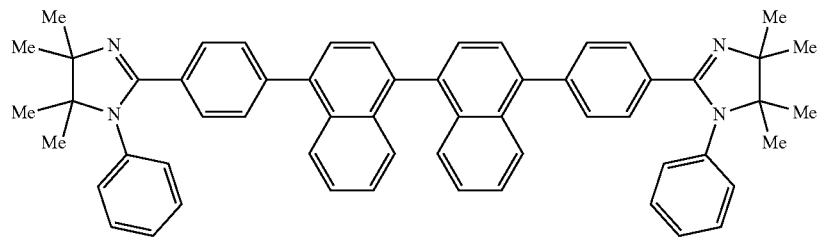
(1-2-591)
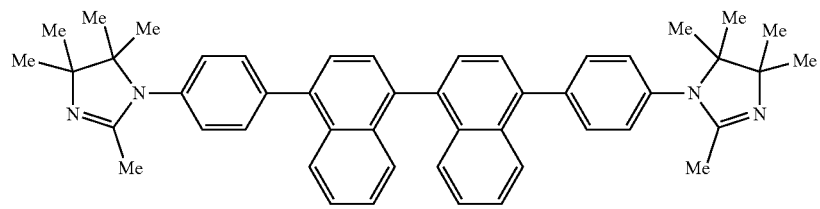
(1-2-592)
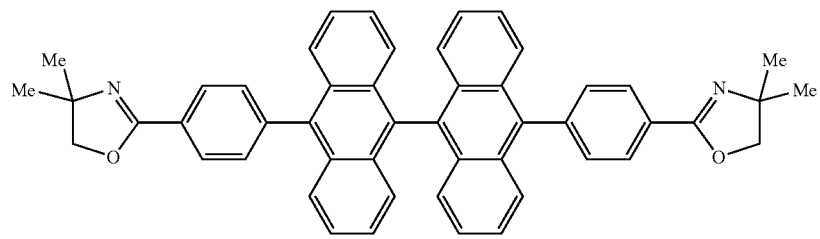
(1-2-601)
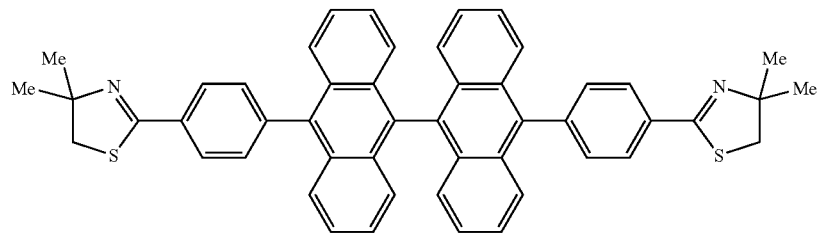
(1-2-602)
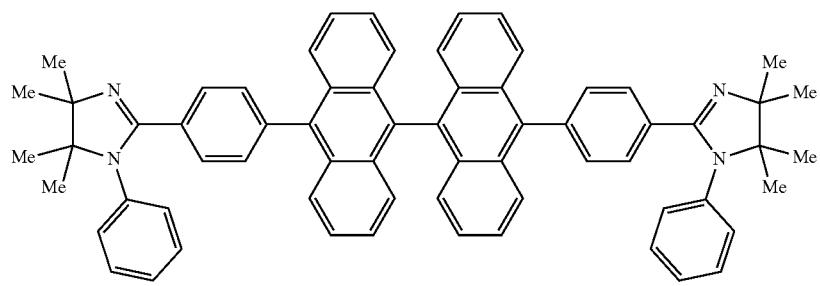
(1-2-603)
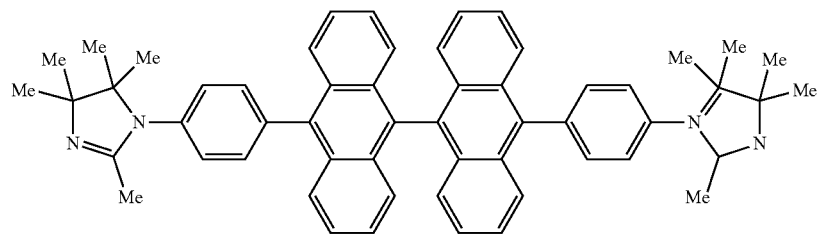
(1-2-604)

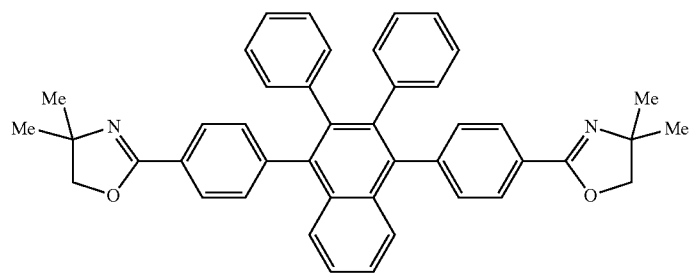
(1-2-605)
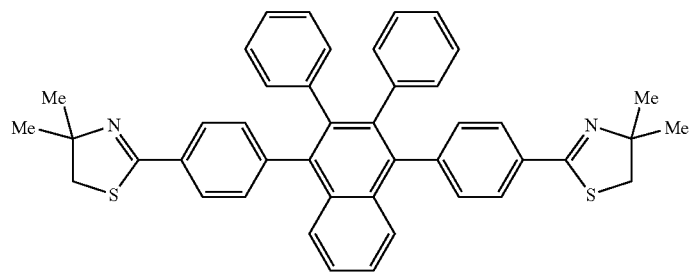
(1-2-606)
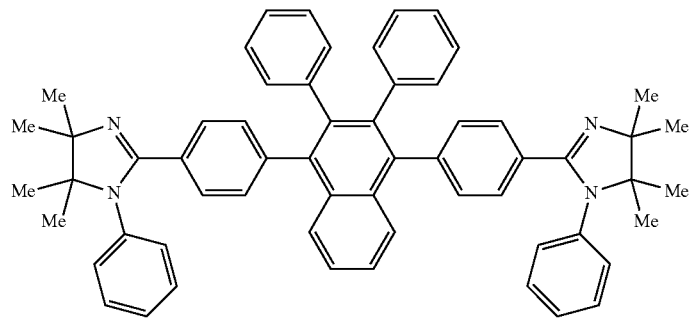
(1-2-607)
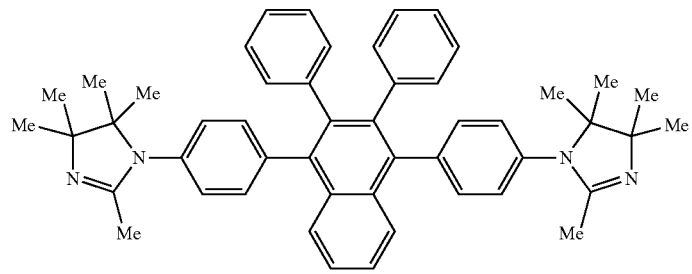
(1-2-608)
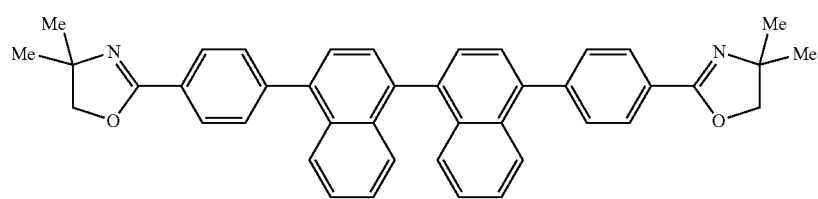
(1-2-609)
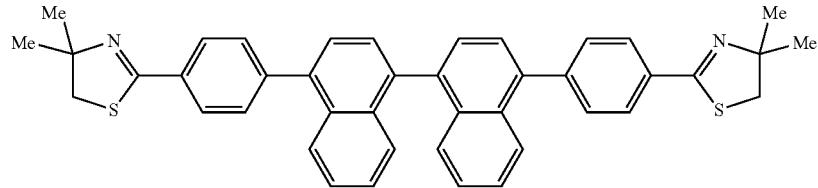
(1-2-610)

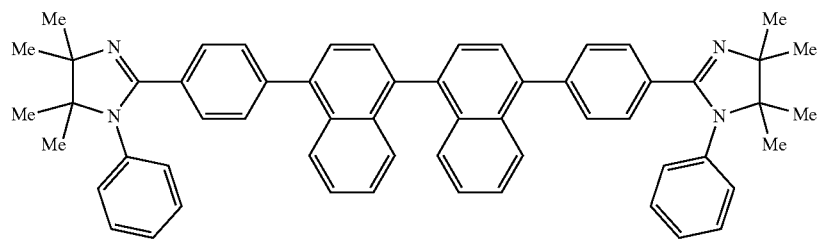 (1-2-611)
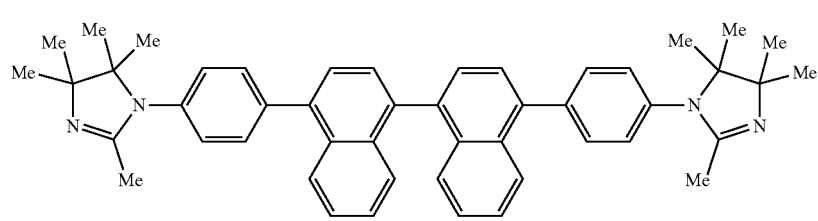 (1-2-612)
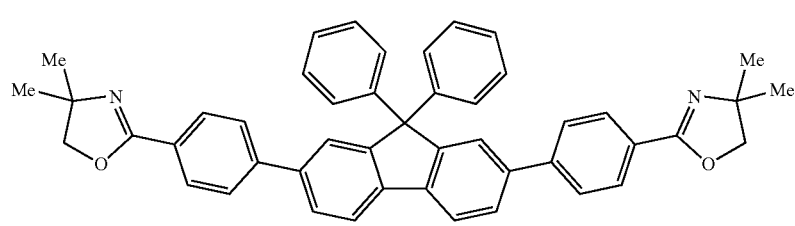 (1-2-621)
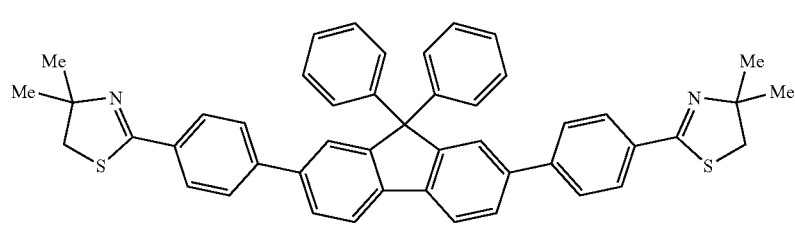 (1-2-622)
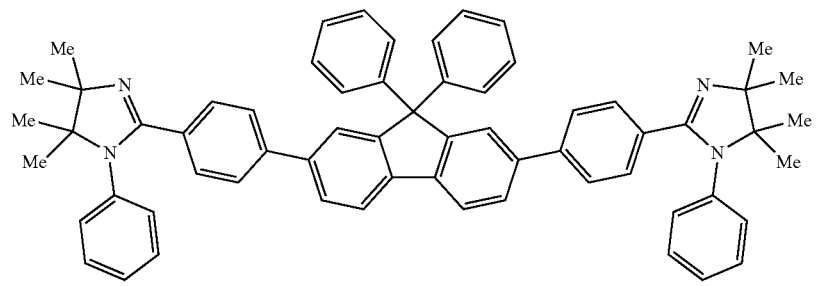 (1-2-623)
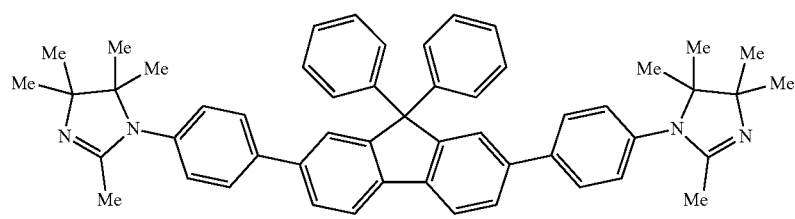 (1-2-624)

-continued
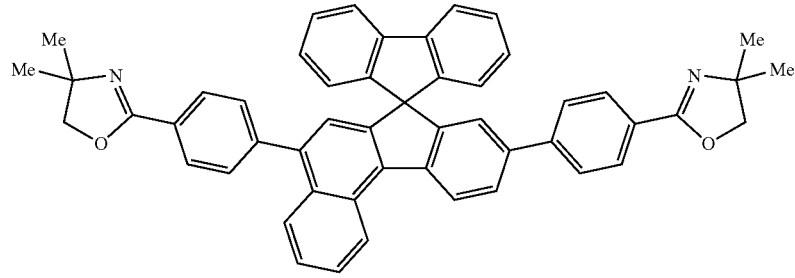
(1-2-625)
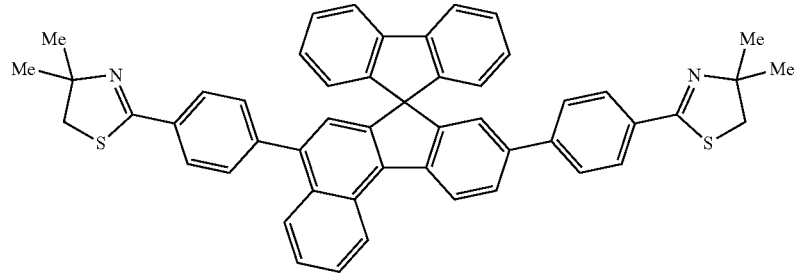
(1-2-626)
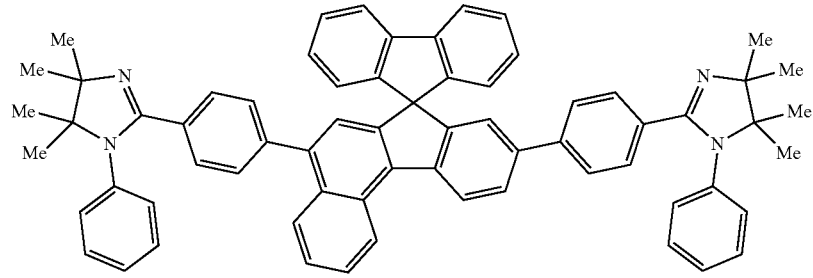
(1-2-627)
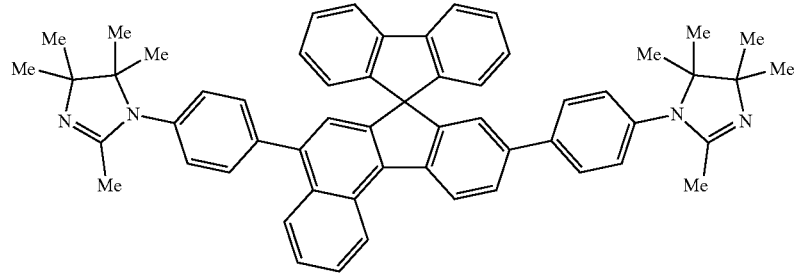
(1-2-628)
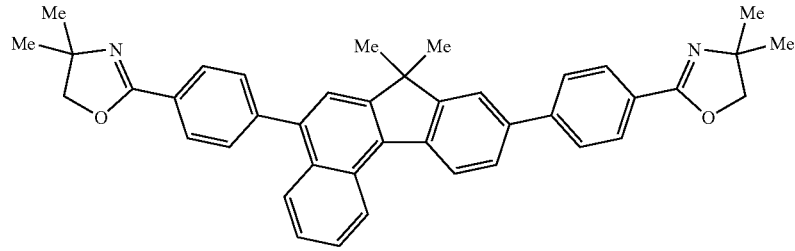
(1-2-629)
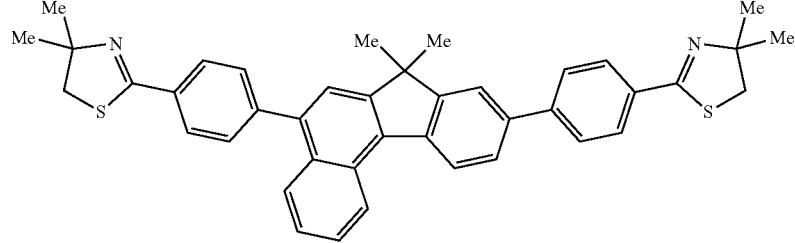
(1-2-630)

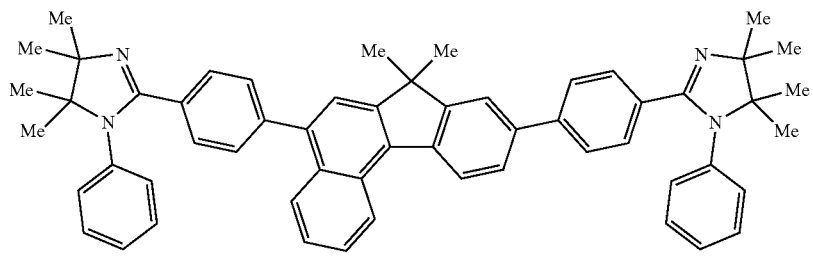
(1-2-631)
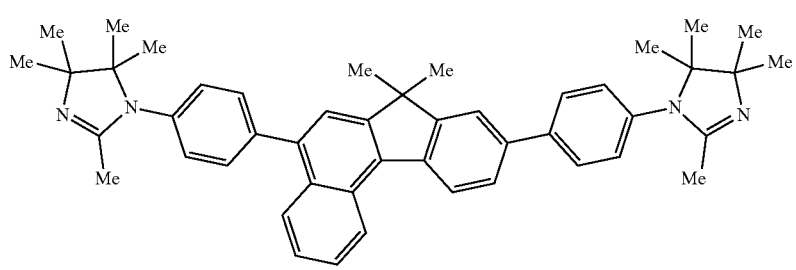
(1-2-632)
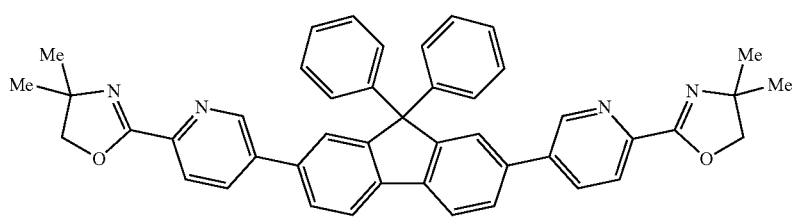
(1-2-641)
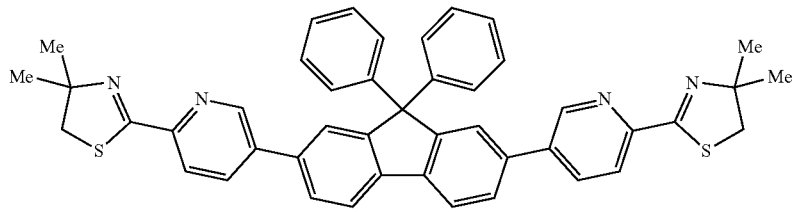
(1-2-642)
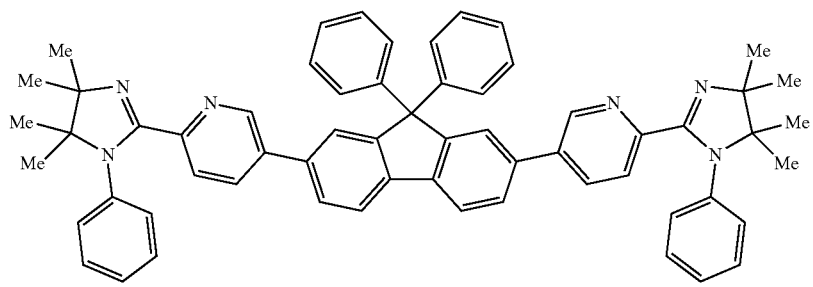
(1-2-643)
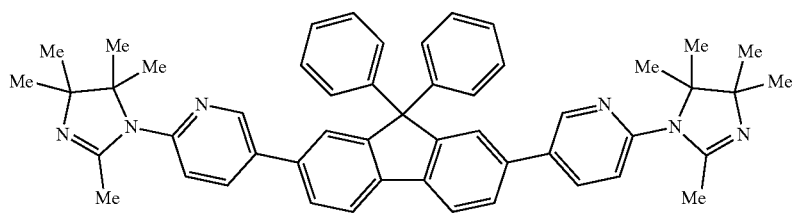
(1-2-644)

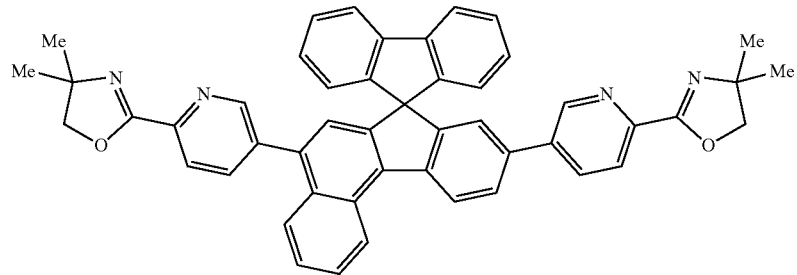
(1-2-645)
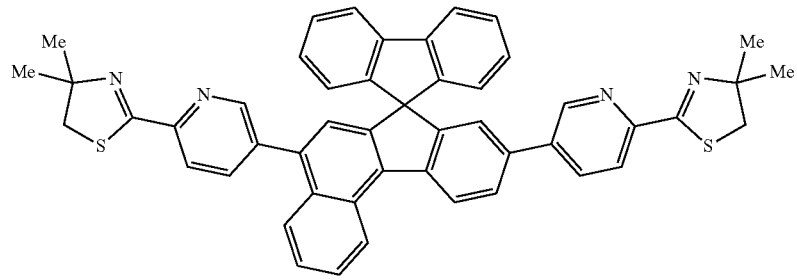
(1-2-646)
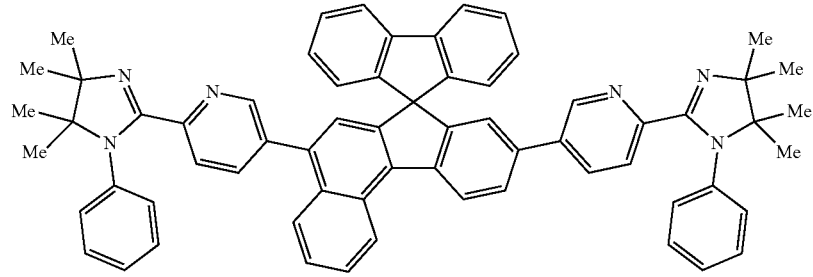
(1-2-647)
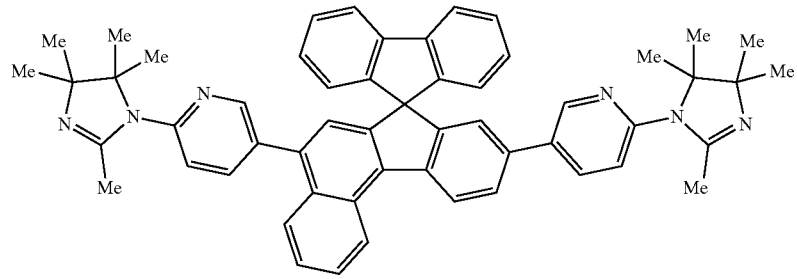
(1-2-648)
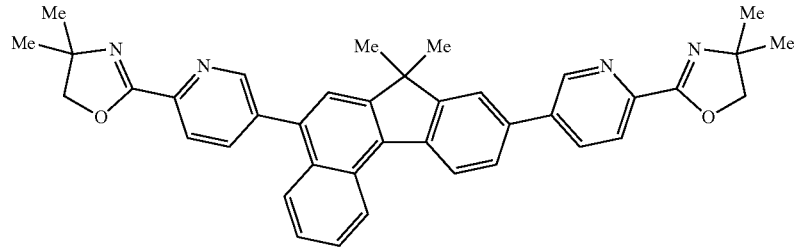
(1-2-649)

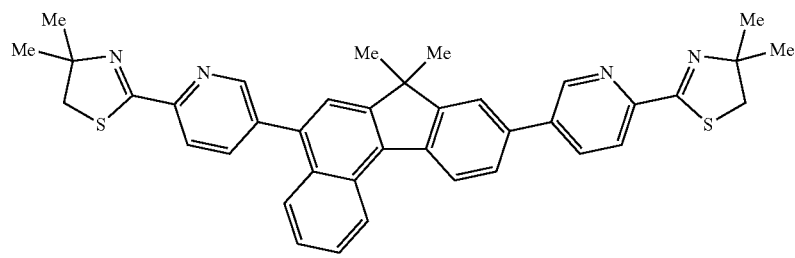
(1-2-650)
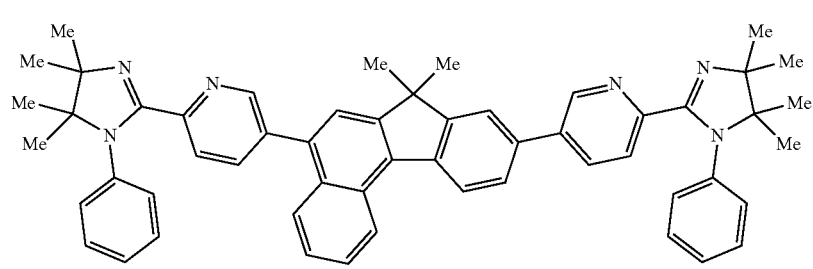
(1-2-651)
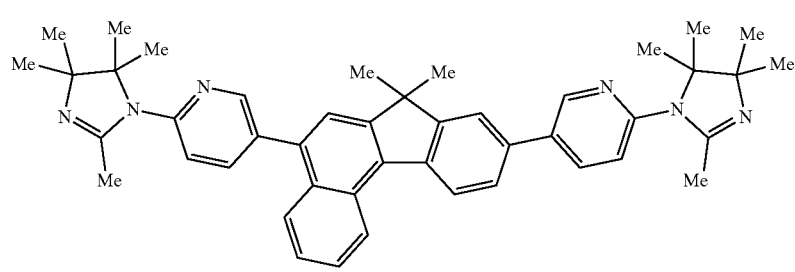
(1-2-652)
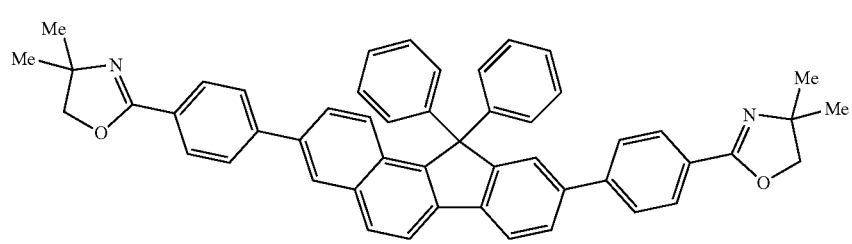
(1-2-661)
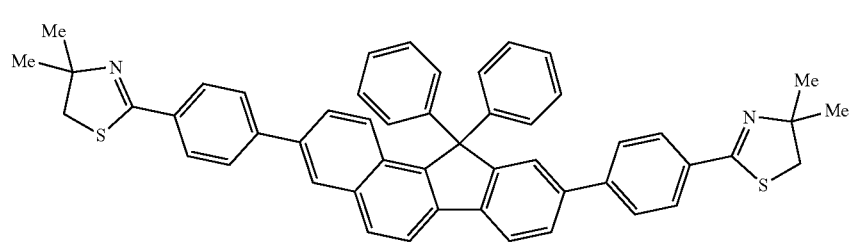
(1-2-662)
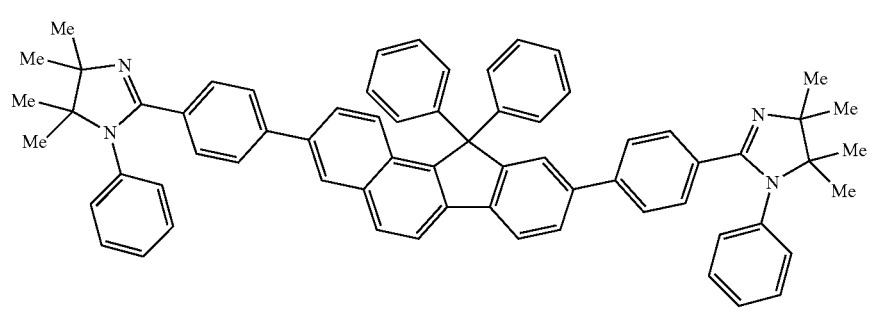
(1-2-663)

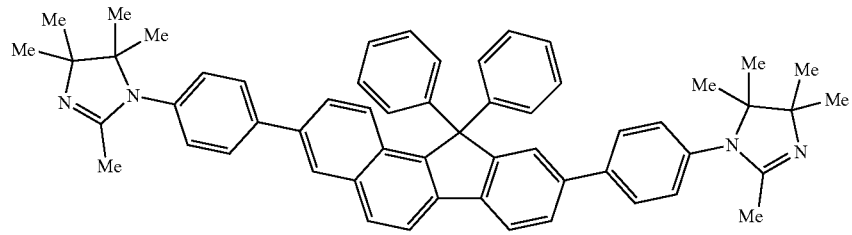
(1-2-664)
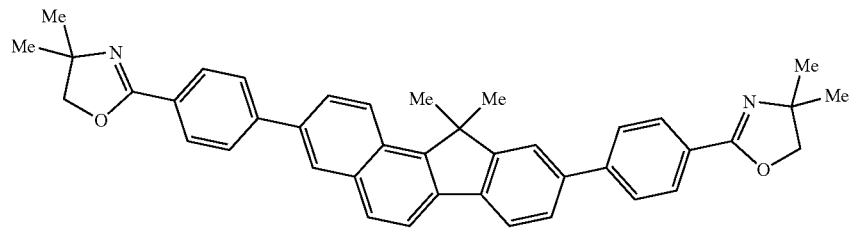
(1-2-665)
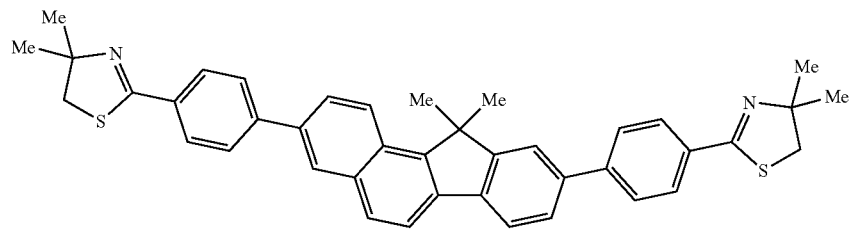
(1-2-666)
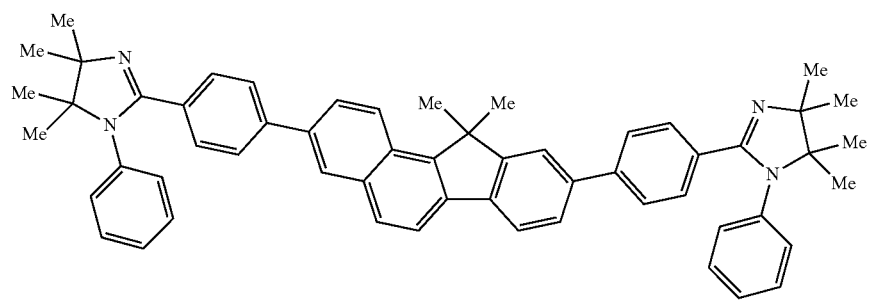
(1-2-667)
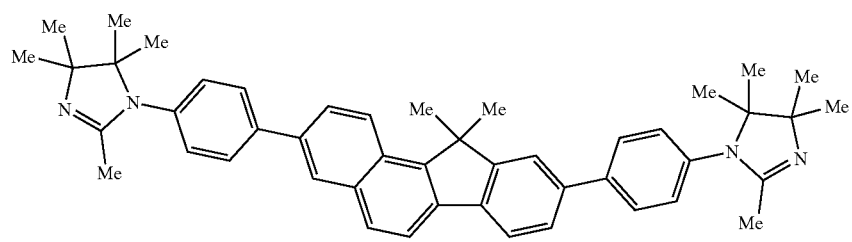
(1-2-668)
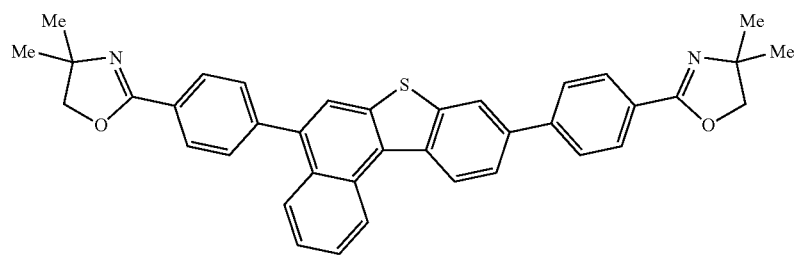
(1-2-669)

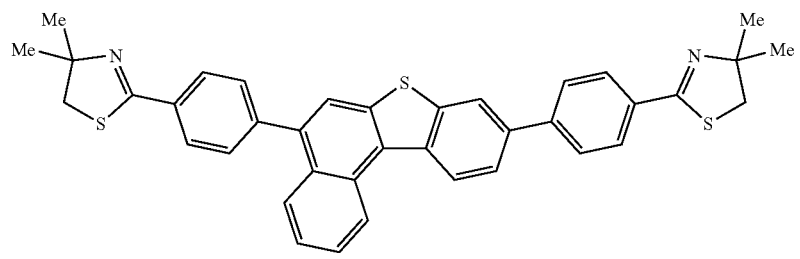
(1-2-670)
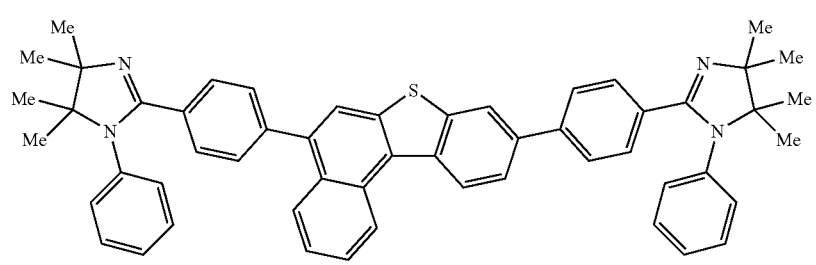
(1-2-671)
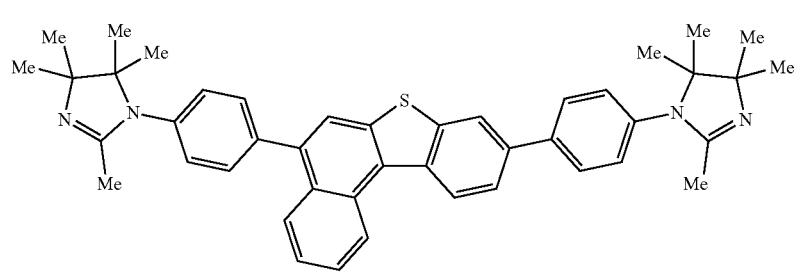
(1-2-672)
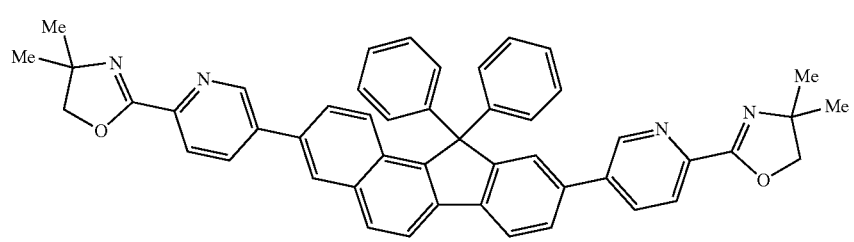
(1-2-681)
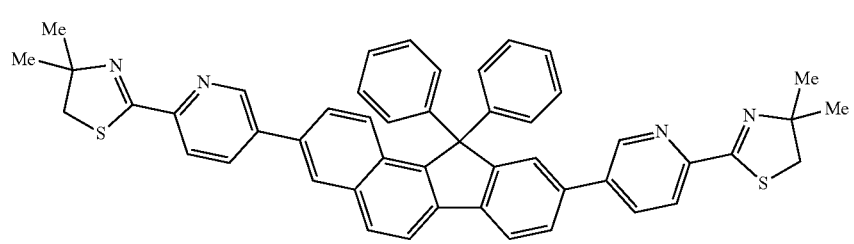
(1-2-682)
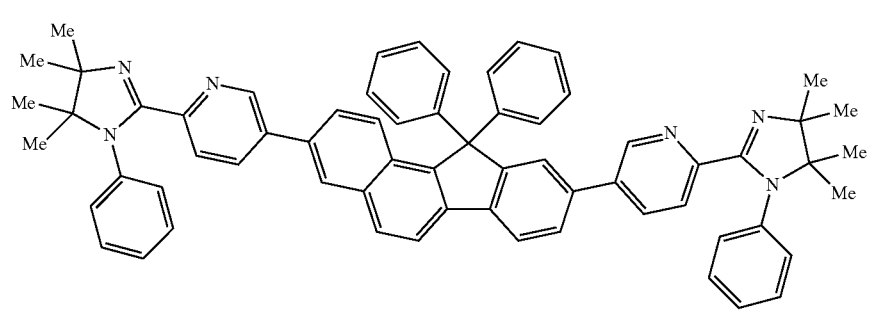
(1-2-683)

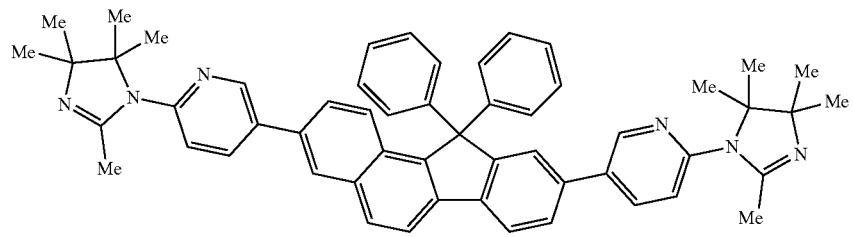
(1-2-684)
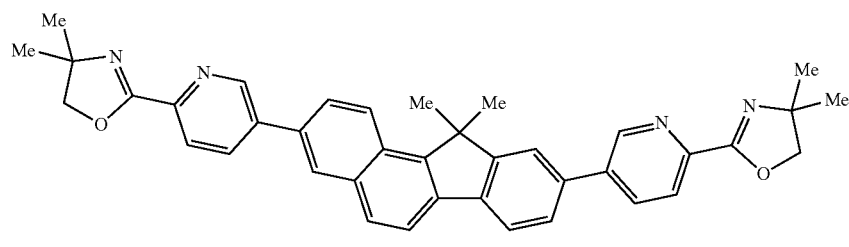
(1-2-685)
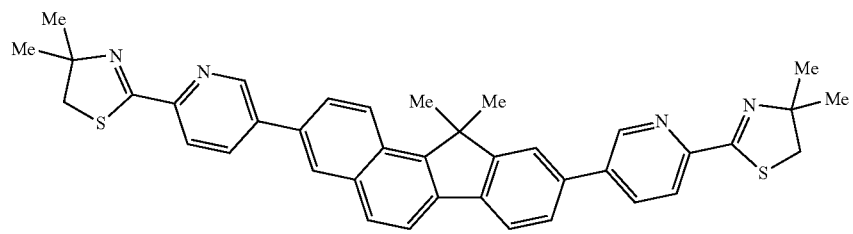
(1-2-686)
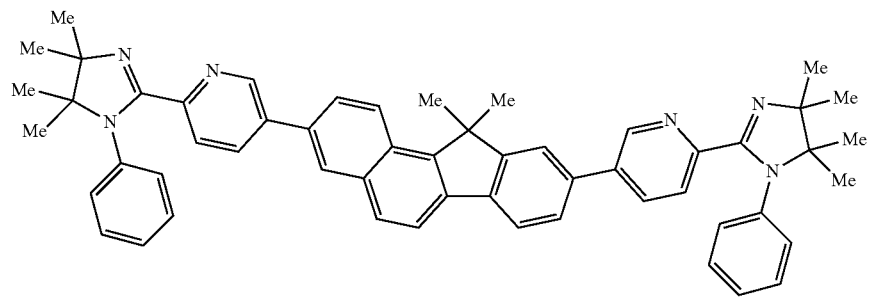
(1-2-687)
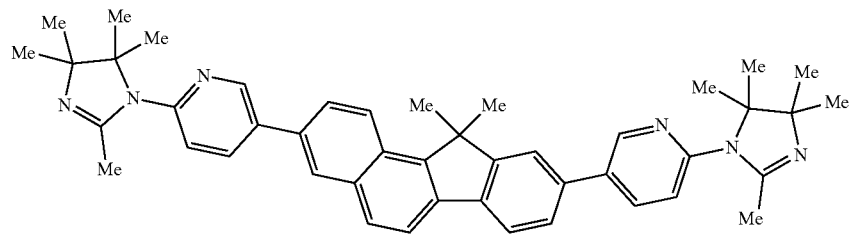
(1-2-688)
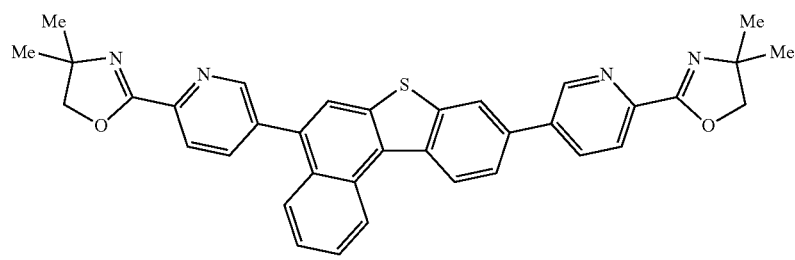
(1-2-689)

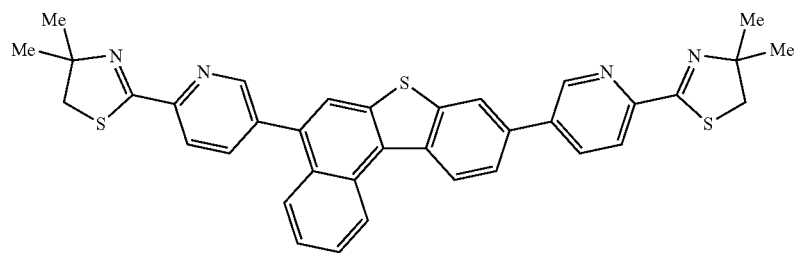
(1-2-690)
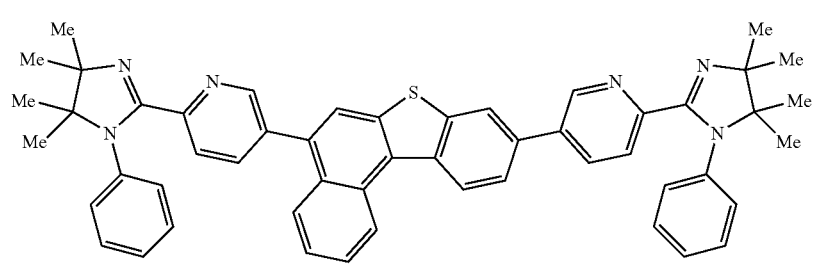
(1-2-691)
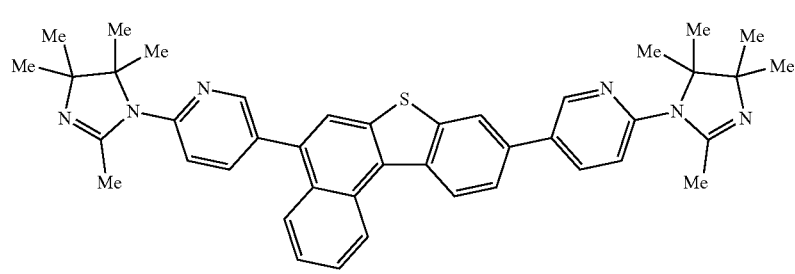
(1-2-692)
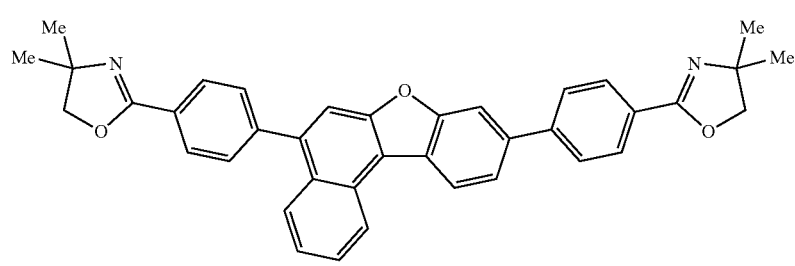
(1-2-701)
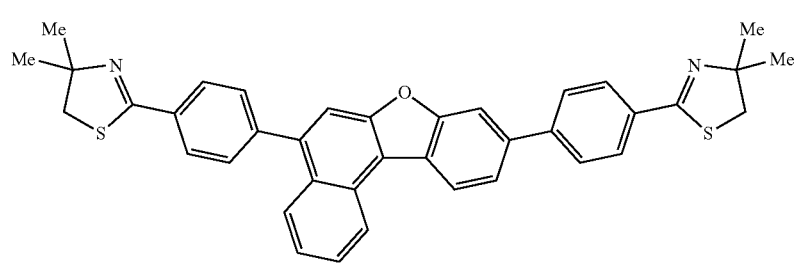
(1-2-702)
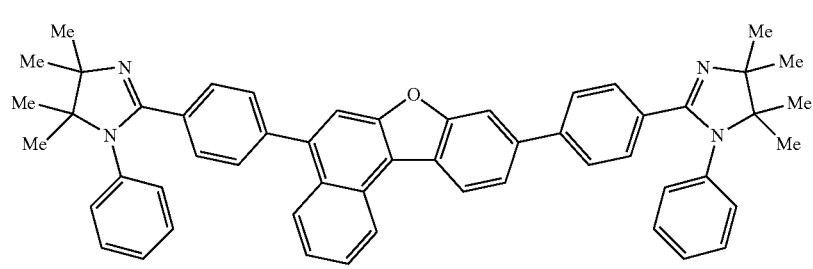
(1-2-703)

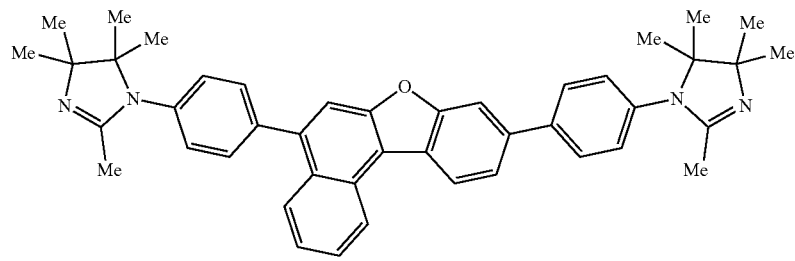
(1-2-704)
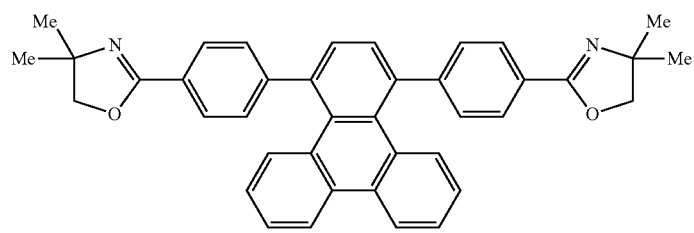
(1-2-705)
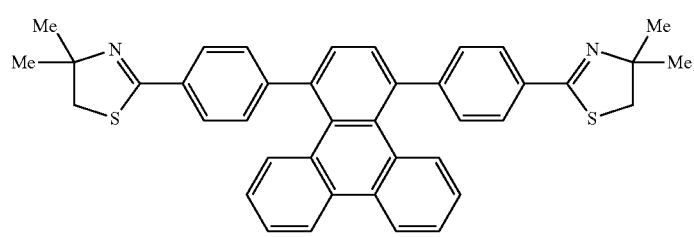
(1-2-706)
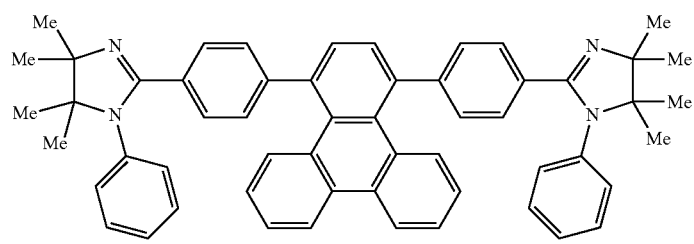
(1-2-707)
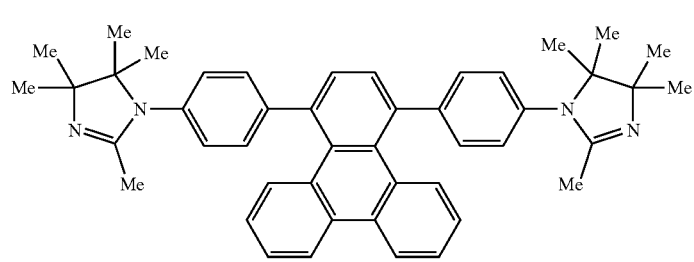
(1-2-708)
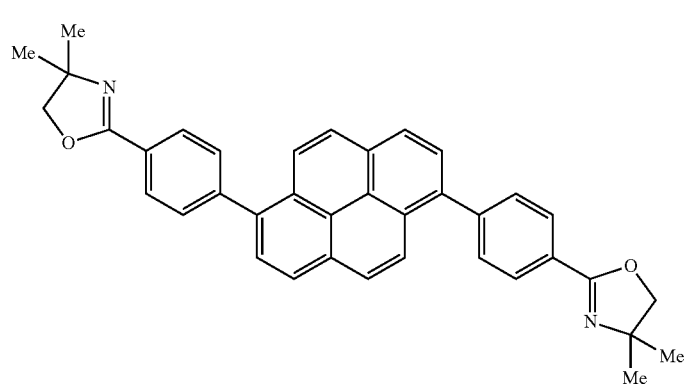
(1-2-709)

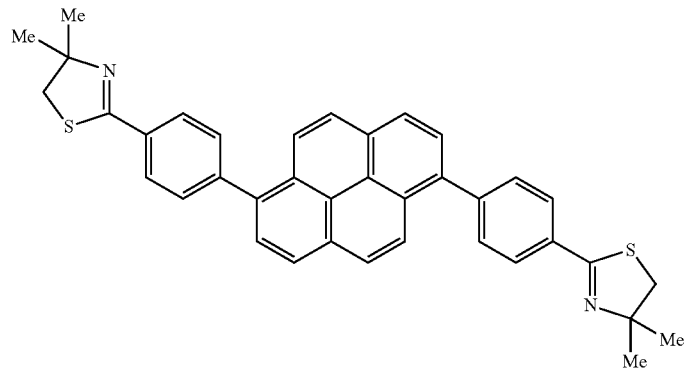
(1-2-710)
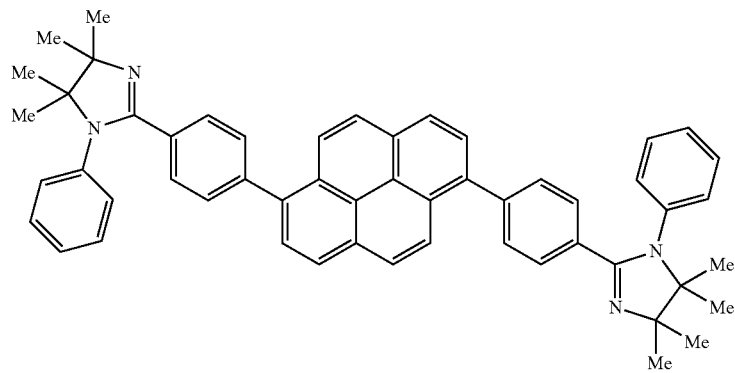
(1-2-711)
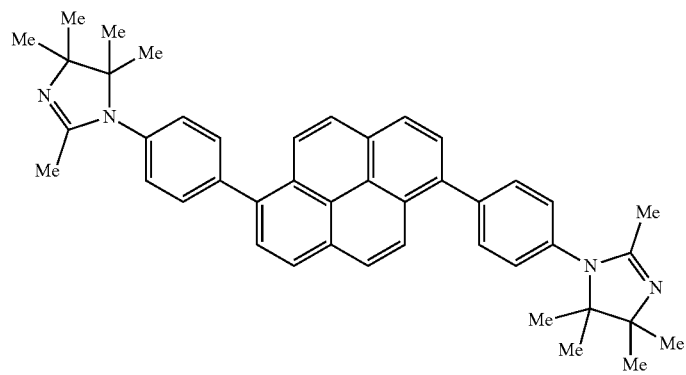
(1-2-712)
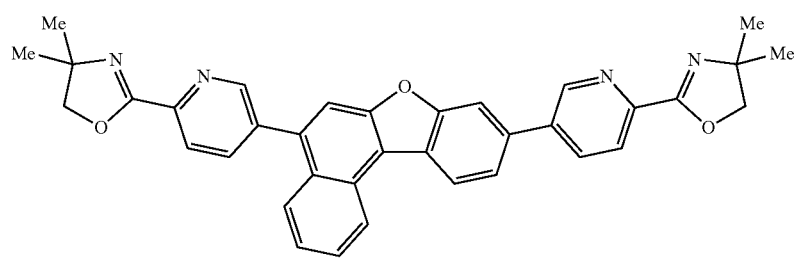
(1-2-721)
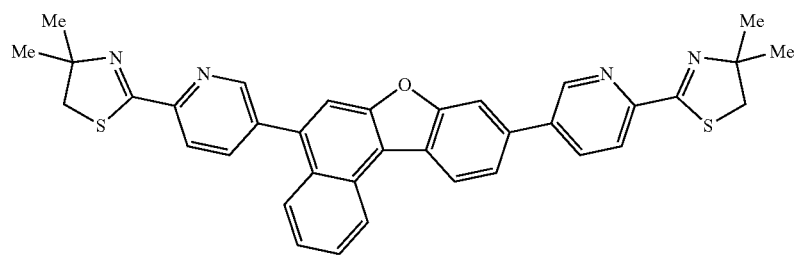
(1-2-722)

-continued
(1-2-723)
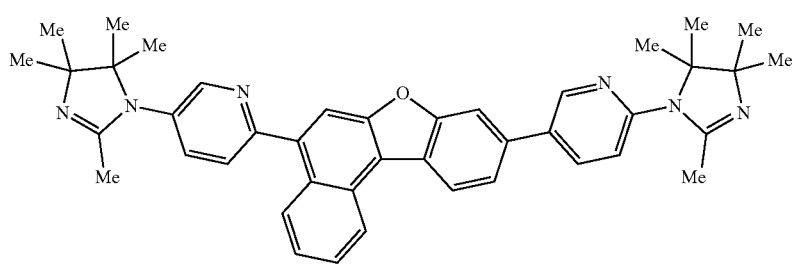
(1-2-724)
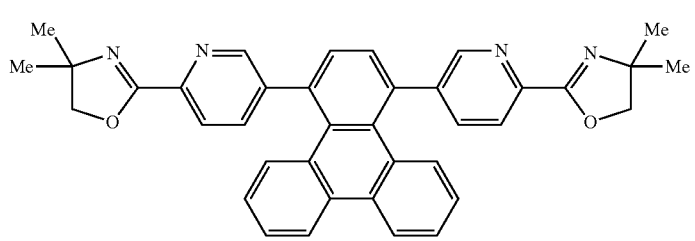
(1-2-725)
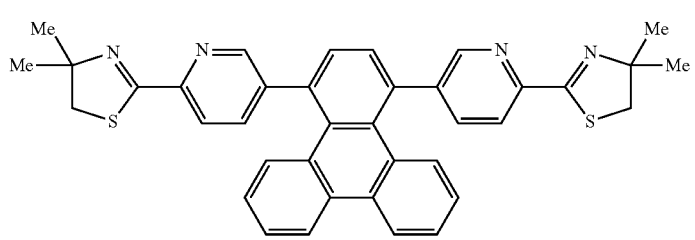
(1-2-726)
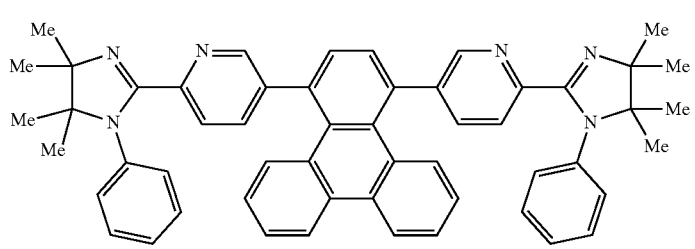
(1-2-727)
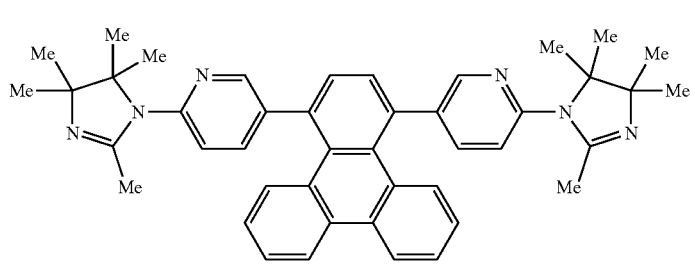
(1-2-728)

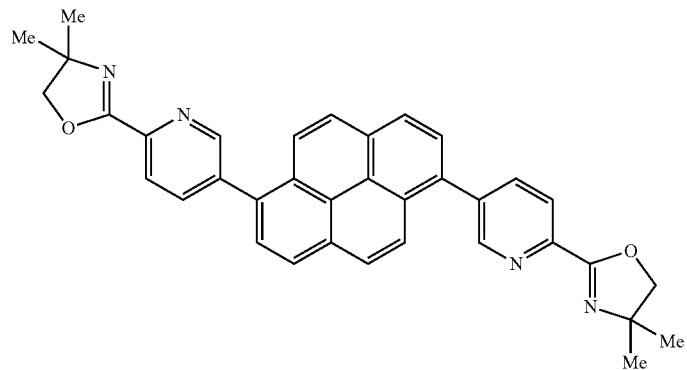
(1-2-729)
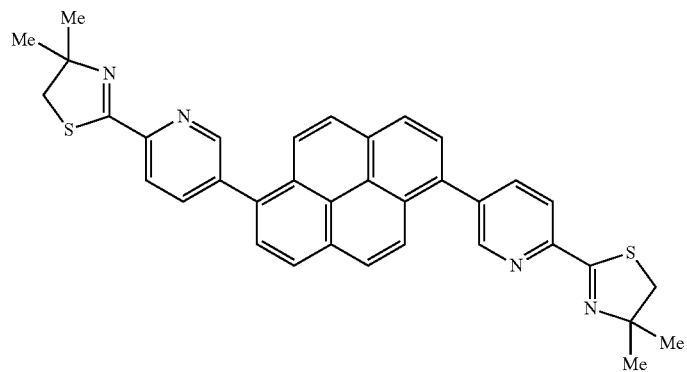
(1-2-730)
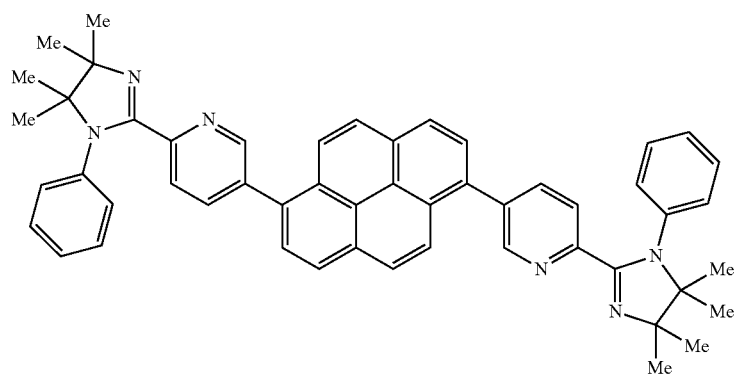
(1-2-731)
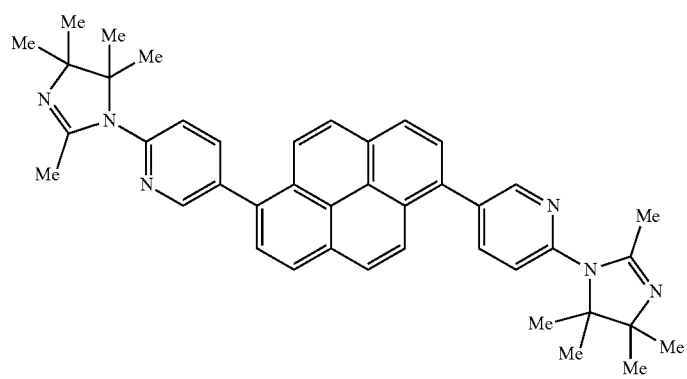
(1-2-732)

-continued
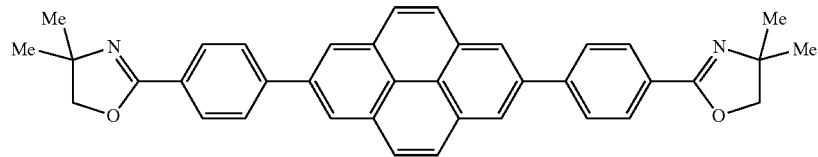
(1-2-741)
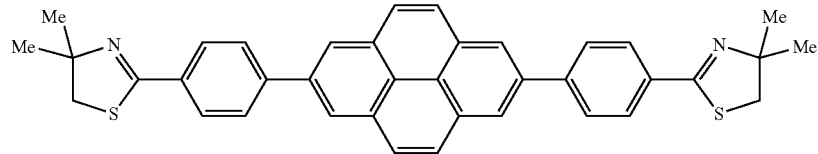
(1-2-742)
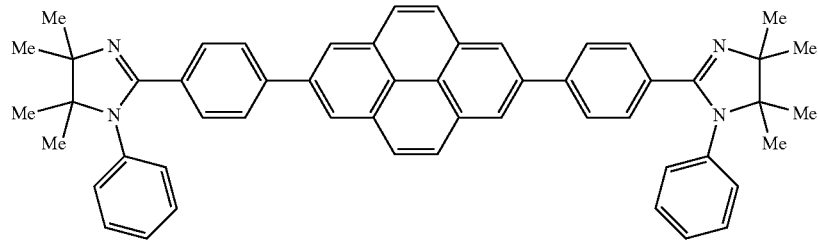
(1-2-743)
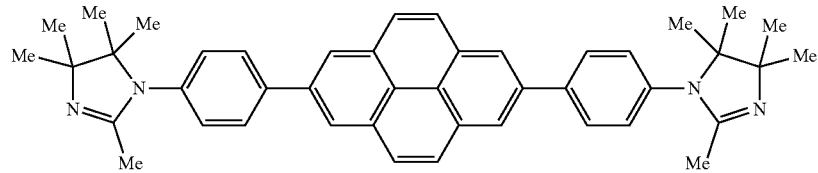
(1-2-744)
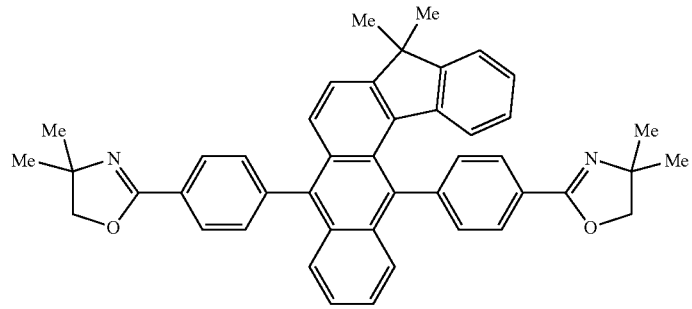
(1-2-745)
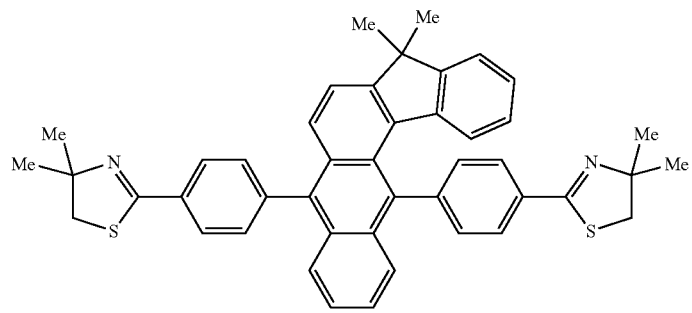
(1-2-746)

-continued
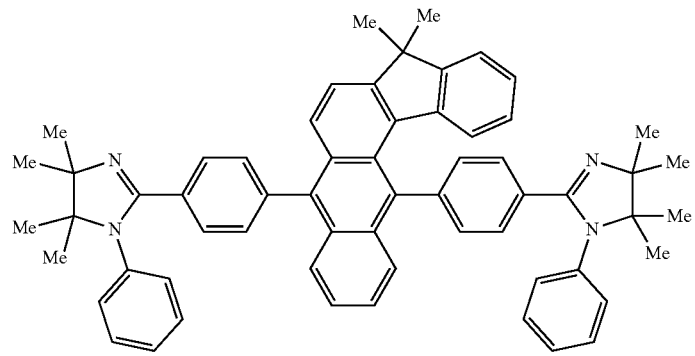
(1-2-747)
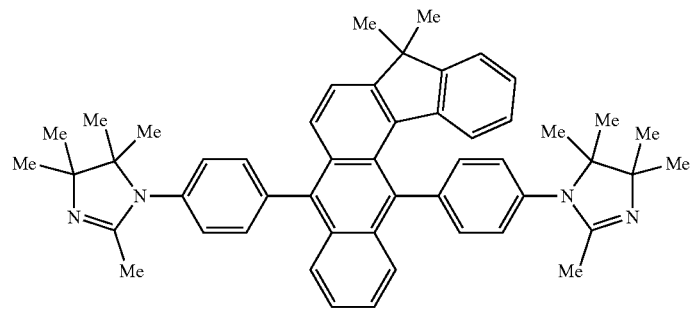
(1-2-748)
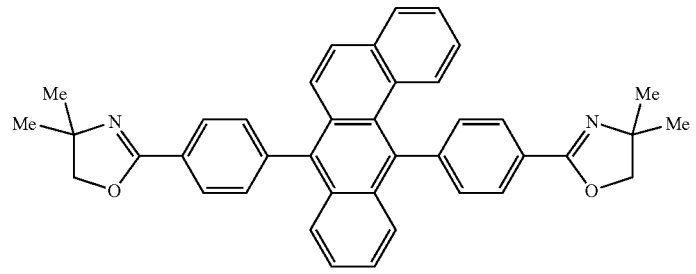
(1-2-749)
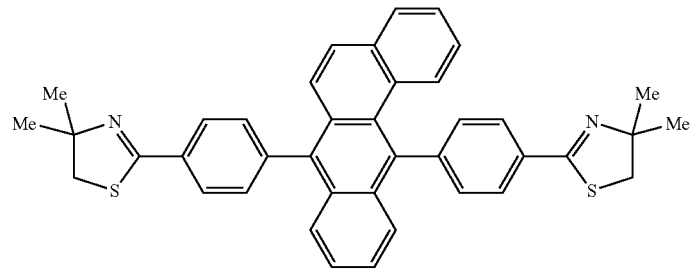
(1-2-750)
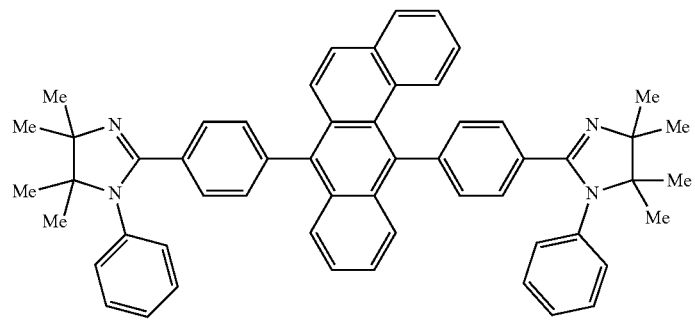
(1-2-751)

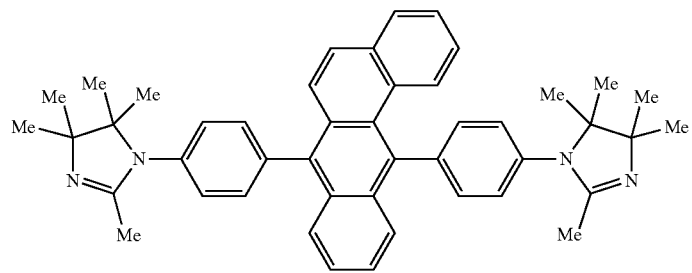
(1-2-752)
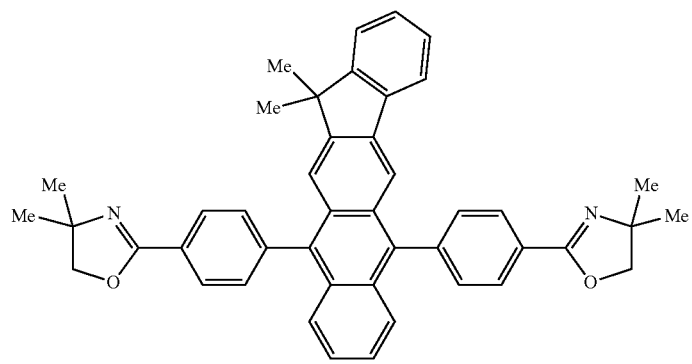
(1-2-761)
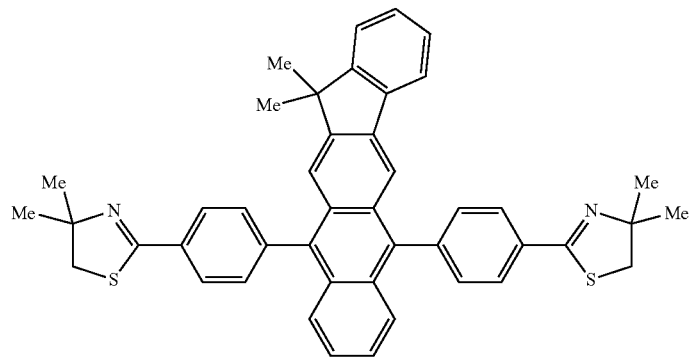
(1-2-762)
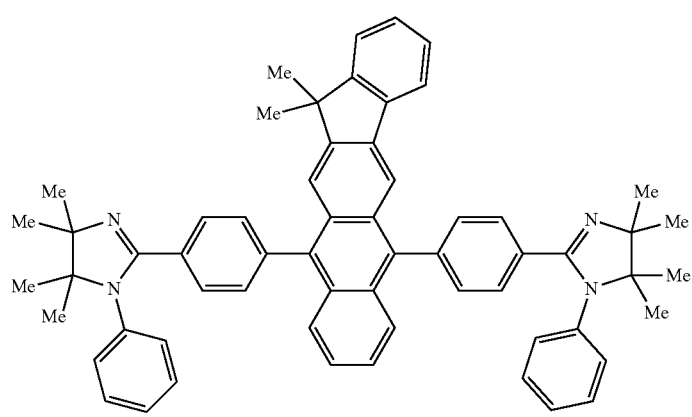
(1-2-763)

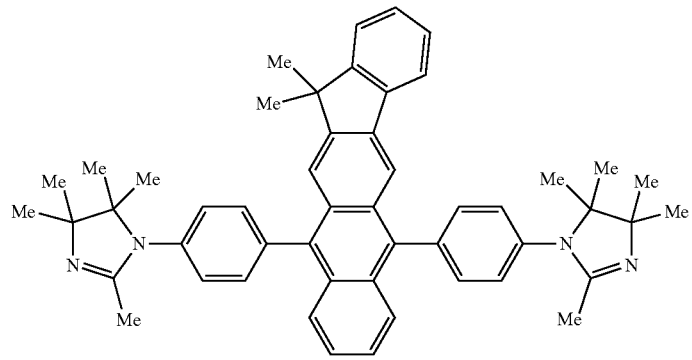
(1-2-764)
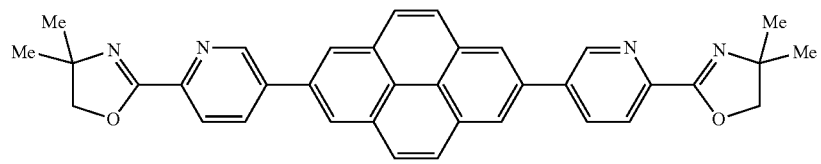
(1-2-771)
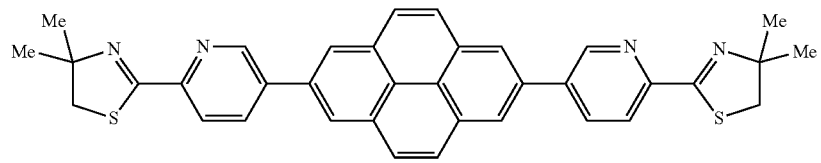
(1-2-772)
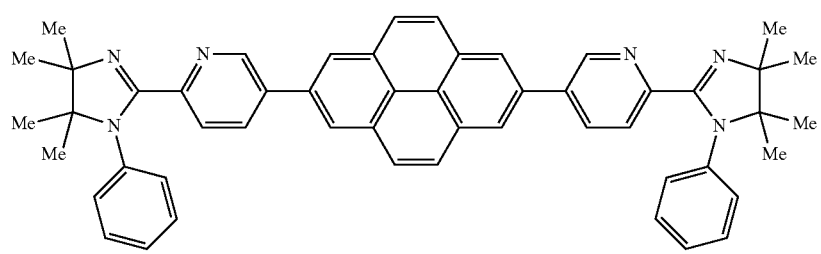
(1-2-773)
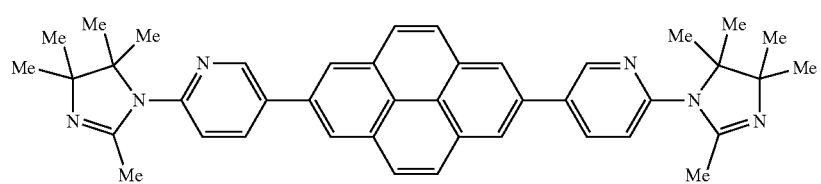
(1-2-774)
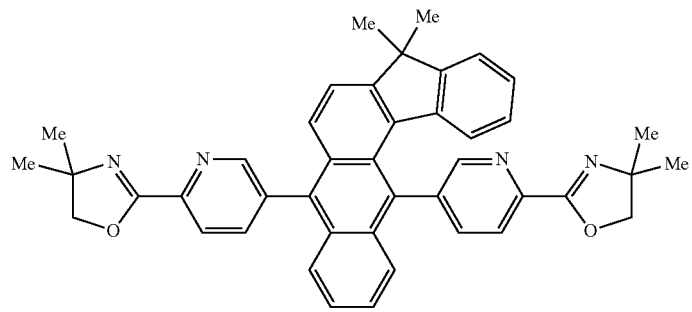
(1-2-775)

-continued
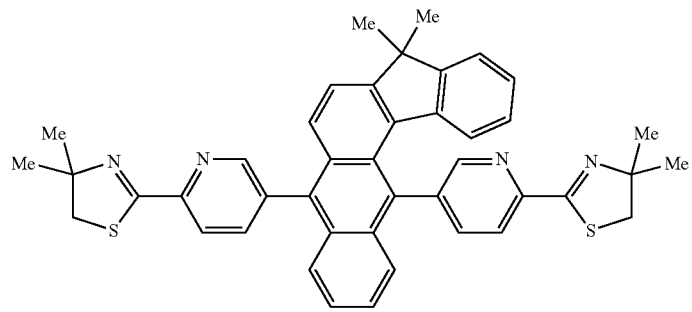
(1-2-776)
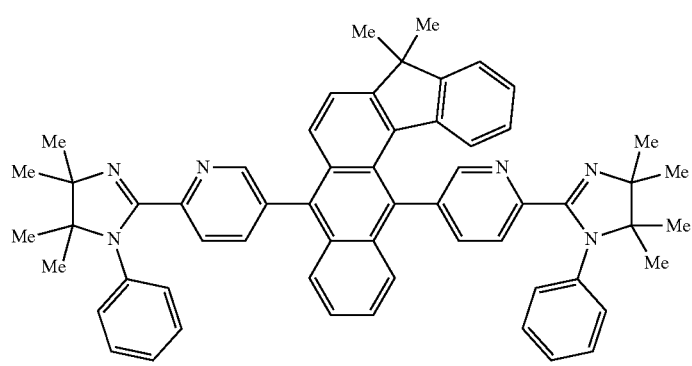
(1-2-777)
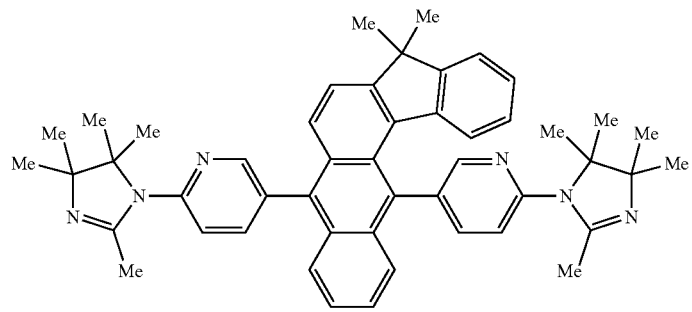
(1-2-778)
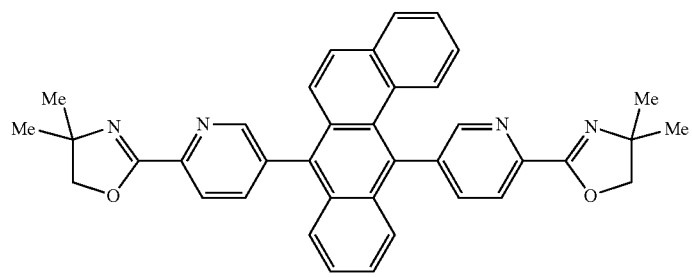
(1-2-779)
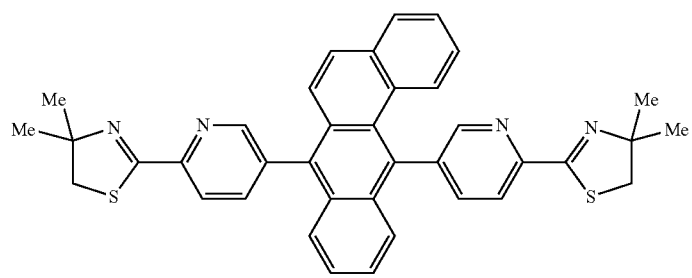
(1-2-780)

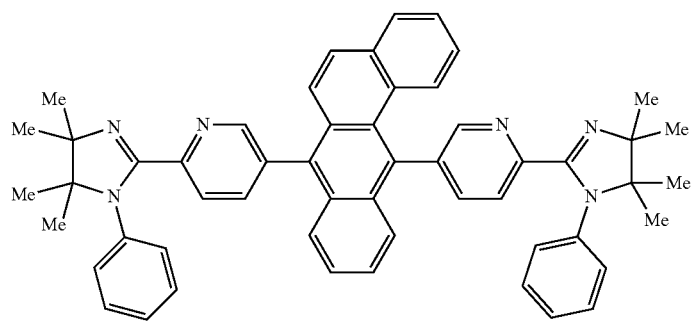
(1-2-781)
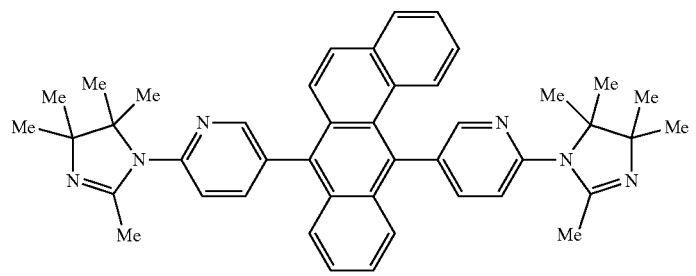
(1-2-782)
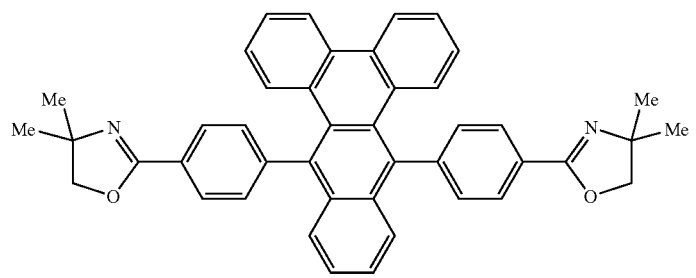
(1-2-791)
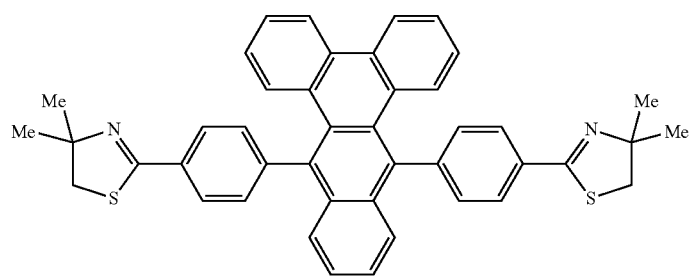
(1-2-792)
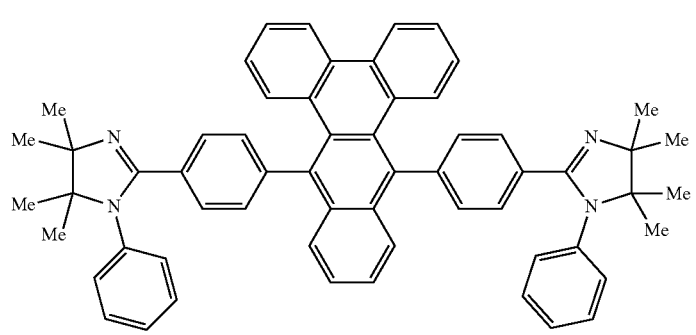
(1-2-793)

(1-2-794)
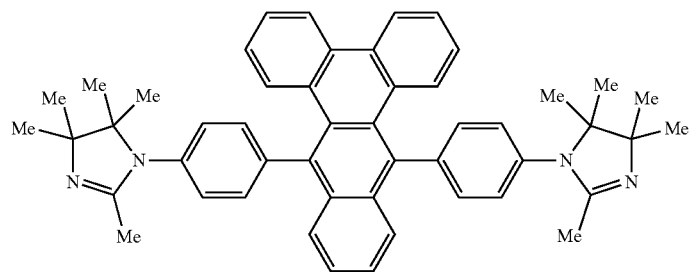
(1-2-795)
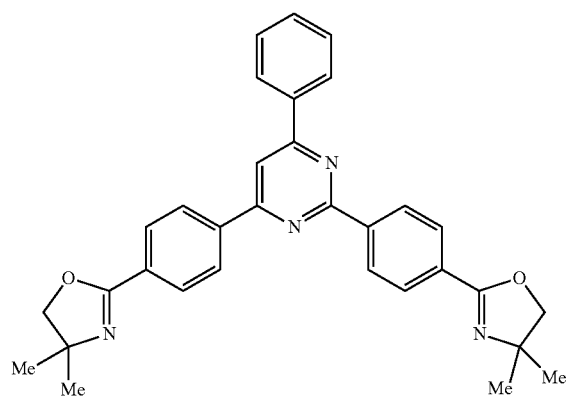
(1-2-796)
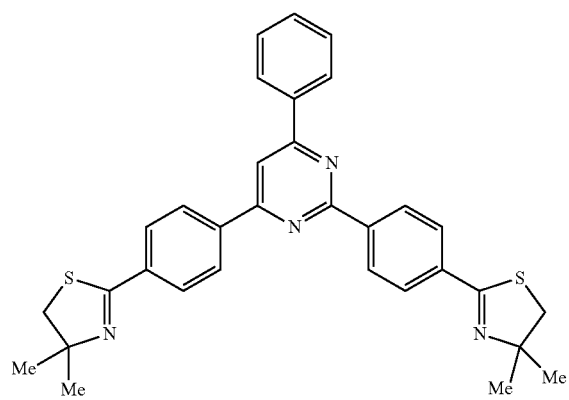
(1-2-797)
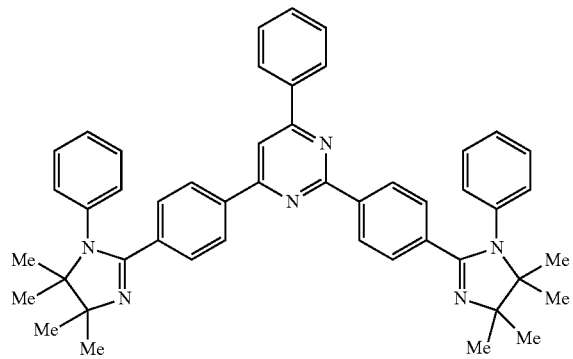
(1-2-798)
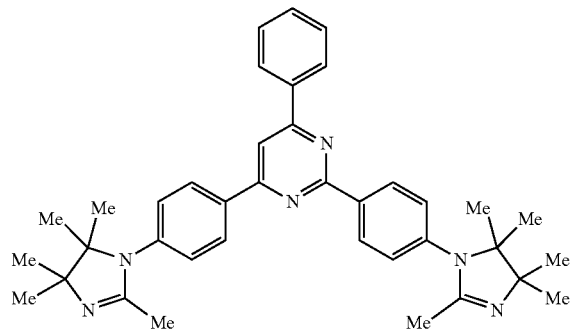
(1-2-799)
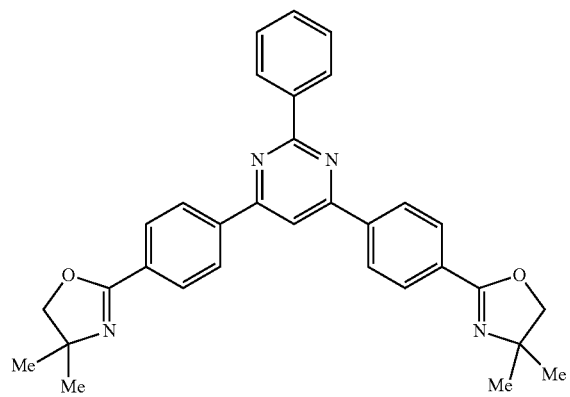
(1-2-800)
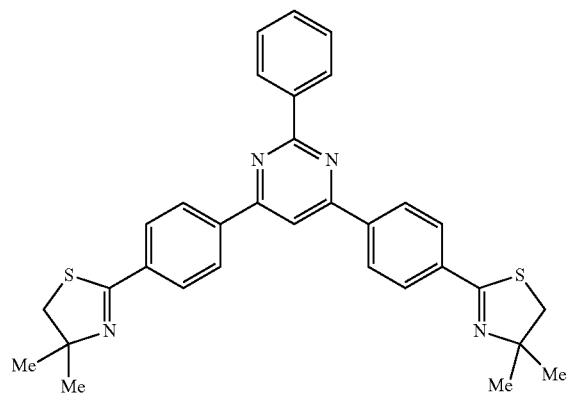

-continued
(1-2-801)
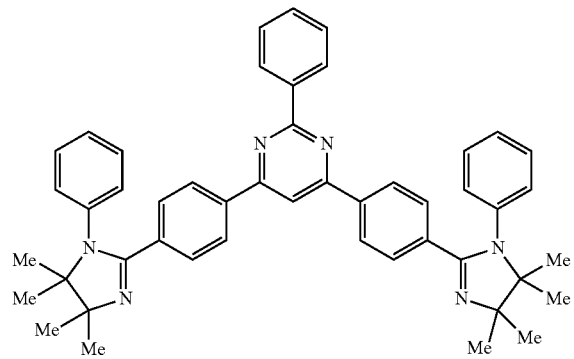
(1-2-802)
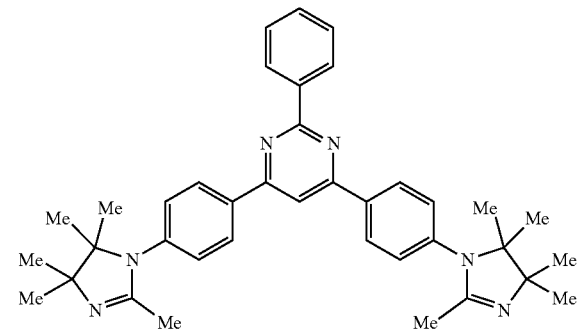
(1-2-811)
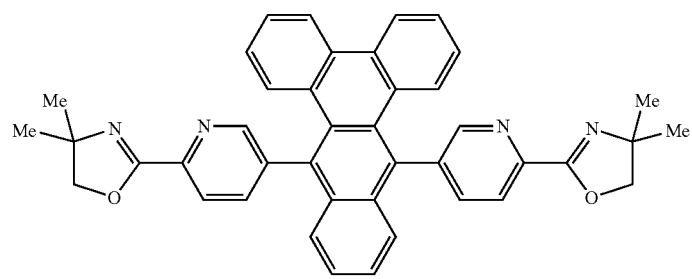
(1-2-812)
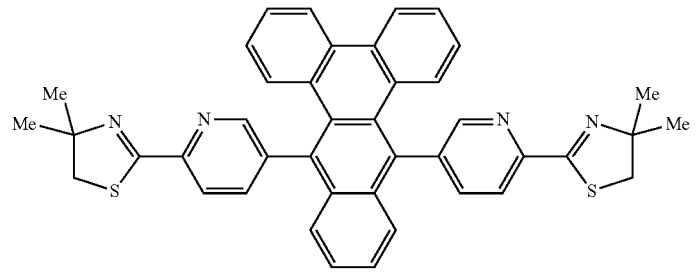
(1-2-813)
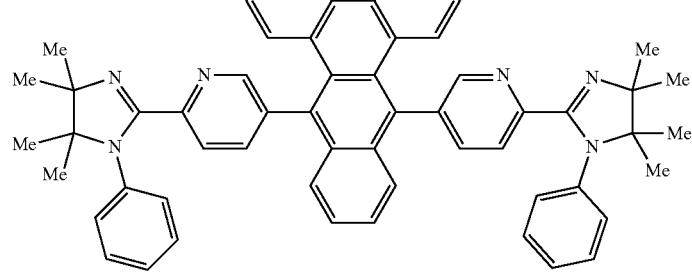
(1-2-814)
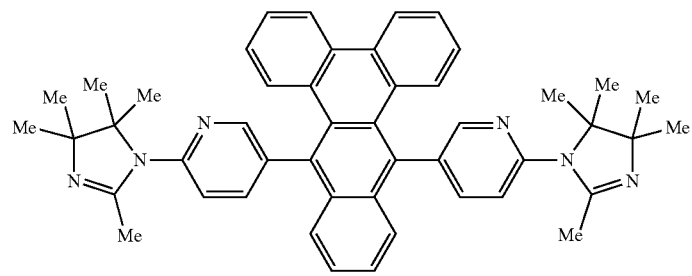

-continued
(1-2-815)
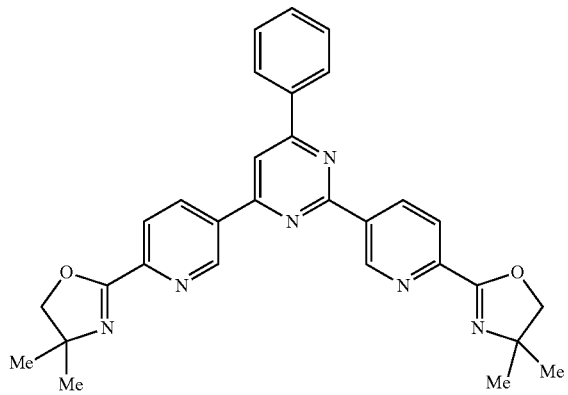
(1-2-816)
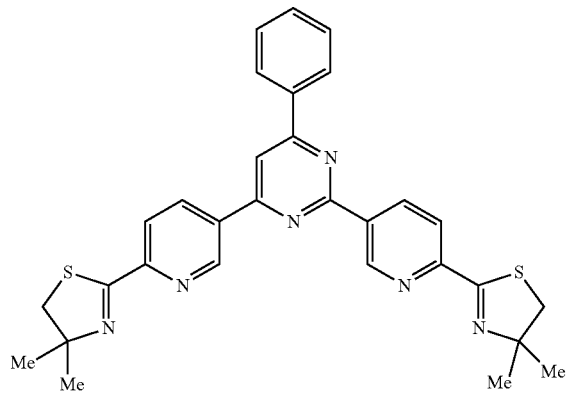
(1-2-817)
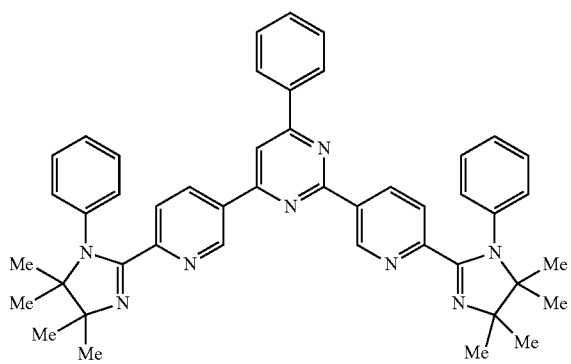
(1-2-818)
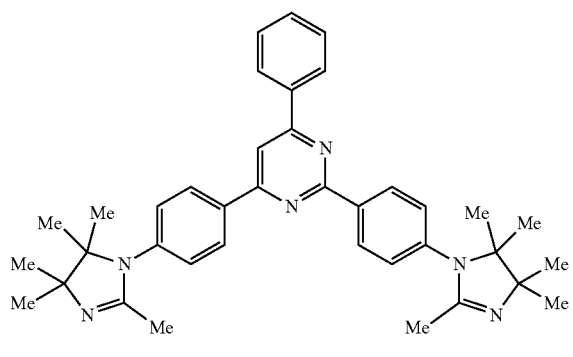
(1-2-819)
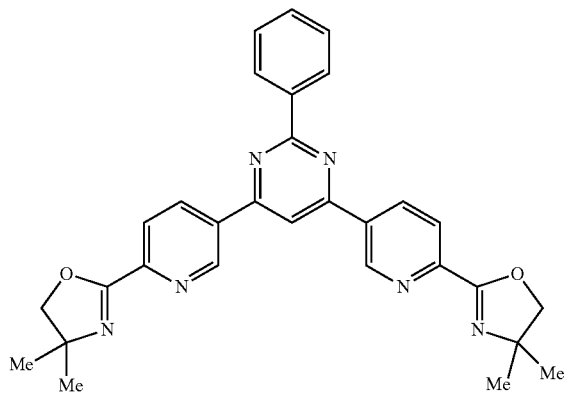
(1-2-820)
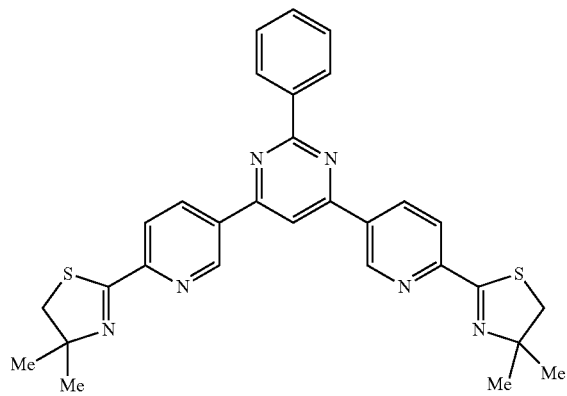
(1-2-821)
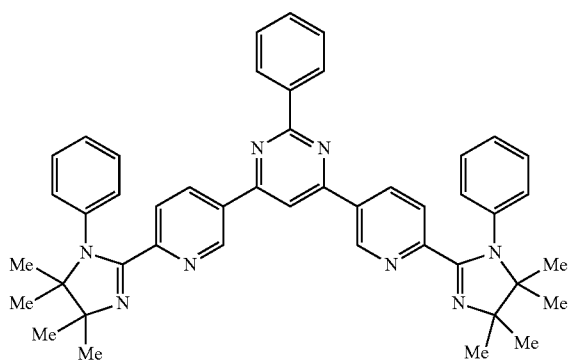
(1-2-822)
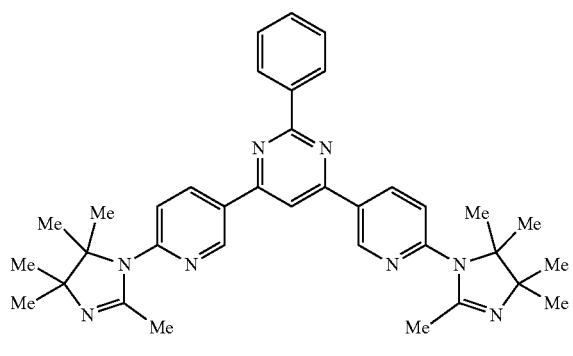

-continued
(1-2-831)
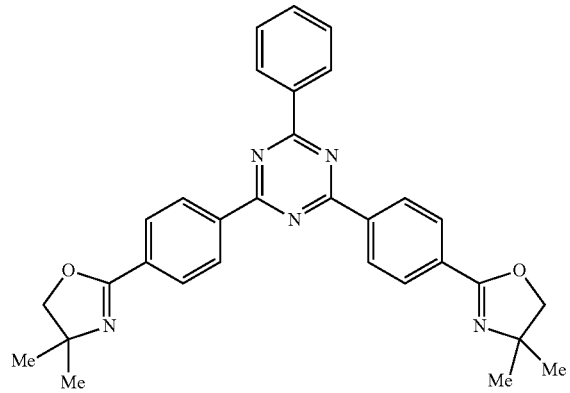
(1-2-832)
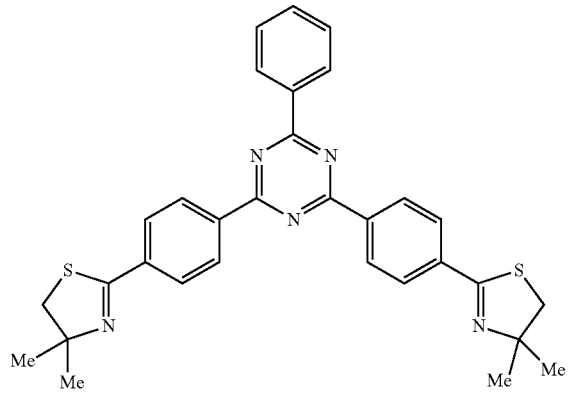
(1-2-833)
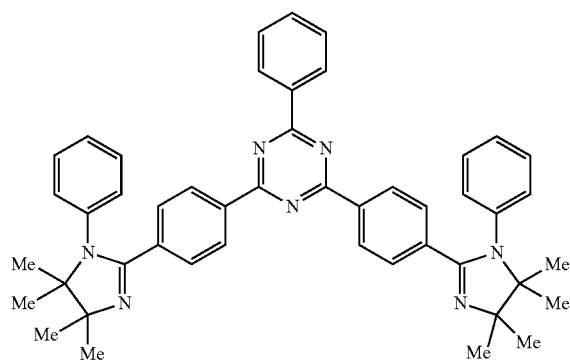
(1-2-834)
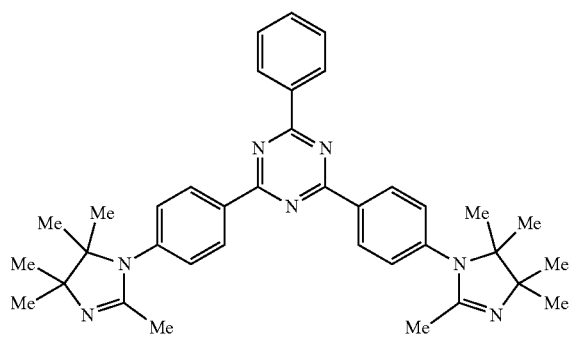
(1-2-835)
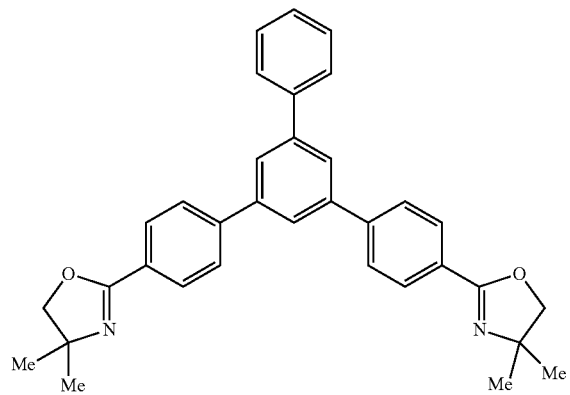
(1-2-836)
(1-2-837)
(1-2-838)
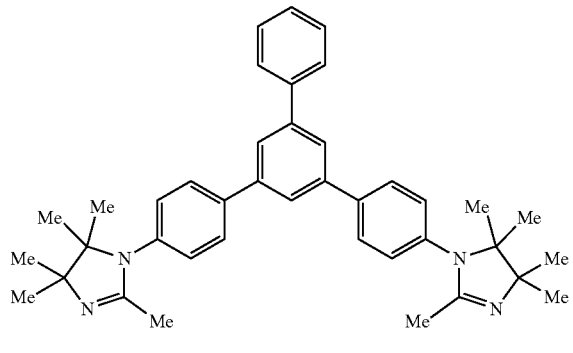

-continued
(1-2-839)
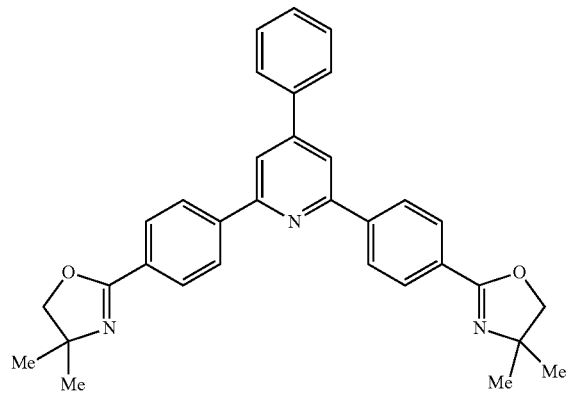
(1-2-840)
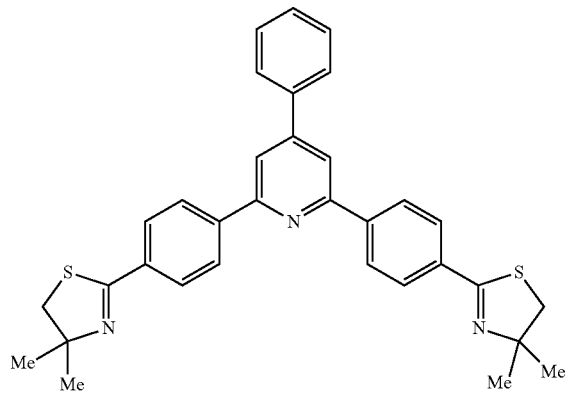
(1-2-841)
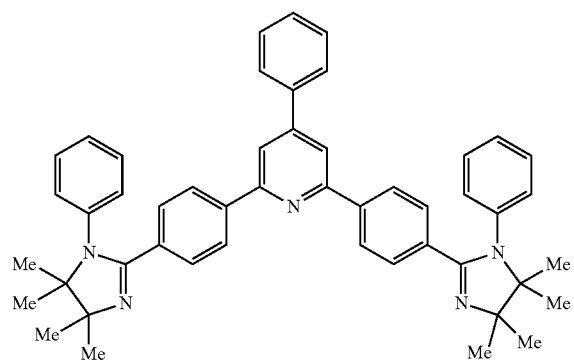
(1-2-842)
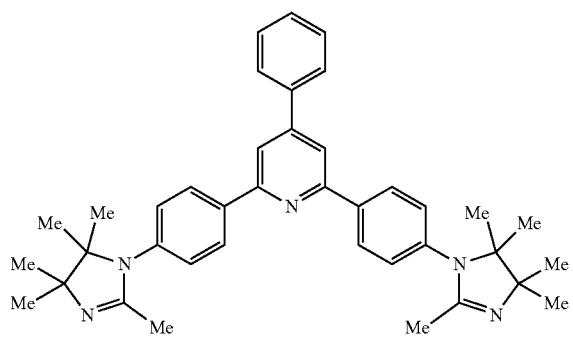
(1-2-851)
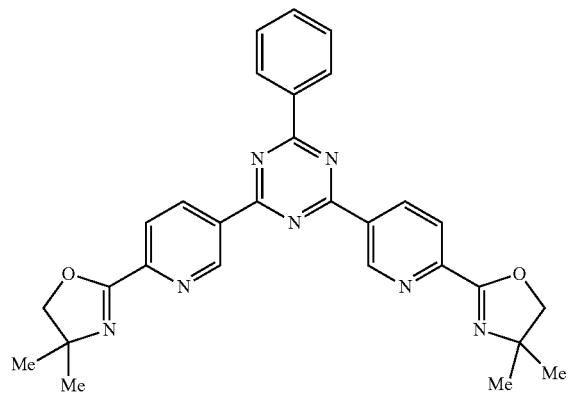
(1-2-852)
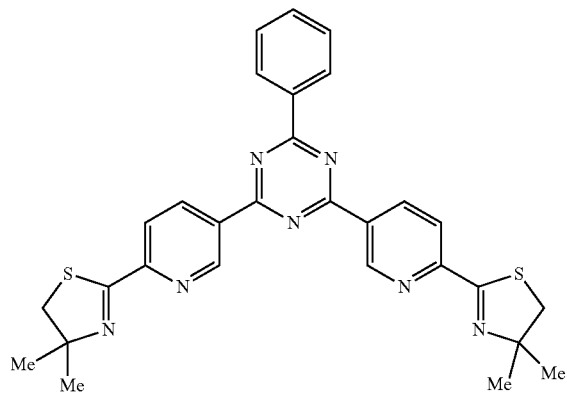
(1-2-853)
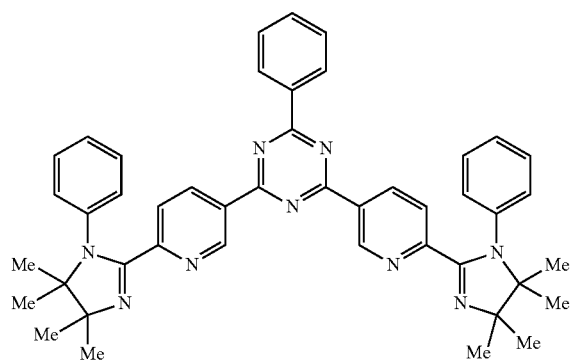
(1-2-854)
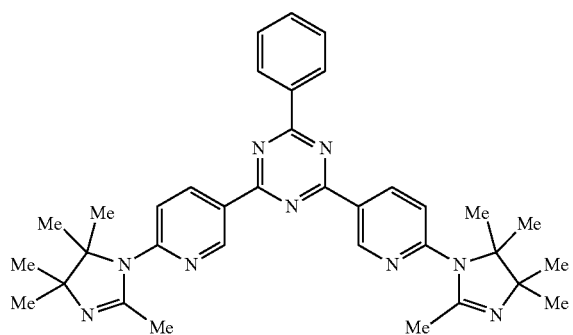

-continued
(1-2-855)
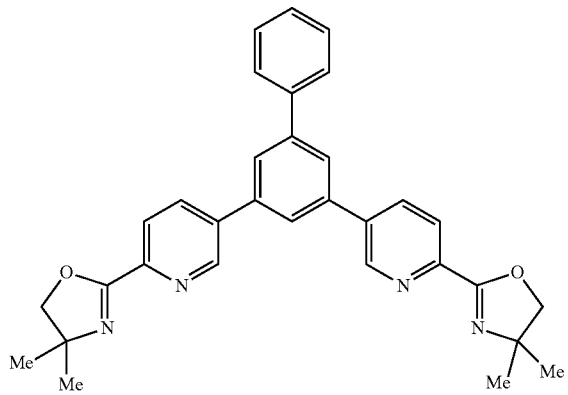
(1-2-856)
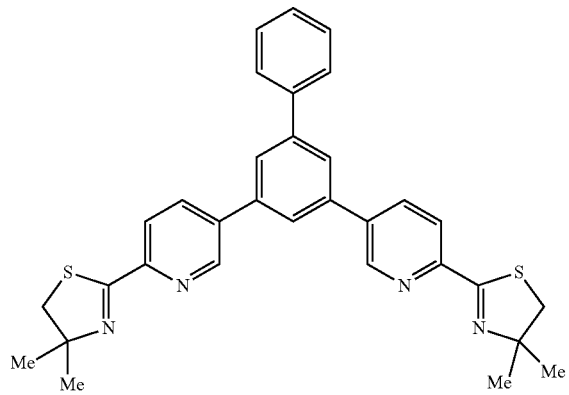
(1-2-857)
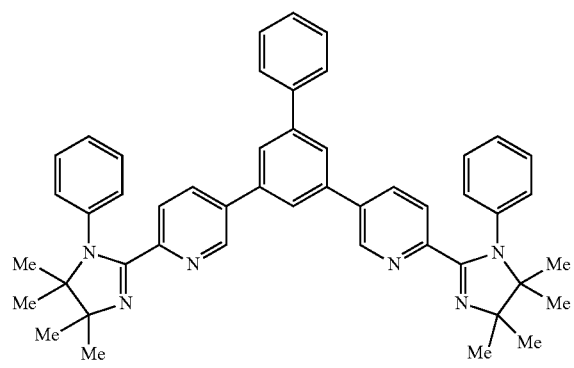
(1-2-858)
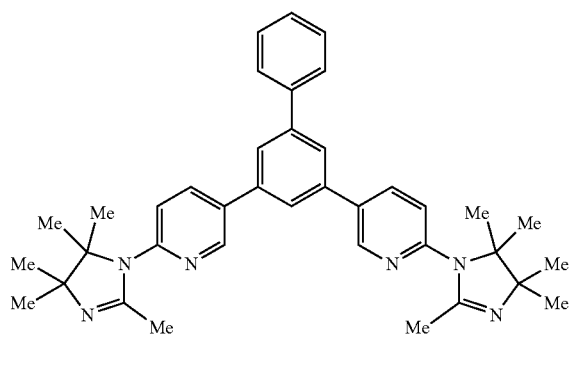
(1-2-859)
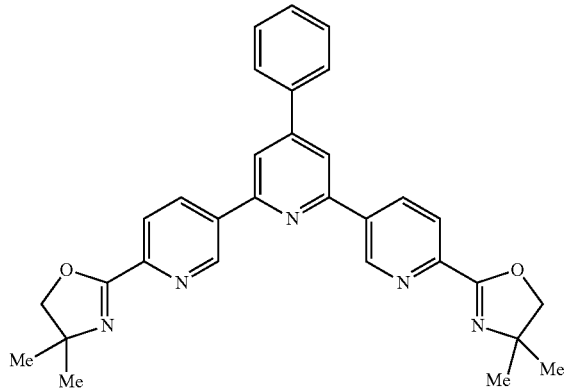
(1-2-860)
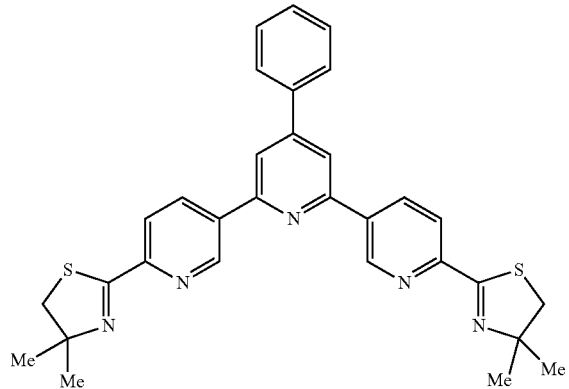
(1-2-861)
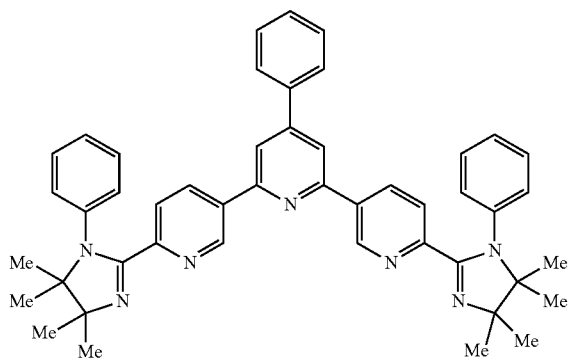
(1-2-862)
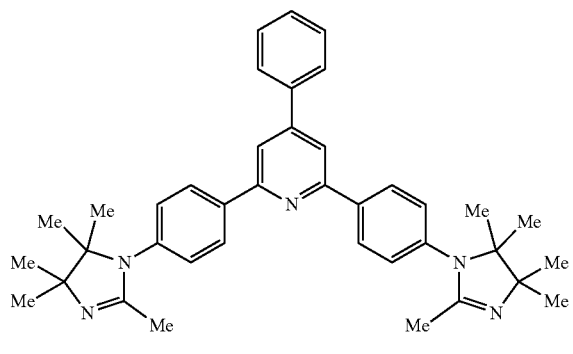

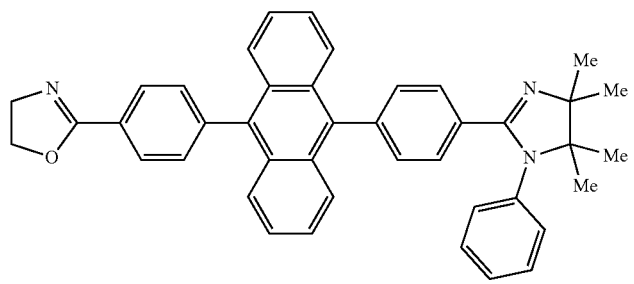
(1-2-871)
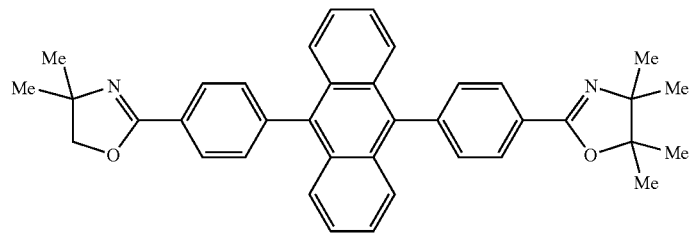
(1-2-872)
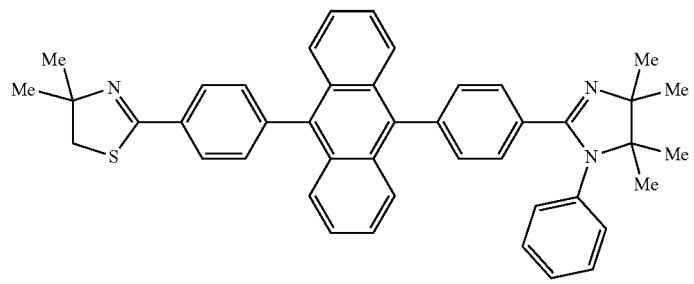
(1-2-873)
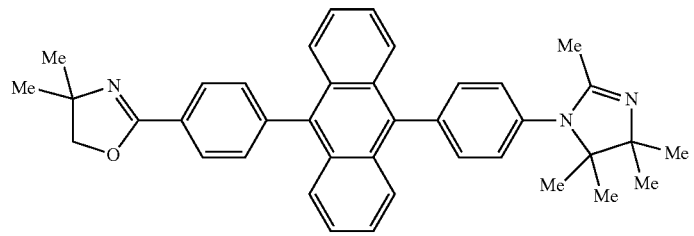
(1-2-874)
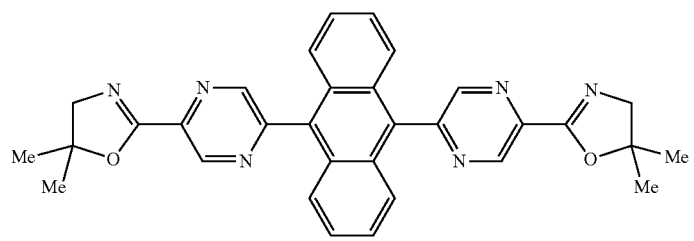
(1-2-875)
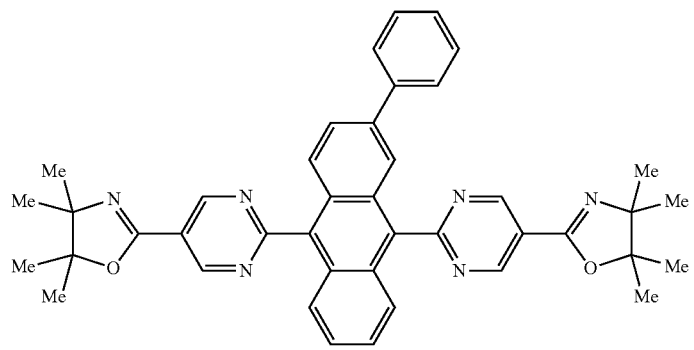
(1-2-876)

(1-2-877)
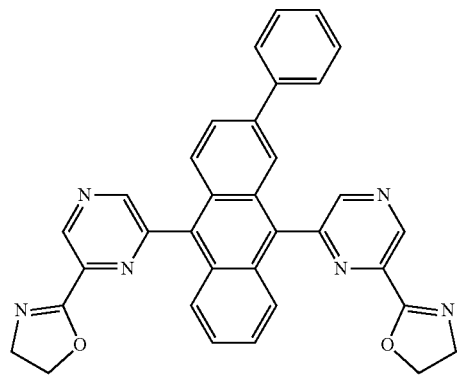
(1-2-878)
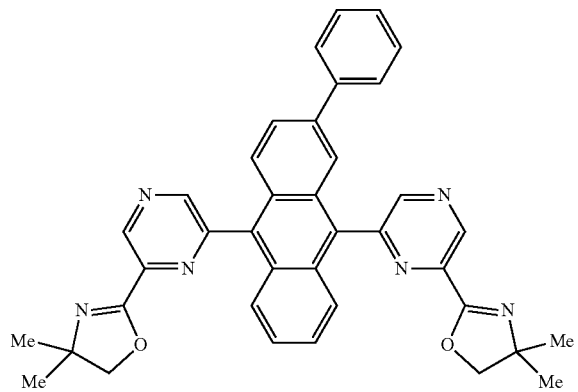
(1-2-879)
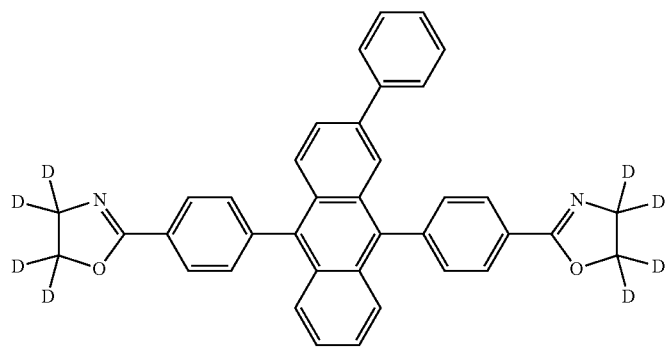
(1-2-880)
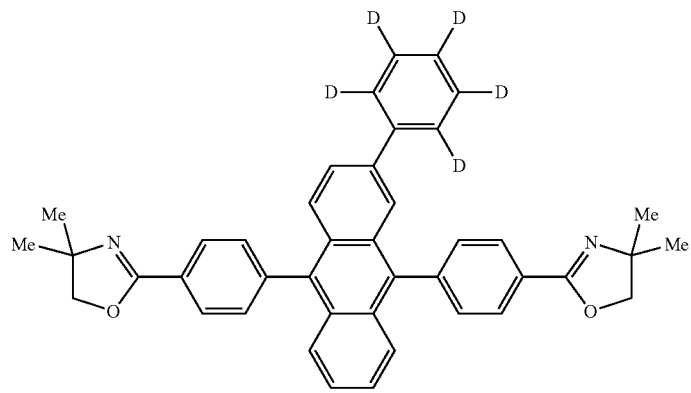
(1-2-881)
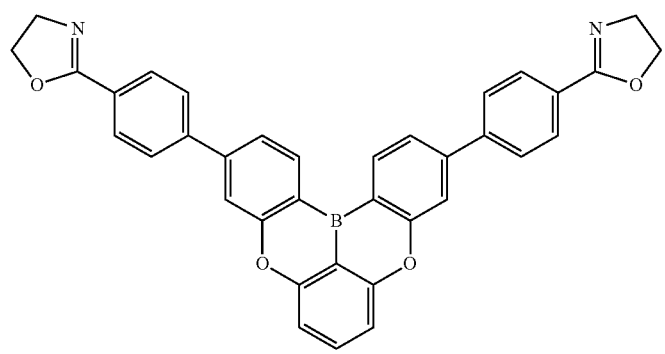

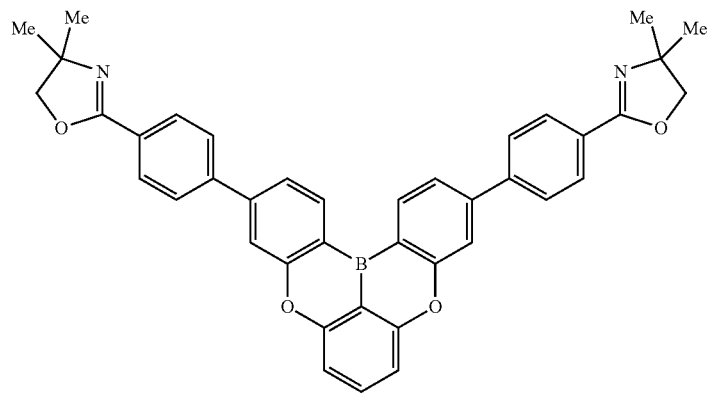
(1-2-882)
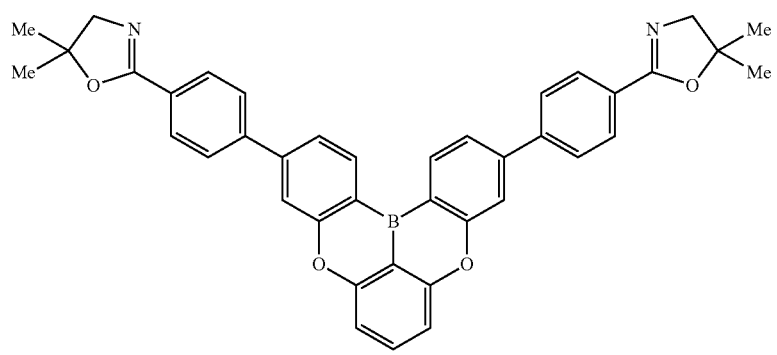
(1-2-883)
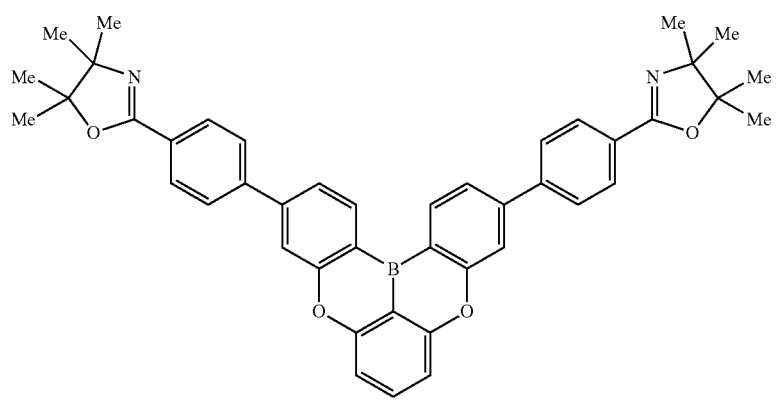
(1-2-884)
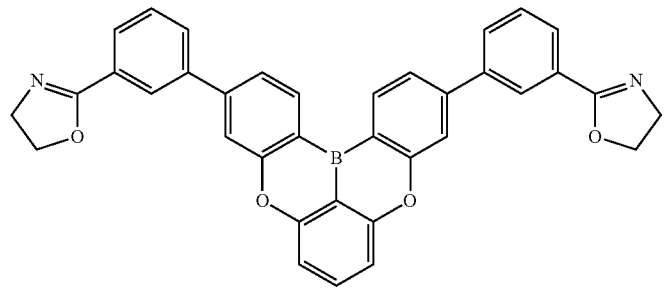
(1-2-885)

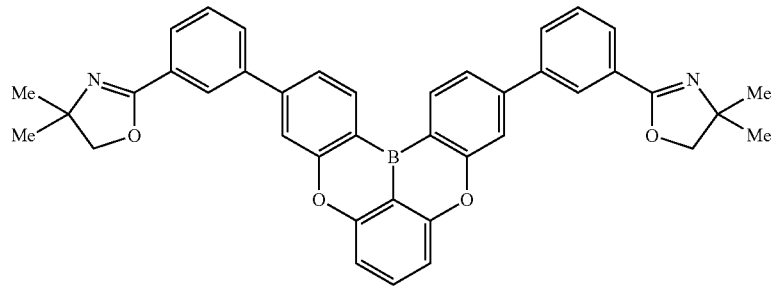
(1-2-886)
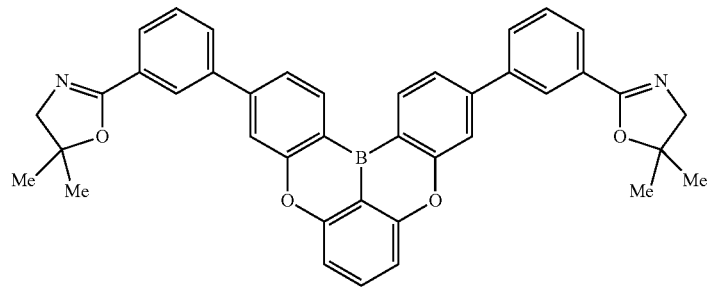
(1-2-887)
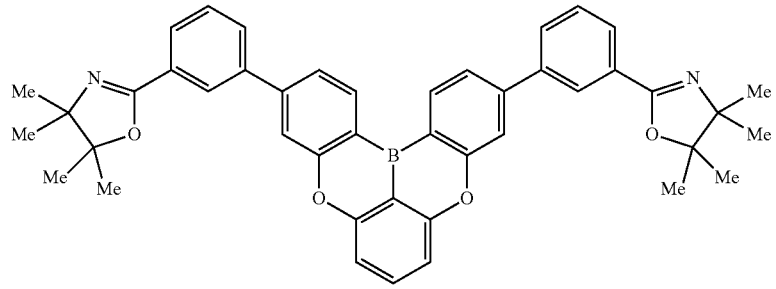
(1-2-888)
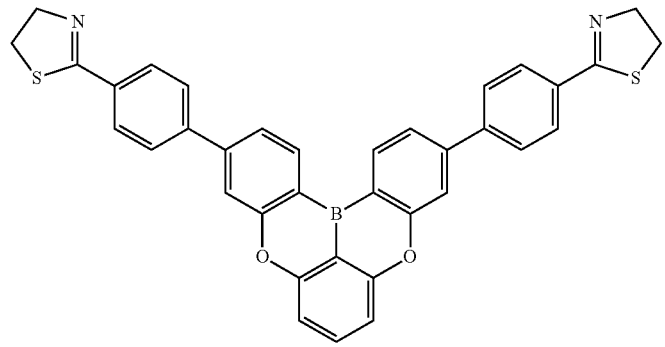
(1-2-891)
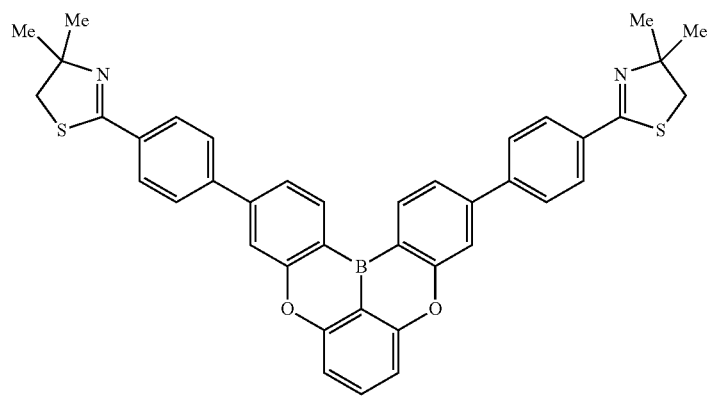
(1-2-892)

-continued
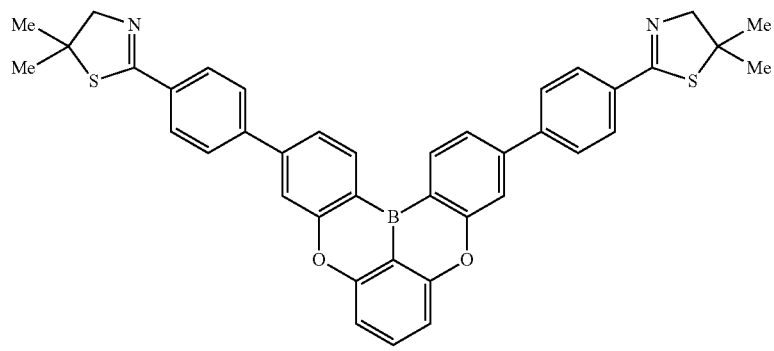
(1-2-893)
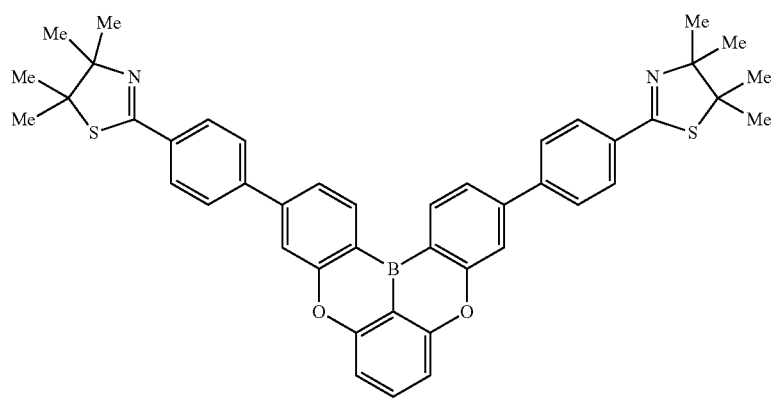
(1-2-894)
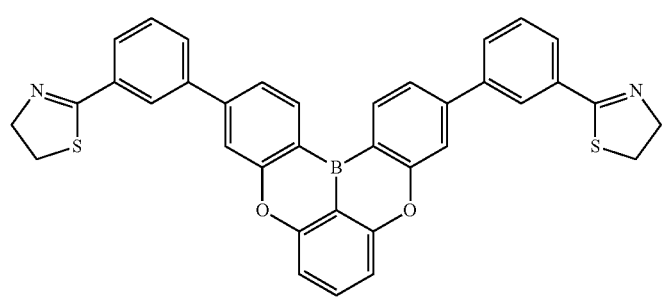
(1-2-895)
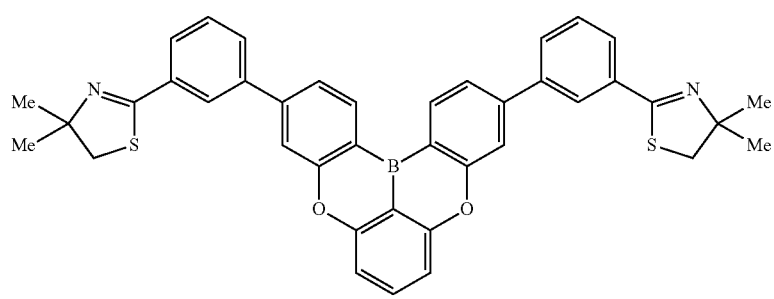
(1-2-896)
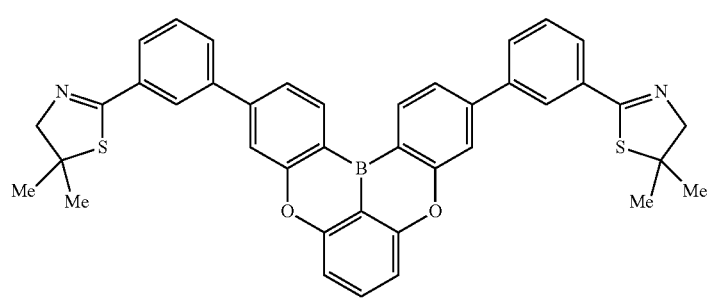
(1-2-897)

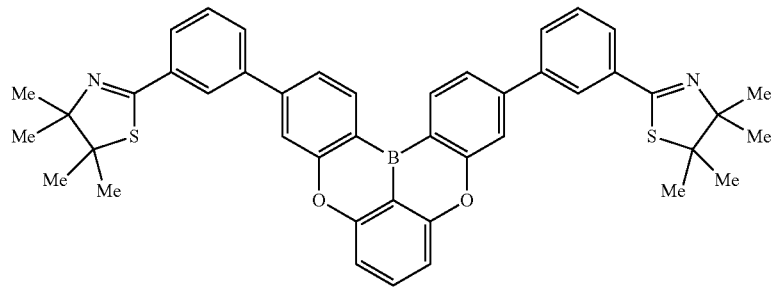
(1-2-898)
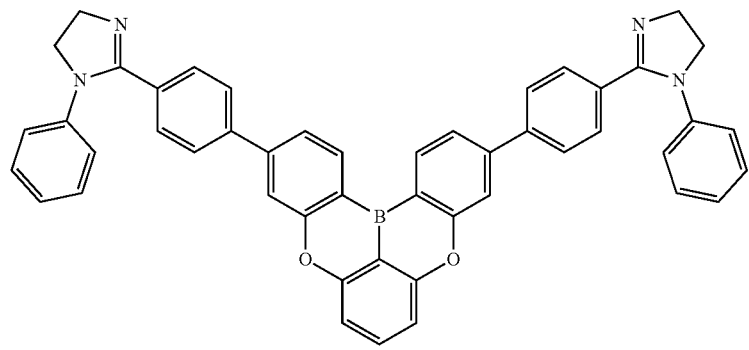
(1-2-901)
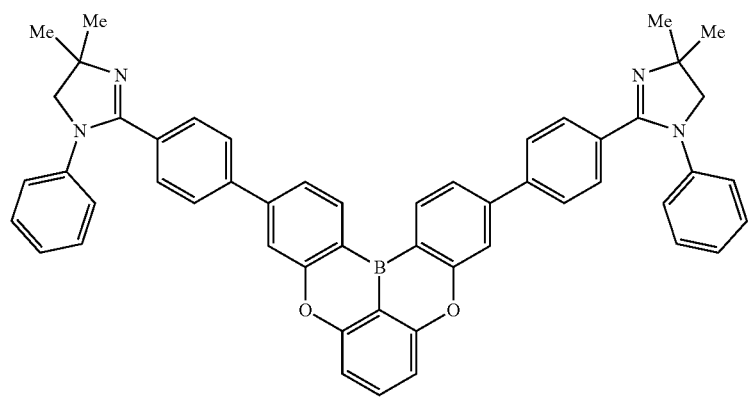
(1-2-902)
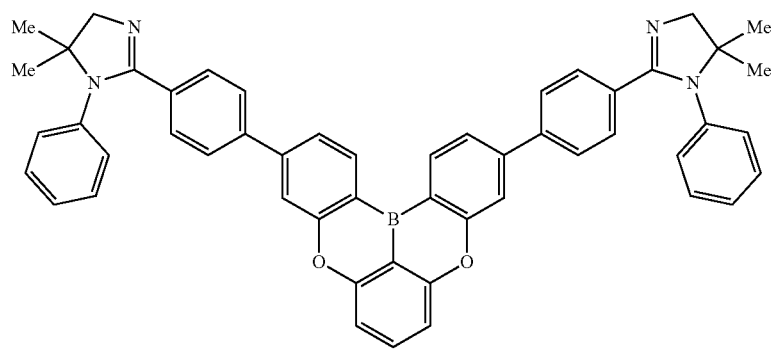
(1-2-903)

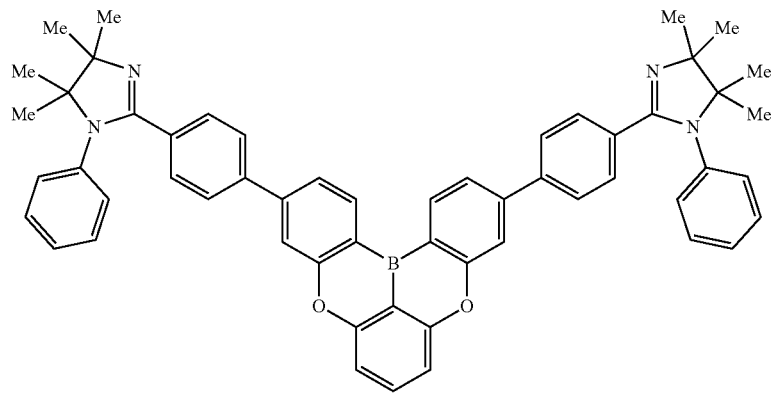
(1-2-904)
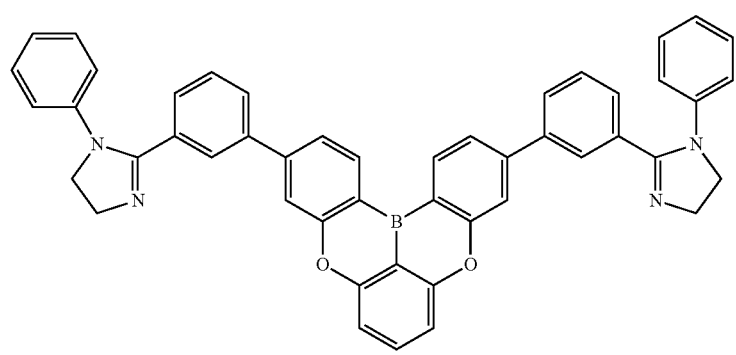
(1-2-905)
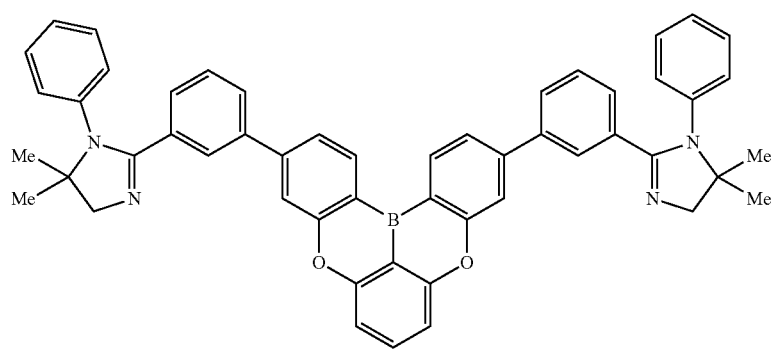
(1-2-906)
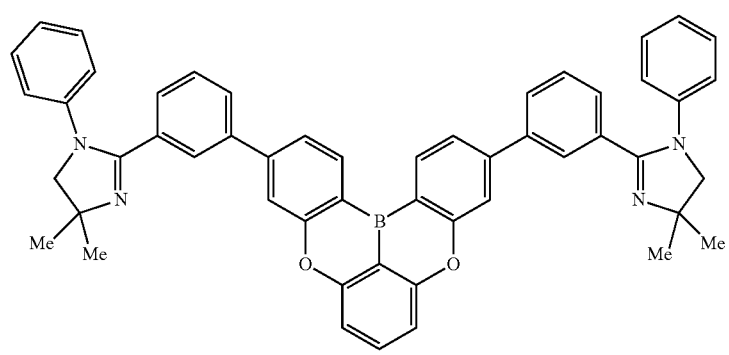
(1-2-907)

-continued
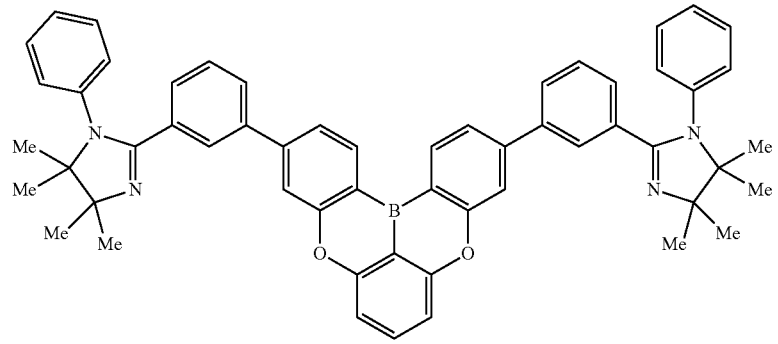
(1-2-908)
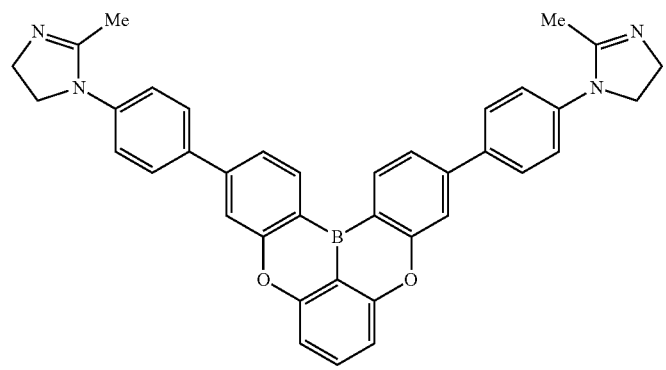
(1-2-911)
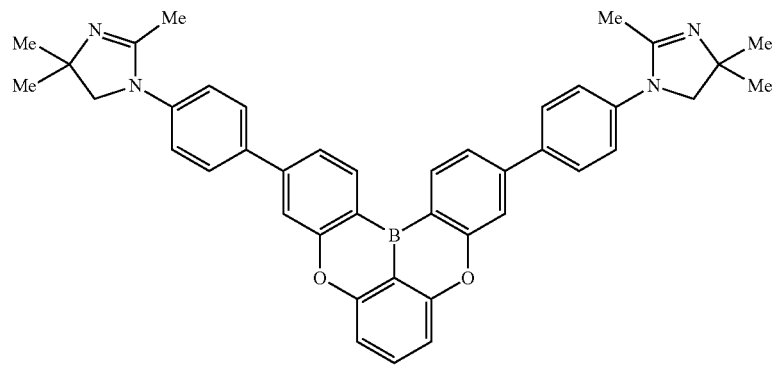
(1-2-912)
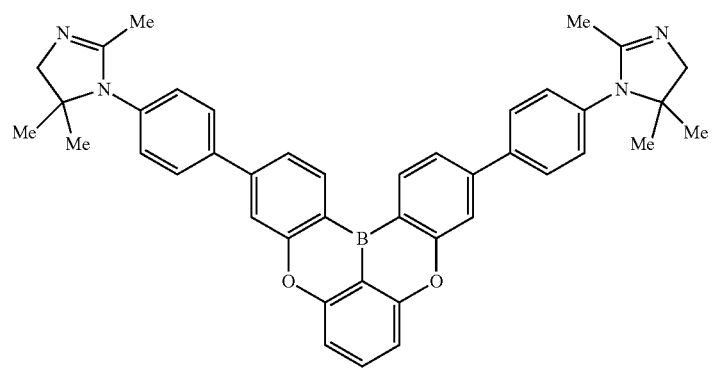
(1-2-913)

-continued
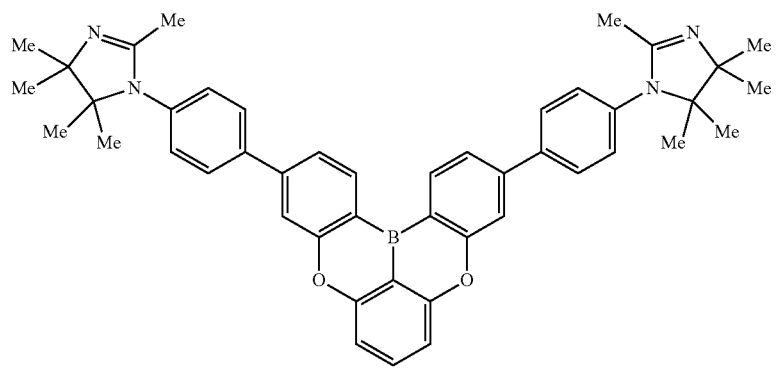
(1-2-914)
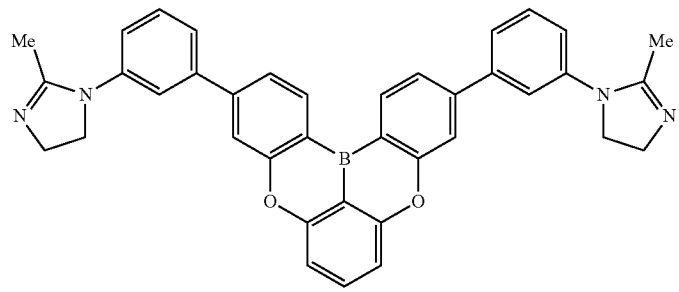
(1-2-915)
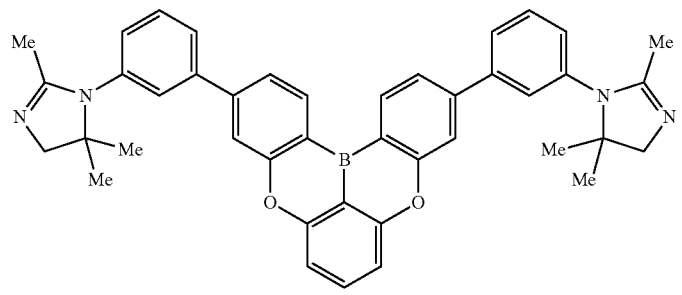
(1-2-916)
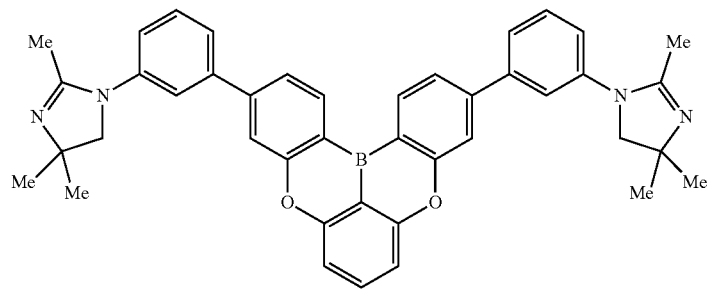
(1-2-917)
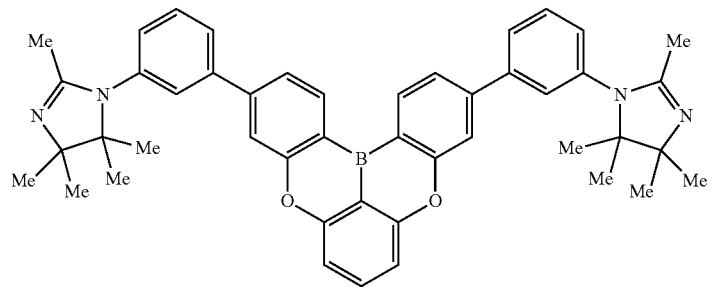
(1-2-918)

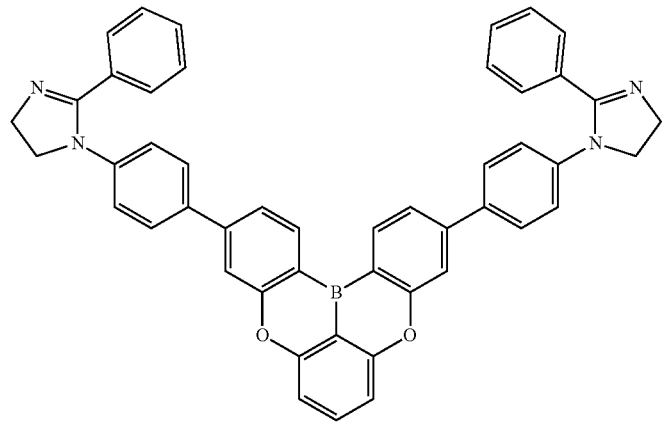
(1-2-921)
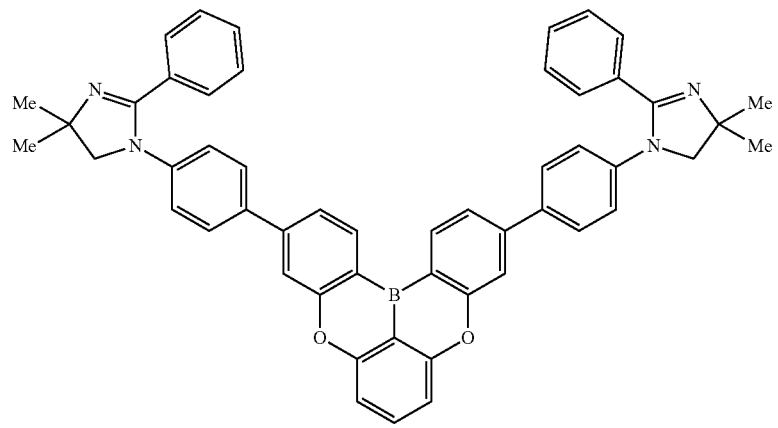
(1-2-922)
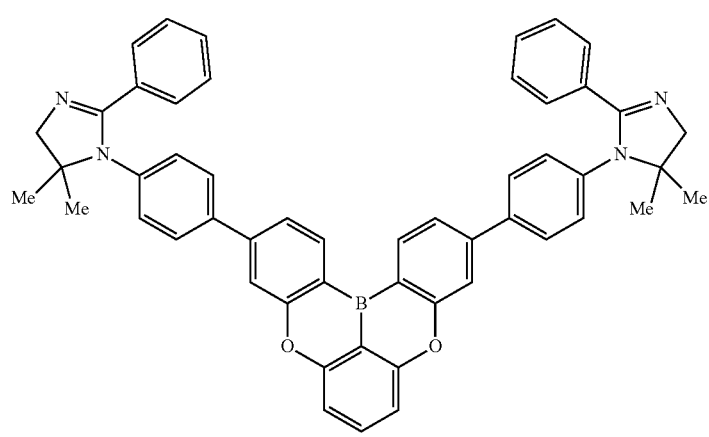
(1-2-923)

-continued
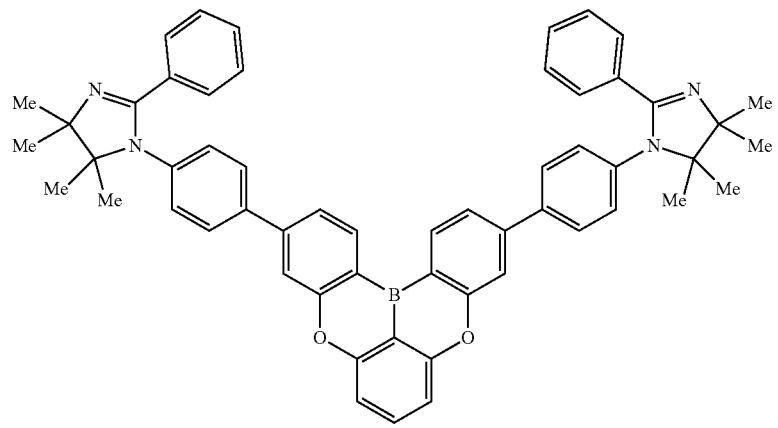
(1-2-924)
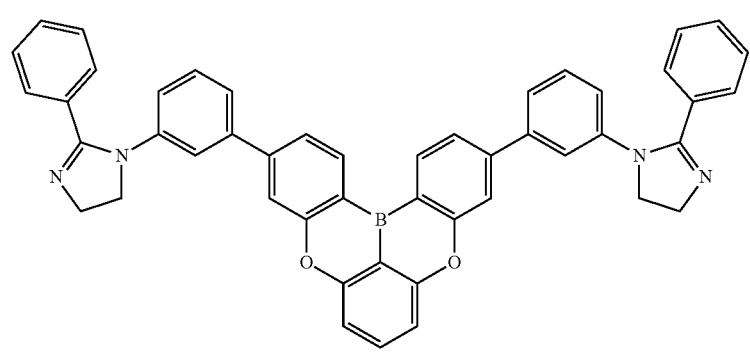
(1-2-925)
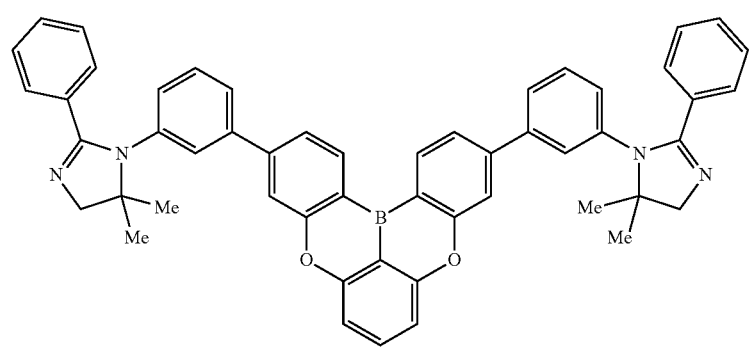
(1-2-926)
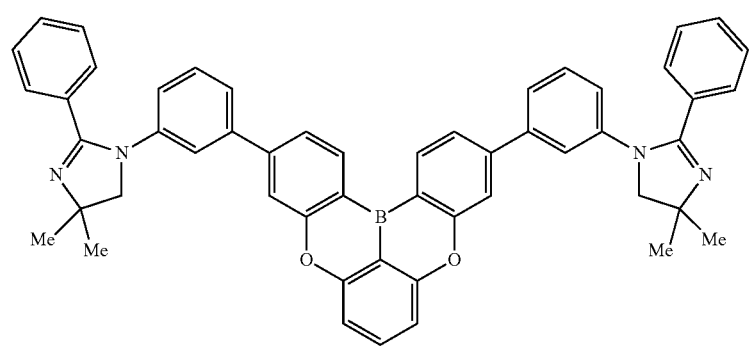
(1-2-927)

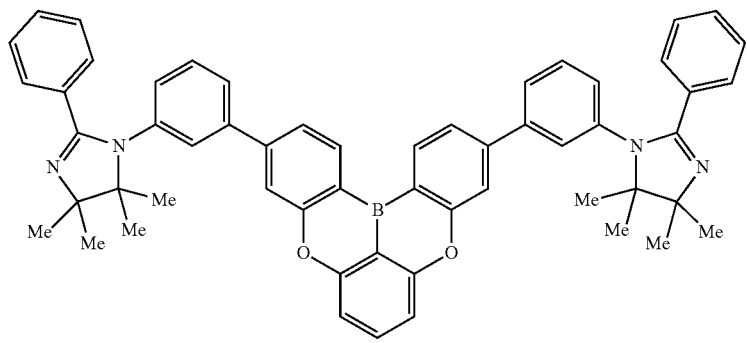
(1-2-928)
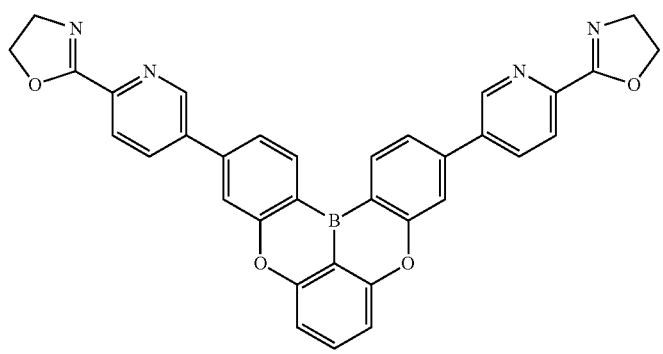
(1-2-931)
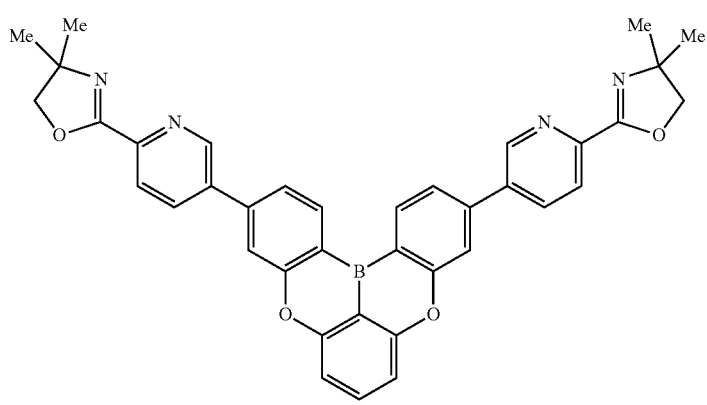
(1-2-932)
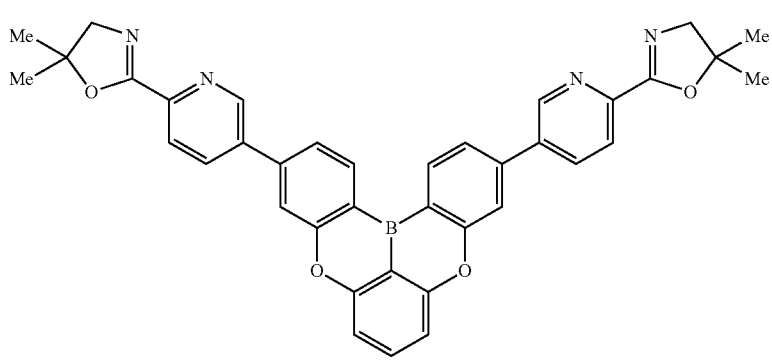
(1-2-933)

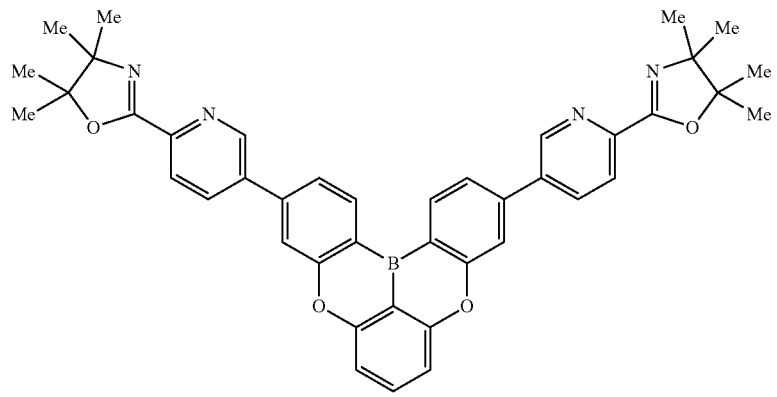
(1-2-934)
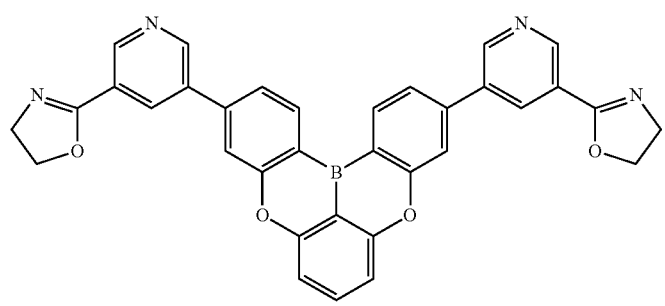
(1-2-935)
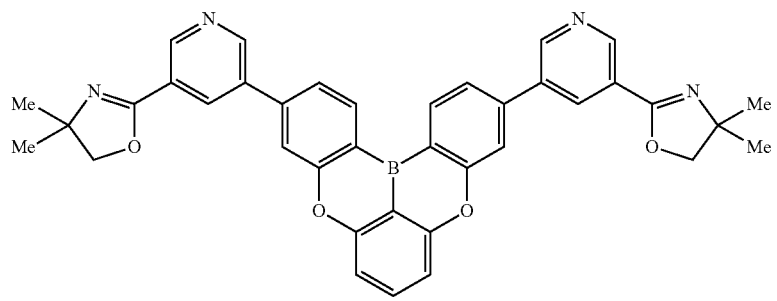
(1-2-936)
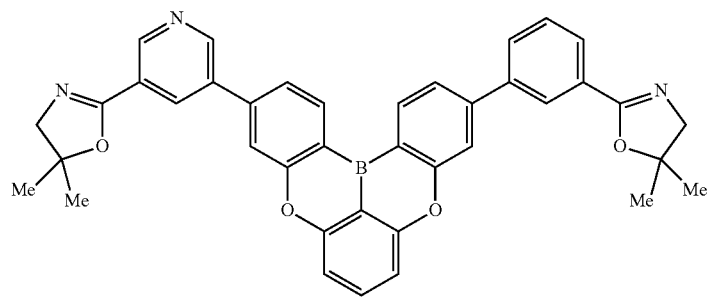
(1-2-937)
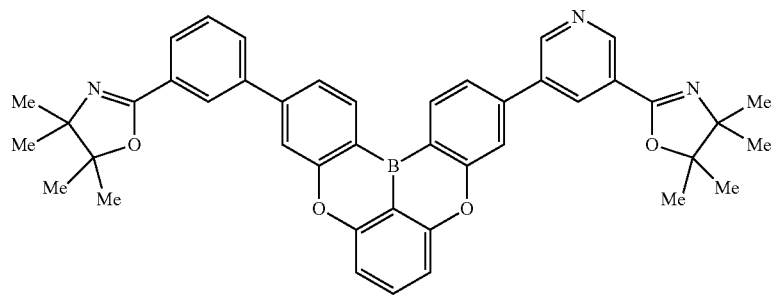
(1-2-938)

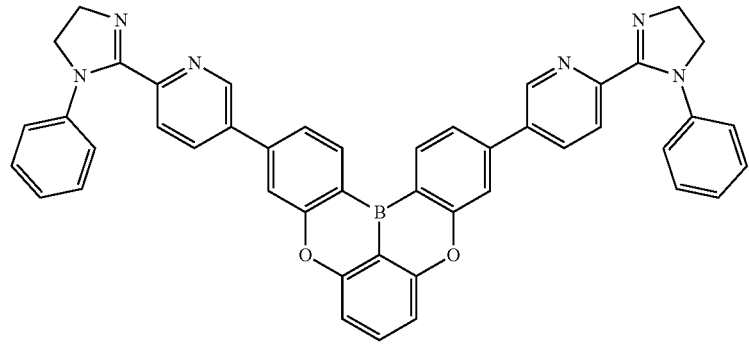
(1-2-941)
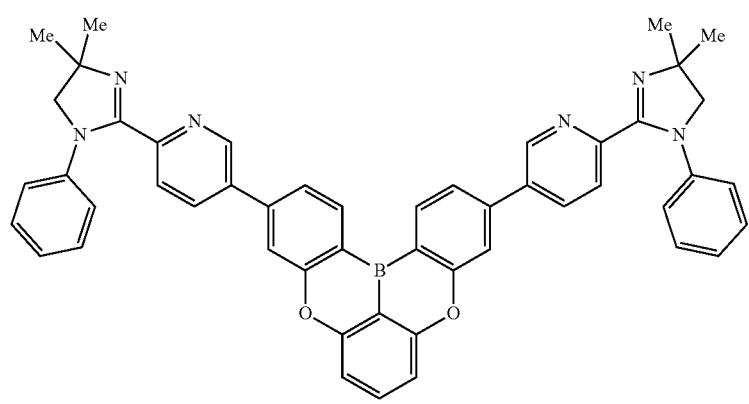
(1-2-942)
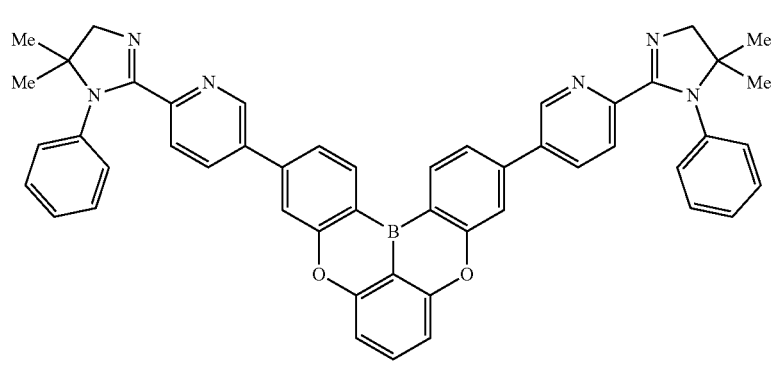
(1-2-943)
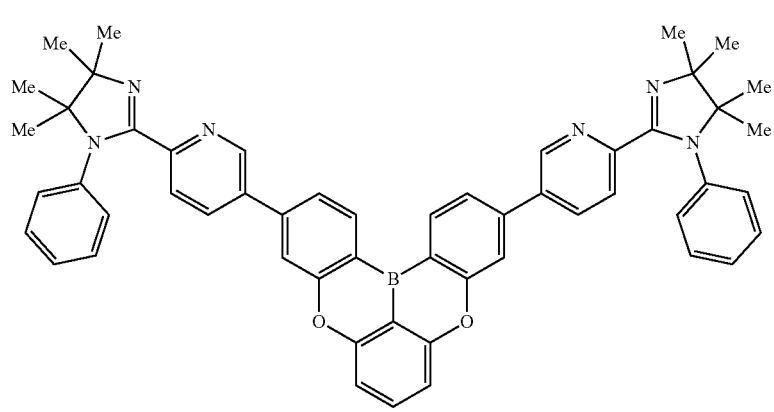
(1-2-944)

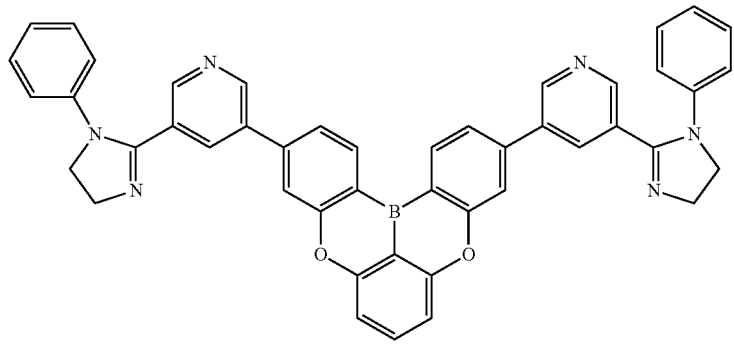
(1-2-945)
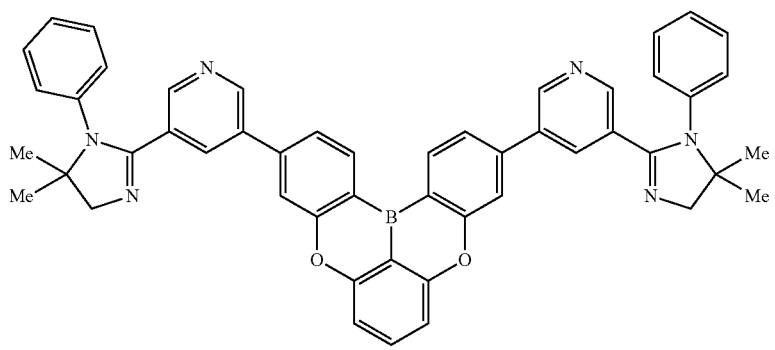
(1-2-946)
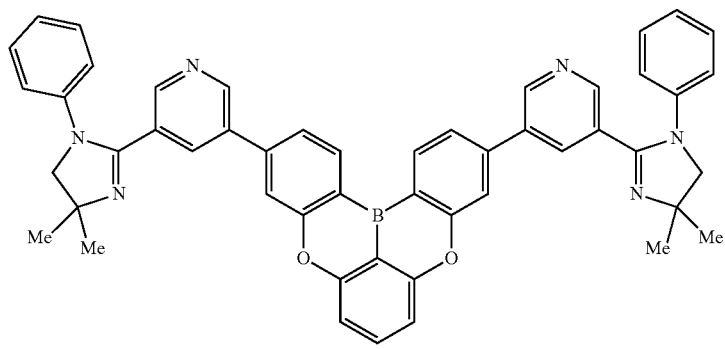
(1-2-947)
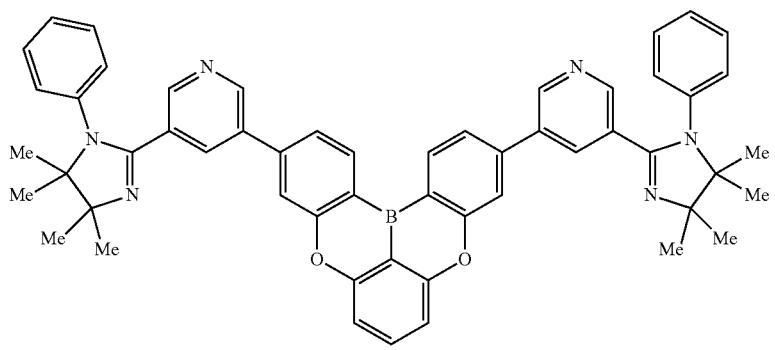
(1-2-948)

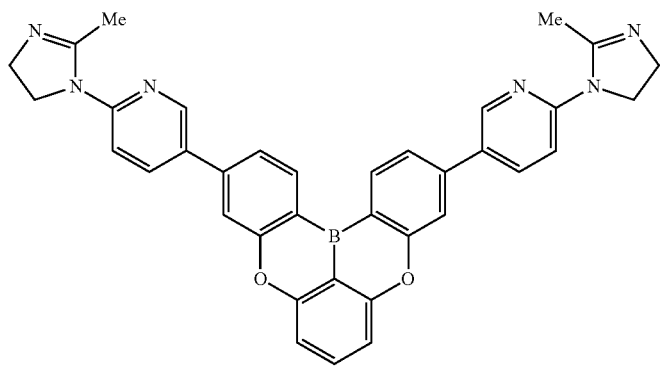
(1-2-951)
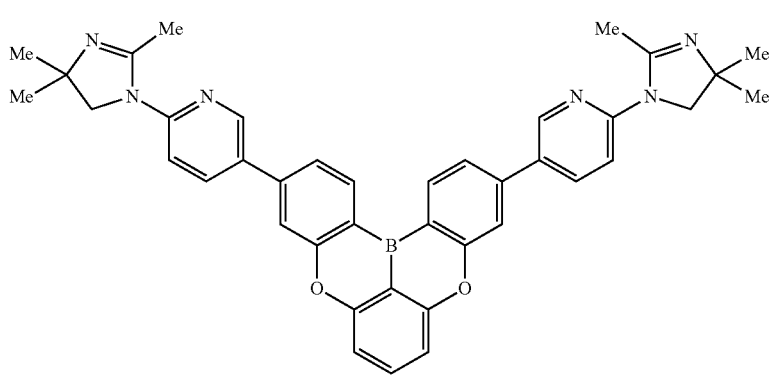
(1-2-952)
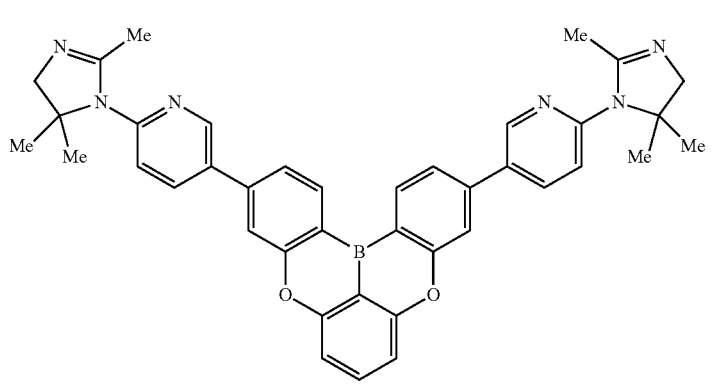
(1-2-953)
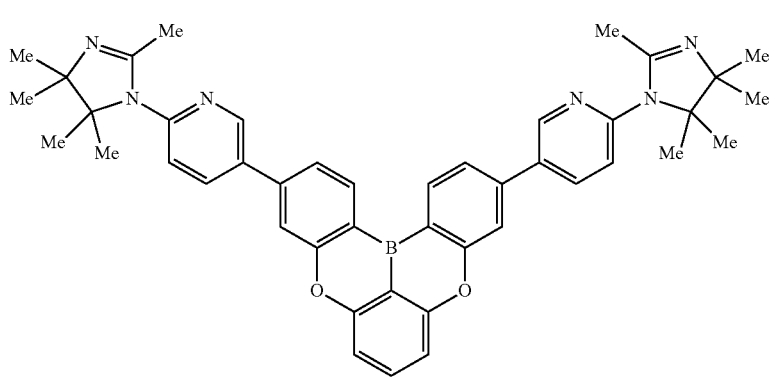
(1-2-954)

-continued
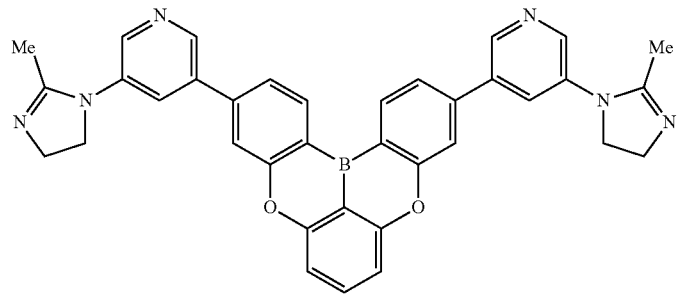
(1-2-955)
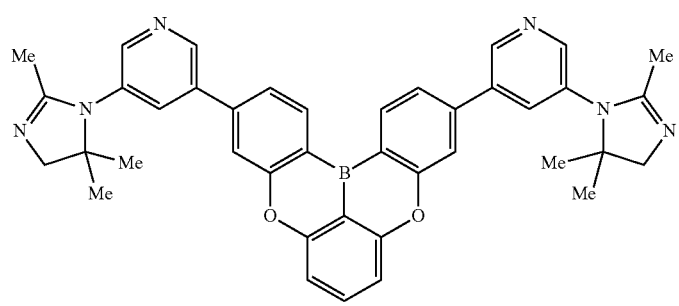
(1-2-956)
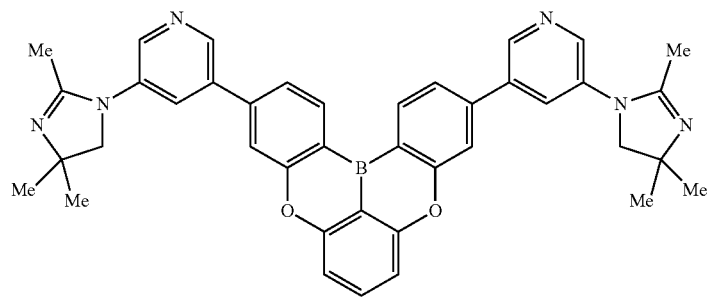
(1-2-957)
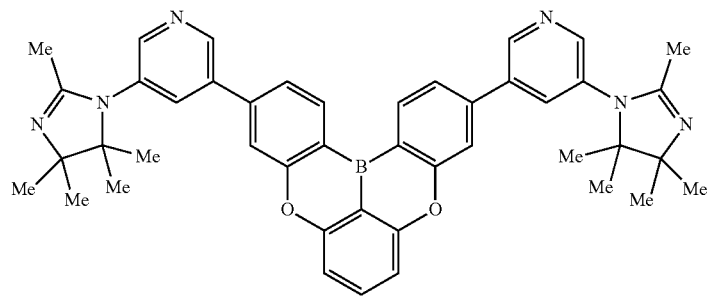
(1-2-958)
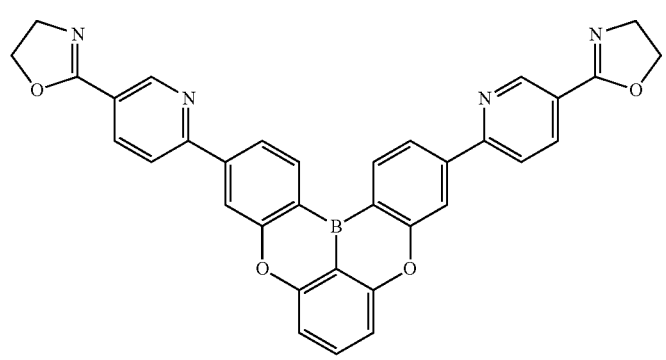
(1-2-961)

-continued
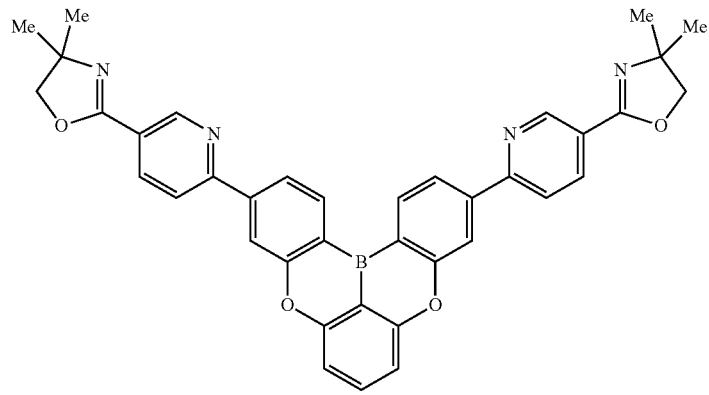
(1-2-962)
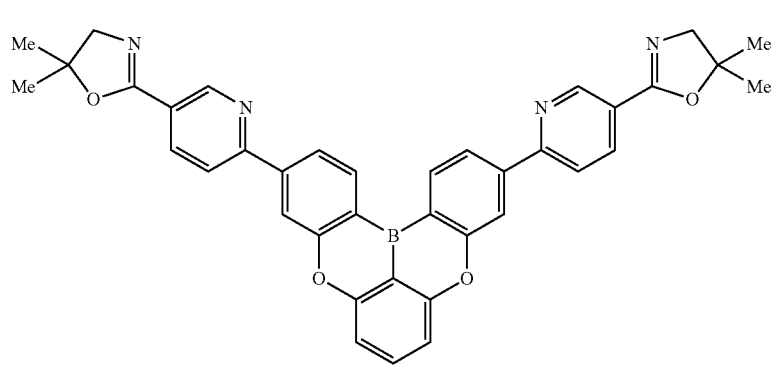
(1-2-963)
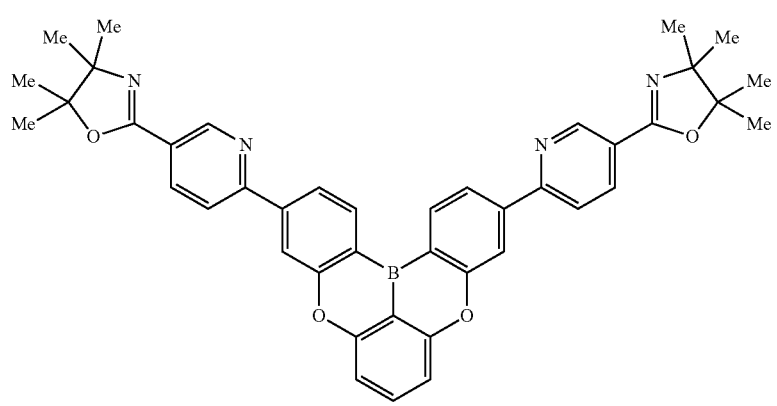
(1-2-964)
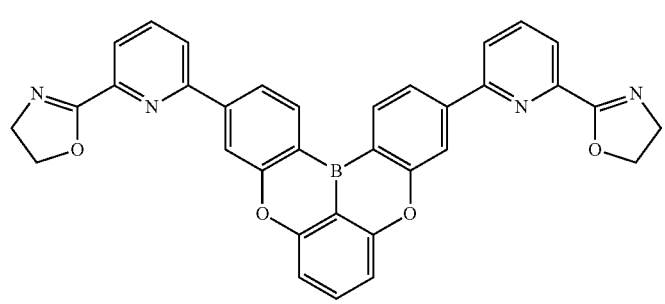
(1-2-965)

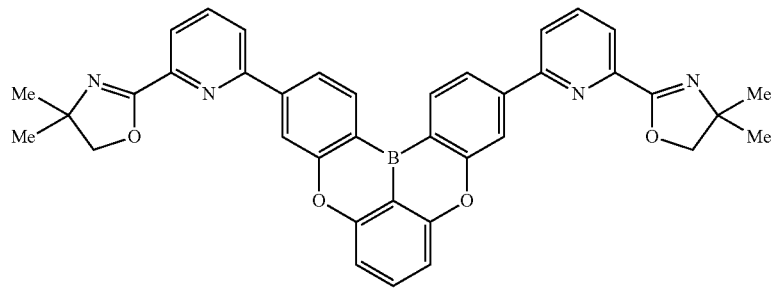
(1-2-966)
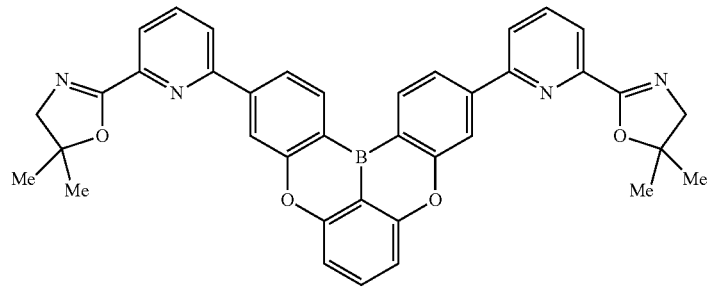
(1-2-967)
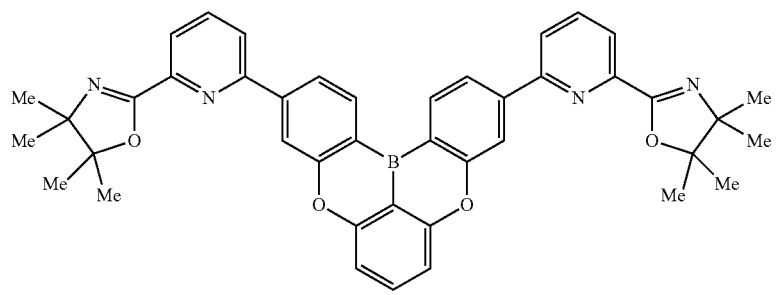
(1-2-968)
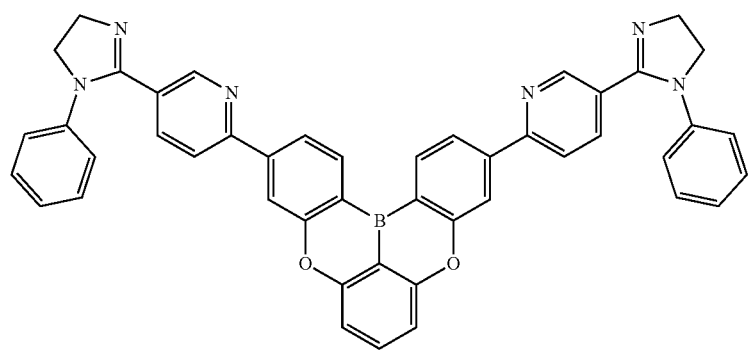
(1-2-971)
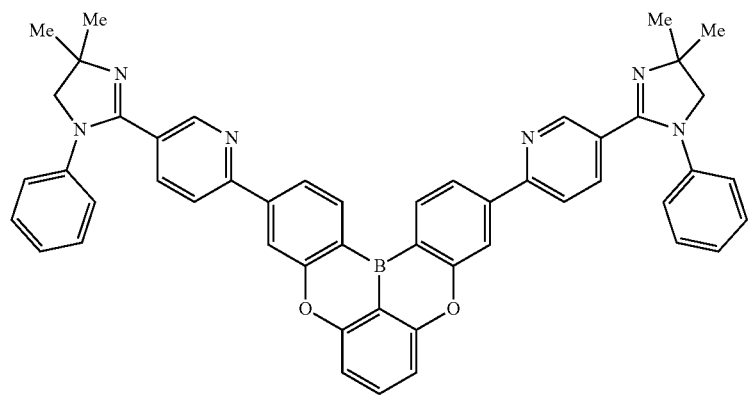
(1-2-972)

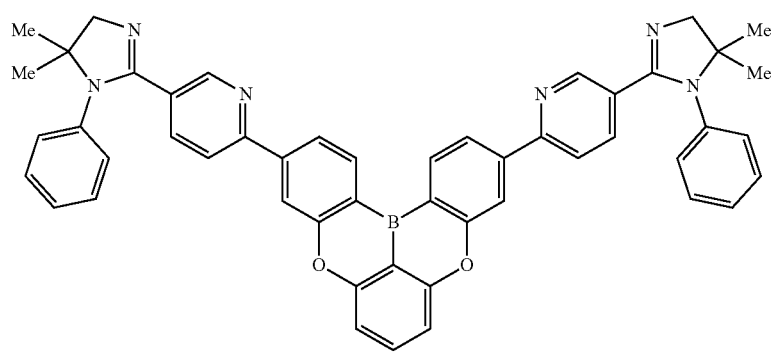
(1-2-973)
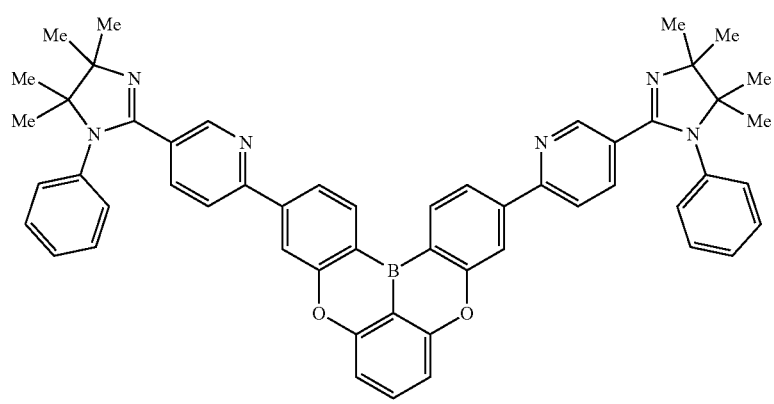
(1-2-974)
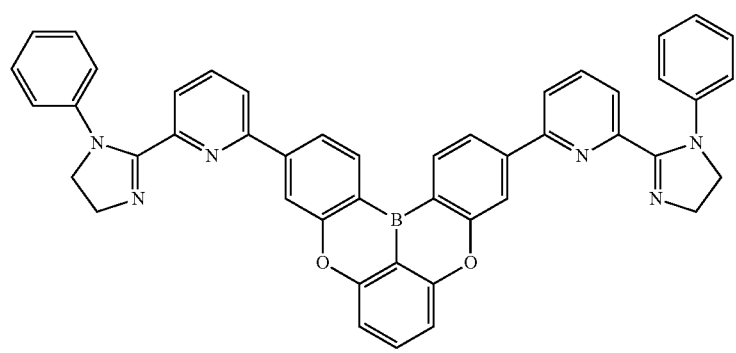
(1-2-975)
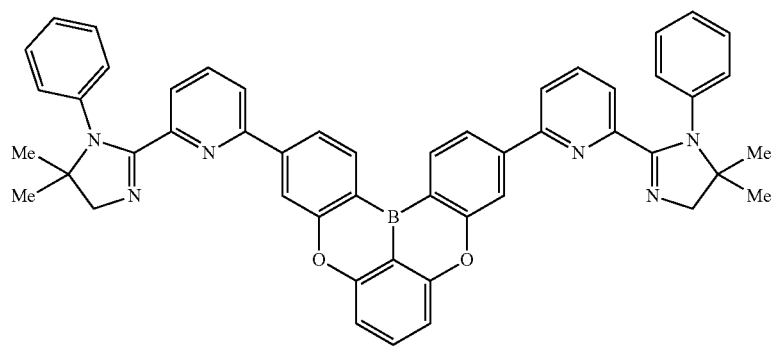
(1-2-976)

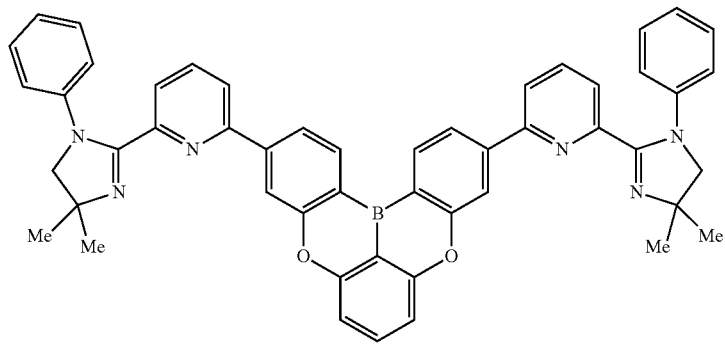
(1-2-977)
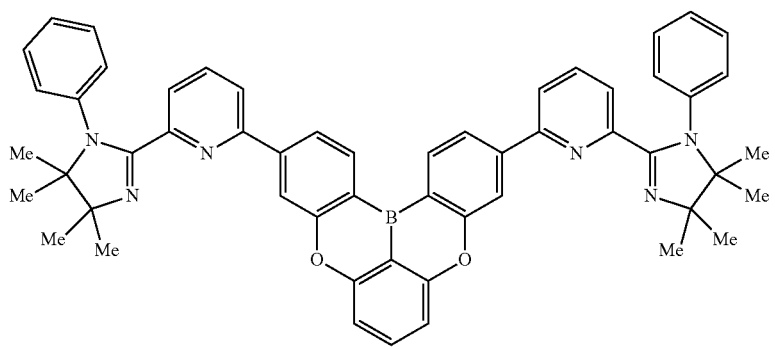
(1-2-978)
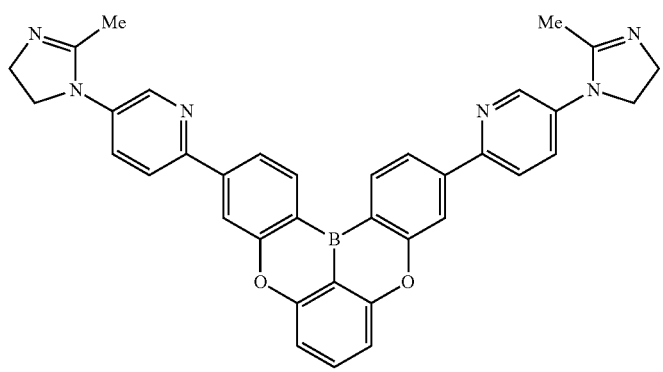
(1-2-981)
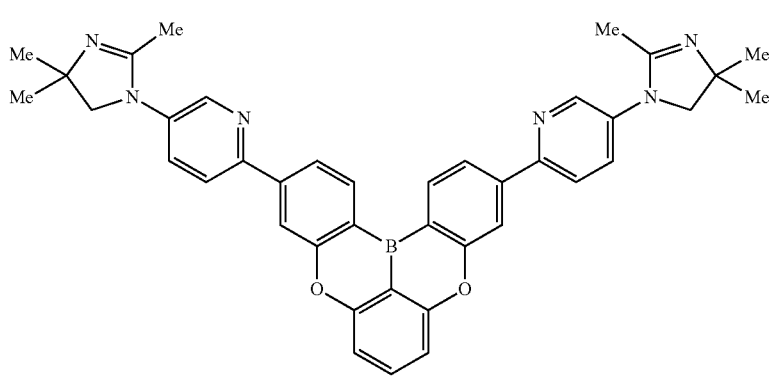
(1-2-982)

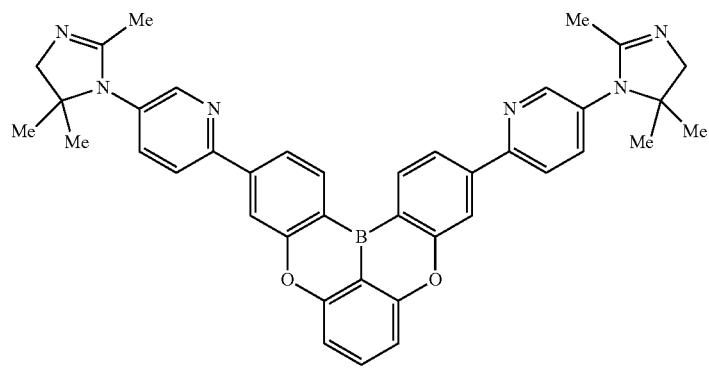
(1-2-983)
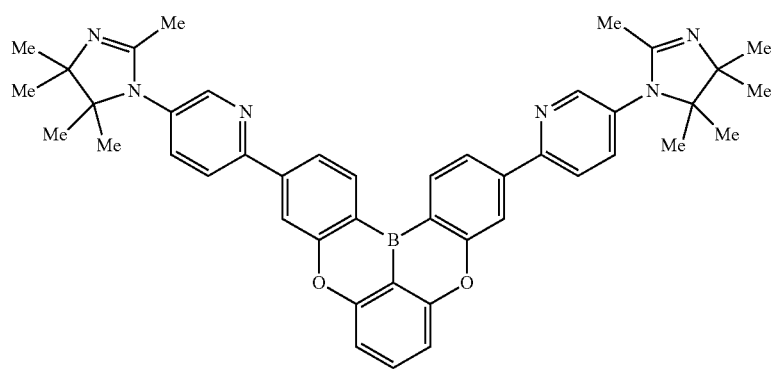
(1-2-984)
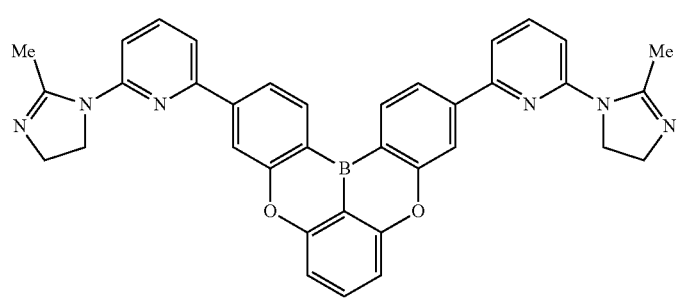
(1-2-985)
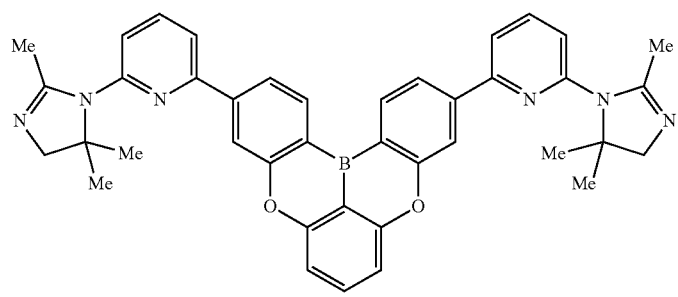
(1-2-986)
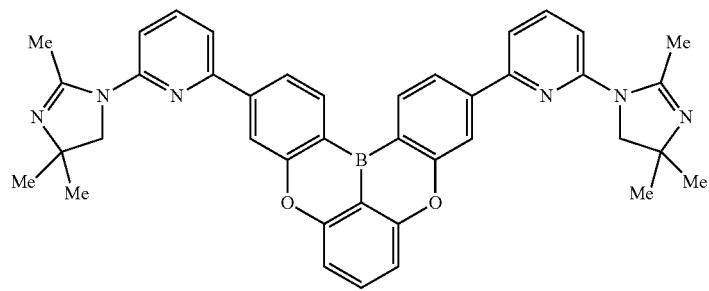
(1-2-987)

(1-2-988)
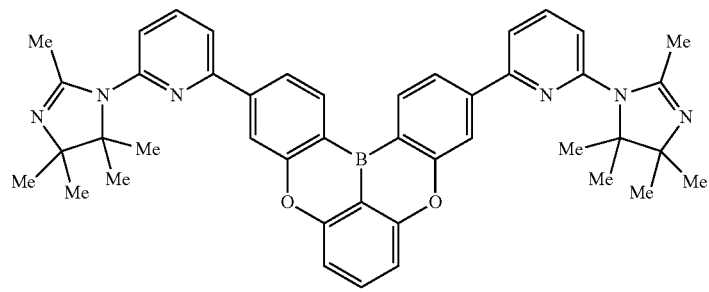
(1-2-991)
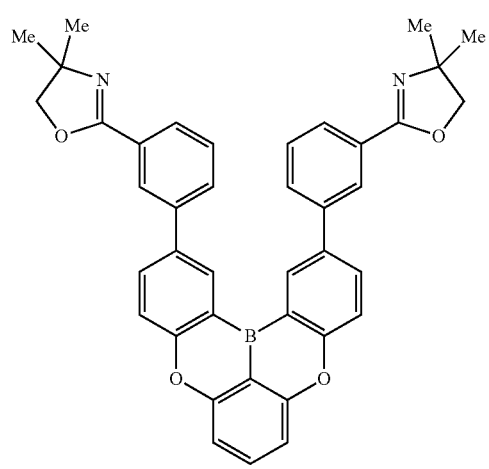
(1-2-992)
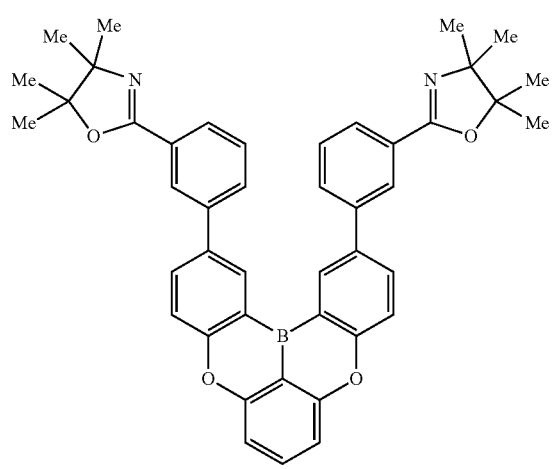
(1-2-993)
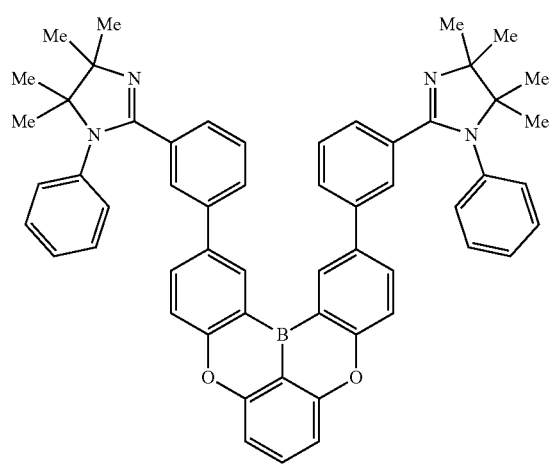
(1-2-994)
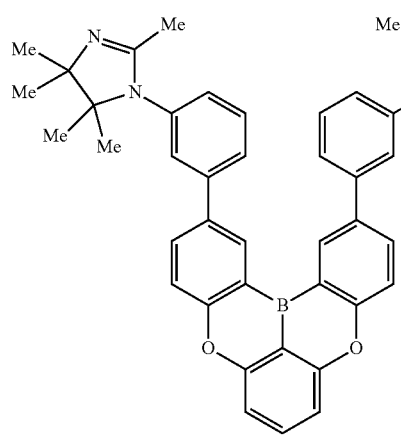

(1-2-995)
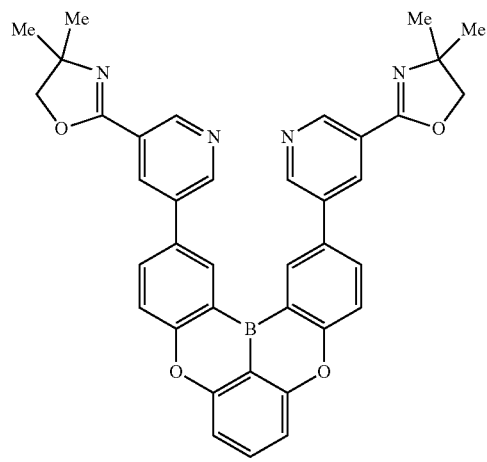
(1-2-996)
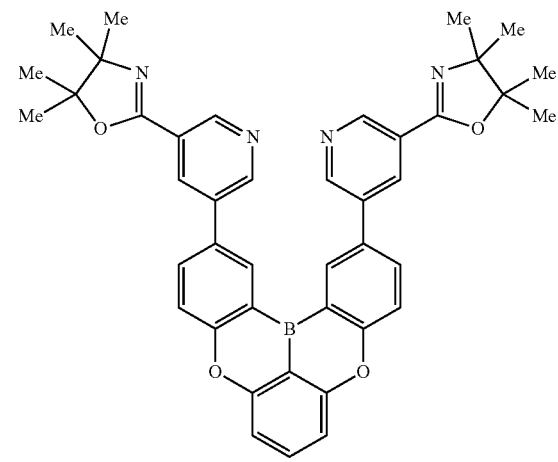
(1-2-997)
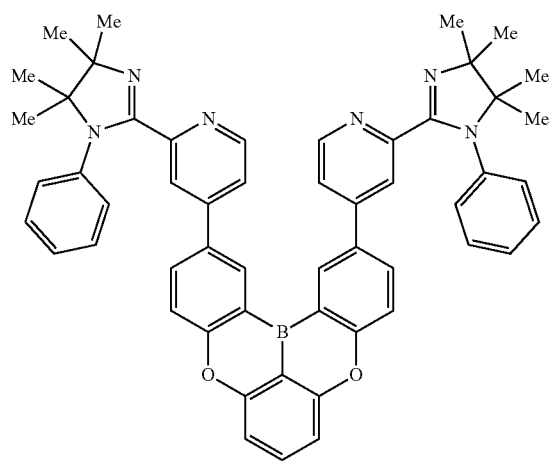
(1-2-998)
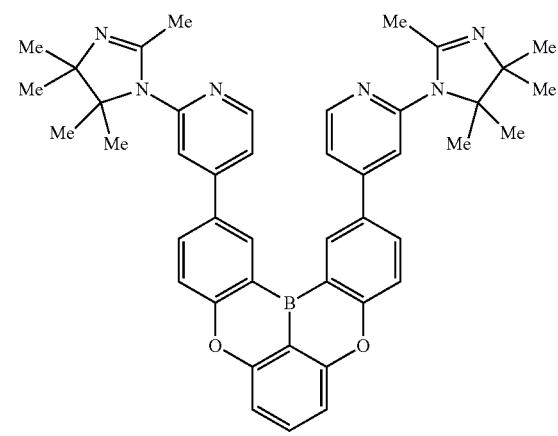
(1-2-1001)
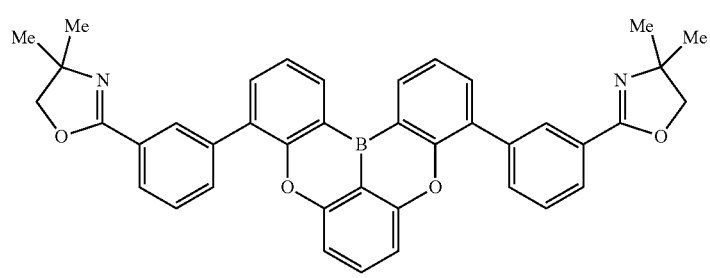
(1-2-1002)
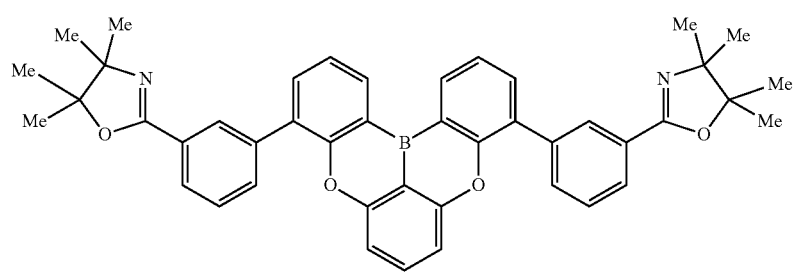

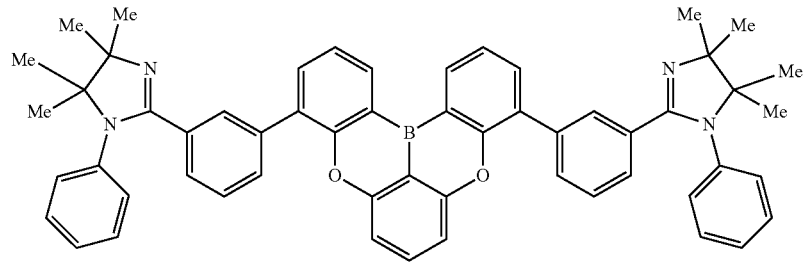
(1-2-1003)
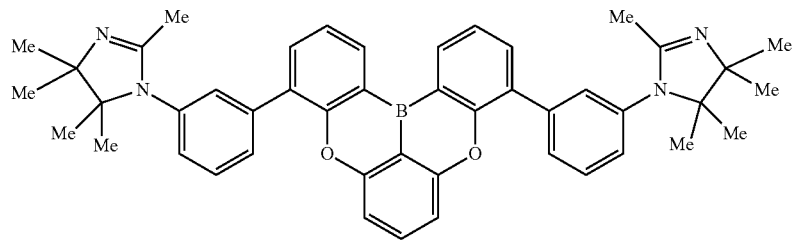
(1-2-1004)
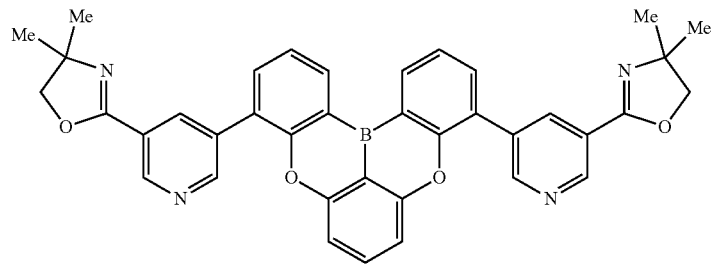
(1-2-1005)
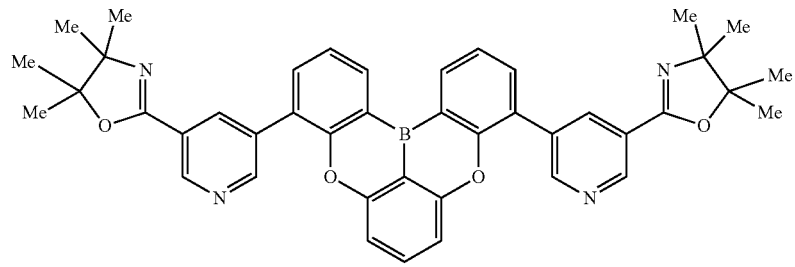
(1-2-1006)
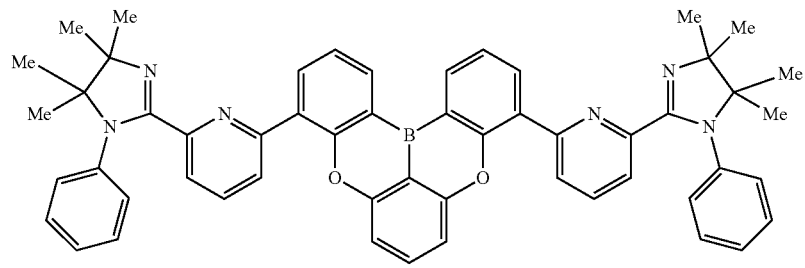
(1-2-1007)
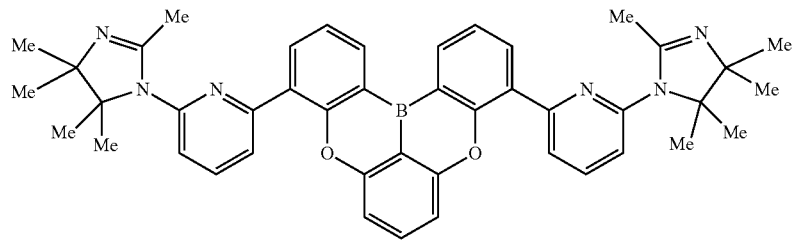
(1-2-1008)

-continued
(1-2-1011)
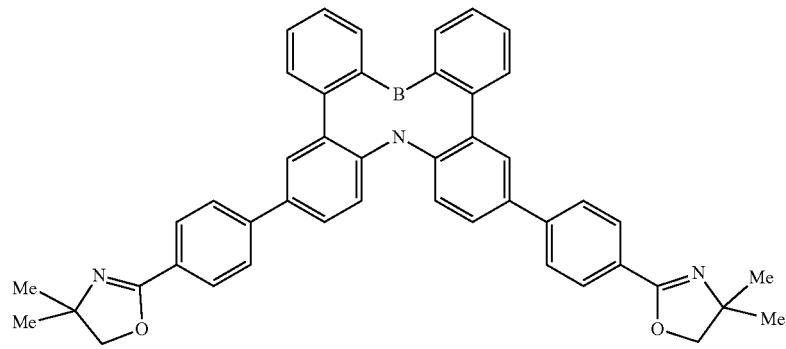
(1-2-1012)
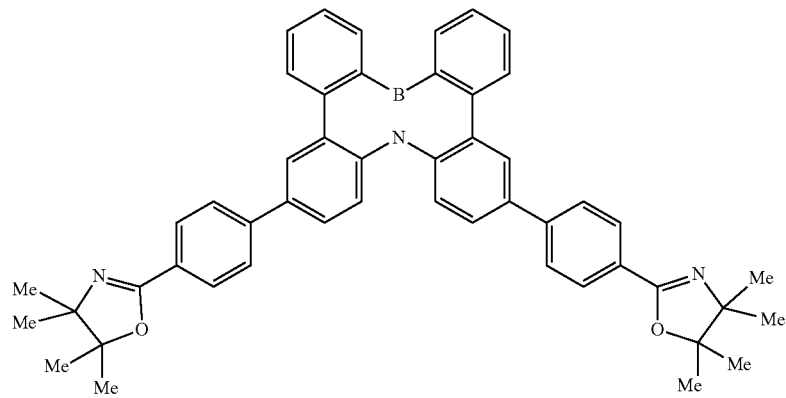
(1-2-1013)
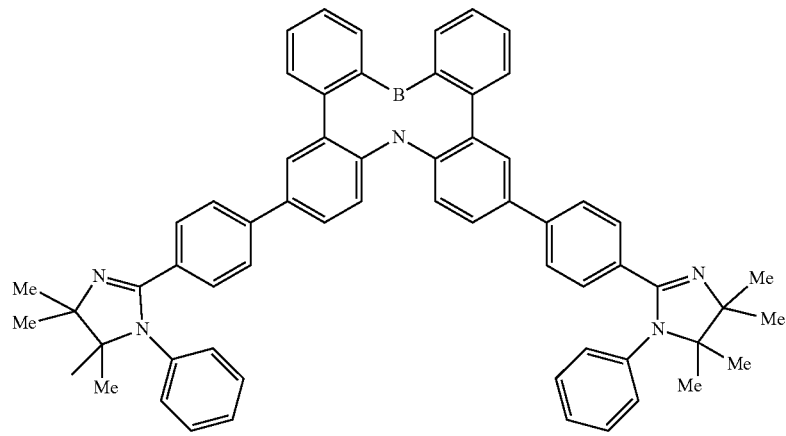
(1-2-1014)
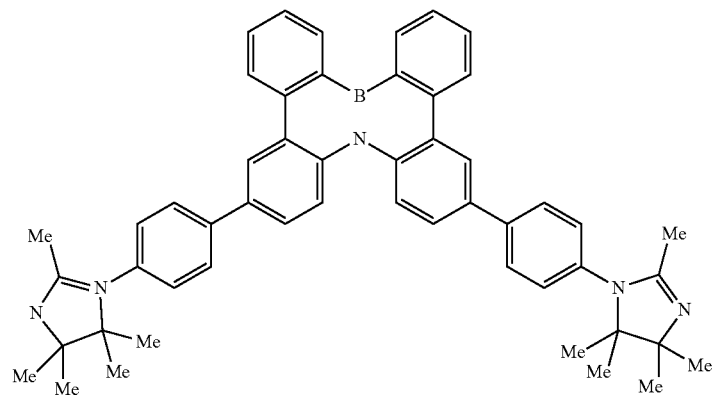

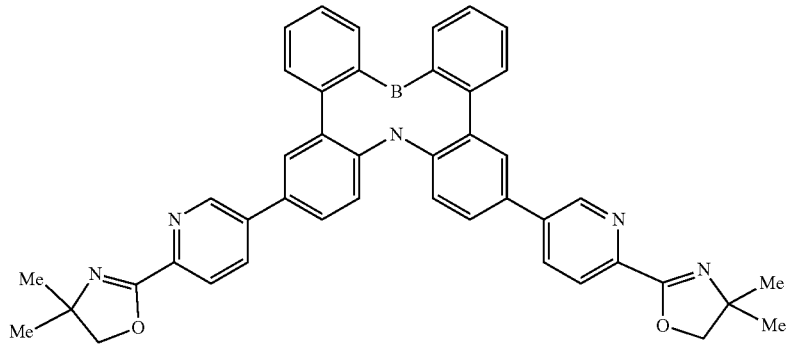
(1-2-1015)
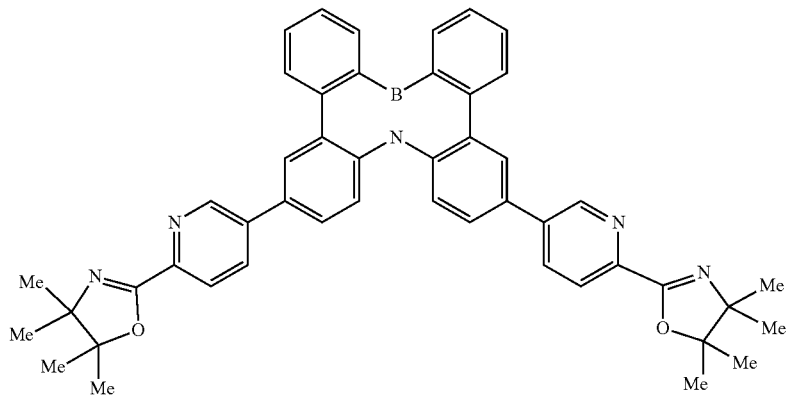
(1-2-1016)
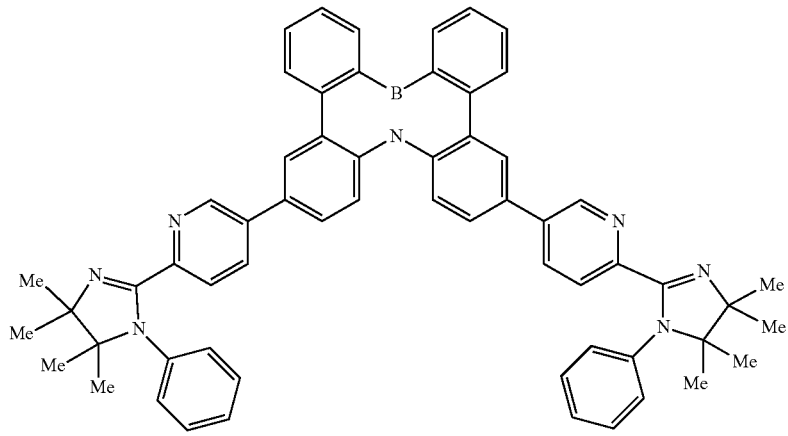
(1-2-1017)
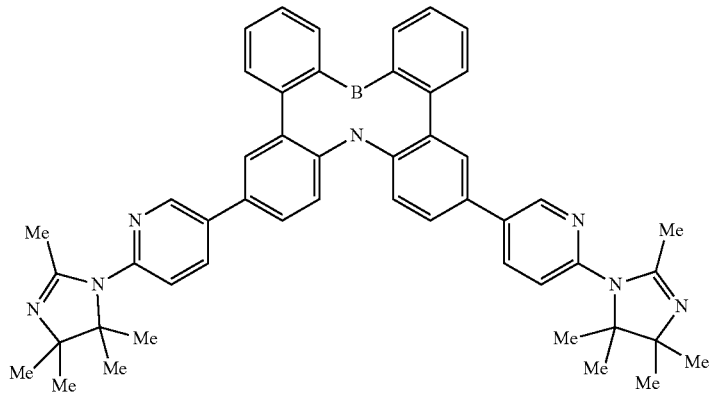
(1-2-1018)

-continued
(1-2-1021)
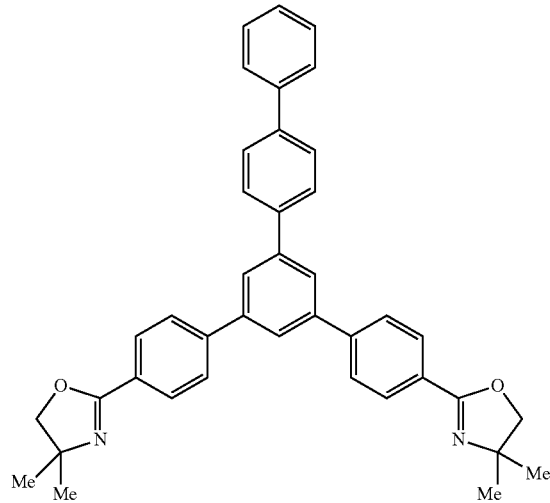
(1-2-1022)
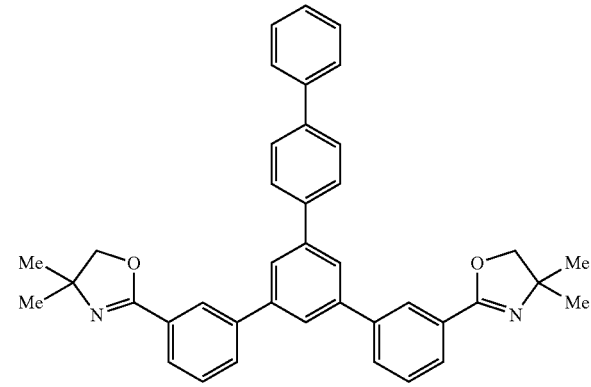
(1-2-1023)
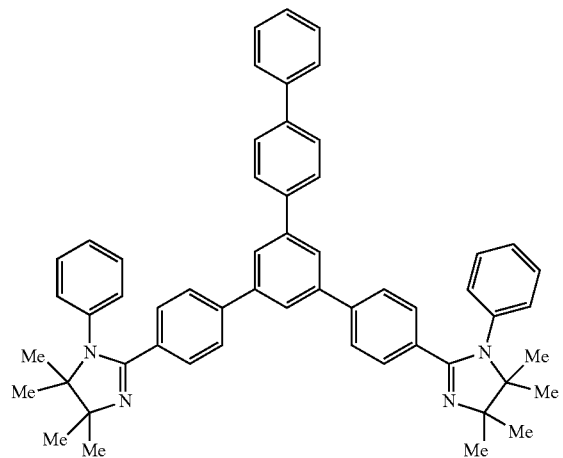
(1-2-1024)
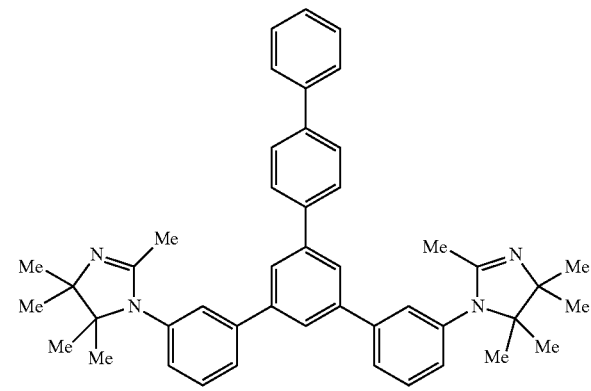
(1-2-1025)
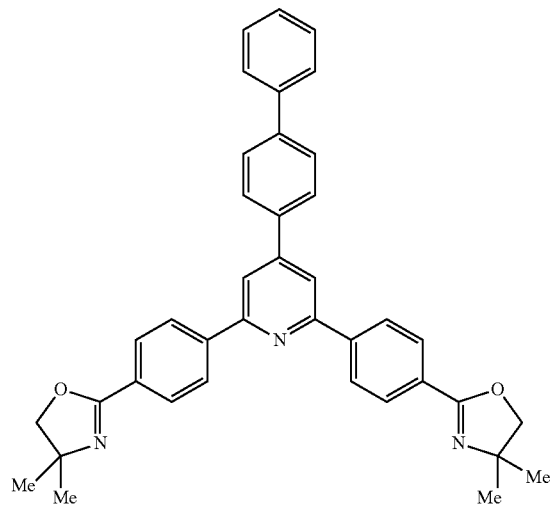
(1-2-1026)
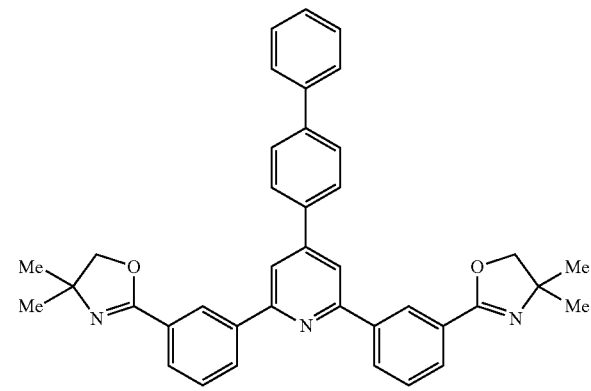

(1-2-1027)
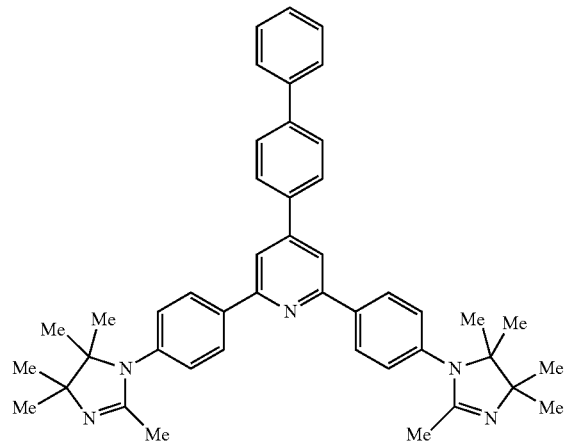
(1-2-1028)
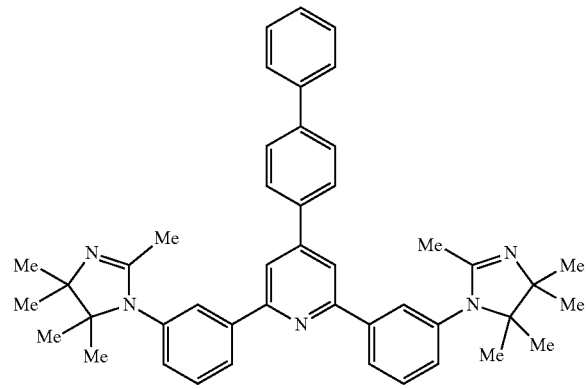
(1-2-1031)
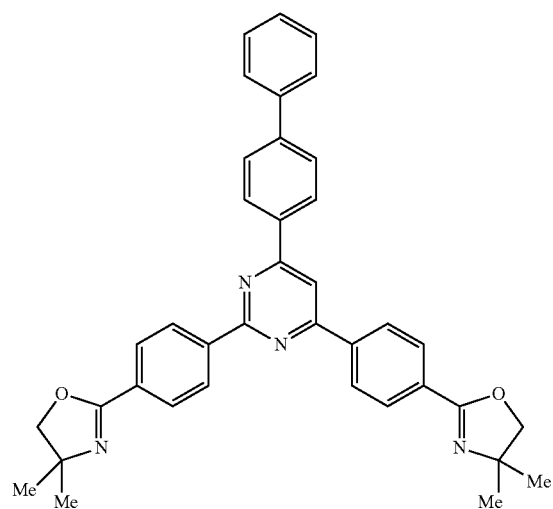
(1-2-1032)
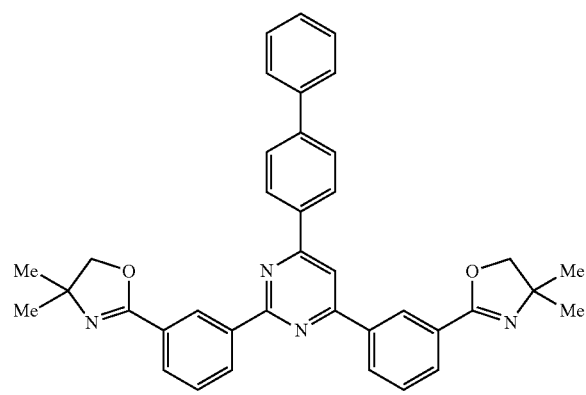
(1-2-1033)
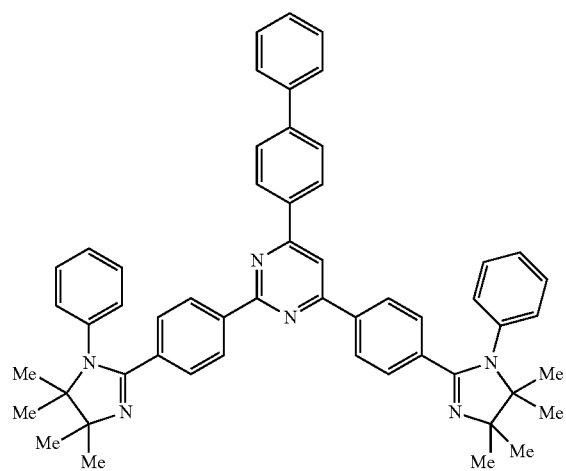
(1-2-1034)
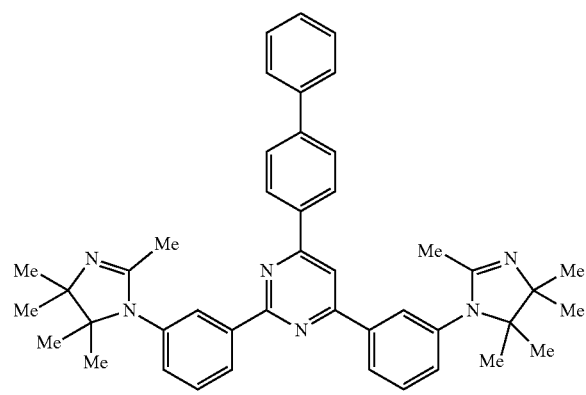

-continued
(1-2-1035)
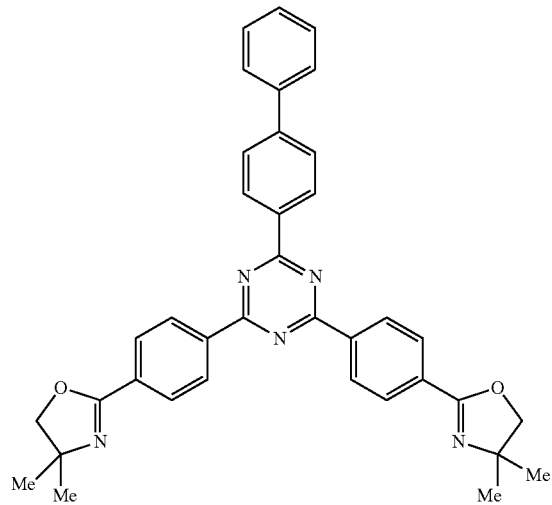
(1-2-1036)
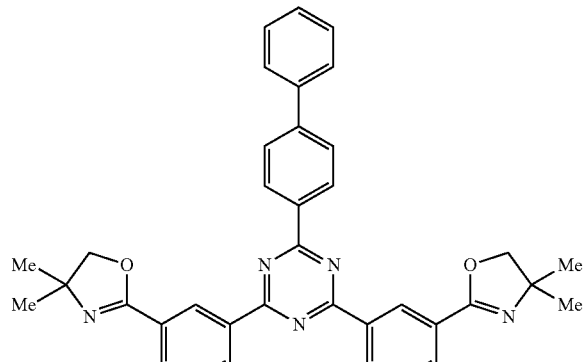
(1-2-1037)
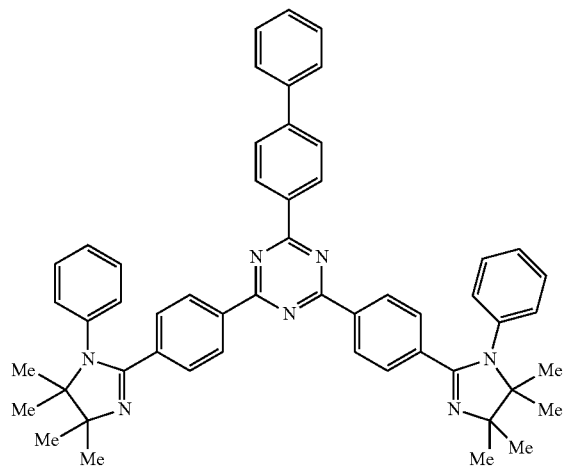
(1-2-1038)
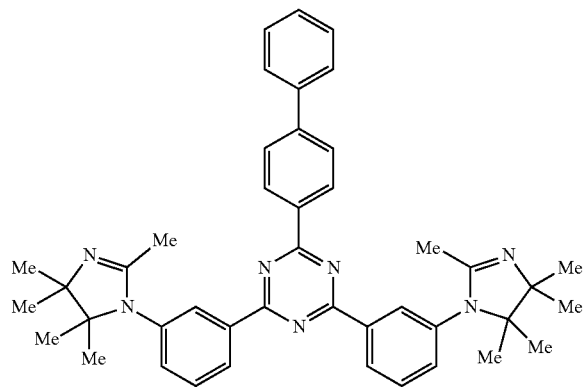
(1-2-1041)
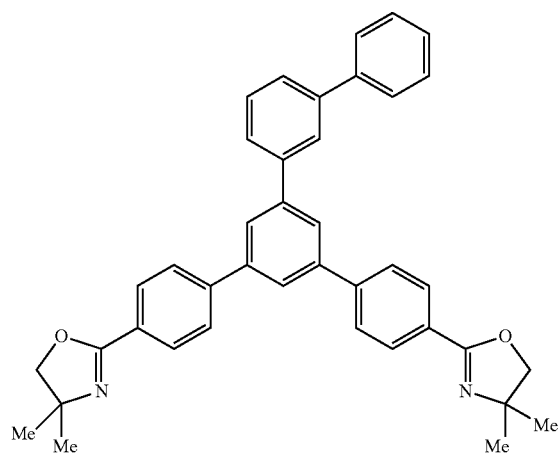
(1-2-1042)
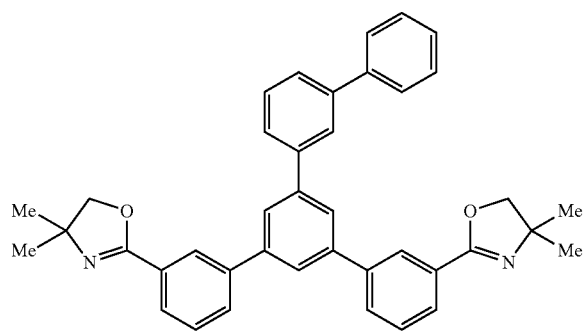

-continued
(1-2-1043)
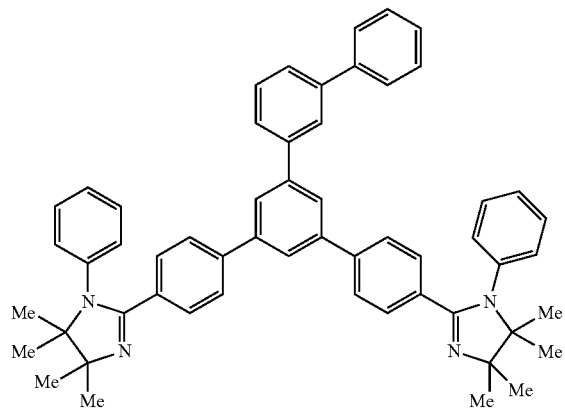
(1-2-1044)
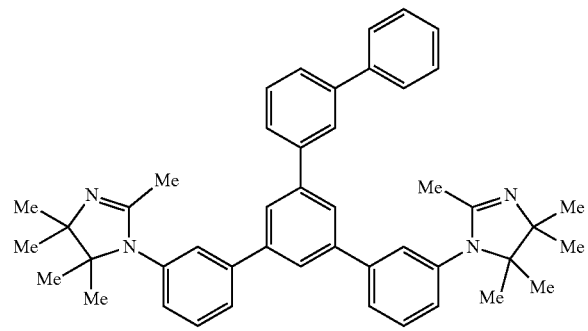
(1-2-1045)
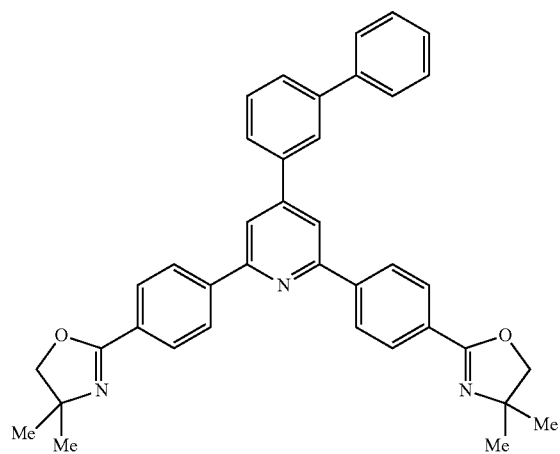
(1-2-1046)
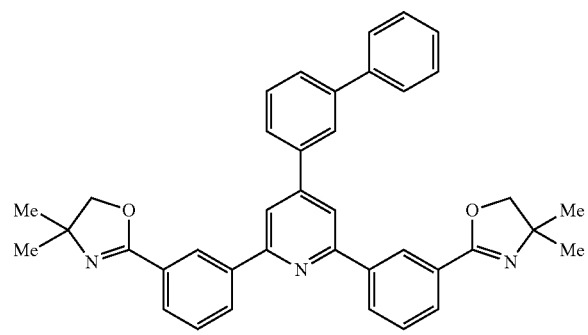
(1-2-1047)
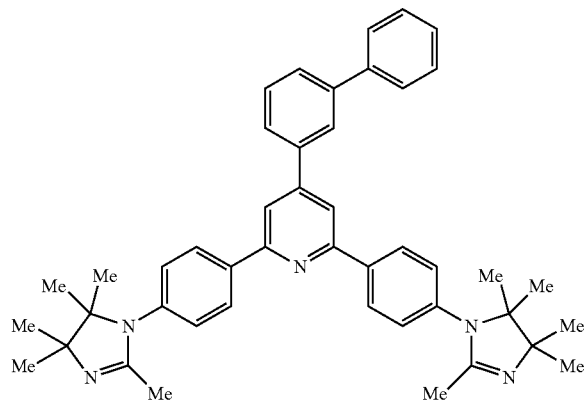
(1-2-1048)
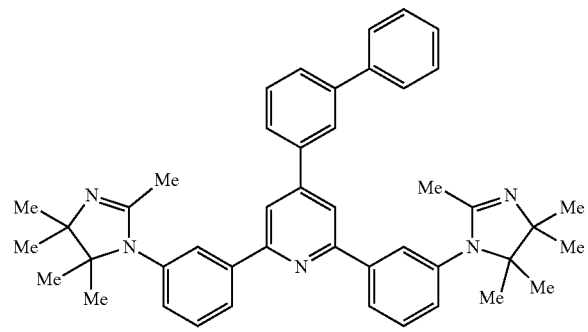

-continued
(1-2-1051)
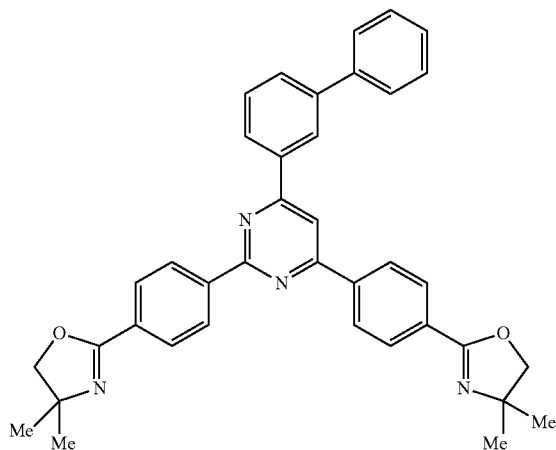
(1-2-1052)
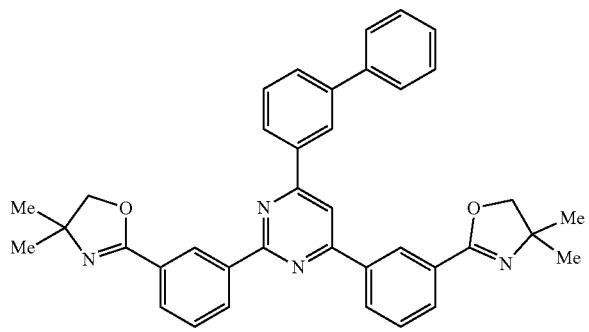
(1-2-1053)
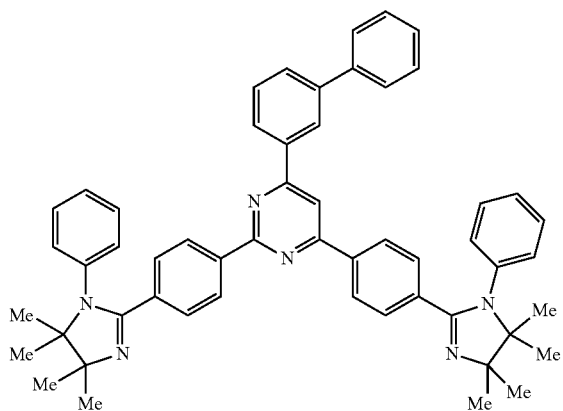
(1-2-1054)
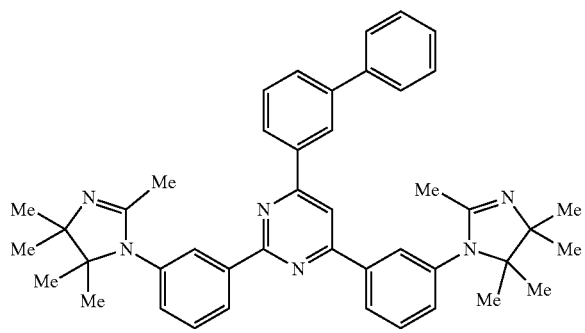
(1-2-1055)
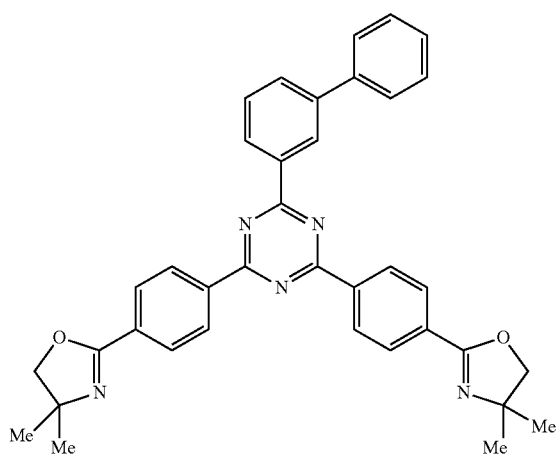
(1-2-1056)
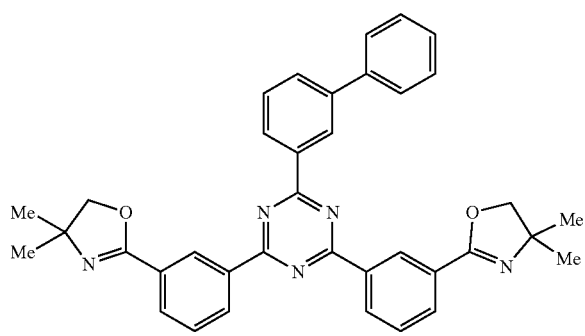

(1-2-1057)
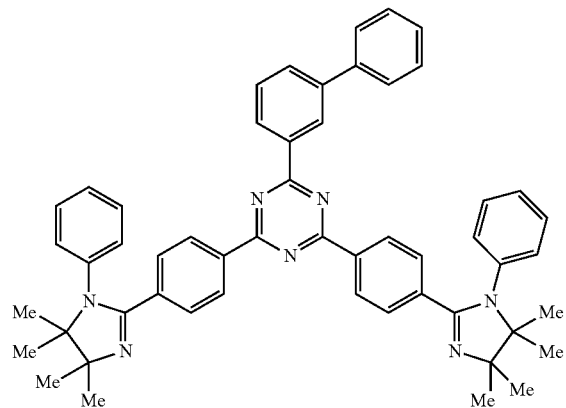
(1-2-1058)
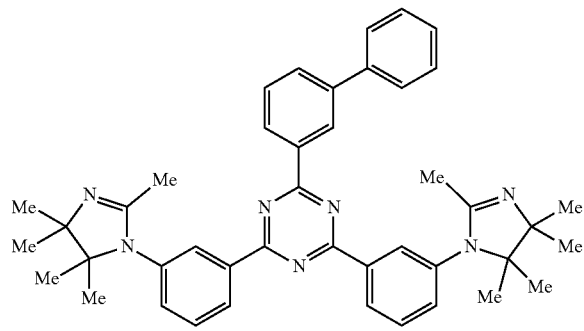
(1-2-1061)
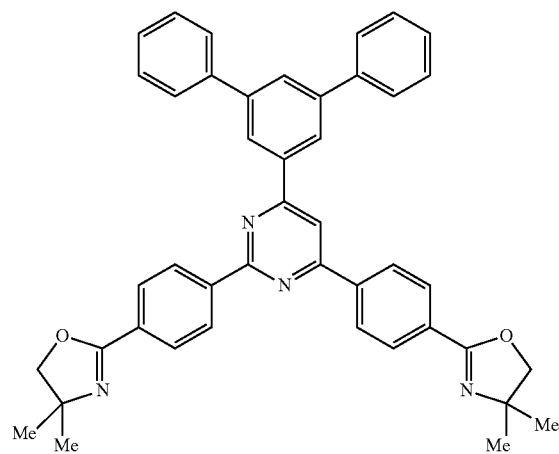
(1-2-1062)
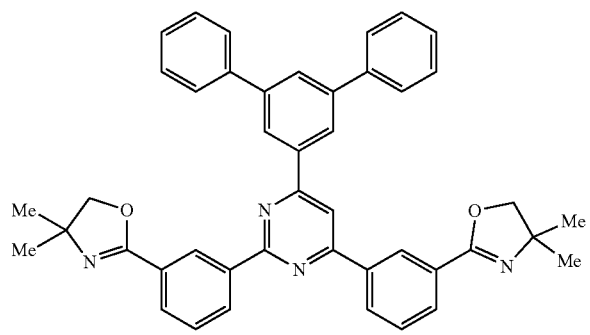
(1-2-1063)
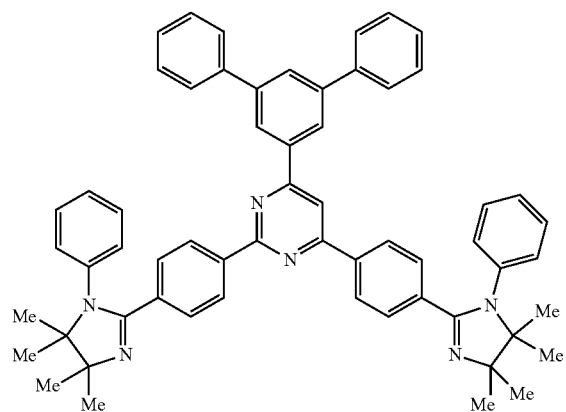
(1-2-1064)
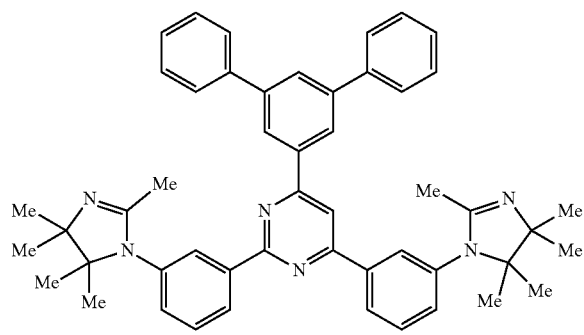

-continued
(1-2-1065)
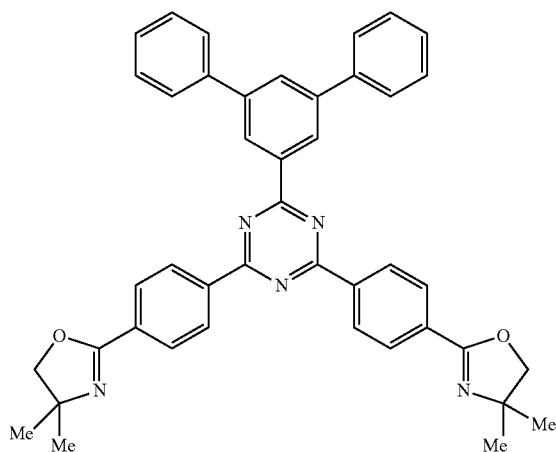
(1-2-1066)
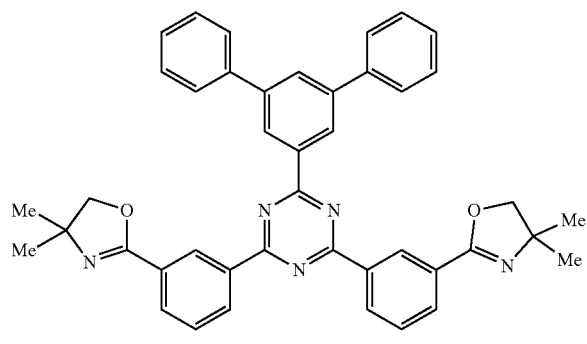
(1-2-1067)
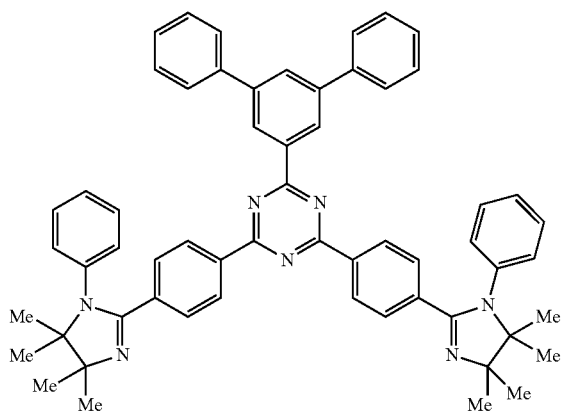
(1-2-1068)
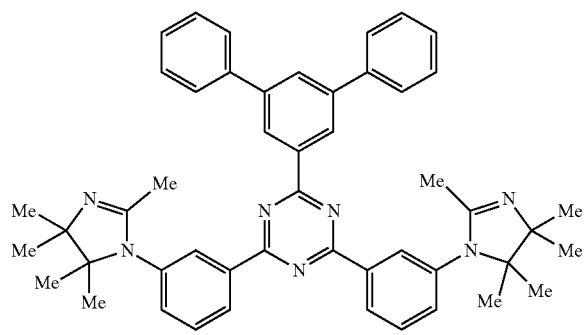
(1-2-1071)
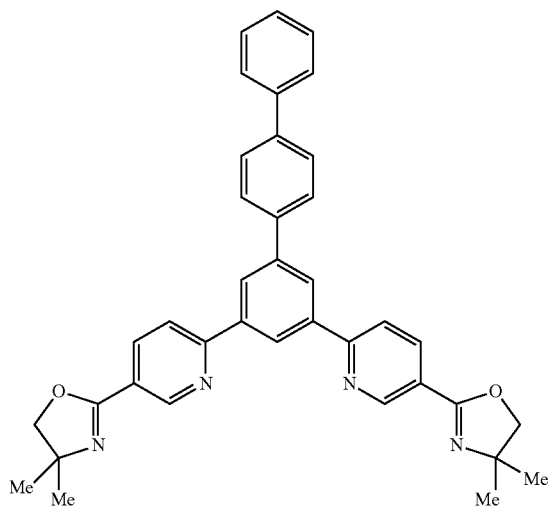
(1-2-1072)
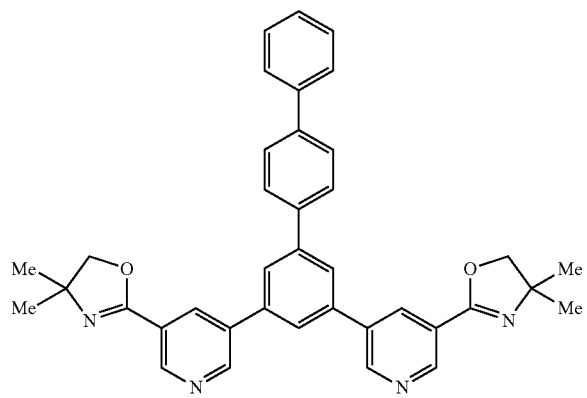

-continued
(1-2-1073)
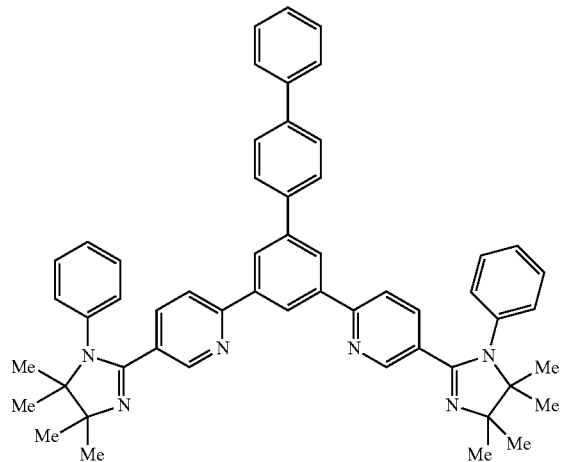
(1-2-1074)
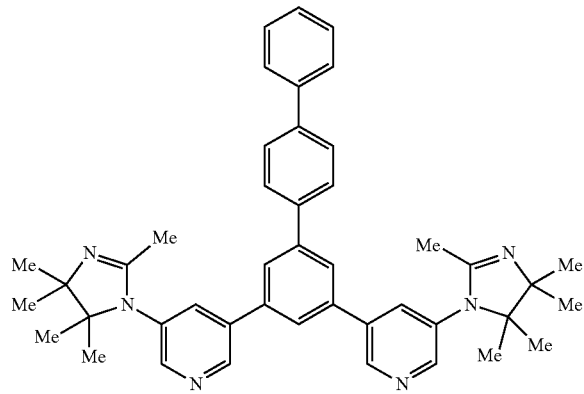
(1-2-1075)
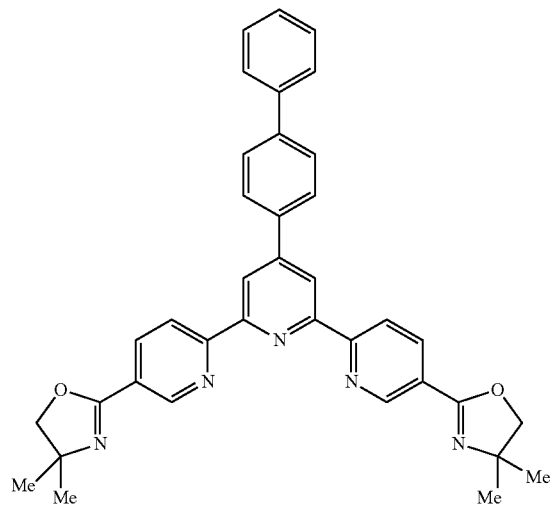
(1-2-1076)
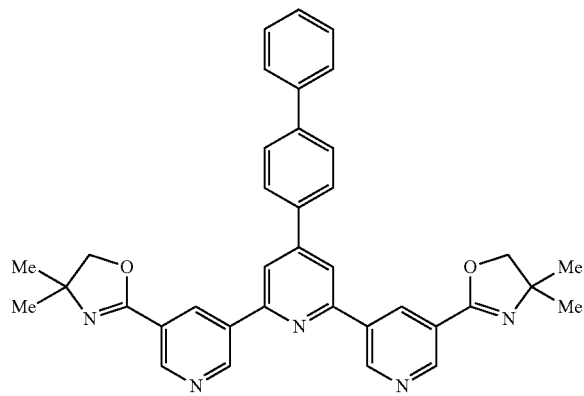
(1-2-1077)
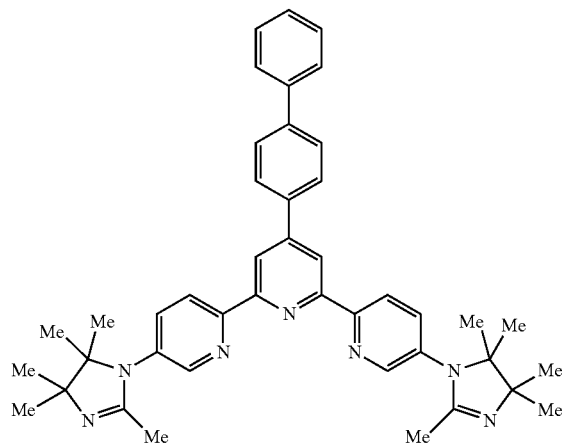
(1-2-1078)
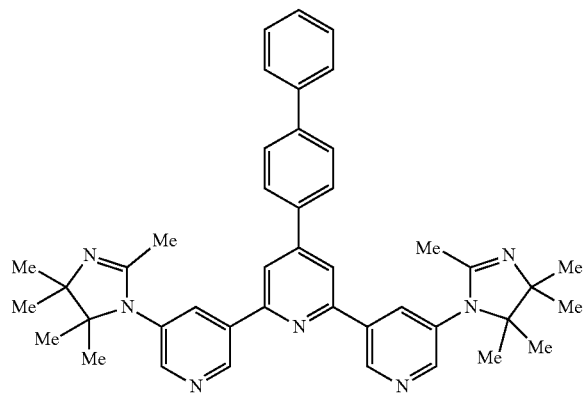

-continued
(1-2-1081)
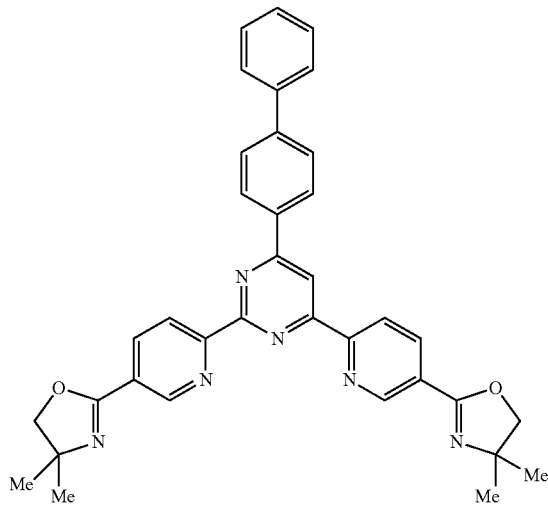
(1-2-1082)
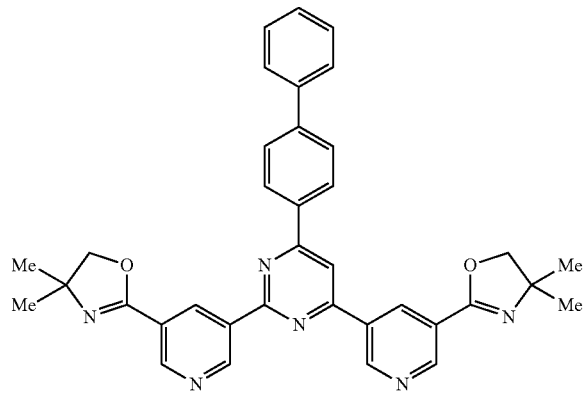
(1-2-1083)
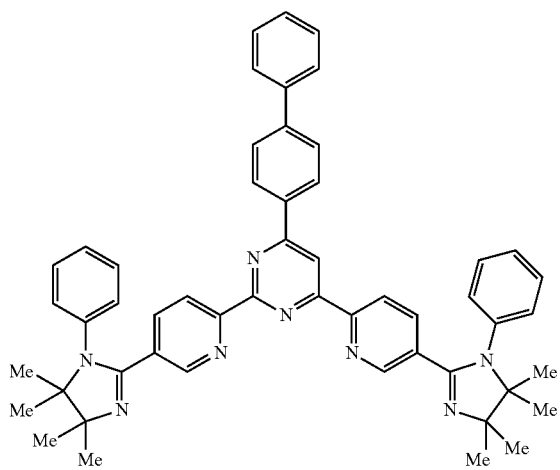
(1-2-1084)
(1-2-1085)
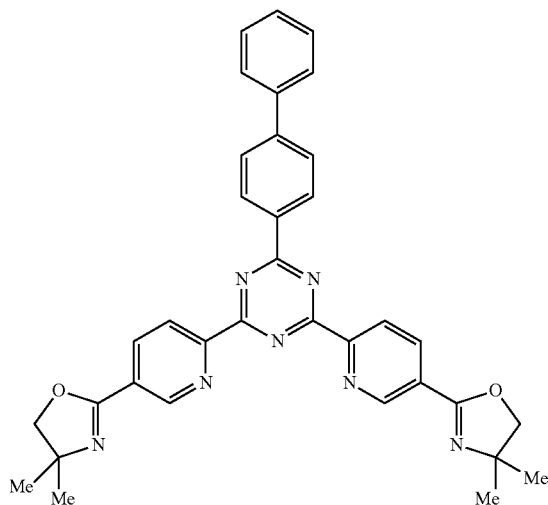
(1-2-1086)
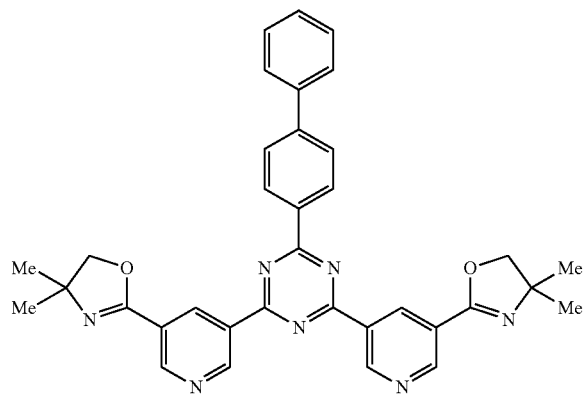

-continued
(1-2-1087)
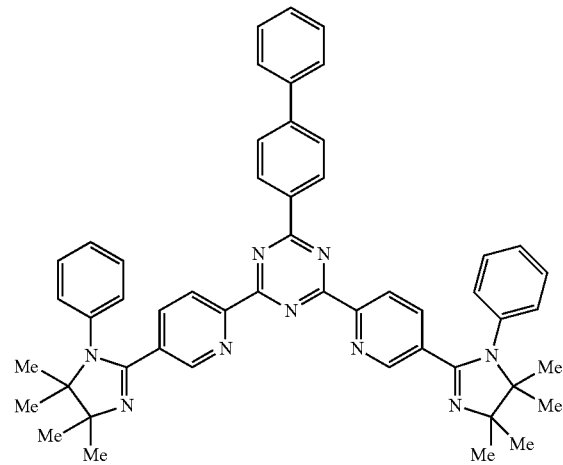
(1-2-1088)
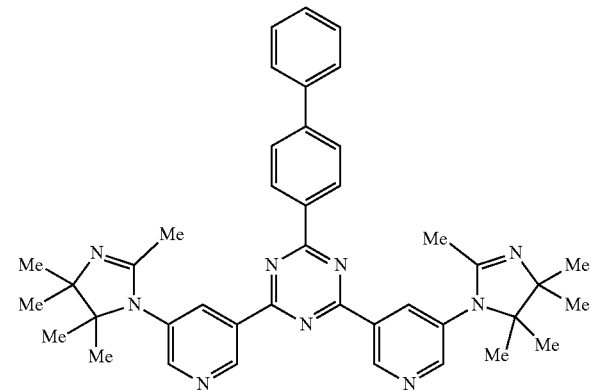
(1-2-1091)
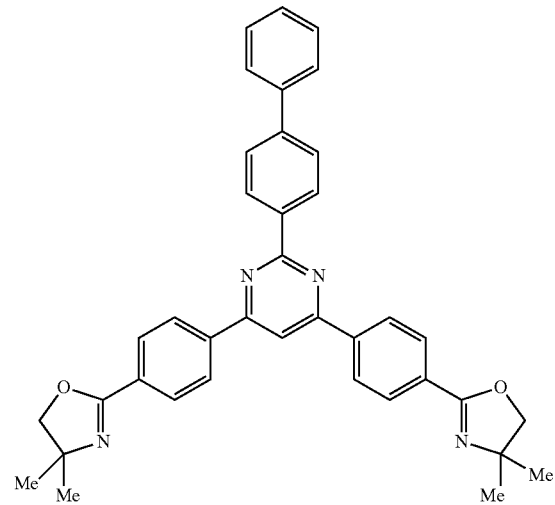
(1-2-1092)
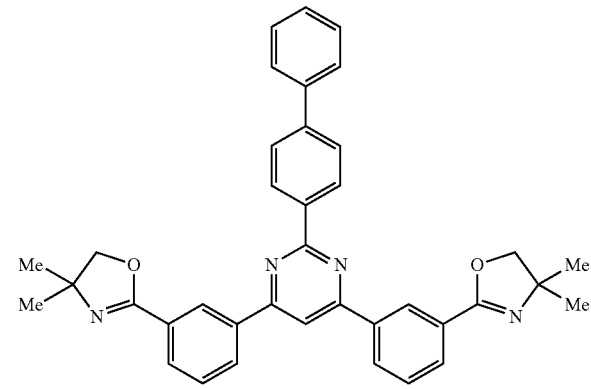
(1-2-1093)
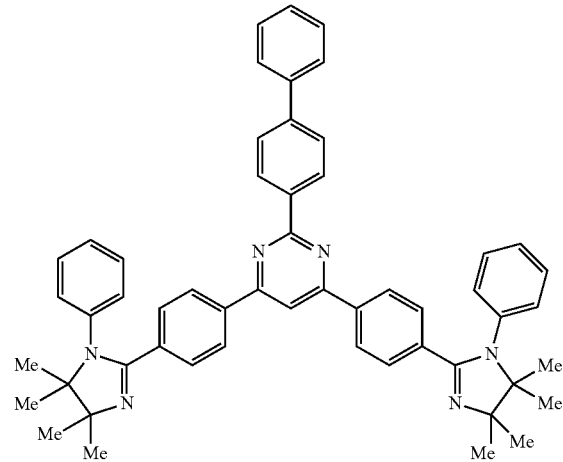
(1-2-1094)
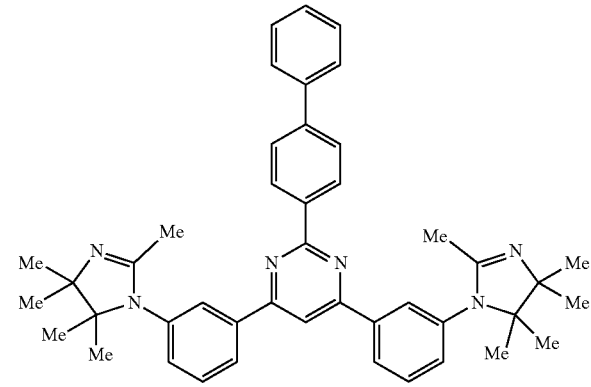

(1-2-1095)
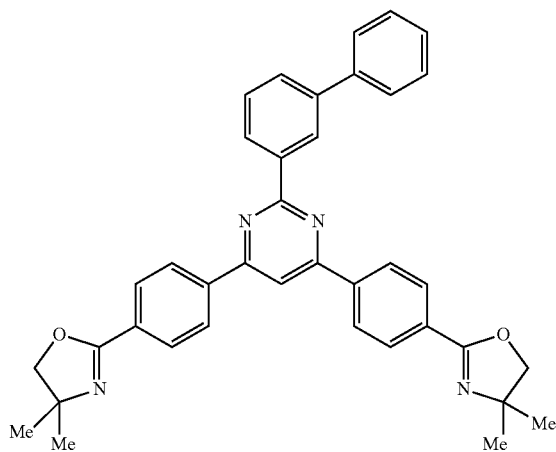
(1-2-1096)
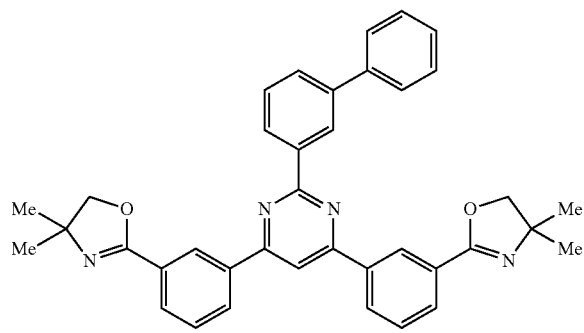
(1-2-1097)
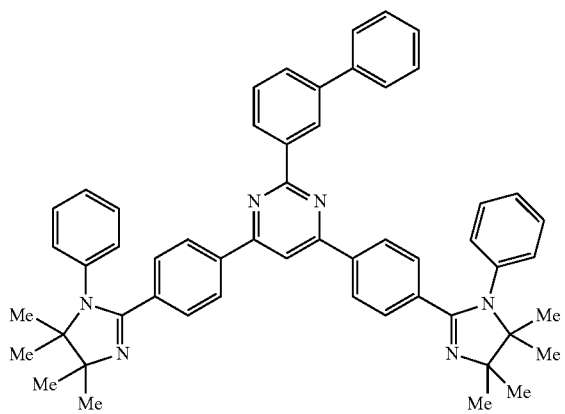
(1-2-1098)
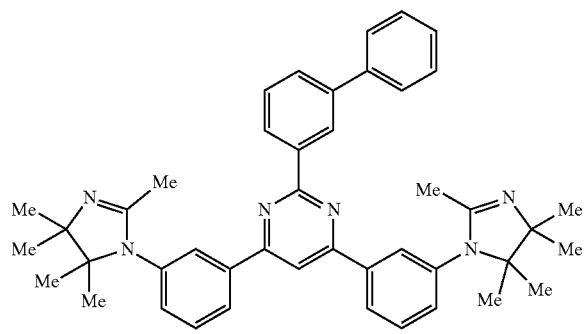
(1-2-1101)
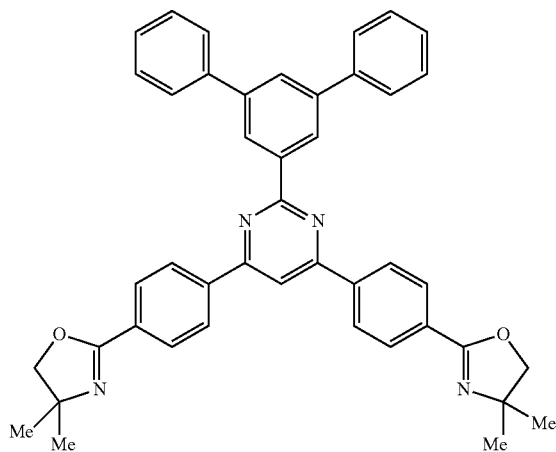
(1-2-1102)
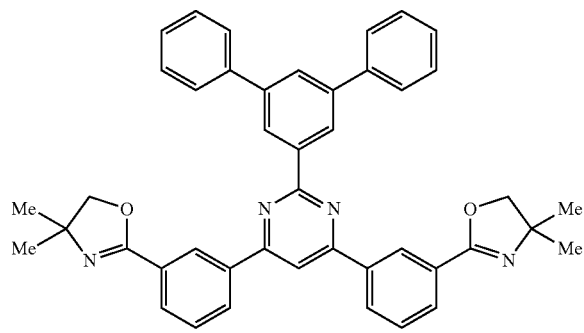

-continued
(1-2-1103)
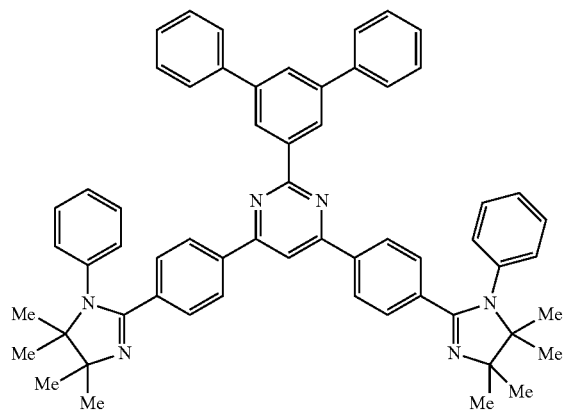
(1-2-1104)
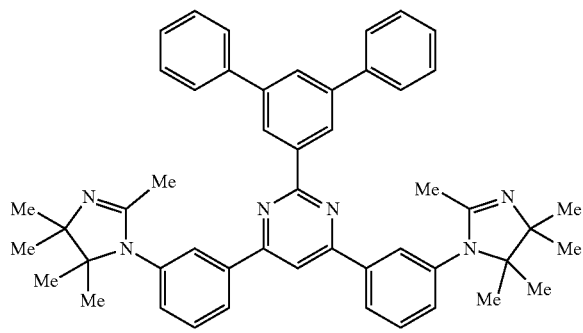
(1-2-1105)
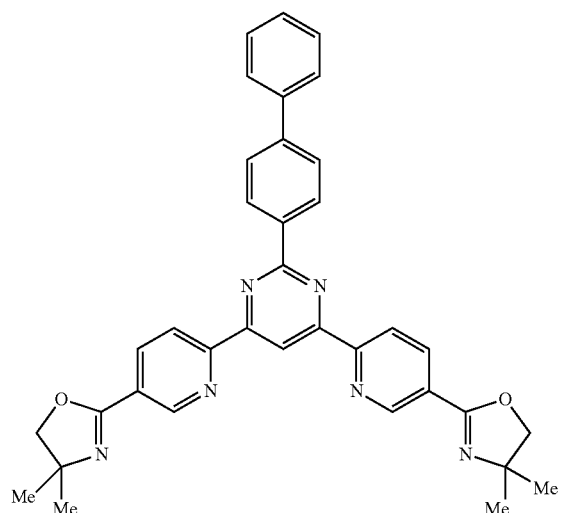
(1-2-1106)
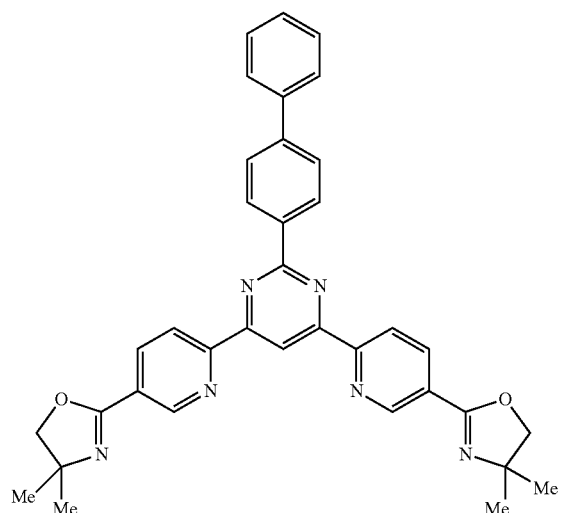
(1-2-1107)
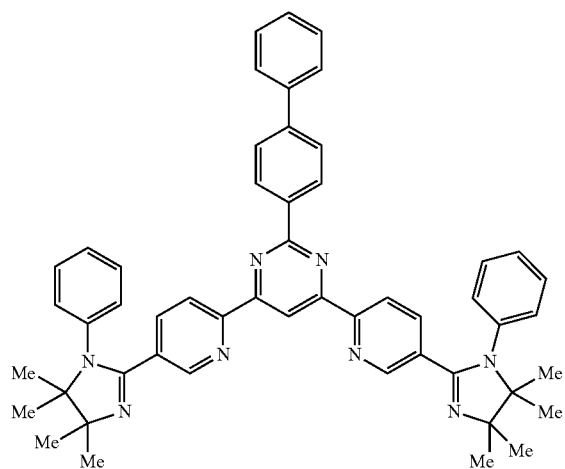
(1-2-1108)
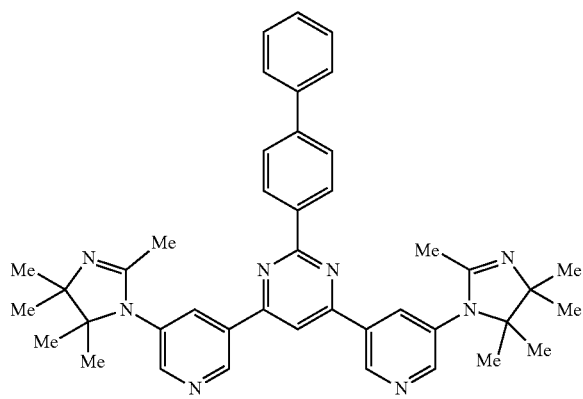

405
406
-continued
(1-2-1111)
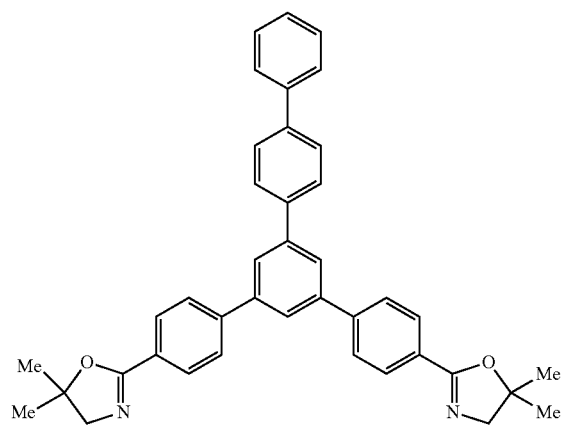
(1-2-1112)
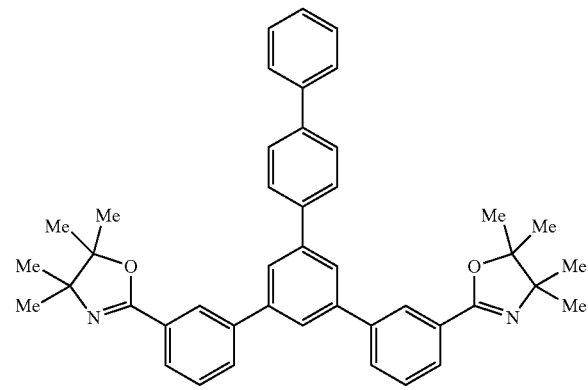
(1-2-113)
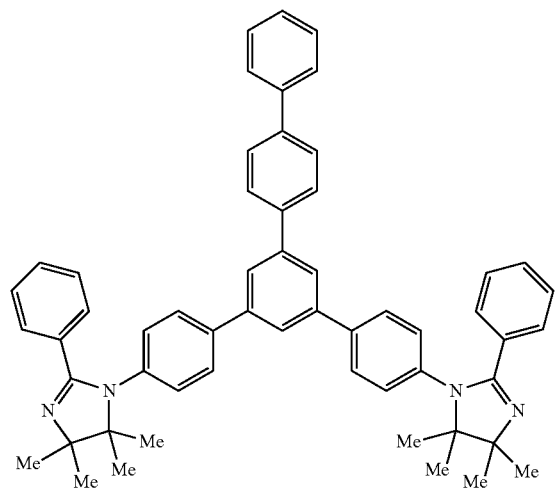
(1-2-114)
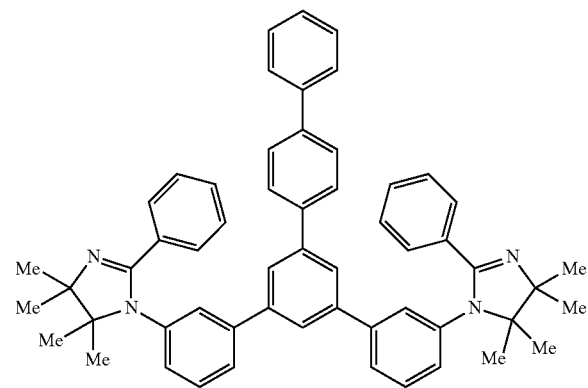
(1-2-1115)
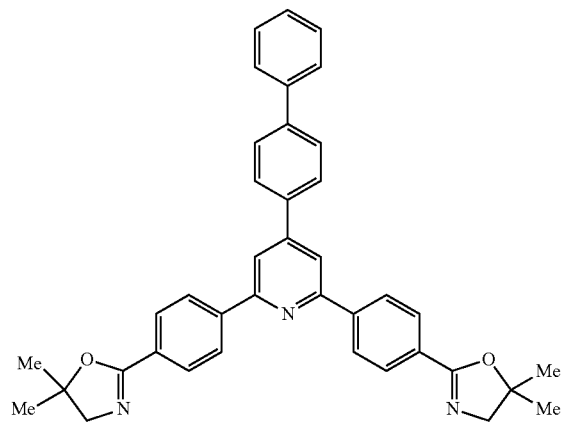
(1-2-1116)
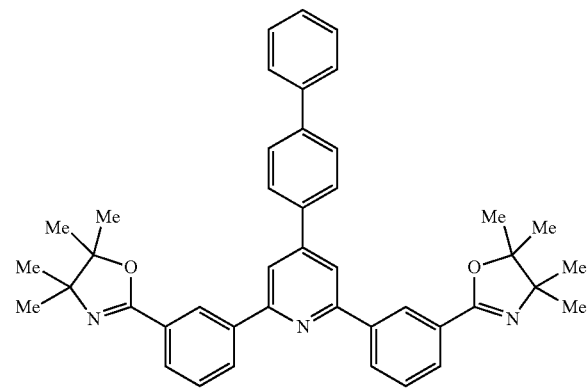

-continued
407
(1-2-1117)
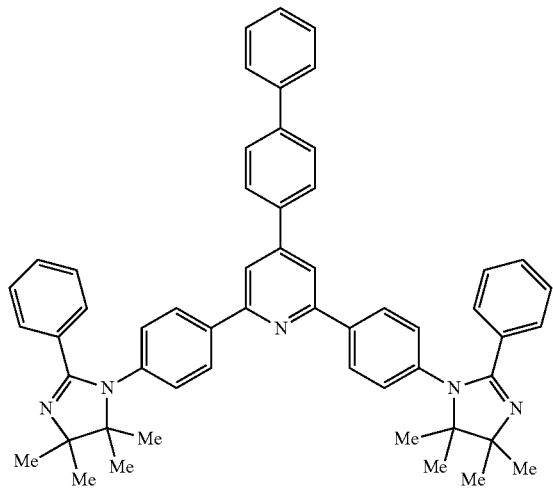
408
(1-2-1118)
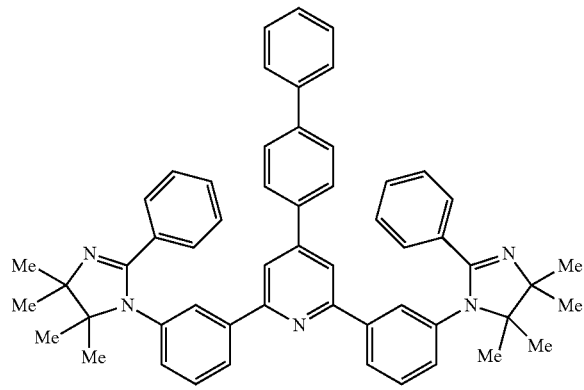
(1-2-1121)
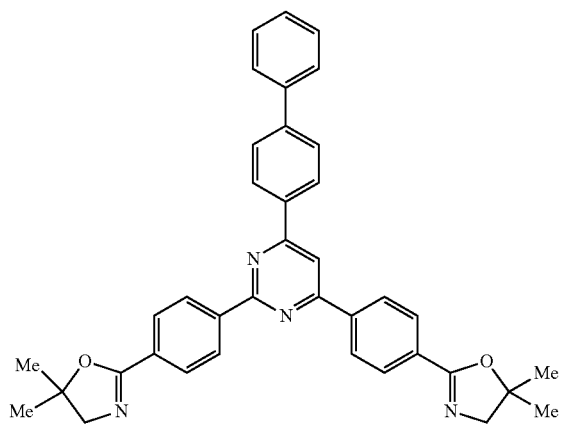
(1-2-1122)
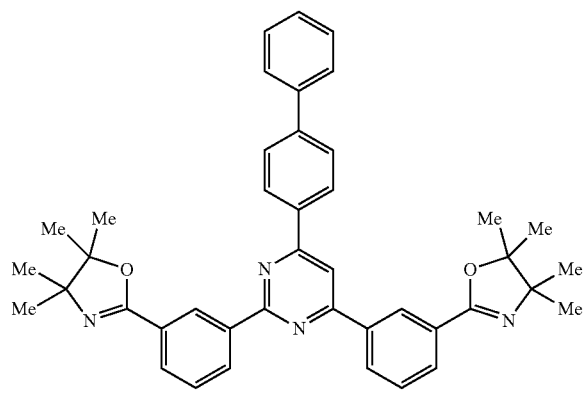
(1-2-1123)
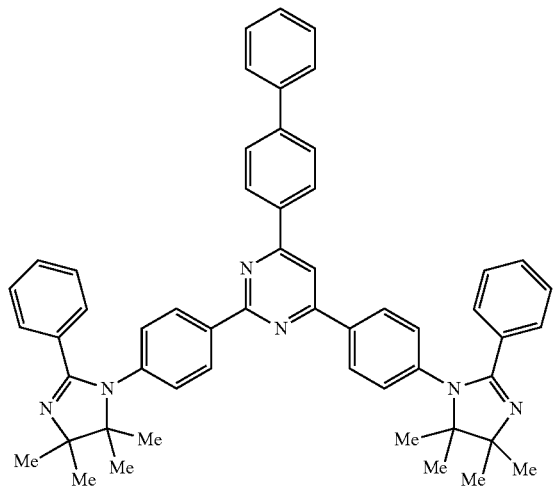
(1-2-1124)
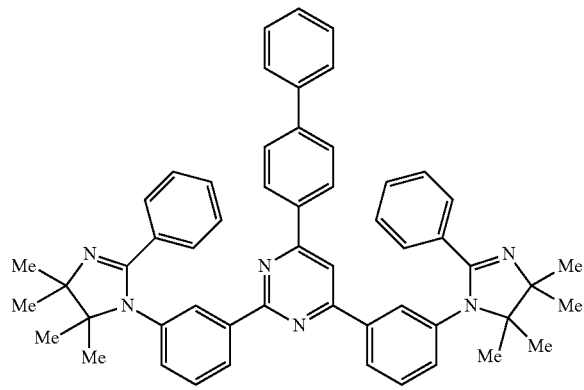

-continued
(1-2-1125)
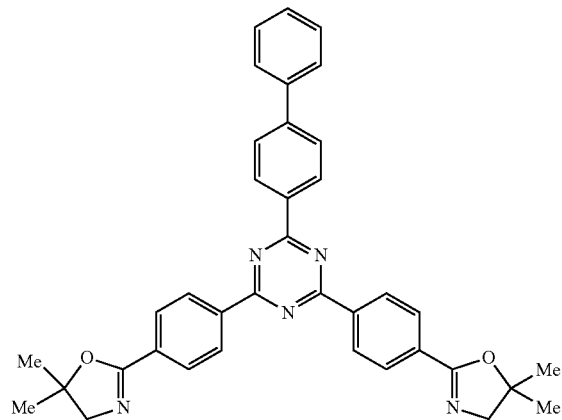
(1-2-1126)
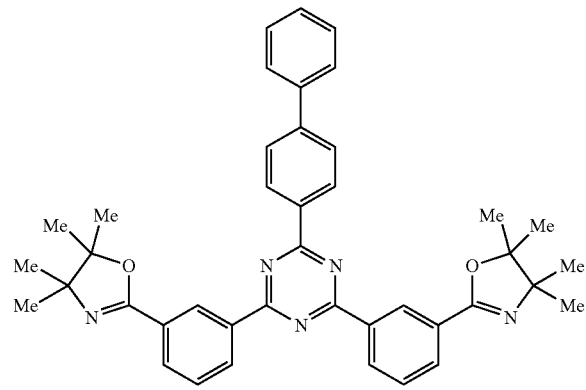
(1-2-1127)
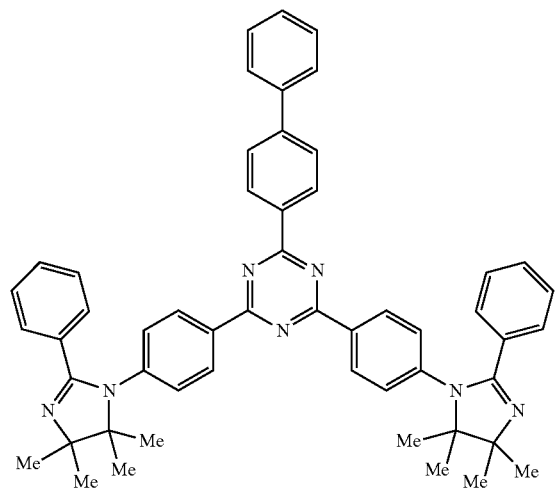
(1-2-1128)
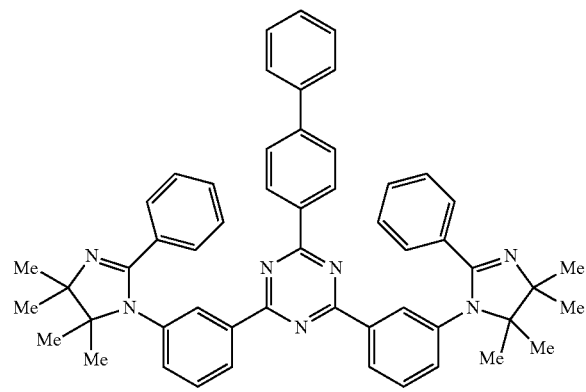
(1-2-1131)
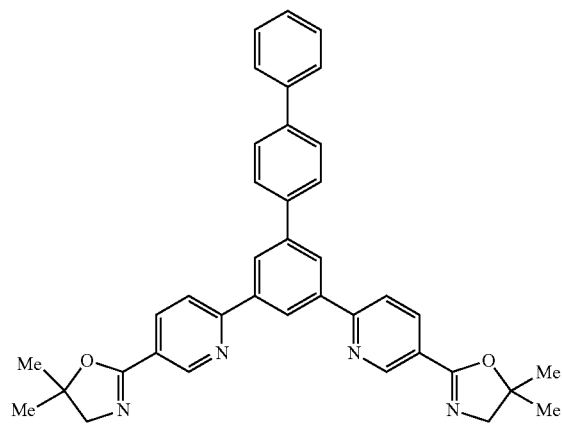
(1-2-1132)
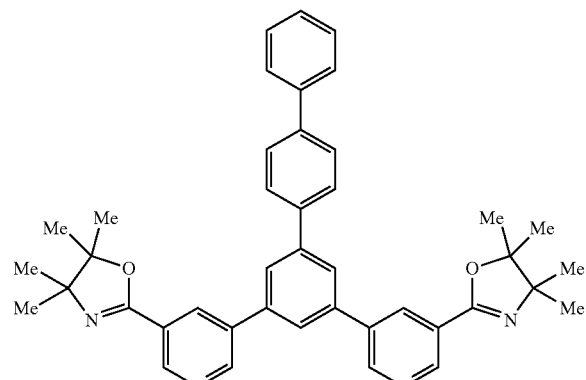

411                                                       412
(1-2-1133)                                              (1-2-1134)
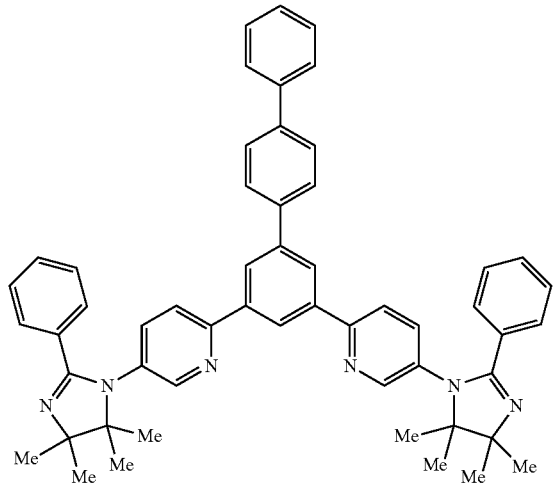    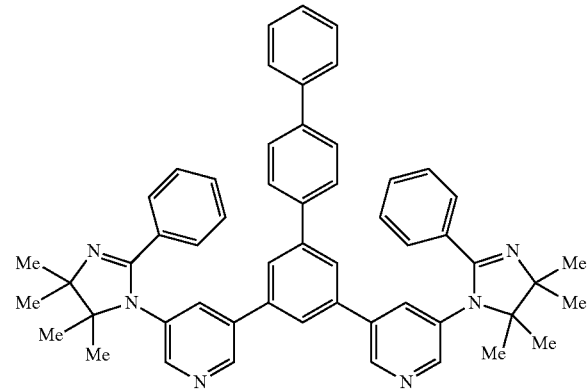
(1-2-1135)                                              (1-2-1136)
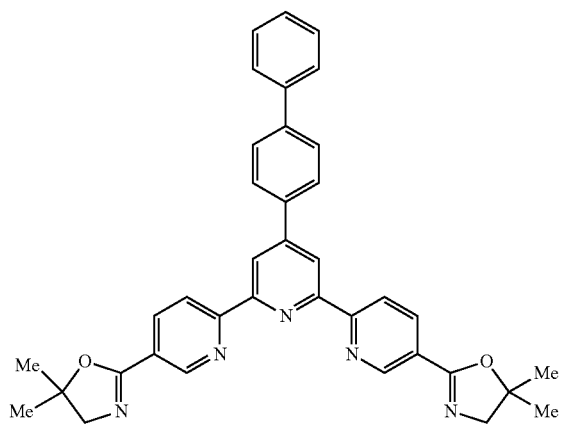    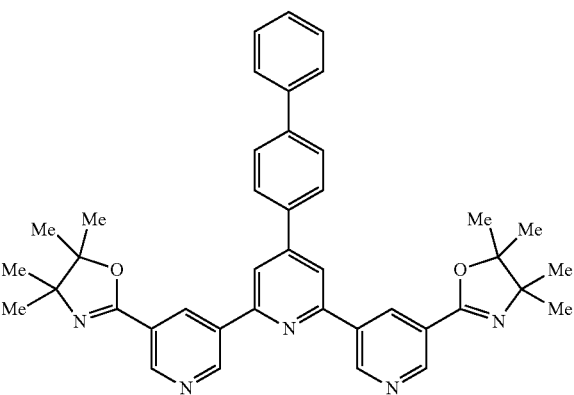
(1-2-1137)                                              (1-2-1138)
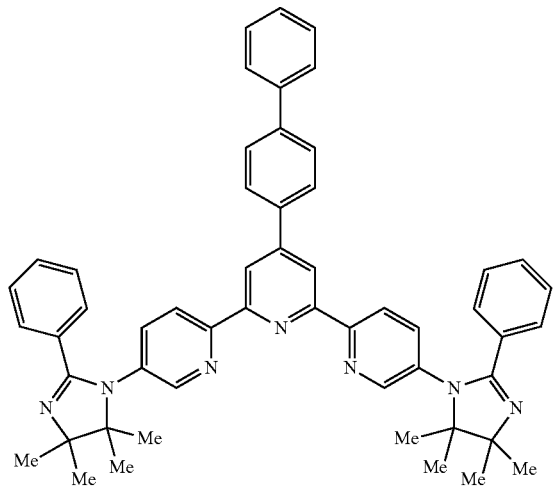    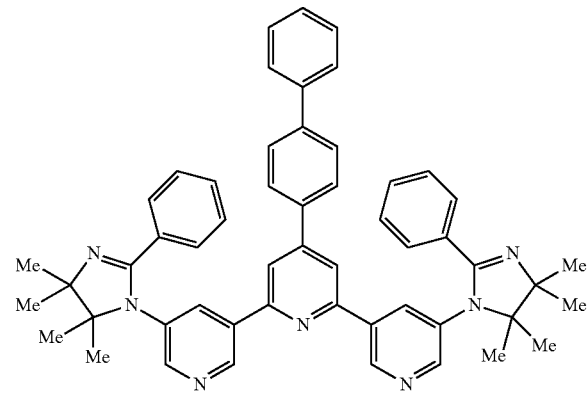

-continued
(1-2-1141)
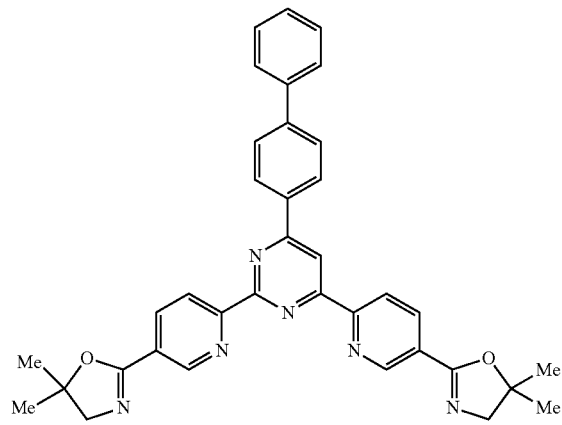
(1-2-1142)
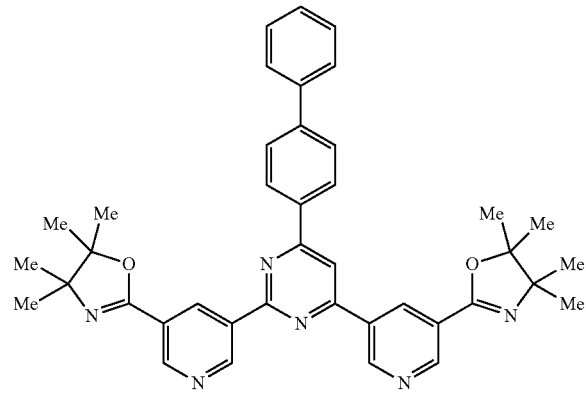
(1-2-1143)
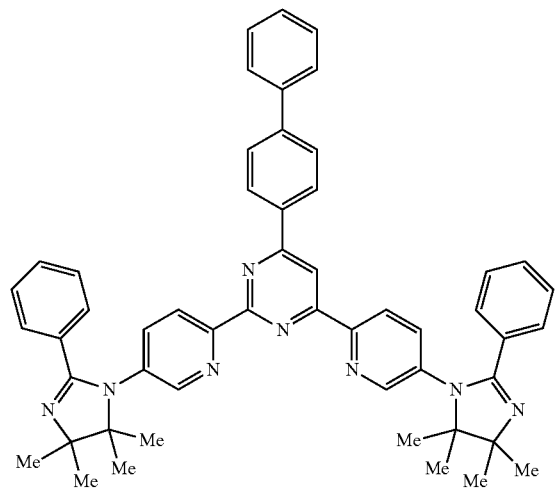
(1-2-1144)
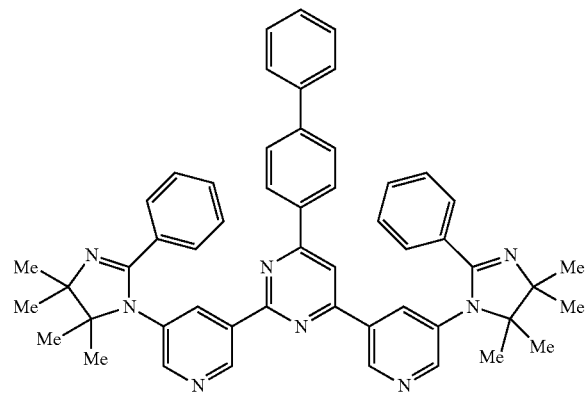
(1-2-1145)
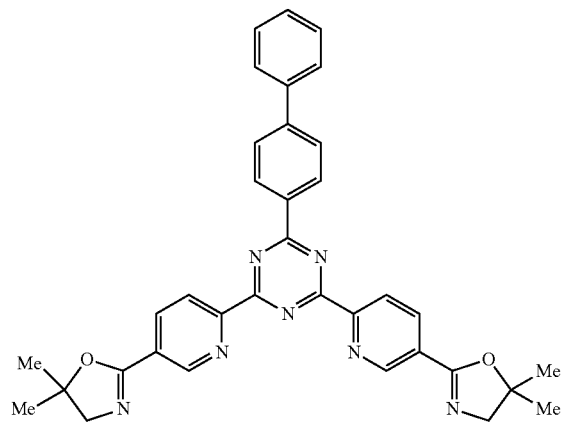
(1-2-1146)
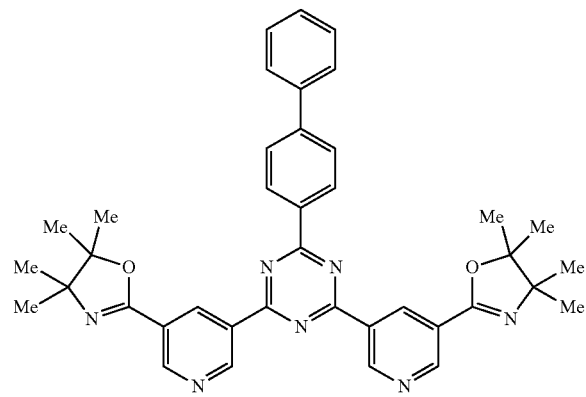

-continued
(1-2-1147)
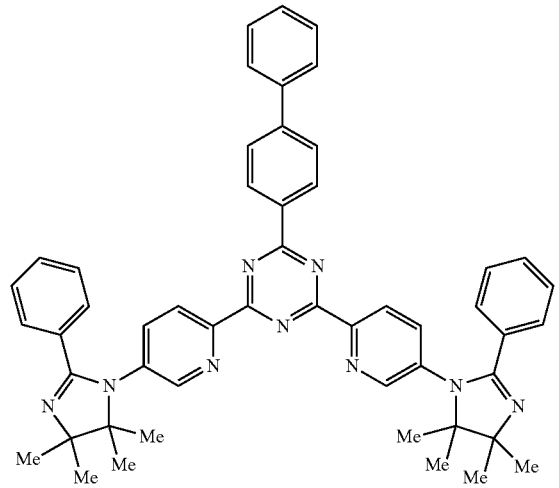
(1-2-1148)
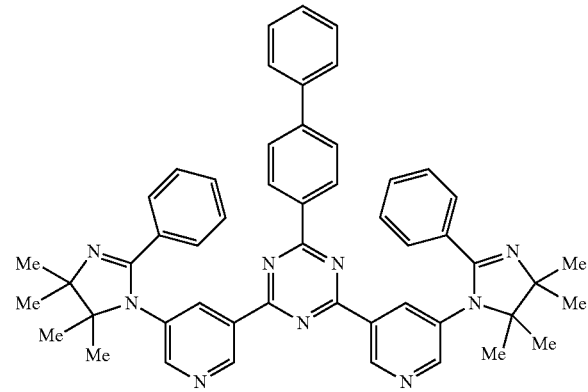
(1-2-1151)
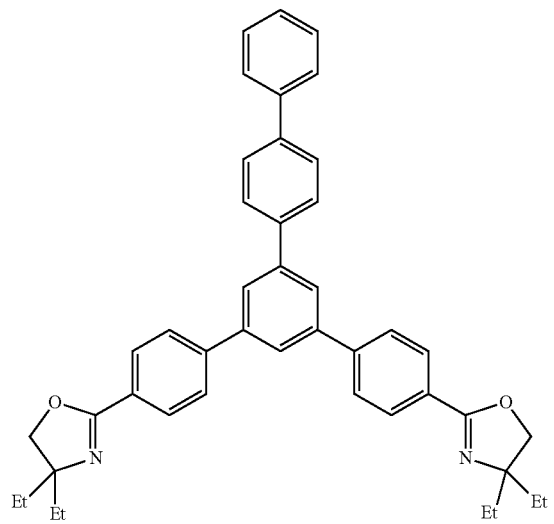
(1-2-1152)
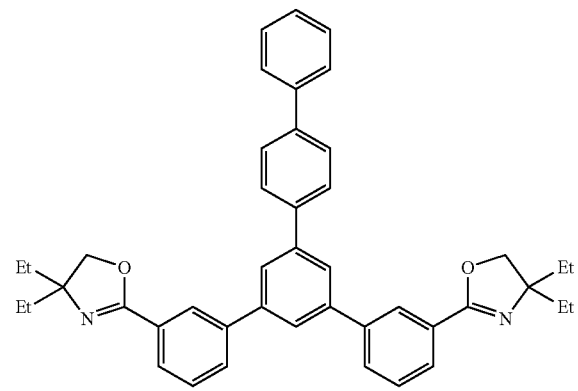
(1-2-1153)
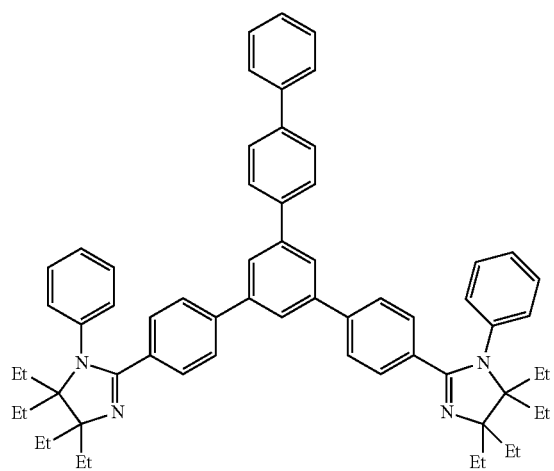
(1-2-1154)
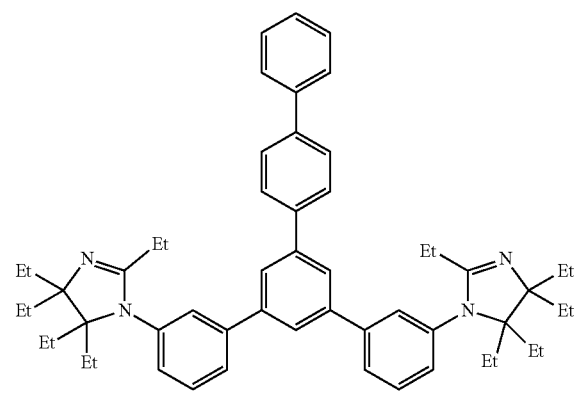

417 418
-continued
(1-2-1155)
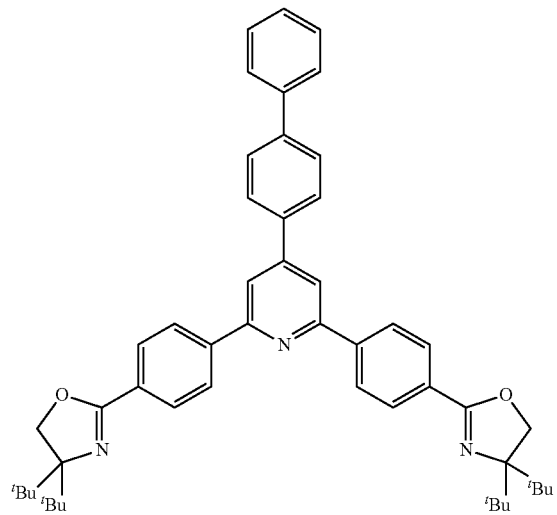
(1-2-1156)
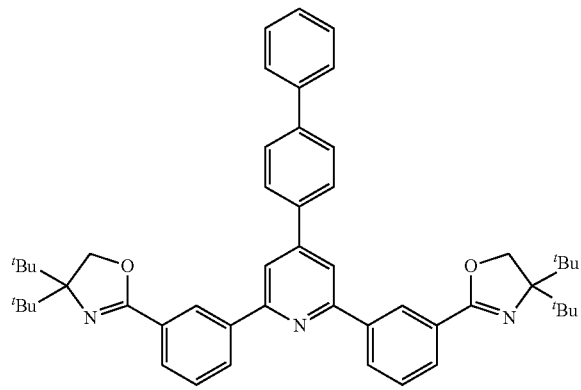
(1-2-1157)
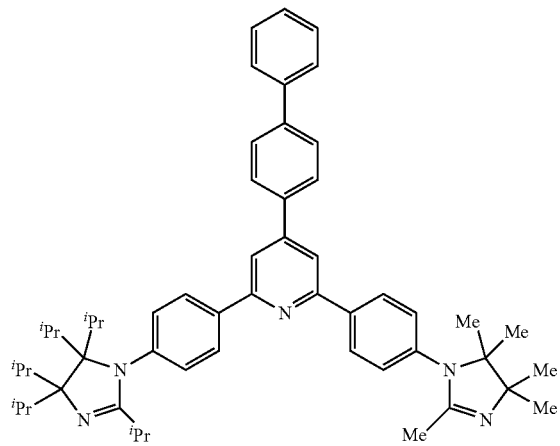
(1-2-1158)
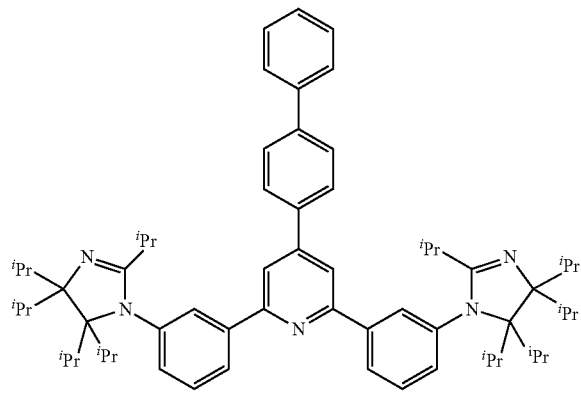
(1-2-1161)
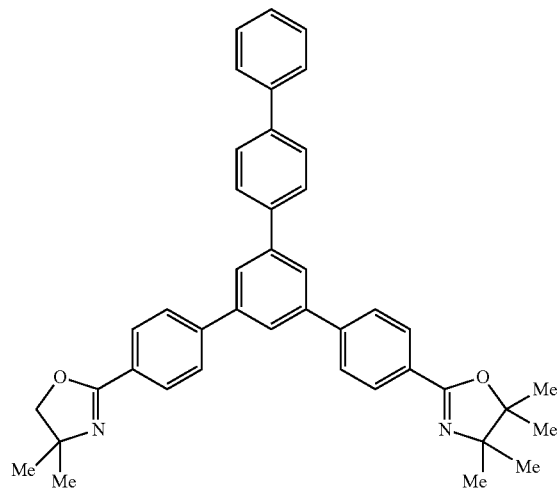
(1-2-1162)
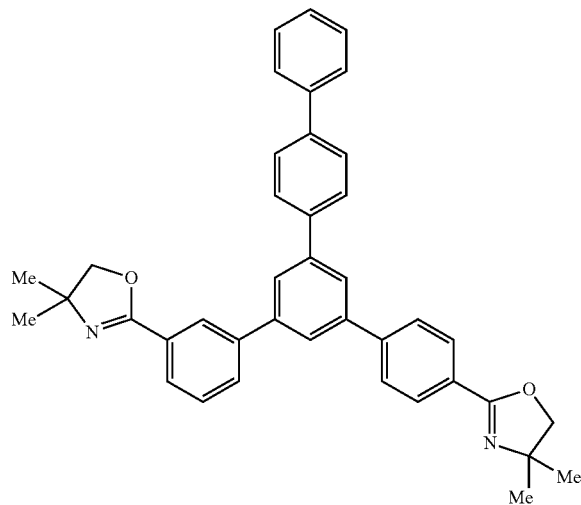

(1-2-1163)
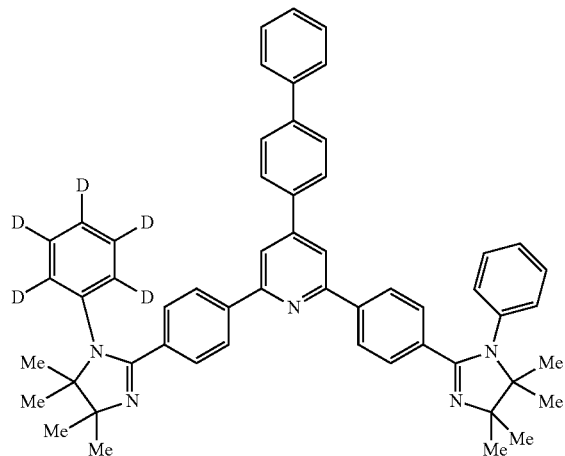
(1-2-1164)
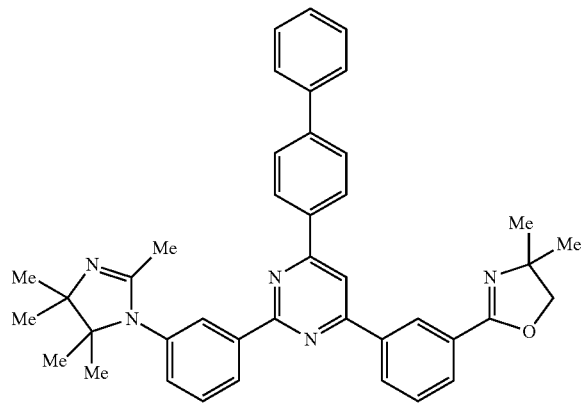
(1-2-1165)
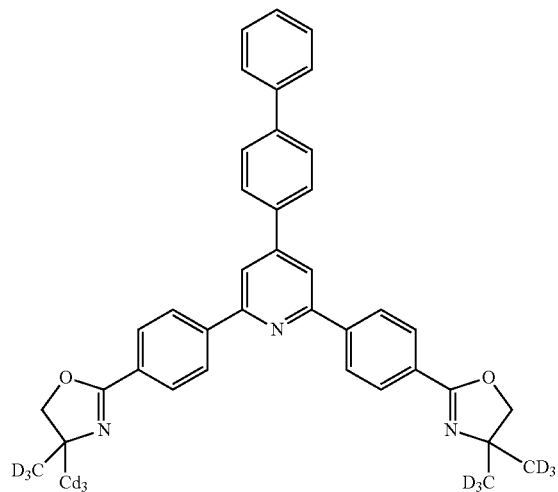
(1-2-1166)
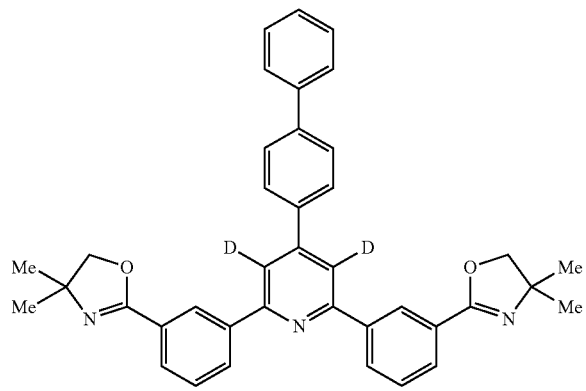
(1-2-1167)
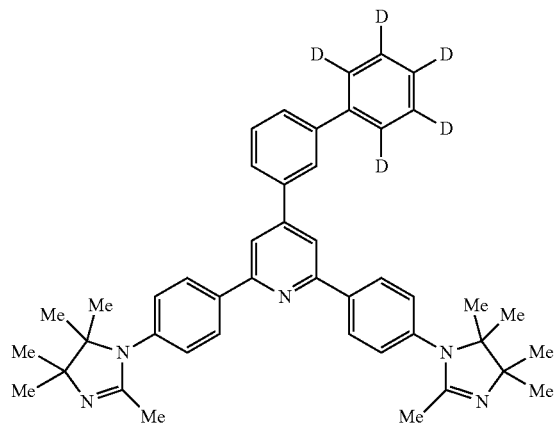
(1-2-1168)
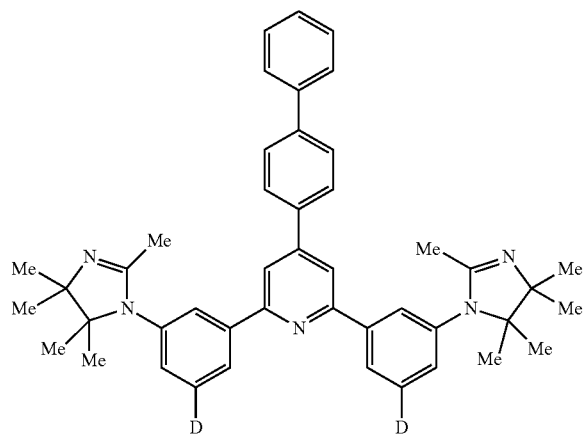

-continued
(1-3-1)
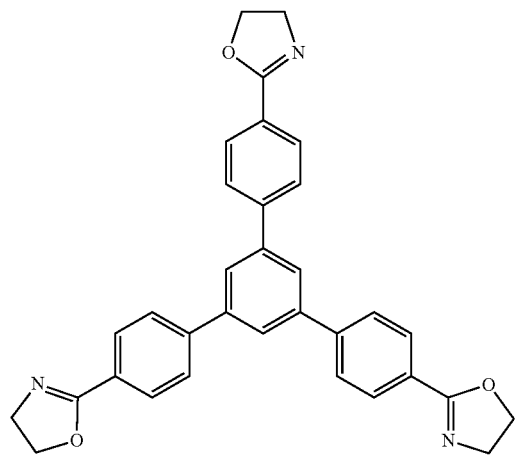
(1-3-2)
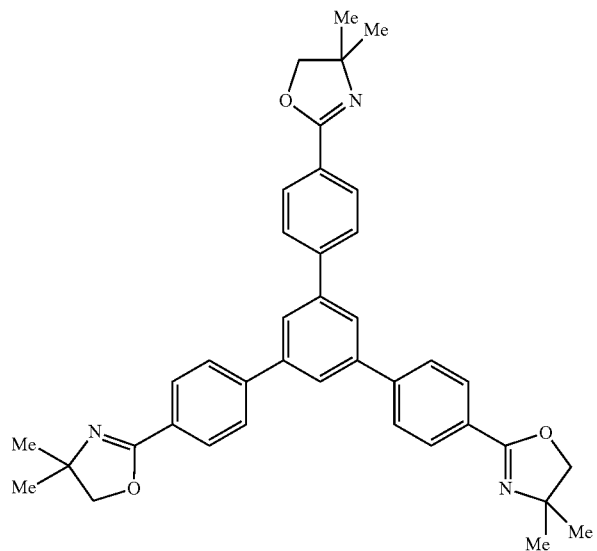
(1-3-3)
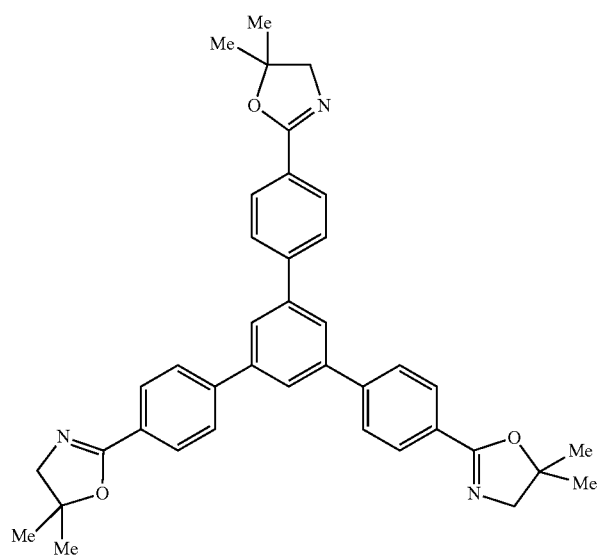
(1-3-4)
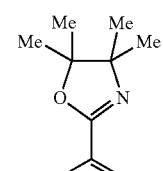
(1-3-5)
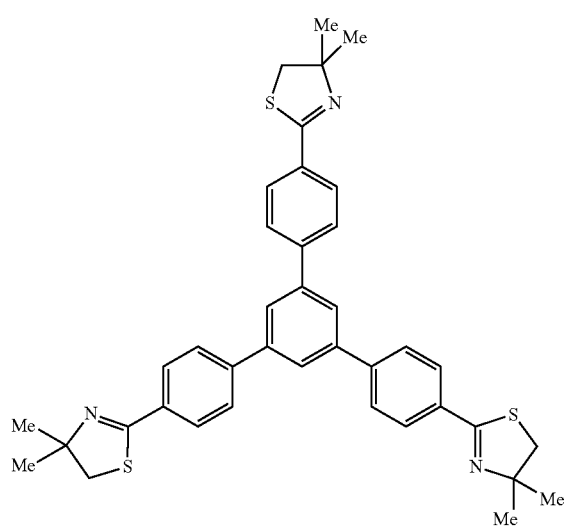
(1-3-6)
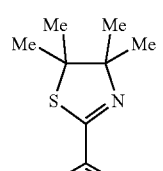
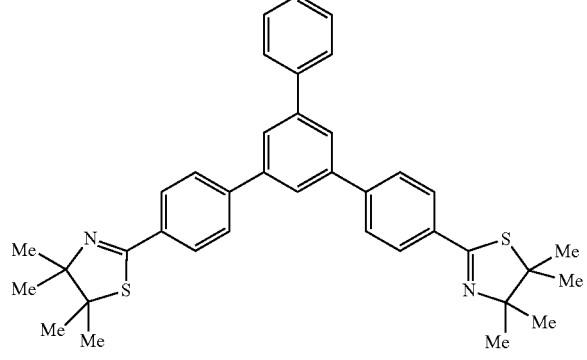

423
(1-3-7)
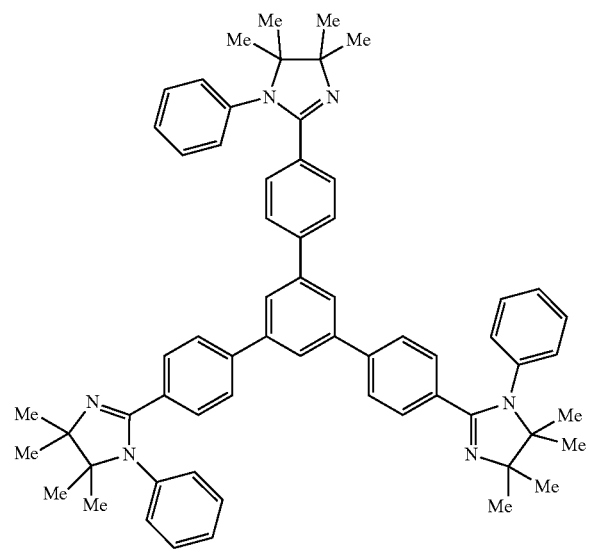
424
(1-3-8)
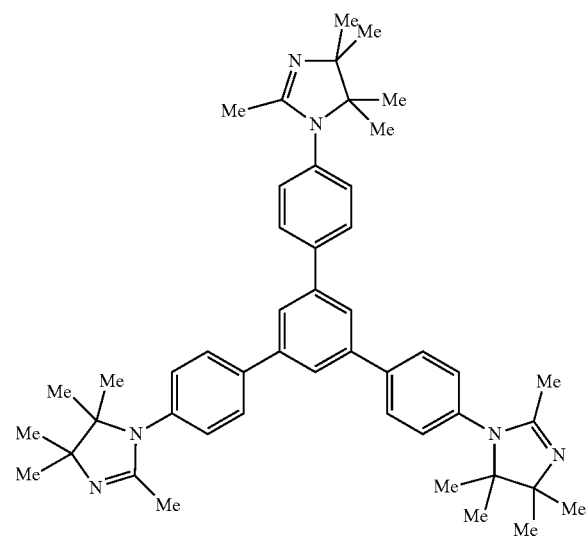
(1-3-9)
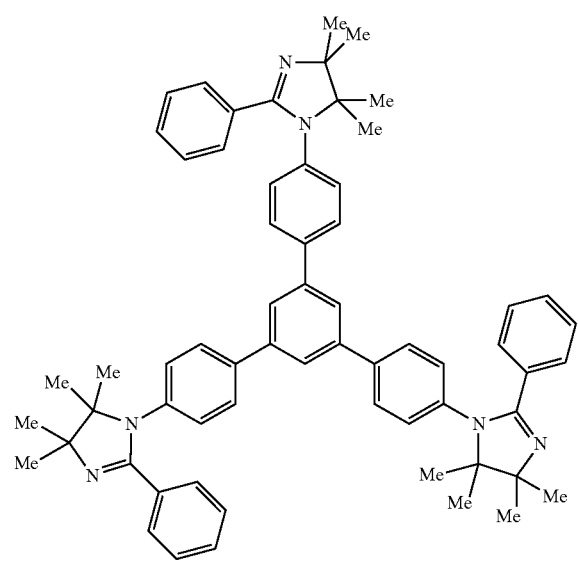
(1-3-11)
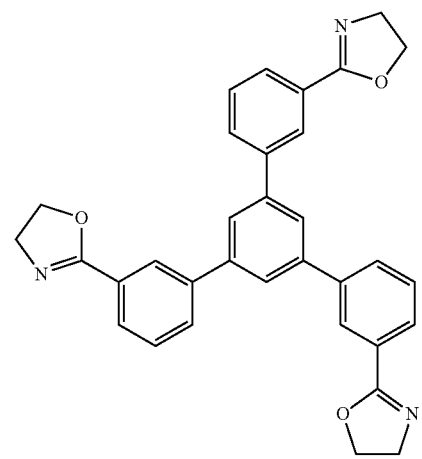

-continued
(1-3-12)
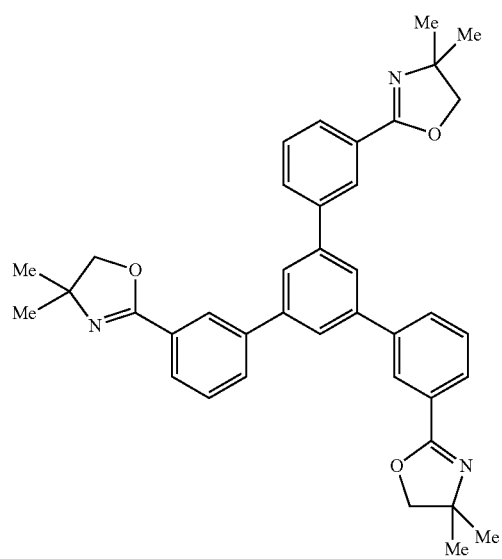
(1-3-13)
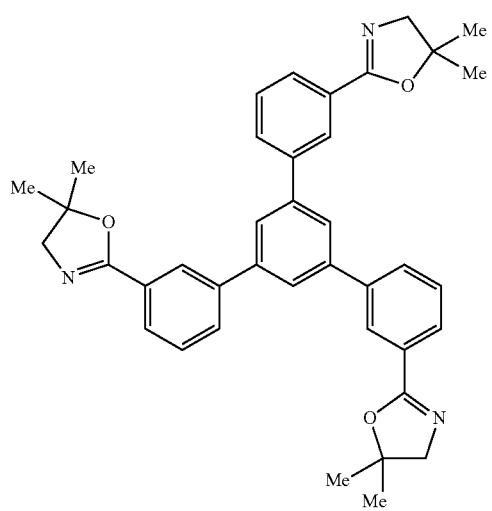
(1-3-14)
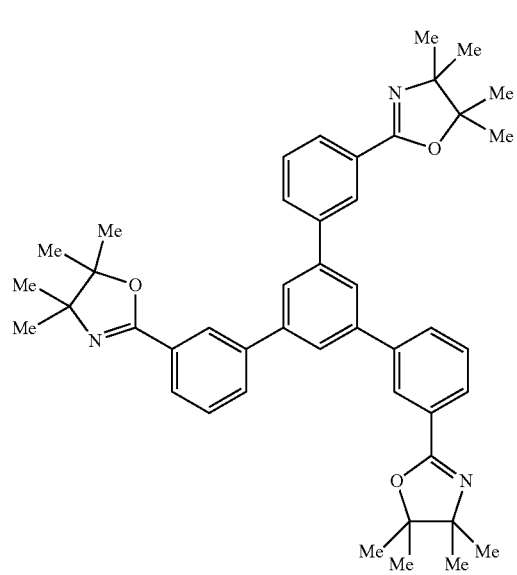
(1-3-15)
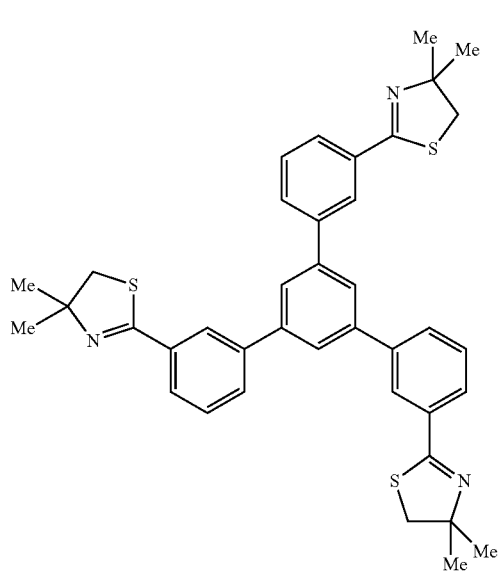
(1-3-16)
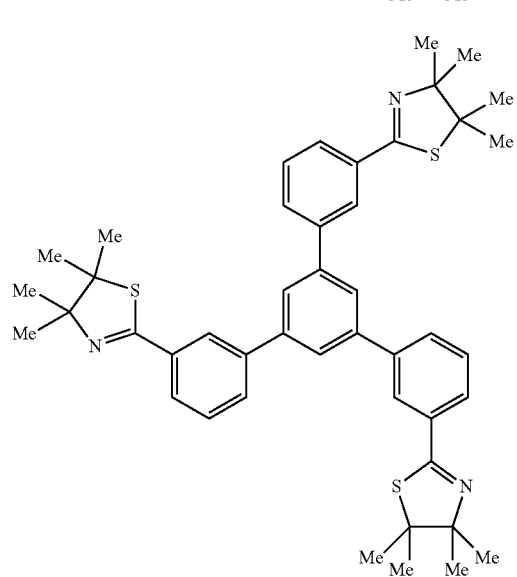
(1-3-17)
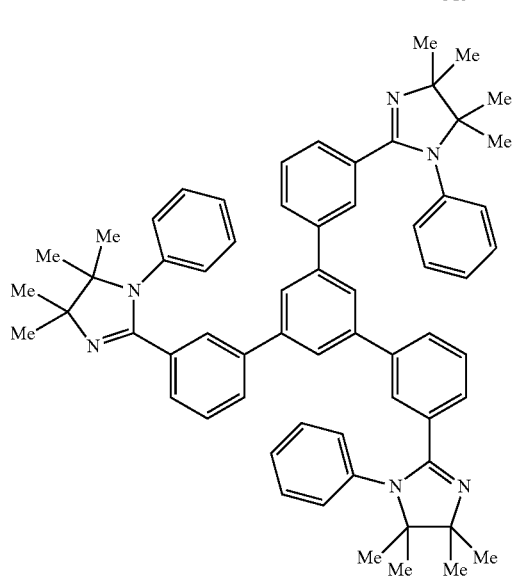

(1-3-18)
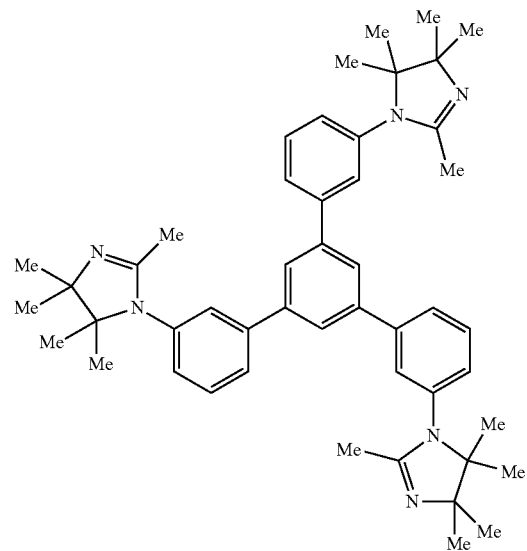
(1-3-19)
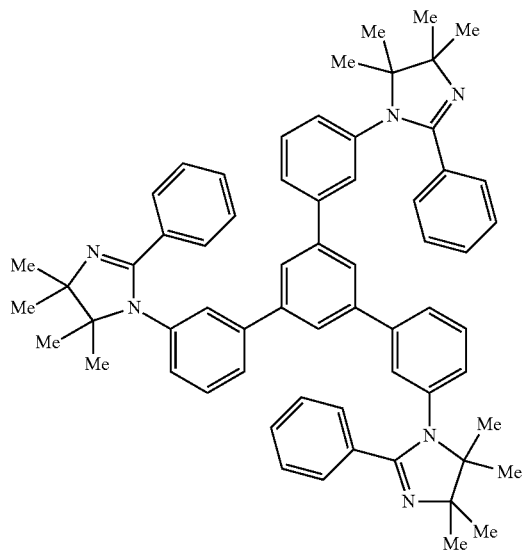
(1-3-21)
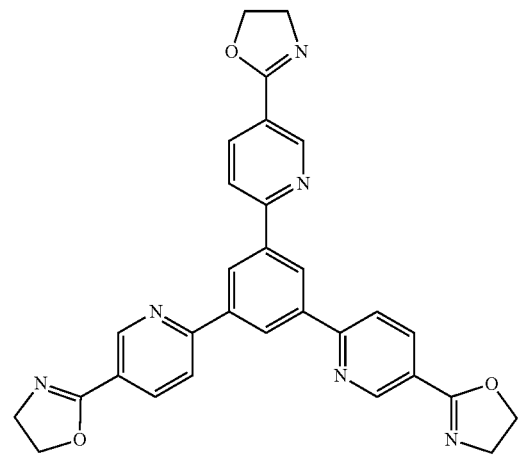
(1-3-22)
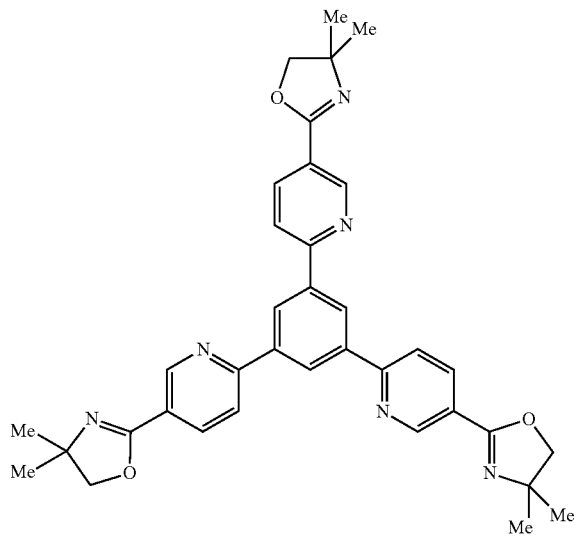

(1-3-23)
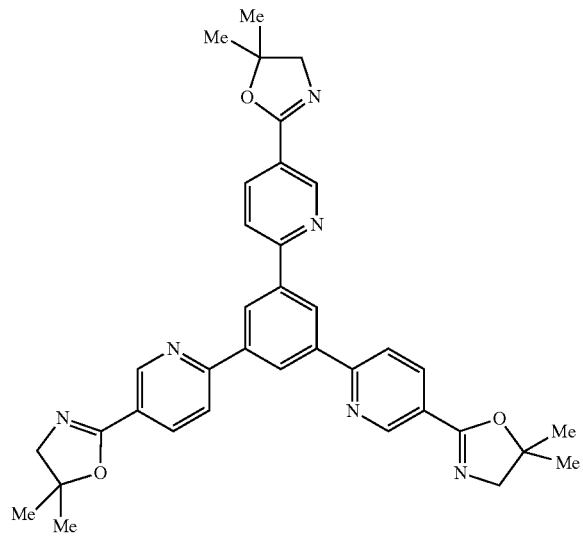
(1-3-24)
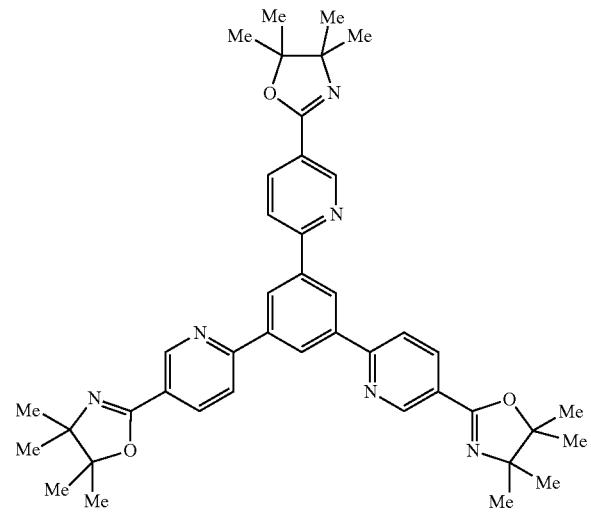
(1-3-25)
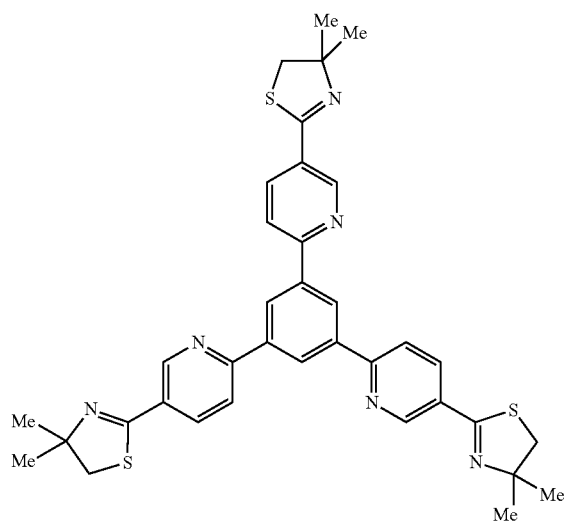
(1-3-26)
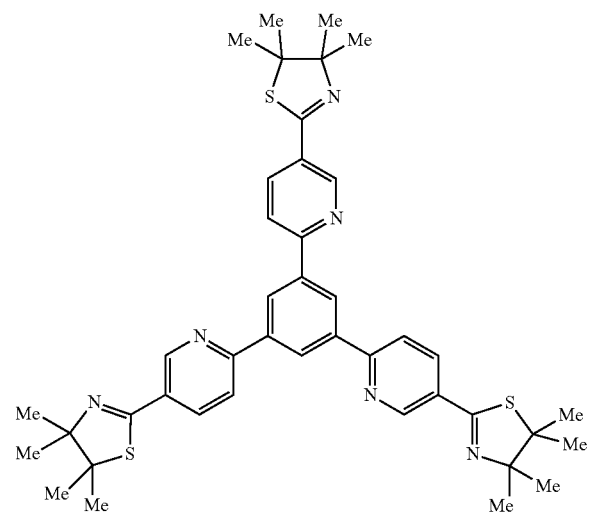
(1-3-27)
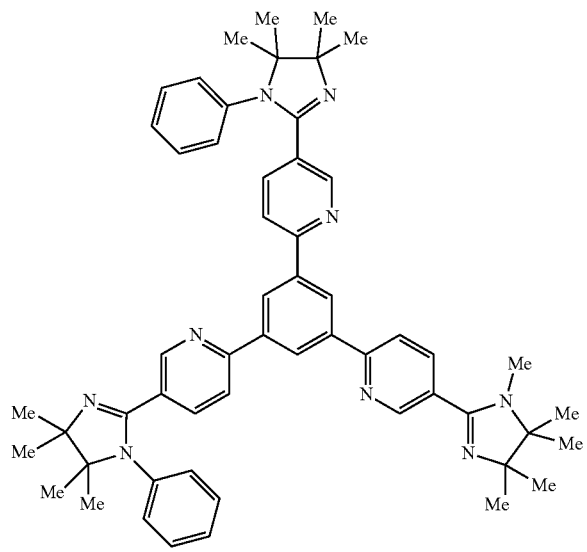
(1-3-28)
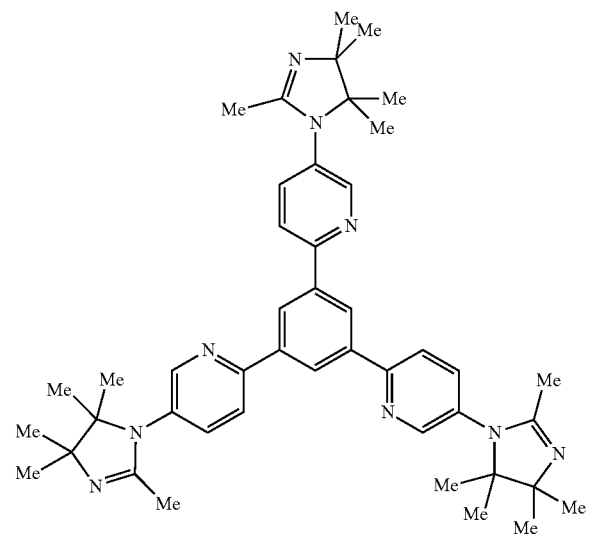

-continued
(1-3-29)
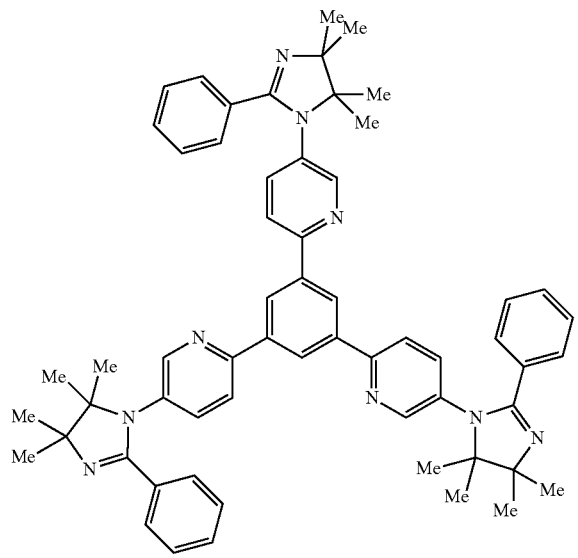
(1-3-31)
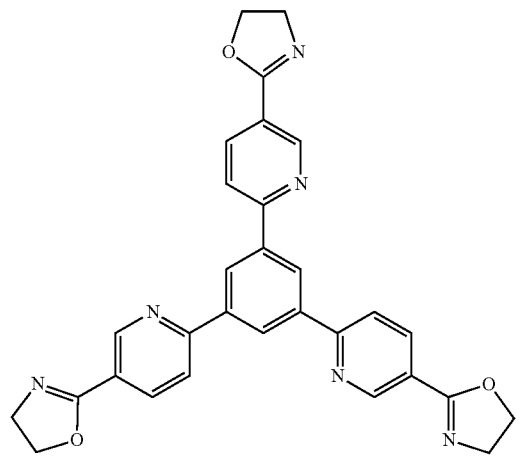
(1-3-32)
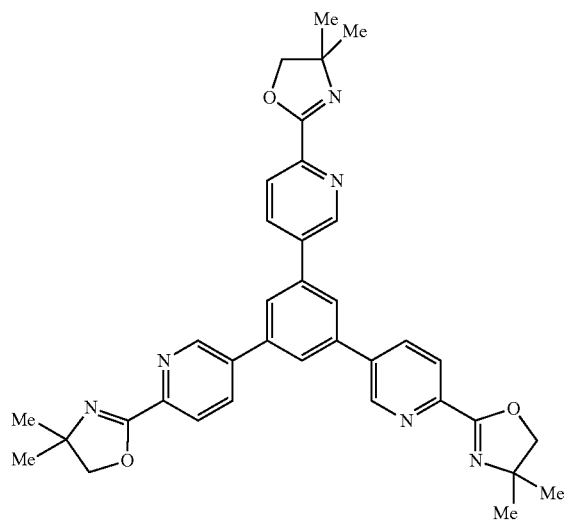
(1-3-33)
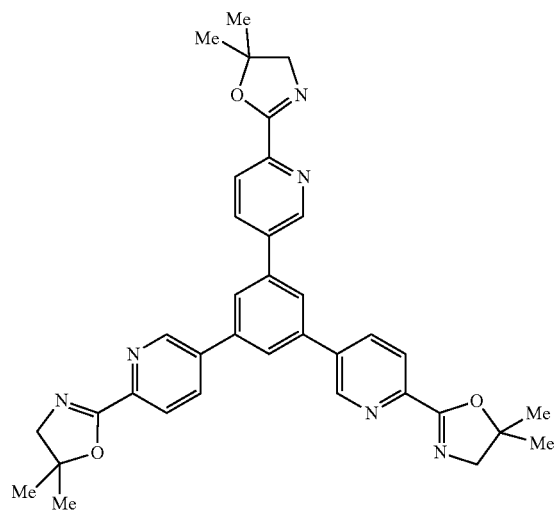
(1-3-34)
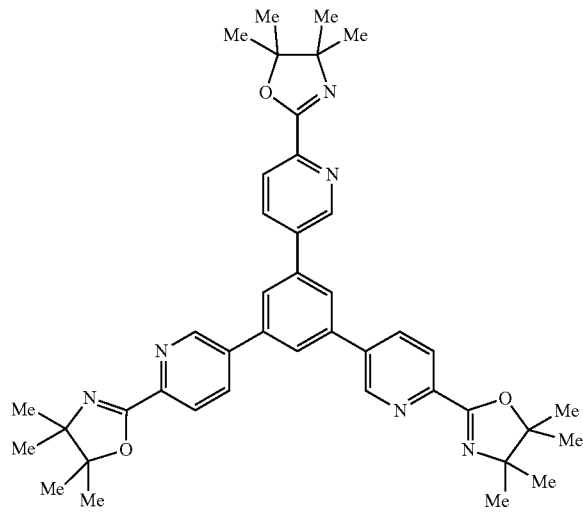
(1-3-35)
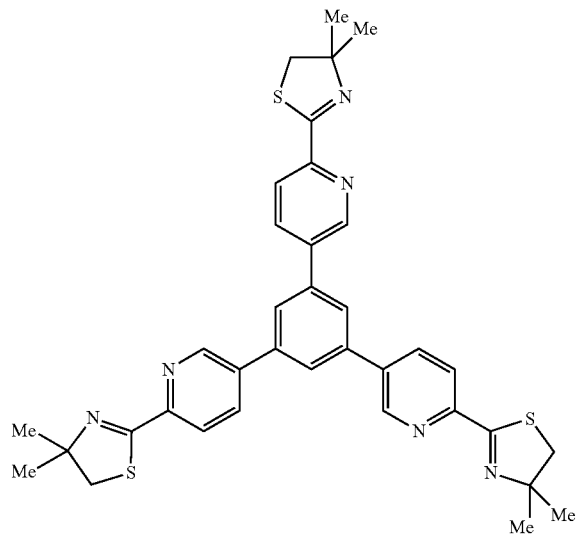

(1-3-36)
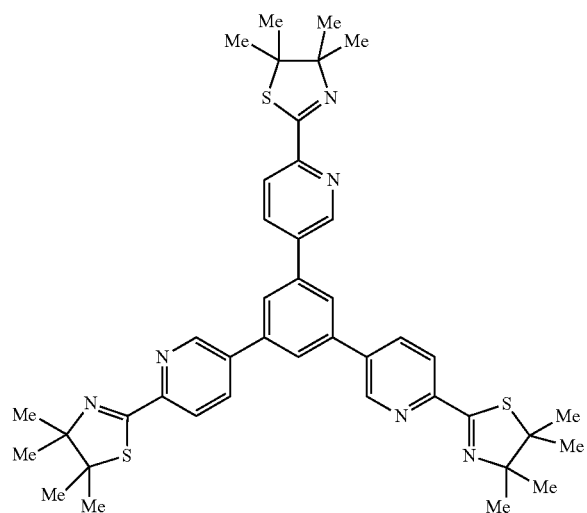
(1-3-37)
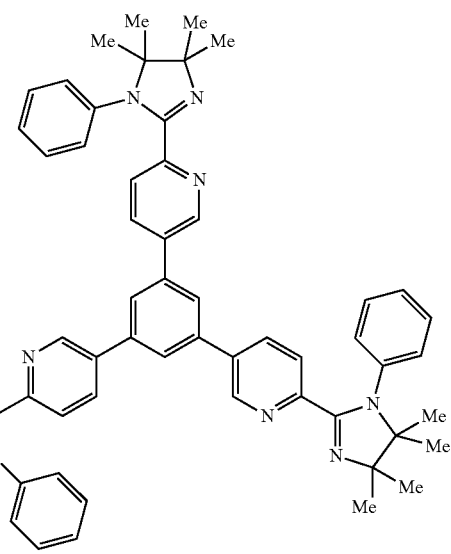
(1-3-38)
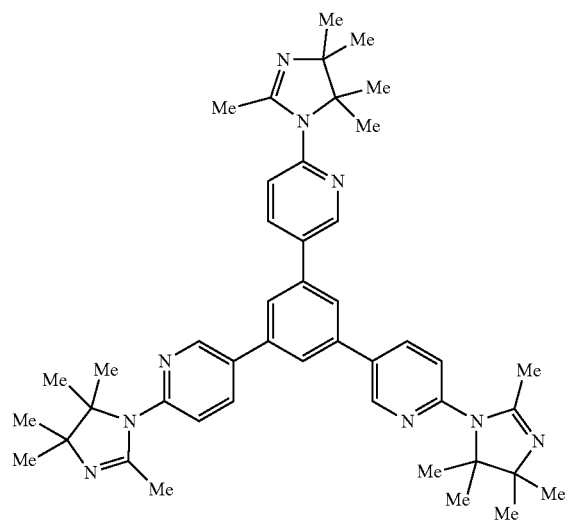
(1-3-39)
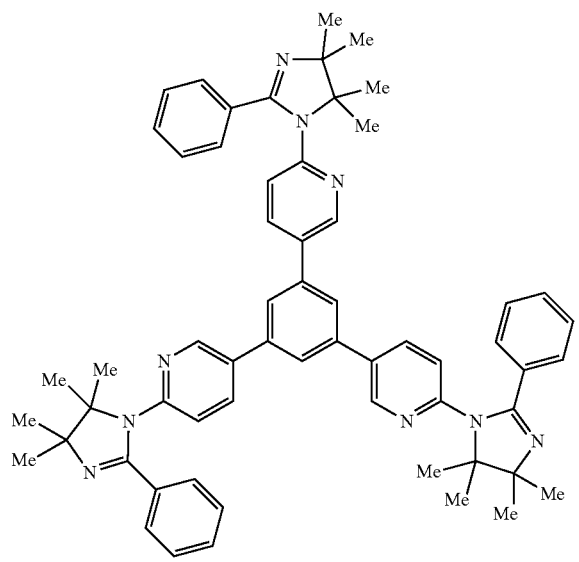

-continued
(1-3-41)
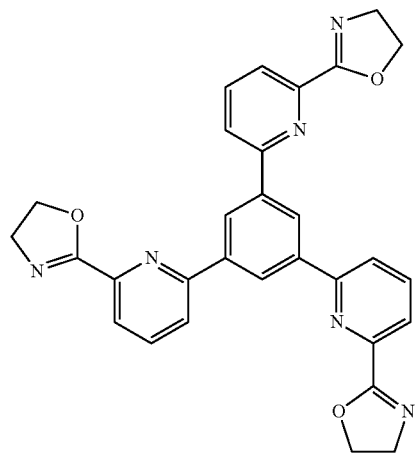
(1-3-42)
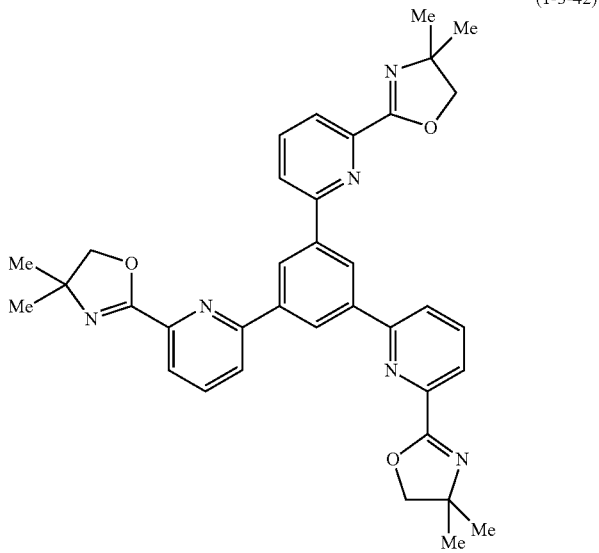
(1-3-43)
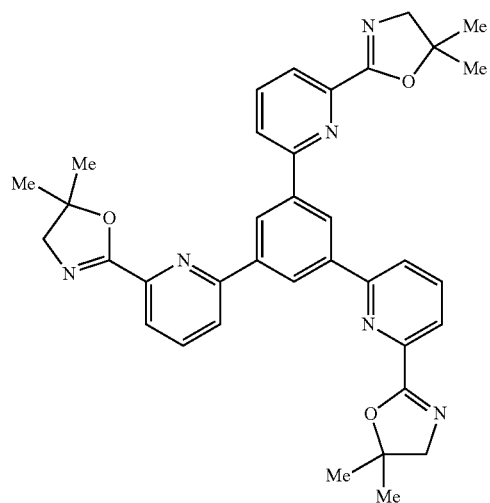
(1-3-44)
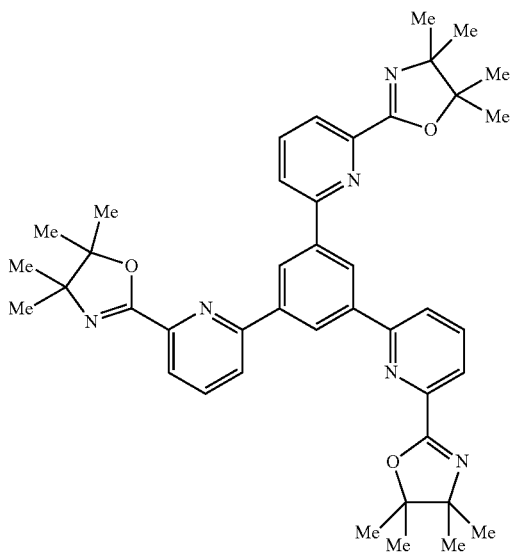
(1-3-45)
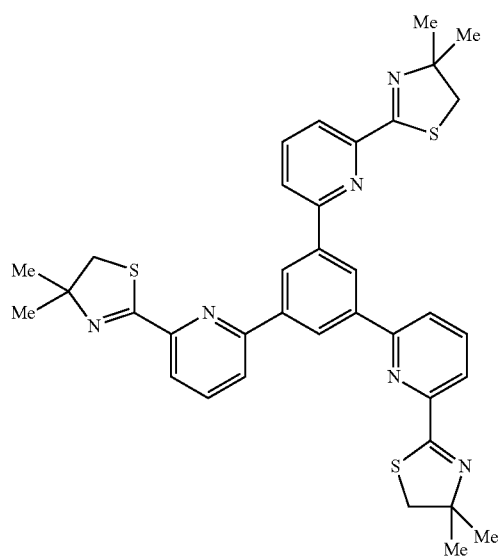
(1-3-46)
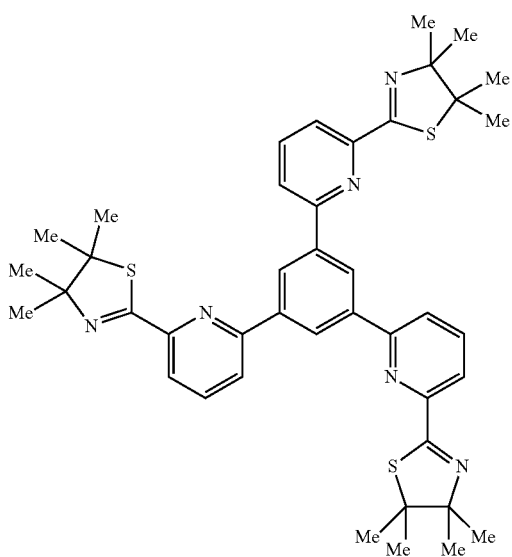

-continued
(1-3-47)
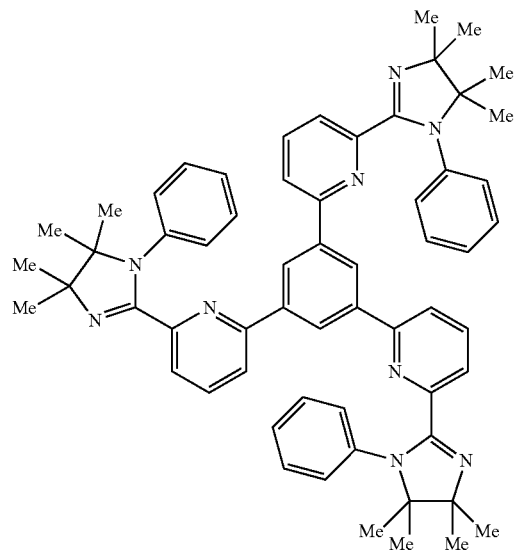
(1-3-48)
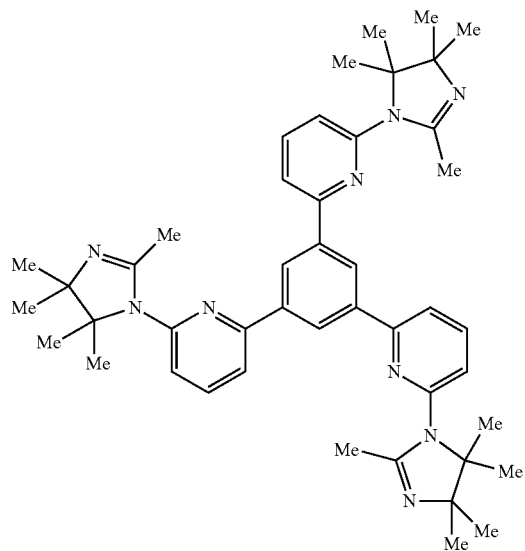
(1-3-49)
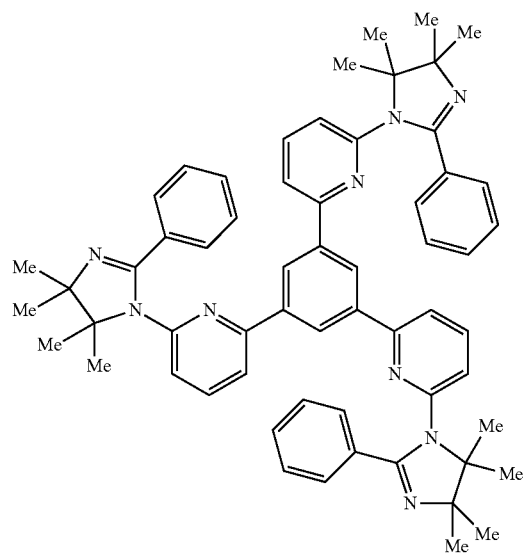
(1-3-51)
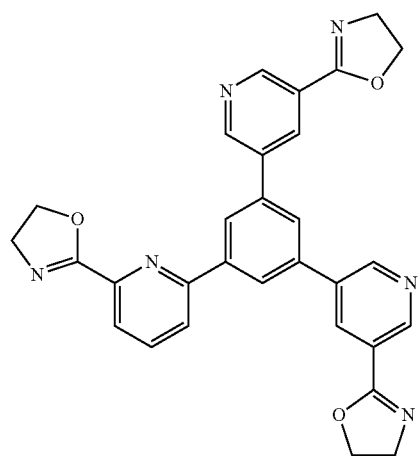

(1-3-52)
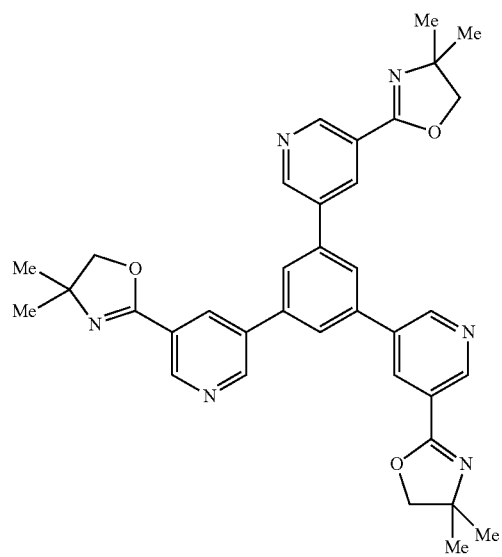
(1-3-53)
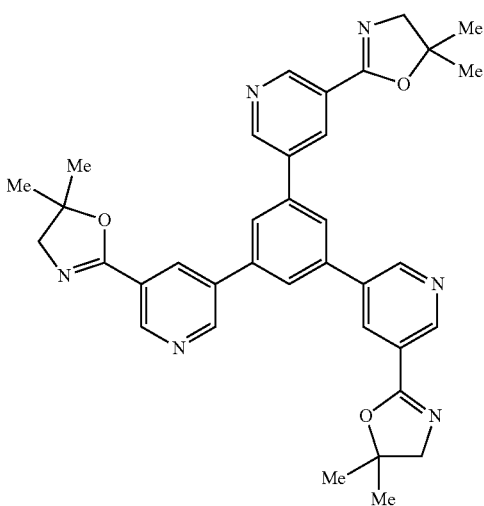
(1-3-54)
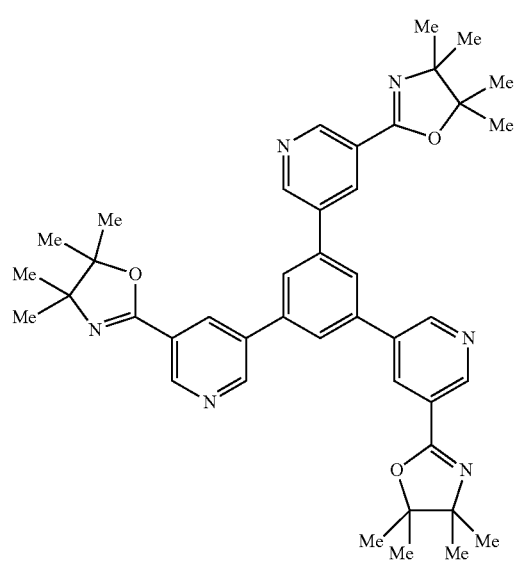
(1-3-55)
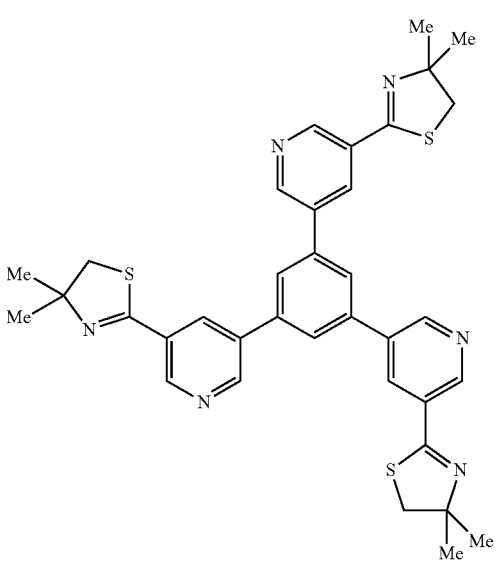
(1-3-56)
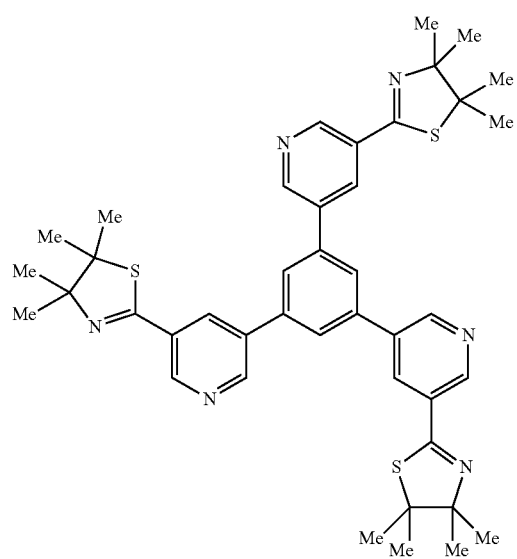
(1-3-57)
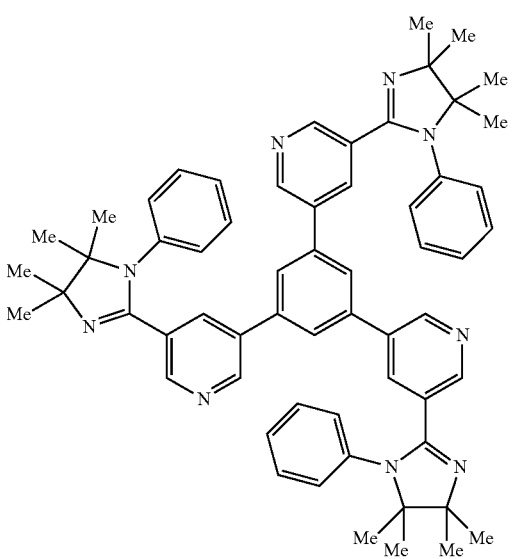

-continued
(1-3-58)
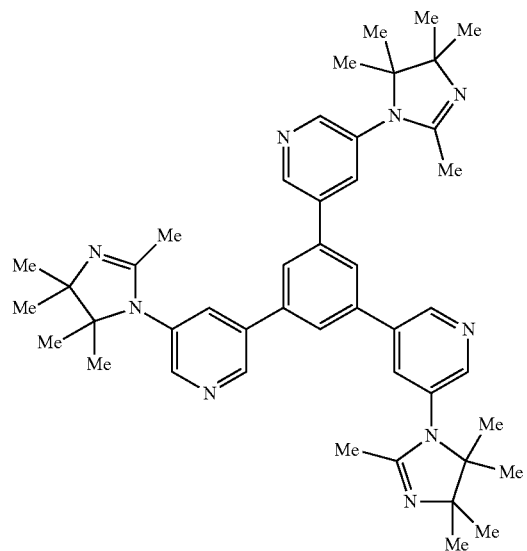
(1-3-59)
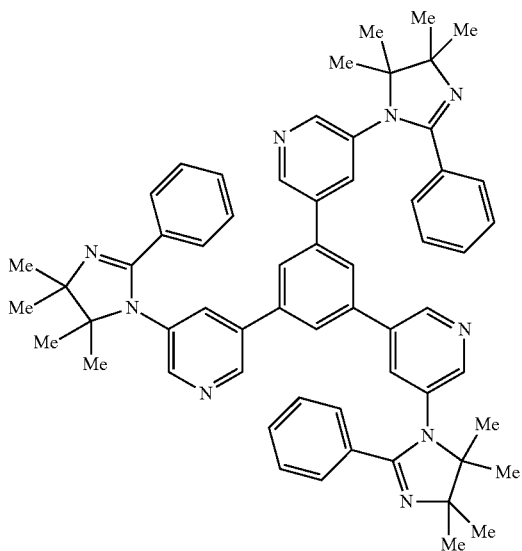
(1-3-61)
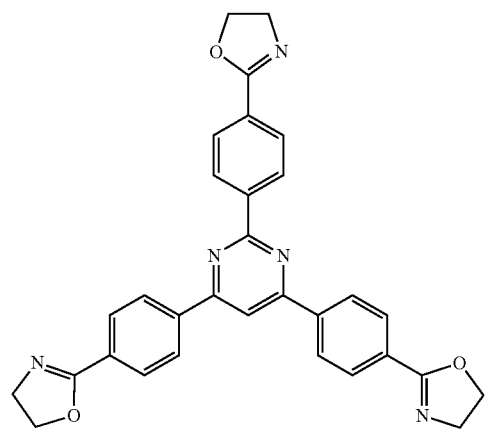
(1-3-62)
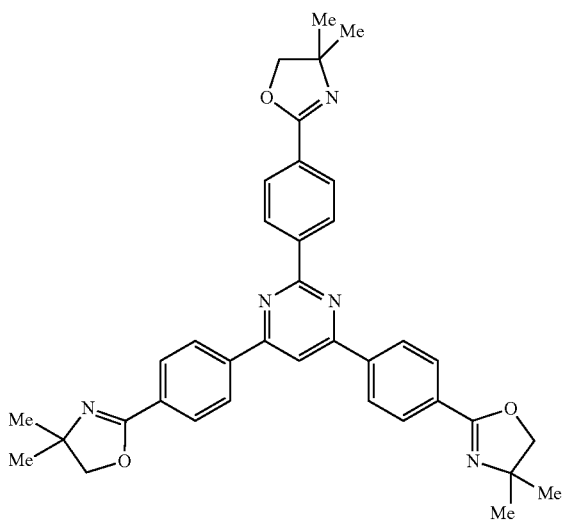
(1-3-63)
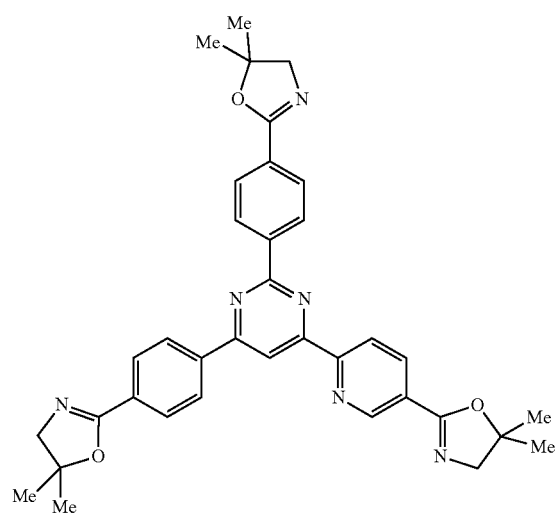
(1-3-64)
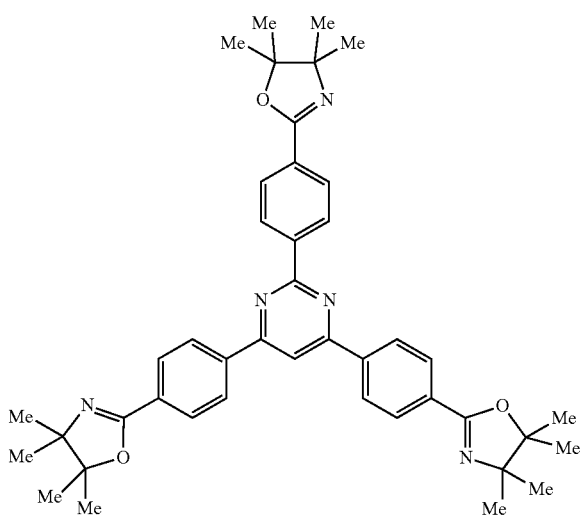

(1-3-65)
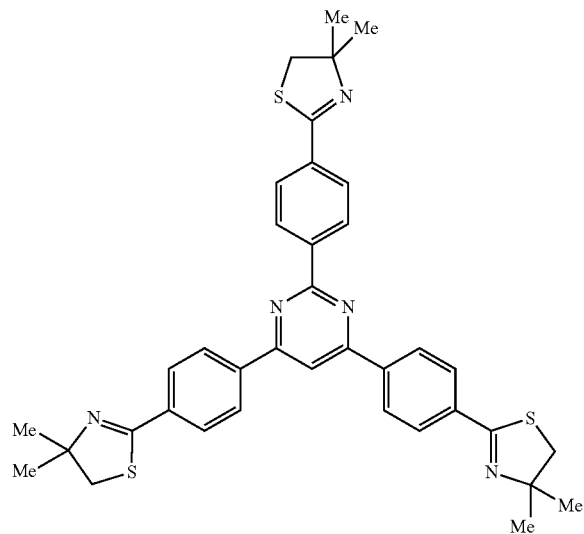
(1-3-66)
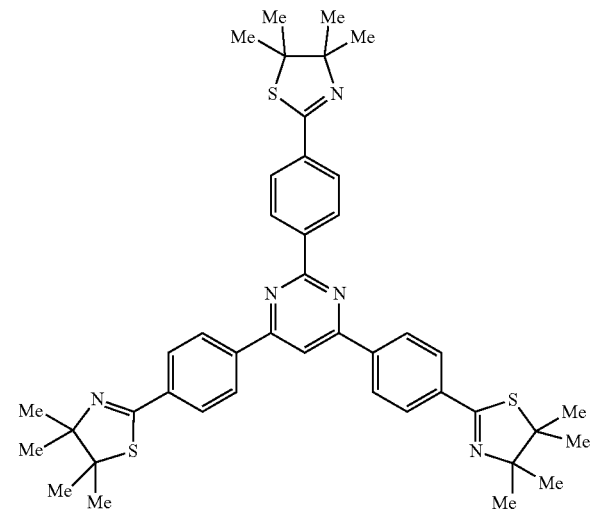
(1-3-67)
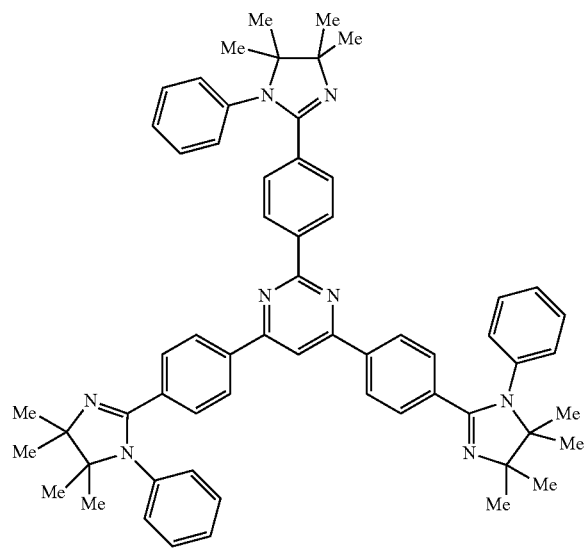
(1-3-68)
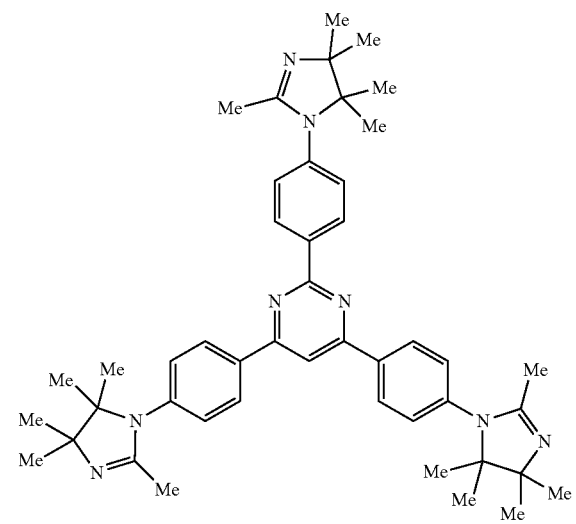

(1-3-69)
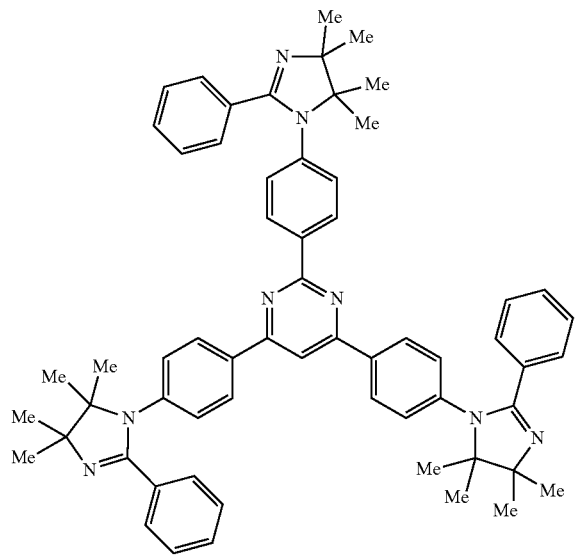
(1-3-71)
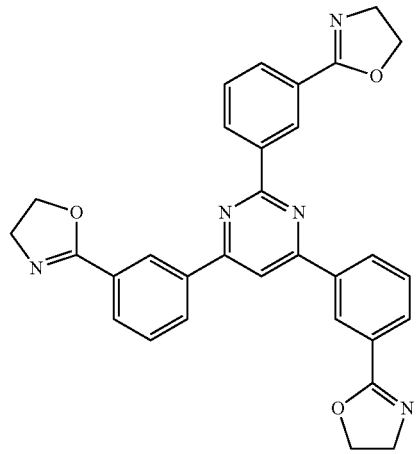
(1-3-72)
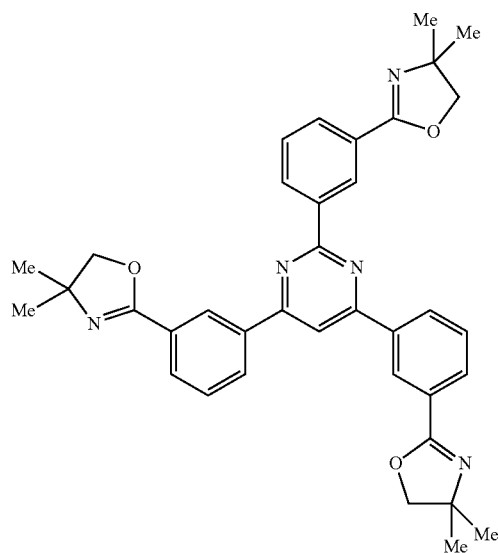
(1-3-73)
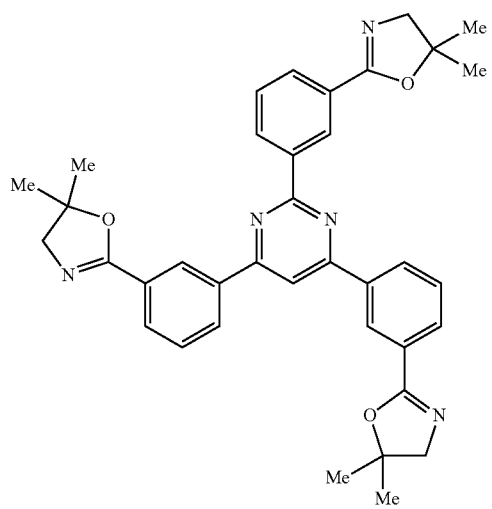
(1-3-74)
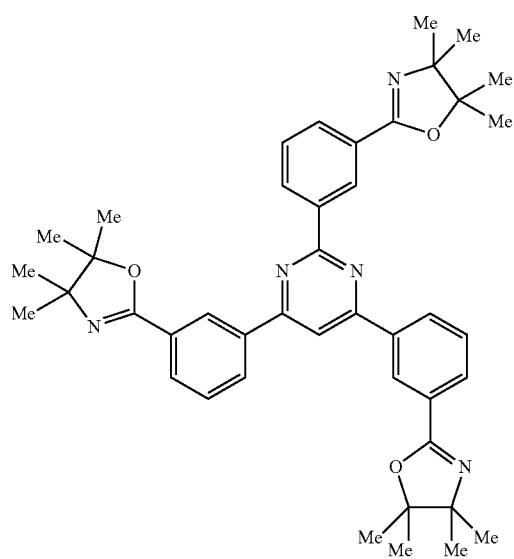
(1-3-75)
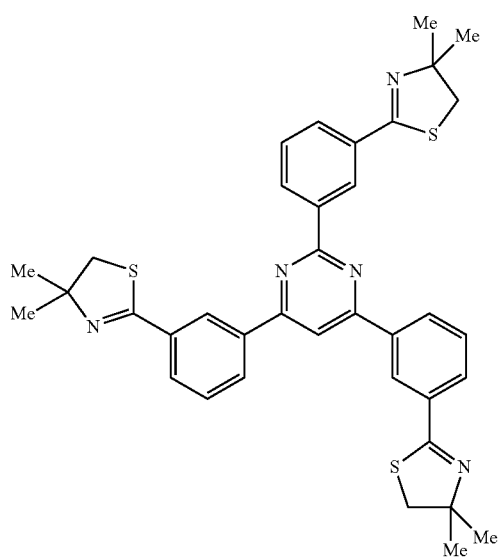

-continued
(1-3-76)
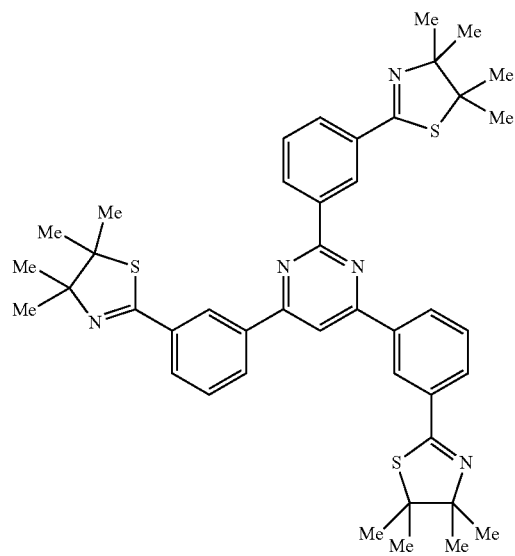
(1-3-77)
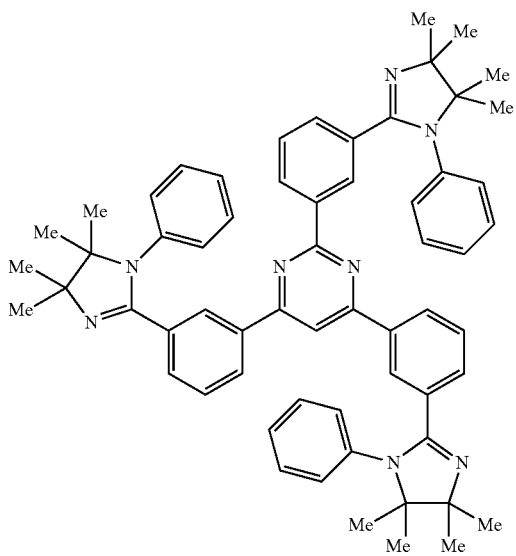
(1-3-78)
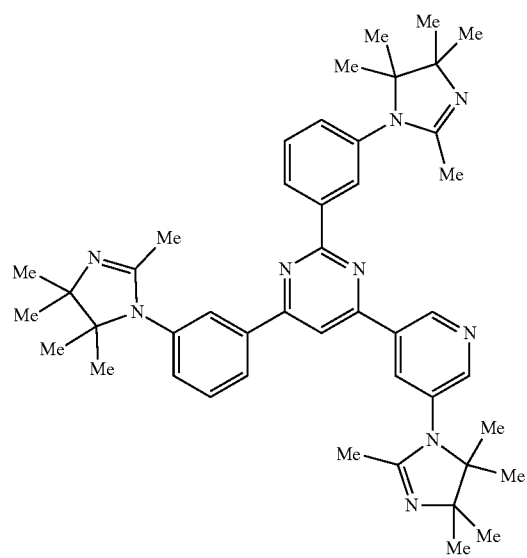
(1-3-79)
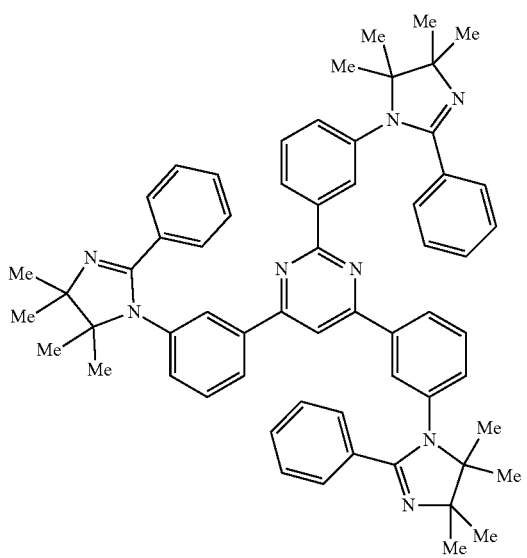
(1-3-81)
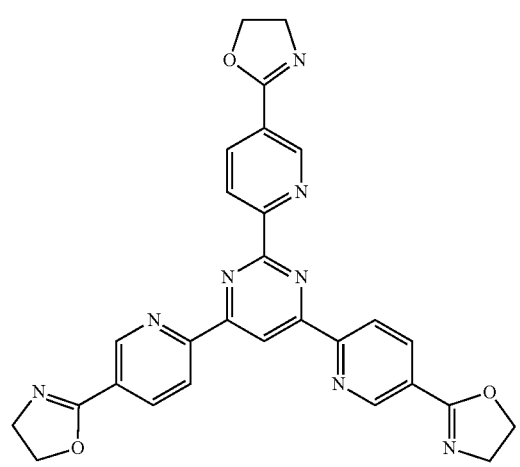
(1-3-82)
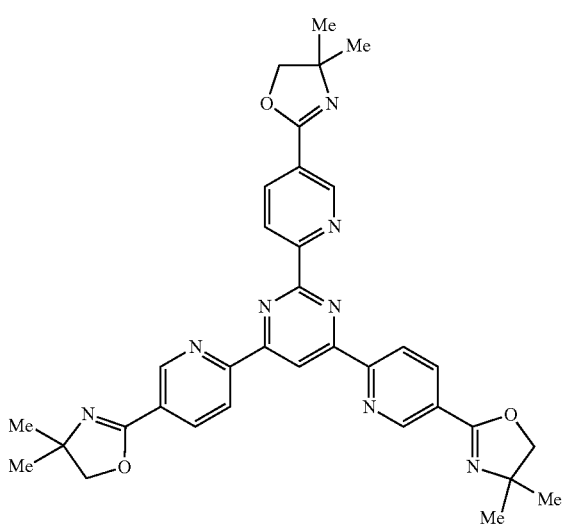

(1-3-83)
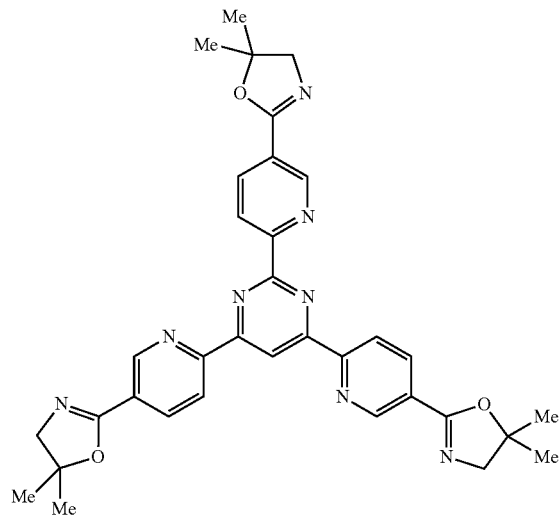
(1-3-84)
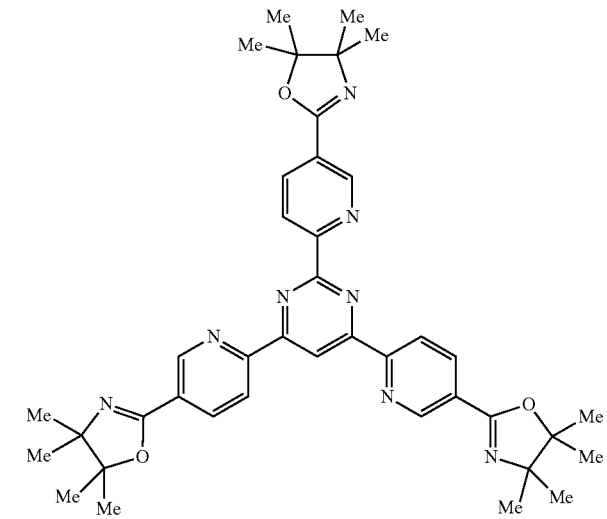
(1-3-85)
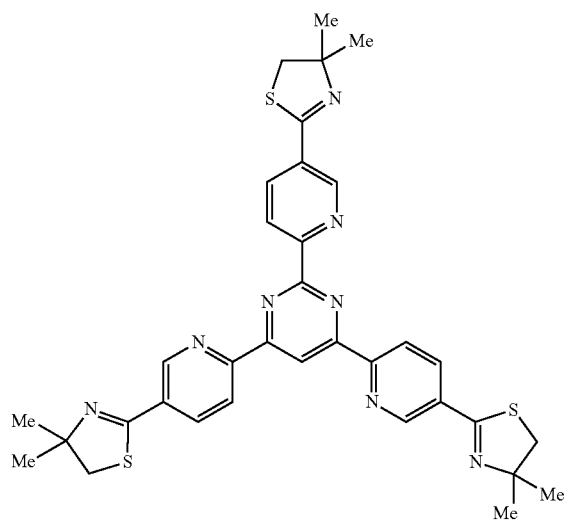
(1-3-86)
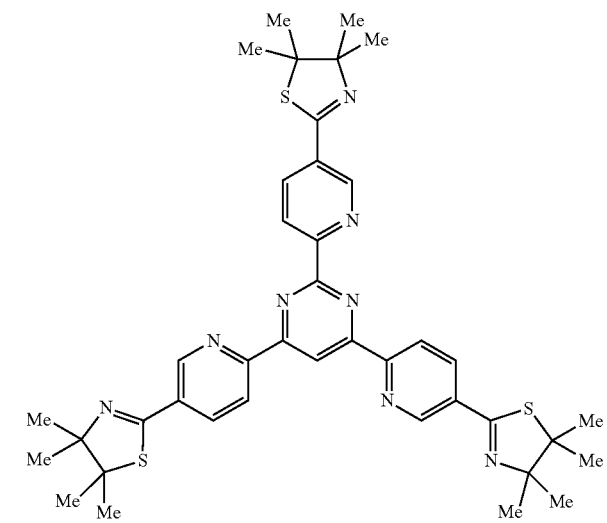
(1-3-87)
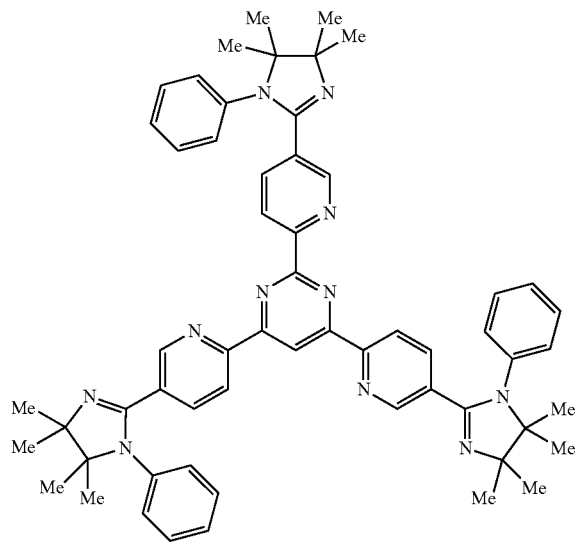
(1-3-88)
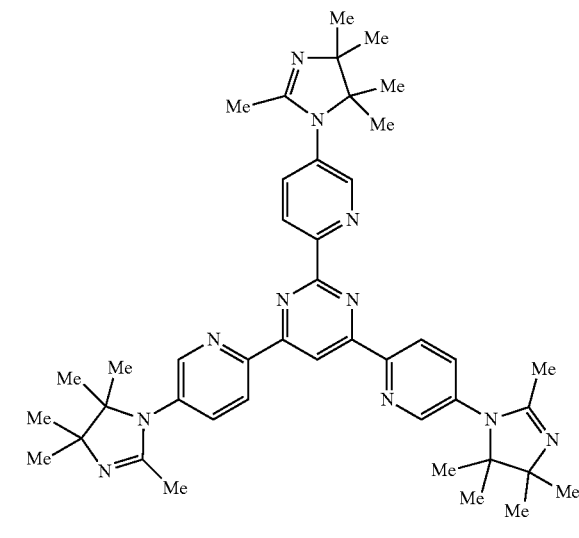

-continued
(1-3-89)
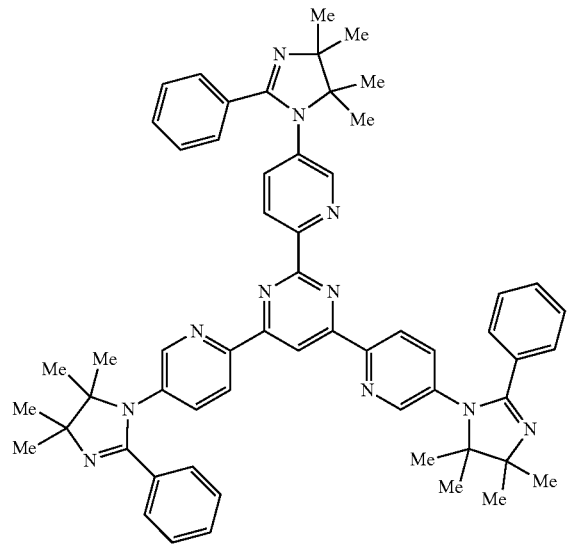
(1-3-91)
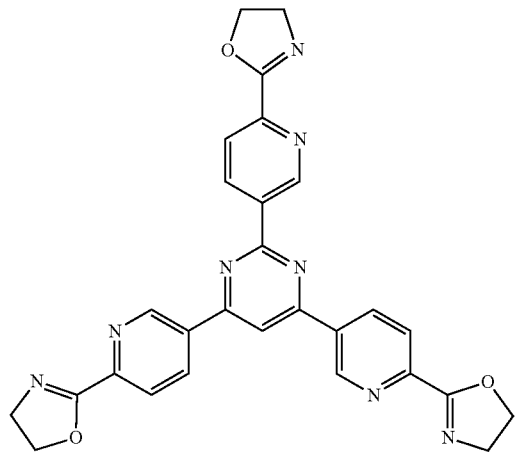
(1-3-92)
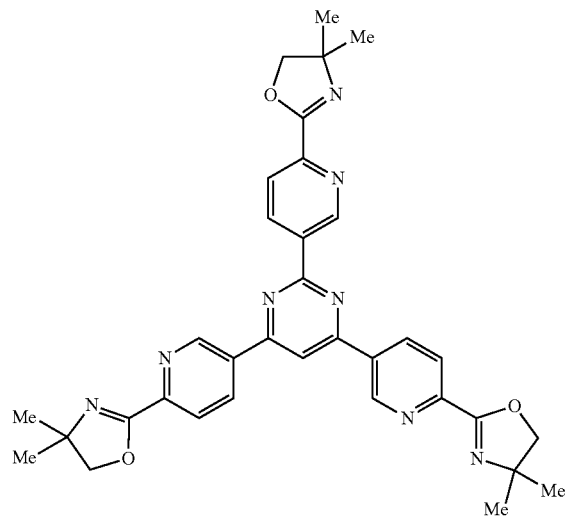
(1-3-93)
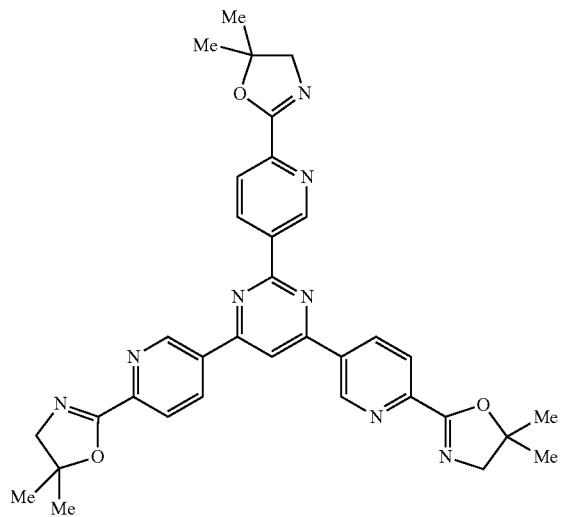
(1-3-94)
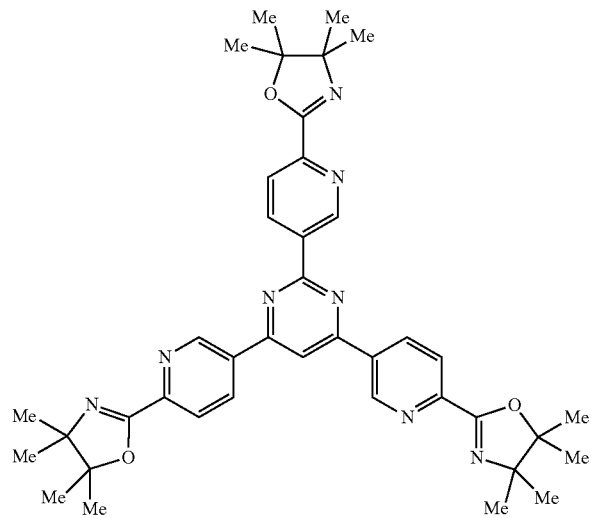
(1-3-95)
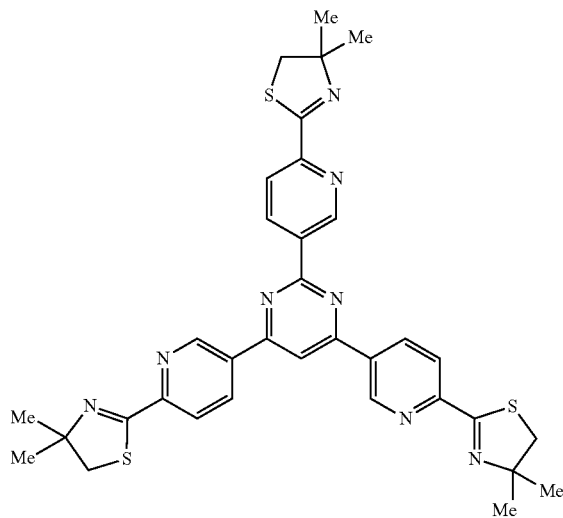

-continued
(1-3-96)
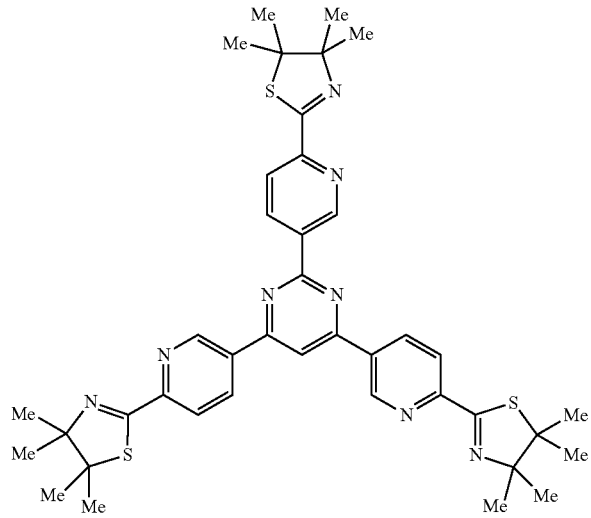
(1-3-97)
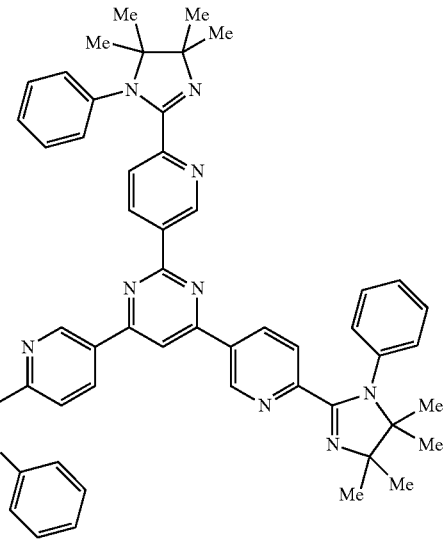
(1-3-98)
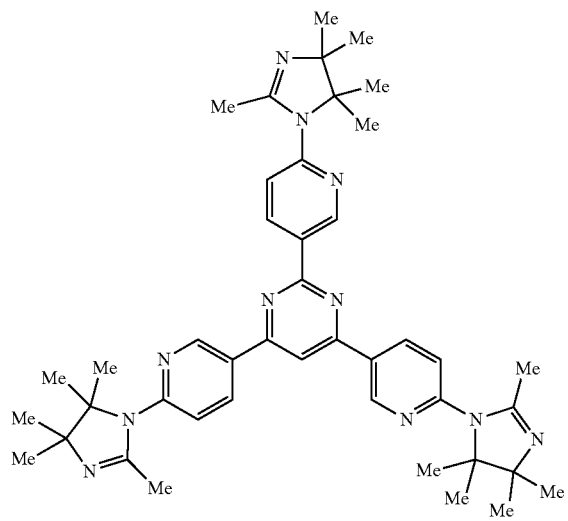
(1-3-99)
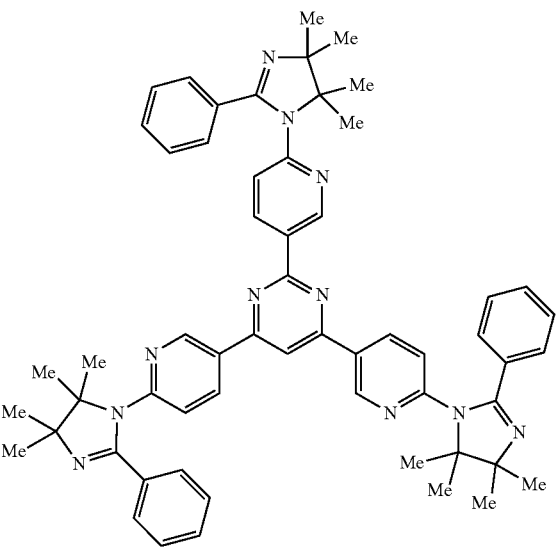

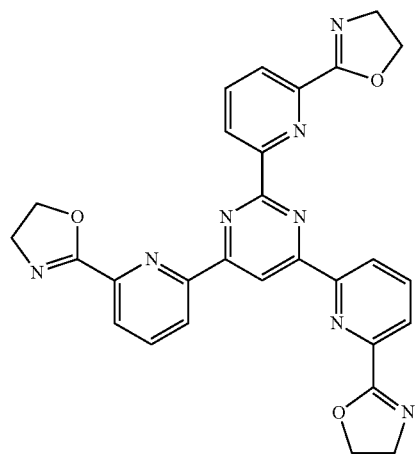
(1-3-101)
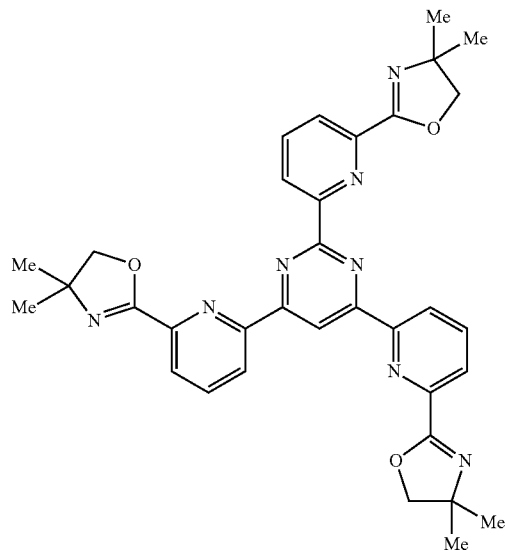
(1-3-102)
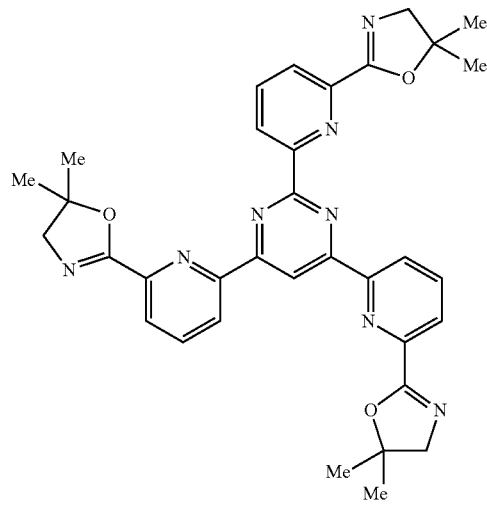
(1-3-103)
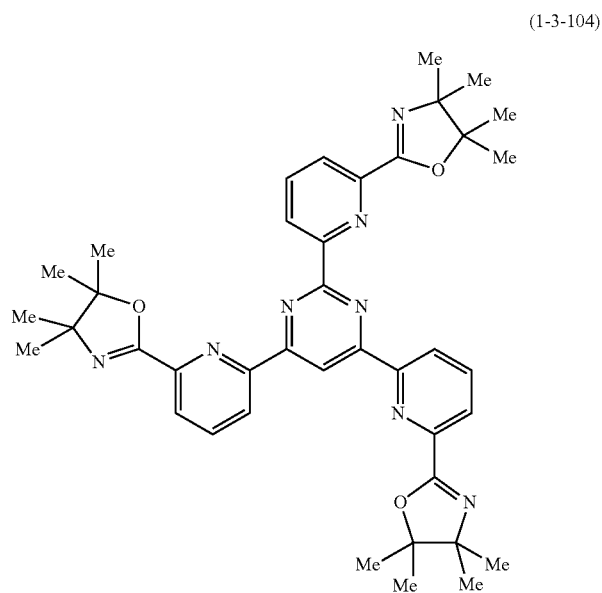
(1-3-104)

(1-3-105)
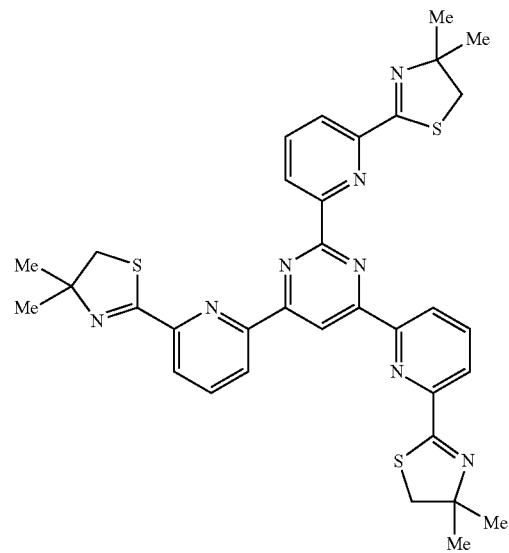
(1-3-106)
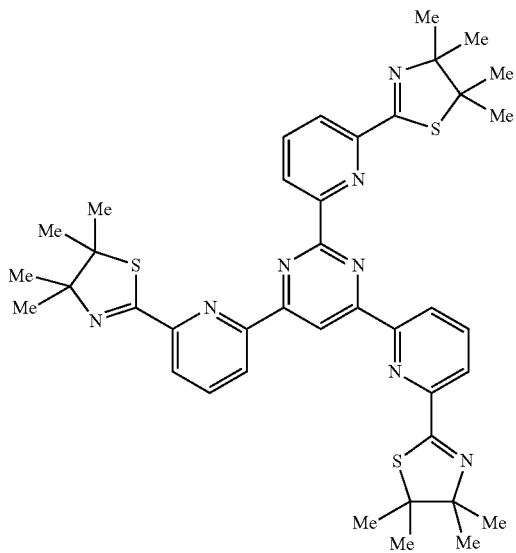
(1-3-107)
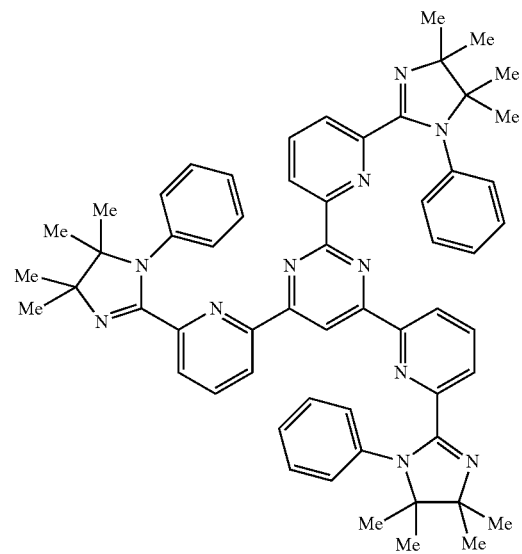
(1-3-108)
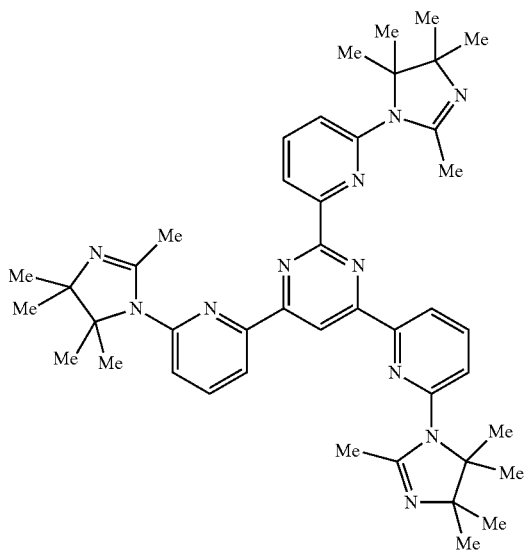

(1-3-109)
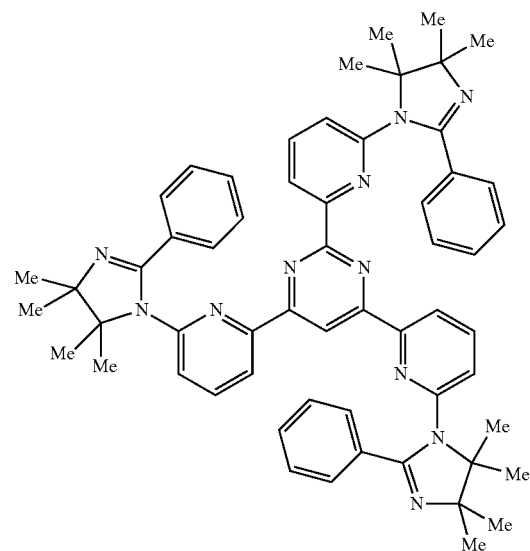
(1-3-111)
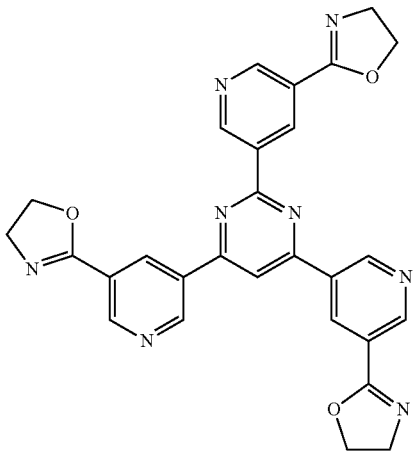
(1-3-112)
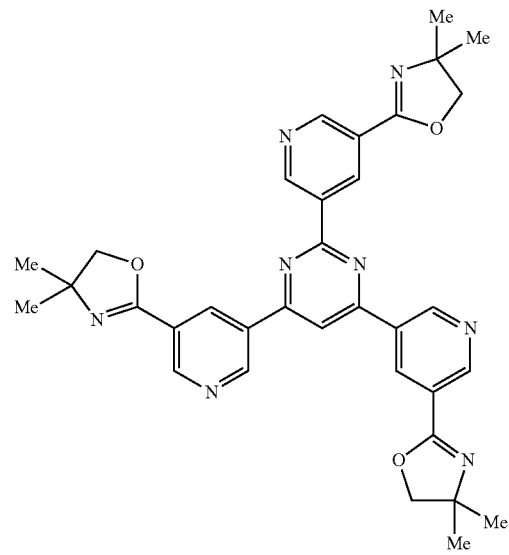
(1-3-113)
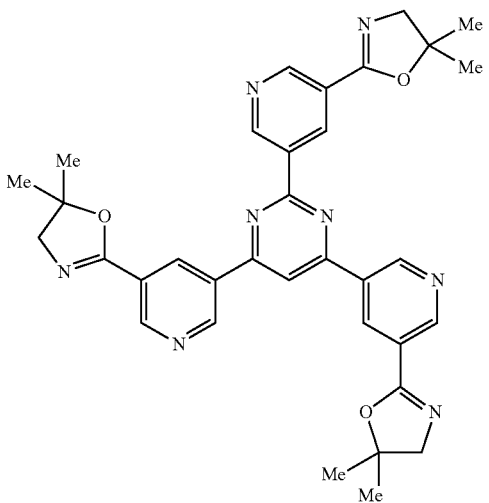

-continued
(1-3-114)
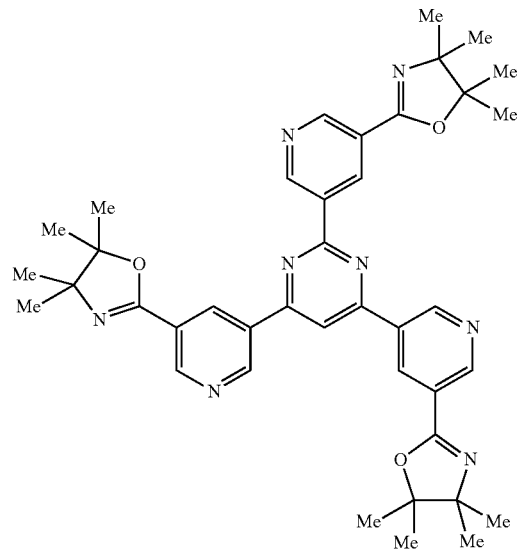
(1-3-115)
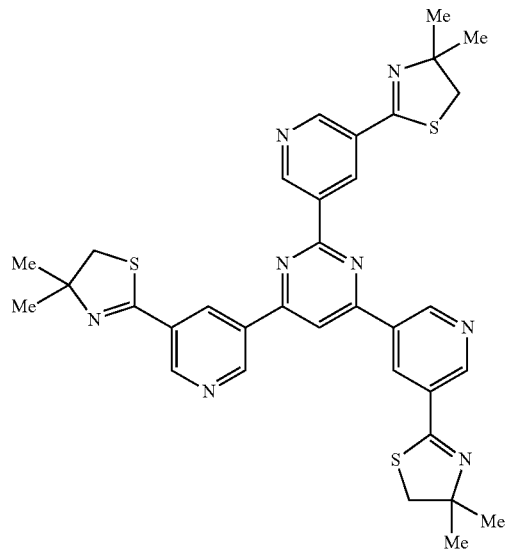
(1-3-116)
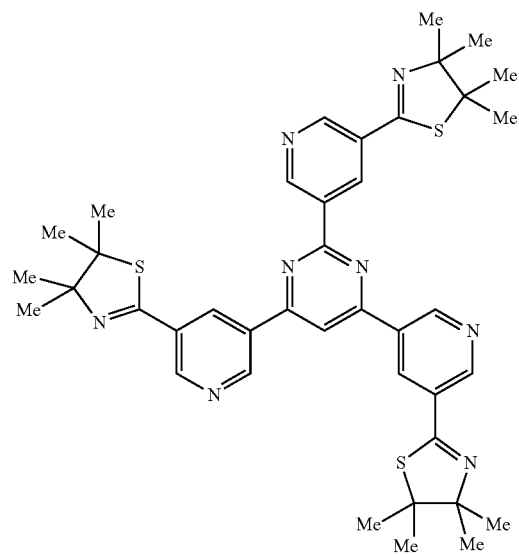
(1-3-117)
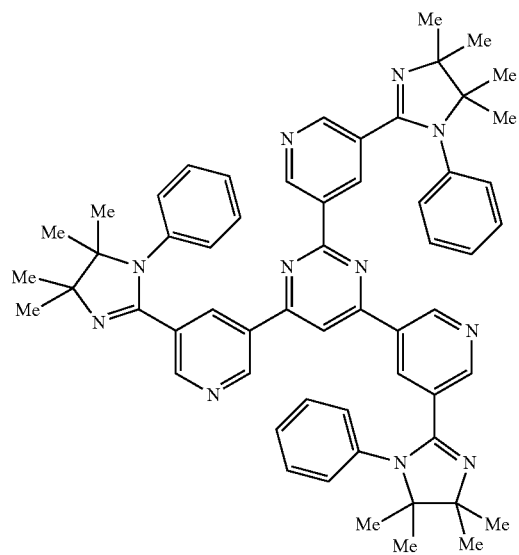

-continued
(1-3-118)
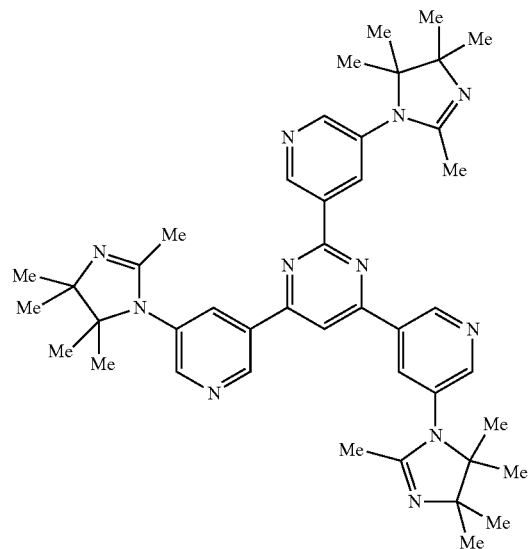
(1-3-119)
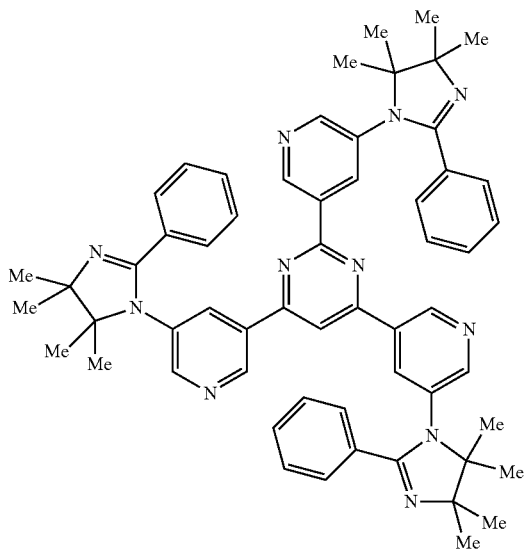
(1-3-121)
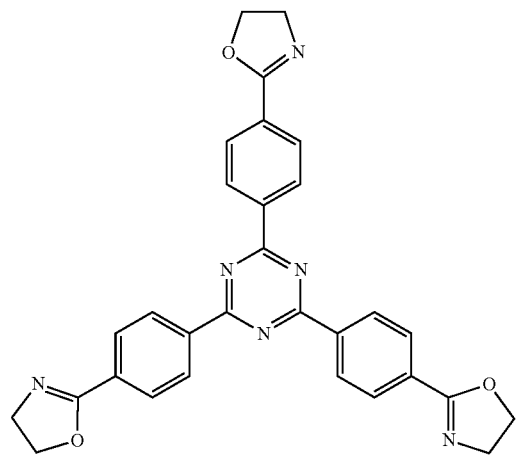
(1-3-122)
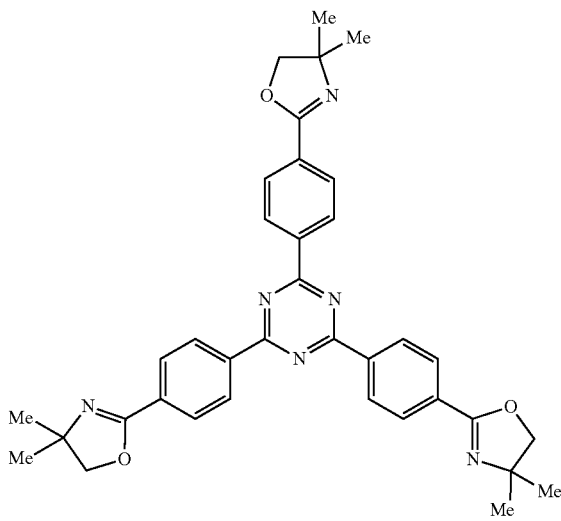
(1-3-123)
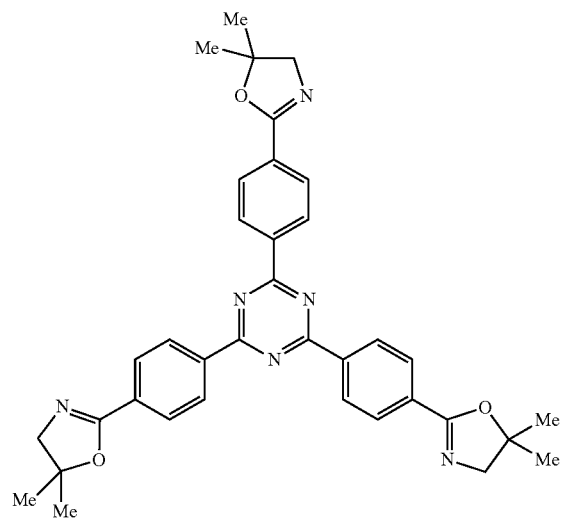
(1-3-124)
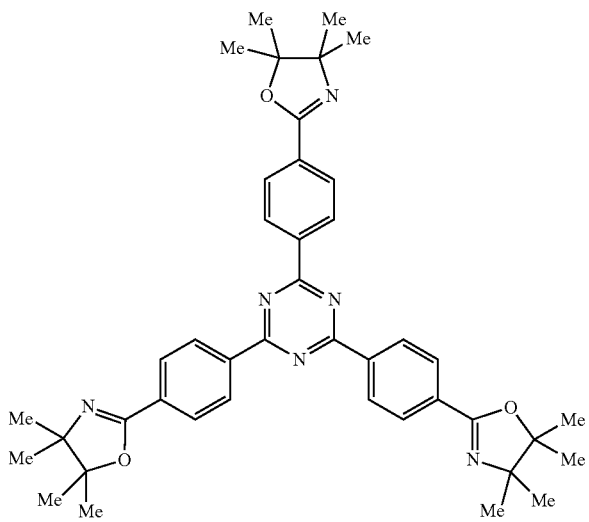

-continued
(1-3-125)
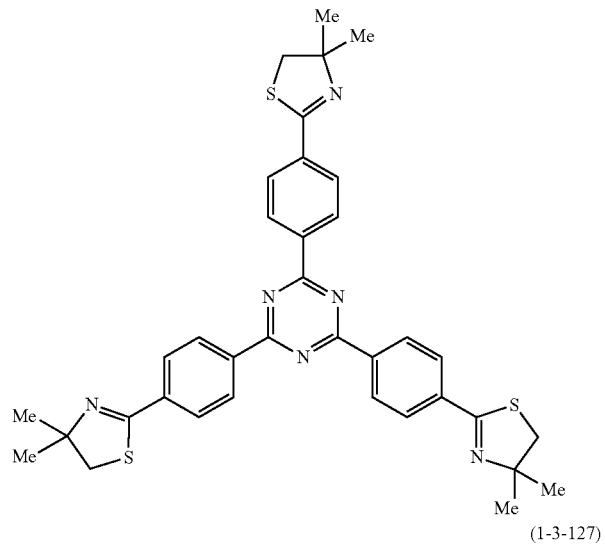
(1-3-126)
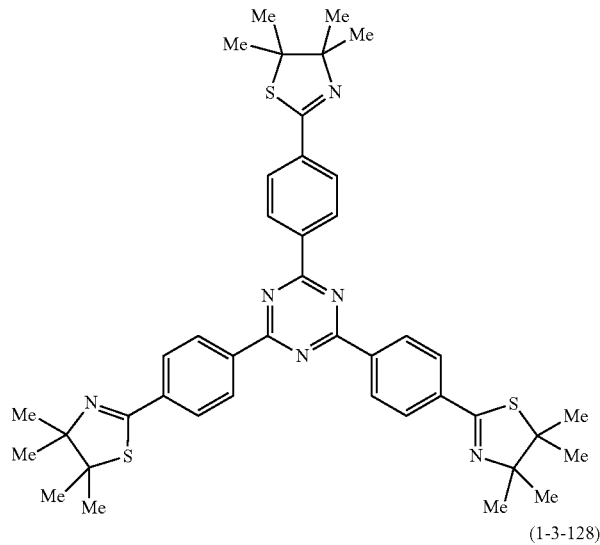
(1-3-127)
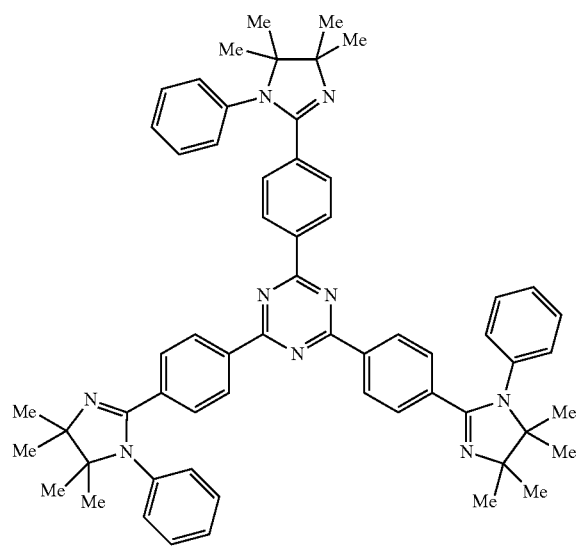
(1-3-128)
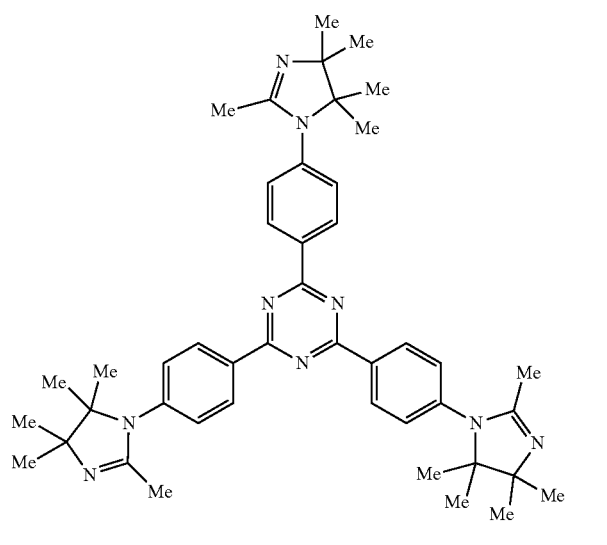
(1-3-129)
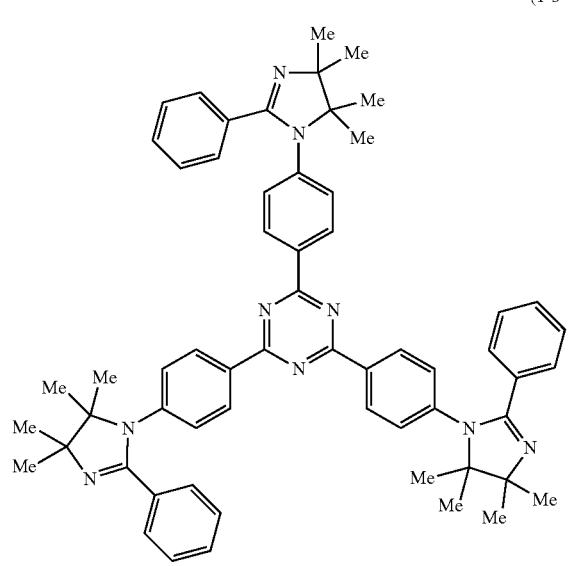
(1-3-131)
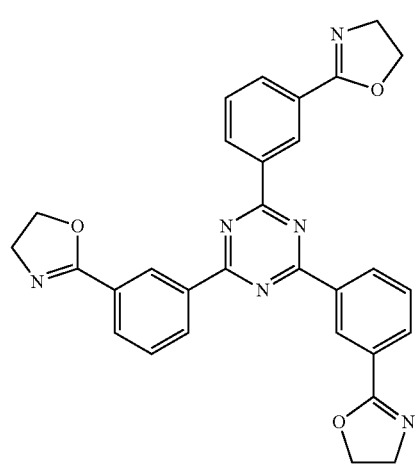

-continued
(1-3-132)
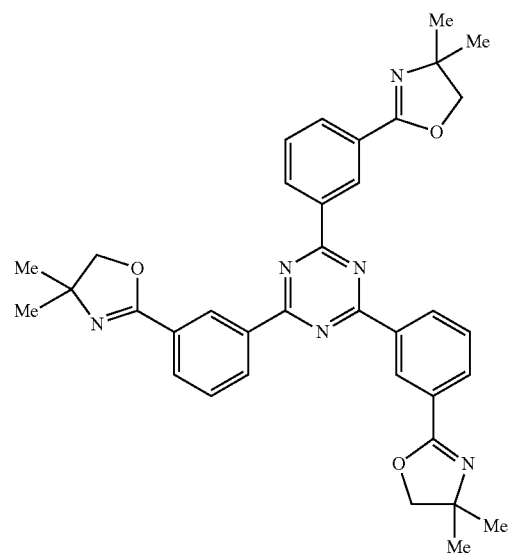
(1-3-133)
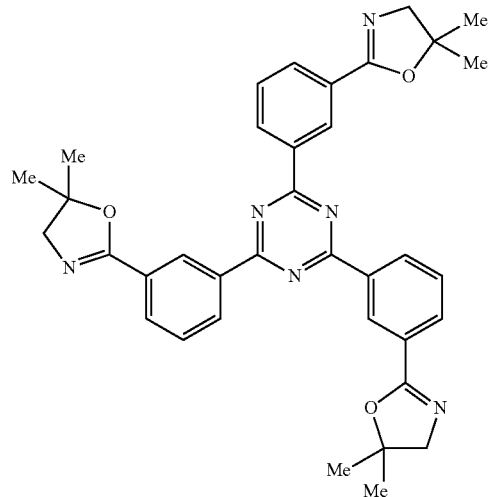
(1-3-134)
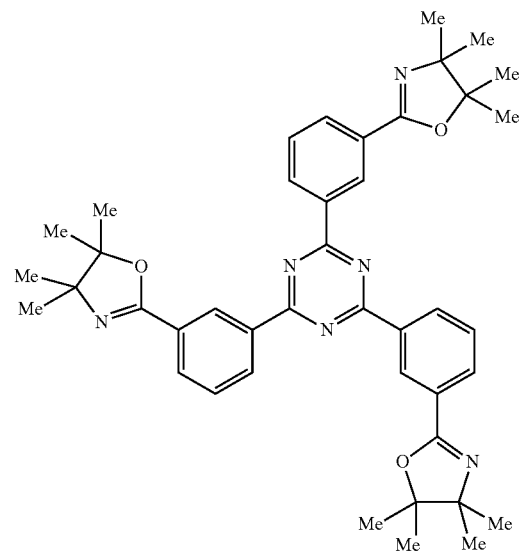
(1-3-135)
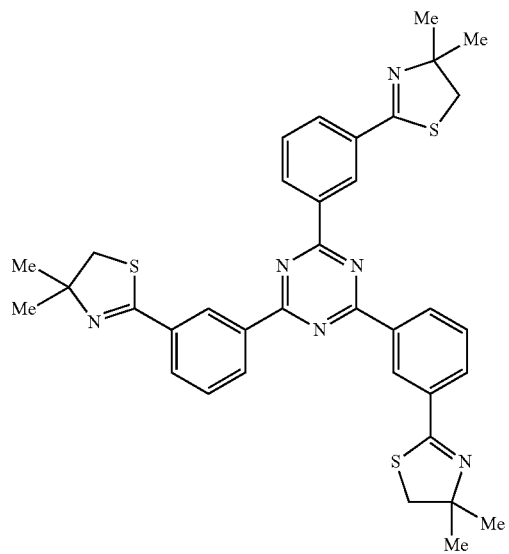

-continued
(1-3-136)
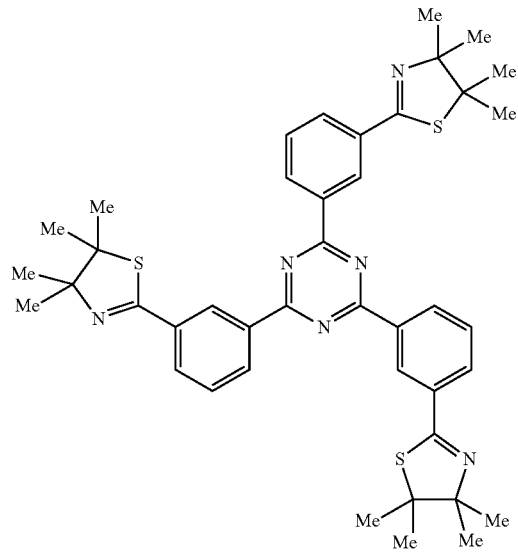
(1-3-137)
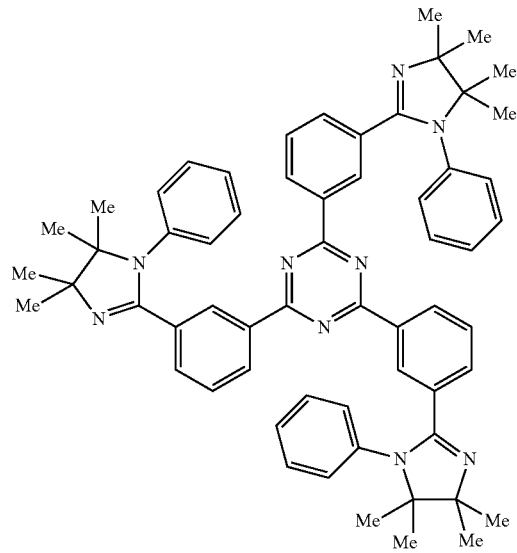
(1-3-138)
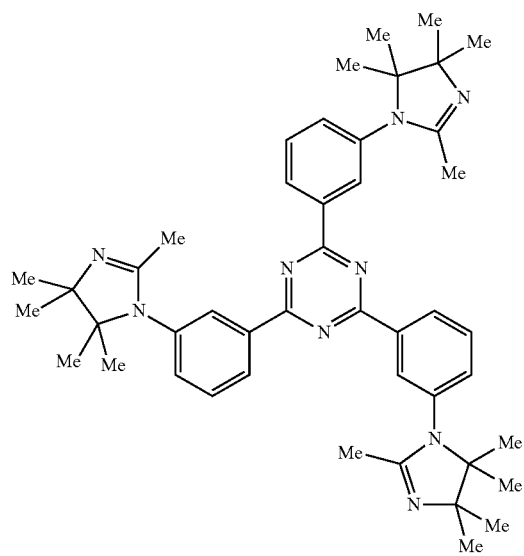
(1-3-139)
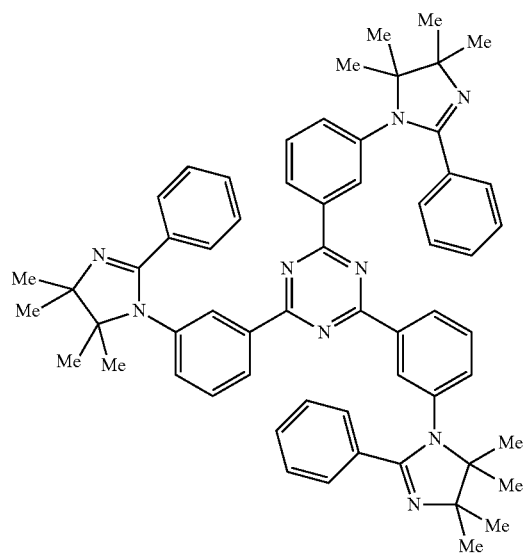
(1-3-141)
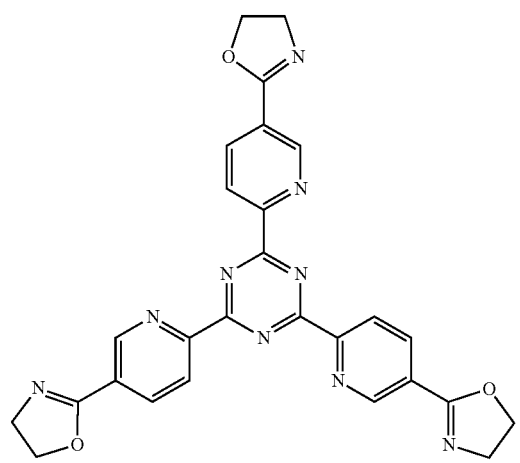
(1-3-142)
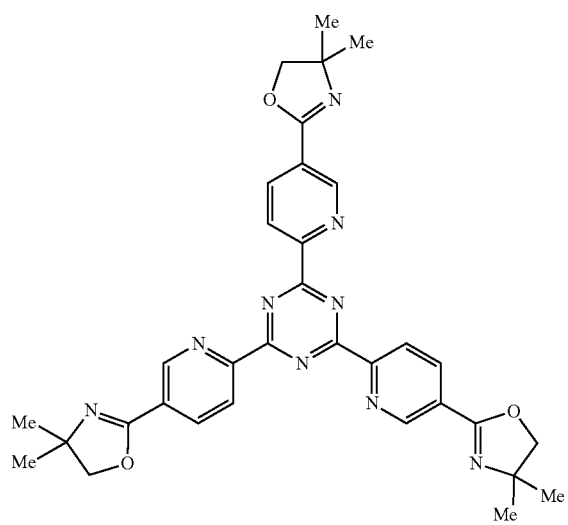

-continued
(1-3-143)
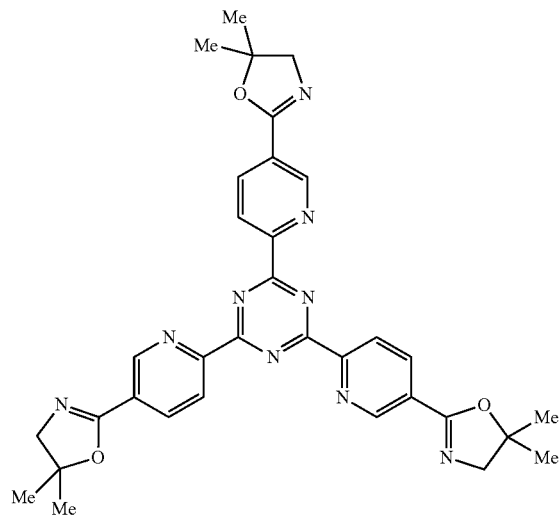
(1-3-144)
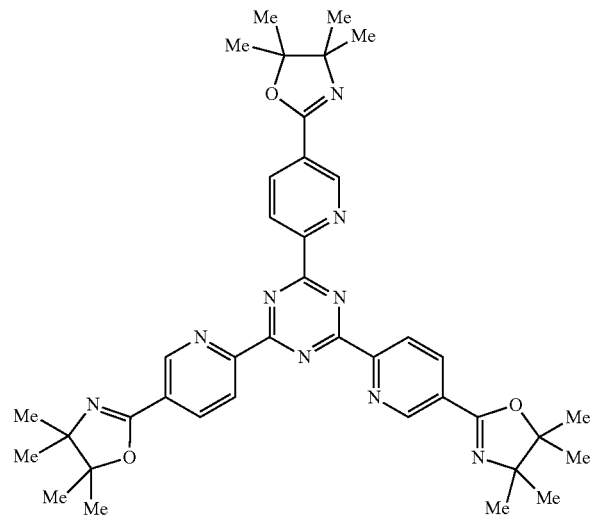
(1-3-145)
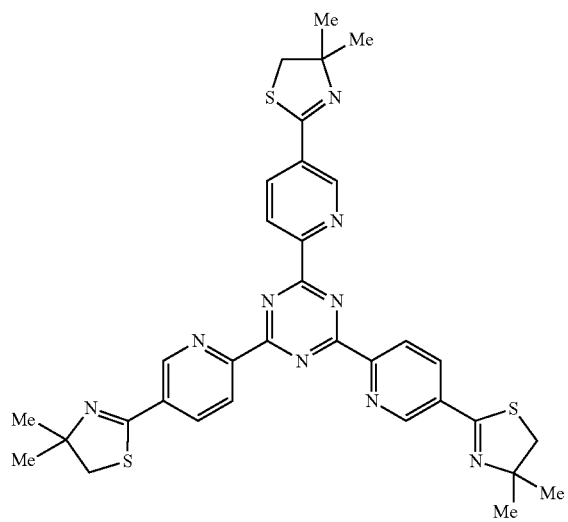
(1-3-146)
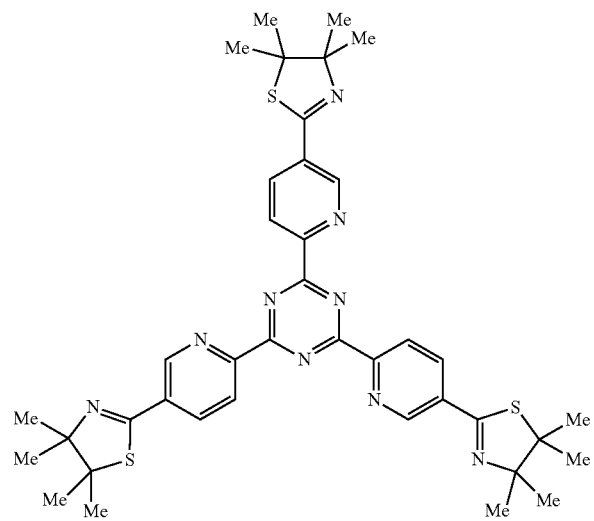
(1-3-147)
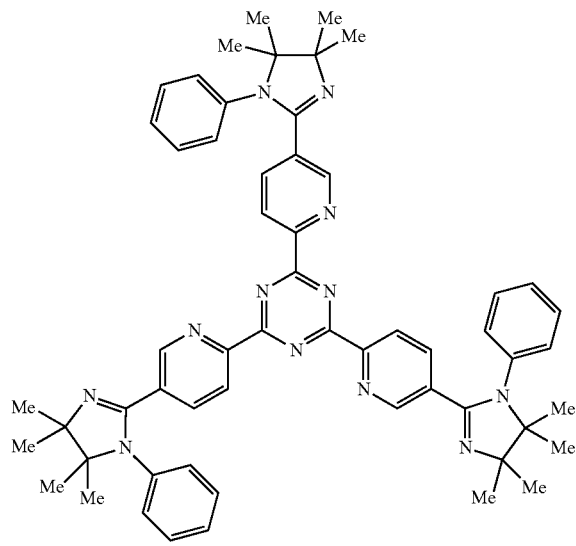
(1-3-148)
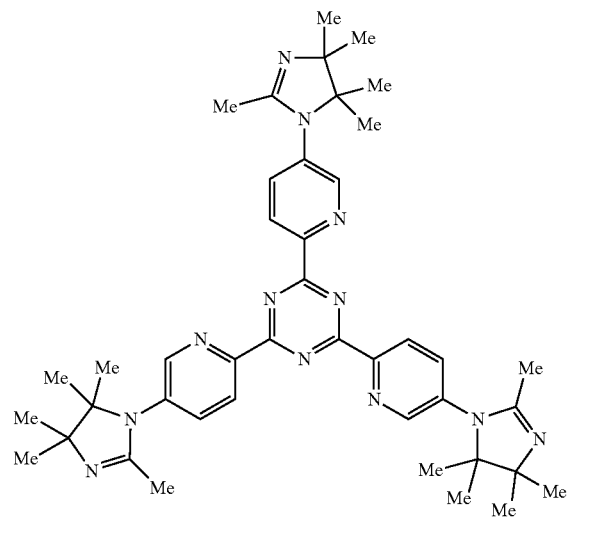

-continued
(1-3-149)
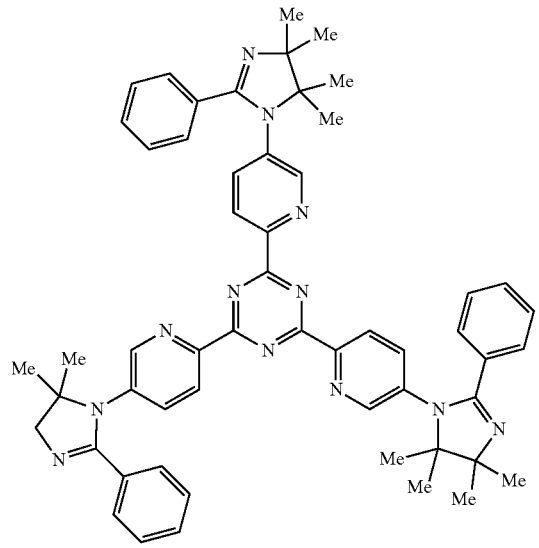
(1-3-151)
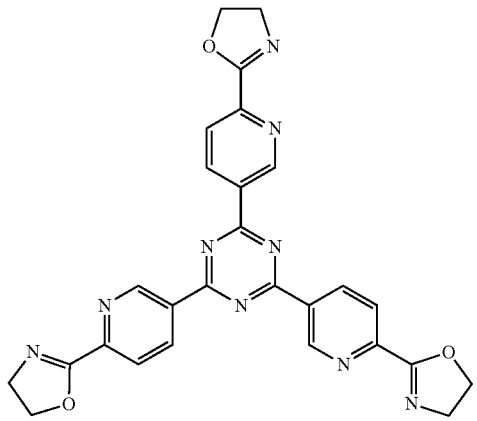
(1-3-152)
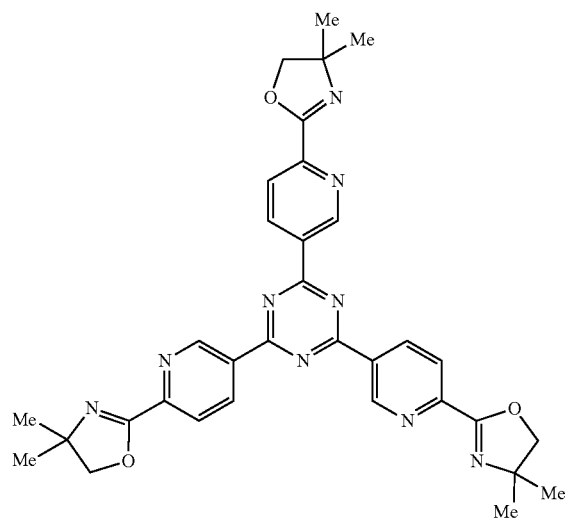
(1-3-153)
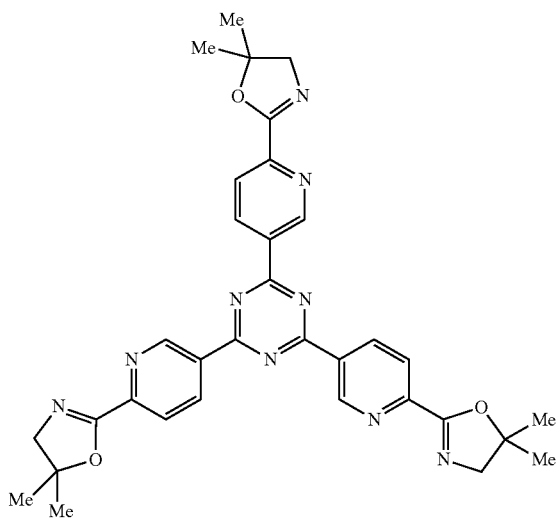
(1-3-154)
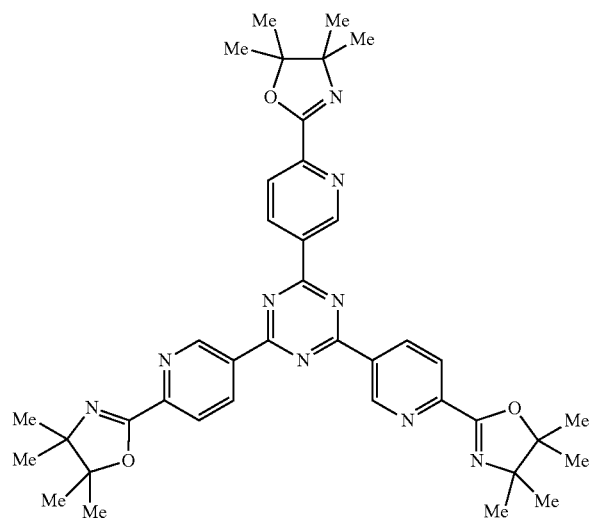
(1-3-155)
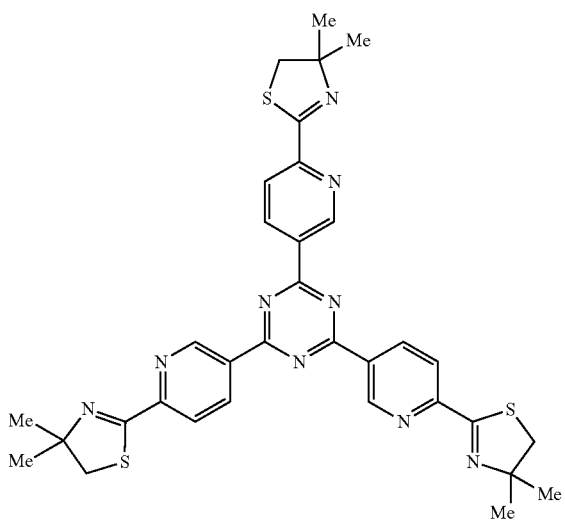

(1-3-156)
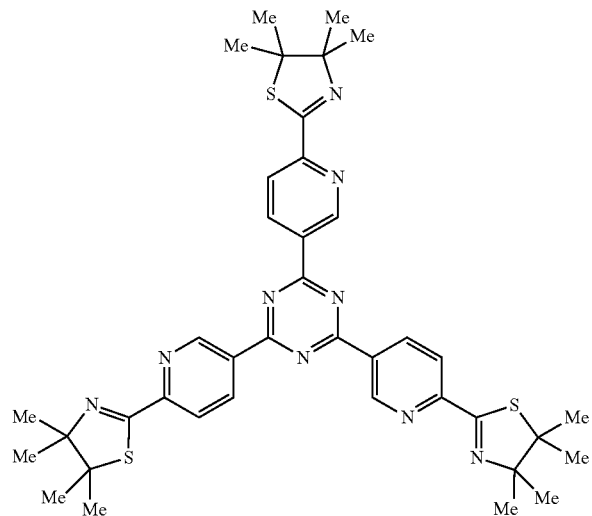
(1-3-157)
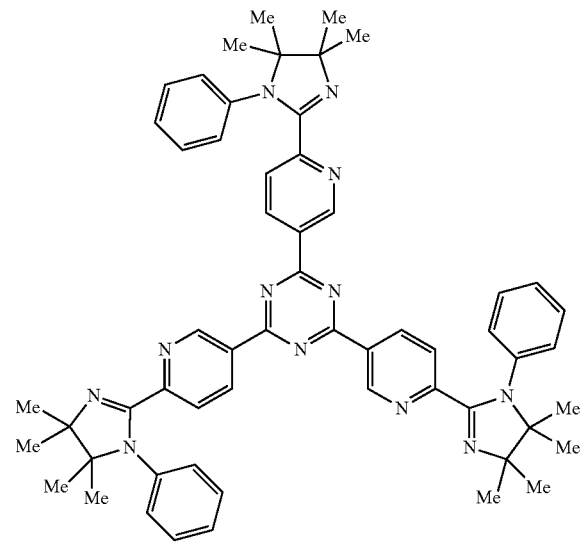
(1-3-158)
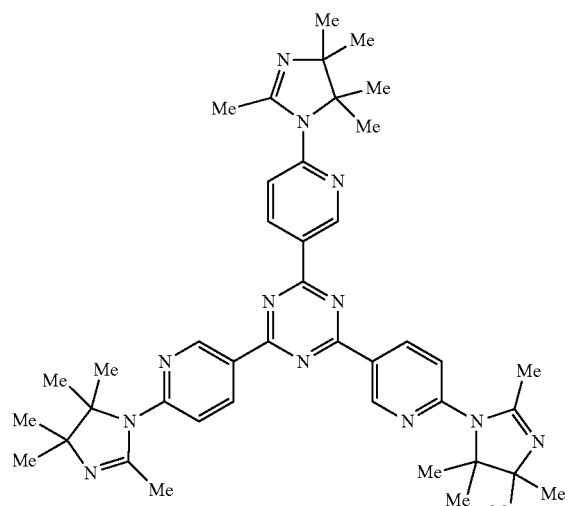
(1-3-159)
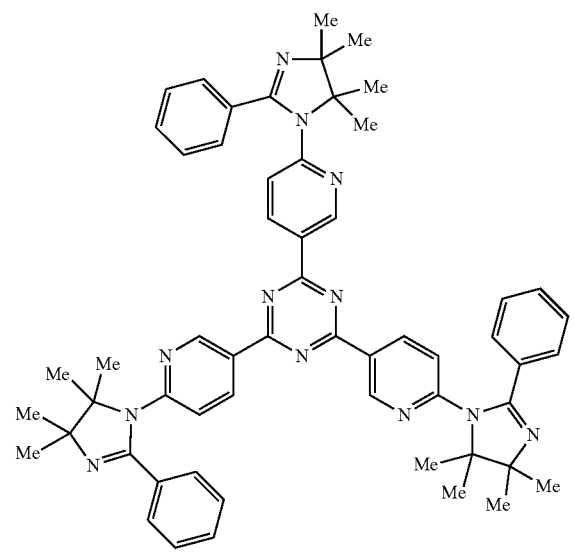
(1-3-161)
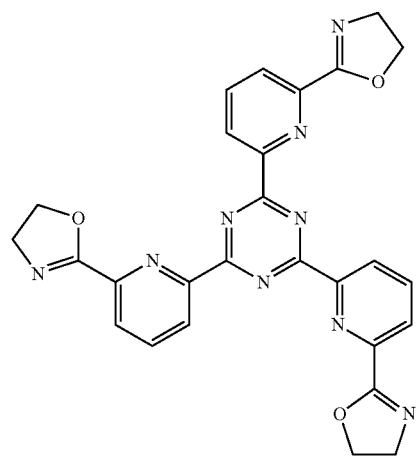
(1-3-162)
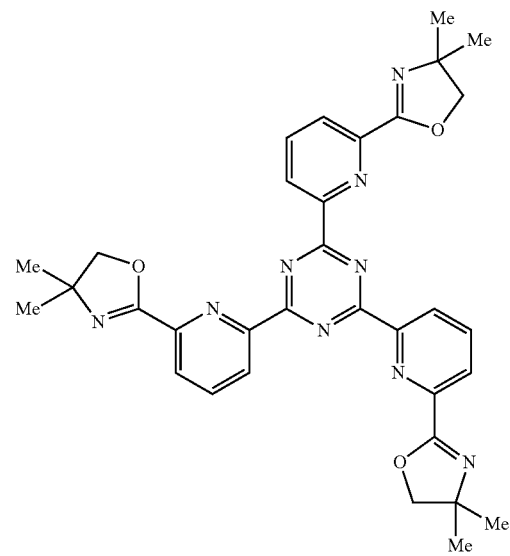

-continued
(1-3-163)
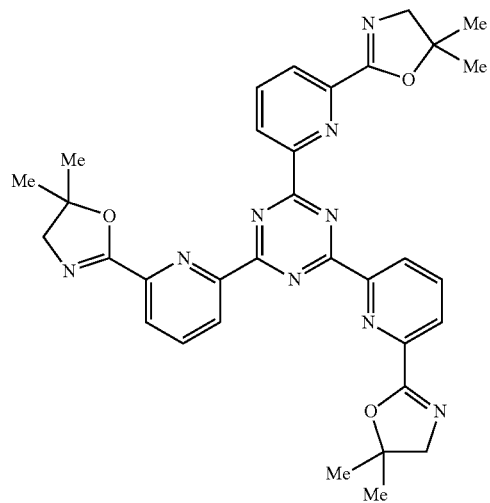
(1-3-164)
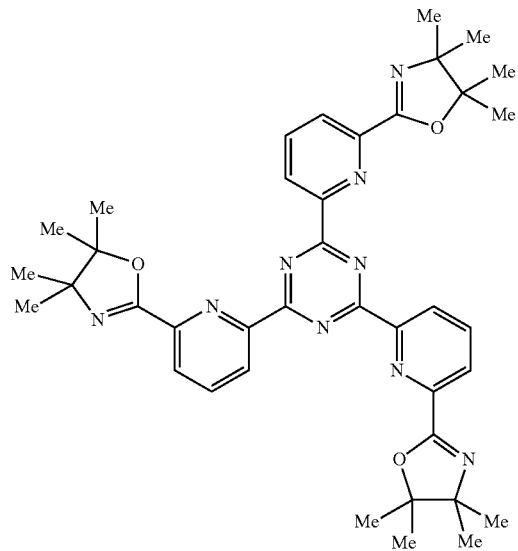
(1-3-165)
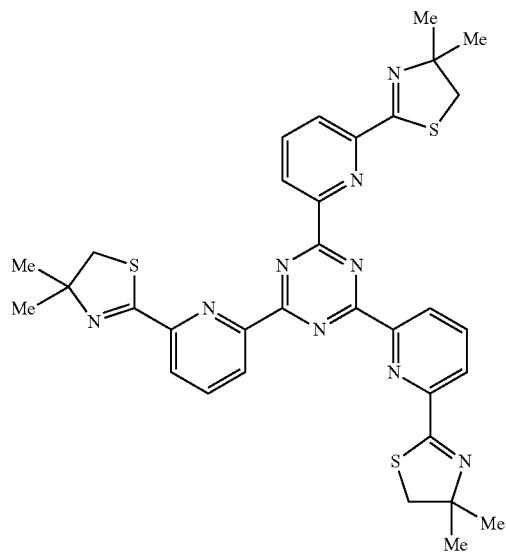
(1-3-166)
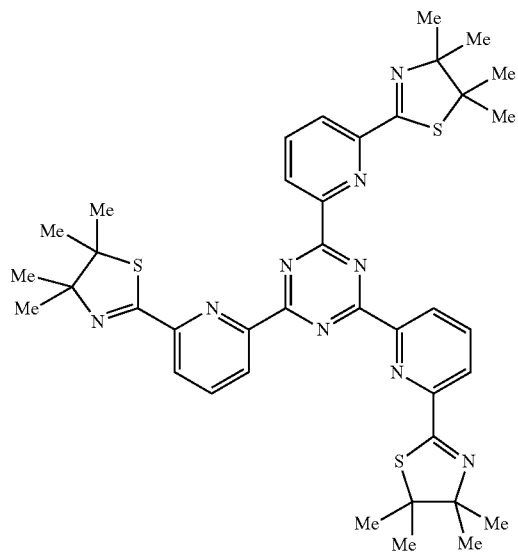

(1-3-167)
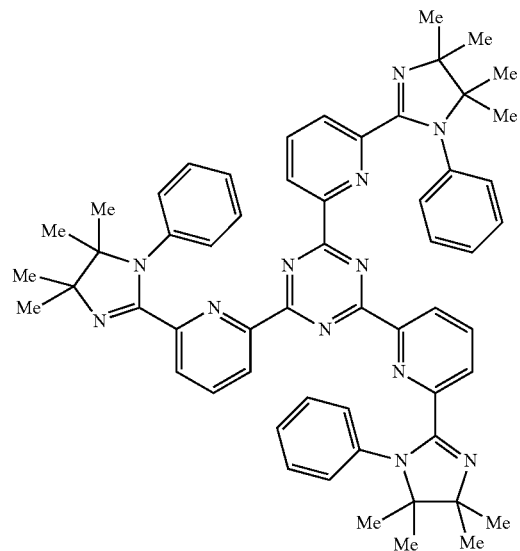
(1-3-168)
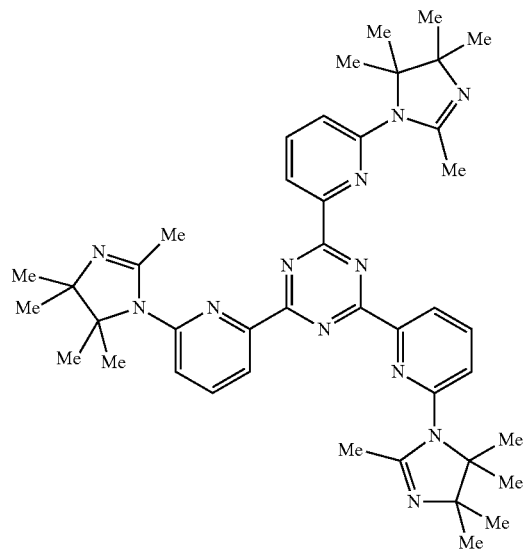
(1-3-169)
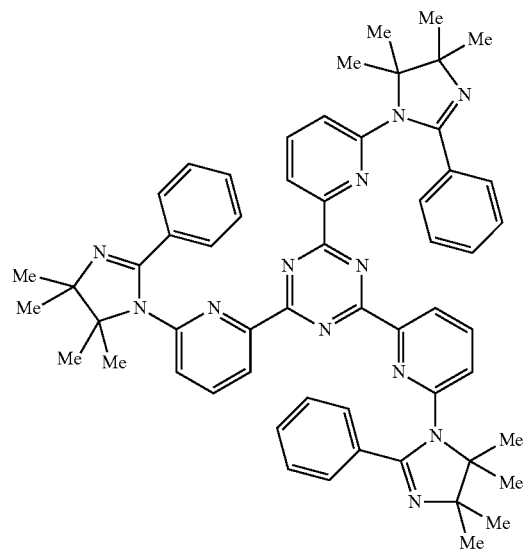
(1-3-171)
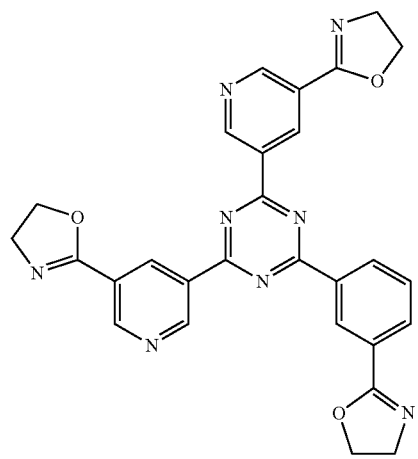

-continued
(1-3-172)
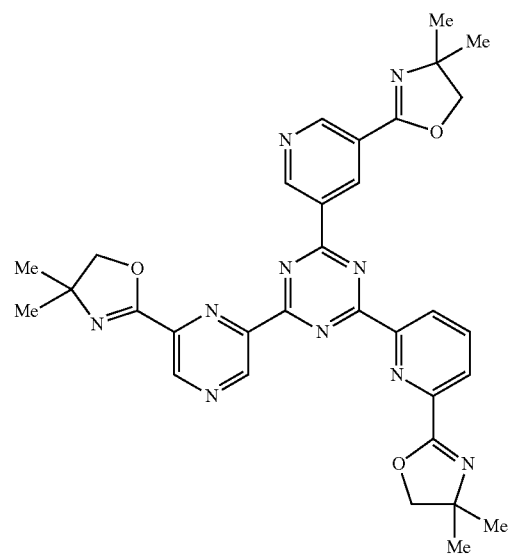
(1-3-173)
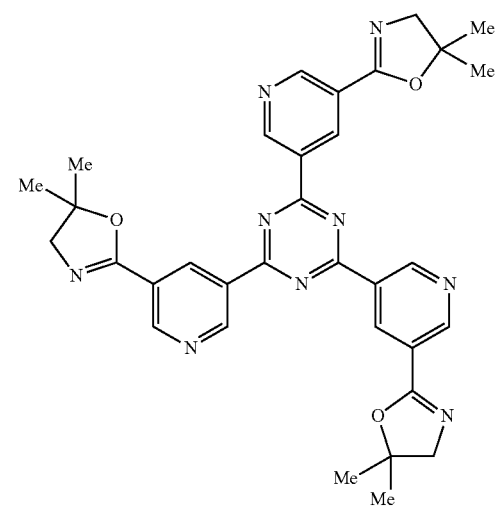
(1-3-174)
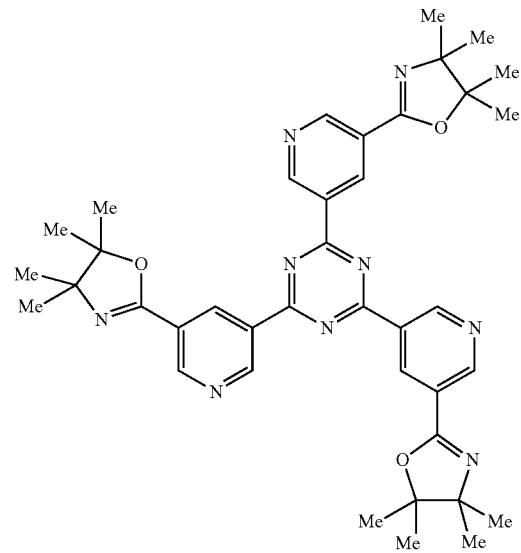
(1-3-175)
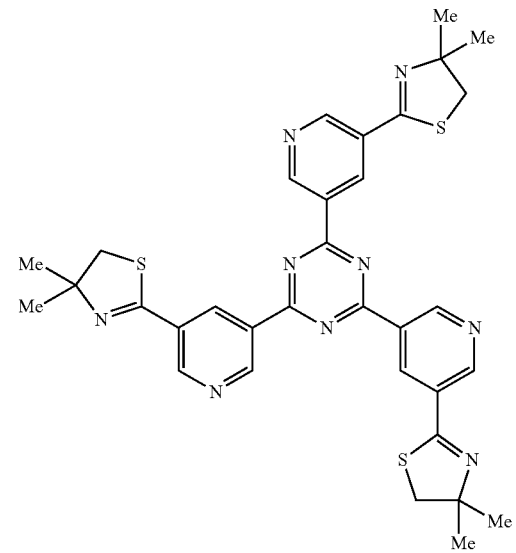

(1-3-176)
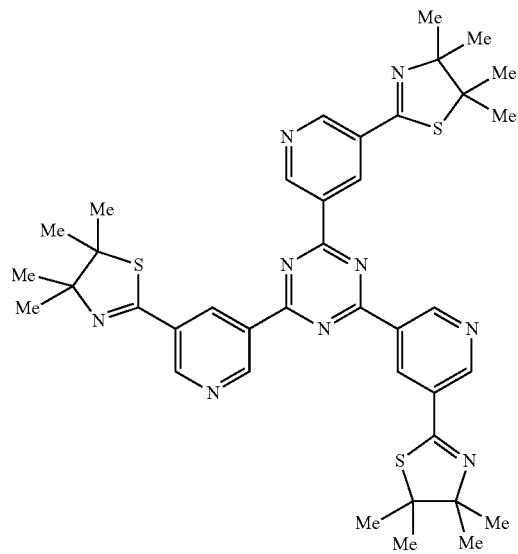
(1-3-177)
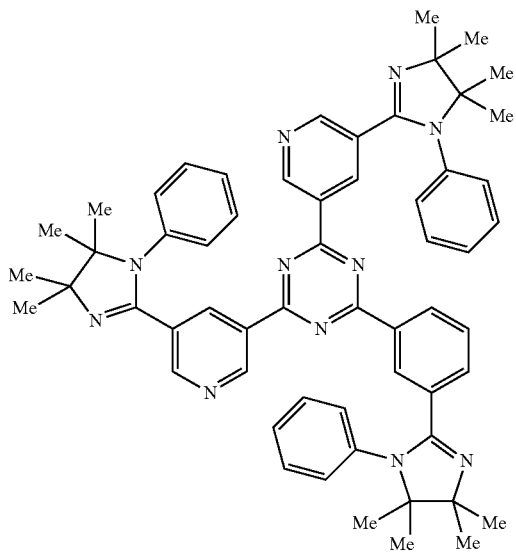
(1-3-178)
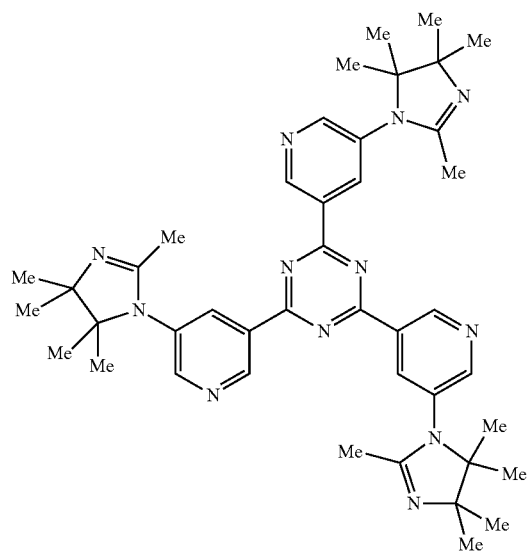
(1-3-179)
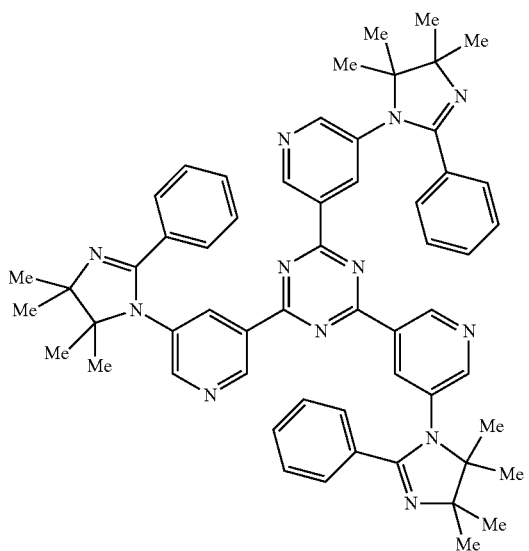
(1-4-1)
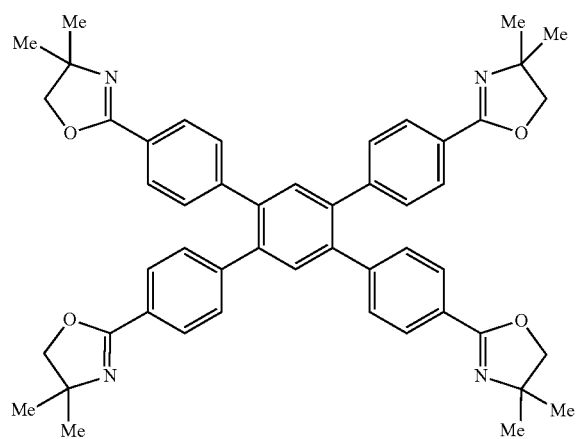
(1-4-2)
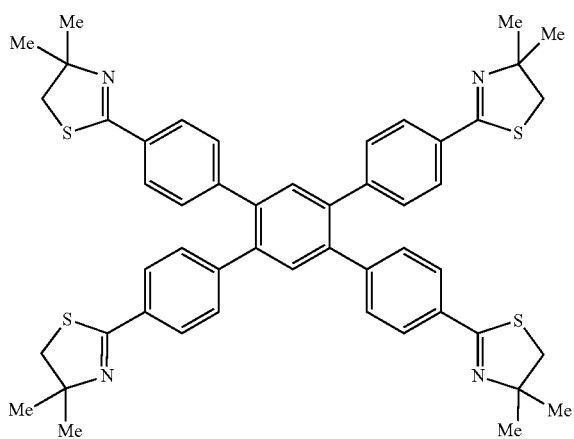

-continued
(1-4-3)
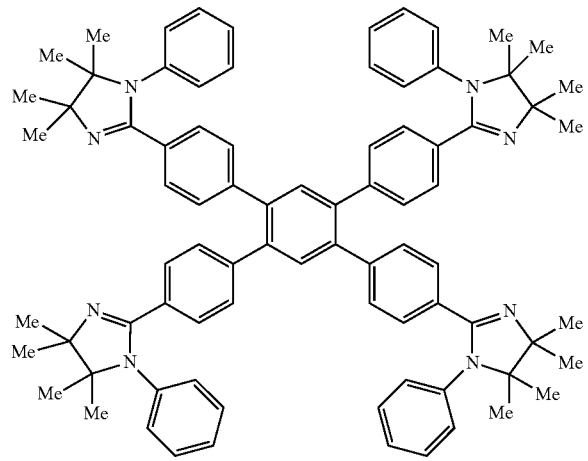
(1-4-4)
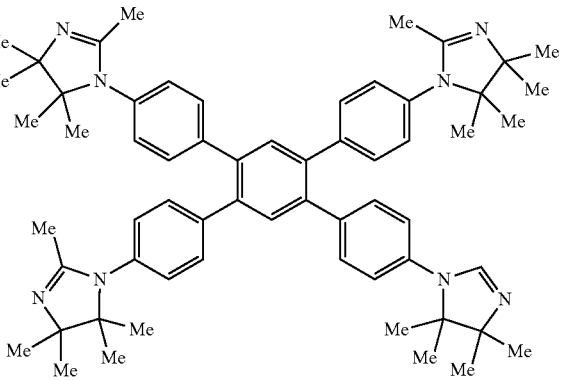
(1-4-5)
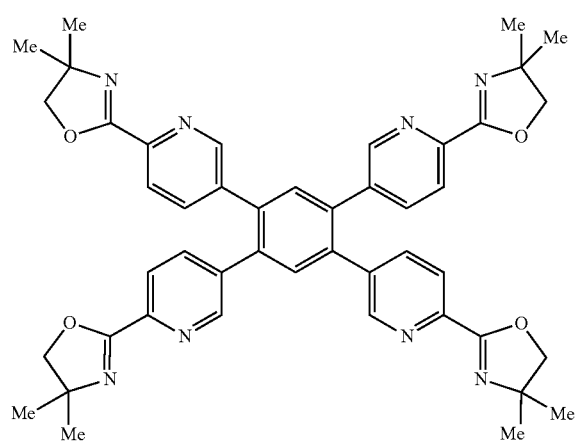
(1-4-6)
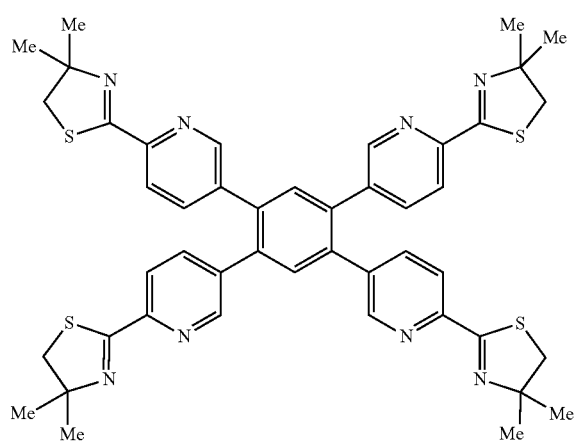
(1-4-7)
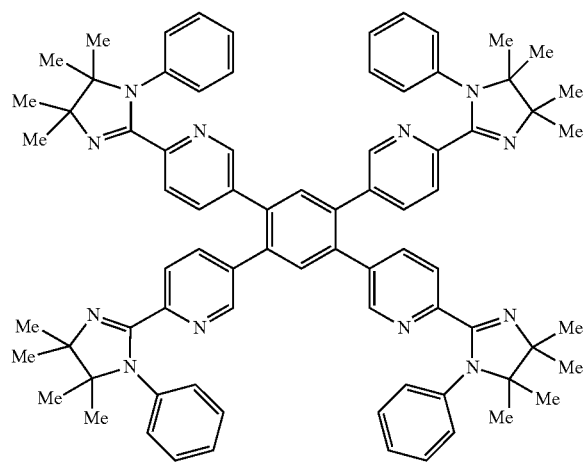
(1-4-8)
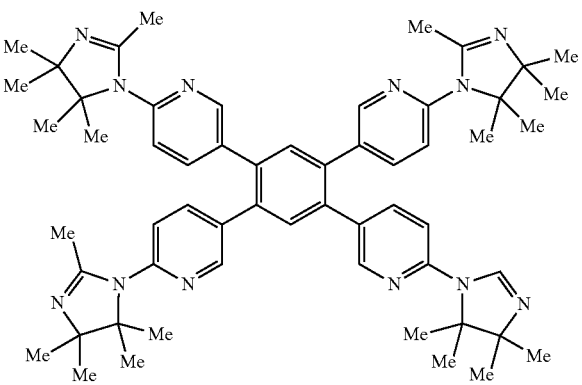

-continued
(1-4-11)
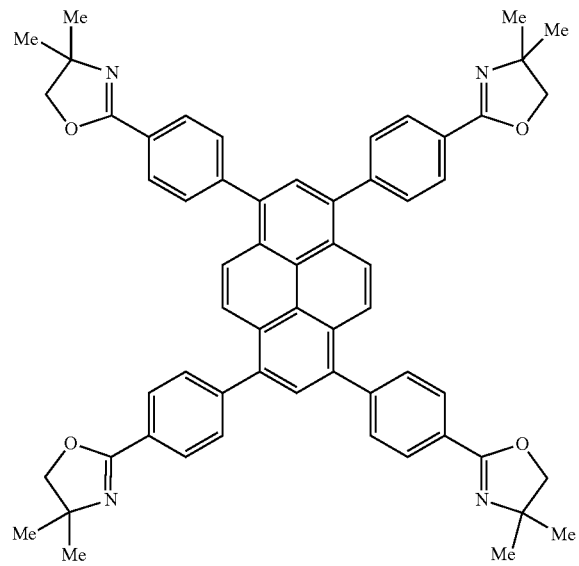
(1-4-12)
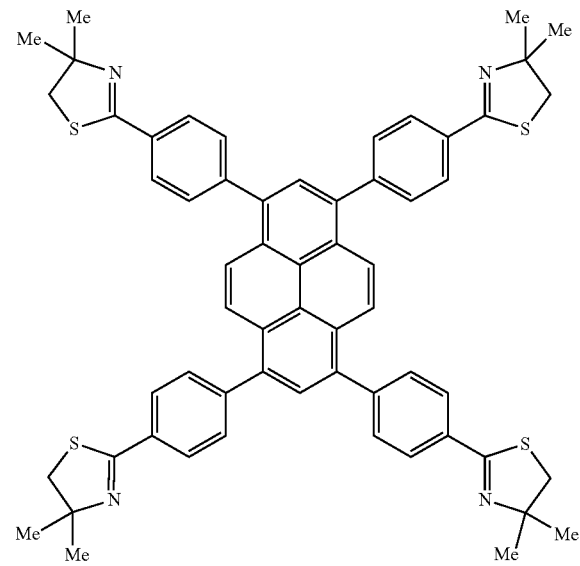
(1-4-13)
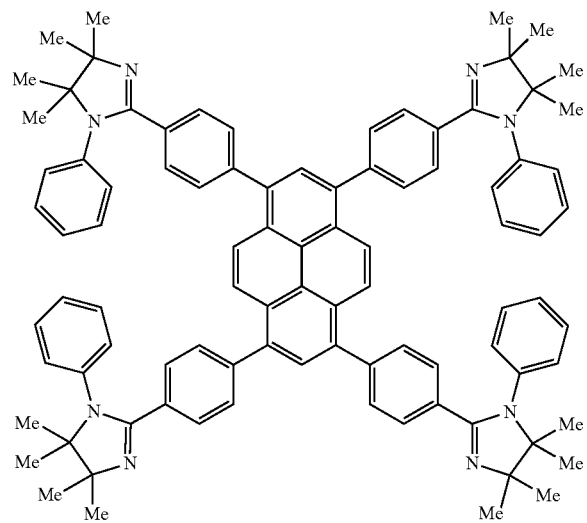
(1-4-14)
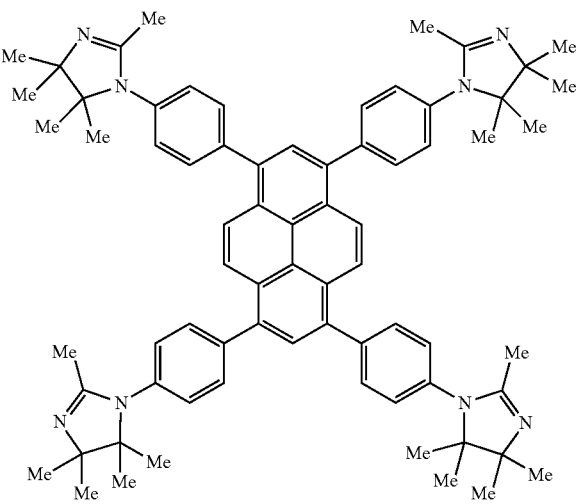

-continued (1-4-15)

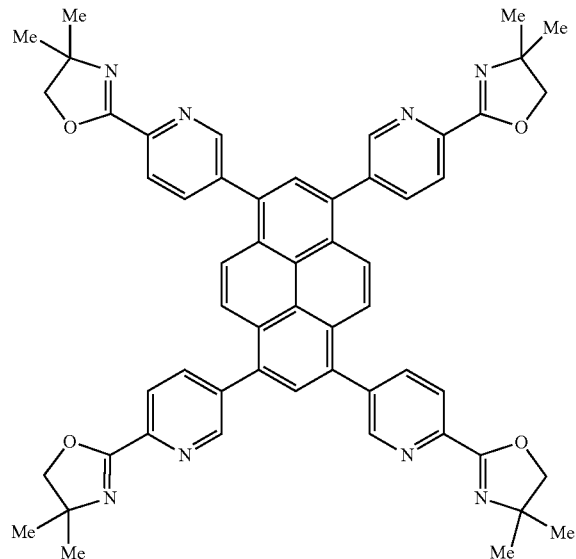

(1-4-16)

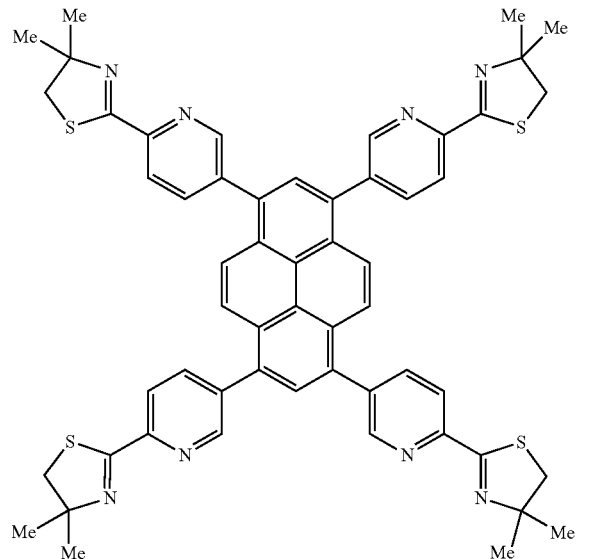

(1-4-17)

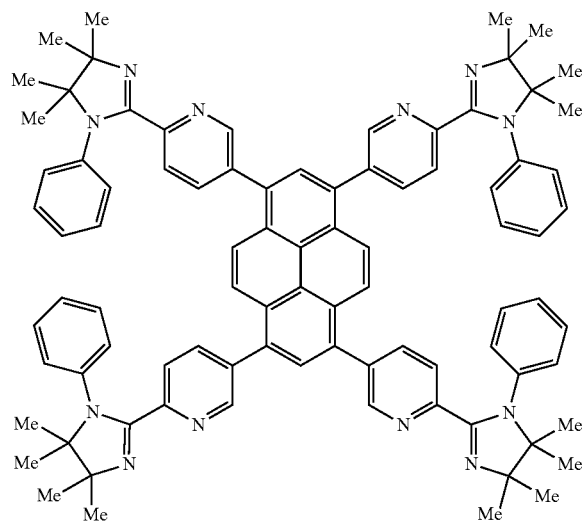

(1-4-18)

Among the compounds exemplified above, the compounds represented by formulas (1-1-1) to (1-1-160), (1-1-261) to (1-1-318), (1-2-1) to (1-2-49), (1-2-101) to (1-2-668), (1-2-681) to (1-2-688), (1-2-795) to (1-2-802), (1-2-815) to (1-2-862), (1-2-881) to (1-2-1018), (1-2-1021) to (1-2-1168), (1-3-1) to (1-3-179), and (1-4-1) to (1-4-8) are preferable, compounds represented by formulas (1-1-1) to (1-1-79), (1-1-101) to (1-1-160), (1-1-261) to (1-1-318), (1-2-1) to (1-2-49), (1-2-101) to (1-2-580), (1-2-621) to (1-2-668), (1-2-681) to (1-2-688), (1-2-795) to (1-2-802), (1-2-815) to (1-2-862), (1-2-881) to (1-2-1008), (1-2-1021) to (1-2-1168), (1-3-1) to (1-3-59), and (1-3-121) to (1-3-179) are more preferable, compounds represented formulas (1-1-101) to (1-1-160), (1-2-1) to (1-2-49), (1-2-401) to (1-2-459), (1-2-521) to (1-2-580), (1-2-101) to (1-2-160), (1-2-1021) to (1-2-1168), and (1-3-1) to (1-3-59) are particularly preferable, and compounds represented formulas (1-2-1021) to (1-2-1168) are most preferable.

<Method for Synthesizing Azoline Ring-Containing Compound>

Next, a method for manufacturing the azoline ring-containing compound of the present invention will be described. Basically, the compound of the present invention can be synthesized using a known compound by a known synthesis method such as a Suzuki coupling reaction or a Negishi coupling reaction (for example, described in "Metal-Catalyzed Cross-Coupling Reactions-Second, Completely Revised and Enlarged Edition"). The compound of the present invention can be also synthesized by combining both reactions. A scheme for synthesizing the azoline ring-containing compound represented by the above general formula (1) is exemplified below.

Examples of a method for manufacturing the compound of the present invention include: (1) a method for synthesizing a group obtained by bonding oxazoline, thiazoline, or imidazoline corresponding to the azoline ring portion to a benzene ring, a naphthalene ring, a pyridine ring, a pyrimidine ring, a pyrazine ring, a pyridazine ring, or the like corresponding to the linking portion L (hereinafter, these groups may be collectively referred to as "oxazoline/thiazoline/imidazoline derivative-containing moiety"), and bonding the resulting group to various aromatic hydrocarbon compounds or aromatic heterocyclic compounds corresponding to the core portion φ; (2) a method for bonding a benzene ring, a naphthalene ring, a pyridine ring, a pyrimidine ring, a pyrazine ring, a pyridazine ring, or the like having a functional group serving as a cyclization precursor such as a cyano group and corresponding to the linking portion L to an aromatic hydrocarbon compound or an aromatic heterocyclic compound corresponding to the core portion φ, and then cyclizing the functional group serving as a cyclization precursor with an amino alcohol, an aminothiol, ethylenediamine, or the like to form oxazoline, thiazoline, or imidazoline corresponding to the azoline ring portion in the compound; and (3) a method for synthesizing a type of compound in which the linking portion L is bonded at a 1-position of imidazoline corresponding to the azoline ring portion, including bonding a benzene ring, a naphthalene ring, a pyridine ring, a pyrimidine ring, a pyrazine ring, a pyridazine ring, or the like having a group (halogen atom or the like) capable of being bonded at the 1-position of imidazoline and corresponding to the linking portion L to an aromatic hydrocarbon compound or an aromatic heterocyclic compound corresponding to the core portion φ, and then introducing the imidazoline into the linking portion L.

(1) Method for bonding "oxazoline/thiazoline/imidazoline derivative-containing moiety" to aromatic hydrocarbon compound or aromatic heterocyclic compound <Synthesis of Phenyloxazoline having Reactive Substituent>

Referring to a method described, for example, in "Journal of Organic Chemistry, Vol. 39, No 18, 1974, p 2784", according to the following reaction formula (1), an acid chloride of benzoic acid having a reactive substituent is caused to react with an amino alcohol to synthesize an amido alcohol, then the resulting amido alcohol is caused to react with thionyl chloride to obtain a hydrochloride of phenyloxazoline, the resulting hydrochloride of phenyloxazoline is neutralized with an aqueous sodium hydroxide solution, and phenyloxazoline having a reactive substituent can be thereby synthesized.

Reaction formula (1)

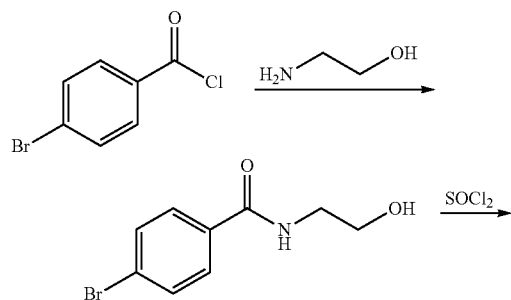

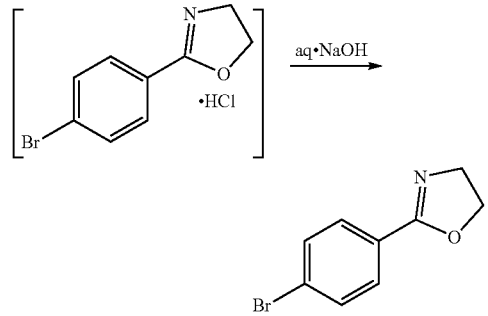

Furthermore, referring to a method described, for example, in "Chemische Berichte, Vol. 124, Issue 5, 1991, p 1173", according to the following reaction formula (2), benzonitrile is caused to react with an amino alcohol using zinc chloride as a catalyst, and phenyloxazoline having a reactive substituent can be thereby also synthesized.

Reaction formula (2)

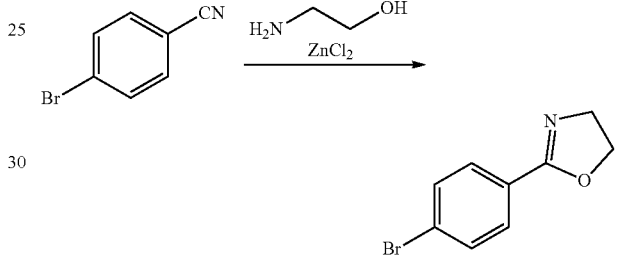

In addition, these oxazoline derivatives can be also synthesized by appropriately combining other methods described in review articles such as "Tetrahedoron, Vol. 50, No 8, 1994, p 2297".

In the above reaction formulas (1) and (2), a synthesis method using 2-aminoethanol as an amino alcohol serving as a raw material of an oxazoline ring has been exemplified. However, using 2-amino-2-methyl-1-propanol, 1-amino-2-methyl-2-propanol, 3-amino-2,3-dimethyl-2-butanol, or the like as a raw material, a target compound corresponding to each of these compounds can be obtained.

In the above reaction formula (1), a synthesis method using p-bromobenzoic acid chloride has been exemplified. However, using m-bromobenzoic acid chloride, 6-bromo-2-picolinic acid chloride, 5-bromo-3-picolinic acid chloride, 6-bromo-3-picolinic acid chloride, 5-bromo-2-picolinic acid chloride, 5-bromopyrazine-2-carboxylic acid chloride, 2-bromopyrimidine-5-carboxylic acid chloride, or the like as a raw material instead of p-bromobenzoic acid chloride, a target compound corresponding thereto can be also obtained. Furthermore, using a chloro compound or an iodo compound instead of a bromo compound, a target compound corresponding thereto can be also obtained. As for the acid chloride, corresponding benzoic acid is caused to react with thionyl chloride or the like, and is thereby converted into the acid chloride to be used.

In the above reaction formula (2), a synthesis method using p-bromobenzonitrile has been exemplified. However, using m-bromobenzonitrile, 2-bromo-6-cyanopyridine, 3-bromo-5-cyanopyridine, 2-bromo-5-cyanopyridine, 5-bromo-2-cyanopyridine, 2-bromo-5-cyanopyrazine, 2-bromo-5-cyanopyrimidine, or the like instead of p-bromobenzonitrile as a raw material, a target compound corresponding thereto can be also obtained. Furthermore, using a chloro compound or an iodo compound instead of a bromo compound, a target compound corresponding thereto can be also obtained.

In addition, using an acid chloride or a nitrile having an alkoxy group as a substituent, such as p-methoxybenzoic acid chloride or p-methoxybenzonitrile instead of the above reaction formulas (1) and (2), an oxazoline ring is formed. Thereafter, the resulting oxazoline ring is subjected to demethylation using boron tribromide, pyridine hydrochloride, or the like, and then is subjected to trifluoromethane sulfonic acid esterification, and a target compound can be thereby also obtained.

<Synthesis of Phenylthiazoline having Reactive Substituent>

Referring to a method described, for example, in "Chemical Reviews, Vol. 109, No. 3, 2009, p 1371", according to the following reaction formula (3), benzonitrile having a reactive substituent is caused to react with an aminothiol using zinc chloride as a catalyst, and phenylthiazoline having a reactive substituent can be thereby synthesized.

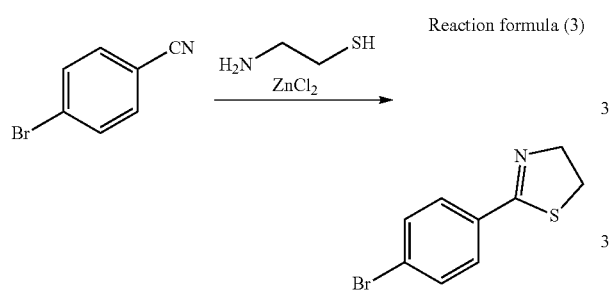

Reaction formula (3)

In addition, these thiazoline derivatives can be also synthesized by appropriately combining other methods described in review articles such as "Chemical Reviews, Vol. 109, No. 3, 2009, p 1371".

In the above reaction formula (3), a synthesis method using 2-aminoethanethiol as an aminothiol serving as a raw material of a thiazoline ring has been exemplified. However, using 2-amino-2-methyl-1-propanethiol, 1-amino 2-methyl-2-propanethiol, or 3-amino-2,3-dimethyl-2-thiol as a raw material, a target compound corresponding to each of these compounds can be obtained.

In the above reaction formula (3), a synthesis method using p-bromobenzonitrile has been exemplified. However, using m-bromobenzonitrile, 2-bromo-6-cyanopyridine, 3-bromo-5-cyanopyridine, 2-bromo-5-cyanopyridine, 5-bromo-2-cyanopyridine, 2-bromo-5-cyanopyrazine, 2-bromo-5-cyanopyrimidine, or the like instead of p-bromobenzonitrile as a raw material, a target compound corresponding thereto can be also obtained. Furthermore, using a chloro compound or an iodo compound instead of a bromo compound, a target compound corresponding thereto can be also obtained. In addition, using a nitrile having an alkoxy group as a substituent, such as p-methoxybenzonitrile, a thiazoline ring is formed. Thereafter, the resulting thiazoline ring is subjected to demethylation using boron tribromide, pyridine hydrochloride, or the like, and then is subjected to trifluoromethane sulfonic acid esterification, and a target compound can be thereby also obtained.

<Synthesis of Phenylimidazoline having Reactive Substituent>

First, a method for synthesizing a type of compound in which the linking portion L is bonded at a 2-position of imidazoline will be described. Referring to a method described, for example, in "Tetrahedoron, Vol. 63, 2007, p 1474" or "TetrahedronLetters Vol. 46, 2005, p 2197", according to the following reaction formula (4), benzaldehyde having a reactive substituent is caused to react with ethylenediamine using potassium carbonate/iodine or N-bromosuccinimide (NBS), and a precursor of phenylimidazoline having a reactive substituent can be thereby synthesized. Subsequently, according to the following reaction formula (5), using a Ullmann reaction using copper or a monovalent copper salt, particularly copper bromide cited in "Journal of Organic Chemistry. Vol. 48, 3470" or a Buchwald-Hartwig reaction using a palladium catalyst, phenylimidazoline is caused to react with iodobenzene, and phenylimidazoline having a reactive substituent can be thereby obtained.

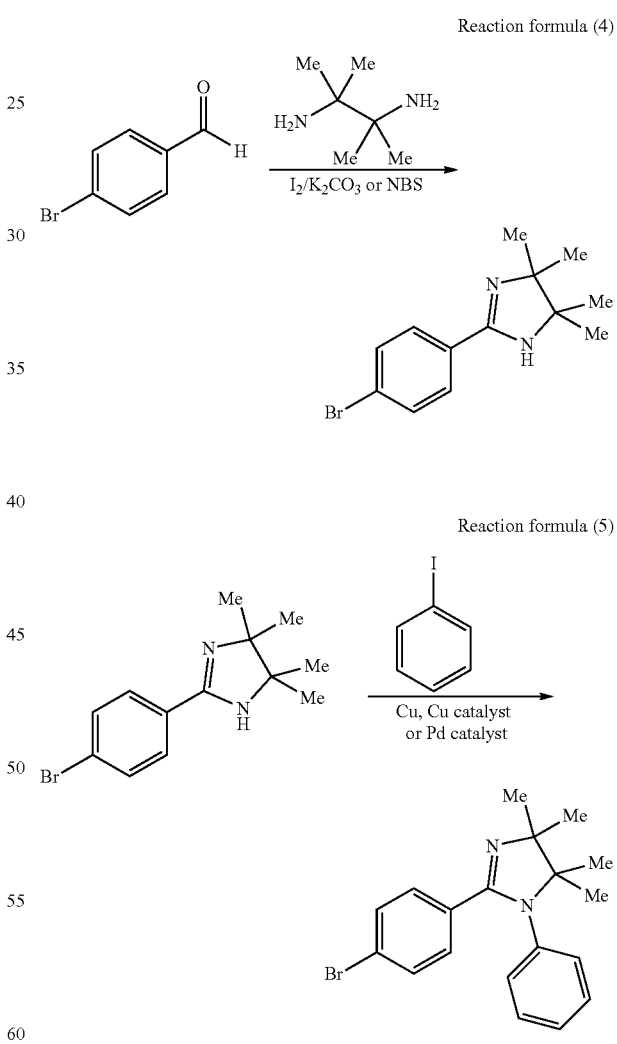

Reaction formula (4)

Reaction formula (5)

In addition, these imidazoline derivatives can be also synthesized by appropriately combining other methods described in review articles such as "Advanced Synthetic Catalysis, Vol. 351, 2009, p 489".

In the above reaction formula (4), a synthesis method using 2,3-dimethylbutane-2,3-diamine as a diamine serving as a raw material of an imidazoline ring has been exemplified. However, using ethylenediamine, 2-methylpropane-1,2-diamine, or the like as a raw material, a target compound corresponding to each of these compounds can be also obtained. Furthermore, hydrochlorides of these diamines can be similarly used by neutralizing the diamines in a reaction system or outside the reaction system.

In the above reaction formula (4), a synthesis method using p-bromobenzaldehyde has been exemplified. However, using m-bromobenzaldehyde, 2-bromo-6-formylpyridine, 3-bromo-5-formylpyridine, 2-bromo-5-formylpyridine, 5-bromo-2-formylpyridine, 2-bromo-5-formylpyrazine, 2-bromo-5-formylpyrimidine, or the like instead of p-bromobenzaldehyde as a raw material, a target compound corresponding thereto can be also obtained. Furthermore, using a chloro compound or an iodo compound instead of a bromo compound, a target compound corresponding thereto can be also obtained. In addition, using an aldehyde having an alkoxy group as a substituent, such as p-methoxybenzaldehyde, an imidazoline compound is synthesized. Thereafter, the resulting imidazoline compound is subjected to demethylation using boron tribromide, pyridine hydrochloride, or the like, and then is subjected to trifluoromethane sulfonic acid esterification, and a target compound can be thereby also obtained.

Next, a method for synthesizing a type of compound in which the linking portion L is bonded at a 1-position of imidazoline will be described. Referring to a method described, for example, in "Advanced Synthetic Catalysis, Vol. 351, 2009, p 489", according to the following reaction formula (6), ethane imidate is caused to react with ethylenediamine, and an imidazoline ring can be thereby synthesized. Furthermore, according to the following reaction formula (6'), ethylenediamine is caused to react with an orthotriester using an acid catalyst, and an imidazoline ring can be also synthesized. As the acid catalyst, a sulfonic acid such as p-toluenesulfonic acid can be used. However, a sulfonic acid-fixed catalyst such as Taycacure SAC-15 (trade name: Tayca Corporation) can be also used. Incidentally, ethylenediamine used here can be used by neutralizing ethylenediamine hydrochloride with a base such as potassium carbonate just before use as in the following reaction formula (6"), and thereby preparing a free base of ethylenediamine. Subsequently, according to the following reaction formula (7), using a Ullmann reaction using copper or a monovalent copper salt, particularly copper bromide cited in "Journal of Organic Chemistry. Vol. 48, 3470" or a Buchwald-Hartwig reaction using a palladium catalyst, an imidazoline ring is caused to react with bromobenzene (linking portion L having a reactive substituent), and phenylimidazoline having a reactive substituent can be thereby obtained.

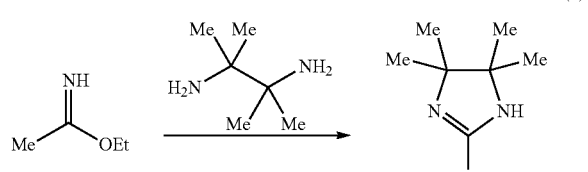

Reaction formula (6)

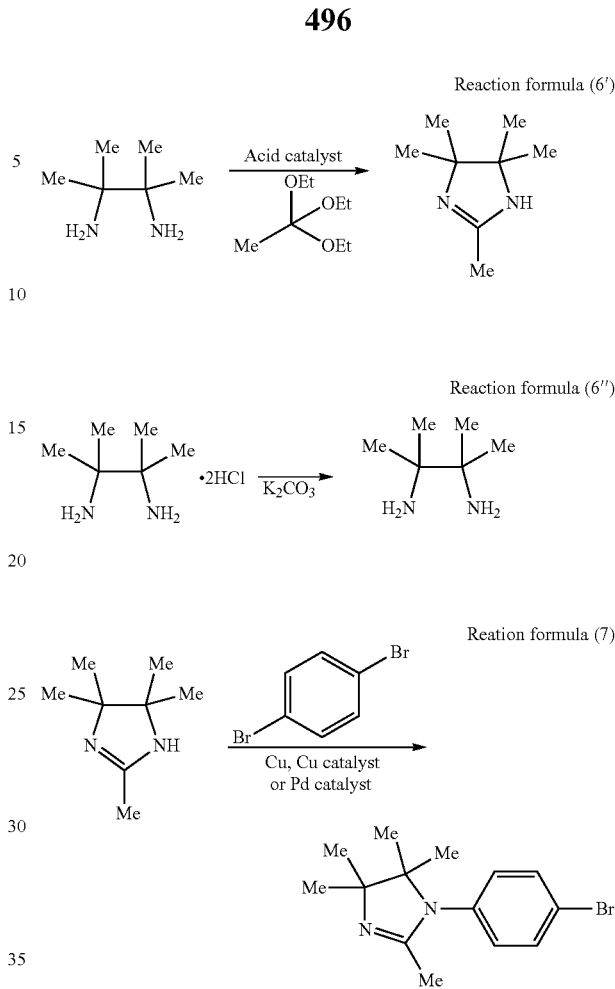

In the above reaction formula (6), a synthesis method using 2,3-dimethylbutane-2,3-diamine as a diamine serving as a raw material of an imidazoline ring has been exemplified. However, using ethylenediamine, 2-methylpropane-1,2-diamine, or the like as a raw material, a target compound corresponding to each of these compounds can be also obtained. Furthermore, hydrochlorides of these diamines can be similarly used by neutralizing the diamines in a reaction system or outside the reaction system. In addition, a synthesis method using ethyl ethane imidate has been exemplified. However, using ethyl propane imidate, ethyl butane imidate, or the like as a raw material, a target compound corresponding to each of these compounds can be also obtained. A target compound can be obtained similarly using a methyl ester instead of an ethyl ester. Hydrochlorides of these imidates can be similarly used by neutralizing the imide acid esters in the reaction system or outside the reaction system. A nitrile is treated with a hydrochloric acid alcohol solution using a method described, for example, in "Chemical Reviews Vol. 61, No. 2, p 179", a hydrochloride of a corresponding imidate is obtained. Therefore, the resulting hydrochloride is appropriately neutralized, and can be used as a raw material.

In the above reaction formula (7), the synthesis method using p-dibromobenzene has been exemplified. However, using m-dibromobenzene, 2,6-dibromopyridine, 2,5-dibromopyridine, 3,5-dibromopyridine, 2,4-dibromopyrimidine, 2,5-dibromopyrimidine, 4,6-dibromopyrimidine, 2,6-dibromopyrazine, 2,5-dibromopyrazine, 3,6-dibromopyridazine, or the like as a raw material, a target compound corresponding thereto can be also obtained. Furthermore, using not a dibromo compound but a dichloro compound such as 2,6-dichloropyridine, a diiodo compound, bis(trifluoromethanesulfonate), or a mixture thereof (for example, 1-bromo-4-iodobenzene), a target compound corresponding thereto can be also obtained.

In addition, benzene or a pyridine derivative having a halogen atom and an alkoxy group as a substituent, such as bromoanisole, is caused to react with imidazoline instead of the above reaction formulas (6) and (7). Thereafter, the resulting product is subjected to demethylation using boron tribromide or pyridine hydrochloride, and then is subjected to trifluoromethane sulfonic acid esterification, and a target compound can be thereby also obtained.

Incidentally, in the above reaction formulas (1) to (7), the synthesis method in the case where the linking portion L or the like has no substituent has been exemplified. However, using a raw material having a substituent at a desired position, a target compound in which the linking portion L or the like has a substituent can be obtained.

Next, a method for bonding the "oxazoline/thiazoline/imidazoline derivative-containing moiety" to various aromatic hydrocarbon compounds or aromatic heterocyclic compounds will be described using anthracene as an example.
<Synthesis of Anthracene having Reactive Substituent>
<9,10-dibromoanthracene>

As illustrated in the following reaction formula (8), 9,10-dibromoanthracene is obtained by brominating anthracene with a suitable brominating agent. Examples of the suitable brominating agent include bromine and N-brominated succinimide (NBS).

Reaction formula (8)

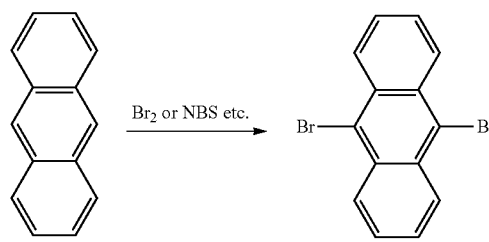

Incidentally, in a case where an anthracene derivative having a substituent (alkyl, cycloalkyl, aryl, or the like) at a 2-position is desired, by Suzuki coupling between anthracene substituted by a halogen atom or triflate at a 2-position and boronic acid (or boronate) of a group corresponding to the substituent, an anthracene derivative having a substituent at a 2-position can be synthesized. In addition, other examples of the method include a synthesis method by Negishi coupling between anthracene substituted by a halogen atom or triflate at a 2-position and a zinc complex of a group corresponding to the substituent. Furthermore, other examples of the method include a synthesis method by Suzuki coupling between 2-anthracene boronic acid (or boronate) and a group corresponding to the substituent substituted by a halogen atom or triflate, and a synthesis method by Negishi coupling between a 2-anthracene zinc complex and a group corresponding to the substituent substituted by a halogen atom or triflate. Incidentally, an anthracene derivative having a substituent at a position other than a 2-position can be similarly synthesized using a raw material having a halogen atom, triflate, boronic acid (or boronate), or a zinc complex by which anthracene is substituted at a desired position.

<9,10-dianthracene Zinc Complex>

As illustrated in the following reaction formula (9), 9,10-dibromoanthracene is lithiated with an organolithium reagent, or is converted into a Grignard reagent using magnesium or an organomagnesium reagent, the resulting product is caused to react with zinc chloride or a zinc chloride tetramethylethylenediamine complex (ZnCl₂.TMEDA), and a 9,10-dianthracene zinc complex can be thereby synthesized. In the reaction formula (9), R' represents a linear or branched alkyl group, but preferably represents a linear alkyl group having 1 to 4 carbon atoms or a branched alkyl group having 3 or 4 carbon atoms. Note that similar synthesis can be performed using a chloride or an iodide instead of a bromide such as 9,10-dibromoanthracene.

Reaction formula (9)

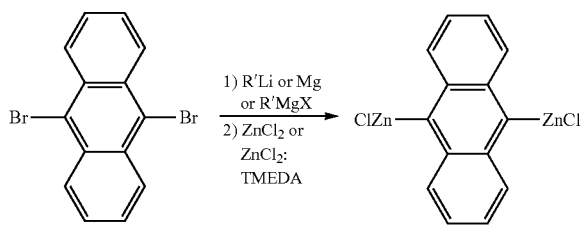

<9,10-anthracenediboronic acid (or boronate)>

As illustrated in the following reaction formula (10), 9,10-dibromoanthracene is lithiated with an organolithium reagent, or is converted into a Grignard reagent using magnesium or an organomagnesium reagent, the resulting product is caused to react with trimethyl borate, triethyl borate, triisopropyl borate, or the like, and 9,10-anthracenediboronate can be thereby synthesized. Furthermore, the 9,10-anthracenediboronate is hydrolyzed in the following reaction formula (11), and 9,10-anthracenediboronic acid can be thereby synthesized. In reaction formulas (10) and (11), R' represents a linear or branched alkyl group, but preferably represents a linear alkyl group having 1 to 4 carbon atoms or a branched alkyl group having 3 or 4 carbon atoms.

Reaction formula (10)

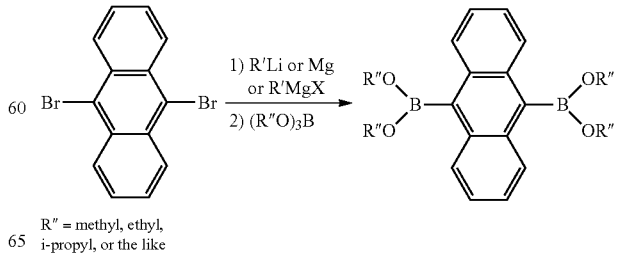

R" = methyl, ethyl, i-propyl, or the like

Reaction formula (11)

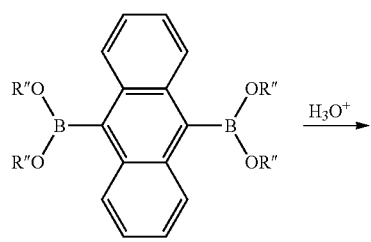

R″ = methyl, ethyl, i-propyl, or the like

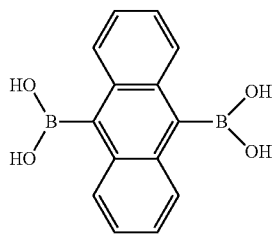

As illustrated in the following reaction formula (12), 9,10-dibromoanthracene and bis(pinacolato) diboron or 4,4,5,5-tetramethyl-1,3,2-dioxaborolane are subjected to a coupling reaction using a palladium catalyst and a base, and similar 9,10-anthracenediboronate can be thereby synthesized.

Reaction formula (12)

Note that similar synthesis can be performed using a chloride or an iodide instead of a bromide such as 9,10-dibromoanthracene in the above reaction formula (9), (10), or (12), or using a chloride, an iodide, or triflate instead of a bromide in the above reaction formula (10).

In the above reaction formulas (8) to (12), the anthracene derivative has been illustrated as an example of an aromatic hydrocarbon or an aromatic heterocyclic ring having a reactive substituent. However, an aromatic hydrocarbon or an aromatic heterocyclic ring having various reactive substituents can be obtained using an aromatic hydrocarbon or an aromatic heterocyclic ring having halogen atoms or triflates at 2 to 4 positions as a raw material. In addition, a substituent can be appropriately introduced into an aromatic hydrocarbon or an aromatic heterocyclic ring having various reactive substituents using a raw material having a substituent at a desired position.

<Method for Boding Anthracene having Reactive Substituent to "oxazoline/thiazoline/imidazoline derivative-containing moiety">

As described above, for the "oxazoline/thiazoline/imidazoline derivative-containing moiety", a bromo compound (reaction formulas (1) to (7)) can be synthesized, and for anthracene having a reactive substituent, a bromo compound (reaction formula (8)), a zinc chloride complex (reaction formula (9)), boronic acid, and boronate (reaction formulas (10) to (12)) can be synthesized. Therefore, by performing Suzuki coupling or Negishi coupling as illustrated in the following reaction formulas (13) and (14), a target compound can be synthesized.

Reaction formula (13)

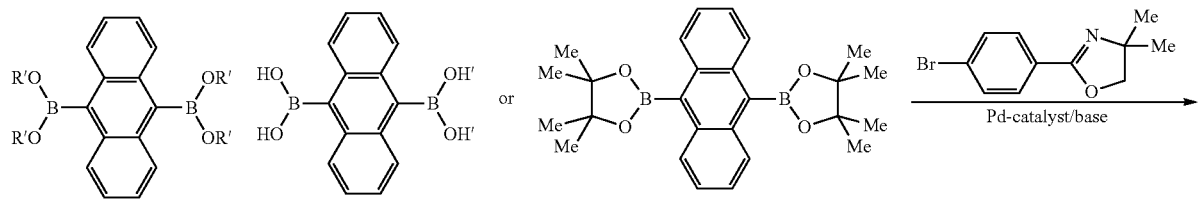

R′ = methyl, ethyl, i-propyl, or the like

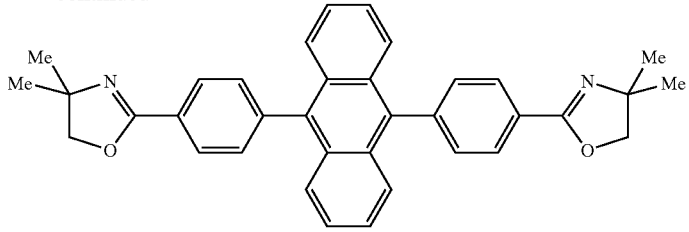

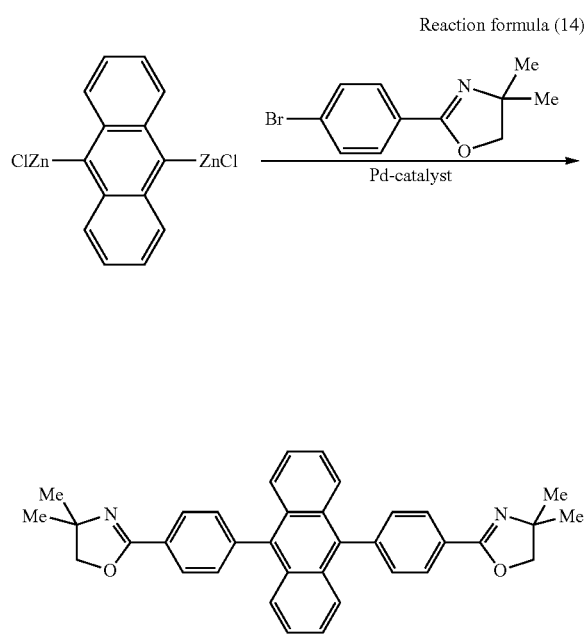

Reaction formula (14)

By bonding the "oxazoline/thiazoline/imidazoline derivative-containing moiety" to anthracene referring to the coupling reaction used in the above description, the azoline ring-containing compound of the present invention can be synthesized.

The case where the "oxazoline/thiazoline/imidazoline derivative-containing moiety" is a bromide has been exemplified here. However, by preparing a zinc complex or boronic acid/boronate according to the methods illustrated in the above formulas (9) to (12), and then performing Suzuki coupling or Negishi coupling according to the methods illustrated in the above formulas (13) and (14), the azoline ring-containing compound of the present invention can be also synthesized.

In this final coupling reaction, in order to cause two or more "oxazoline/thiazoline/imidazoline derivative-containing moieties" of an azoline ring-containing compound represented by general formula (1) to have different structures, first, anthracene having a reactive substituent is caused to react with a compound of an "oxazoline/thiazoline/imidazoline derivative-containing moiety" with a value less than an equivalent, and then this intermediate is caused to react with a compound of an "oxazoline/thiazoline/imidazoline derivative-containing moiety" different from the preceding compound (that is, reacted in two or more stages).

(2) Method for Bonding Group having Functional Group Serving as cyclization precursor to aromatic hydrocarbon compound or the like, and then performing cyclization reaction to synthesize compound in which azoline ring has substituent Subsequently, a method for introducing a group having a functional group serving as a cyclization precursor such as a cyano group into an aromatic hydrocarbon compound or an aromatic heterocyclic compound, and then performing a cyclization reaction to obtain a target compound in which an oxazoline, thiazoline, or imidazoline ring has a substituent will be described by taking anthracene as an example.

<Synthesis of Anthracene having Functional Group Serving as Cyclization Precursor such as Cyano Group>

For anthracene having a reactive substituent, a bromo compound (reaction formula (8)), a zinc chloride complex (reaction formula (9)), boronic acid, and a boronate (reaction formulas (10) to (12)) can be synthesized, and therefore anthracene having a substituent of a cyanophenyl group can be synthesized with reference to the coupling reaction used in the above description as illustrated in the following reaction formulas (15) and (16).

Reaction formula (15)

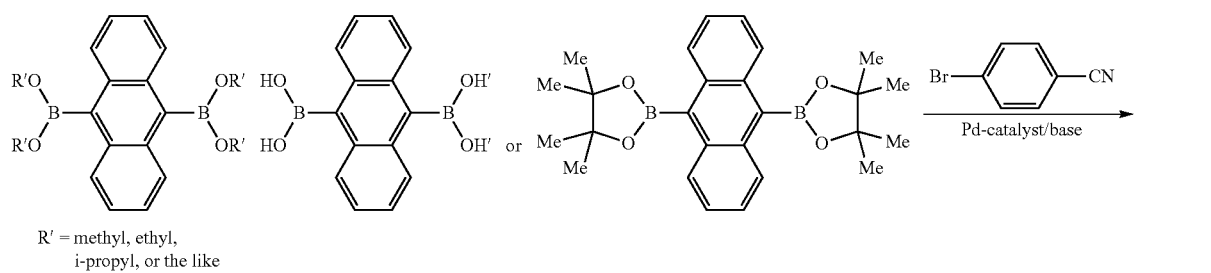

R' = methyl, ethyl, i-propyl, or the like

-continued

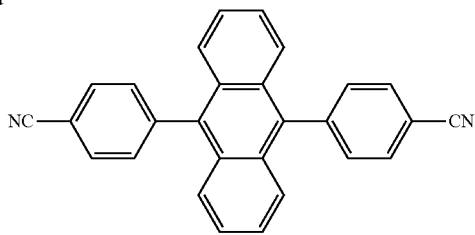

Reaction formula (16)

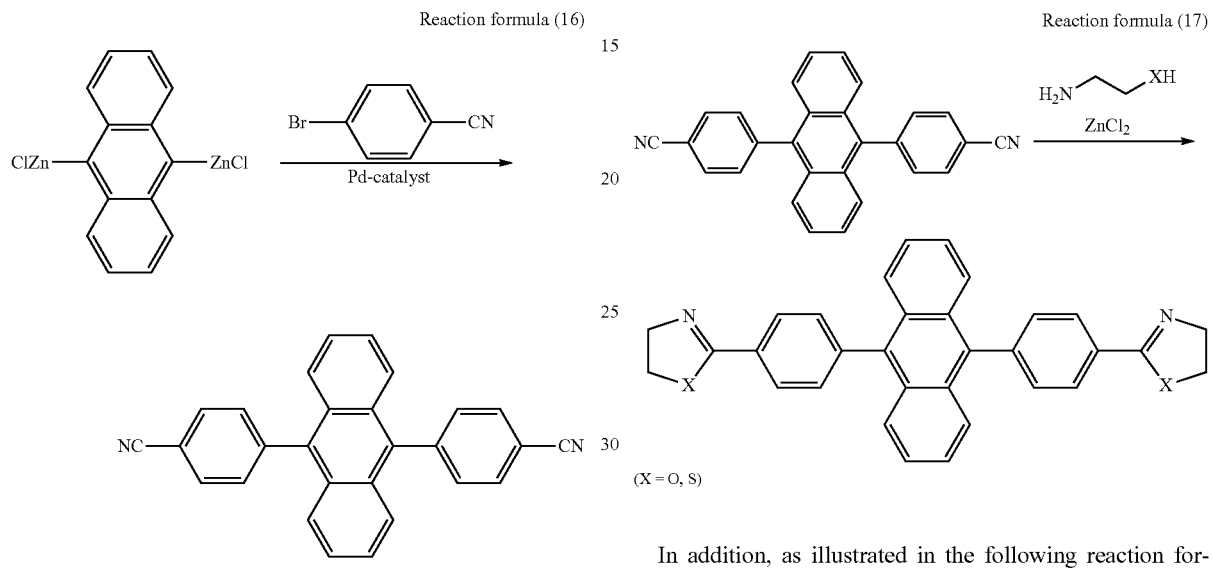

Reaction formula (17)

(X = O, S)

Subsequently, by performing a cyclization reaction using an amino alcohol or an aminothiol as illustrated in the above reaction formulas (2) and (3), the oxazoline ring-containing compound or the thiazoline ring-containing compound of the present invention can be synthesized as illustrated in the following reaction formula (17).

In addition, as illustrated in the following reaction formulas (18) to (21), by synthesizing anthracene having a substituent of a formylphenyl group according to the methods illustrated in the above reaction formulas (15) and (16), then forming an imidazoline ring according to the method illustrated in the above reaction formula (4), and arylating a nitrogen atom by a method as illustrated in the above reaction formula (5), the imidazoline ring-containing compound of the present invention can be also synthesized.

Reaction formula (18)

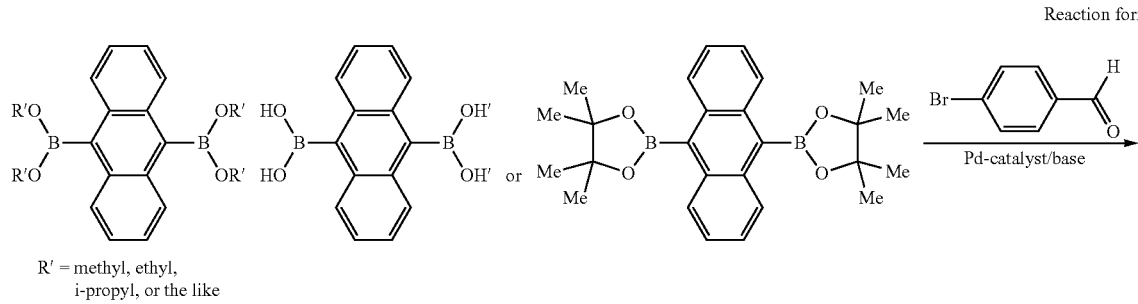

R' = methyl, ethyl, i-propyl, or the like

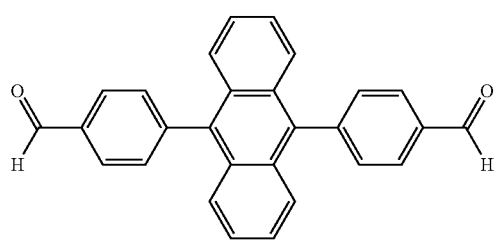

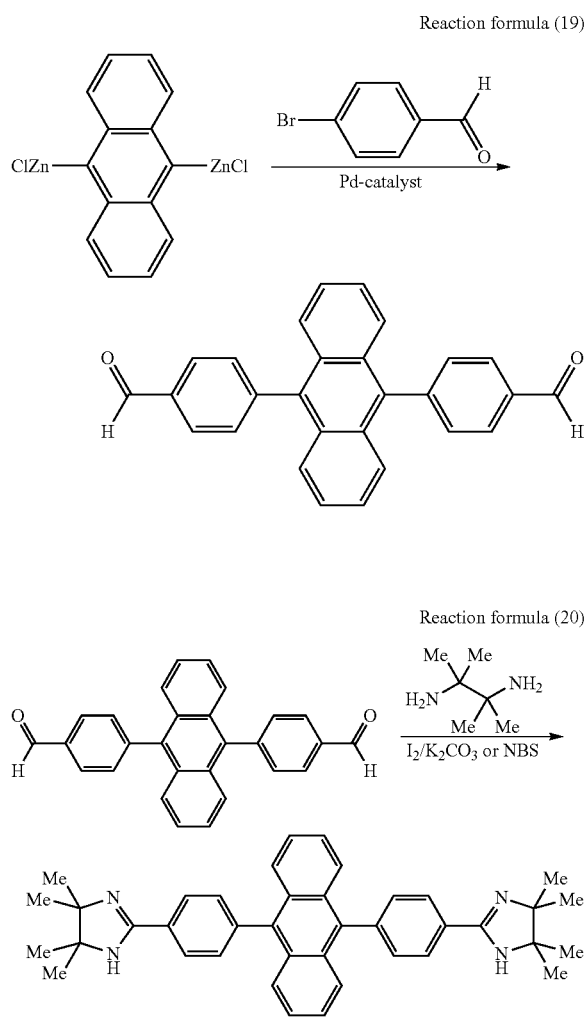

Reaction formula (19)

Reaction formula (20)

In addition, by converting a benzonitrile or a benzaldehyde having a reactive functional group into a zinc complex according to the method illustrated in the above reaction formula (9), or by converting a benzonitrile or a benzaldehyde having a reactive functional group into boronic acid/boronate according to the method illustrated in the above reaction formulas (10) to (12), and then causing the resulting product to react with dibromoanthracene by Suzuki coupling or Negishi coupling, a similar compound can be also obtained. As the zinc complex or boronic acid/boronate of benzonitrile used here, a commercially available product can be used.

(3) Method for synthesizing a type of compound in which linking portion L is bonded at 1-position of imidazoline Next, a method for synthesizing a type of compound in which the linking portion L is bonded at a 1-position of imidazoline will be described by taking pyridine as an example below. The method includes bonding a benzene ring, a naphthalene ring, a pyridine ring, a pyrimidine ring, a pyrazine ring, a pyridazine ring, or the like having a group (halogen atom or the like) capable of being bonded at a 1-position of imidazoline and corresponding to the linking portion L to an aromatic hydrocarbon compound or an aromatic heterocyclic compound corresponding to the core portion φ, and then introducing the imidazoline into the linking portion L.

<Synthesis of Pyridine Compound having Group Serving as Bonding Precursor such as Halogen Atom>

As illustrated in the following reaction formula (22), by causing biphenyl-4-carboxaldehyde to react with 4-iodoacetophenone in acetic acid in the presence of ammonium acetate, a pyridine compound having p-iodophenyl groups at 2,6-positions can be synthesized. Here, a method using biphenyl-4-carboxaldehyde, 4-iodoacetophenone, and ammonium acetate has been described. However, by a commonly used pyridine synthesis method, a pyridine compound having a group serving as a bonding precursor such as a halogen atom can be also synthesized similarly.

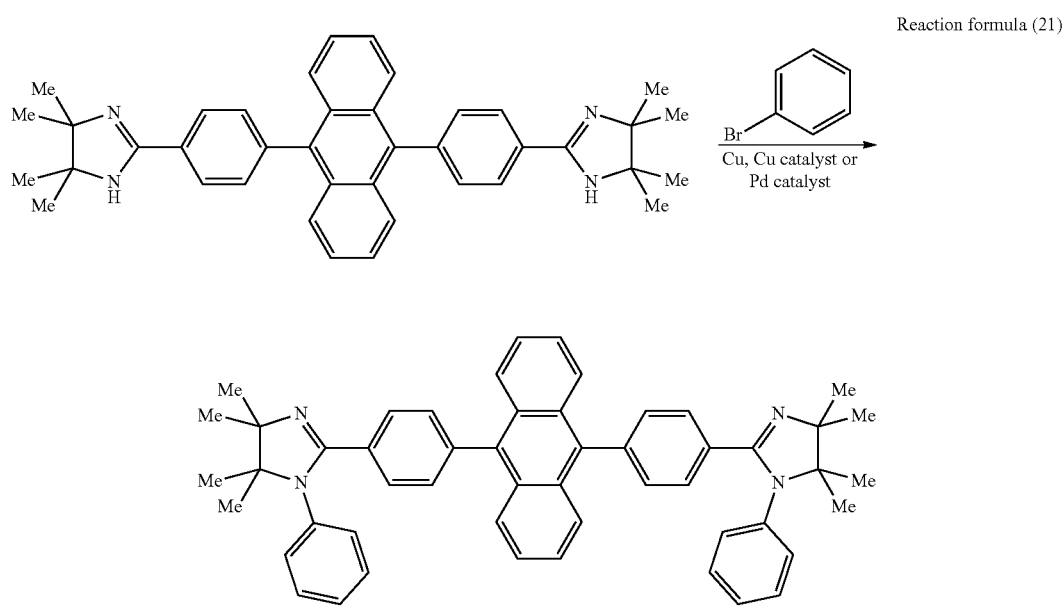

Reaction formula (21)

Reaction formula (22)

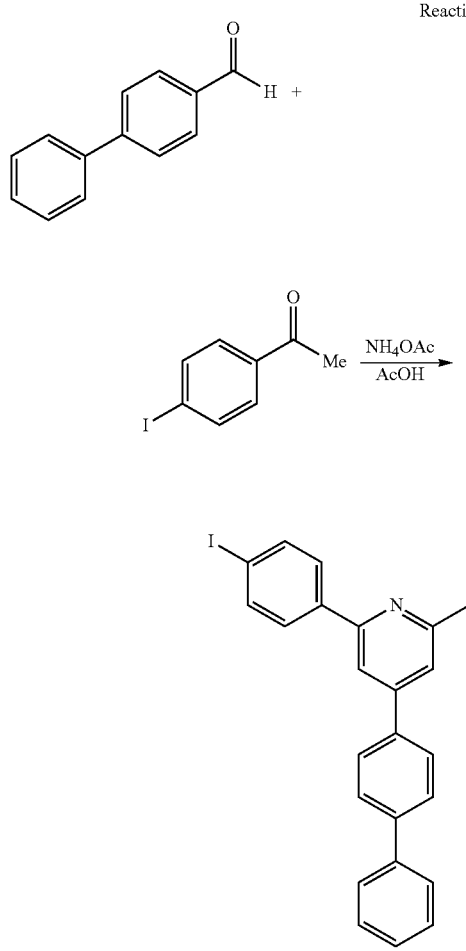

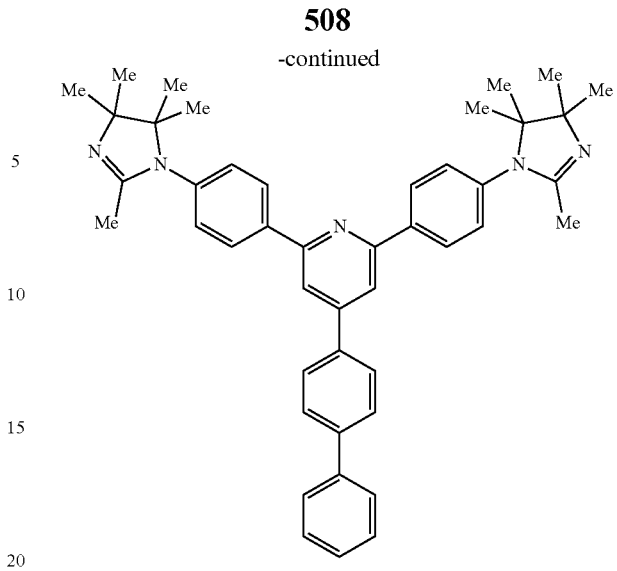

Subsequently, according to the method illustrated in the above reaction formula (7), as illustrated in the following reaction formula (23), a compound in which 1-imidazoline is bonded to a pyridine compound having a group serving as a bonding precursor such as a halogen atom can be synthesized.

Reaction formula (23)

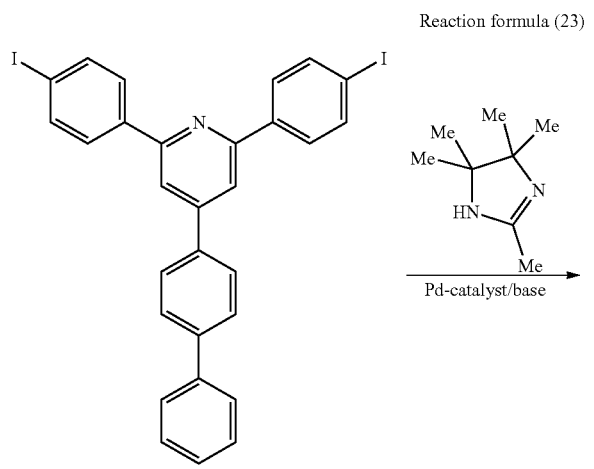

The type of compound in which the linking portion L is bonded at a 1-position of imidazoline can be also synthesized by the following procedure. For example, various aromatic hydrocarbon compounds or aromatic heterocyclic compounds having a functional group capable of causing a Suzuki coupling reaction or a Negishi coupling reaction, such as boronic acid, a boronate, or a zinc chloride complex and corresponding to the core portion φ are caused to react with a largely excessive amount of a benzene ring, a naphthalene ring, a pyridine ring, a pyrimidine ring, a pyrazine ring, a pyridazine ring, or the like having two groups serving as a bonding precursor such as a halogen atom and corresponding to the linking portion L by the Suzuki coupling reaction or the Negishi coupling reaction. A precursor compound in which the linking portion L (benzene ring, naphthalene ring, pyridine ring, pyrimidine ring, pyrazine ring, or pyridazine ring) having a halogen atom is bonded to the core portion φ (aromatic hydrocarbon compound or aromatic heterocyclic compound) can be thereby synthesized. A compound in which 1-imidazoline is bonded can be synthesized using this precursor compound by the method illustrated in the above reaction formula (23).

<Reagent used in Reaction>

Specific examples of a palladium catalyst used in the coupling reaction include tetrakis(triphenylphosphine) palladium(0): $Pd(PPh_3)_4$, bis(triphenylphosphine) palladium (II) dichloride: $PdCl_2(PPh_3)_2$, palladium(II) acetate: $Pd(OAc)_2$, tris(dibenzylideneacetone)dipalladium(0): $Pd_2(dba)_3$, a tris(dibenzylideneacetone) dipalladium(0) chloroform complex: $Pd_2(dba)_3 \cdot CHCl_3$, bis(dibenzylideneacetone) palladium(0): $Pd(dba)_2$, bis(tri-t-butylphosphino) palladium (0): Pd $(t-Bu_3P)_2$, [1,1'-bis(diphenylphosphino) ferrocene] palladium(II) dichloride: $Pd(dppf)Cl_2$, a [1,1'-bis(diphenylphosphino) ferrocene] palladium(II) dichloridedichloromethane complex (1:1): $Pd(dppf)Cl_2 \cdot CH_2Cl_2$, and $PdCl_2$ $[P(t-Bu)_2-(p-NMe_2-Ph)]_2$: $(A-^{ta}Phos)_2PdCl_2$ (Pd-132: trademark; manufactured by Johnson Matthey Co., Ltd.).

In order to accelerate the reaction, a phosphine compound may be optionally added to these palladium compounds. Specific examples of the phosphine compound include tri (t-butyl) phosphine, tricyclohexylphosphine, 1-(N,N-dimethylaminomethyl)-2-(di-t-butylphosphino) ferrocene, 1-(N, N-dibutylaminomethyl)-2-(di-t-butylphosphino) ferrocene, 1-(methoxymethyl)-2-(di-t-butylphosphino) ferrocene, 1,1'-bis(di-t-butylphosphino) ferrocene, 2,2'-bis(di-t-butylphosphino)-1,1'-binaphthyl, 2-methoxy-2'-(di-t-butylphosphino)-1,1'-binaphthyl, and 2-dicyclohexylphosphino-2',6'-dimethoxybiphenyl.

Specific examples of a base used in the reaction include sodium carbonate, potassium carbonate, cesium carbonate, sodium hydrogencarbonate, sodium hydroxide, potassium hydroxide, barium hydroxide, sodium ethoxide, sodium t-butoxide, sodium acetate, potassium acetate, tripotassium phosphate, and potassium fluoride.

In order to accelerate the reaction, a quaternary ammonium salt may be added as a phase transfer catalyst. Specific examples of the phase transfer catalyst include tetra-n-butylammonium bromide, cetyltrimethylammonium bromide, benzyltrimethylammonium bromide, and dodecyltrimethylammonium bromide.

Specific examples of a solvent used in the reaction include benzene, toluene, xylene, 1,2,4-trimethylbenzene, N,N-dimethylformamide, 1,2-dimethoxy ethane, t-butyl methyl ether, cyclopentyl methyl ether, tetrahydrofuran, 1,4-dioxane, methanol, ethanol, isopropyl alcohol, and t-butyl alcohol. These solvents can be appropriately selected, and may be used singly or as a mixed solvent. At least one of the above solvents can be mixed with water to be used. Water can be also used as a single solvent.

The azoline ring-containing compound of the present invention includes a compound in which at least a part of hydrogen atoms are substituted by deuterium atoms. Such a compound can be synthesized using a raw material deuterated at a desired portion in a similar manner to the above.

When the azoline ring-containing compound of the present invention is used for an electron injection layer or an electron transport layer in an organic EL element, the organic EL element is stable when an electric field is applied thereto. This means that the compound of the present invention is excellent as an electron injection material or an electron transport material of an electroluminescent element. The electron injection layer referred to herein is a layer for receiving electrons from a cathode to an organic layer, and the electron transport layer is a layer for transporting the injected electrons to a light emitting layer. The electron transport layer can also serve as the electron injection layer. Materials used for the two layers are referred to as an electron injection material and an electron transport material, respectively.

<Description of Organic EL Element>

The azoline ring-containing compound according to the present invention can be used, for example, as a material of an organic electroluminescent element. Hereinafter, an organic EL element according to the present embodiment will be described in detail based on the drawings. FIG. 1 is a schematic cross-sectional view illustrating the organic EL element according to the present embodiment.

<Structure of Organic Electroluminescent Element>

An organic electroluminescent element 100 illustrated in FIG. 1 includes a substrate 101, an anode 102 disposed on the substrate 101, a hole injection layer 103 disposed on the anode 102, a hole transport layer 104 disposed on the hole injection layer 103, a light emitting layer 105 disposed on the hole transport layer 104, an electron transport layer 106 disposed on the light emitting layer 105, an electron injection layer 107 disposed on the electron transport layer 106, and a cathode 108 disposed on the electron injection layer 107.

Incidentally, the organic electroluminescent element 100 may be configured, by reversing the manufacturing order, to include, for example, the substrate 101, the cathode 108 disposed on the substrate 101, the electron injection layer 107 disposed on the cathode 108, the electron transport layer 106 disposed on the electron injection layer 107, the light emitting layer 105 disposed on the electron transport layer 106, the hole transport layer 104 disposed on the light emitting layer 105, the hole injection layer 103 disposed on the hole transport layer 104, and the anode 102 disposed on the hole injection layer 103.

Not all of the above layers are essential. The configuration includes the anode 102, the light emitting layer 105, and the cathode 108 as a minimum constituent unit, and optionally includes the hole injection layer 103, the hole transport layer 104, the electron transport layer 106, and the electron injection layer 107. Each of the above layers may be formed of a single layer or a plurality of layers.

A form of layers constituting the organic electroluminescent element may be, in addition to the above configuration form of "substrate/anode/hole injection layer/hole transport layer/light emitting layer/electron transport layer/electron injection layer/cathode", a configuration form of "substrate/anode/hole transport layer/light emitting layer/electron transport layer/electron injection layer/cathode", "substrate/anode/hole injection layer/light emitting layer/electron transport layer/electron injection layer/cathode", "substrate/anode/hole injection layer/hole transport layer/light emitting layer/electron injection layer/cathode", "substrate/anode/hole injection layer/hole transport layer/light emitting layer/electron transport layer/cathode", "substrate/anode/light emitting layer/electron transport layer/electron injection layer/cathode", "substrate/anode/hole transport layer/light emitting layer/electron injection layer/cathode", "substrate/anode/hole transport layer/light emitting layer/electron transport layer/cathode", "substrate/anode/hole injection layer/light emitting layer/electron injection layer/cathode", "substrate/anode/hole injection layer/light emitting layer/electron transport layer/cathode", "substrate/anode/light emitting layer/electron transport layer/cathode", or "substrate/anode/light emitting layer/electron injection layer/cathode".

<Substrate in Organic Electroluminescent Element>

The substrate 101 serves as a support of the organic electroluminescent element 100, and usually, quartz, glass, a metal, a plastic, and the like are used. The substrate 101 is formed into a plate shape, a film shape, or a sheet shape according to a purpose, and for example, a glass plate, a metal plate, a metal foil, a plastic film, and a plastic sheet are used therefor. Among these examples, a glass plate and a plate made of a transparent synthetic resin such as polyester, polymethacrylate, polycarbonate, or polysulfone are preferable. For a glass substrate, soda lime glass, alkali-free glass, and the like are used. The thickness is only required to be sufficient for maintaining mechanical strength. Therefore, the thickness is only required to be 0.2 mm or more, for example. The upper limit value of the thickness is, for example, 2 mm or less, and preferably 1 mm or less. Regarding a material of glass, glass having fewer ions eluted from the glass is desirable, and therefore alkali-free glass is preferable. However, soda lime glass which has been subjected to barrier coating with $SiO_2$ or the like is also commercially available, and therefore this soda lime glass can be used. Furthermore, the substrate 101 may be provided with a gas barrier film such as a dense silicon oxide film on at least one surface in order to increase a gas barrier property. Particularly in a case of using a plate, a film, or a sheet made of a synthetic resin having a low gas barrier property as the substrate 101, a gas barrier film is preferably provided.

<Anode in Organic Electroluminescent Element>

The anode 102 plays a role of injecting a hole into the light emitting layer 105. Incidentally, in a case where the hole injection layer 103 and/or the hole transport layer 104 are/is disposed between the anode 102 and the light emitting layer 105, a hole is injected into the light emitting layer 105 through these layers.

Examples of a material to form the anode 102 include an inorganic compound and an organic compound. Examples of the inorganic compound include a metal (aluminum, gold, silver, nickel, palladium, chromium, and the like), a metal oxide (indium oxide, tin oxide, indium-tin oxide (ITO), indium-zinc oxide (IZO), and the like), a metal halide (copper iodide and the like), copper sulfide, carbon black, ITO glass, and Nesa glass. Examples of the organic compound include an electrically conductive polymer including polythiophene such as poly(3-methylthiophene), polypyrrole, and polyaniline. In addition to these compounds, a material can be appropriately selected for use from materials used as an anode of an organic electroluminescent element.

A resistance of a transparent electrode is not limited as long as a sufficient current can be supplied for light emission of a luminescent element. However, a low resistance is desirable from a viewpoint of consumption power of the luminescent element. For example, an ITO substrate having a resistance of $300\Omega/\square$ or less functions as an element electrode. However, a substrate having a resistance of about $10\Omega/\square$ can be also supplied at present, and therefore it is particularly desirable to use a low resistance product having a resistance of, for example, 100 to $5\Omega/\square$, preferably 50 to $5\Omega/\square$. The thickness of ITO can be arbitrarily selected according to a resistance value, but an ITO having a thickness of 50 to 300 nm is often used.

<Hole Injection Layer and Hole Transport Layer in Organic Electroluminescent Element>

The hole injection layer 103 plays a role of efficiently injecting a hole that migrates from the anode 102 into the light emitting layer 105 or the hole transport layer 104. The hole transport layer 104 plays a role of efficiently transporting a hole injected from the anode 102 or a hole injected from the anode 102 through the hole injection layer 103 to the light emitting layer 105. The hole injection layer 103 and the hole transport layer 104 are each formed by laminating and mixing one or more kinds of hole injection/transport materials, or by a mixture of a hole injection/transport material and a polymer binder. Furthermore, a layer may be formed by adding an inorganic salt such as iron (III) chloride to the hole injection/transport material.

A hole injection/transport substance needs to efficiently inject/transport a hole from a positive electrode between electrodes to which an electric field is applied, and desirably has a high hole injection efficiency and transports an injected hole efficiently. For this purpose, a substance which has low ionization potential, large hole mobility, and further has excellent stability, and in which impurities serving as traps are not easily generated at the time of manufacturing and at the time of use, is preferable.

As a material to form the hole injection layer 103 and the hole transport layer 104, any compound can be selected for use among compounds that have been conventionally used as charge transport materials for holes in a photoconductive material, p-type semiconductors, and known compounds used in a hole injection layer and a hole transport layer of an organic electroluminescent element. Specific examples thereof include a heterocyclic compound including a carbazole derivative (N-phenylcarbazole, polyvinylcarbazole, and the like), a biscarbazole derivative such as bis(N-arylcarbazole) or bis(N-alkylcarbazole), a triarylamine derivative (a polymer having an aromatic tertiary amino in a main chain or a side chain, 1,1-bis(4-di-p-tolylaminophenyl)cyclohexane, N,N'-diphenyl-N,N'-di(3-methylphenyl)-4,4'-diaminobiphenyl, N,N'-diphenyl-N,N'-dinaphthyl-4,4'-diaminobiphenyl, N,N'-diphenyl-N,N'-di(3-methylphenyl)-4,4'-diphenyl-1,1'-diamine, N,N'-dinaphthyl-N,N'-diphenyl-4,4'-diphenyl-1,1'-diamine, $N^4,N^{4'}$-diphenyl-$N^4,N^{4'}$-bis(9-phenyl-9H-carbazol-3-yl)-[1,1'-biphenyl]-4,4'-diamine, $N^4,N^4,N^{4'},N^{4'}$-tetra[1,1'-biphenyl]-4-yl)-[1,1'-biphenyl]-4,4'-diamine, a triphenylamine derivative such as 4,4',4"-tris(3-methylphenyl(phenyl)amino)triphenylamine, a starburst amine derivative, and the like), a stilbene derivative, a phthalocyanine derivative (non-metal, copper phthalocyanine, and the like), a pyrazoline derivative, a hydrazone-based compound, a benzofuran derivative, a thiophene derivative, an oxadiazole derivative, a quinoxaline derivative (for example, 1,4,5,8,9,12-hexaazatriphenylene-2,3,6,7,10,11-hexacarbonitrile, and the like), and a porphyrin derivative, and a polysilane. Among the polymer-based materials, a polycarbonate, a styrene derivative, a polyvinylcarbazole, a polysilane, and the like having the above monomers in side chains are preferable. However, there is no particular limitation as long as a compound can form a thin film needed for manufacturing a luminescent element, can inject a hole from an anode, and can transport a hole.

Furthermore, it is also known that electroconductivity of an organic semiconductor is strongly affected by doping into the organic semiconductor. Such an organic semiconductor matrix substance is formed of a compound having a good electron-donating property, or a compound having a good electron-accepting property. For doping with an electron-donating substance, a strong electron acceptor such as tetracyanoquinonedimethane (TCNQ) or 2,3,5,6-tetrafluorotetracyano-1,4-benzoquinonedimethane (F4TCNQ) is known (see, for example, "M. Pfeiffer, A. Beyer, T. Fritz, K. Leo, Appl. Phys. Lett., 73(22), 3202-3204 (1998" and "J. Blochwitz, M. Pheiffer, T. Fritz, K. Leo, Appl. Phys. Lett., 73(6), 729-731 (1998)"). These compounds generate a so-called hole by an electron migrating process in an electron-donating type base substance (hole transport substance). Electroconductivity of the base substance depends on the number and mobility of the holes fairly significantly. Known examples of a matrix substance having a hole transport characteristic include a benzidine derivative (TPD and the like), a starburst amine derivative (TDATA and the like), and a specific metal phthalocyanine (particularly, zinc phthalocyanine (ZnPc) and the like) (JP 2005-167175 A).

<Light Emitting Layer in Organic Electroluminescent Element>

The light emitting layer 105 emits light by recombining a hole injected from the anode 102 and an electron injected from the cathode 108 between electrodes to which an electric field is applied. A material to form the light emitting layer 105 is only required to be a compound which is excited by recombination between a hole and an electron and emits light (luminescent compound), and is preferably a compound which can form a stable thin film shape, and exhibits a strong light emission (fluorescence) efficiency in a solid state.

The light emitting layer may be formed of a single layer or a plurality of layers, and each layer is formed of a material for a light emitting layer (a host material and a dopant material). Each of the host material and the dopant material may be formed of a single kind, or a combination of a plurality of kinds. The dopant material may be included in the host material wholly or partially. Regarding a doping method, doping can be performed by a co-deposition method with a host material, or alternatively, a dopant material may be mixed in advance with a host material, and then vapor deposition may be performed simultaneously.

The amount of use of a host material depends on the kind of the host material, and is only required to be determined according to a characteristic of the host material. The reference of the amount of use of a host material is preferably from 50 to 99.999% by weight, more preferably from 80 to 99.95% by weight, and still more preferably from 90 to 99.9% by weight with respect to the total amount of a material for a light emitting layer.

The amount of use of a dopant material depends on the kind of the dopant material, and is only required to be determined according to a characteristic of the dopant material. The reference of the amount of use of a dopant is preferably from 0.001 to 50% by weight, more preferably from 0.05 to 20% by weight, and still more preferably from 0.1 to 10% by weight with respect to the total amount of a material for a light emitting layer. The amount of use within the above range is preferable, for example, from a viewpoint of being able to prevent a concentration quenching phenomenon.

Examples of a host material include a fused ring derivative of anthracene, pyrene, or the like conventionally known as a luminous body, a bisstyryl derivative such as a bis-styrylanthracene derivative or a distyrylbenzene derivative, a tetraphenylbutadiene derivative, a cyclopentadiene derivative, a fluorene derivative, and a benzofluorene derivative.

Furthermore, a dopant material is not particularly limited, but known compounds can be used. The dopant material can be selected from various materials according to a desired color of emitted light. Specific examples of the dopant material include a fused ring derivative of phenanthrene, anthracene, pyrene, tetracene, pentacene, perylene, naphthopyrene, dibenzopyrene, rubrene, chrysene, or the like, a benzoxazole derivative, a benzothiazole derivative, a benzimidazole derivative, a benzotriazole derivative, an oxazole derivative, an oxadiazole derivative, a triazole derivative, an imidazole derivative, a thiadiazole derivative, a triazole derivative, a pyrazoline derivative, a stilbene derivative, a thiophene derivative, a tetraphenylbutadiene derivative, a cyclopentadiene derivative, a bisstyryl derivative such as a bisstyrylanthracene derivative or a distyrylbenzene derivative (JP 1-245087 A), a bisstyrylarylene derivative (JP 2-247278 A), a diazaindacene derivative, a furan derivative, a benzofuran derivative, an isobenzofuran derivative such as phenylisobenzofuran, dimesitylisobenzofuran, di(2-methylphenyl)isobenzofuran, di(2-trifluoromethylphenyl)isobenzofuran, or phenylisobenzofuran, a dibenzofuran derivative, a coumarin derivative such as a 7-dialkylaminocoumarin derivative, a 7-piperidinocoumarin derivative, a 7-hydroxycoumarin derivative, a 7-methoxycoumarin derivative, a 7-acetoxycoumarin derivative, a 3-benzothiazolylcoumarin derivative, a 3-benzimidazolylcoumarin derivative, or a 3-benzoxazolylcoumarin derivative, a dicyanomethylenepyran derivative, a dicyanomethylenethiopyran derivative, a polymethine derivative, a cyanine derivative, an oxobenzoanthracene derivative, a xanthene derivative, a rhodamine derivative, a fluorescein derivative, a pyrylium derivative, a carbostyryl derivative, an acridine derivative, an oxazine derivative, a phenylene oxide derivative, a quinacridone derivative, a quinazoline derivative, a pyrrolopyridine derivative, a furopyridine derivative, a 1,2,5-thiadiazolopyrene derivative, a pyromethene derivative, a perinone derivative, a pyrrolopyrrole derivative, a squarylium derivative, a violanthrone derivative, a phenazine derivative, an acridone derivative, a deazaflavine derivative, a fluorene derivative, and a benzofluorene derivative.

If the examples are listed for each color of emitted light, examples of blue to bluish green dopant materials include an aromatic hydrocarbon compound such as naphthalene, anthracene, phenanthrene, pyrene, triphenylene, perylene, fluorene, indene, or chrysene, and derivatives thereof, an aromatic heterocyclic compound such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthyridine, quinoxaline, pyrrolopyridine, or thioxanthene, and derivatives thereof, a distyrylbenzene derivative, a tetraphenylbutadiene derivative, a stilbene derivative, an aldazine derivative, a coumarin derivative, an azole derivative such as imidazole, triazole, thiadiazole, carbazole, oxazole, oxadiazole, or triazole, and metal complexes thereof, and an aromatic amine derivative represented by N,N'-diphenyl-N,N'-di(3-methylphenyl)-4,4'-diphenyl-1,1'-diamine.

Furthermore, examples of a green to yellow dopant material include a coumarin derivative, a phthalimide derivative, a naphthalimide derivative, a perinone derivative, a pyrrolopyrrole derivative, a cyclopentadiene derivative, an acridone derivative, a quinacridone derivative, and a naphthacene derivative such as rubrene. Furthermore, suitable examples of the green-yellow dopant material include compounds obtained by introducing a substituent capable of shifting a wavelength to a longer wavelength, such as an aryl, a heteroaryl, an arylvinyl, an amino, or cyano to the above compounds listed as examples of the blue to bluish green dopant material.

Furthermore, examples of an orange to red dopant material include a naphthalimide derivative such as bis(diisopropylphenyl)perylene tetracarboxylic acid imide, a perinone derivative, a rare earth complex such as a Eu complex containing acetylacetone, benzoylacetone, phenanthroline, or the like as a ligand, 4-(dicyanomethylene)-2-methyl-6-(p-dimethylaminostyryl)-4H-pyran and an analogue thereof, a metal phthalocyanine derivative such as magnesium phthalocyanine or aluminum chlorophthalocyanine, a rhodamine compound, a deazaflavine derivative, a coumarin derivative, a quinacridone derivative, a phenoxazine derivative, an oxazine derivative, a quinazoline derivative, a pyrrolopyridine derivative, a squarylium derivative, a violanthrone derivative, a phenazine derivative, a phenoxazone derivative, and a thiadiazolopyrene derivative. Furthermore, suitable examples of the orange to red dopant material include compounds obtained by introducing a substituent capable of shifting a wavelength to a longer wavelength, such as an aryl, a heteroaryl, an arylvinyl, an amino, or cyano to the above compounds listed as examples of the blue to bluish green and green to yellow dopant materials.

In addition to the above compounds, a dopant can be appropriately selected for use from compounds and the like described in "Kagaku Kogyo (Chemical Industry)", June 2004, p. 13, and reference documents and the like described therein.

Among the dopant materials described above, an amine having a stilbene structure, aperylene derivative, aborane derivative, an aromatic amine derivative, a coumarin derivative, a pyran derivative, and a pyrene derivative are particularly preferable.

An amine having a stilbene structure is represented by the following formula, for example.

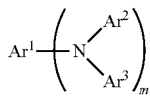

In the formula, Ar¹ represents an m-valent group derived from an aryl having 6 to 30 carbon atoms, and Ar² and Ar³ each independently represent an aryl having 6 to 30 carbon atoms, while at least one of Ar¹ to Ar³ has a stilbene structure, Ar¹ to Ar³ may be substituted by an aryl, a heteroaryl, an alkyl, a trisubstituted silyl (a silyl trisubstituted by an aryl and/or an alkyl), or a cyano, and m represents an integer of 1 to 4.

The amine having a stilbene structure is more preferably a diaminostilbene represented by the following formula.

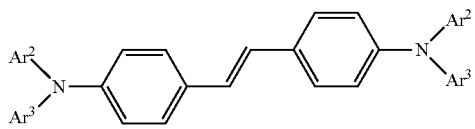

In the formula, Ar² and Ar³ each independently represent an aryl having 6 to 30 carbon atoms, while Ar² and Ar³ may be substituted by an aryl, a heteroaryl, an alkyl, a trisubstituted silyl (a silyl trisubstituted by an aryl and/or an alkyl), or a cyano.

Specific examples of the aryl having 6 to 30 carbon atoms include phenyl, naphthyl, acenaphthylenyl, fluorenyl, phenalenyl, phenanthrenyl, anthryl, fluoranthenyl, triphenylenyl, pyrenyl, chrysenyl, naphthacenyl, peryle, stilbenyl, distyrylphenyl, distyrylbiphenylyl, and distyrylfluorenyl.

Specific examples of the amine having a stilbene structure include N,N,N',N'-tetra(4-biphenylyl)-4,4'-diaminostilbene, N,N,N',N'-tetra(1-naphthyl)-4,4'-diaminostilbene, N,N,N',N'-tetra(2-naphthyl)-4,4'-diaminostilbene, N,N'-di(2-naphthyl)-N,N'-diphenyl-4,4'-diaminostilbene, N,N'-di(9-phenanthryl)-N,N'-diphenyl-4,4'-diaminostilbene, 4,4'-bis[4"-bis(diphenylamino)styryl]-biphenyl, 1,4-bis[4'-bis(diphenylamino)styryl]-benzene, 2,7-bis[4'-bis(diphenylamino)styryl]-9,9-dimethylfluorene, 4,4'-bis(9-ethyl-3-carbazovinylene)-biphenyl, and 4,4'-bis(9-phenyl-3-carbazovinylene)-biphenyl.

Furthermore, amines having a stilbene structure described in JP 2003-347056 A, JP 2001-307884 A, and the like may also be used.

Examples of the perylene derivative include 3,10-bis(2,6-dimethylphenyl)perylene, 3,10-bis(2,4,6-trimethylphenyl)perylene, 3,10-diphenylperylene, 3,4-diphenylperylene, 2,5,8,11-tetra-t-butylperylene, 3,4,9,10-tetraphenylperylene, 3-(1'-pyrenyl)-8,11-di(t-butyl)perylene, 3-(9'-anthryl)-8,11-di(t-butyl)perylene, and 3,3'-bis(8,11-di(t-butyl)perylenyl).

Furthermore, perylene derivatives described in JP 11-97178 A, JP 2000-133457 A, JP 2000-26324 A, JP 2001-267079 A, JP 2001-267078A, JP2001-267076A, JP 2000-34234A, JP2001-267075 A, JP 2001-217077 A, and the like may also be used.

Examples of the borane derivative include 1,8-diphenyl-10-(dimesitylboryl) anthracene, 9-phenyl-10-(dimesitylboryl) anthracene, 4-(9'-anthryl) dimesitylborylnaphthalene, 4-(10'-phenyl-9'-anthryl) dimesitylborylnaphthalene, 9-(dimesitylboryl) anthracene, 9-(4'-biphenylyl)-10-(dimesitylboryl) anthracene, and 9-(4'-(N-carbazolyl)phenyl)-10-(dimesitylboryl) anthracene.

Furthermore, borane derivatives described in WO 2000/40586 A and the like may also be used.

An aromatic amine derivative is represented by the following formula, for example.

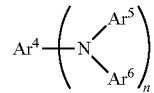

In the formula, Ar⁴ represents an n-valent group derived from an aryl having 6 to 30 carbon atoms, and Ar⁵ and Ar⁶ each independently represent an aryl having 6 to 30 carbon atoms, while Ar⁴ to Ar⁶ may be substituted by an aryl, a heteroaryl, an alkyl, a trisubstituted silyl (a silyl trisubstituted by an aryl and/or an alkyl), or a cyano, and n represents an integer of 1 to 4.

Particularly, an aromatic amine derivative in which Ar⁴ represents a divalent group derived from anthracene, chrysene, fluorene, benzofluorene, or pyrene, Ar⁵ and Ar⁶ each independently represent an aryl having 6 to 30 carbon atoms, Ar⁴ to Ar⁶ may be substituted by an aryl, a heteroaryl, an alkyl, a trisubstituted silyl (a silyl trisubstituted by an aryl and/or an alkyl), or a cyano, and n represents 2, is more preferable.

Specific examples of the aryl having 6 to 30 carbon atoms include phenyl, naphthyl, acenaphthylenyl, fluorenyl, phenalenyl, phenanthrenyl, anthryl, fluoranthenyl, triphenylenyl, pyrenyl, chrysenyl, naphthacenyl, perylenyl, and pentacenyl.

Examples of a chrysene-based aromatic amine derivative include N,N,N',N'-tetraphenylchrysene-6,12-diamine, N,N,N',N'-tetra(p-tolyl)chrysene-6,12-diamine, N,N,N',N'-tetra(m-tolyl)chrysene-6,12-diamine, N,N,N',N'-tetrakis(4-isopropylphenyl)chrysene-6,12-diamine, N,N,N',N'-tetra(naphthalen-2-yl)chrysene-6,12-dimine, N,N'-diphenyl-N,N'-di(p-tolyl)chrysene-6,12-diamine, N,N'-diphenyl-N,N'-bis(4-ethylphenyl)chrysene-6,12-diamine, N,N'-diphenyl-N,N'-bis(4-ethylphenyl)chrysene-6,12-diamine, N,N'-diphenyl-N,N'-bis(4-isopropylphenyl)chrysene-6,12-diamine, N,N'-diphenyl-N,N'-bis(4-t-butylphenyl)chrysene-6,12-diamine, and N,N'-bis(4-isopropylphenyl)-N,N'-di(p-tolyl)chrysene-6,12-diamine.

Furthermore, examples of a pyrene-based aromatic amine derivative include N,N,N',N'-tetraphenylpyrene-1,6-diamine, N,N,N',N'-tetra(p-tolyl)pyrene-1,6-diamine, N,N,N',N'-tetra(m-tolyl)pyrene-1,6-diamine, N,N,N',N'-tetrakis(4-isopropyophenyl)pyrene-1,6-diamine, N,N,N',N'-tetrakis(3,4-dimethylphenyl)pyrene-1,6-diamine, N,N'-diphenyl-N,N'-di(p-tolyl)pyrene-1,6-diamine, N,N'-diphenyl-N,N'-bis(4-ethylphenyl)pyrene-1,6-diamine, N,N'-diphenyl-N,N'-bis(4-ethylphenyl)pyrene-1,6-diamine, N,N'-diphenyl-N,N'-bis(4-isopropylphenyl)pyrene-1,6-diamine, N,N'-diphenyl-N,N'-bis(4-t-butylphenyl)pyrene-1,6-diamine, N,N'-bis(4-isopropylphenyl)-N,N'-di(p-tolyl)pyrene-1,6-diamine, N,N,N',N'-tetrakis(3,4-dimethylphenyl)-3,8-diphenylpyrene-1,6-diamine, N,N,N,N-tetraphenylpyrene-1,8-diamine, N,N'-bis(biphenyl-4-yl)-N,N'-diphenylpyrene-1,8-diamine, and N¹,N⁶-diphenyl-N¹,N⁶-bis(4-trimethylsilanyl-phenyl)-1H,8H-pyrene-1,6-diamine.

Furthermore, examples of an anthracene-based aromatic amine derivative include N,N,N,N-tetraphenylanthracene-9,10-diamine, N,N,N',N'-tetra(p-tolyl)anthracene-9,10-diamine, N,N,N',N'-tetra(m-tolyl)anthracene-9,10-diamine, N,N,N',N'-tetrakis(4-isopropylphenyl)anthracene-9,10-diamine, N,N'-diphenyl-N,N'-di(p-tolyl)anthracene-9,10-diamine, N,N'-diphenyl-N,N'-di(m-tolyl)anthracene-9,10-diamine, N,N'-diphenyl-N,N'-bis(4-ethylphenyl)anthracene-9,10-diamine, N,N'-diphenyl-N,N'-bis(4-ethylphenyl)anthracene-9,10-diamine, N,N'-diphenyl-N,N'-bis(4-isopropylphenyl)anthracene-9,10-diamine, N,N'-diphenyl-N,N'-bis(4-t-butylphenyl)anthracene-9,10-diamine, N,N'-bis(4-isopropylphenyl)-N,N'-di(p-tolyl)anthracene-9,10-diamine, 2,6-di-t-butyl-N,N,N',N'-tetra(p-tolyl)anthracene-9,10-diamine, 2,6-di-t-butyl-N,N'-diphenyl-N,N'-bis(4-isopropylphenyl)anthracene-9,10-diamine, 2,6-di-t-butyl-N,N'-bis(4-isopropylphenyl)-N,N'-di(p-tolyl)anthracene-9,10-diamine, 2,6-dicyclohexyl-N,N'-bis(4-isopropylphenyl)-N,N'-di(p-tolyl)anthracene-9,10-diamine, 2,6-dicyclohexyl-N,N'-bis(4-isopropylphenyl)-N,N'-bis(4-t-butylphenyl)anthracene-9,10-diamine, 9,10-bis(4-diphenylaminophenyl)anthracene, 9,10-bis(4-di(1-naphthylamino)phenyl)anthracene, 9,10-bis(4-di(2-naphthylamino)phenyl)anthracene, 10-di-p-tolylamino-9-(4-di-p-tolylamino-1-naphthyl)anthracene, 10-diphenylamino-9-(4-diphenylamino-1-naphthyl)anthracene, and 10-diphenylamino-9-(6-diphenylamino-2-naphthyl)anthracene.

Furthermore, other examples include [4-(4-diphenylamino-phenyl)naphthalen-1-yl]-diphenylamine, [6-(4-diphenylamino-phenyl)naphthalen-2-yl]-diphenylamine, 4,4'-bis[4-diphenylaminonaphthalen-1-yl]biphenyl, 4,4'-bis[6-diphenylaminonaphthalen-2-yl]biphenyl, 4,4"-bis[4-diphenylaminonaphthalen-1-yl]-p-terphenyl, and 4,4"-bis[6-diphenylaminonaphthalen-2-yl]-p-terphenyl.

Furthermore, an aromatic amine derivative described in JP 2006-156888 A or the like may also be used.

Examples of the coumarin derivative include coumarin-6 and coumarin-334.

Furthermore, a coumarin derivative described in JP 2004-43646 A, JP 2001-76876 A, JP 6-298758 A, or the like may also be used.

Examples of the pyran derivative include DCM and DCJTB described below.

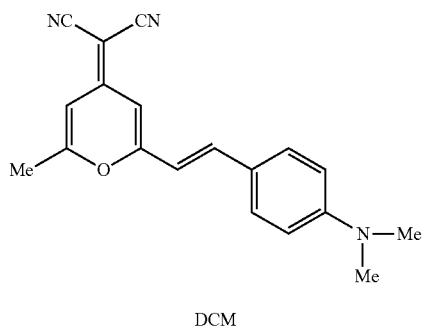

DCM

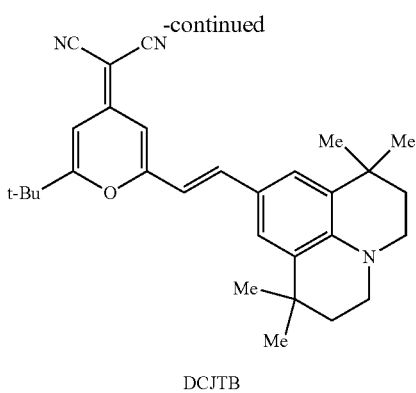

DCJTB

Furthermore, a pyran derivative described in JP 2005-126399 A, JP 2005-097283 A, JP 2002-234892 A, JP 2001-220577 A, JP 2001-081090 A, JP 2001-052869 A, or the like may also be used.

<Electron Injection Layer and Electron Transport Layer in Organic Electroluminescent Element>

The electron injection layer 107 plays a role of efficiently injecting an electron migrating from the cathode 108 into the light emitting layer 105 or the electron transport layer 106. The electron transport layer 106 plays a role of efficiently transporting an electron injected from the cathode 108, or an electron injected from the cathode 108 through the electron injection layer 107 to the light emitting layer 105. The electron transport layer 106 and the electron injection layer 107 are each formed by laminating and mixing one or more kinds of electron transport/injection materials, or by a mixture of an electron transport/injection material and a polymer binder.

The electron injection/transport layer manages injection of an electron from a cathode and further manages transport of an electron, and desirably has a high electron injection efficiency and can efficiently transport an injected electron. For this purpose, a substance which has high electron affinity and large electron mobility, and further has excellent stability, and in which impurities serving as traps are not easily generated at the time of manufacturing and at the time of use, is preferable. However, when a transport balance between a hole and an electron is considered, in a case where the electron injection/transport layer mainly plays a role of efficiently preventing a hole coming from an anode from flowing toward a cathode side without being recombined, even if electron transport ability is not so high, the electron injection/transport layer has an effect of enhancing a light emission efficiency equally to a material having high electron transport ability. Therefore, the electron injection/transport layer according to the present embodiment may also include a function of a layer capable of efficiently preventing migration of a hole.

As the material to form the electron transport layer 106 or the electron injection layer 107 (electron transport material), the azoline ring-containing compound represented by the above general formula (1) can be used. Furthermore, a material can be arbitrarily selected for use from compounds that have been conventionally used as electron transfer compounds in a photoconductive material, and known compounds used in an electron injection layer and an electron transport layer of an organic electroluminescent element.

A material used in an electron transport layer or an electron injection layer preferably includes at least one selected from a compound formed of an aromatic ring or a heteroaromatic ring including one or more kinds of atoms selected from carbon, hydrogen, oxygen, sulfur, silicon, and phosphorus atoms, a pyrrole derivative and a fused ring derivative thereof, and a metal complex having an electron-accepting nitrogen atom. Specific examples of the material include a fused ring-based aromatic ring derivative of naphthalene, anthracene, or the like, a styryl-based aromatic ring derivative represented by 4,4'-bis(diphenylethenyl)biphenyl, a perinone derivative, a coumarin derivative, a naphthalimide derivative, a quinone derivative such as anthraquinone or diphenoquinone, a phosphorus oxide derivative, a carbazole derivative, and an indole derivative. Examples of the metal complex having an electron-accepting nitrogen atom include a hydroxyazole complex such as a hydroxyphenyloxazole complex, an azomethine complex, a tropolone metal complex, a flavonol metal complex, and a benzoquinoline metal complex. These materials are used singly, but may also be used in a mixture with other materials.

Furthermore, specific examples of other electron transfer compounds include a pyridine derivative, a naphthalene derivative, an anthracene derivative, a phenanthroline derivative, a perinone derivative, a coumarin derivative, a naphthalimide derivative, an anthraquinone derivative, a diphenoquinone derivative, a diphenylquinone derivative, a perylene derivative, an oxadiazole derivative (1,3-bis[(4-t-butylphenyl)-1,3,4-oxadiazolyl]phenylene and the like), a thiophene derivative, a triazole derivative (N-naphthyl-2,5-diphenyl-1,3,4-triazole and the like), a thiadiazole derivative, a metal complex of an oxine derivative, a quinolinol-based metal complex, a quinoxaline derivative, a polymer of a quinoxaline derivative, a benzazole compound, a gallium complex, a pyrazole derivative, a perfluorinated phenylene derivative, a triazine derivative, a pyrazine derivative, a benzoquinoline derivative (2,2'-bis(benzo[h]quinolin-2-yl)-9,9'-spirobifluorene and the like), an imidazopyridine derivative, a borane derivative, a benzimidazole derivative (tris(N-phenylbenzimidazol-2-yl)benzene and the like), a benzoxazole derivative, a benzothiazole derivative, a quinoline derivative, an oligopyridine derivative such as terpyridine, a bipyridine derivative, a terpyridine derivative (1,3-bis (4'-(2,2': 6'2"-terpyridinyl)) benzene and the like), a naphthyridine derivative (bis(1-naphthyl)-4-(1,8-naphthyridin-2-yl)phenylphosphine oxide and the like), an aldazine derivative, a carbazole derivative, an indole derivative, a phosphorus oxide derivative, and a bisstyryl derivative.

Furthermore, a metal complex having an electron-accepting nitrogen atom can be also used, and examples thereof include a quinolinol-based metal complex, a hydroxyazole complex such as a hydroxyphenyloxazole complex, an azomethine complex, a tropolone metal complex, a flavonol metal complex, and a benzoquinoline metal complex.

The materials described above are used singly, but may also be used in a mixture with other materials.

Among the materials described above, a quinolinol-based metal complex, a bipyridine derivative, a phenanthroline derivative, and a borane derivative are preferable.

The quinolinol-based metal complex is a compound represented by the following general formula (E-1).

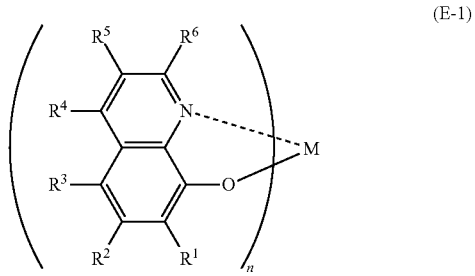

In the formula, $R^1$ to $R^6$ each independently represent a hydrogen atom, a fluorine atom, an alkyl, an aralkyl, an alkenyl, a cyano, an alkoxy, or an aryl, M represents Li, Al, Ga, Be, or Zn, and n represents an integer of 1 to 3.

Specific examples of the quinolinol-based metal complex include 8-quinolinollithium, tris(8-quinolinolato)aluminum, tris(4-methyl-8-quinolinolato)aluminum, tris(5-methyl-8-quinolinolato)aluminum, tris(3,4-dimethyl-8-quiolinolato)aluminum, tris(4,5-dimethyl-8-quinolinolato)aluminum, tris (4,6-dimethyl-8-quinolinolato)aluminum, bis(2-methyl-8-quinolinolato) (phenolato)aluminum, bis(2-methyl-8-quinolinolato) (2-methylphenolato)aluminum, bis(2-methyl-8-quinolinolato) (3-methylphenolato)aluminum, bis (2-methyl-8-quinolinolato) (4-methylphenolato)aluminum, bis(2-methyl-8-quinolinolato) (2-phenylphenolato)aluminum, bis(2-methyl-8-quinolinolato) (3-phenylphenolato) aluminum, bis(2-methyl-8-quinolinolato) (4-phenylphenolato)aluminum, bis(2-methyl-8-quinolinolato) (2,3-dimethylphenolato)aluminum, bis(2-methyl-8-quinolinolato) (2,6-dimethylphenolato)aluminum, bis(2-methyl-8-quinolinolato) (3,4-dimethylphenolato)aluminum, bis(2-methyl-8-quinolinolato) (3,5-dimethylphenolato)aluminum, bis(2-methyl-8-quinolinolato) (3,5-di-t-butylphenolato)aluminum, bis(2-methyl-8-quinolinolato) (2,6-diphenylphenolato)aluminum, bis(2-methyl-8-quinolinolato) (2,4,6-triphenylphenolato)aluminum, bis(2-methyl-8-quinolinolato) (2,4,6-trimethylphenolato)aluminum, bis(2-methyl-8-quinolinolato) (2,4,5,6-tetramethylphenolato)aluminum, bis(2-methyl-8-quinolinolato) (1-naphtholato) aluminum, bis(2-methyl-8-quinolinolato) (2-naphtholato) aluminum, bis(2,4-dimethyl-8-quinolinolato) (2-phenylphenolato)aluminum, bis(2,4-dimethyl-8-quinolinolato) (3-phenylphenolato)aluminum, bis(2,4-dimethyl-8-quinolinolato) (4-phenylphenolato)aluminum, bis(2,4-dimethyl-8-quinolinolato) (3,5-dimethylphenolato)aluminum, bis(2,4-dimethyl-8-quinolinolato) (3,5-di-t-butylphenolato) aluminum, bis(2-methyl-8-quinolinolato)aluminum-p-oxo-bis(2-methyl-8-quinolinolato)aluminum, bis(2,4-dimethyl-8-quinolinolato)aluminum-p-oxo-bis(2,4-dimethyl-8-quinolinolato)aluminum, bis(2-methyl-4-ethyl-8-quinolinolato)aluminum-p-oxo-bis(2-methyl-4-ethyl-8-quinolinolato)aluminum, bis(2-methyl-4-methoxy-8-quinolinolato)aluminum-p-oxo-bis(2-methyl-4-methoxy-8-quinolinolato)aluminum, bis(2-methyl-5-cyano-8-quinolinolato)aluminum-p-oxo-bis(2-methyl-5-cyano-8-quinolinolato)aluminum, bis(2-methyl-5-trifluoromethyl-8-quinolinolato)aluminum-p-oxo-bis(2-methyl-5-trifluoromethyl-8-quiolinolato)aluminum, and bis(10-hydroxybenzo[h]quinoline)beryllium.

The bipyridine derivative is a compound represented by the following general formula (E-2).

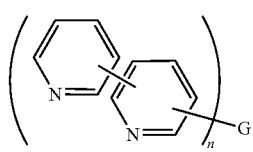 (E-2)

In the formula, G represents a simple bond or an n-valent linking group, and n represents an integer of 2 to 8. A carbon not used for a pyridine-pyridine bond or a pyridine-G bond may be substituted by an aryl, a heteroaryl, an alkyl, or a cyano.

Examples of G in general formula (E-2) include groups represented by the following structural formulas. Note that R's in the following structural formulas each independently represent a hydrogen atom, methyl, ethyl, isopropyl, cyclohexyl, phenyl, 1-naphthyl, 2-naphthyl, biphenylyl, or terphenylyl.

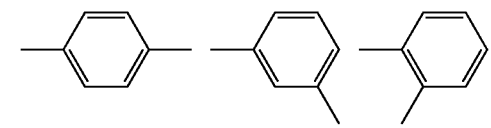

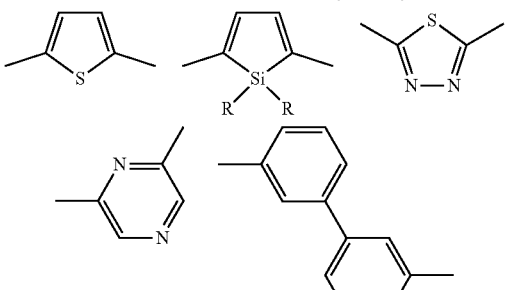

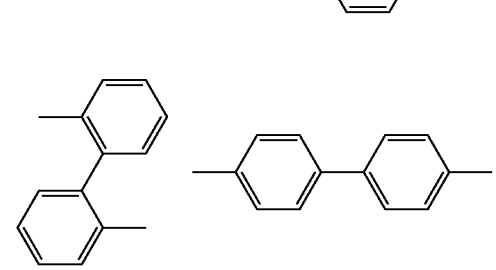

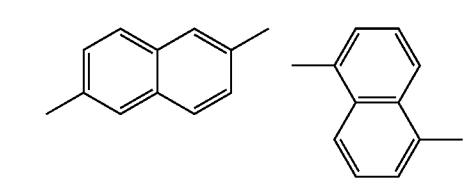

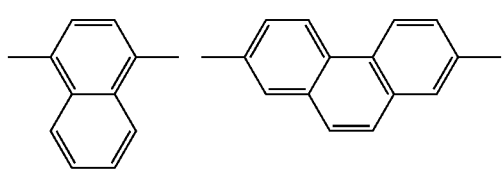

-continued

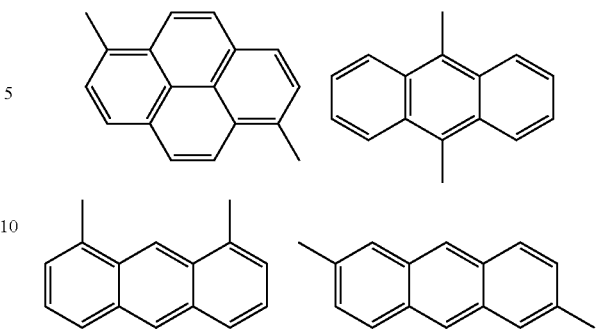

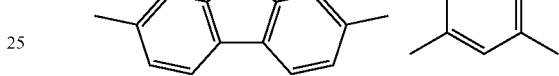

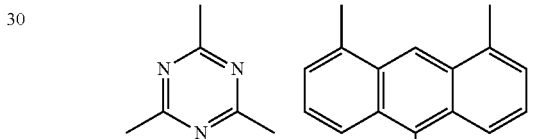

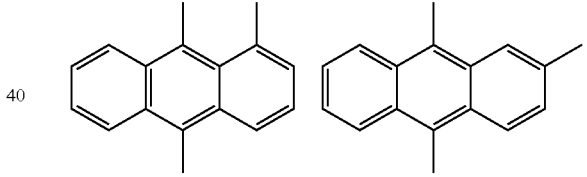

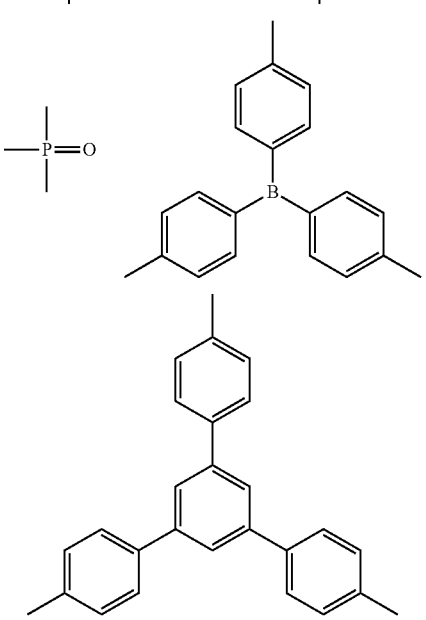

523
-continued

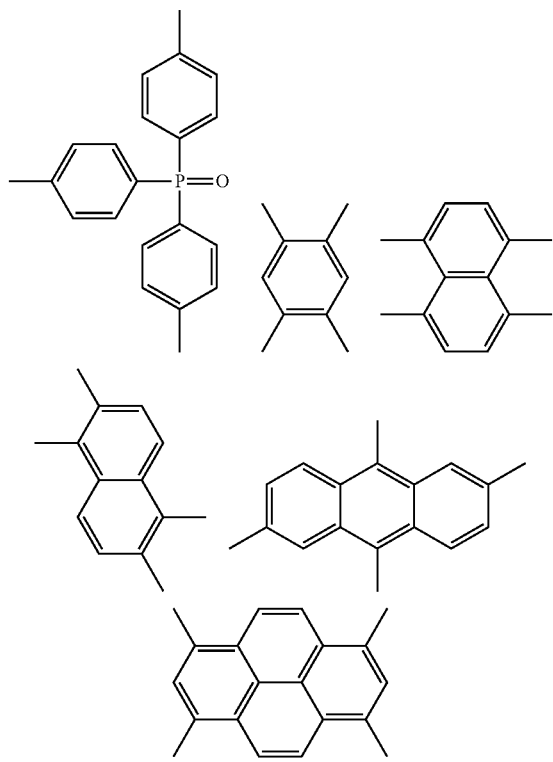

Specific examples of the pyridine derivative include 2,5-bis(2,2'-pyridin-6-yl)-1,1-dimethyl-3,4-diphenylsilole, 2,5-bis(2,2'-pyridin-6-yl)-1,1-dimethyl-3,4-dimesitylsilole, 2,5-bis(2,2'-pyridin-5-yl)-1,1-dimethyl-3,4-diphenylsilole, 2,5-bis(2,2'-pyridin-5-yl)-1,1-dimethyl-3,4-dimesitylsilole, 9,10-di(2,2'-pyridin-6-yl)anthracene, 9,10-di(2,2'-pyridin-5-yl)anthracene, 9,10-di(2,3'-pyridin-6-yl)anthracene, 9,10-di(2,3'-pyridin-5-yl)anthracene, 9,10-di(2,3'-pyridin-6-yl)-2-phenylanthracene, 9,10-di(2,3'-pyridin-5-yl)-2-phenylanthracene, 9,10-di(2,2'-pyridin-6-yl)-2-phenylanthracene, 9,10-di(2,2'-pyridin-5-yl)-2-phenylanthracene, 9,10-di(2,4'-pyridin-6-yl)-2-phenylanthracene, 9,10-di(2,4'-pyridin-5-yl)-2-phenylanthracene, 9,10-di(3,4'-pyridin-6-yl)-2-phenylanthracene, 9,10-di(3,4'-pyridin-5-yl)-2-phenylanthracene, 3,4-diphenyl-2,5-di(2,2'-pyridin-6-yl)thiophene, 3,4-diphenyl-2,5-di(2,3'-pyridin-5-yl)thiophene, and 6',6"-di(2-pyridyl)-2,2':4',4":2",2'"-quaterpyridine.

The phenanthroline derivative is a compound represented by the following general formula (E-3-1) or (E-3-2).

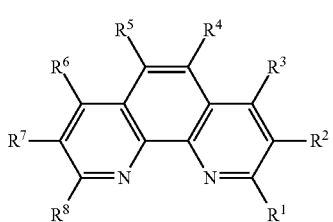

(E-3-1)

524
-continued

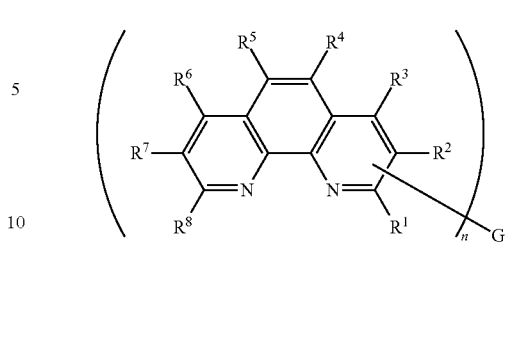

(E-3-2)

In the formula, $R^1$ to $R^8$ each independently represent a hydrogen atom, an alkyl (a methyl, an ethyl, an isopropyl, a hydroxyethyl, a methoxymethyl, a trifluoromethyl, a t-butyl, a cyclopentyl, a cyclohexyl, a benzyl, or the like), an alkyloxy (a methoxy, an ethoxy, an isopropoxy, a butoxy, or the like), an aryloxy (a phenoxy, a 1-naphthyloxy, a 4-tolyloxy, or the like), a halogen atom (a fluorine atom, a chlorine atom, a bromine atom, an iodine atom, or the like), an aryl (a phenyl, a naphthyl, a p-tolyl, a p-chlorophenyl, or the like), an alkylthio (a methylthio, an ethylthio, an isopropylthio, or the like), an arylthio (a phenylthio or the like), a cyano, a nitro, and a heterocyclic ring (a pyrrole, a pyrrolidyl, a pyrazolyl, an imidazolyl, a pyridyl, a benzimidazolyl, a benzthiazolyl, a benzoxazolyl, or the like). An alkyl or a halogen atom is preferable. A methyl, an ethyl, an isopropyl, or a fluorine atom is more preferable. Adjacent groups may be bonded to each other to form a fused ring. G represents a simple bond or an n-valent linking group, and n represents an integer of 2 to 8. Examples of G of general formula (E-3-2) include the same groups as those described in the section of the bipyridine derivative. In the above formula (E-3-2), any one of $R^1$ to $R^8$ is bonded to G.

Specific examples of the phenanthroline derivative include 4,7-diphenyl-1,10-phenanthroline, 2,9-dimethyl-4,7-diphenyl-1,10-phenanthroline, 9,10-di(1,10-phenanthrolin-2-yl)anthracene, 2,6-di(1,10-phenanthrolin-5-yl)pyridine, 1,3,5-tri(1,10-phenanthrolin-5-yl)benzene, 9,9'-difluoro-bi(1,10-phenanthrolin-5-yl), bathocuproine, and 1,3-bis(2-phenyl-1,10-phenanthrolin-9-yl)benzene.

Particularly, a case of using a phenanthroline derivative in an electron transport layer or an electron injection layer will be described. In order to obtain stable light emission over a long time, a material having excellent thermal stability or thin film formability is desired. Among phenanthroline derivatives, a phenanthroline derivative in which a substituent itself has a three-dimensional steric structure, a phenanthroline derivative having a three-dimensional steric structure as a result of steric repulsion between a substituent and a phenanthroline skeleton or between a substituent and an adjacent substituent, or a phenanthroline derivative having a plurality of phenanthroline skeletons linked together, is preferable. Furthermore, in a case of linking a plurality of phenanthroline skeletons, a compound containing a conjugated bond, a substituted or unsubstituted aromatic hydrocarbon, or a substituted or unsubstituted heterocyclic aromatic ring in a linked unit, is more preferable.

The borane derivative is a compound represented by the following general formula (E-4), specific examples of which are disclosed in JP 2007-27587 A.

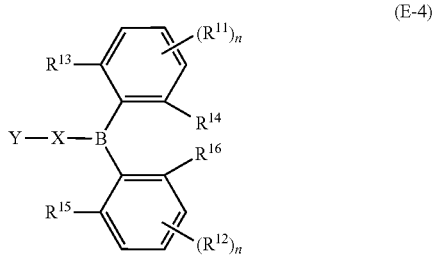

(E-4)

In the formula, $R^{11}$ and $R^{12}$ each independently represent at least one of a hydrogen atom, an alkyl, an optionally substituted aryl, a substituted silyl, an optionally substituted nitrogen-containing heterocyclic ring, and cyano, $R^{13}$ to $R^{16}$ each independently represent an optionally substituted alkyl or an optionally substituted aryl, X represents an optionally substituted arylene, Y represents an optionally substituted aryl having 16 or fewer carbon atoms, a substituted boryl, or an optionally substituted carbazolyl, and n's each independently represent an integer of 0 to 3. Examples of a substituent in a case of being "optionally substituted" or "substituted" include an aryl, a heteroaryl, and an alkyl.

Among compounds represented by the above general formula (E-4), a compound represented by the following general formula (E-4-1) is preferable, and compounds represented by the following general formulas (E-4-1-1) to (E-4-1-4) are more preferable.

Specific examples of the compounds include 9-[4-(4-dimesitylborylnaphthalen-1-yl) phenyl]carbazole and 9-[4-(4-dimesitylborylnaphthalen-1-yl) naphthalen-1-yl]carbazole.

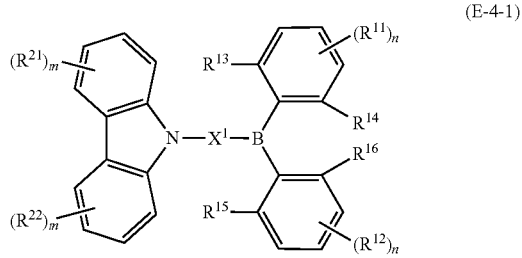

(E-4-1)

In the formula, $R^{11}$ and $R^{12}$ each independently represent at least one of a hydrogen atom, an alkyl, an optionally substituted aryl, a substituted silyl, an optionally substituted nitrogen-containing heterocyclic ring, and cyano, $R^{13}$ to $R^{16}$ each independently represent an optionally substituted alkyl or an optionally substituted aryl, $R^{21}$ and $R^{22}$ each independently represent at least one of a hydrogen atom, an alkyl, an optionally substituted aryl, a substituted silyl, an optionally substituted nitrogen-containing heterocyclic ring, and cyano, $X^1$ represents an optionally substituted arylene having 20 or fewer carbon atoms, n's each independently represent an integer of 0 to 3, and m's each independently represent an integer of 0 to 4. Examples of a substituent in a case of being "optionally substituted" or "substituted" include an aryl, a heteroaryl, and an alkyl.

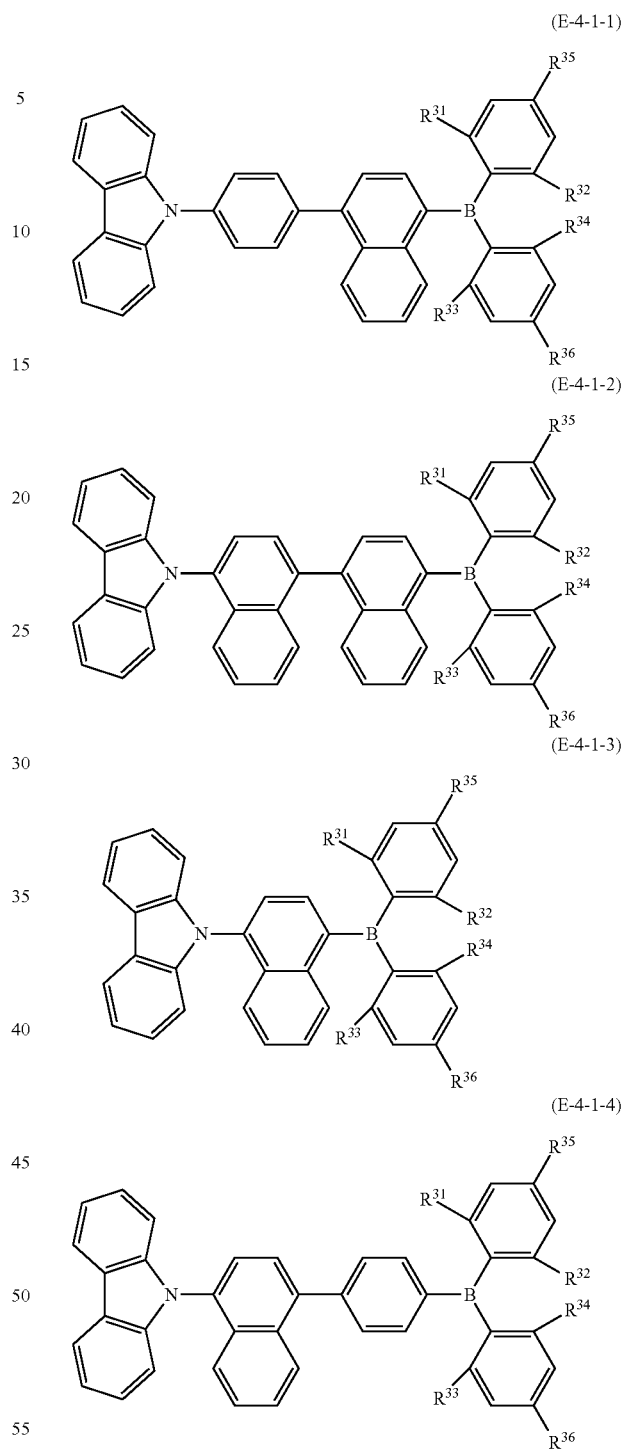

In each of the formulas, $R^{31}$ to $R^{34}$ each independently represent any one of methyl, isopropyl, and phenyl, and $R^{35}$ and $R^{36}$ each independently represent any one of a hydrogen atom, methyl, isopropyl, and phenyl.

Among compounds represented by the above general formula (E-4), a compound represented by the following general formula (E-4-2) is preferable, and a compound represented by the following general formula (E-4-2-1) is more preferable.

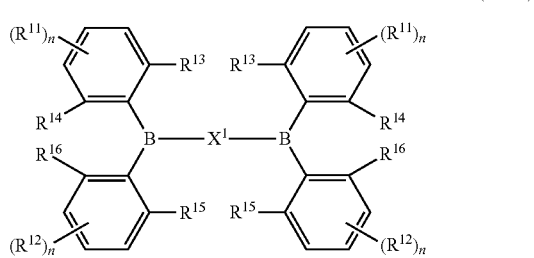

(E-4-2)

In the formula, $R^{11}$ and $R^{12}$ each independently represent at least one of a hydrogen atom, an alkyl, an optionally substituted aryl, a substituted silyl, an optionally substituted nitrogen-containing heterocyclic ring, and cyano, $R^{13}$ to $R^{16}$ each independently represent an optionally substituted alkyl or an optionally substituted aryl, $X^1$ represents an optionally substituted arylene having 20 or fewer carbon atoms, and n's each independently represent an integer of 0 to 3. Examples of a substituent in a case of being "optionally substituted" or "substituted" include an aryl, a heteroaryl, and an alkyl.

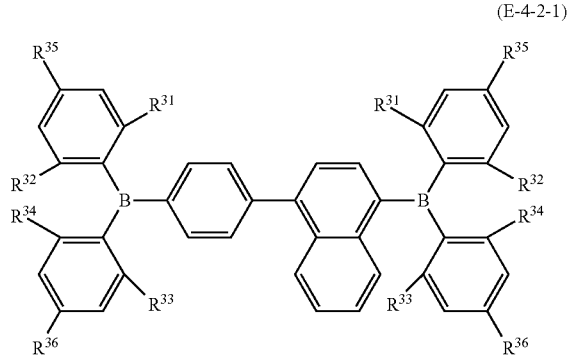

(E-4-2-1)

In the formula, $R^{31}$ to $R^{34}$ each independently represent any one of methyl, isopropyl, and phenyl, and $R^{35}$ and $R^{36}$ each independently represent any one of a hydrogen atom, methyl, isopropyl, and phenyl.

Among compounds represented by the above general formula (E-4), a compound represented by the following general formula (E-4-3) is preferable, and a compound represented by the following general formula (E-4-3-1) or (E-4-3-2) is more preferable.

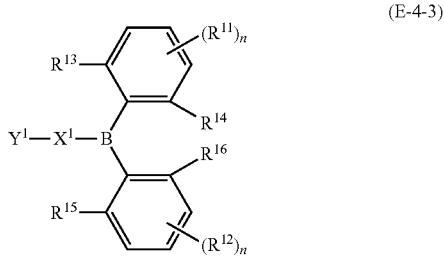

(E-4-3)

In the formula, $R^{11}$ and $R^{12}$ each independently represent at least one of a hydrogen atom, an alkyl, an optionally substituted aryl, a substituted silyl, an optionally substituted nitrogen-containing heterocyclic ring, and cyano, $R^{13}$ to $R^{16}$ each independently represent an optionally substituted alkyl or an optionally substituted aryl, $X^1$ represents an optionally substituted arylene having 10 or fewer carbon atoms, $Y^1$ represents an optionally substituted aryl having 14 or fewer carbon atoms, and n's each independently represent an integer of 0 to 3. Examples of a substituent in a case of being "optionally substituted" or "substituted" include an aryl, a heteroaryl, and an alkyl.

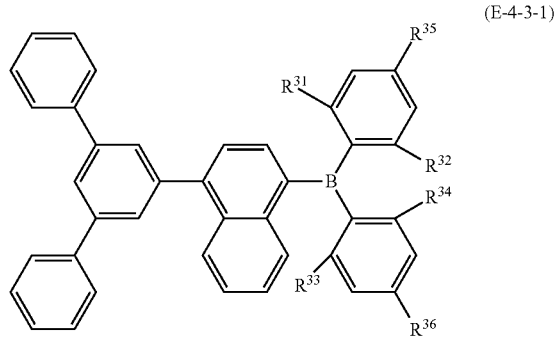

(E-4-3-1)

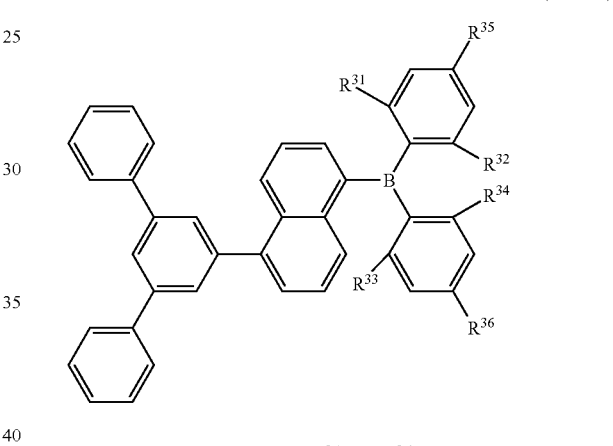

(E-4-3-2)

In each of the formulas, $R^{31}$ to $R^{34}$ each independently represent any one of methyl, isopropyl, and phenyl, and $R^{35}$ and $R^{36}$ each independently represent any one of a hydrogen atom, methyl, isopropyl, and phenyl.

The benzimidazole derivative is a compound represented by the following general formula (E-5).

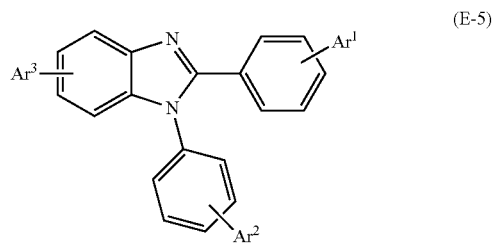

(E-5)

In the formula, $Ar^1$ to $Ar^3$ each independently represent a hydrogen atom or an optionally substituted aryl having 6 to 30 carbon atoms. Examples of a substituent in a case of being "optionally substituted" include an aryl, a heteroaryl, an alkyl, and a cyano. Particularly, a benzimidazole derivative in which $Ar^1$ is an anthryl optionally substituted by an aryl, a heteroaryl, an alkyl, or a cyano is preferable.

Specific examples of the aryl having 6 to 30 carbon atoms include phenyl, 1-naphthyl, 2-naphthyl, acenaphthylen-1-yl, acenaphthylen-3-yl, acenaphthylen-4-yl, acenaphthylen-5-yl, fluoren-1-yl, fluoren-2-yl, fluoren-3-yl, fluoren-4-yl, fluoren-9-yl, phenalen-1-yl, phenalen-2-yl, 1-phenanthryl, 2-phenanthryl, 3-phenanthryl, 4-phenanthryl, 9-phenanthryl, 1-anthryl, 2-anthryl, 9-anthryl, fluoranthen-1-yl, fluoranthen-2-yl, fluoranthen-3-yl, fluoranthen-7-yl, fluoranthen-8-yl, triphenylen-1-yl, triphenylen-2-yl, pyren-1-yl, pyren-2-yl, pyren-4-yl, chrysen-1-yl, chrysen-2-yl, chrysen-3-yl, chrysen-4-yl, chrysen-5-yl, chrysen-6-yl, naphthacen-1-yl, naphthacen-2-yl, naphthacen-5-yl, perylen-1-yl, perylen-2-yl, perylen-3-yl, pentacen-1-yl, pentacen-2-yl, pentacen-5-yl, and pentacen-6-yl.

Specific examples of the benzimidazole derivative include 1-phenyl-2-(4-(10-phenylanthracen-9-yl)phenyl)-1H-benzo[d]imidazole, 2-(4-(10-(naphthalen-2-yl)anthracen-9-yl)phenyl)-1-phenyl-1H-benzo[d]imidazole, 2-(3-(10-(naphthalen-2-yl)anthracen-9-yl)phenyl)-1-phenyl-1H-benzo[d]imidazole, 5-(10-(naphthlen-2-yl)anthracen-9-yl)-1,2-diphenyl-1H-benzo[d]imidazole, 1-(4-(10-(naphthalen-2-yl)anthracen-9-yl)phenyl)-2-phenyl-1H-benzo[d]imidazole, 2-(4-(9,10-di(naphthalen-2-yl)anthracen-2-yl)phenyl)-1-phenyl-1H-benzo[d]imidazole, 1-(4-(9,10-di(naphthalen-2-yl)anthracen-2-yl)phenyl)-2-phenyl-1H-benzo[d]imidazole, and 5-(9,10-di(naphthalen-2-yl)anthracen-2-yl)-1,2-diphenyl-1H-benzo[d]imidazole.

An electron transport layer or an electron injection layer may further contain a substance capable of reducing a material to form the electron transport layer or the electron injection layer. As this reducing substance, various substances are used as long as having reducibility to a certain extent. For example, at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal, can be suitably used.

Preferable examples of the reducing substance include alkali metals such as Na (work function 2.36 eV), K (work function 2.28 eV), Rb (work function 2.16 eV), and Cs (work function 1.95 eV); and alkaline earth metals such as Ca (work function 2.9 eV), Sr (work function 2.0 to 2.5 eV), and Ba (work function 2.52 eV). A reducing substance having a work function of 2.9 eV or less is particularly preferable. Among these substances, an alkali metal such as K, Rb, or Cs is a more preferable reducing substance, Rb or Cs is a still more preferable reducing substance, and Cs is the most preferable reducing substance. These alkali metals have particularly high reducing ability, and can enhance emission luminance of an organic EL element or can lengthen a lifetime thereof by adding the alkali metals in a relatively small amount to a material to form an electron transport layer or an electron injection layer. Furthermore, as the reducing substance having a work function of 2.9 eV or less, a combination of two or more kinds of these alkali metals is also preferable, and particularly, a combination including Cs, for example, a combination of Cs with Na, a combination of Cs with K, a combination of Cs with Rb, or a combination of Cs with Na and K, is preferable. By inclusion of Cs, reducing ability can be efficiently exhibited, and emission luminance of an organic EL element is enhanced or a lifetime thereof is lengthened by adding Cs to a material to form an electron transport layer or an electron injection layer.

<Cathode in Organic Electroluminescent Element>

The cathode 108 plays a role of injecting an electron to the light emitting layer 105 through the electron injection layer 107 and the electron transport layer 106.

A material to form the cathode 108 is not particularly limited as long as being a substance capable of efficiently injecting an electron to an organic layer. However, a material similar to the materials to form the anode 102 can be used. Among these materials, a metal such as tin, indium, calcium, aluminum, silver, copper, nickel, chromium, gold, platinum, iron, zinc, lithium, sodium, potassium, cesium, or magnesium, and alloys thereof (a magnesium-silver alloy, a magnesium-indium alloy, an aluminum-lithium alloy such as lithium fluoride/aluminum, and the like) are preferable. In order to enhance element characteristics by increasing an electron injection efficiency, lithium, sodium, potassium, cesium, calcium, magnesium, or an alloy containing these low work function-metals is effective. However, many of these low work function-metals are generally unstable in air. In order to ameliorate this problem, for example, a method using an electrode having high stability obtained by doping an organic layer with a trace amount of lithium, cesium, or magnesium is known. Other examples of a dopant that can be used include an inorganic salt such as lithium fluoride, cesium fluoride, lithium oxide, or cesium oxide. However, the dopant is not limited thereto.

Furthermore, in order to protect an electrode, a metal such as platinum, gold, silver, copper, iron, tin, aluminum, or indium, an alloy using these metals, an inorganic substance such as silica, titania, or silicon nitride, polyvinyl alcohol, vinyl chloride, a hydrocarbon-based polymer compound, or the like may be laminated as a preferable example. A method for manufacturing these electrodes is not particularly limited as long as being able to obtain conduction, and examples thereof include resistance heating vapor deposition, electron beam vapor deposition, sputtering, ion plating, and coating.

<Binder that may be used in each Layer>

The materials used in the above-described hole injection layer, hole transport layer, light emitting layer, electron transport layer, and electron injection layer can form each layer by being used singly. However, it is also possible to use the materials by dispersing the materials in a solvent-soluble resin such as polyvinyl chloride, polycarbonate, polystyrene, poly(N-vinylcarbazole), polymethyl methacrylate, polybutyl methacrylate, polyester, polysulfone, polyphenylene oxide, polybutadiene, a hydrocarbon resin, a ketone resin, a phenoxy resin, polyamide, ethyl cellulose, a vinyl acetate resin, an ABS resin, or a polyurethane resin; or a curable resin such as a phenolic resin, a xylene resin, a petroleum resin, a urea resin, a melamine resin, an unsaturated polyester resin, an alkyd resin, an epoxy resin, or a silicone resin, as a polymer binder.

<Method for Manufacturing Organic Electroluminescent Element>

Each layer constituting an organic electroluminescent element can be formed by forming thin films of materials to constitute each layer by a method such as a vapor deposition method, resistance heating vapor deposition, electron beam vapor deposition, sputtering, a molecular lamination method, a printing method, a spin coating method, a casting method, or a coating method. The film thickness of each layer thus formed is not particularly limited, and can be appropriately set according to a property of a material, but is usually within a range of 2 nm to 5000 nm. The film thickness can be usually measured using a crystal oscillation type film thickness measuring apparatus or the like. In a case of forming a thin film using a vapor deposition method, vapor deposition conditions depend on the kind of a material, an intended crystal structure of a film, an association structure, and the like. It is preferable to appropriately set the vapor deposition conditions generally in ranges of a vapor deposition crucible heating temperature of +50 to +400° C., a degree of vacuum of $10^{-6}$ to $10^{-3}$ Pa, a rate of vapor deposition of 0.01 to 50 nm/sec, a substrate temperature of −150 to +300° C., and a film thickness of 2 nm to 5 μm.

Next, as an example of a method for manufacturing an organic electroluminescent element, a method for manufacturing an organic electroluminescent element formed of anode/hole injection layer/hole transport layer/light emitting layer including host material and dopant material/electron transport layer/electron injection layer/cathode will be described. A thin film of an anode material is formed on an appropriate substrate by a vapor deposition method or the like to manufacture an anode, and then thin films of a hole injection layer and a hole transport layer are formed on this anode. A thin film is formed thereon by co-depositing a host material and a dopant material to obtain a light emitting layer. An electron transport layer and an electron injection layer are formed on this light emitting layer, and a thin film formed of a substance for a cathode is further formed by a vapor deposition method or the like to obtain a cathode. An intended organic electroluminescent element is thereby obtained. Incidentally, in manufacturing the above organic electroluminescent element, it is also possible to manufacture the element by reversing the manufacturing order, that is, in order of a cathode, an electron injection layer, an electron transport layer, a light emitting layer, a hole transport layer, a hole injection layer, and an anode.

In a case where a direct current voltage is applied to the organic electroluminescent element thus obtained, it is only required to apply the voltage by using an anode as a positive polarity and using a cathode as a negative polarity. By applying a voltage of about 2 to 40 V, light emission can be observed from a transparent or semitransparent electrode side (the anode or the cathode, or both the electrodes). This organic electroluminescent element also emits light also in a case where a pulse current or an alternating current is applied. Note that a waveform of an alternating current applied may be any waveform.

<Application Examples of Organic Electroluminescent Element>

The present invention can be also applied to a display apparatus including an organic electroluminescent element, a lighting apparatus including an organic electroluminescent element, or the like.

The display apparatus or lighting apparatus including an organic electroluminescent element can be manufactured by a known method such as connecting the organic electroluminescent element according to the present embodiment to a known driving apparatus, and can be driven by appropriately using a known driving method such as direct driving, pulse driving, or alternating driving.

Examples of the display apparatus include a panel display such as a color flat panel display; and a flexible display such as a flexible color organic electroluminescent (EL) display (see, for example, JP 10-335066A, JP 2003-321546A, and JP 2004-281086 A). Examples of a display method of the display include a matrix method and/or a segment method. Note that the matrix display and the segment display may co-exist in the same panel.

The matrix refers to a system in which pixels for display are arranged two-dimensionally as in a lattice form or a mosaic form, and characters or images are displayed by an assembly of pixels. The shape or size of the pixel depends on intended use. For example, for display of images and characters of a personal computer, a monitor, or a television, square pixels each having a size of 300 μm or less on each side are usually used, and in a case of a large-sized display such as a display panel, pixels having a size in the order of millimeters on each side are used. In a case of monochromic display, it is only required to arrange pixels of the same color. However, in a case of color display, display is performed by arranging pixels of red, green, and blue. In this case, typically, delta type display and stripe type display are available. For this matrix driving method, either a line sequential driving method or an active matrix method may be employed. The line sequential driving method has an advantage of having a simpler structure. However, in consideration of operation characteristics, the active matrix method may be superior. Therefore, it is necessary to use the line sequential driving method and the active matrix method properly according to intended use.

In the segment method (type), a pattern is formed so as to display predetermined information, and a determined region emits light. Examples of the segment method include display of time or temperature in a digital clock or a digital thermometer, display of a state of operation in an audio instrument or an electromagnetic cooker, and panel display in an automobile.

Examples of the lighting apparatus include a lighting apparatuses for indoor lighting or the like, and a backlight of a liquid crystal display apparatus (see, for example, JP 2003-257621 A, JP 2003-277741 A, and JP 2004-119211 A). The backlight is mainly used for enhancing visibility of a display apparatus that is not self-luminous, and is used in a liquid crystal display apparatus, a timepiece, an audio apparatus, an automotive panel, a display panel, a sign, and the like. Particularly, in a backlight for use in a liquid crystal display apparatus, among the liquid crystal display apparatuses, for use in a personal computer in which thickness reduction has been a problem to be solved, in consideration of difficulty in thickness reduction because a conventional type backlight is formed from a fluorescent lamp or a light guide plate, a backlight using the luminescent element according to the present embodiment is characterized by its thinness and light weightness.

EXAMPLES

Hereinafter, the present invention will be described more specifically by way of Examples, but the present invention is not limited thereto. First, a synthesis example of an azoline-containing compound will be described below.

Synthesis of compound (1-2-1): 2-phenyl-9,10-bis (4-(oxazolin-2-yl) phenyl) anthracene Synthesis of 4-bromo-N-(2-hydroxyethyl) benzamide

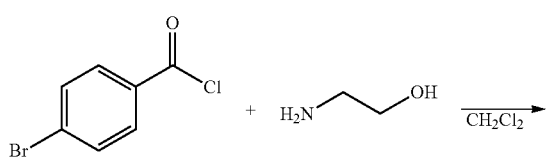

-continued

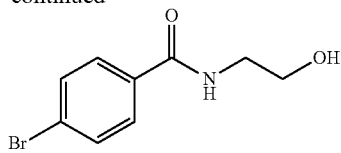

4-Bromobenzoyl chloride (22.5 g) and dichloromethane (100 mL) were put in a flask and were cooled to 0° C. under a nitrogen atmosphere. A solution obtained by dissolving ethanolamine (12.5 g) in dichloromethane (100 mL) was slowly added thereto using a dropping funnel. This solution was stirred at room temperature for 6 hours, and then water was added thereto to stop the reaction. The organic layer was separated, and then was dried and concentrated. Toluene was poured thereinto after concentration, and a precipitate was generated. Therefore, the precipitate was filtered to obtain a target compound (18.3 g).

Synthesis of 2-(4-bromophenyl) oxazoline

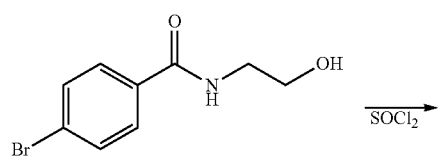

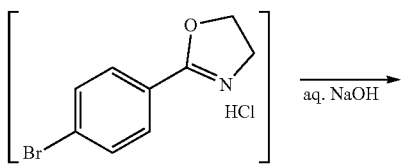

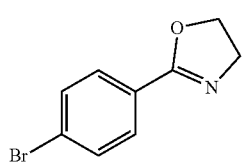

4-Bromo-N-(2-hydroxyethyl) benzamide (18.0 g) was put in a flask, thionyl chloride (20 mL) was slowly added thereto under a nitrogen atmosphere, and the resulting mixture was stirred at room temperature for 0.5 hours. Dry toluene was added to the solution, and a precipitate as a hydrochloride of a target compound was generated. Therefore, the precipitate after filtration was dissolved in water (400 mL), and a solution obtained by dissolving sodium hydroxide (3.5 g) in water (50 mL) was slowly added dropwise to the solution. Toluene was added to the resulting suspension for liquid separation. The organic layer was separated, dried, and concentrated, and a precipitate generated by pouring heptane was filtered to obtain a target compound (10.5 g).

Synthesis of 2-phenyl-9,10-bis(4-(oxazolin-2-yl) phenyl)anthracene

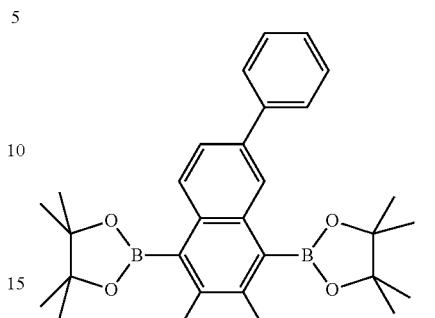

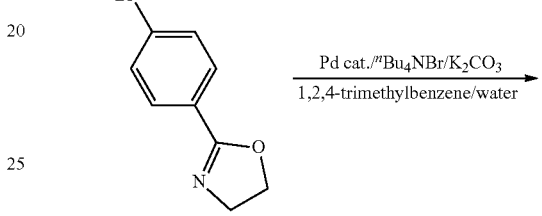

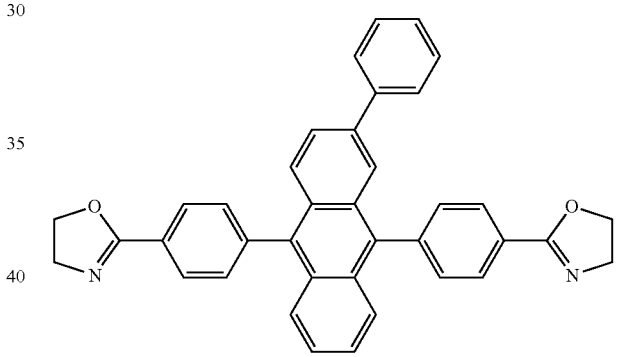

9,10-bis (4,4,5,5-tetramethyl-1,3,2-dioxaborolanyl)-2-phenylanthracene (4.0 g) synthesized according to description in WO 2007/029696A, 2-(4-bromophenyl) oxazoline (4.8 g), potassium carbonate (4.3 g), tetra-n-butylammonium bromide (0.51 g), bis (di-t-butyl (4-dimethylaminophenyl) phosphine) dichloropalladium (0.17 g), 1,2,4-trimethylbenzene (20 mL), and water (2 mL) were put in a flask, and were stirred under a nitrogen atmosphere at a reflux temperature for 7.5 hours. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)), and then was purified by sublimation to obtain 2-phenyl-9,10-bis (4-(oxazolin-2-yl) phenyl) anthracene (2.8 g) as a target compound (1-2-1).

The structure of the compound thus obtained was identified by NMR measurement.

$^1$H-NMR (CDCl$_3$): δ=8.2 (d, 4H), 7.9 (d, 1H), 7.7 (d, 1H), 7.7-7.5 (m, 9H), 7.4-7.3 (m, 5H), 4.5 (t, 4H), 4.2 (t, 4H).

Synthesis of compound (1-2-2) 2-phenyl-9,10-bis (4-(4,4-dimethyloxazolin-2-yl) phenyl) anthracene

Synthesis of 4-bromo-N-(1-hydroxy-2-methylpropan-2-yl) benzamide

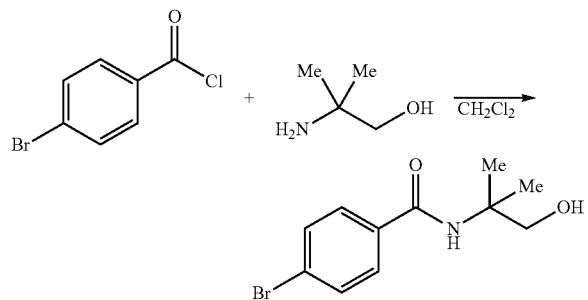

4-Bromobenzoyl chloride (28.7 g) and dichloromethane (100 mL) were put in a flask, and were cooled to 0° C. under a nitrogen atmosphere. A solution obtained by dissolving 2-amino-2-methylpropan-1-ol (23.3 g) in dichloromethane (100 mL) was slowly added thereto using a dropping funnel. This solution was stirred at room temperature for 6 hours, and then water was added thereto to stop the reaction. The organic layer was separated, and then was dried and concentrated. Toluene was poured thereinto after concentration, and a precipitate was generated. Therefore, the precipitate was filtered to obtain a target compound (25.3 g).

Synthesis of 2-(4-bromophenyl)-4,4-dimethyloxazoline

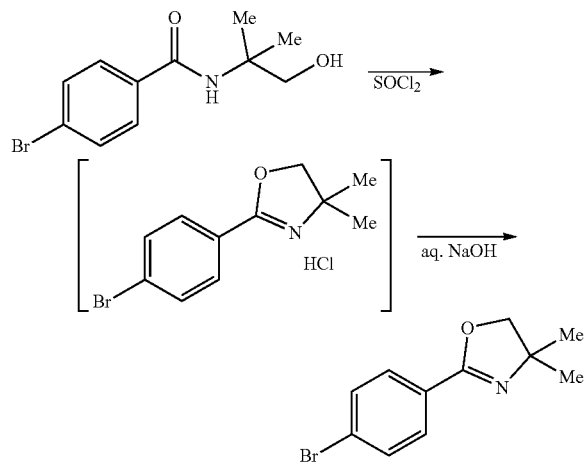

4-Bromo-N-(1-hydroxy-2-methylpropan-2-yl) benzamide (25.0 g) was put in a flask, thionyl chloride (20 mL) was slowly added thereto under a nitrogen atmosphere, and the resulting mixture was stirred at room temperature for 0.5 hours. Dry toluene was added to the solution, and a precipitate as a hydrochloride of a target compound was generated. Therefore, the precipitate after filtration was dissolved in water (400 mL), and a solution obtained by dissolving sodium hydroxide (4.4 g) in water (50 mL) was slowly added dropwise to the solution. Toluene was added to the resulting suspension for liquid separation. The organic layer was separated, dried, and concentrated, and the precipitate generated by pouring heptane was filtered to obtain a target compound (19.2 g).

Synthesis of 2-phenyl-9,10-bis (4-(4,4-dimethyloxazolin-2-yl) phenyl) anthracene

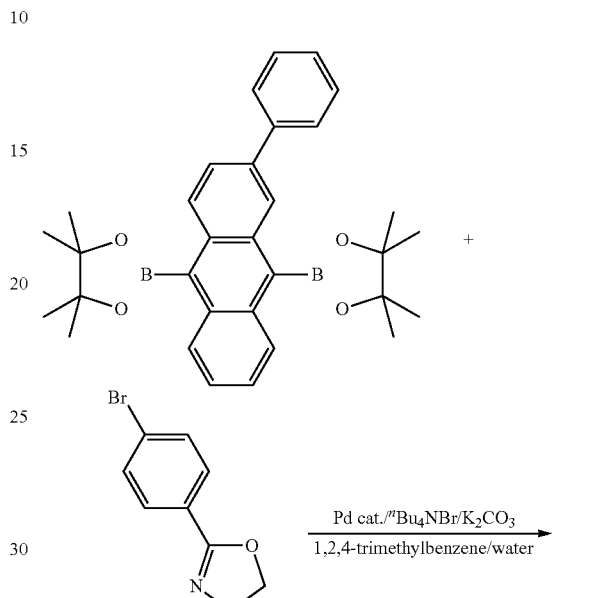

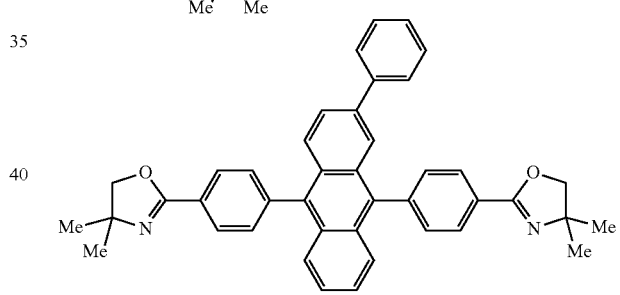

9,10-bis (4,4,5,5-tetramethyl-1,3,2-dioxaborolanyl)-2-phenylanthracene (4.0 g) synthesized according to description in WO 2007/029696 A), 2-(4-bromophenyl)-4,4-dimethyl oxazoline (4.8 g), potassium carbonate (4.4 g), tetra-n-butylammonium bromide (0.51 g), bis (di-t-butyl (4-dimethylaminophenyl) phosphine) dichloropalladium (0.17 g), 1,2,4-trimethylbenzene (20 mL), and water (2 mL) were put in a flask, and were stirred under a nitrogen atmosphere at a reflux temperature for 7.5 hours. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)), and then was purified by sublimation to obtain 2-phenyl-9,10-bis (4-(4,4-dimethyloxazolin-2-yl) phenyl) anthracene (3.0 g) as a target compound (1-2-2).

The structure of the compound thus obtained was identified by NMR measurement.

¹H-NMR (CDCl₃): δ=8.2 (m, 4H), 7.9 (d, 1H), 7.7 (d, 1H), 7.7-7.6 (m, 3H), 7.6-7.5 (m, 6H), 7.4 (t, 2H), 7.3 (m, 3H), 4.2 (s, 4H), 1.5 (s, 12H).

Synthesis of compound (1-3-2): 1,3,5-tris (4-(4,4-dimethyloxazolin-2-ylphenyl)) benzene

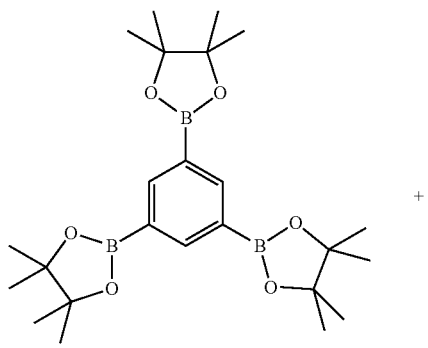

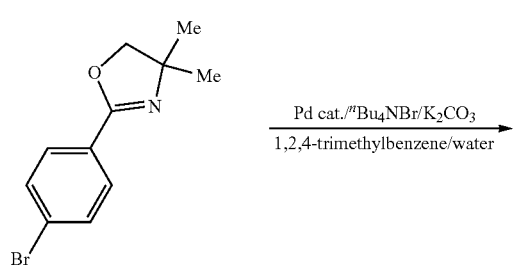

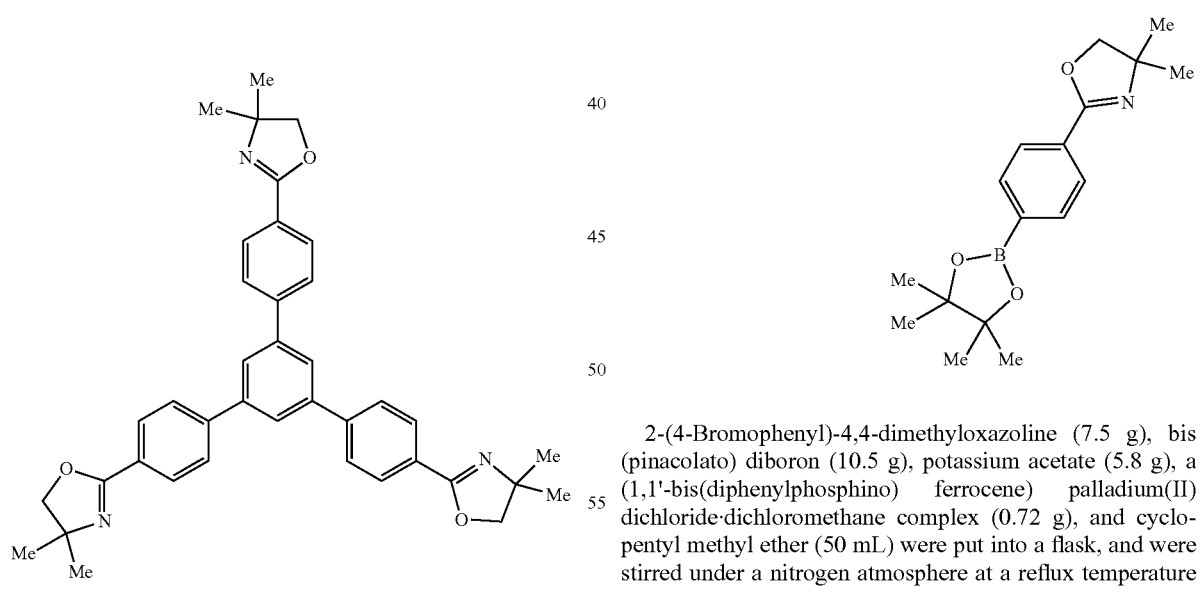

1,3,5-tris (4,4,5,5-tetramethyl-1,3,2-dioxaborolan-2-yl) benzene (3.0 g), 2-(4-bromophenyl)-4,4-dimethyloxazoline (6.0 g), potassium carbonate (5.5 g), tetra-n-butylammonium bromide (0.84 g), bis (di-t-butyl (4-dimethylaminophenyl) phosphine) dichloropalladium (0.14 g), 1,2,4-trimethylbenzene (20 mL), and water (2 mL) were put in a flask, and were stirred under a nitrogen atmosphere at a reflux temperature for 6 hours. The reaction solution was cooled to room temperature, water was added thereto, and toluene was further added thereto for liquid separation extraction. An organic layer was separated, and was then dried and concentrated. A crude product was purified with a NH silica gel column (developing solution: toluene), and then was purified by sublimation to obtain 1,3,5-tris(4-(4,4-dimethyloxazolin-2-ylphenyl)) benzene (3.5 g) as a target compound (1-3-2).

The structure of the compound thus obtained was identified by NMR measurement.

¹H-NMR(CDCl₃): δ=8.1 (d, 6H), 7.8 (s, 3H), 7.7 (d, 6H), 4.1 (s, 6H), 1.4 (s, 18H).

Synthesis of compound (1-2-102): 2,7-bis (4-(4,4-dimethyloxazolin-2-yl) phenyl)-9,9'-spirobi[fluorene]

Synthesis of 2-(4-(4,4,5,5-tetramethyl-1,3,2-dioxaborolan-2-yl) phenyl)-4,4-dimethyloxazoline 2-(4-Bromophenyl)-4,4-dimethyloxazoline (7.5 g), bis (pinacolato) diboron (10.5 g), potassium acetate (5.8 g), a (1,1'-bis(diphenylphosphino) ferrocene) palladium(II) dichloride·dichloromethane complex (0.72 g), and cyclopentyl methyl ether (50 mL) were put into a flask, and were stirred under a nitrogen atmosphere at a reflux temperature for 7 hours. The reaction solution was cooled to room temperature, water was added thereto, and toluene was further added thereto for liquid separation extraction. An organic layer was separated, and was then dried and concentrated. The resulting product was caused to pass through an activated carbon short column (developing solution: toluene). Thereafter, the resulting product was concentrated and reprecipitated with heptane to obtain a target compound (4.5 g).

Synthesis of 2,7-bis (4-(4,4-dimethyloxazolin-2-yl) phenyl)-9,9'-spirobi [fluorene]

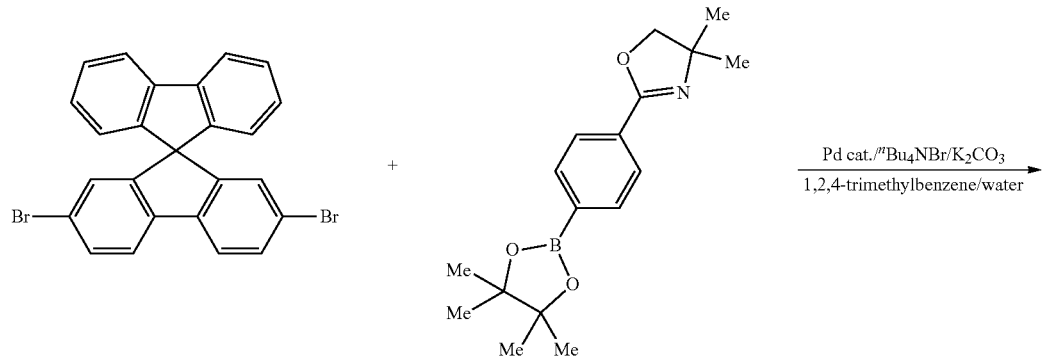

2,7-Dibromo-9,9'-spirobi [fluorene] (3.0 g), 2-(4-(4,4,5, 5-tetramethyl-1,3,2-dioxaborolan-2-yl) phenyl)-4,4-dimethyloxazoline (4.2 g), potassium carbonate (3.5 g), tetra-n-butylammonium bromide (0.82 g), bis(di-t-butyl (4-dimethylaminophenyl)phosphine)dichloropalladium (0.13g), 1,2,4-trimethylbenzene (20 mL), and water (2 mL) were put in a flask, and were stirred under a nitrogen atmosphere at a reflux temperature for 4 hours. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)), and then was purified by sublimation to obtain 2,7-bis (4-(4,4-dimethyl-oxazolin-2-yl) phenyl)-9,9'-spirobi[fluorene] (3.4 g)) as a target compound (1-2-102).

The structure of the compound thus obtained was identified by NMR measurement.

$^1$H-NMR (CDCl$_3$): δ=7.9 (m, 8H), 7.7 (dd, 2H), 7.5 (d, 4H), 7.4 (t, 2H), 7.1 (t, 2H), 7.0 (s, 2H), 6.8 (d, 2H), 4.1 (s, 4H), 1.4 (s, 12H).

Synthesis of compound (1-1-108): 2-(4-(9,10-di (naphthalen-2-yl) anthraces-2-yl) phenyl)-4,4,5,5-tetramethyl-1-phenyl-1H-imidazoline Synthesis of 2-(4-bromophenyl)-4,4,5,5-tetramethyl-1H-imidazoline

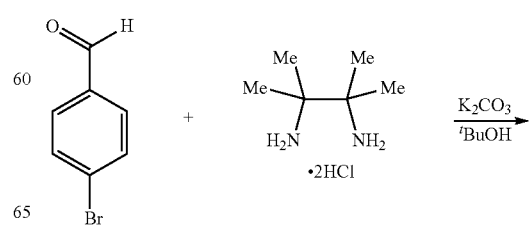

-continued

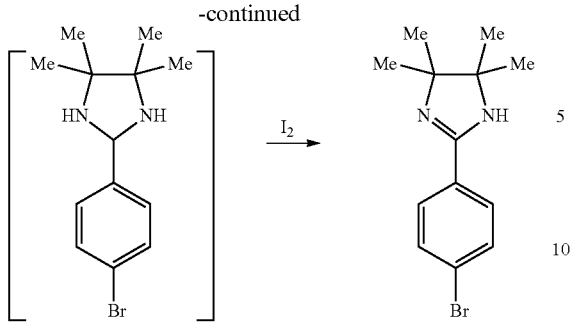

4-Bromobenzaldehyde (3.9 g), 2,3-dimethyl-2,3-butanediamine dihydrochloride (4.0 g), potassium carbonate (29.2 g), and t-butanol (120 mL) were put in a flask, and were stirred at 30° C. for 1 hour. Iodine (6.7 g) was added thereto, and the mixture was stirred at 70° C. for 7 hours. After completion of the reaction, the reaction was stopped with an aqueous sodium thiosulfate solution. Thereafter, ethyl acetate was added thereto for liquid separation, and the organic layer was dried and concentrated. A crude product was purified with a NH silica gel column (developing solution: ethyl acetate) to obtain a target compound (5.5 g).

Synthesis of 2-(4-bromophenyl)-4,4,5,5-tetramethyl-1-phenyl-1H-imidazoline

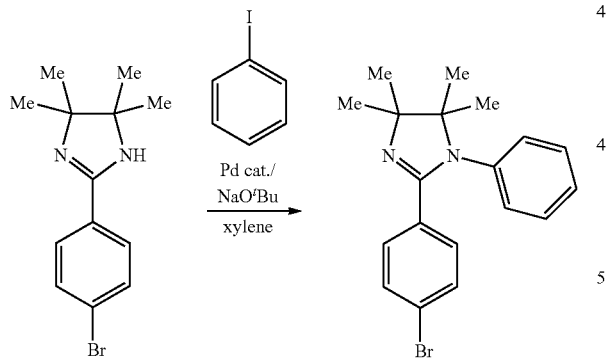

2-(4-Bromophenyl)-4,4,5,5-tetramethyl-1H-imidazoline (1.4 g), iodobenzene (2.9 g), sodium t-butoxide (0.92 g), bis(di-t-butyl (4-dimethylaminophenyl) phosphine) dichloropalladium (0.10 g), and xylene (10 mL) were put in a flask and were stirred at reflux temperature for 7 hours. The reaction solution was cooled to room temperature, water was added thereto, and toluene was further added thereto for liquid separation extraction. An organic layer was separated, and was then dried and concentrated. A crude product was purified with a NH silica gel column (developing solution: toluene/ethyl acetate=9/1 (volume ratio)) to obtain a target compound (1.6 g).

Synthesis of 2-(4-(9,10-di(naphthalen-2-yl) anthraces-2-yl) phenyl)-4,4,5,5-tetramethyl-1-phenyl-1H-imidazoline

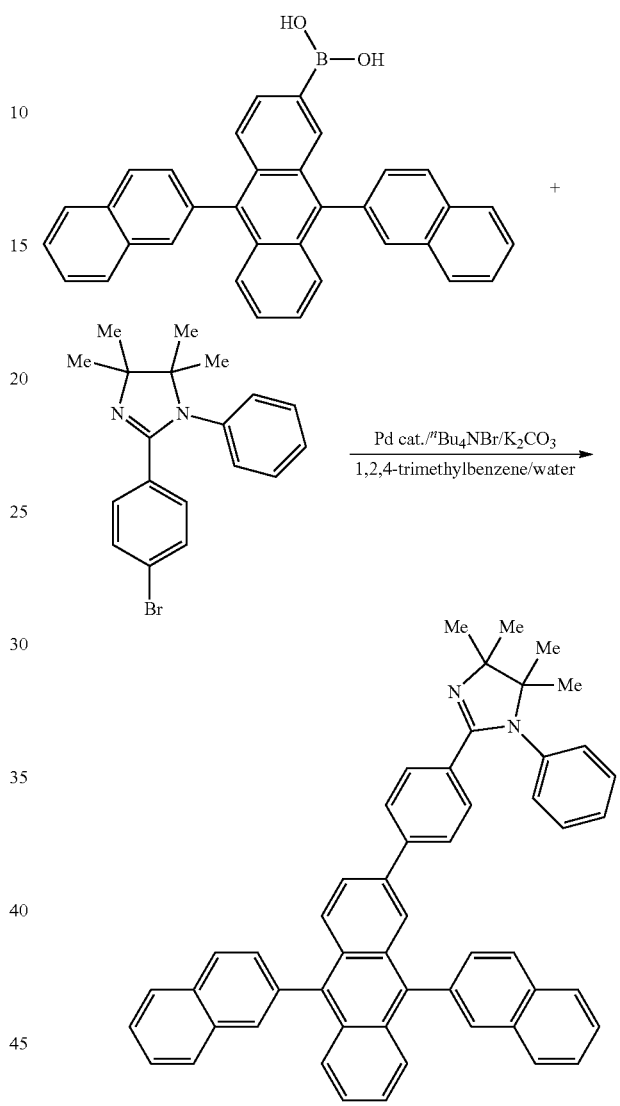

2-(4-Bromophenyl)-4,4,5,5-tetramethyl-1-phenyl-1H-imidazoline (1.6 g), (9,10-di(naphthalen-2-yl) anthraces-2-yl) boronic acid (2.1 g), potassium carbonate (1.2 g), tetra-n-butylammonium bromide (0.43 g), bis(di-t-butyl (4-dimethylaminophenyl)phosphine)dichloropalladium (0.09 g), 1,2,4-trimethylbenzene (20 mL), and water (2 mL) were put in a flask, and were stirred under a nitrogen atmosphere at a reflux temperature for 7.5 hours. The reaction solution was cooled to room temperature, water was added thereto, and toluene was further added thereto for liquid separation extraction. An organic layer was separated, and was then dried and concentrated. A crude product was purified with a NH silica gel column (developing solution: toluene), and then was purified by sublimation to obtain 2-(4-(9,10-di(naphthalen-2-yl) anthraces-2-yl) phenyl)-4,4,5,5-tetramethyl-1-phenyl-1H-imidazoline (1.4 g) as a target compound (1-1-108).

The structure of the compound thus obtained was identified by NMR measurement.

¹H-NMR (CDCl₃): δ=8.1 (dd, 2H), 8.0 (m, 4H), 7.9 (m, 3H), 7.8 (d, 1H), 7.7 (m, 2H), 7.6 (m, 6H), 7.5 (dd, 1H), 7.4-7.3 (m, 6H), 7.1 (t, 2H), 7.0 (t, 1H), 6.8 (d, 2H), 1.2 (s, 6H), 1.2 (s, 3H), 1.1 (s, 3H).

Synthesis of compound (1-2-22): 2-phenyl-9,10-bis (2-(4,4-dimethyloxazolin-2-yl) pyridin-5-yl) anthracene Synthesis of 5-bromo-2-(4,4-dimethyloxazolin-2-yl) pyridine

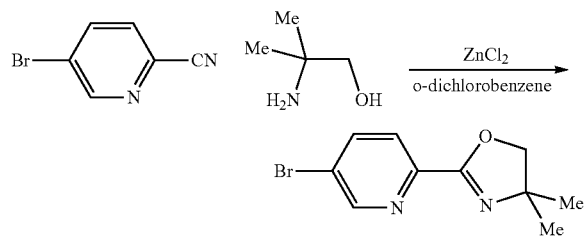

2-Cyano-5-bromopyridine (20 g), 2-amino-2-methyl-1-propanol (49 g), zinc chloride (0.4 g), and o-dichlorobenzene (200 mL) were put in a flask, and were stirred under a nitrogen atmosphere for 17 hours while being heated under reflux. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)) to obtain 5-bromo-2-(4,4-dimethyloxazolin-2-yl) pyridine (23.1 g) as a target compound.

Synthesis of compound (1-2-22)

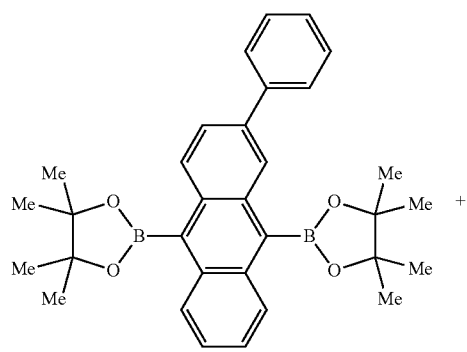

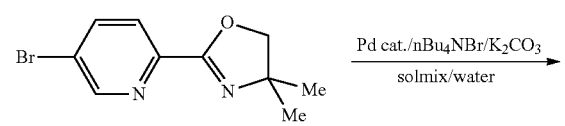

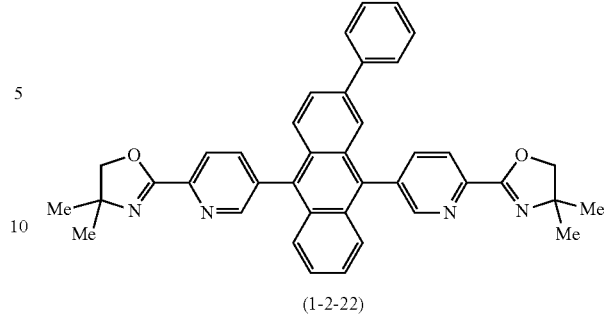

(1-2-22)

2-Phenyl-9,10-bis (4,4,5,5-tetramethyl-1,3,2-dioxaborolan-2-yl) anthracene (4.0 g) synthesized according to description in WO 2007/029696 A, 5-bromo-2-(4,4-dimethyloxazolin-2-yl) pyridine (2.4 g), potassium carbonate (2.2 g), bis(di-t-butyl (4-dimethylaminophenyl) phosphine) dichloropalladium (0.1 g), Solmix (trade name: Japan Alcohol Trading Co., Ltd.) (10 mL), and water (5 mL) were put in a flask, and were stirred under a nitrogen atmosphere at a reflux temperature for 7 hours. The reaction solution was cooled to room temperature, water was added thereto, and toluene was further added thereto for liquid separation extraction. An organic layer was separated, and was then dried and concentrated. A crude product was purified with a NH silica gel column (developing solution: toluene/ethyl acetate=9/1 (volume ratio)), and then was purified by sublimation to obtain compound (1-2-22) (1.3 g) as a target compound.

The structure of the compound thus obtained was identified by NMR measurement.

¹H-NMR (CDCl₃): δ=8.9 (m, 2H), 8.3 (m, 2H), 8.0 (m, 2H), 7.8 (s, 1H), 7.7 (m, 2H), 7.6 (m, 2H), 7.6 (d, 2H), 7.4 (m, 4H), 7.3 (t, 1H), 4.3 (s, 4H), 1.5 (s, 12H).

Synthesis of compound (1-2-146) 2,7-bis(5-(4,4-dimethyloxazolin-2-yl) pyridin-3-yl)-9,9'-spirobi [fluorene]

Synthesis of 3-(5-bromopyridin-3-yl)-4,4-dimethyloxazoline

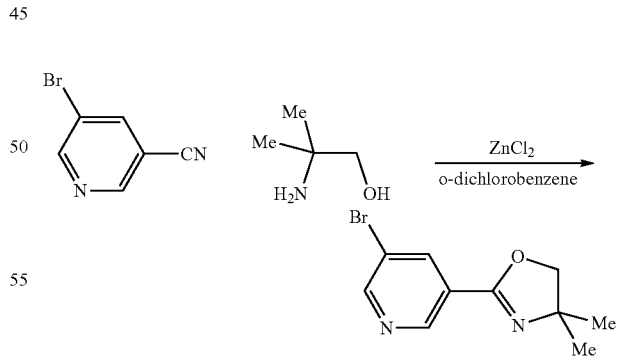

3-Bromo-5-cyanopyridine (5 g), 2-amino-2-methyl-1-propanol (24 g), zinc chloride (0.1 g), and o-dichlorobenzene (50 mL) were put in a flask, and were stirred under a nitrogen atmosphere for 16 hours while being heated under reflux. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)) to obtain 3-(5-bromopyridin-3-yl)-4,4-dimethyloxazoline (5.7 g) as a target compound.

Synthesis of compound (1-2-146)

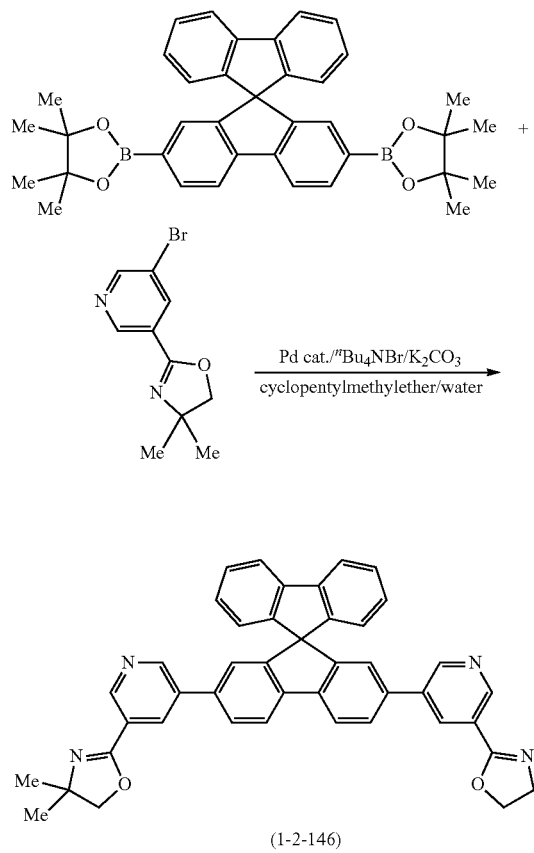

(1-2-146)

2,7-bis (4,4,5,5-tetramethyl-1,3,2-dioxaborolan-2-yl)-9,9'-spirobi [fluorene] (1.4 g) synthesized according to description in WO 2015/141608 A, 3-(5-bromopyridin-3-yl)-4,4-dimethyloxazoline (1.4 g), potassium carbonate (1.4 g), bis (di-t-butyl (4-dimethylaminophenyl) phosphine) dichloropalladium (0.1 g), tetra-n-butylammonium bromide (0.3 g), cyclopentyl methyl ether (20 mL), and water (2 mL) were put in a flask, and were stirred under a nitrogen atmosphere at a reflux temperature for 5 hours. The reaction solution was cooled to room temperature, water was added thereto, and toluene was further added thereto for liquid separation extraction. An organic layer was separated, and was then dried and concentrated. A crude product was purified with a NH silica gel column (developing solution: toluene/ethyl acetate=9/1 (volume ratio)), and then was purified by sublimation to obtain compound (1-2-146) (1.4 g) as a target compound.

The structure of the compound thus obtained was identified by NMR measurement.

$^1$H-NMR (CDCl$_3$): δ=9.0 (d, 2H), 8.8 (d, 2H), 8.2 (t, 2H), 8.0 (d, 2H), 7.9 (d, 2H), 7.7 (dd, 2H), 7.4 (t, 2H), 7.1 (t, 2H), 7.0 (d, 2H), 6.8 (d, 2H), 4.1 (s, 4H), 1.4 (s, 12H).

Synthesis of compound (1-2-402): 2,7-bis(3-(4,4-dimethyloxazolin-2-yl) phenyl) triphenylene Synthesis of 2,7-bis(3-cyanophenyl) triphenylene

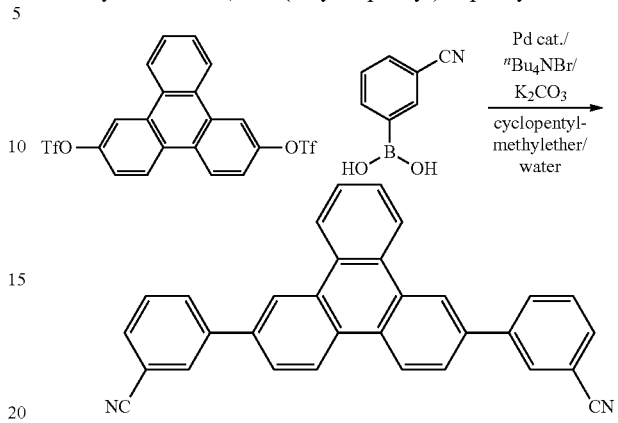

2,7-Bis (trifluoromethanesulfonyloxy) triphenylene (5.0 g) synthesized by a method described in WO 2007/029696 A, 3-cyanophenylboronic acid (3,4 g), bis (di-t-butyl (4-dimethylaminophenyl) phosphine) dichloropalladium (0.2 g), potassium carbonate (5.3 g), tetra-n-butylammonium bromide (0.6 g), cyclopentyl methyl ether (30 mL), and water (3 mL) were put in a flask, and were stirred under a nitrogen atmosphere for 8 hours while being heating under reflux. The resulting product was cooled, and then water was added thereto. Thereafter, a precipitate was filtered, and was washed with Solmix (trade name: Nippon Alcohol Trading Co., Ltd.) and then with ethyl acetate. The obtained crude product was dissolved in hot chlorobenzene, and was filtered through a silica gel short column to obtain a target compound (2.1 g).

Synthesis of compound (1-2-402)

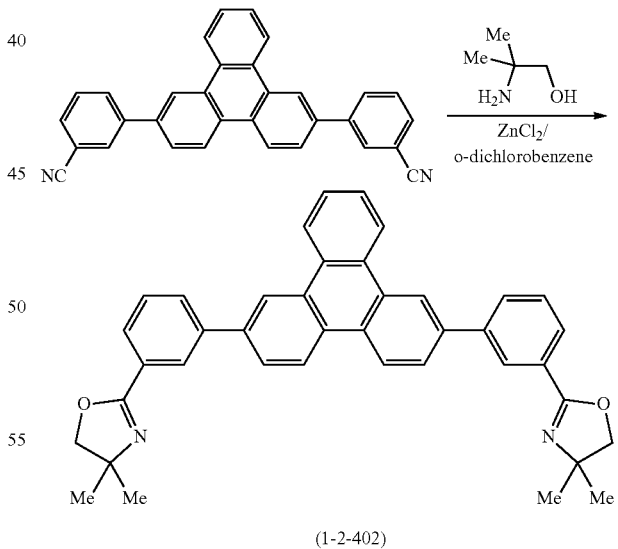

(1-2-402)

2,7-Bis (3-cyanophenyl) triphenylene (2.0 g), 2-amino-2-methyl-1-propanol (4.1 g), zinc chloride (0.2 g), and o-dichlorobenzene (30 mL) were put in a flask, and were stirred under a nitrogen atmosphere at 150° C. for 24 hours. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)), and then was purified by sublimation to obtain compound (1-2-402) (2.1 g) as a target compound.

The structure of the compound thus obtained was identified by NMR measurement.

$^1$H-NMR (CDCl$_3$): δ=8.8 (d, 2H), 8.7 (dd, 2H), 8.6 (d, 2H), 8.4 (m, 2H), 8.0 (dt, 2H), 7.9 (td, 4H), 7.7 (dd, 2H), 7.5 (t, 2H), 4.2 (s, 4H), 1.4 (s, 12H).

Synthesis of compound (1-2-522): 9,9'-bis (4-(4,4-dimethyloxazolin-2-yl) phenyl)-9H, 9'H-3,3'-bicarbazole Synthesis of 9,9'-bis (4-cyanophenyl)-9H, 9'H-3,3'-bicarbazole

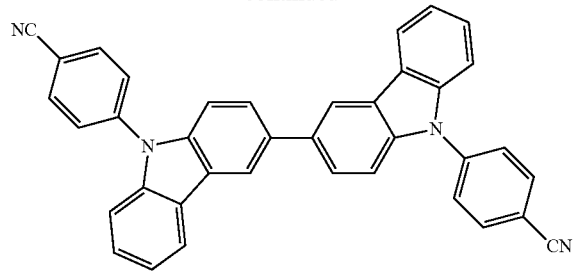

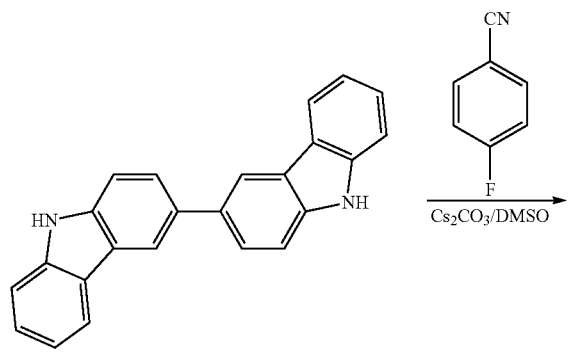

9H, 9'H-3,3'-Bicarbazole (1.0 g), 4-fluorobenzonitrile (1.1 g), cesium carbonate (3.9 g), and dimethylsulfoxide (10 mL) were put in a flask, and were stirred under a nitrogen atmosphere at 120° C. for 6 hours. The resulting product was cooled, and then a precipitate generated by adding water to the solution was filtered. This precipitate was washed with Solmix (trade name: Nippon Alcohol Trading Co., Ltd.). Thereafter, the obtained crude product was dissolved in hot chlorobenzene, and the resulting solution was filtered through a NH silica gel short column. The precipitate obtained by concentrating the filtrate was filtered and dried to obtain a target compound (1.6 g).

Synthesis of compound (1-2-522)

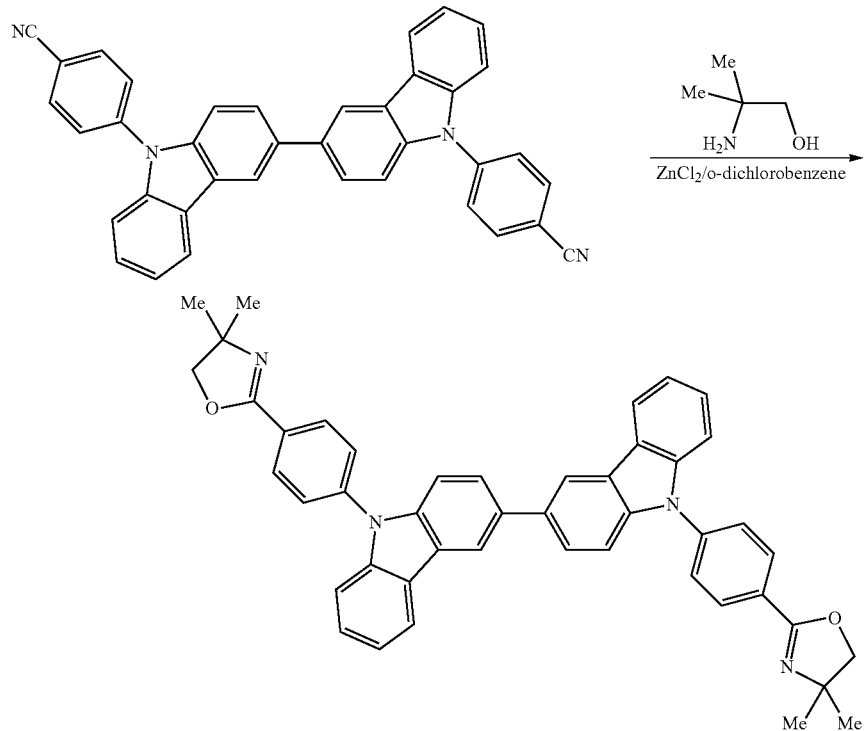

(1-2-522)

9,9'-Bis (4-cyanophenyl)-9H, 9'H-3,3'-bicarbazole (1.6 g), 2-amino-2-methyl-1-propanol (2.7 g), zinc chloride 0.01 g), and o-dichlorobenzene (30 mL) were put in a flask, and were stirred under a nitrogen atmosphere at 150° C. for 26 hours. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)), and then was purified by sublimation to obtain compound (1-2-522) (0.8 g) as a target compound.

The structure of the compound thus obtained was identified by NMR measurement.

$^1$H-NMR (CDCl$_3$): δ=8.4 (m, 2H), 8.2 (m, 6H), 7.8 (dd, 2H), 7.7 (d, 4H), 7.5 (d, 2H), 7.5-7.4 (m, 4H), 7.3 (t, 2H), 4.2 (s, 4H), 1.4 (s, 12H).

Synthesis of compound (1-2-1022): 3,5-bis(3-(4,4-dimethyloxazolin-2-yl) phenyl)-1,1':4',1"-terphenyl Synthesis of 3,5-dibromo-1,1':4',1"-terphenyl

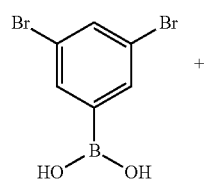

+

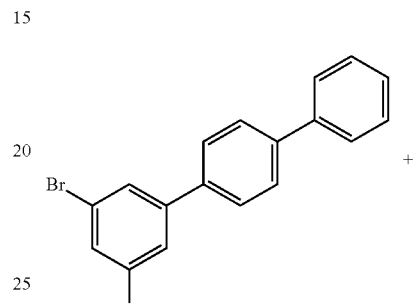

3,5-Dibromophenylboronic acid (5.0 g), 4-iodo-1,1'-biphenyl (6.0 g), palladium acetate (0.04 g), triphenylphosphine (0.09 g), potassium carbonate (4.9 g), tetra-n-butylammonium bromide (1.2 g), cyclopentyl methyl ether (30 mL), and water (3 mL) were put in a flask, and were stirred under a nitrogen atmosphere for 6 hours while being heated under reflux. The reaction solution was cooled to room temperature, water was added thereto, and toluene was further added thereto for liquid separation extraction. An organic layer was separated, and was then dried and concentrated. A crude product was purified with a silica gel column (developing solution: toluene/heptane=1/1 (volume ratio)) to obtain 3,5-dibromo-1,1':4',1"-terphenyl (3.6 g) as a target compound.

Synthesis of 3,5-bis (3-cyanophenyl)-1,1':4',1"-terphenyl

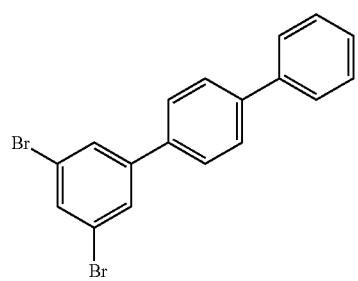

+

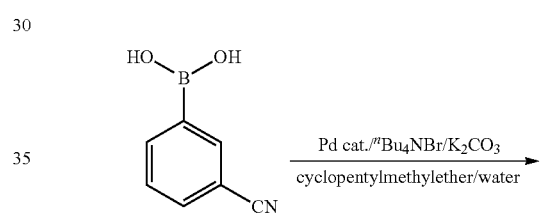

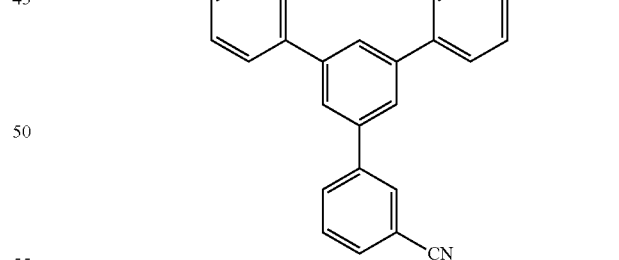

3,5-Dibromo-1,1':4',1"-terphenyl (3.6 g), 3-cyanophenylboronic acid (4.1 g), bis(di-t-butyl (4-dimethylaminophenyl) phosphine) dichloropalladium (0.1 g), potassium carbonate (5.1 g), tetra-n-butylammonium bromide (0.6 g), cyclopentyl methyl ether (20 mL), and water (2 mL) were put in a flask, and were stirred under a nitrogen atmosphere for 8 hours while being heated under reflux. The resulting product was cooled. Thereafter, water was added thereto, and then a precipitate was filtered. The obtained crude product was dissolved in hot chlorobenzene, and was filtered through a silica gel short column to obtain a target compound (1.6 g).

551

Synthesis of compound (1-2-1022)

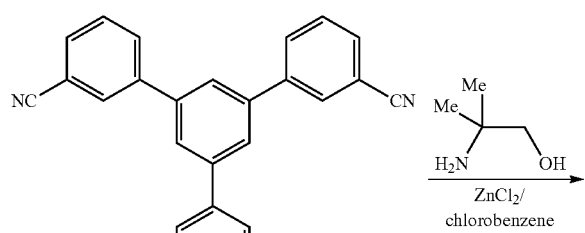

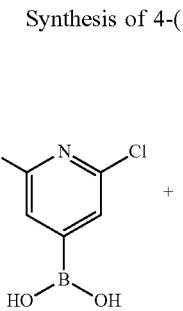

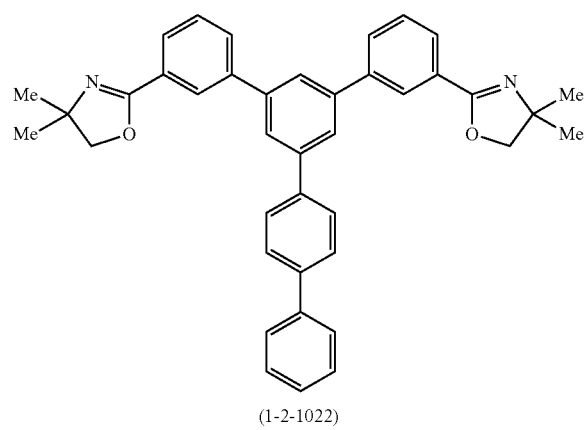

(1-2-1022)

3,5-Bis(3-cyanophenyl)-1,1':4',1''-terphenyl (1.6 g), 2-amino-2-methyl-1-propanol (3.3 g), zinc chloride (0.05 g), and chlorobenzene (20 mL) were put in a flask, and were stirred under a nitrogen atmosphere for 40 hours while being heated under reflux. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)), and then was purified by sublimation to obtain compound (1-2-1022) (1.0 g) as a target compound.

The structure of the compound thus obtained was identified by NMR measurement.

$^1$H-NMR (CDCl$_3$): δ=8.3 (t, 2H), 8.0 (dt, 2H), 7.9 (d, 2H), 7.8 (m, 5H), 7.7 (m, 2H), 7.7 (m, 2H), 7.5 (t, 2H), 7.5 (t, 2H), 7.4 (tt, 1H), 4.1 (s, 4H), 1.4 (s, 12H).

552

Synthesis of compound (1-2-1025): 4-([1,1'-biphenyl]-4-yl)-2,6-bis(4-(4,4-dimethyloxazolin-2-yl)phenyl) pyridine Synthesis of 4-([1,1'-biphenyl]-4-yl)-2,6-dichloropyridine 2,6-Dichloropyridin-4-yl boronic acid (1.7 g), 4-iodo-1,1'-biphenyl (5.0 g), dichlorobis(triphenylphosphine) palladium (0.06 g), potassium carbonate (2.5 g), tetra-n-butylammonium bromide (0.6 g), toluene (20 mL), and water (2 mL) were put in a flask, and were stirred under a nitrogen atmosphere for 5 hours while being heated under reflux. The reaction solution was cooled to room temperature, water was added thereto, and toluene was further added thereto for liquid separation extraction. An organic layer was separated, and was then dried and concentrated. A crude product was purified with a silica gel column (developing solution: toluene/heptane=1/1 (volume ratio), and then 3/1 (volume ratio)) to obtain 4-([1,1'-biphenyl]-4-yl)-2,6-dichloropyridine (1.8 g) as a target compound.

Synthesis of compound (1-2-1025)

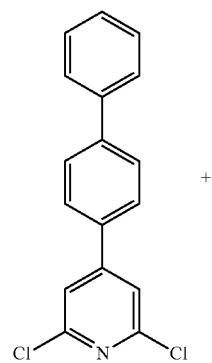

-continued

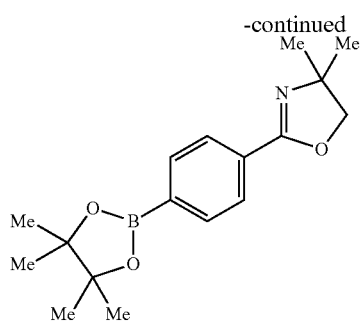

Pd cat./
$^n$Bu$_4$NBr/K$_2$CO$_3$
cyclopentylmethylether/ water

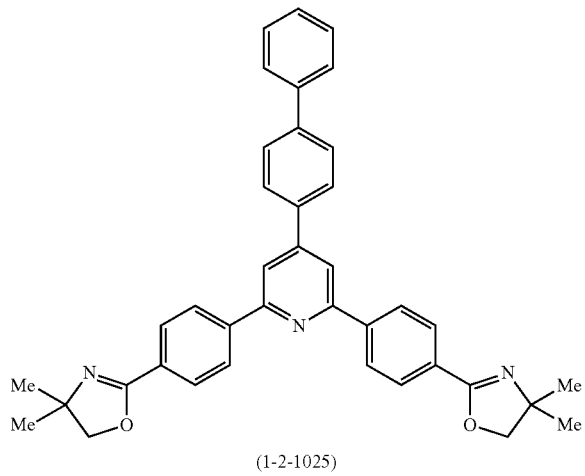

(1-2-1025)

4-([1,1'-Biphenyl]-4-yl)-2,6-dichloropyridine (1.4 g), 4,4-dimethyl-2-(4-(4,4,5,5-tetramethyl-1,3,2-dioxaborolan-2-yl) phenyl) oxazoline (4.2 g), bis (di-t-butyl (4-dimethylaminophenyl) phosphine) dichloropalladium (0.1 g), potassium carbonate (2.6 g), tetra-n-butylammonium bromide (0.3 g), cyclopentyl methyl ether (20 mL), and water (2 mL) were put in a flask, and were stirred under a nitrogen atmosphere for 7 hours while being heated under reflux. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=7/3 (volume ratio)), and then was purified by sublimation to obtain compound (1-2-1025) (1.1 g) as a target compound.

The structure of the compound thus obtained was identified by NMR measurement.

$^1$H-NMR (CDCl$_3$): δ=8.3 (d, 4H), 8.1 (d, 4H), 8.0 (s, 2H), 7.8 (d, 2H), 7.8 (d, 2H), 7.7 (m, 2H), 7.5 (t, 2H), 7.4 (tt, 1H), 4.2 (s, 4H), 1.4 (s, 12H).

Synthesis of compound (1-2-1026): 4-([1,1'-biphenyl]-4-yl)-2,6-bis(3-(4,4-dimethyloxazolin-2-yl) phenyl) pyridine Synthesis of 4-([1,1'-biphenyl]-4-yl)-2,6-bis(3-cyanophenyl) pyridine

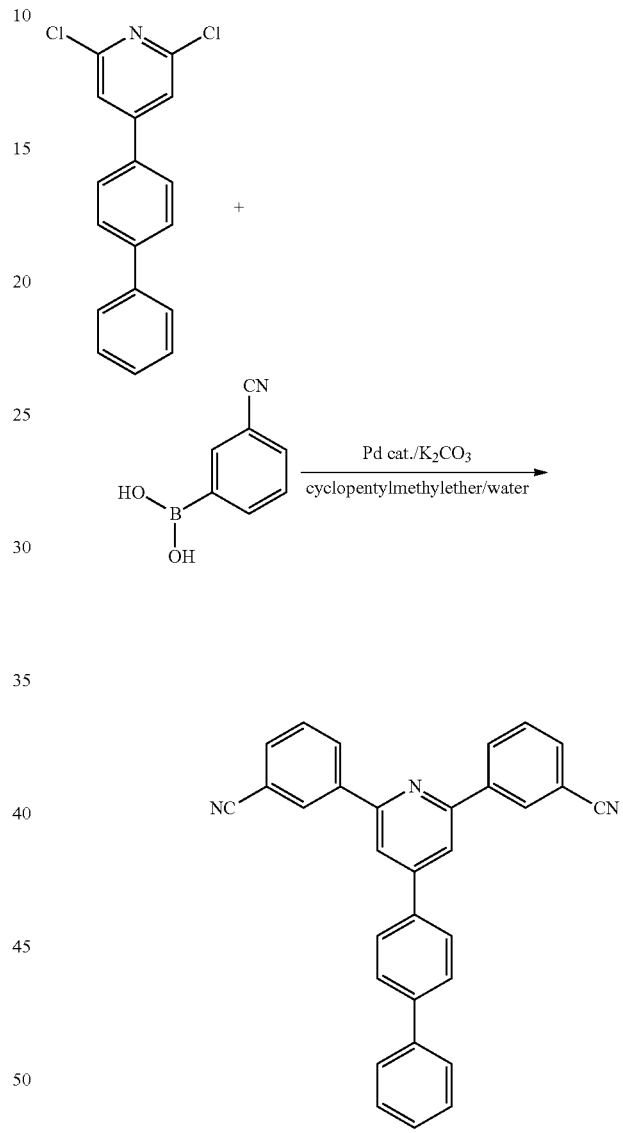

4-([1,1'-Biphenyl]-4-yl)-2,6-dichloropyridine (3.3 g), 3-cyanophenyl boronic acid (4.8 g), PEPPSI-IPr (trade name: Aldrich) (0.04 g) as a palladium catalyst, potassium carbonate (5.1 g), cyclopentyl methyl ether (30 mL), and water (3 mL) were put in a flask, and were stirred under a nitrogen atmosphere for 0.5 hours while being heated under reflux. The resulting product was cooled, and then water was added thereto. Thereafter, a precipitate was filtered, and was washed with Solmix (trade name: Nippon Alcohol Trading Co., Ltd.). The obtained crude product was dissolved in hot chlorobenzene and was filtered through a silica gel short column to obtain 4-([1,1'-biphenyl]-4-yl)-2,6-bis(3-cyanophenyl) pyridine (4.2 g).

Synthesis of compound (1-2-1026)

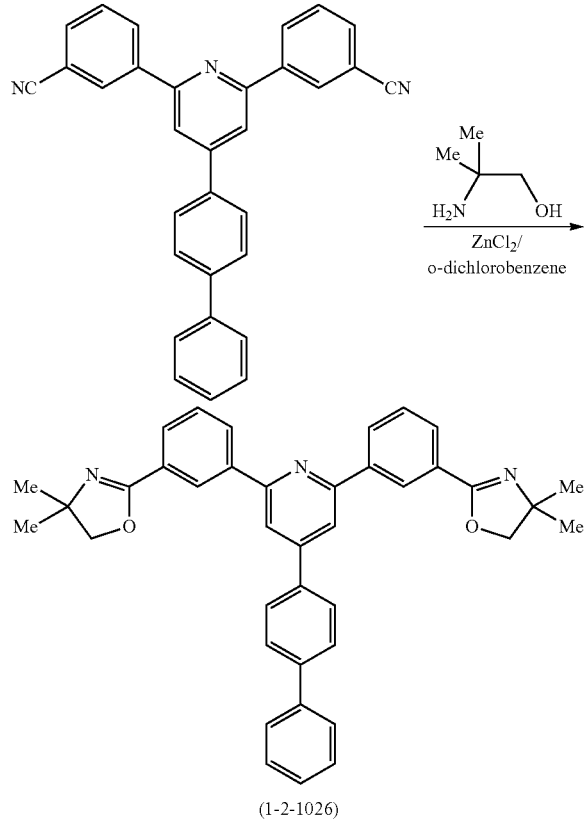

(1-2-1026)

4-([1,1'-Biphenyl]-4-yl)-2,6-bis(3-cyanophenyl) pyridine (4.0 g), 2-amino-2-methyl-1-propanol (8.2 g), zinc chloride (0.1 g), and o-dichlorobenzene (30 mL) were put in a flask, and were stirred under a nitrogen atmosphere for 24 hours while being heated under reflux. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)), and then was purified by sublimation to obtain compound (1-2-1026) (3.8 g) as a target compound.

The structure of the compound thus obtained was identified by NMR measurement.

$^1$H-NMR (CDCl$_3$): δ=8.7 (t, 2H), 8.4 (dt, 2H), 8.0 (dt, 2H), 8.0 (s, 2H), 7.9 (dt, 2H), 7.8 (dt, 2H), 7.7 (m, 2H), 7.6 (t, 2H), 7.5 (t, 2H), 7.4 (tt, 1H), 4.2 (s, 4H), 1.4 (s, 12H).

Synthesis of compound (1-2-1027): 4-([1,1'-biphenyl]-4-yl)-2,6-bis((4-(2,4,4,5,5-pentamethyl-1H-imidazolin-1-yl) phenyl) pyridine Synthesis of 2,4,4,5,5-pentamethyl-1H-imidazoline

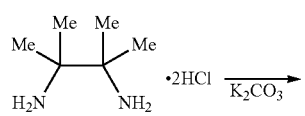

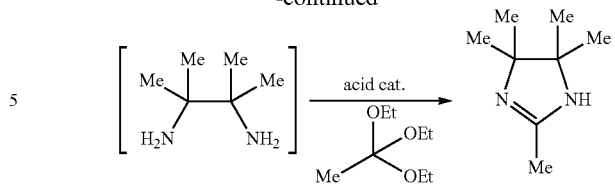

2,3-Dimethylbutane-2,3-diamine·dihydrochloride (6.5 g) was put in a flask, and was dissolved in water (20 mL). Potassium carbonate (20 g) was added thereto for neutralization and absorption of water. Thereafter, a free base of 2,3-dimethylbutane-2,3-diamine was washed off with ethyl acetate (400 mL), and the resulting ethyl acetate solution was concentrated to obtain free 2,3-dimethylbutane-2,3-diamine. Triethyl orthoacetate (25 mL) and Taycacure SAC-15 (trade name: Tayca Corporation) (70 mg) as an acid catalyst were added thereto, and the resulting mixture was stirred under a nitrogen atmosphere at a reflux temperature for 10 hours. The reaction solution was cooled to room temperature, and Taycacure SAC-15 (trade name: Tayca Corporation) was removed by filtration. Thereafter, the reaction solution was concentrated, and a colorless crystal started to be precipitated. Heptane (5 mL) was added thereto, and the resulting mixture was cooled in an ice bath to precipitate a colorless crystals, followed by filtration and drying to obtain 2,4,4,5,5-pentamethyl-1H-imidazoline (1.8 g) as a target compound.

Synthesis of 4-([1,1'-biphenyl]-4-yl)-2,6-bis(4-iodophenyl) pyridine

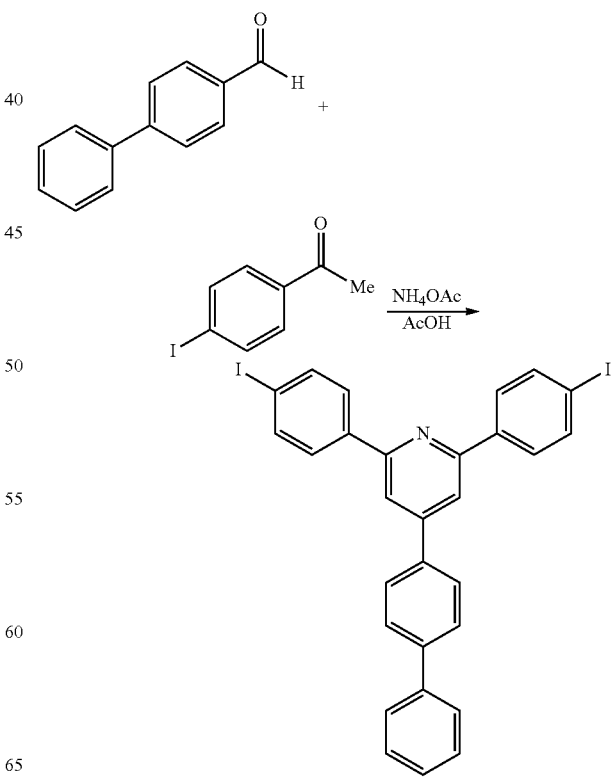

Biphenyl-4-carboxaldehyde (5.0 g), 4-iodoacetophenone (13.5 g), ammonium acetate (4.2 g), and acetic acid (50 mL) were put in a flask, and were stirred under a nitrogen atmosphere for 40 hours while being heated under reflux. The reaction solution was cooled to room temperature, water was added thereto, and a precipitate was filtered. This precipitate was washed with Solmix (trade name: Japan Alcohol Trading Co., Ltd.) and then with ethyl acetate, and the ethyl acetate washing solution was concentrated to obtain a crude product. The crude product was purified with a silica gel column (developing solution: toluene/heptane=1/1 (volume ratio)) to obtain 4-([1,1'-biphenyl]-4-yl)-2,6-bis(4-iodophenyl) pyridine (1.8 g) as a target compound.

Synthesis of compound (1-2-1027)

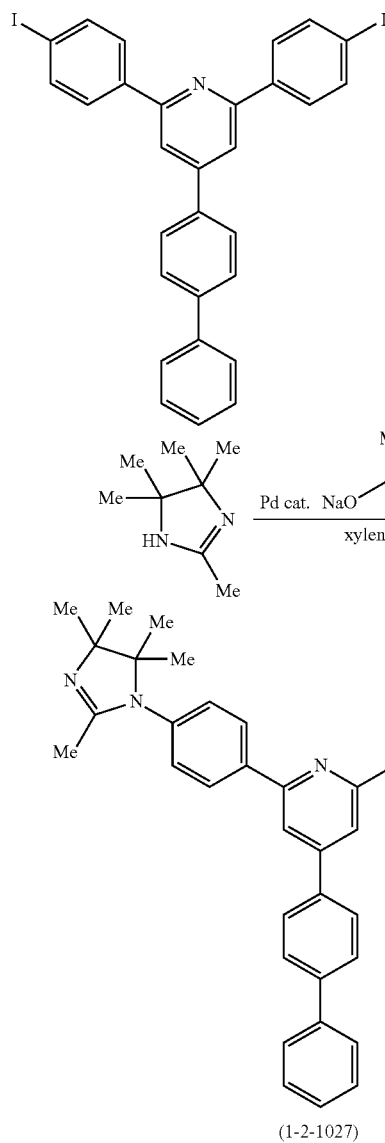

(1-2-1027)

4-([1,1'-Biphenyl]-4-yl)-2,6-bis(4-iodophenyl) pyridine (1.6 g), 2,4,4,5,5-pentamethyl-1H-imidazoline (0.8 g), sodium t-amylate (1.1 g), bis (di-t-butyl (4-dimethylaminophenyl) phosphine) dichloropalladium (0.05 g), and xylene (20 mL) were put in a flask, and were stirred under a nitrogen atmosphere at a reflux temperature for 6 hours. The reaction solution was cooled to room temperature, water was added thereto, and toluene was further added thereto for liquid separation extraction. An organic layer was separated, and was then dried and concentrated. A crude product was purified with a NH silica gel column (developing solution: toluene/ethyl acetate/isopropyl alcohol=1/1/0.05 (volume ratio)), and then was purified by sublimation to obtain compound (1-2-1027) (1.0 g) as a target compound.

The structure of the compound thus obtained was identified by NMR measurement.

$^1$H-NMR (CDCl$_3$): δ=8.2 (d, 4H), 8.0 (s, 2H), 7.9 (d, 2H), 7.8 (d, 2H), 7.7 (m, 2H), 7.5 (t, 2H), 7.4 (tt, 1H), 7.2 (d, 4H), 1.9 (s, 6H), 1.2 (s, 12H), 1.1 (s, 12H).

Synthesis of compound (1-2-1031): 6-([1,1'-biphenyl]-4-yl)-2,4-bis (4-(4,4-dimethyloxazolin-2-yl) phenyl) pyrimidine

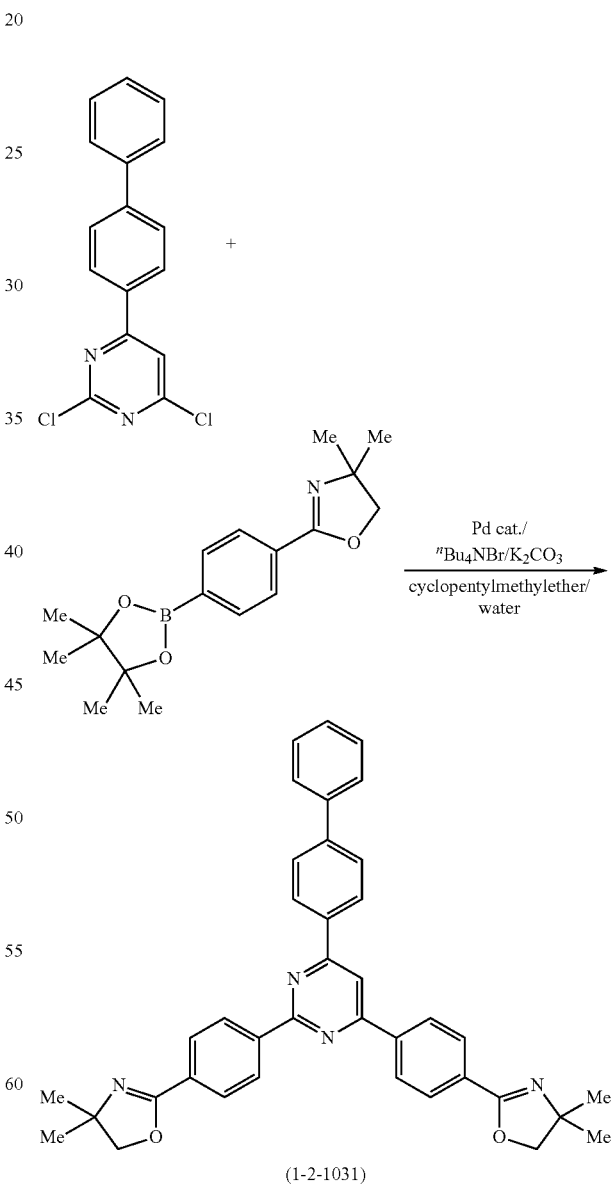

(1-2-1031)

4-([1,1'-Biphenyl]-4-yl)-2,6-dichloropyrimidine (1.6 g) synthesized by a method described in WO 2012/096263 A, 4,4-dimethyl-2-(4-(4,4,5,5-tetramethyl-1,3,2-dioxaborolan-2-yl) phenyl) oxazoline (4.8 g), bis(di-t-butyl (4-dimethylaminophenyl) phosphine) dichloropalladium (0.1 g), potassium carbonate (2.9 g), tetra-n-butylammonium bromide (0.3 g), cyclopentyl methyl ether (20 mL), and water (2 mL) were put in a flask, and were stirred under a nitrogen atmosphere for 10 hours while being heated under reflux. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=4/1 (volume ratio)), and then was purified by sublimation to obtain compound (1-2-1031) (1.2 g).

The structure of the compound thus obtained was identified by NMR measurement.

$^1$H-NMR (CDCl$_3$): δ=8.8 (d, 2H), 8.4 (d, 2H), 8.3 (d, 2H), 8.1 (m, 5H), 7.8 (d, 2H), 7.7 (d, 2H), 7.4 (t, 2H), 7.4 (t, 1H), 4.2 (s, 4H), 1.4 (s, 12H).

Synthesis of compound (1-2-1035): 4-([1,1'-biphenyl]-4-yl)-2,6-bis(4-(4,4-dimethyloxazolin-2-yl) phenyl) triazine Synthesis of 4-([1,1'-biphenyl]-4-yl)-2,6-bis(4-cyanophenyl) triazine

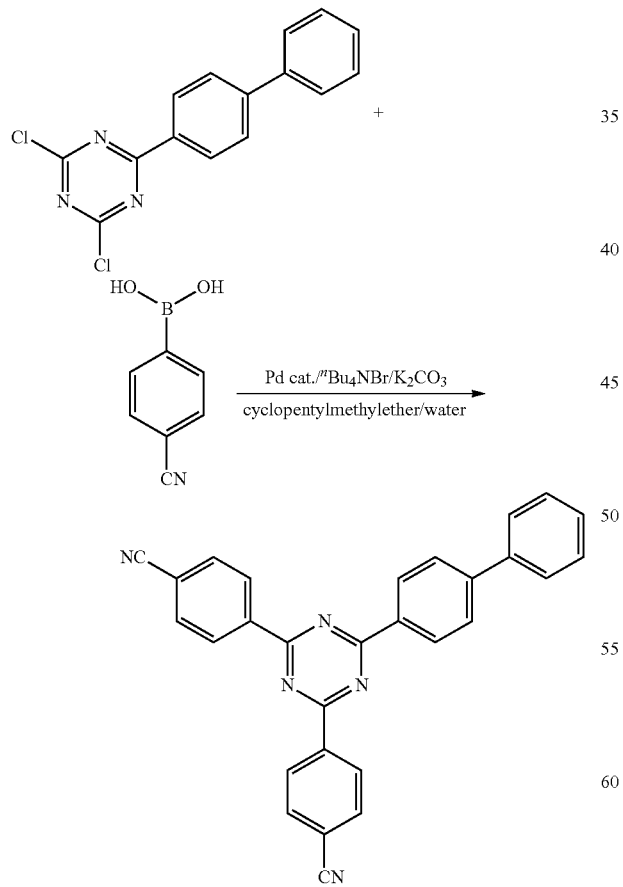

4-([1,1'-Biphenyl]-4-yl)-2,6-dichlorotriazine (3.2 g), 4-cyanophenyl boronic acid (4.7 g), bis(di-t-butyl (4-dimethylaminophenyl) phosphine) dichloropalladium (0.2 g), potassium carbonate (5.9 g), tetra-n-butylammonium bromide (0.7 g), cyclopentyl methyl ether (40 mL), and water (4 mL) were put in a flask, and were stirred under a nitrogen atmosphere for 8 hours while being heated under reflux. The reaction solution was cooled to room temperature, and then water was added thereto. Thereafter, a precipitate was filtered, and was washed with Solmix (trade name: Nippon Alcohol Trading Co., Ltd.) and then with ethyl acetate. The obtained crude product was dissolved in hot chlorobenzene, and was filtered through a silica gel short column to obtain a target compound (4.0 g).

Synthesis of compound (1-2-1035)

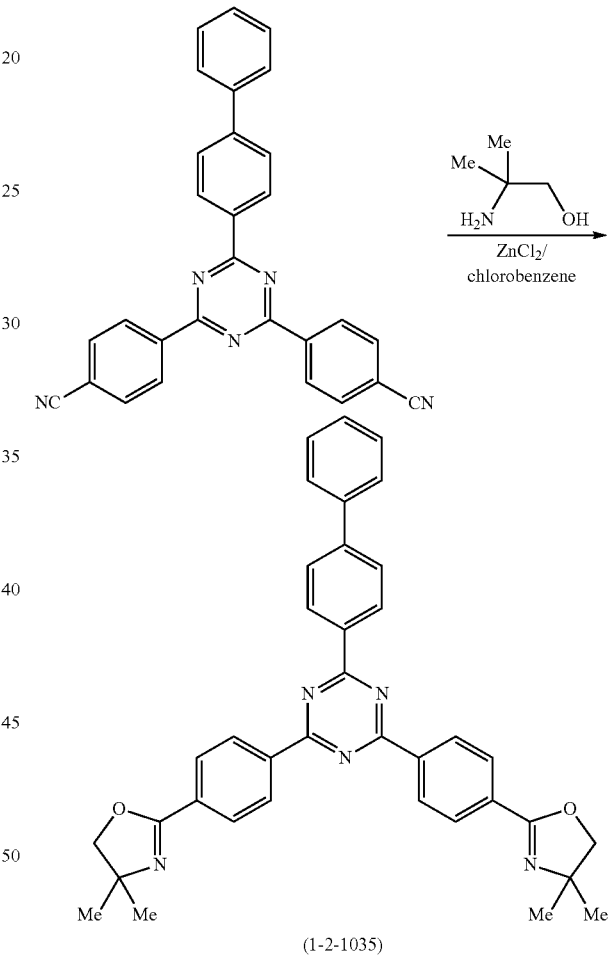

(1-2-1035)

4-([1,1'-Biphenyl]-4-yl)-2,6-bis(4-cyanophenyl) triazine (3.9 g), 2-amino-2-methyl-1-propanol (8.0 g), zinc chloride (0.1 g), and chlorobenzene (50 mL) were put in a flask, and were stirred under a nitrogen atmosphere at 150° C. for 57 hours. The reaction solution was cooled to room temperature, water was added thereto, and toluene was further added thereto for liquid separation extraction. An organic layer was separated, and was then dried and concentrated. A crude product was purified with a silica gel column (developing solution: toluene/ethyl acetate=7/3 (volume ratio)), and then was purified by sublimation to obtain compound (1-2-1035) (3.8 g) as a target compound.

The structure of the compound thus obtained was identified by NMR measurement.

$^1$H-NMR (CDCl$_3$): δ=8.8 (m, 6H), 8.1 (d, 4H), 7.8 (d, 2H), 7.7 (d, 2H), 7.5 (t, 2H), 7.4 (t, 1H), 4.2 (s, 4H), 1.4 (s, 12H).

Synthesis of compound (1-3-8): 1,3,5-tris(4-(2,4,4,5,5-pentamethyl-1H-imidazolin-1-yl) phenyl) benzene

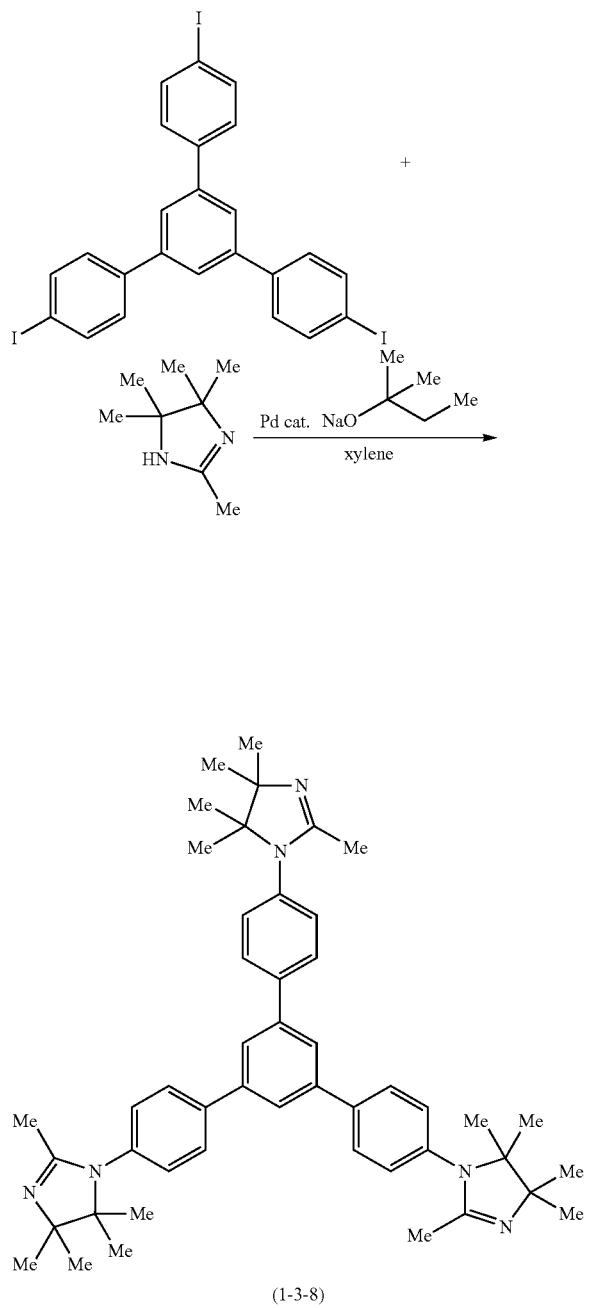

(1-3-8)

1,3,5-tris(4-iodophenyl) benzene (2.0 g), 2,4,4,5,5-pentamethyl-1H-imidazoline(1.5 g),sodium t-amylate (1.9 g), bis(di-t-butyl (4-dimethylaminophenyl) phosphine) dichloropalladium (0.06 g), and xylene (20 mL) were put in a flask, and were stirred under a nitrogen atmosphere at a reflux temperature for 8 hours. The reaction solution was cooled to room temperature, water was added thereto, and toluene was further added thereto for liquid separation extraction. An organic layer was separated, and was then dried and concentrated. A crude product was purified by a NH silica gel column (developing solution: toluene/ethyl acetate/Solmix (trade name: Nippon Alcohol Trading Co., Ltd.)=1/1/0.1 (volume ratio)), and then was purified by sublimation to obtain compound (1-3-8) (1.3 g) as a target compound.

The structure of the compound thus obtained was identified by NMR measurement.

$^1$H-NMR (CDCl$_3$): δ=7.8 (s, 3H), 7.7 (d, 6H), 7.2 (d, 6H), 1.8 (s, 9H), 1.2 (s, 18H), 1.1 (s, 18H).

Hereinafter, Examples of an organic EL element using the compound of the present invention will be described in order to describe the present invention in more detail, but the present invention is not limited thereto.

Organic EL elements according to Examples 1 to 5 and Comparative Examples 1 to 3 were manufactured, and driving voltage (V) and external quantum efficiency (%) during 1000 cd/m$^2$ light emission were measured for each of the organic EL elements. Furthermore, time (hr) to retain luminance of 80% (1200 cd/m$^2$) or more of initial luminance was measured when a constant current driving test was performed with a current density capable of obtaining initial luminance of 1500 cd/m$^2$.

A quantum efficiency of a luminescent element includes an internal quantum efficiency and an external quantum efficiency. The internal quantum efficiency indicates a ratio at which external energy injected as electrons (or holes) into a light emitting layer of a luminescent element is purely converted into photons. Meanwhile, the external quantum efficiency is calculated based on the amount of photons emitted to an outside of the luminescent element. A part of the photons generated in the light emitting layer are absorbed or reflected continuously inside the luminescent element, and are not emitted to the outside of the luminescent element. Therefore, the external quantum efficiency is lower than the internal quantum efficiency.

A method for measuring the external quantum efficiency is as follows. Using a voltage/current generator R6144 manufactured by Advantest Corporation, a voltage at which luminance of an element was 1000 cd/m$^2$ was applied to cause the element to emit light. Using a spectral radiance meter SR-3AR manufactured by TOPCON Co., spectral radiance in a visible light region was measured from a direction perpendicular to a light emitting surface. Assuming that the light emitting surface is a perfectly diffusing surface, a numerical value obtained by dividing a spectral radiance value of each measured wavelength component by wavelength energy and multiplying the obtained value by π is the number of photons at each wavelength. Subsequently, the number of photons is integrated in the observed entire wavelength region, and this number is taken as the total number of photons emitted from the element. A numerical value obtained by dividing an applied current value by an elementary charge is taken as the number of carriers injected into the element. The external quantum efficiency is a numerical value obtained by dividing the total number of photons emitted from the element by the number of carriers injected into the element.

Table 1 indicates a material composition of each layer of the manufactured organic EL elements according to Examples 1 to 6 and Comparative Examples 1 to 6.

TABLE 1

| | Hole Injection layer 1 (40 nm) | Hole Injection layer 2 (5 nm) | Hole Transport layer (25 nm) | Light emitting layer (20 nm) Host | Light emitting layer (20 nm) Dopant | Electron Transport layer (30 nm) | Cathode (1 nm/100 nm) |
|---|---|---|---|---|---|---|---|
| Example 1 | HI-1 | IL | HT-1 | BH | BD | Compound (1-2-1) | Liq/MgAg |
| Example 2 | HI-1 | IL | HT-1 | BH | BD | Compound (1-2-2) | Liq/MgAg |
| Example 3 | HI-1 | IL | HT-1 | BH | BD | Compound (1-3-2) | Liq/MgAg |
| Example 4 | HI-1 | IL | HT-1 | BH | BD | Compound (1-2-102) | Liq/MgAg |
| Example 5 | HI-1 | IL | HT-1 | BH | BD | Compound (1-1-108) | Liq/MgAg |
| Example 6 | HI-1 | IL | HT-1 | BH | BD | Compound (1-2-402) | Liq/MgAg |
| Comparative Example 1 | HI-1 | IL | HT-1 | BH | BD | Compound (A) | Liq/MgAg |
| Comparative Example 2 | HI-1 | IL | HT-1 | BH | BD | Compound (B) | Liq/MgAg |
| Comparative Example 3 | HI-1 | IL | HT-1 | BH | BD | Compound (C) | Liq/MgAg |
| Comparative Example 4 | HI-1 | IL | HT-1 | BH | BD | Compound (D) | Liq/MgAg |
| Comparative Example 5 | HI-1 | IL | HT-1 | BH | BD | Compound (E) | Liq/MgAg |
| Comparative Example 6 | HI-1 | IL | HT-1 | BH | BD | Compound (F) | Liq/MgAg |

* The electron transport layer was formed by mixing a compound in Table 1 with Liq at a weight ratio of 1:1.

In Table 1, "HI-1" represents $N^4,N^{4'}$-diphenyl-$N^4,N^{4'}$-bis(9-phenyl-9H-carbazol-3-yl)-[1,1'-biphenyl]-4,4'-diamine, "IL" represents 1,4,5,8,9,12-hexaazatriphenylene hexacarbonitrile, "HT-1" represents N-([1,1'-biphenyl]-4-yl)-9,9-dimethyl-N-(4-(9-phenyl-9H-carbazol-3-yl) phenyl)-9H-fluorene-2-amine, "BH" represents 9-phenyl-10-(4-phenylnaphthalene-1-yl) anthracene, "BD" represents 7,7-dimethyl-$N^5,N^9$-diphenyl-$N^5,N^9$-bis(4-(trimethylsilyl)phenyl)-7H-benzo[c]fluorene-5,9-diamine, compound (A) represents 9,10-bis(4-(3-pyridylphenyl))-2-phenylanthracene, compound (B) represents 1,3,5-tris(3-(3-pyridylphenyl)) benzene, compound (C) represents 2,7-bis(4-(5-methyl-3-pyridylphenyl))-5,5'-(9,9'-spirobi[fluorene]), compound (D) represents 2-4-(9,10-di(naphthalene-2-yl)anthracene-2-yl) phenyl)-1-phenyl-1H-benzo [d] imidazole, compound (E) represents 9,10-bis(4-(2-oxazolylphenyl))-2-phenylanthracene, and compound (F) represents 2,7-bis(4-(2-thiazolyl) phenyl) triphenylene. Chemical structures of these compounds are illustrated below together with a chemical structure of "Liq" used for the cathode.

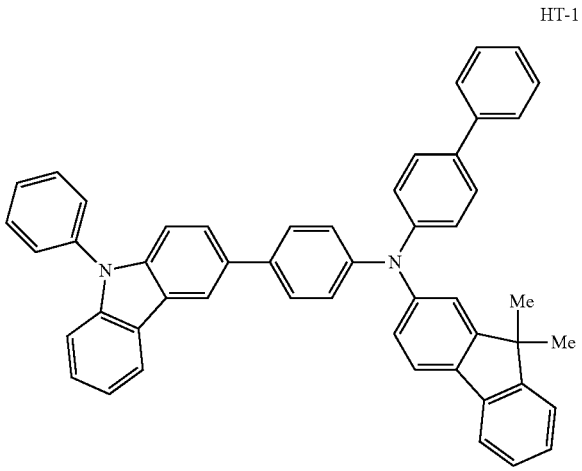

HT-1

-continued

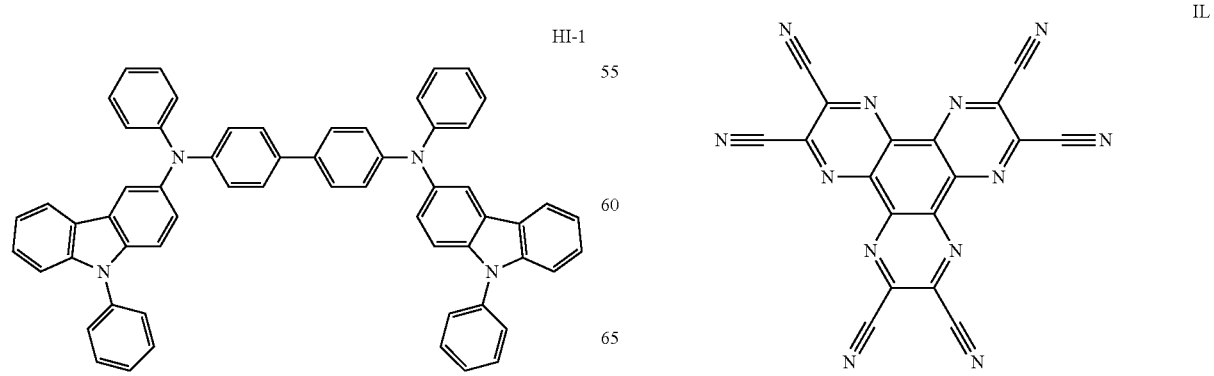

HI-1

IL

BH
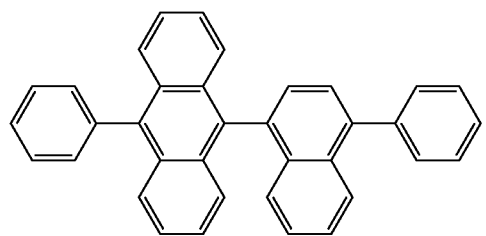

BD
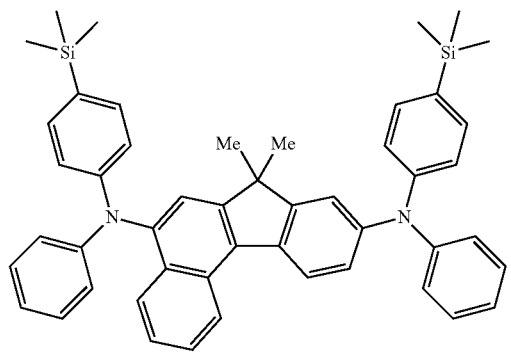

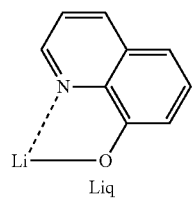
Liq

A
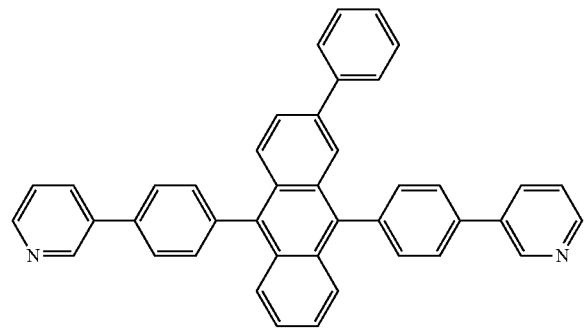

B
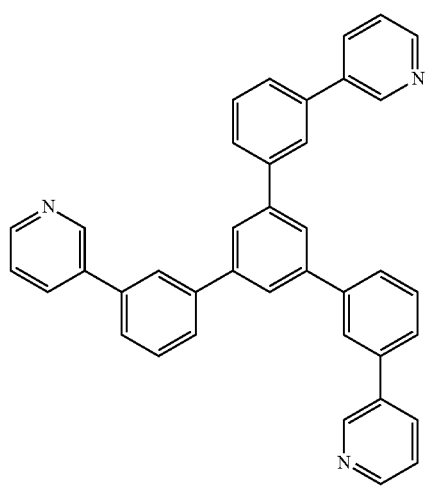

C
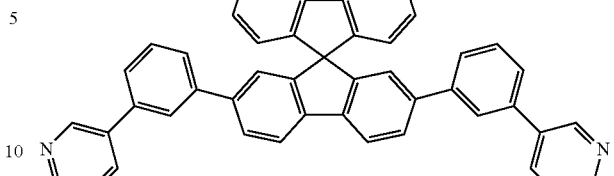

D
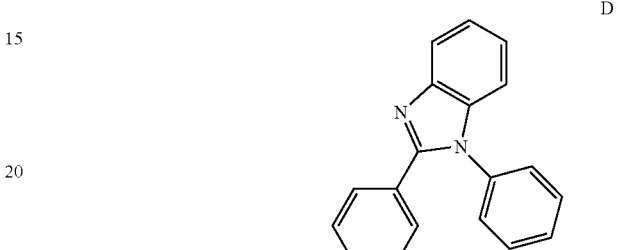

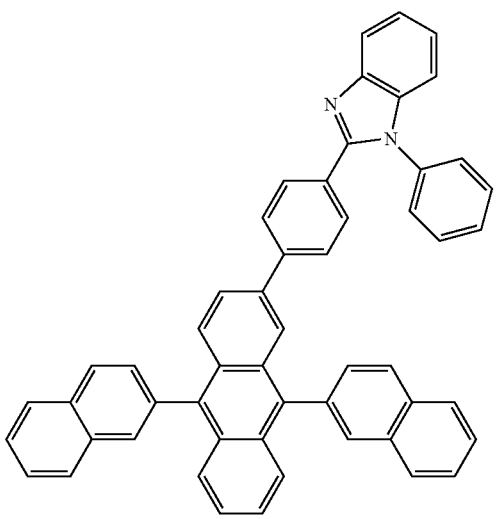

E
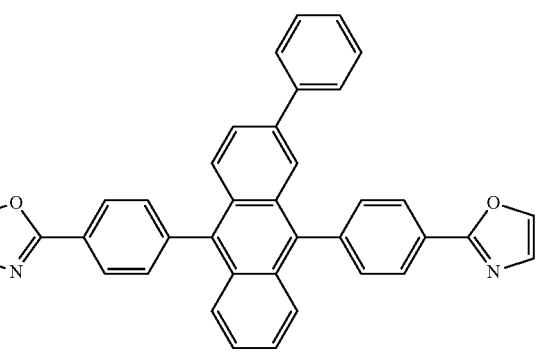

F
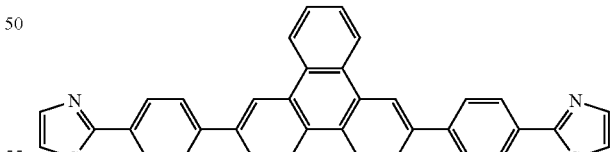

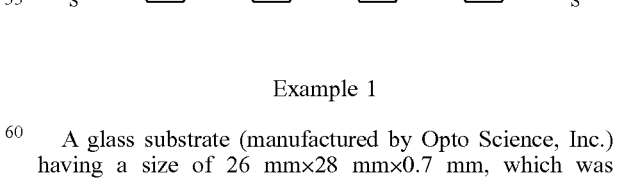

Example 1

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Show a Shinku Co., Ltd.), and a vapor deposition boat made of molybdenum and containing HI-1, a vapor deposition boat made of molybdenum and containing IL, a vapor deposition boat made of molybdenum and containing HT-1, a vapor deposition boat made of molybdenum and containing BH, a vapor deposition boat made of molybdenum and containing BD, a vapor deposition boat made of molybdenum and containing compound (1-2-1) of the present invention, a vapor deposition boat made of molybdenum and containing Liq, a vapor deposition boat made of tungsten and containing magnesium, and a vapor deposition boat made of tungsten and containing silver were mounted in the apparatus.

Layers as described below were formed sequentially on the ITO film of the transparent supporting substrate. The pressure in a vacuum chamber was reduced to $5 \times 10^{-4}$ Pa. First, the vapor deposition boat containing HI-1 was heated, and vapor deposition was performed so as to obtain a film thickness of 40 nm. Furthermore, the vapor deposition boat containing IL was heated, and vapor deposition was performed so as to obtain a film thickness of 5 nm to form a hole injection layer formed of two layers. Subsequently, the vapor deposition boat containing HT-1 was heated, and vapor deposition was performed so as to obtain a film thickness of 25 nm to form a hole transport layer. Subsequently, the vapor deposition boat containing BH and the vapor deposition boat containing BD were heated simultaneously, and vapor deposition was performed so as to obtain a film thickness of 20 nm to form a light emitting layer. A vapor deposition rate was adjusted such that a weight ratio between BH and BD was approximately 95: 5. Subsequently, the vapor deposition boat containing compound (1-2-1) and the vapor deposition boat containing Liq were heated simultaneously, and vapor deposition was performed so as to obtain a film thickness of 30 nm to form an electron transport layer. A vapor deposition rate was adjusted such that a weight ratio between compound (1-2-1) and Liq was approximately 1: 1. The vapor deposition rate for each layer was 0.01 to 1 nm/sec.

Thereafter, the vapor deposition boat containing Liq was heated, and vapor deposition was performed at a vapor deposition rate of 0.01 to 0.1 nm/sec so as to obtain a film thickness of 1 nm. Subsequently, the boat containing magnesium and the boat containing silver were simultaneously heated, and vapor deposition was performed so as to obtain a film thickness of 100 nm to form a cathode, and an organic EL element was obtained. At this time, the vapor deposition rate was adjusted in a range between 0.1 nm to 10 nm/sec such that the ratio of the numbers of atoms between magnesium and silver was 10:1.

When characteristics during 1000 cd/m$^2$ light emission were measured using the ITO electrode as an anode and the Mg/Ag electrode as a cathode, the driving voltage was 3.41 V, and the external quantum efficiency was 6.42%. Time to retain luminance of 80% (1200 cd/m$^2$) or more of the initial luminance was 141 hours.

Example 2

An organic EL element was obtained according to the method of Example 1 except that compound (1-2-1) was replaced with compound (1-2-2). When characteristics during 1000 cd/m$^2$ light emission were measured, the driving voltage was 3.65 V, and the external quantum efficiency was 6.25%. Time to retain luminance of 80% (1200 cd/m$^2$) or more of the initial luminance was 331 hours.

Example 3

An organic EL element was obtained according to the method of Example 1 except that compound (1-2-1) was replaced with compound (1-3-2). When characteristics during 1000 cd/m$^2$ light emission were measured, the driving voltage was 4.75 V, and the external quantum efficiency was 7.25%. Time to retain luminance of 80% (1200 cd/m$^2$) or more of the initial luminance was 55 hours.

Example 4

An organic EL element was obtained according to the method of Example 1 except that compound (1-2-1) was replaced with compound (1-2-102). When characteristics during 1000 cd/m$^2$ light emission were measured, the driving voltage was 3.72 V, and the external quantum efficiency was 8.16%. Time to retain luminance of 80% (1200 cd/m$^2$) or more of the initial luminance was 154 hours.

Example 5

An organic EL element was obtained according to the method of Example 1 except that compound (1-2-1) was replaced with compound (1-1-108). When characteristics during 1000 cd/m$^2$ light emission were measured, the driving voltage was 4.55 V, and the external quantum efficiency was 5.62%. Time to retain luminance of 80% (1200 cd/m$^2$) or more of the initial luminance was 262 hours.

Example 6

An organic EL element was obtained according to the method of Example 1 except that compound (1-2-1) was replaced with compound (1-2-402). When characteristics during 1000 cd/m$^2$ light emission were measured, the driving voltage was 5.92 V, and the external quantum efficiency was 6.99%. Time to retain luminance of 80% (1200 cd/m$^2$) or more of the initial luminance was 108 hours.

Comparative Example 1

An organic EL element was obtained according to the method of Example 1 except that compound (1-2-1) was replaced with compound (A). When characteristics during 1000 cd/m$^2$ light emission were measured, the driving voltage was 3.51 V, and the external quantum efficiency was 5.24%. Time to retain luminance of 80% (1200 cd/m$^2$) or more of the initial luminance was 77 hours.

Comparative Example 2

An organic EL element was obtained according to the method of Example 1 except that compound (1-2-1) was replaced with compound (B). When characteristics during 1000 cd/m$^2$ light emission were measured, the driving voltage was 5.17 V, and the external quantum efficiency was 5.70%. Time to retain luminance of 80% (1200 cd/m$^2$) or more of the initial luminance was 63 hours.

Comparative Example 3

An organic EL element was obtained according to the method of Example 1 except that compound (1-2-1) was replaced with compound (C). When characteristics during 1000 cd/m$^2$ light emission were measured, the driving voltage was 3.98 V, and the external quantum efficiency was 6.45%. Time to retain luminance of 80% (1200 cd/m$^2$) or more of the initial luminance was 160 hours.

Comparative Example 4

An organic EL element was obtained according to the method of Example 1 except that compound (1-2-1) was replaced with compound (D). When characteristics during 1000 cd/m² light emission were measured, the driving voltage was 5.11 V, and the external quantum efficiency was 4.65%. Time to retain luminance of 80% (1200 cd/m²) or more of the initial luminance was 119 hours.

Comparative Example 5

An organic EL element was obtained according to the method of Example 1 except that compound (1-2-1) was replaced with compound (E). When characteristics during 1000 cd/m² light emission were measured, the driving voltage was 3.55 V, and the external quantum efficiency was 5.92%. Time to retain luminance of 80% (1200 cd/m²) or more of the initial luminance was 99 hours.

Comparative Example 6

An organic EL element was obtained according to the method of Example 1 except that compound (1-2-1) was replaced with compound (F). When characteristics during 1000 cd/m² light emission were measured, the driving voltage was 3.85 V, and the external quantum efficiency was 6.42%. Time to retain luminance of 80% (1200 cd/m²) or more of the initial luminance was 29 hours.

Results of Examples 1 to 6 and Comparative Examples 1 to 6 are summarized in Table 2.

TABLE 2

| | | Characteristics during 1000 cd/m² light emission | | Time (hr) to retain luminance of |
|---|---|---|---|---|
| | Electron Transport layer | Voltage (V) | Quantum efficiency (%) | 80% or more of initial luminance |
| Example 1 | Compound (1-2-1) | 3.41 | 6.42 | 141 |
| Example 2 | Compound (1-2-2) | 3.65 | 6.25 | 331 |
| Example 3 | Compound (1-3-2) | 4.75 | 7.25 | 55 |
| Example 4 | Compound (1-2-102) | 3.72 | 8.16 | 154 |
| Example 5 | Compound (1-1-108) | 4.55 | 5.62 | 262 |
| Example 6 | Compound (1-2-402) | 5.92 | 6.99 | 108 |
| Comparative Example 1 | Compound (A) | 3.51 | 5.24 | 77 |
| Comparative Example 2 | Compound (B) | 5.17 | 5.70 | 63 |
| Comparative Example 3 | Compound (C) | 3.98 | 6.45 | 160 |
| Comparative Example 4 | Compound (D) | 5.11 | 4.65 | 119 |
| Comparative Example 5 | Compound (E) | 3.55 | 5.92 | 99 |
| Comparative Example 6 | Compound (F) | 3.85 | 6.42 | 29 |

* The electron transport layer was formed by mixing a compound in Table 2 with Liq at a weight ratio of 1:1.

Table 3 indicates a material composition of each layer of the manufactured organic EL elements according to Examples 7 to 16 and Comparative Examples 7 to 10.

TABLE 3

| | Hole Injection layer 1 | Hole Injection layer 2 | Hole Transport layer | Blocking layer | Light emitting layer (25 nm) | | Electron transport layer | Cathode |
|---|---|---|---|---|---|---|---|---|
| | (40 nm) | (5 nm) | (15 nm) | (10 nm) | Host | Dopant | (30 nm) | (1 nm/100 nm) |
| Example 7 | HI-1 | IL | HT-1 | BL | BH2 | BD2 | Compound (1-2-22) | Liq/MgAg |
| Example 8 | HI-1 | IL | HT-1 | BL | BH2 | BD2 | Compound (1-2-146) | Liq/MgAg |
| Example 9 | HI-1 | IL | HT-1 | BL | BH2 | BD2 | Compound (1-2-522) | Liq/MgAg |
| Example 10 | HI-1 | IL | HT-1 | BL | BH2 | BD2 | Compound (1-2-1022) | Liq/MgAg |
| Example 11 | HI-1 | IL | HT-1 | BL | BH2 | BD2 | Compound (1-2-1025) | Liq/MgAg |
| Example 12 | HI-1 | IL | HT-1 | BL | BH2 | BD2 | Compound (1-2-1026) | Liq/MgAg |
| Example 13 | HI-1 | IL | HT-1 | BL | BH2 | BD2 | Compound (1-2-1027) | Liq/MgAg |
| Example 14 | HI-1 | IL | HT-1 | BL | BH2 | BD2 | Compound (1-2-1031) | Liq/MgAg |
| Example 15 | HI-1 | IL | HT-1 | BL | BH2 | BD2 | Compound (1-2-1035) | Liq/MgAg |
| Example 16 | HI-1 | IL | HT-1 | BL | BH2 | BD2 | Compound (1-3-8) | Liq/MgAg |

TABLE 3-continued

| | Hole Injection layer 1 (40 nm) | Hole Injection layer 2 (5 nm) | Hole Transport layer (15 nm) | Blocking layer (10 nm) | Light emitting layer (25 nm) Host | Light emitting layer (25 nm) Dopant | Electron transport layer (30 nm) | Cathode (1 nm/100 nm) |
|---|---|---|---|---|---|---|---|---|
| Comparative Example 7 | HI-1 | IL | HT-1 | BL | BH2 | BD2 | Compound (G) | Liq/MgAg |
| Comparative Example 8 | HI-1 | IL | HT-1 | BL | BH2 | BD2 | Compound (H) | Liq/MgAg |
| Comparative Example 9 | HI-1 | IL | HT-1 | BL | BH2 | BD2 | Compound (I) | Liq/MgAg |
| Comparative Example 10 | HI-1 | IL | HT-1 | BL | BH2 | BD2 | Compound (J) | Liq/MgAg |

* The electron transport layer was formed by mixing a compound in Table 3 with Liq at a weight ratio of 1:1.

In Table 3, "HI-1", "IL", "HT-1", and "Liq" represent the same compounds as those in Table 1. "BL" represents N,N-bis(4-(dibenzo[b,d]furan-4-yl phenyl [1,1':4',1''-terphenyl]-4-amine, "BH2" represents 2-(10-phenylanthracen-9-yl)naphtho[2,3-b]benzofuran, "BD2" represents $N^1,N^6$-di ([1,1'-biphenyl]-2-yl)-$N^1,N^6$-bis(dibenzo[b,d]furan-4-yl) pyren-1,6-diamine, compound (G) represents 9,10-bis(2-(2-oxazolyl) pyridin-5-yl)-2-phenylanthracene, compound (H) represents 4',4''-bis(benzo (d) thiazol-2-yl)-1,1':3',1''-terphenyl, compound (I) represents 2-(4-((diphenylboryl) oxy-[1,1'-biphenyl]-3-yl)-4,4-dimethyloxazoline, and compound (J) represents 2,9-bis(2-benzo[d]oxazolyl)-5,6-diphenyl-1,10-phenanthroline. Chemical structures of these compounds are illustrated below.

BL

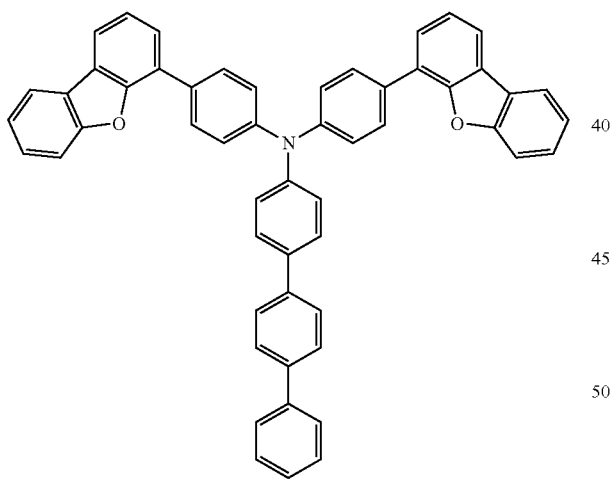

BH2

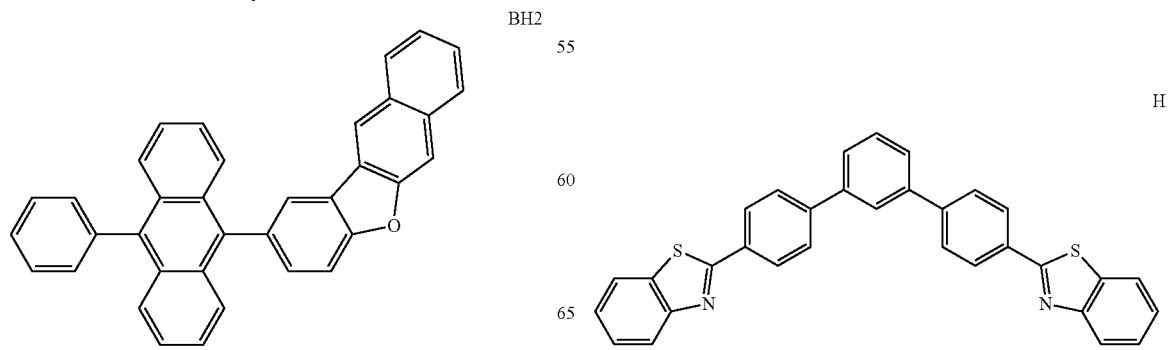

BD2

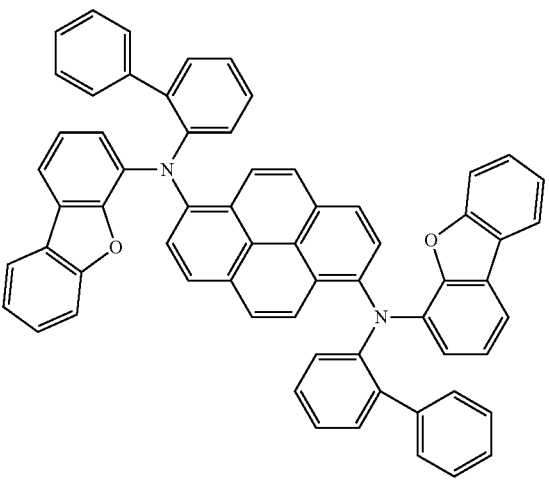

G

H

I

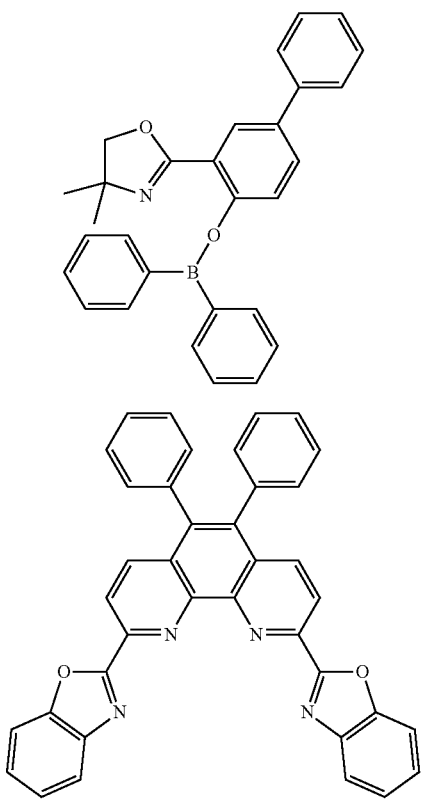

J

Example 7

A glass substrate (manufactured by Opto Science, Inc.) having a size of 26 mm×28 mm×0.7 mm, which was obtained by forming a film of ITO having a thickness of 180 nm by sputtering, and polishing the ITO film to 150 nm, was used as a transparent supporting substrate. This transparent supporting substrate was fixed to a substrate holder of a commercially available vapor deposition apparatus (manufactured by Show a Shinku Co., Ltd.), and a vapor deposition boat made of molybdenum and containing HI-1, a vapor deposition boat made of molybdenum and containing IL, a vapor deposition boat made of molybdenum and containing HT-1, a vapor deposition boat made of molybdenum and containing BL, a vapor deposition boat made of molybdenum and containing BH2, a vapor deposition boat made of molybdenum and containing BD2, a vapor deposition boat made of molybdenum and containing compound (1-2-22) of the present invention, a vapor deposition boat made of molybdenum and containing Liq, a vapor deposition boat made of tungsten and containing magnesium, and vapor deposition boat made of tungsten and containing silver were mounted in the apparatus.

Layers as described below were formed sequentially on the ITO film of the transparent supporting substrate. The pressure in a vacuum chamber was reduced to $5\times10^{-4}$ Pa. First, the vapor deposition boat containing HI-1 was heated, and vapor deposition was performed so as to obtain a film thickness of 40 nm. Furthermore, the vapor deposition boat containing IL was heated, and vapor deposition was performed so as to obtain a film thickness of 5 nm to form a hole injection layer formed of two layers. Subsequently, the vapor deposition boat containing HT-1 was heated, and vapor deposition was performed so as to obtain a film thickness of 15 nm to form a hole transport layer.

Subsequently, the vapor deposition boat containing BL was heated, and vapor deposition was performed so as to obtain a film thickness of 10 nm to form a blocking layer. Subsequently, the vapor deposition boat containing compound BH2 and the vapor deposition boat containing BD2 were heated simultaneously, and vapor deposition was performed so as to obtain a film thickness of 25 nm to form a light emitting layer. A vapor deposition rate was adjusted such that a weight ratio between BH2 and BD2 was approximately 95: 5. Subsequently, the vapor deposition boat containing compound (1-2-22) and the vapor deposition boat containing Liq were heated simultaneously, and vapor deposition was performed so as to obtain a film thickness of 30 nm to form an electron transport layer. The vapor deposition rate was adjusted such that a weight ratio between compound (1-2-22) and Liq was approximately 1: 1. The vapor deposition rate for each layer was 0.01 to 1 nm/sec.

Thereafter, the vapor deposition boat containing Liq was heated, and vapor deposition was performed at a vapor deposition rate of 0.01 to 0.1 nm/sec so as to obtain a film thickness of 1 nm. Subsequently, the boat containing magnesium and the boat containing silver were simultaneously heated, and vapor deposition was performed so as to obtain a film thickness of 100 nm to form a cathode, and an organic EL element was obtained. At this time, the vapor deposition rate was adjusted in a range between 0.1 nm to 10 nm/sec such that the ratio of the numbers of atoms between magnesium and silver was 10: 1.

When characteristics during 1000 cd/m² light emission were measured using the ITO electrode as an anode and the Mg/Ag electrode as a cathode, the driving voltage was 3.82 V, and the external quantum efficiency was 5.95%. Time to retain luminance of 80% (1200 cd/m²) or more of the initial luminance was 150 hours.

Example 8

An organic EL element was obtained according to the method of Example 7 except that compound (1-2-22) was replaced with compound (1-2-146). When characteristics during 1000 cd/m² light emission were measured, the driving voltage was 3.78 V, and the external quantum efficiency was 7.31%. Time to retain luminance of 80% (1200 cd/m²) or more of the initial luminance was 140 hours.

Example 9

An organic EL element was obtained according to the method of Example 7 except that compound (1-2-22) was replaced with compound (1-2-522). When characteristics during 1000 cd/m² light emission were measured, the driving voltage was 4.60 V, and the external quantum efficiency was 5.88%. Time to retain luminance of 80% (1200 cd/m²) or more of the initial luminance was 121 hours.

Example 10

An organic EL element was obtained according to the method of Example 7 except that compound (1-2-22) was replaced with compound (1-2-1022). When characteristics during 1000 cd/m² light emission were measured, the driving voltage was 3.55 V, and the external quantum efficiency was 6.10%. Time to retain luminance of 80% (1200 cd/m²) or more of the initial luminance was 412 hours.

Example 11

An organic EL element was obtained according to the method of Example 7 except that compound (1-2-22) was replaced with compound (1-2-1025). When characteristics during 1000 cd/m² light emission were measured, the driving voltage was 3.24 V, and the external quantum efficiency was 6.22%. Time to retain luminance of 80% (1200 cd/m²) or more of the initial luminance was 523 hours.

Example 12

An organic EL element was obtained according to the method of Example 7 except that compound (1-2-22) was replaced with compound (1-2-1026). When characteristics during 1000 cd/m² light emission were measured, the driving voltage was 3.35 V, and the external quantum efficiency was 6.41%. Time to retain luminance of 80% (1200 cd/m²) or more of the initial luminance was 540 hours.

Example 13

An organic EL element was obtained according to the method of Example 7 except that compound (1-2-22) was replaced with compound (1-2-1027). When characteristics during 1000 cd/m² light emission were measured, the driving voltage was 3.85 V, and the external quantum efficiency was 6.02%. Time to retain luminance of 80% (1200 cd/m²) or more of the initial luminance was 365 hours.

Example 14

An organic EL element was obtained according to the method of Example 7 except that compound (1-2-22) was replaced with compound (1-2-1031). When characteristics during 1000 cd/m² light emission were measured, the driving voltage was 3.63 V, and the external quantum efficiency was 6.05%. Time to retain luminance of 80% (1200 cd/m²) or more of the initial luminance was 565 hours.

Example 15

An organic EL element was obtained according to the method of Example 7 except that compound (1-2-22) was replaced with compound (1-2-1035). When characteristics during 1000 cd/m² light emission were measured, the driving voltage was 4.45 V, and the external quantum efficiency was 5.86%. Time to retain luminance of 80% (1200 cd/m²) or more of the initial luminance was 580 hours.

Example 16

An organic EL element was obtained according to the method of Example 7 except that compound (1-2-22) was replaced with compound (1-3-8). When characteristics during 1000 cd/m² light emission were measured, the driving voltage was 3.92 V, and the external quantum efficiency was 6.10%. Time to retain luminance of 80% (1200 cd/m²) or more of the initial luminance was 145 hours.

Comparative Example 7

An organic EL element was obtained according to the method of Example 7 except that compound (1-2-22) was replaced with compound (G). When characteristics during 1000 cd/m² light emission were measured, the driving voltage was 4.52 V, and the external quantum efficiency was 4.31%. Time to retain luminance of 80% (1200 cd/m²) or more of the initial luminance was 95 hours.

Comparative Example 8

An organic EL element was obtained according to the method of Example 7 except that compound (1-2-22) was replaced with compound (H). When characteristics during 1000 cd/m² light emission were measured, the driving voltage was 8.20 V, and the external quantum efficiency was 1.2%. Time to retain luminance of 80% (1200 cd/m²) or more of the initial luminance was 8 hours.

Comparative Example 9

An organic EL element was obtained according to the method of Example 7 except that compound (1-2-22) was replaced with compound (I). When characteristics during 1000 cd/m² light emission were measured, the driving voltage was 6.31 V, and the external quantum efficiency was 1.8%. Time to retain luminance of 80% (1200 cd/m²) or more of the initial luminance was 30 hours.

Comparative Example 10

An organic EL element was obtained according to the method of Example 7 except that compound (1-2-22) was replaced with compound (J). When characteristics during 1000 cd/m² light emission were measured, the driving voltage was 5.62 V, and the external quantum efficiency was 4.20%. Time to retain luminance of 80% (1200 cd/m²) or more of the initial luminance was 75 hours.

Results of Examples 7 to 16 and Comparative Examples 7 to 10 are summarized in Table 4.

TABLE 4

| | | Characteristics during 1000 cd/m light emission | | Time (hr) to retain luminance of |
|---|---|---|---|---|
| | Electron transport layer | Voltage (V) | Quantum efficiency (%) | 80% or more of initial luminance |
| Example 7 | Compound (1-2-22) | 3.82 | 5.95 | 150 |
| Example 8 | Compound (1-2-146) | 3.78 | 7.31 | 140 |
| Example 9 | Compound (1-2-522) | 4.60 | 5.88 | 121 |
| Example 10 | Compound (1-2-1022) | 3.55 | 6.10 | 412 |
| Example 11 | Compound (1-2-1025) | 3.24 | 6.22 | 523 |
| Example 12 | Compound (1-2-1026) | 3.35 | 6.41 | 540 |
| Example 13 | Compound (1-2-1027) | 3.85 | 6.02 | 365 |
| Example 14 | Compound (1-2-1031) | 3.63 | 6.05 | 565 |
| Example 15 | Compound (1-2-1035) | 4.45 | 5.86 | 580 |
| Example 16 | Compound (1-3-8) | 3.92 | 6.10 | 145 |

TABLE 4-continued

| | | Characteristics during 1000 cd/m light emission | | Time (hr) to retain luminance of 80% or more of initial luminance |
|---|---|---|---|---|
| | Electron transport layer | Voltage (V) | Quantum efficiency (%) | |
| Comparative Example 7 | Compound (G) | 4.52 | 4.31 | 95 |
| Comparative Example 8 | Compound (H) | 8.20 | 1.2 | 8 |
| Comparative Example 9 | Compound (I) | 6.31 | 1.8 | 30 |
| Comparative Example 10 | Compound (J) | 5.62 | 4.20 | 75 |

* The electron transport layer was formed by mixing a compound in Table 4 with Liq at a weight ratio of 1:1.

INDUSTRIAL APPLICABILITY

According to the preferred embodiment of the present invention, it is possible to provide an organic EL element which achieves characteristics required for an organic EL element, such as a low driving voltage, a high quantum efficiency, and long element lifetime in a well-balanced manner, particularly has the high quantum efficiency, and to provide a high-performance display apparatus such as a full-color display.

REFERENCE SIGNS LIST

100 Organic electroluminescent element
101 Substrate
102 Anode
103 Hole injection layer
104 Hole transport layer
105 Light emitting layer
106 Electron transport layer
107 Electron injection layer
108 Cathode

The invention claimed is:
1. An azoline ring-containing compound represented by the following formula (1),

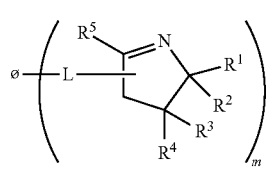

(1)

wherein:
formula (1) represents a structure in which m "group(s) formed by an azoline ring and L" is/are bonded to φ,
in formula (1), m represents an integer of 1 to 4, and when m represents 2 to 4, "groups formed by an azoline ring and L" may be the same as or different from one another,
in formula (1), φ is selected from the group consisting of monovalent groups (in this case m=1) represented by the following formulas (φ1-1) to (φ1-11), monovalent groups (in this case m=1) represented by the following formulas (φ1-14) to (φ1-18), divalent groups (in this case m=2) represented by the following formulas (φ2-1) and (φ2-4) to (φ2-34), trivalent groups (in this case m=3) represented by the following formulas (φ3-2) and (φ3-3), and tetravalent groups (in this case m=4) represented by the following formulas (φ4-1) and (φ4-2),

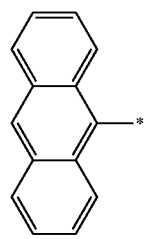
(φ1-1)

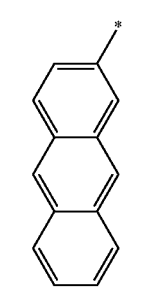
(φ1-2)

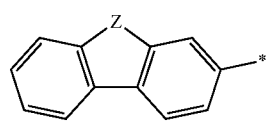
(φ1-3)

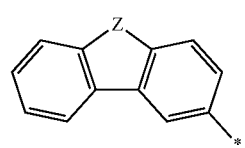
(φ1-4)

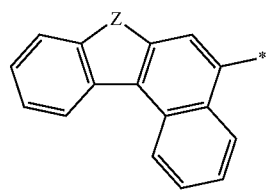
(φ1-5)

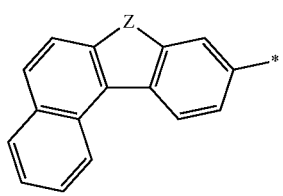
(φ1-6)

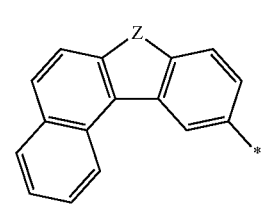
(φ1-7)

(φ1-8)
(φ1-9)
(φ1-10)
(φ1-11)
(φ1-14)
(φ1-15)
(φ1-16)
(φ1-17)
(φ1-18)
(φ2-1)
(φ2-4)
(φ2-5)
(φ2-6)
(φ2-7)

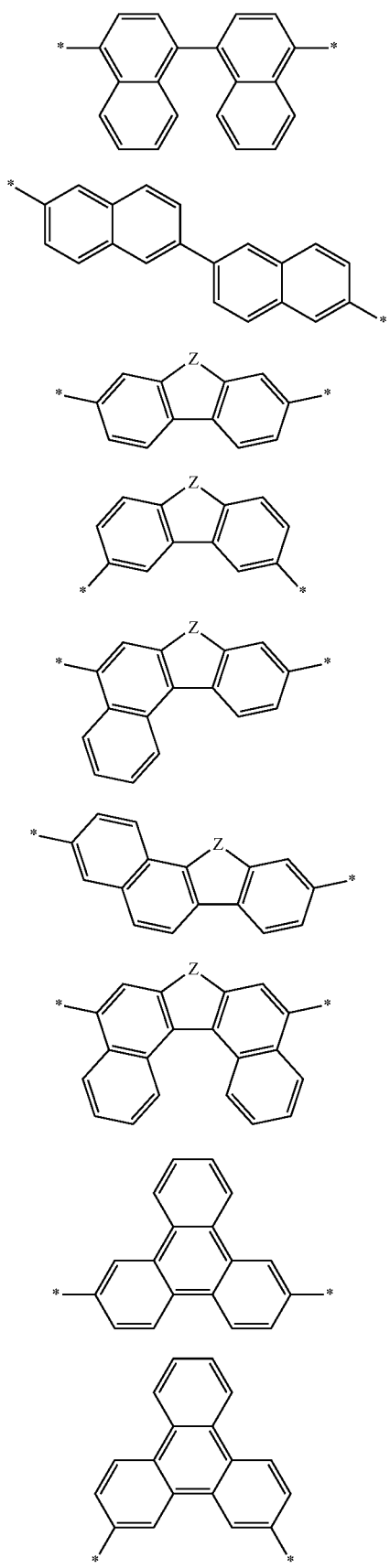
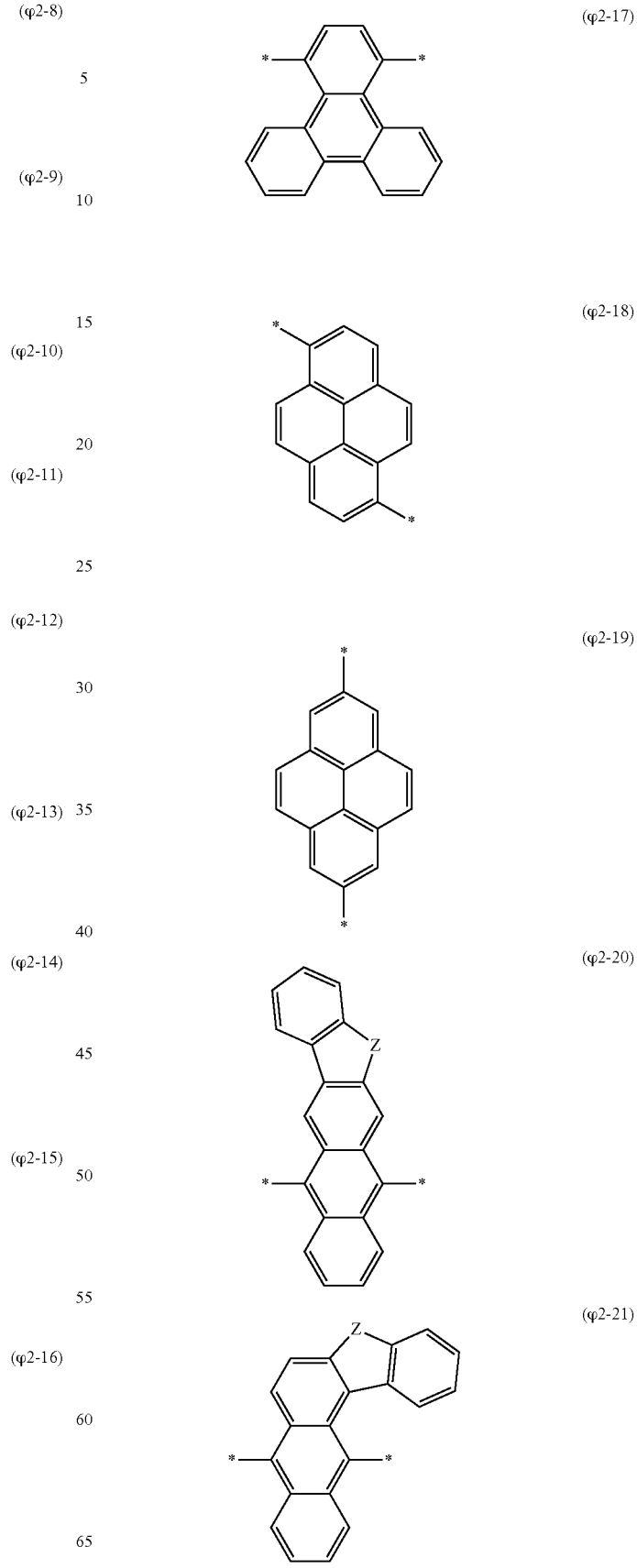

(φ2-22)
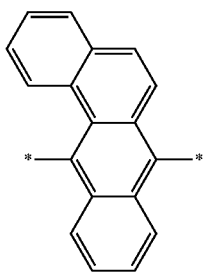
(φ2-23)
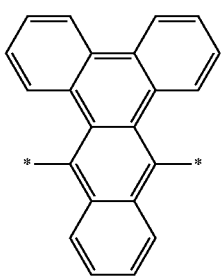
(φ2-24)
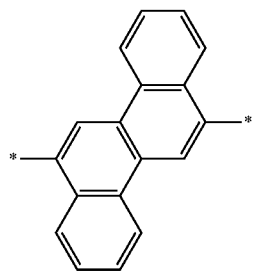
(φ2-25)
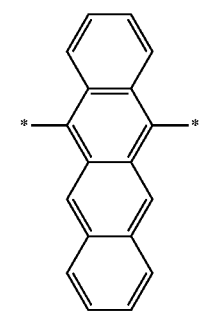
(φ2-26)
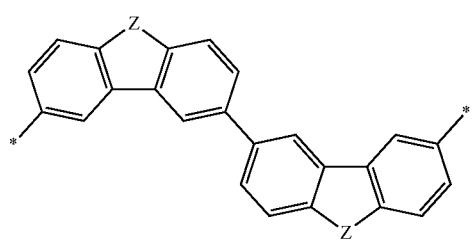
(φ2-27)
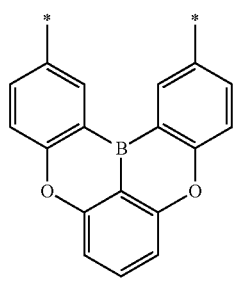
(φ2-28)
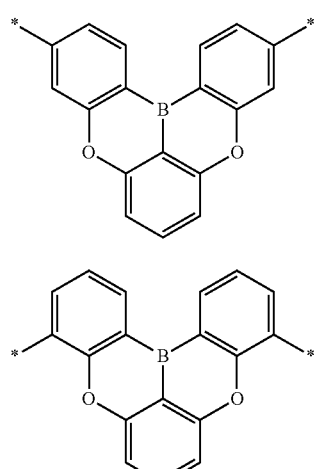
(φ2-29)
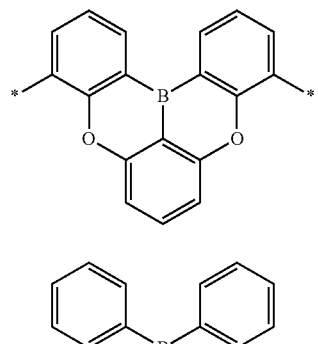
(φ2-30)
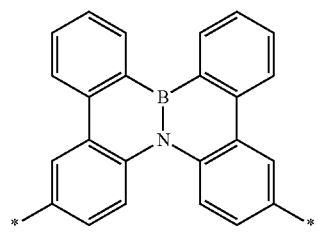
(φ2-31)
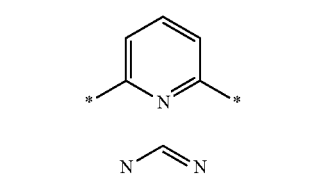
(φ2-32)
(φ2-33)
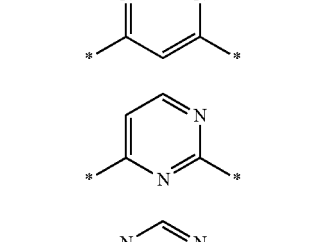
(φ2-34)
(φ3-2)
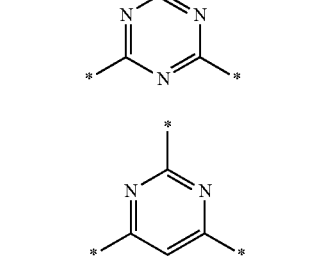

-continued (φ3-3)

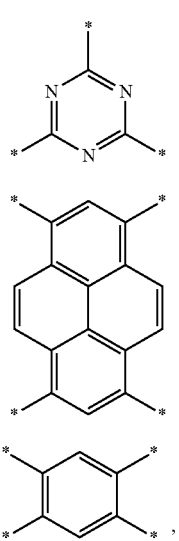

(φ4-1)

(φ4-2)

wherein a straight line(s) * extending outward in the structural formulas of φ means a bond(s) with L, Z in the structural formulas of φ represents >CR$_2$, >N—Ar, >N-L, —O—, or —S—, R's in >CR$_2$ each independently represent an alkyl having 1 to 4 carbon atoms, an aryl having 6 to 12 carbon atoms, or a heteroaryl having 2 to 12 carbon atoms, R's may be bonded to each other to form a ring, Ar in >N—Ar represents an aryl having 6 to 12 carbon atoms or a heteroaryl having 2 to 12 carbon atoms, and L in >N-L represents L in the formula (1), and at least one hydrogen atom in φ may be substituted by an alkyl having 1 to 6 carbon atoms, an unsubstituted aryl having 6 to 18 carbon atoms, or an unsubstituted heteroaryl having 2 to 18 carbon atoms, in formula (1), Y's each independently represent —O—, —S—, or >N—Ar, Ar represents an aryl having 6 to 12 carbon atoms or a heteroaryl having 2 to 12 carbon atoms, at least one hydrogen atom in Ar may be substituted by an alkyl having 1 to 4 carbon atoms, an aryl having 6 to 12 carbon atoms, or a heteroaryl having 2 to 12 carbon atoms, and $R^1$, $R^2$, $R^3$, $R^4$ and $R^5$ each independently represent a hydrogen atom or an alkyl having 1 to 4 carbon atoms, with the proviso that at least one of Ar in the >N—Ar and the $R^1$, $R^2$, $R^3$, $R^4$ and $R^5$ is a moiety bonded to L, in formula (1), L's are each independently selected from the group consisting of a divalent group represented by the following formula (L-1) and a divalent group represented by the following formula (L-2), (L-1)

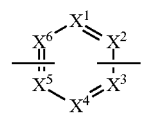

(L-2)

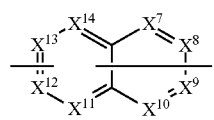

in formula (L-1), $X^1$, $X^2$, $X^3$, $X^4$, $X^5$ and $X^6$ each independently represent =CR$^6$- or =N—, at least two of $X^1$, $X^2$, $X^3$, $X^4$, $X^5$ and $X^6$ each represent=CR$^6$-, R$^6$'s in two=CR$^6$'s in $X^1$, $X^2$, $X^3$, $X^4$, $X^5$ and $X^6$ are each a moiety bonded to φ or an azoline ring, and R$^6$'s in the other=CR$^6$'s- each represent a hydrogen atom, in formula (L-2), $X^7$, $X^8$, $X^9$, $x^{10}$, $X^{11}$, $X^{12}$, $X^{13}$ and $X^{14}$ each independently represent =CR$^6$-or =N—, at least two of $X^7$, $X^8$, $X^9$, $x^{10}$, $X^{11}$, $x^{12}$, $x^{13}$ and $X^{14}$ each represent=CR$^6$-, R$^6$'s in two=CR$^6$'s in $X^7$, $X^8$, $X^9$, $x^{10}$, $X^{11}$, $X^{12}$, $X^{13}$ and $X^{14}$ are each a moiety bonded to φ or an azoline ring, and R$^6$'s in the other=CR$^6$-'s each represent a hydrogen atom, at least one hydrogen atom in L may be substituted by an alkyl having 1 to 4 carbon atoms, an aryl having 6 to 10 carbon atoms, or a heteroaryl having 2 to 10 carbon atoms, and at least one hydrogen atom in the compound represented by formula (1) may be substituted by a deuterium atom.

2. The azoline ring-containing compound according to claim 1, represented by the following formula (2-1) or (2-2), (2-1)

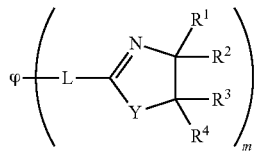

(2-2)

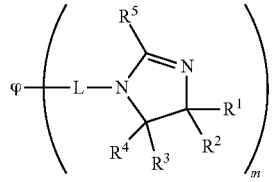

wherein:

formulas (2-1) and (2-2) represent a structure in which m "group(s) formed by an azoline ring and L" is/are bonded to φ, in formulas (2-1) and (2-2), m represents an integer of 1 to 4, and when m represents 2 to 4, "groups formed by an azoline ring and L" may be the same as or different from one another, in formulas (2-1) and (2-2), φ is selected from the group consisting of monovalent groups (in this case m=1) represented by the following formulas (φ1-1) to (φ1-11), monovalent groups (in this case m=1) represented by the following formulas (φ1-14) to (φ1-18), divalent groups (in this case m=2) represented by the following formulas (φ2-1) and (φ2-4) to (φ2-34), trivalent groups (in this case m=3) represented by the following formulas (φ3-2) and (φ3-3), and tetravalent groups (in this case m=4) represented by the following formulas (φ4-1) and (φ4-2),

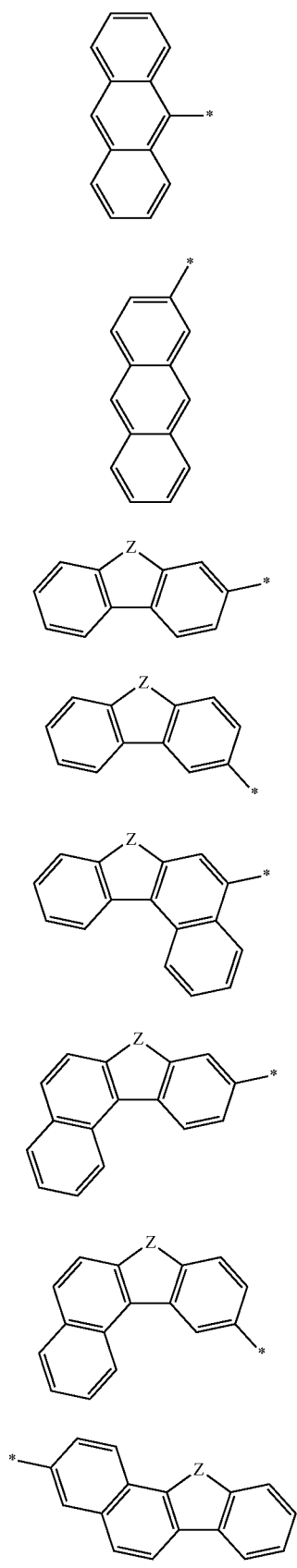
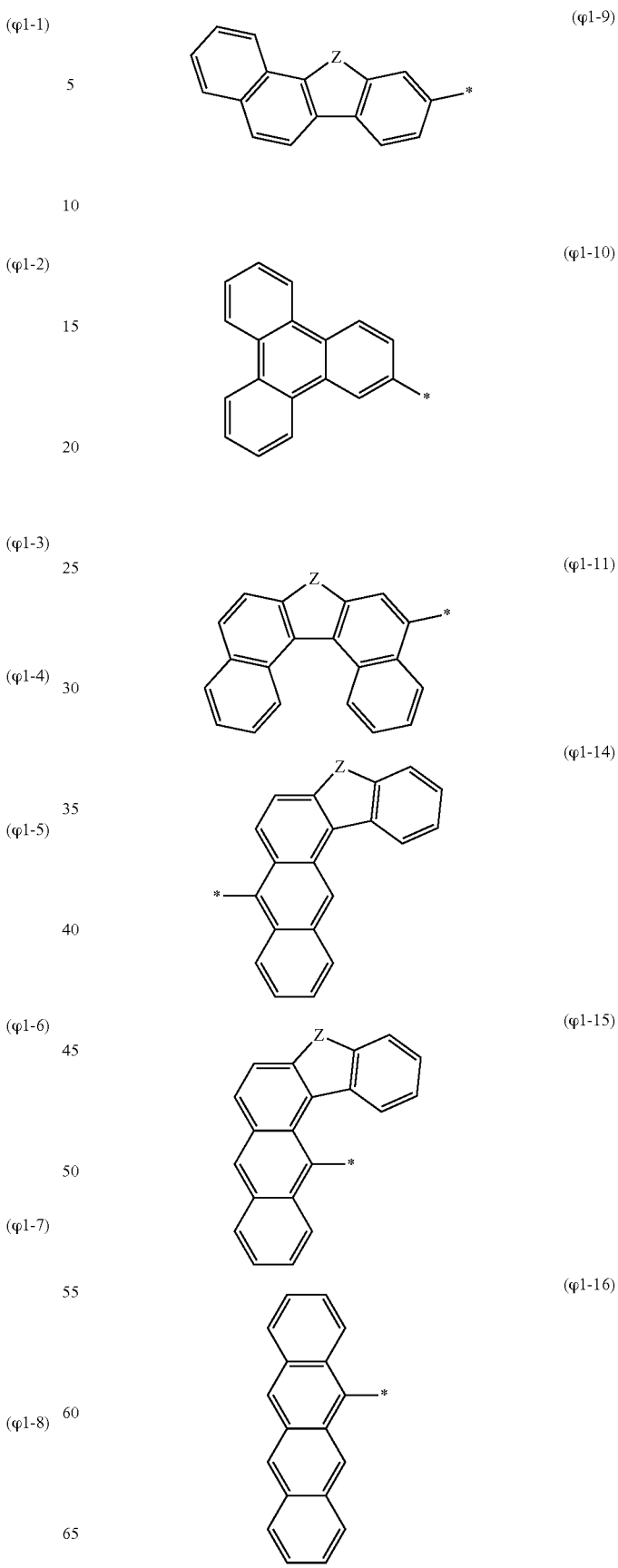

(φ1-17)
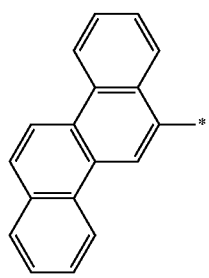
(φ1-18)
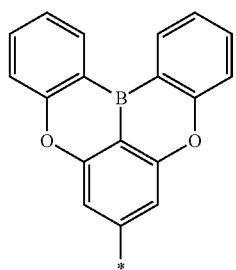
(φ2-1)
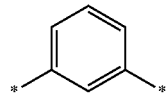
(φ2-4)
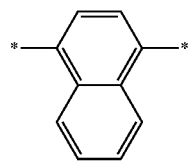
(φ2-5)
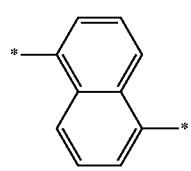
(φ2-6)
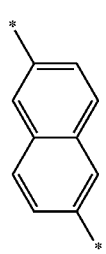
(φ2-7)
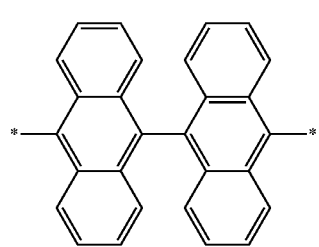
(φ2-8)
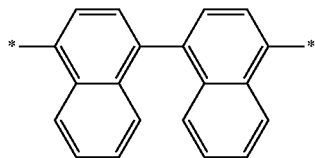
(φ2-9)
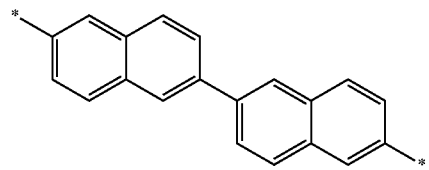
(φ2-10)
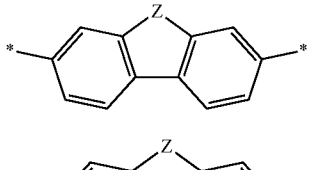
(φ2-11)
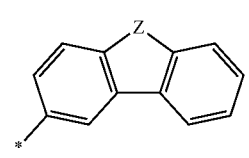
(φ2-12)
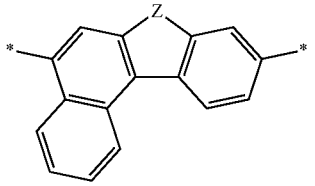
(φ2-13)
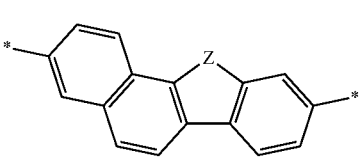
(φ2-14)
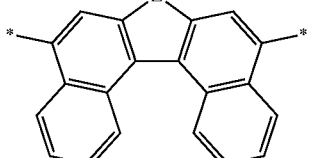
(φ2-15)
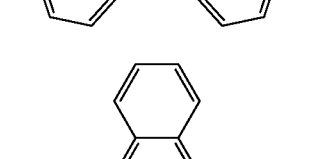
(φ2-16)
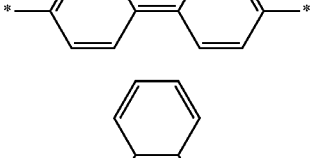
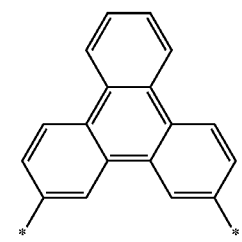

(φ2-17)
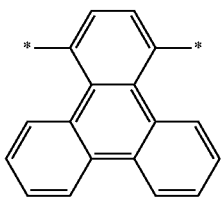
(φ2-18)
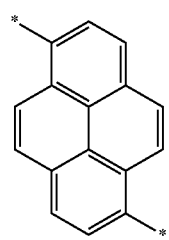
(φ2-19)
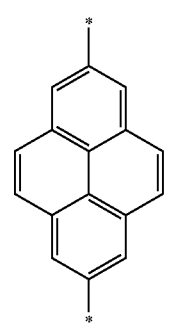
(φ2-20)
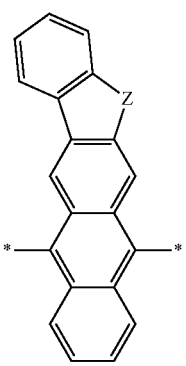
(φ2-21)
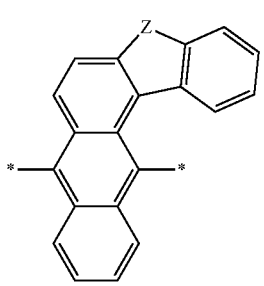
(φ2-22)
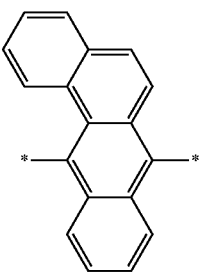
(φ2-23)
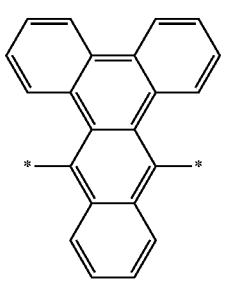
(φ2-24)
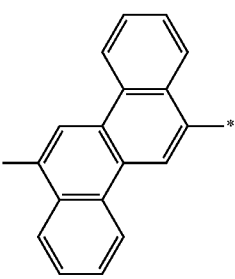
(φ2-25)
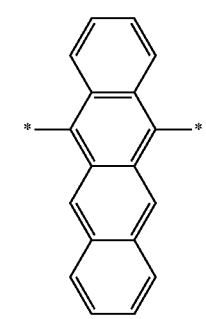
(φ2-26)
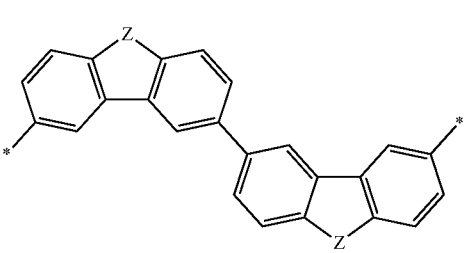

(φ2-27)
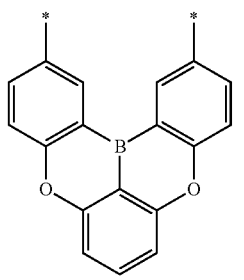

(φ2-28)
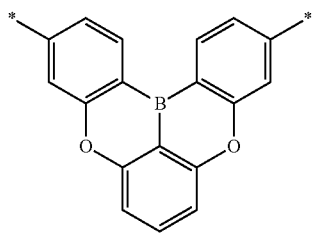

(φ2-29)
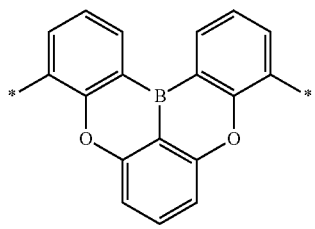

(φ2-30)
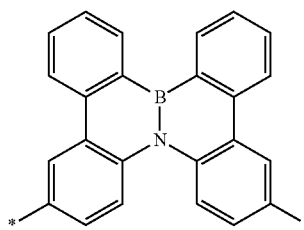

(φ2-31)
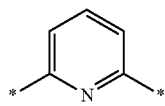

(φ2-32)
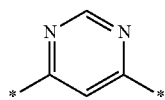

(φ2-33)
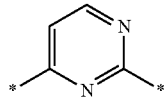

(φ2-34)
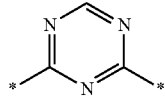

(φ3-2)
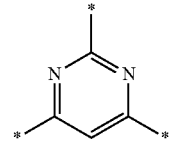

(φ3-3)
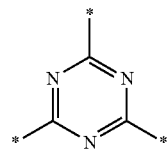

(φ4-1)
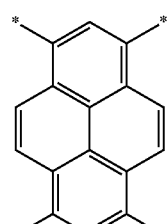

(φ4-2)
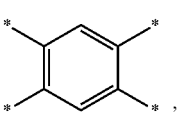

wherein a straight line(s) * extending outward in the structural formulas of φ means a bond(s) with L, Z in the structural formulas of φ represents >CR$_2$, >N—Ar, >N-L, —O—, or —S—, R's in >CR$_2$ each independently represent an alkyl having 1 to 4 carbon atoms, an aryl having 6 to 12 carbon atoms, or a heteroaryl having 2 to 12 carbon atoms, R's may be bonded to each other to form a ring, Ar in >N—Ar represents an aryl having 6 to 12 carbon atoms or a heteroaryl having 2 to 12 carbon atoms, and L in >N-L represents L in the formula (2-1) or (2-2), and at least one hydrogen atom in φ may be substituted by an alkyl having 1 to 6 carbon atoms, an aryl having 6 to 18 carbon atoms, or a heteroaryl having 2 to 18 carbon atoms, in formula (2-1), Y's each independently represent —O—, —S—, or >N—Ar, Ar represents an aryl having 6 to 12 carbon atoms or a heteroaryl having 2 to 12 carbon atoms, and at least one hydrogen atom in Ar may be substituted by an alkyl having 1 to 4 carbon atoms, an aryl having 6 to 12 carbon atoms, or a heteroaryl having 2 to 12 carbon atoms, in formula (2-1), $R^1$, $R^2$, $R^3$ and $R^4$ each independently represent a hydrogen atom or an alkyl having 1 to 4 carbon atoms, with the proviso that $R^1$ and $R^2$ are the same as each other and $R^3$ and $R^4$ are the same as each other, in formula (2-2), $R^1$, $R^2$, $R^3$, $R^4$ and $R^5$ each independently represent a hydrogen atom or an alkyl having 1 to 4 carbon atoms, with the proviso that $R^1$ and $R^2$ are the same as each other and $R^3$ and $R^4$ are the same as each other, in formulas (2-1) and (2-2), L's are each independently selected from the group consisting of a divalent group represented by the following formula (L-1) and a divalent group represented by the following formula (L-2), (L-1)

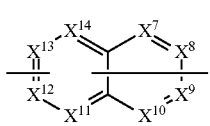
(L-2)

in formula (L-1), $X^1$, $X^2$, $X^3$, $X^4$, $X^5$ and $X^6$ each independently represent $=CR^6-$ or $=N-$, at least two of $X^1$, $X^2$, $X^3$, $X^4$, $X^5$ and $X^6$ each represent $=CR^6-$, $R^6$'s in two $=CR^6$'s in $X^1$, $X^2$, $X^3$, $X^4$, $X^5$ and $X^6$ are each a moiety bonded to $\varphi$ or an azoline ring, and $R^6$'s in the other $=CR^6-$'s each represent a hydrogen atom, in formula (L-2), $X^7$, $X^8$, $X^9$, $x^{10}$, $x^{11}$, $X^{12}$, $X^{13}$ and $X^{14}$ each independently represent $=CR^6-$or $=N-$, at least two of $X^7$, $X^8$, $X^9$, $X^{10}$, $x^{11}$, $X^{12}$, $x^{13}$ and $X^{14}$ each represent $=CR^6-$, $R^6$'s in two $=CR^6$'s in $X^7$, $X^8$, $X^9$, $X^{10}$, $X^{11}$, $X^{12}$, $X^{13}$ and $X^{14}$ are each a moiety bonded to $\varphi$ or an azoline ring, and $R^6$'s in the other $=CR^6-$'s each represent a hydrogen atom, at least one hydrogen atom in L may be substituted by an alkyl having 1 to 4 carbon atoms, an aryl having 6 to 10 carbon atoms, or a heteroaryl having 2 to 10 carbon atoms, and at least one hydrogen atom in the compound represented by formula (2-1) or (2-2) may be substituted by a deuterium atom.

3. The azoline ring-containing compound according to claim 1, wherein L represents a divalent group of a ring selected from the group consisting of benzene, naphthalene, pyridine, pyrazine, pyrimidine, pyridazine, triazine, quinoline, isoquinoline, naphthyridine, phthalazine, quinoxaline, quinazoline, cinnoline, and pteridine, and at least one hydrogen atom of L may be substituted by an alkyl having 1 to 4 carbon atoms, an aryl having 6 to 10 carbon atoms, or a heteroaryl having 2 to 10 carbon atoms.

4. The azoline ring-containing compound according to claim 1, wherein Ar in >N—Ar as Y or Z is selected from the group consisting of phenyl, naphthyl, pyridinyl, pyrazinyl, pyrimidinyl, pyridazinyl, triazinyl, quinolinyl, isoquinolinyl, naphthyridinyl, phthalazinyl, quinoxalinyl, quinazolinyl, cinnolinyl, and pteridinyl, and at least one hydrogen atom of Ar in >N—Ar as Y may be substituted by an alkyl having 1 to 4 carbon atoms or an aryl having 6 to 10 carbon atoms.

5. The azoline ring-containing compound according to claim 1, wherein $R^1$, $R^2$, $R^3$ and $R^4$ each independently represent a hydrogen atom or an alkyl having 1 to 4 carbon atoms, with the proviso that $R^1$ and $R^2$ are the same as each other, $R^3$ and $R^4$ are the same as each other, and not all of $R^1$, $R^2$, $R^3$ and $R^4$ represent hydrogen atoms simultaneously, and m represents 1 or 2, and when m represents 2, groups formed by an azoline ring and L are the same as each other.

6. The azoline ring-containing compound according to claim 1, wherein:

φ is selected from the group consisting of divalent groups represented by the following formulas (φ2-1), (φ2-31), (φ2-32), (φ2-33), and (φ2-34),

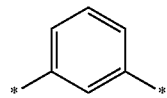
(φ2-1)

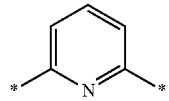
(φ2-31)

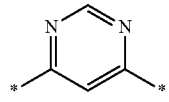
(φ2-32)

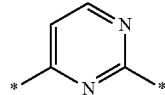
(φ2-33)

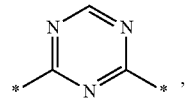
(φ2-34)

and at least one hydrogen atom of φ may be substituted by an aryl having 6 to 18 carbon atoms, L represents a divalent group of a ring selected from the group consisting of benzene, pyridine, pyrazine, pyrimidine, pyridazine, and triazine, and at least one hydrogen atom of L may be substituted by an alkyl having 1 to 4 carbon atoms, an aryl having 6 to 10 carbon atoms, or a heteroaryl having 2 to 14 carbon atoms, Ar in >N—Ar as Y is selected from the group consisting of phenyl, pyridinyl, pyrazinyl, pyrimidinyl, pyridazinyl, and triazinyl, and at least one hydrogen atom of the Ar may be substituted by an alkyl having 1 to 4 carbon atoms or an aryl having 6 to 10 carbon atoms, $R^1$, $R^2$, $R^3$ and $R^4$ each independently represent a hydrogen atom or an alkyl having 1 to 4 carbon atoms, with the proviso that $R^1$ and $R^2$ are the same as each other, $R^3$ and $R^4$ are the same as each other, and not all of $R^1$, $R^2$, $R^3$ and $R^4$ represent hydrogen atoms simultaneously, and m represents 2, and groups formed by an azoline ring and L are the same as each other.

7. An electron transport material or an electron injection layer material, comprising the azoline ring-containing compound according to claim 1.

8. An organic electroluminescent element comprising: a pair of electrodes formed of an anode and a cathode; a light emitting layer disposed between the pair of electrodes; and an electron transport layer and/or an electron injection layer disposed between the cathode and the light emitting layer and comprising the material according to claim 7.

9. The organic electroluminescent element according to claim 8, wherein at least one of the electron transport layer and the electron injection layer further comprises at least one selected from the group consisting of a quinolinol-based metal complex, a bipyridine derivative, a phenanthroline derivative, and a borane derivative.

10. The organic electroluminescent element according to claim 8, wherein at least one of the electron transport layer and the electron injection layer further comprises at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

11. A display apparatus or a lighting apparatus comprising the organic electroluminescent element according to claim 8.

12. An azoline ring-containing compound represented by any one of the following formulas (1-1-108), (1-2-2) and (1-2-102), (1-1-108)

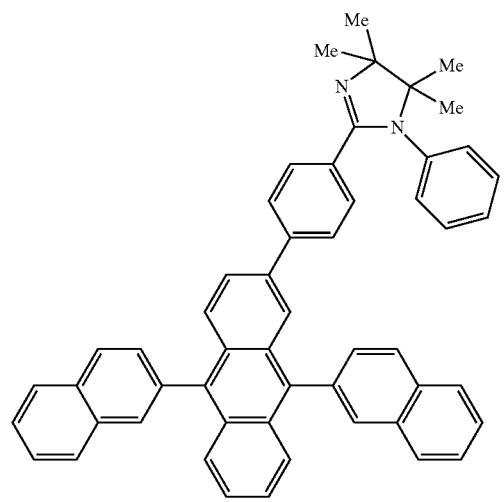

(1-2-2)

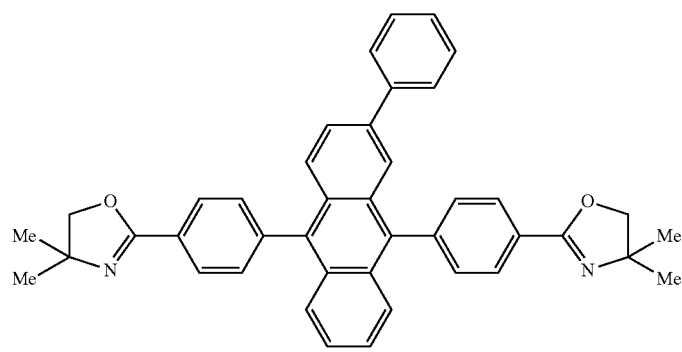

(1-2-102)

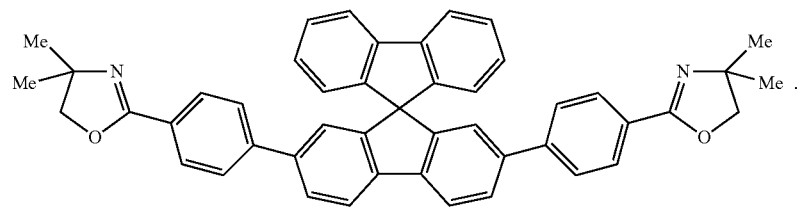

13. An azoline ring-containing compound represented by any one of the following formulas (1-2-22), (1-2-146), (1-2-402) and (1-2-522),
(1-2-22)
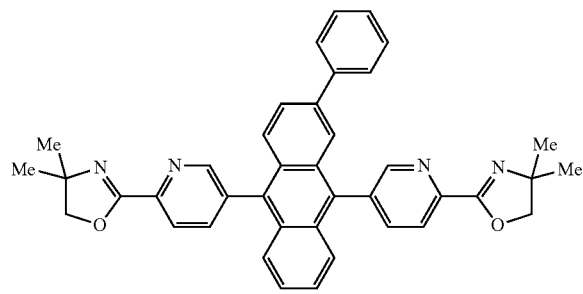
(1-2-146)
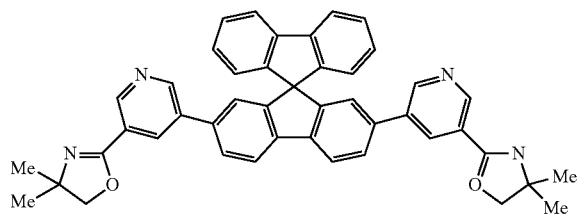
(1-2-402)
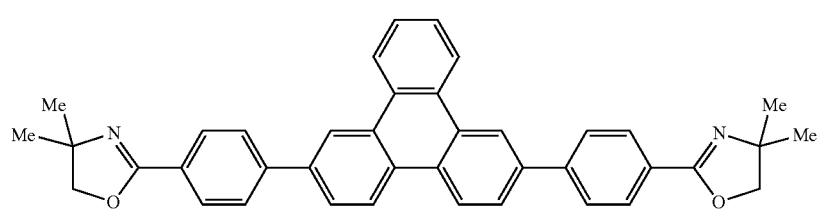
(1-2-522)
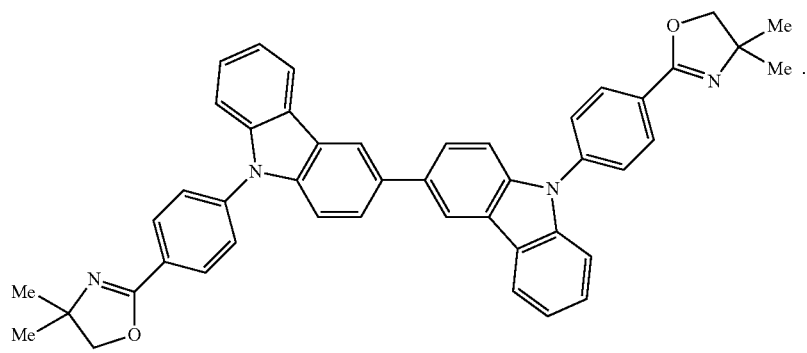
14. An azoline ring-containing compound represented by any one of the following formulas (1-2-1022), (1-2-1025), (1-2-1026), (1-2-1027), (1-2-1031) and (1-2-1035),
(1-2-1022)
-continued
(1-2-1025)
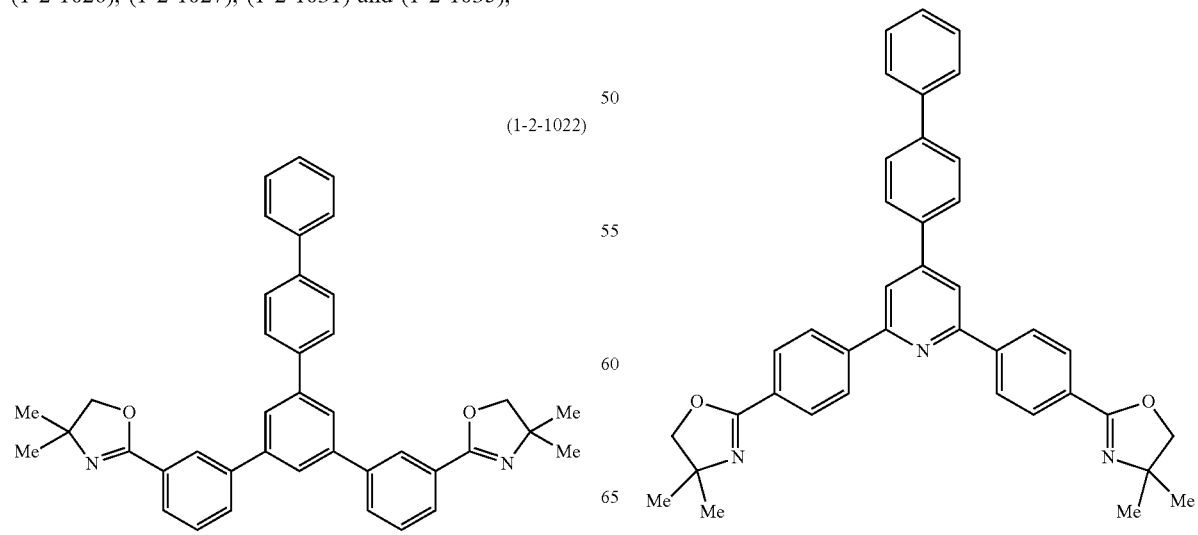

-continued (1-2-1026)

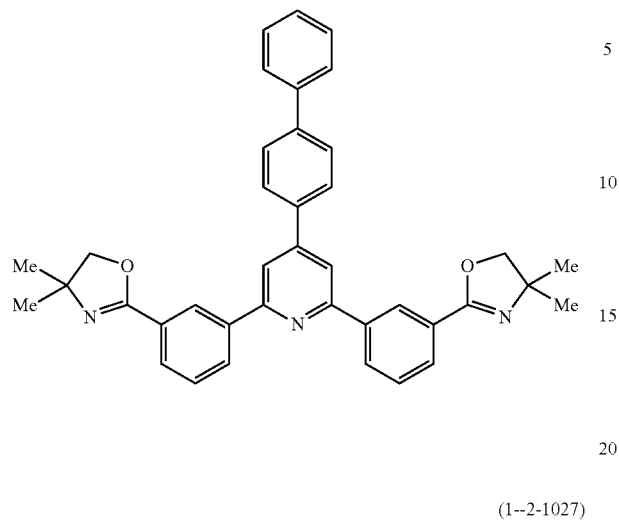

(1-2-1027)

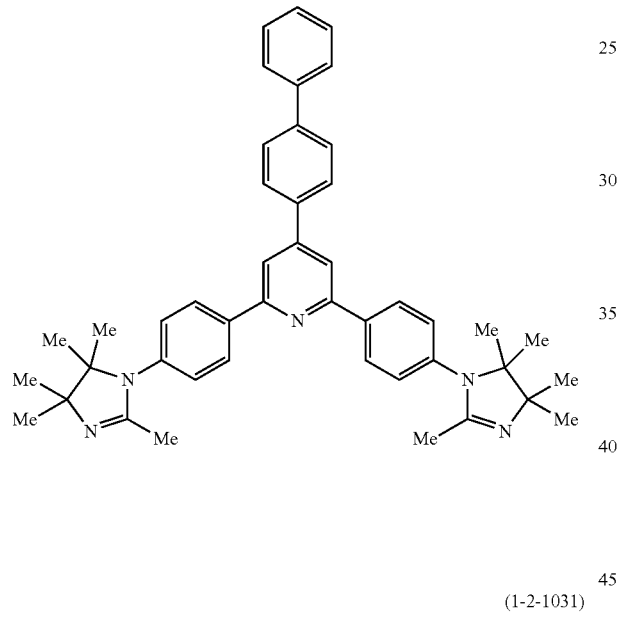

(1-2-1031)

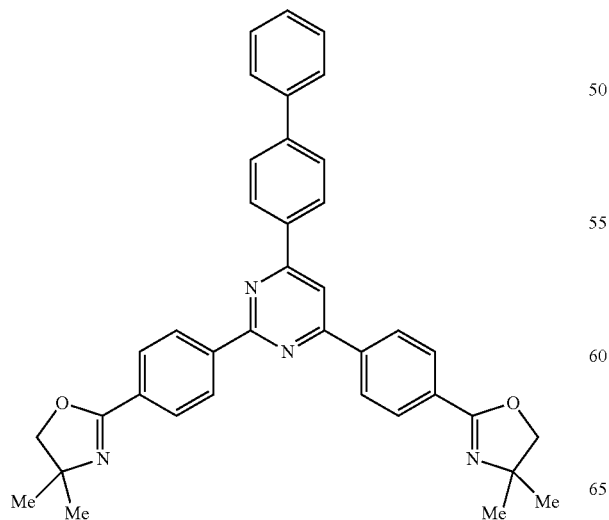

-continued (1-2-1035)

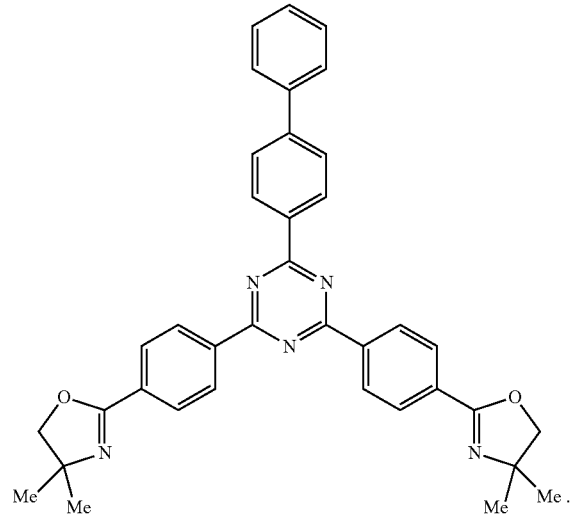

15. An azoline ring-containing compound represented by the following formula (1),

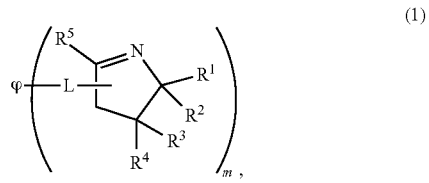

(1)

wherein:
formula (1) represents a structure in which m "group(s) formed by an azoline ring and L" is/are bonded to φ, in formula (1), m represents an integer of 1 to 4, and when m represents 2 to 4, "groups formed by an azoline ring and L" may be the same as or different from one another, in formula (1), φ is selected from the group consisting of monovalent groups (in this case m=1) represented by the following formulas (φ1-1) to (φ1-11), monovalent groups (in this case m=1) represented by the following formulas (φ1-14) to (φ1-18), divalent groups (in this case m=2) represented by the following formulas (φ2-1) to (φ2-34), trivalent groups (in this case m=3) represented by the following formulas (φ3-2) and (φ3-3), and tetravalent groups (in this case m=4) represented by the following formulas (φ4-1) and (φ4-2), (φ1-1)

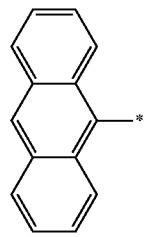

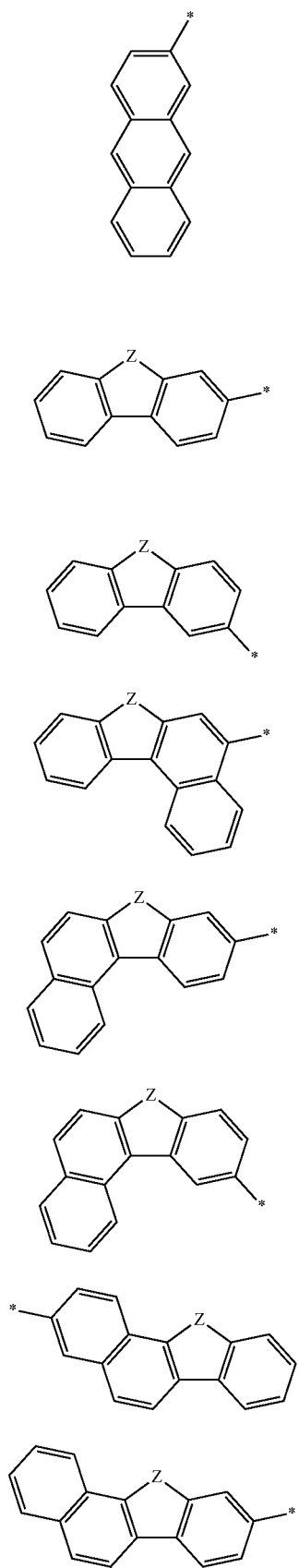
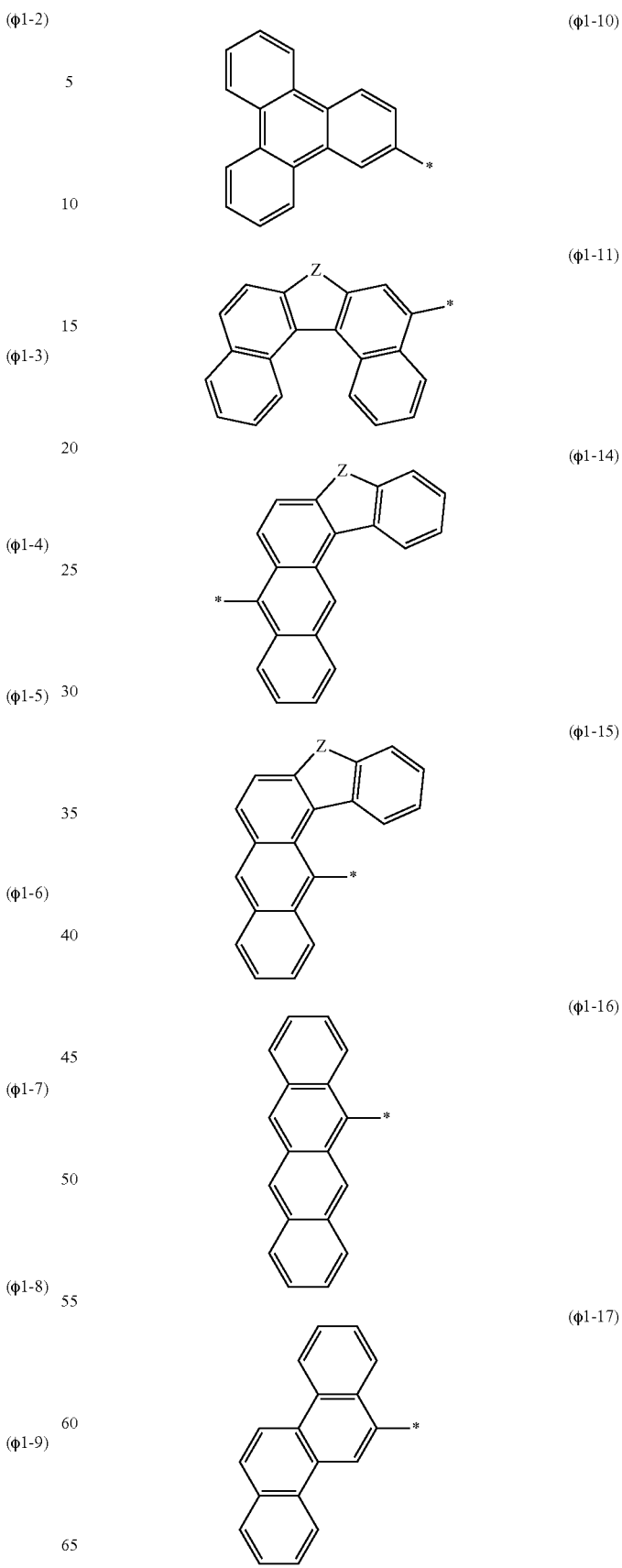

-continued
(φ1-18)
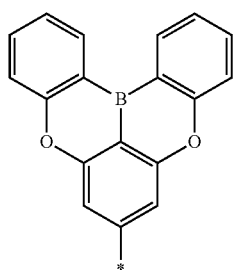
(φ2-1)
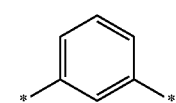
(φ2-2)
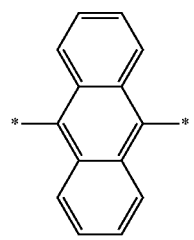
(φ2-3)
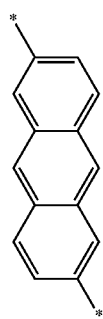
(φ2-4)
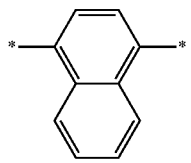
(φ2-5)
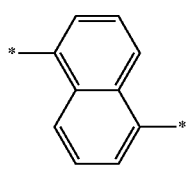
(φ2-6)
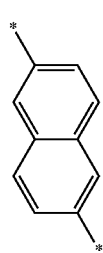
-continued
(φ2-7)
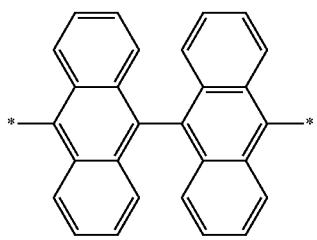
(φ2-8)
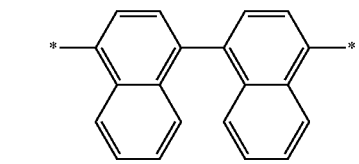
(φ2-9)
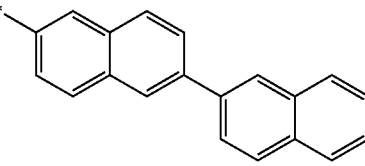
(φ2-10)
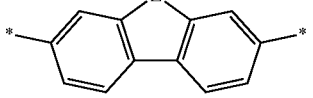
(φ2-11)
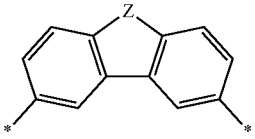
(φ2-12)
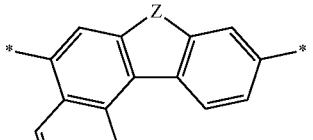
(φ2-13)
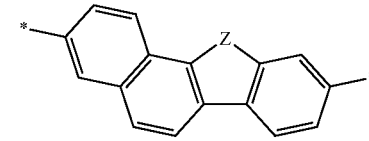
(φ2-14)
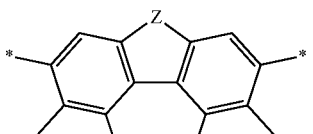
(φ2-15)
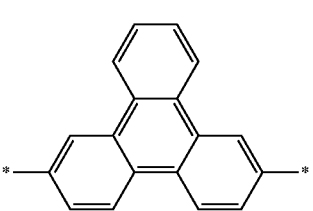

-continued
(φ2-16)
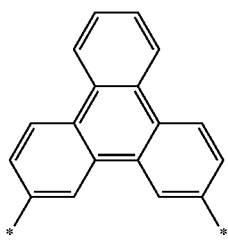
(φ2-17)
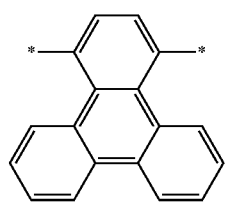
(φ2-18)
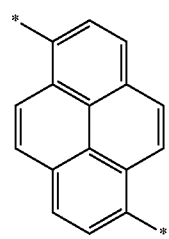
(φ2-19)
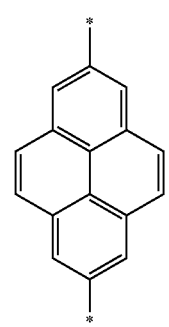
(φ2-20)
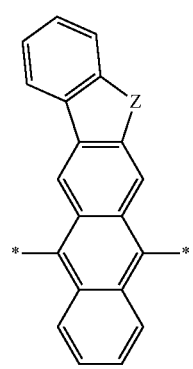
-continued
(φ2-21)
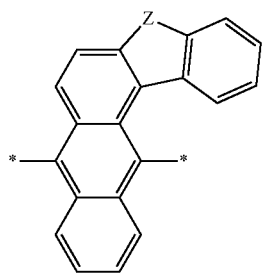
(φ2-22)
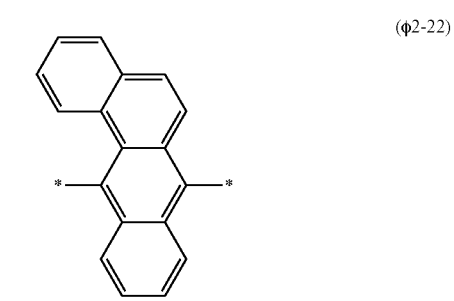
(φ2-23)
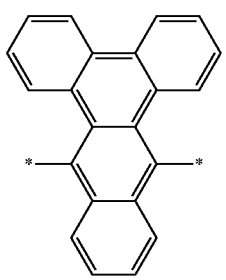
(φ2-24)
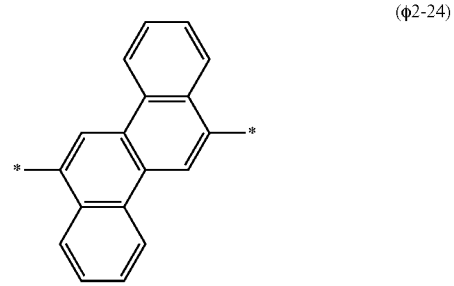
(φ2-25)
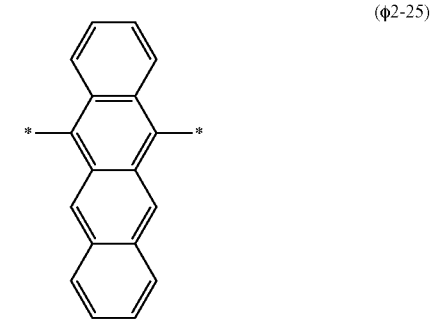

609
-continued (φ2-26)
(φ2-27)
(φ2-28)
(φ2-29)
(φ2-30)
(φ2-31)
(φ2-32)
(φ2-33)

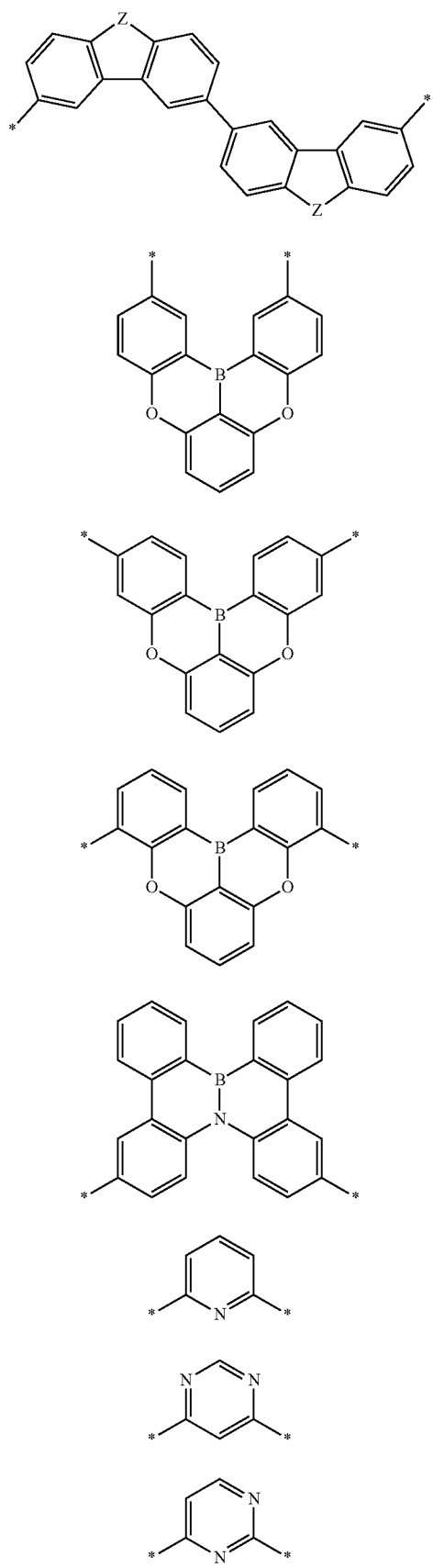

610
-continued

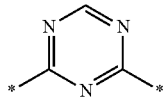
(φ2-34)

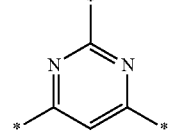
(φ3-2)

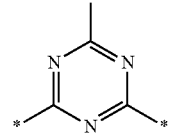
(φ3-3)

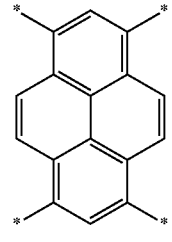
(φ4-1)

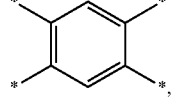
(φ4-2)

wherein a straight line(s) * extending outward in the structural formulas of φ means a bond(s) with L,
Z in the structural formulas of φ represents >CR$_2$, >N—Ar, >N-L, —O—, or —S—, R's in >CR$_2$ each independently represent an alkyl having 1 to 4 carbon atoms, an aryl having 6 to 12 carbon atoms, or a heteroaryl having 2 to 12 carbon atoms, R's may be bonded to each other to form a ring, Ar in >N—Ar represents an aryl having 6 to 12 carbon atoms or a heteroaryl having 2 to 12 carbon atoms, and L in >N-L represents L in the formula (1),
and at least one hydrogen atom in φ may be substituted by an alkyl having 1 to 6 carbon atoms, an unsubstituted aryl having 6 to 18 carbon atoms, or an unsubstituted heteroaryl having 2 to 18 carbon atoms,
in formula (1), Y's each independently represent —O—, —S—, or >N—Ar, Ar represents an aryl having 6 to 12 carbon atoms or a heteroaryl having 2 to 12 carbon atoms, at least one hydrogen atom in Ar may be substituted by an alkyl having 1 to 4 carbon atoms, an aryl having 6 to 12 carbon atoms, or a heteroaryl having 2 to 12 carbon atoms, and $R^1$, $R^2$, $R^3$, $R^4$ and $R^5$ each independently represent a hydrogen atom or an alkyl having 1 to 4 carbon atoms, with the proviso that $R^1$ and $R^2$ are the same as each other, $R^3$ and $R^4$ are the same as each other, and not all of $R^1$, $R^2$, $R^3$ and $R^4$ represent hydrogen atoms simultaneously, and with the proviso that at least one of Ar in the >N—Ar and the $R^1$, $R^2$, $R^3$, $R^4$ and $R^5$ is a moiety bonded to L,
in formula (1), L's are each independently selected from the group consisting of a divalent group represented by the following formula (L-1) and a divalent group represented by the following formula (L-2),

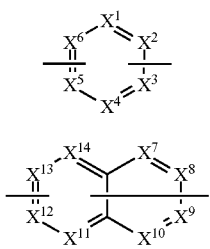
(L-1)

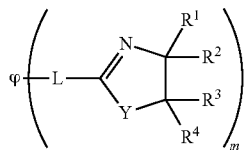
(L-2)

in formula (L-1), $X^1$, $X^2$, $X^3$, $X^4$, $X^5$ and $X^6$ each independently represent =$CR^6$- or =N—, at least two of $X^1$, $X^2$, $X^3$, $X^4$, $X^5$ and $X^6$ each represent =$CR^6$-, $R^6$'s in two =$CR^6$'s in $X^1$, $X^2$, $X^3$, $X^4$, $X^5$ and $X^6$ are each a moiety bonded to φ or an azoline ring, and $R^6$'s in the other =$CR^6$'s- each represent a hydrogen atom, in formula (L-2), $X^7$, $X^8$, $X^9$, $x^{10}$, $X^{11}$, $X^{12}$, $X^{13}$ and $X^{14}$ each independently represent =$CR^6$-or =N—, at least two of $X^7$, $X^8$, $X^9$, $x^{10}$, $X^{11}$, $x^{12}$, $x^{13}$ and $X^{14}$ each represent =$CR^6$-, $R^6$'s in two =$CR^6$'s in $X^7$, $X^8$, $X^9$, $x^{10}$, $X^{11}$, $X^{12}$, $X^{13}$ and $X^{14}$ are each a moiety bonded to φ or an azoline ring, and $R^6$'s in the other =$CR^6$-'s each represent a hydrogen atom, at least one hydrogen atom in L may be substituted by an alkyl having 1 to 4 carbon atoms, an aryl having 6 to 10 carbon atoms, or a heteroaryl having 2 to 10 carbon atoms, and at least one hydrogen atom in the compound represented by formula (1) may be substituted by a deuterium atom.

16. The azoline ring-containing compound according to claim 15, represented by the following formula (2-1) or (2-2),

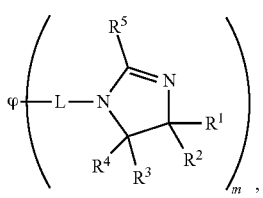

wherein:

formulas (2-1) and (2-2) represent a structure in which m "group(s) formed by an azoline ring and L" is/are bonded to y, in formulas (2-1) and (2-2), m represents an integer of 1 to 4, and when m represents 2 to 4, "groups formed by an azoline ring and L" may be the same as or different from one another, in formulas (2-1) and (2-2), φ is selected from the group consisting of monovalent groups (in this case m=1) represented by the following formulas (φ1-1) to (φ1-11), monovalent groups (in this case m=1) represented by the following formulas (φ1-14) to (φ1-18), divalent groups (in this case m=2) represented by the following formulas (φ2-1) to (φ2-34), trivalent groups (in this case m=3) represented by the following formulas (φ3-2) and (φ3-3), and tetravalent groups (in this case m=4) represented by the following formulas (φ4-1) and (φ4-2),

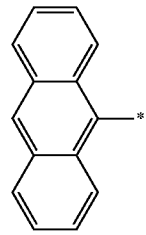
(φ1-1)

(φ1-2)

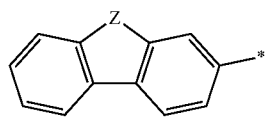
(φ1-3)

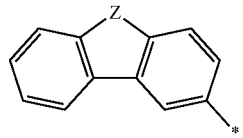
(φ1-4)

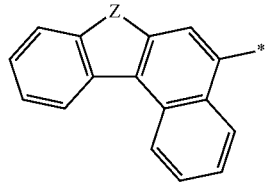
(φ1-5)

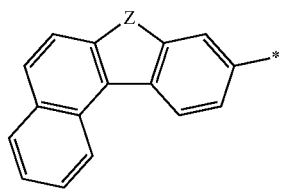
(φ1-6)

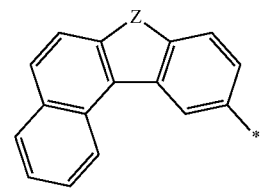
(φ1-7)

-continued
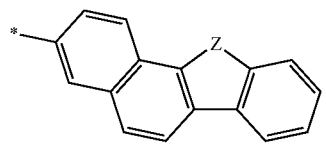
(φ1-8)
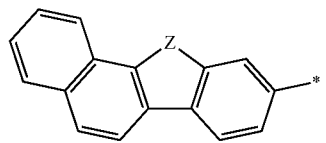
(φ1-9)
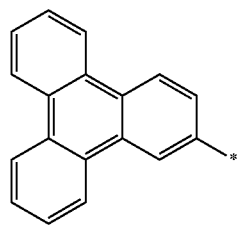
(φ1-10)
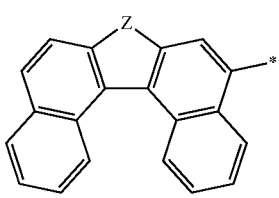
(φ1-11)
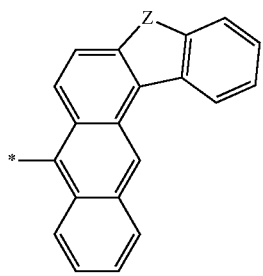
(φ1-14)
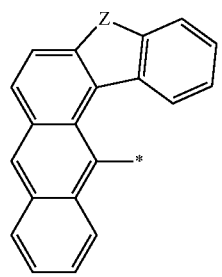
(φ1-15)
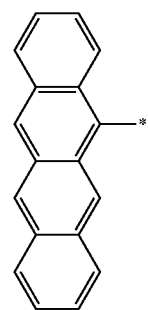
(φ1-16)
-continued
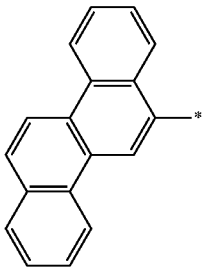
(φ1-17)
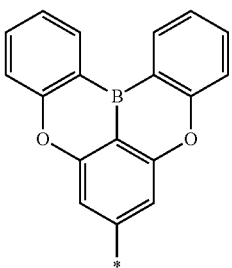
(φ1-18)
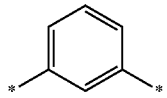
(φ2-1)
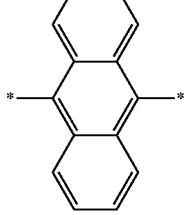
(φ2-2)
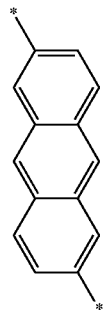
(φ2-3)
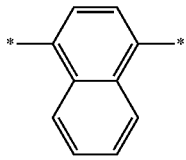
(φ2-4)
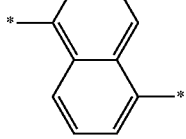
(φ2-5)

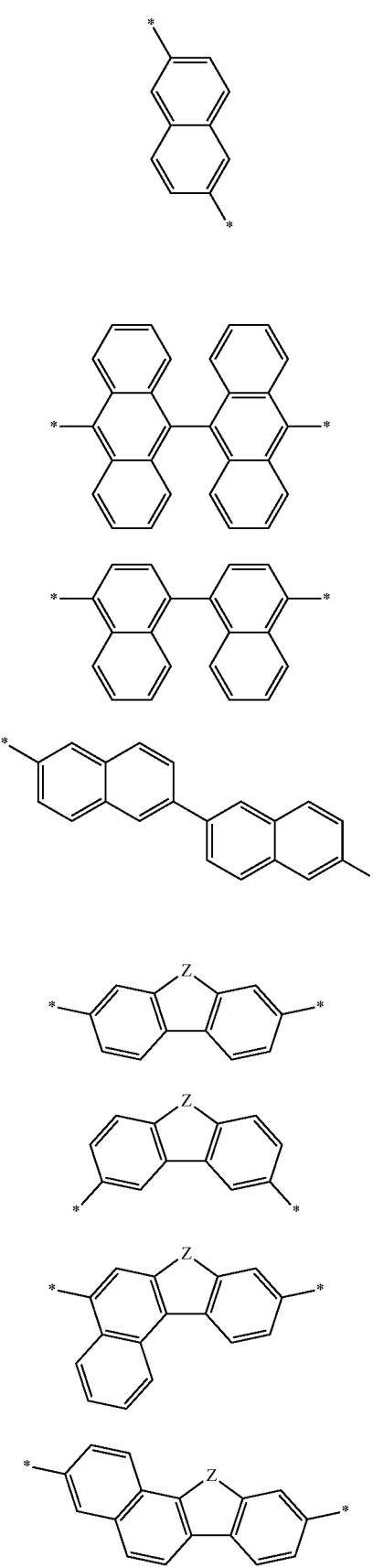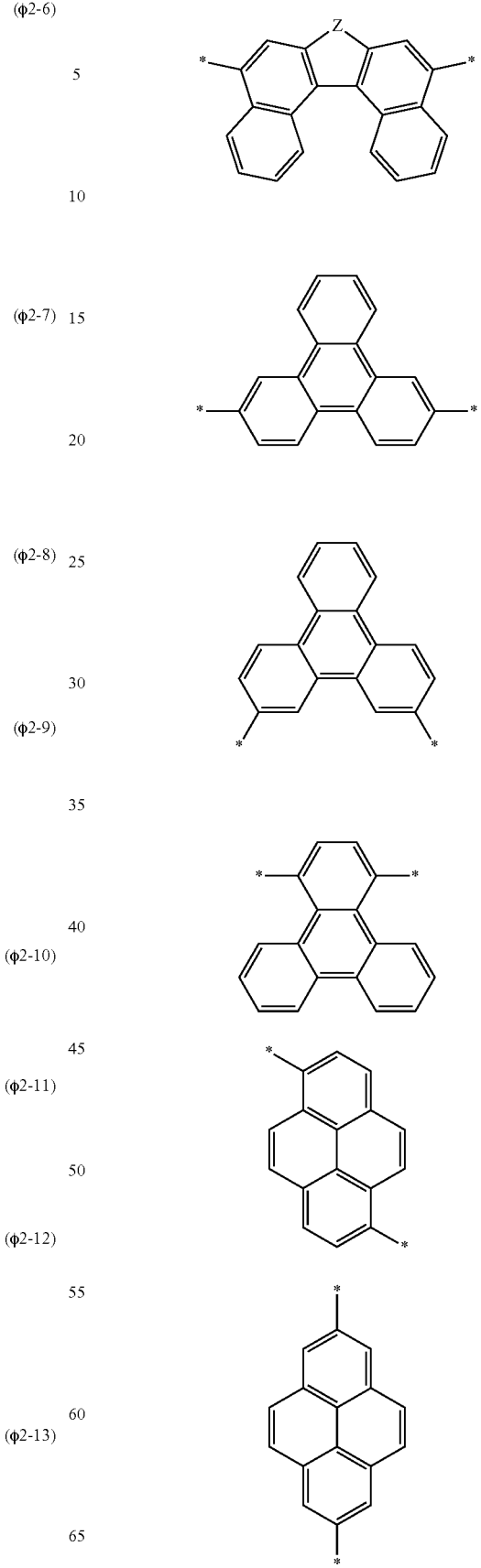

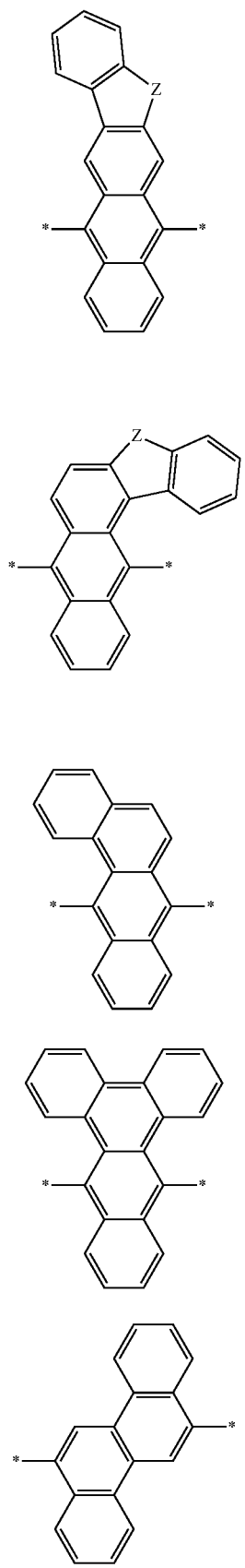
(φ2-20)
(φ2-21)
(φ2-22)
(φ2-23)
(φ2-24)
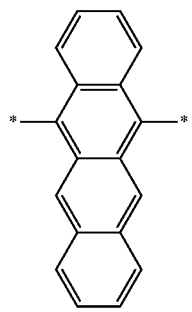
(φ2-25)
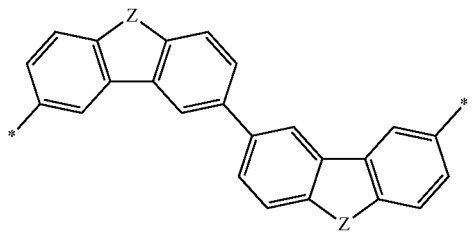
(φ2-26)
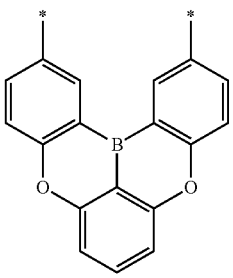
(φ2-27)
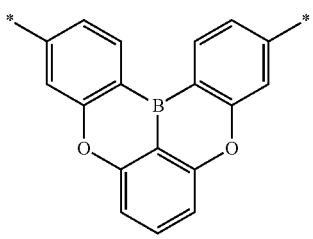
(φ2-28)
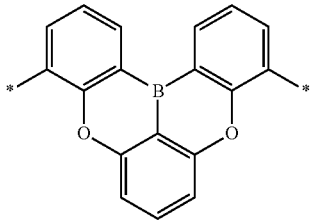
(φ2-29)
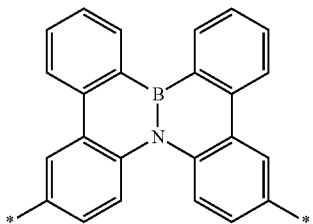
(φ2-30)

(φ2-31)
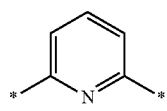

(φ2-32)
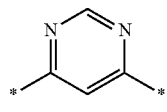

(φ2-33)
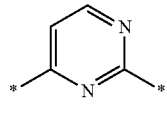

(φ2-34)
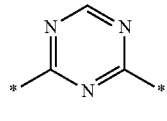

(φ3-2)
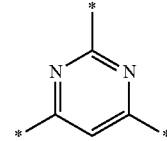

(φ3-3)
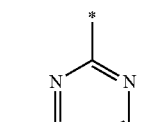

(φ4-1)
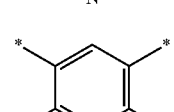

(φ4-2)
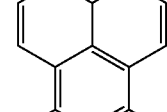

wherein a straight line(s) * extending outward in the structural formulas of φ means a bond(s) with L, Z in the structural formulas of φ represents >CR$_2$, >N—Ar, >N-L, —O—, or —S—, R's in >CR$_2$ each independently represent an alkyl having 1 to 4 carbon atoms, an aryl having 6 to 12 carbon atoms, or a heteroaryl having 2 to 12 carbon atoms, R's may be bonded to each other to form a ring, Ar in >N—Ar represents an aryl having 6 to 12 carbon atoms or a heteroaryl having 2 to 12 carbon atoms, and L in >N-L represents L in the formula (2-1) or (2-2), and at least one hydrogen atom in φ may be substituted by an alkyl having 1 to 6 carbon atoms, an aryl having 6 to 18 carbon atoms, or a heteroaryl having 2 to 18 carbon atoms, in formula (2-1), Y's each independently represent —O—, —S—, or >N—Ar, Ar represents an aryl having 6 to 12 carbon atoms or a heteroaryl having 2 to 12 carbon atoms, and at least one hydrogen atom in Ar may be substituted by an alkyl having 1 to 4 carbon atoms, an aryl having 6 to 12 carbon atoms, or a heteroaryl having 2 to 12 carbon atoms, in formulas (2-1) and (2-2), L's are each independently selected from the group consisting of a divalent group represented by the following formula (L-1) and a divalent group represented by the following formula (L-2), (L-1)
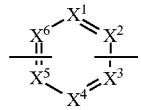

(L-2)
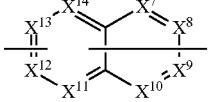

in formula (L-1), $X^1$, $X^2$, $X^3$, $X^4$, $X^5$ and $X^6$ each independently represent =CR$^6$- or =N—, at least two of $X^1$, $X^2$, $X^3$, $X^4$, $X^5$ and $X^6$ each represent =CR$^6$-, R$^6$'s in two =CR$^6$'s in $X^1$, $X^2$, $X^3$, $X^4$, $X^5$ and $X^6$ are each a moiety bonded to φ or an azoline ring, and R$^6$'s in the other =CR$^6$-'s each represent a hydrogen atom, in formula (L-2), $X^7$, $X^8$, $X^9$, $X^{10}$, $X^{11}$, $X^{12}$, $X^{13}$ and $X^{14}$ each independently represent =CR$^6$- or =N—, at least two of $X^7$, $X^8$, $X^9$, $X^{10}$, $X^{11}$, $X^{12}$, $X^{13}$ and $X^{14}$ each represent =CR$^6$-, R$^6$'s in two =CR$^6$'s in $X^7$, $X^8$, $X^9$, $X^{10}$, $X^{11}$, $X^{12}$, $X^{13}$ and $X^{14}$ are each a moiety bonded to φ or an azoline ring, and R$^6$'s in the other =CR$^6$-'s each represent a hydrogen atom, at least one hydrogen atom in L may be substituted by an alkyl having 1 to 4 carbon atoms, an aryl having 6 to 10 carbon atoms, or a heteroaryl having 2 to 10 carbon atoms, and at least one hydrogen atom in the compound represented by formula (2-1) or (2-2) may be substituted by a deuterium atom.

17. The azoline ring-containing compound according to claim 15, wherein L represents a divalent group of a ring selected from the group consisting of benzene, naphthalene, pyridine, pyrazine, pyrimidine, pyridazine, triazine, quinoline, isoquinoline, naphthyridine, phthalazine, quinoxaline, quinazoline, cinnoline, and pteridine, and at least one hydrogen atom of L may be substituted by an alkyl having 1 to 4 carbon atoms, an aryl having 6 to 10 carbon atoms, or a heteroaryl having 2 to 10 carbon atoms.

18. The azoline ring-containing compound according to claim 15, wherein Ar in >N—Ar as Y or Z is selected from the group consisting of phenyl, naphthyl, pyridinyl, pyrazinyl, pyrimidinyl, pyridazinyl, triazinyl, quinolinyl, isoquinolinyl, naphthyridinyl, phthalazinyl, quinoxalinyl, quinazolinyl, cinnolinyl, and pteridinyl, and at least one hydrogen atom of Ar in >N—Ar as Y may be substituted by an alkyl having 1 to 4 carbon atoms or an aryl having 6 to 10 carbon atoms.

19. The azoline ring-containing compound according to claim 15, wherein:

φ is selected from the group consisting of divalent groups represented by the following formulas (φ2-11, (φ2-311 (φ2-321 (φ2-331 and (φ2-341

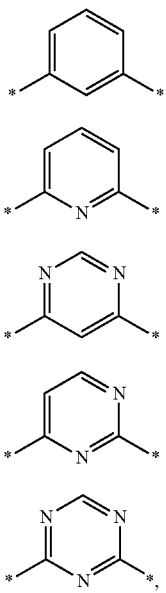

(φ2-1)
(φ2-31)
(φ2-32)
(φ2-33)
(φ2-34)

and at least one hydrogen atom of φ may be substituted by an aryl having 6 to 18 carbon atoms, L represents a divalent group of a ring selected from the group consisting of benzene, pyridine, pyrazine, pyrimidine, pyridazine, and triazine, and at least one hydrogen atom of L may be substituted by an alkyl having 1 to 4 carbon atoms, an aryl having 6 to 10 carbon atoms, or a heteroaryl having 2 to 14 carbon atoms, Ar in >N—Ar as Y is selected from the group consisting of phenyl, pyridinyl, pyrazinyl, pyrimidinyl, pyridazinyl, and triazinyl, and at least one hydrogen atom of the Ar may be substituted by an alkyl having 1 to 4 carbon atoms or an aryl having 6 to 10 carbon atoms, and m represents 2, and groups formed by an azoline ring and L are the same as each other.

20. An electron transport material or an electron injection layer material, comprising the azoline ring-containing compound according to claim 15.

21. An organic electroluminescent element comprising: a pair of electrodes formed of an anode and a cathode; a light emitting layer disposed between the pair of electrodes; and an electron transport layer and/or an electron injection layer disposed between the cathode and the light emitting layer and comprising the material according to claim 20.

22. The organic electroluminescent element according to claim 21, wherein at least one of the electron transport layer and the electron injection layer further comprises at least one selected from the group consisting of a quinolinol-based metal complex, a bipyridine derivative, a phenanthroline derivative, and a borane derivative.

23. The organic electroluminescent element according to claim 21, wherein at least one of the electron transport layer and the electron injection layer further comprises at least one selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal, and an organic complex of a rare earth metal.

24. A display apparatus or a lighting apparatus comprising the organic electroluminescent element according to claim 21.

* * * * *